United States Patent
Yoshimoto et al.

(10) Patent No.: US 9,380,782 B2
(45) Date of Patent: Jul. 5, 2016

(54) TETRAZOLINONE COMPOUNDS AND ITS USE

(71) Applicant: SUMITOMO CHEMICAL COMPANY, LIMITED, Tokyo (JP)

(72) Inventors: Yuya Yoshimoto, Takarazuka (JP);
Teruki Takahashi, Takarazuka (JP);
Daisuke Oohira, Takarazuka (JP);
Shuhei Azuma, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/382,232

(22) PCT Filed: Apr. 26, 2013

(86) PCT No.: PCT/JP2013/062982
§ 371 (c)(1),
(2) Date: Aug. 29, 2014

(87) PCT Pub. No.: WO2013/162077
PCT Pub. Date: Oct. 31, 2013

(65) Prior Publication Data
US 2015/0031733 A1 Jan. 29, 2015

(30) Foreign Application Priority Data

Apr. 27, 2012 (JP) .................................. 2012-102451
Oct. 22, 2012 (JP) .................................. 2012-232587

(51) Int. Cl.
| | |
|---|---|
| *C07D 413/12* | (2006.01) |
| *C07D 417/12* | (2006.01) |
| *A01N 43/78* | (2006.01) |
| *A01N 43/76* | (2006.01) |
| *C07D 277/34* | (2006.01) |

(52) U.S. Cl.
CPC ................ *A01N 43/78* (2013.01); *A01N 43/76* (2013.01); *C07D 277/34* (2013.01); *C07D 413/12* (2013.01); *C07D 417/12* (2013.01)

(58) Field of Classification Search
USPC ........................................................ 548/182
See application file for complete search history.

(56) References Cited

U.S. PATENT DOCUMENTS

2014/0323305 A1   10/2014   Rheinheimer et al.

FOREIGN PATENT DOCUMENTS

| | | |
|---|---|---|
| CN | 1153173 A | 7/1997 |
| JP | 9-208565 A | * 8/1997 |
| WO | WO 96/36229 A1 | 11/1996 |
| WO | WO 99/05139 A1 | 2/1999 |
| WO | 2013/092224 A1 | 6/2013 |

OTHER PUBLICATIONS

The International Preliminary Report on Patentability and the Written Opinion of the International Searching Authority, dated Nov. 6, 2014, issued in the corresponding International Application No. PCT/JP2013/062982.
The First Office Action (including an English translation thereof) issued in the corresponding Chinese Patent Application No. 201380021109.7 on Jul. 16, 2015.
The Second Office Action (including an English translation thereof) issued in the corresponding Chinese Patent Application No. 201380021109.7 on Mar. 28, 2016.

* cited by examiner

*Primary Examiner* — Laura L Stockton
(74) *Attorney, Agent, or Firm* — Birch, Stewart, Kolasch & Birch, LLP

(57) ABSTRACT

The present invention provides a compound having an excellent efficacy for controlling pests. A tetrazolinone compound of a formula (1): [wherein, R1 represents an C6-C16 aryl group, an C1-C12 alkyl group, a C3-C12 cycloalkyl group or an adamantyl group, etc., which each optionally be substituted; R2 represents a hydrogen atom, an C1-C12 alkyl group, or a halogen atom, etc.; R4 and R5 represent independently of each other a hydrogen atom or an C1-C3 alkyl group, etc.; R6, R7, R8 and R9 represent independently of each other a hydrogen atom, a halogen atom, an C1-C12 alkyl group, a C1-C12 haloalkyl group, an C2-C12 alkenyl group, a C3-C12 cycloalkyl group, an C1-C12 alkoxy group or a C1-C12 haloalkoxy group, etc.; X and Y represent independently of each other a sulfur atom or an oxygen atom; Q represents an oxygen atom or a sulfur atom; and R10 represents an C1-C6 alkyl group, etc.] shows an excellent controlling efficacy on pests.

(1)

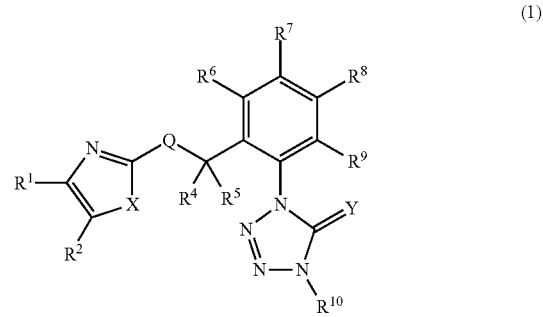

35 Claims, No Drawings

TETRAZOLINONE COMPOUNDS AND ITS USE

This application claims priority to and the benefit of Japanese Patent Application Nos. 2012-102451 filed Apr. 27, 2012 and 2012-232587 filed Oct. 22, 2012, the entire contents of which are incorporated herein by reference.

TECHNICAL FIELD

The present invention relates to tetrazolinone compounds and its use.

BACKGROUND ART

Heretofore, some compounds as active ingredients in pesticides for controlling pests have been widely developed and then provides in practice use.

Also, as pesticides for controlling pests having tetrazolinone ring, compounds having a thiazole backbone represented by the following formula (A):

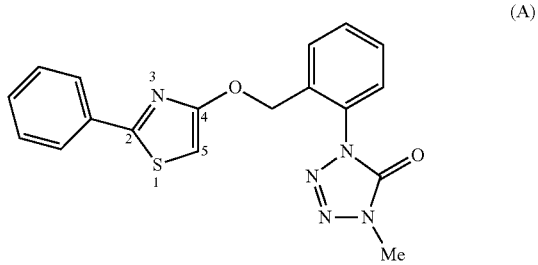 [SMILES: Cn1nnn(-c2ccccc2COc2csc(-c3ccccc3)n2)c1=O]

(A)

wherein a substituent (hereinafter, described as a linker) connecting between a benzene ring directly bound to the tetrazolinone ring and the thiazole backbone is bound at 4-position of the thiazole, have been known (see Patent Document 1).

Compounds having benzothiazole backbone represented by the following formula (B):

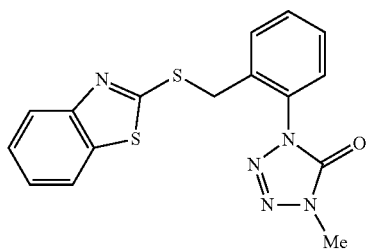

(B)

have been also known (see Patent Document 2).

Further, compounds having a substituent such as methyl group at 6-position of the benzene ring that is directly bound to the tetrazolinone ring in the formula (B), for example, compounds represented by the following formula (C):

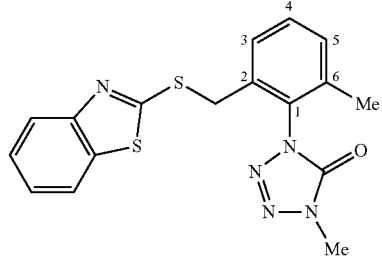

(C)

have been disclosed (see Patent Document 2).

CITATION LIST

Patent Document

Patent Document 1: WO 1996/36229 pamphlet
Patent Document 2: JP 9-208565 A

SUMMARY OF THE INVENTION

An object of the present invention is to provide a compound having an excellent efficacy for controlling pests.

The present inventors have intensively studied to find that compounds having an excellent efficacy for controlling pests and as a result, found that a tetrazolinone compound of the following formula (I) has an excellent efficacy for controlling pests, which thus have completed the present invention.

Specifically, the present invention includes the following [1] to [36].

[1] A tetrazolinone compound of a formula (1):

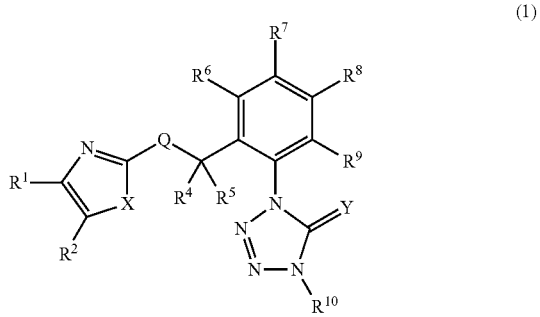

(1)

[wherein, $R^1$ represents an C6-C16 aryl group optionally substituted with one or more substituents selected from the group $P^1$, an C7-C18 aralkyl group optionally substituted with one or more substituents selected from the group $P^1$, an C1-C12 alkyl group optionally substituted with one or more substituents selected from the group $P^1$, an C2-C12 alkenyl group optionally substituted with one or more substituents selected from the group $P^1$, an C2-C12 alkynyl group optionally substituted with one or more substituents selected from the group $P^1$, a C3-C12 cycloalkyl group optionally substituted with one or more substituents selected from the group $P^1$, an C2-C12 acyl group optionally substituted with one or more substituents selected from the group P1, an adamantyl group optionally substituted with one or more substituents selected from the group $P^1$, a C3-C12 trialkylsilyl group, a hydrogen atom or a halogen atom (with the proviso that when the C6-C16 aryl group, the C7-C18 aralkyl group, the C1-C12 alkyl group, the C2-C12 alkenyl group, the C2-C12 alkynyl group, the C3-C12 cycloalkyl group, the C2-C12 acyl group or the adamantyl group has two or more substituents, the substituents may be same or different to each other);

X represents a sulfur atom or an oxygen atom;

$R^2$ represents a hydrogen atom, an C1-C12 alkyl group, a C1-C12 haloalkyl group, an C2-C12 alkenyl group, a C2-C12 haloalkenyl group, an C2-C12 alkynyl group, a C2-C12 haloalkynyl group, an C2-C12 alkoxycarbonyl group, a hydroxycarbonyl group or a halogen atom;

$R^4$ and $R^5$ represent independently of each other a hydrogen atom, a halogen atom or an C1-C3 alkyl group, or $R^4$ and $R^5$ combine each other together with the carbon to which they are attached to form a C3-C6 cycloalkane ring;

$R^6$, $R^7$, $R^8$ and $R^9$ represent independently of each other an C1-C12 alkyl group, a halogen atom, a C1-C12 haloalkyl group, a C3-C12 cycloalkyl group, a C3-C12 halocycloalkyl group, an C1-C12 alkoxy group, a C1-C12 haloalkoxy group, an C1-C12 alkylthio group, a C1-C12 haloalkylthio group, a nitro group, a cyano group, a hydroxyl group, a thiol group, a pentafluorosulfanyl group, an C2-C12 alkenyl group, a C2-C12 haloalkenyl group, an C2-C12 alkynyl group, a C2-C12 haloalkynyl group, a C3-C12 cycloalkyloxy group, a C3-C12 halocycloalkyloxy group, a C3-C12 cycloalkylthio group, an C2-C12 alkenyloxy group, an C2-C12 alkynyloxy group, a C2-C12 haloalkenyloxy group, a C2-C12 haloalkynyloxy group, an C2-C12 alkynythio group, an C2-C12 alkenythio group, a C2-C12 haloalkenythio group, a C2-C12 haloalkynythio group, an C2-C12 acyl group, a C2-C12 haloacyl group, an C2-C12 acyloxy group, an C2-C12 acylthio group, an C2-C12 alkoxycarbonyl group, a C3-C12 trialkylsilyl group, a C5-C14 trialkylsilylethynyl group, an C1-C12 alkylsulfonyl group, a C1-C12 haloalkylsulfonyl group, an C1-C12 alkylsulfinyl group, a C1-C12 haloalkylsulfinyl group, an aminosulfonyl group optionally substituted with an C1-C12 alkyl group, an amino group optionally substituted with an C1-C12 alkyl group, an aminocarbonyl group optionally substituted with an C1-C12 alkyl group, a hydrogen atom, a hydroxycarbonyl group, or a formyl group, or the adjacent $R^6$ and $R^7$, the adjacent $R^7$ and $R^8$, or the adjacent $R^8$ and $R^9$ may connect each other together with the carbon to which they are attached to form a C4-C6 cycloalkene ring, a C5-C6 cycloalkyldiene ring or a benzene ring;

$R^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group;

Y represents an oxygen atom or a sulfur atom;

Q represents an oxygen atom, a sulfur atom or a $NR^{11}$ group; and $R^{11}$ represents a halogen atom, an C1-C6 alkyl group or a C1-C6 haloalkyl group;

Group $P^1$: a group consisting of a halogen atom, an C1-C12 alkyl group, a C1-C12 haloalkyl group, an C1-C12 alkoxy group, a C1-C12 haloalkoxy group, an C1-C12 alkylthio group, a C1-C12 haloalkylthio group, a hydroxycarbonyl group, a formyl group, a nitro group, a cyano group, a hydroxyl group, a thiol group, a pentafluorosulfanyl group, an C2-C12 alkenyl group, a C2-C12 haloalkenyl group, an C2-C12 alkynyl group, a C2-C12 haloalkynyl group, a C3-C12 cycloalkyl group, a C3-C12 halocycloalkyl group, a C3-C12 cycloalkyloxy group, a C3-C12 halocycloalkyloxy group, C3-C12 cycloalkylthio group, an C2-C12 alkenyloxy group, an C2-C12 alkynyloxy group, a C2-C12 haloalkenyloxy group, a C2-C12 haloalkynyloxy group, an C2-C12 alkynythio group, an C2-C12 alkenylthio group, a C2-C12 haloalkenythio group, a C2-C12 haloalkynythio group, an C2-C12 acyl group, a C2-C12 haloacyl group, an C2-C12 acyloxy group, an C2-C12 acylthio group, an C2-C12 alkoxycarbonyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a C3-C12 trialkylsilyl group, a C5-C14 trialkylsilylethynyl group, an C1-C12 alkylsulfonyl group, a C1-C12 haloalkylsulfonyl group, an C6-C16 arylsulfonyl group, a C6-C16 haloarylsulfonyl group, an C1-C12 alkylsulfinyl group, a C1-C12 haloalkylsulfinyl group, an C6-C16 arylsulfinyl group, a C6-C16 haloarylsulfinyl group, a C2-11 polyoxaalkyloxy group, an C2-C5 oxacycloalkyloxy group, an aminocarbonyl group optionally substituted with an C1-C12 alkyl group and/or an C6-C12 aryl group, an aminosulfonyl group optionally substituted with an C1-C12 alkyl group and/or an C6-C12 aryl group, and an amino group optionally substituted with an C1-C12 alkyl group].

[2] The tetrazolinone compound according to [1] wherein
X represents a sulfur atom;
$R^2$, $R^4$ and $R^5$ represent a hydrogen atom;
$R^{10}$ represents a methyl group; and
Y and Q represent an oxygen atom.

[3] The tetrazolinone compound according to [2] wherein
$R^1$ represents an C6-C16 aryl group optionally substituted with one or more substituents selected from group $P^1$, an C1-C12 alkyl group optionally substituted with one or more substituents selected from group $P^1$, an C3-C12 cycloalkyl group optionally substituted with one or more substituents selected from group $P^1$, or an adamantyl group optionally substituted with one or more substituents selected from group $P^1$ (with the proviso that when the C6-C16 aryl group, the C1-C12 alkyl group, the C3-C12 cycloalkyl group, or the adamantyl group has two or more substituents, the substituents may be same or different to each other);

$R^6$ represents independently of each other an C1-C4 alkyl group, a halogen atom, a C1-C4 haloalkyl group, a C3-C4 cycloalkyl group, a C3-C4 halocycloalkyl group, an C1-C4 alkoxy group, a C1-C4 haloalkoxy group, an C1-C4 alkylthio group, a C1-C4 haloalkylthio group, a nitro group, a cyano group, a hydroxyl group, a thiol group, a trimethylsilylethynyl group, a triethylsilylethynyl group, a pentafluorosulfanyl group, an C2-C4 alkenyl group, a C2-C4 haloalkenyl group, an C2-C4 alkynyl group, a C2-C4 haloalkynyl group, a C3-C4 cycloalkyloxy group, a C3-C4 halocycloalkyloxy group, a C3-C4 cycloalkylthio group, an C2-C4 alkenyloxy group, an C2-C4 alkynyloxy group, a C2-C4 haloalkenyloxy group, a C2-C4 haloalkynyloxy group, an C2-C4 alkynythio group, an C2-C4 alkenythio group, a C2-C4 haloalkenythio group, a C2-C4 haloalkynythio group, an amino group optionally substituted with an C1-C4 alkyl group, an C2-C4 acyl group, a C2-C4 haloacyl group, an C2-C4 acyloxy group, an C2-C4 acylthio group, an C2-C4 alkoxycarbonyl group, an aminocarbonyl group optionally substituted with an C1-C3 alkyl group, an aminosulfonyl group optionally substituted with an C1-C3 alkyl group, an C1-C4 alkylsulfonyl group, a C1-C4 haloalkylsulfonyl group, an C1-C4 alkylsulfinyl group, a C1-C4 haloalkylsulfinyl group, a hydroxycarbonyl group, or a formyl group; and $R^7$, $R^8$ and $R^9$ represent independently of each other a hydrogen atom or a fluorine atom.

[4] The tetrazolinone compound according to [3] wherein $R^1$ represents an C6-C16 aryl group optionally substituted with one or more substituents selected from group $P^1$ (with the proviso that when the C6-C16 aryl group has two or more substituents, the substituents may be same or different to each other).

[5] The tetrazolinone compound according to [3] wherein

R$^1$ represents a formula (2):

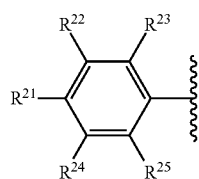

(2)

[wherein

R$^{21}$ represents a hydrogen atom, a halogen atom, a nitro group, a cyano group, a trimethylsilyl group, trimethylsilylethynyl group, a pentafluorosulfanyl group, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C2-C6 alkenyloxy group, an C2-C6 alkynyloxy group, a C2-C6 haloalkenyloxy group, a C2-C6 haloalkynyloxy group, an C2-C6 alkynylthio group, an C2-C6 alkenylthio group, a C2-C6 haloalkenylthio group, a C2-C6 haloalkynylthio group, an amino group optionally substituted with an C1-C6 alkyl group, an C2-C6 acyl group, a C2-C6 haloacyl group, an C2-C6 acyloxy group, an C2-C6 acylthio group, an C1-C6 alkylsulfonyl group, a C1-C6 haloalkylsulfonyl group, an C1-C6 alkylsulfinyl group, a C1-C6 haloalkylsulfinyl group, a C2-C5 polyoxaalkyloxy group, or an C2-C5 oxacycloalkyloxy group; and R$^{22}$, R$^{23}$, R$^{24}$ and R$^{25}$ represent independently of each other a hydrogen atom or a halogen atom].

[6] The tetrazolinone compound according to [5] wherein

R$^{21}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group; and R$^6$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom.

[7] The tetrazolinone compound according to [6] wherein

R$^{21}$ represents a hydrogen atom, a fluorine atom, a chlorine atom, a bromine atom, an iodine atom, a methyl group, an ethyl group, a methoxy group, a methylthio group, a trifluoromethyl group or a trifluoromethoxy group;

R$^{22}$, R$^{23}$, R$^{24}$ and R$^{25}$ represent independently of each other a hydrogen atom or a fluorine atom; and R$^6$ represents a methyl group, an ethyl group, a cyclopropyl group, a chlorine atom, a bromine atom or a methoxy group.

[8] The tetrazolinone compound according to [3] wherein

R$^1$ represents a group of a formula (3):

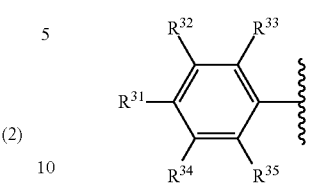

(3)

[wherein

R$^{32}$ represents a hydrogen atom, a halogen atom, a nitro group, a cyano group, a trimethylsilyl group, a trimethylsilylethynyl group, a pentafluorosulfanyl group, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C2-C6 alkenyloxy group, an C2-C6 alkynyloxy group, a C2-C6 haloalkenyloxy group, a C2-C6 haloalkynyloxy group, an C2-C6 alkynylthio group, an C2-C6 alkenylthio group, a C2-C6 haloalkenylthio group, a C2-C6 haloalkynylthio group, an amino group optionally substituted with an C1-C6 alkyl group, an C2-C6 acyl group, a C2-C6 haloacyl group, an C2-C6 acyloxy group, an C2-C6 acylthio group, an C1-C6 alkylsulfonyl group, a C1-C6 haloalkylsulfonyl group, an C1-C6 alkylsulfinyl group, a C1-C6 haloalkylsulfinyl group, a C2-C5 polyoxaalkyloxy group, or an C2-C5 oxacycloalkyloxy group; and R$^{31}$, R$^{33}$, R$^{34}$ and R$^{35}$ represent independently of each other a hydrogen atom or a halogen atom].

[9] The tetrazolinone compound according to [8] wherein

R$^{32}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group;

R$^6$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom.

[10] The tetrazolinone compound according to [9] wherein

R$^{32}$ represents a hydrogen atom, a fluorine atom, a chlorine atom, a bromine atom, an iodine atom, a methyl group, an ethyl group, a methoxy group, a methylthio group, a trifluoromethyl group or a trifluoromethoxy group;

R$^{31}$, R$^{33}$, R$^{34}$ and R$^{35}$ represent independently of each other a hydrogen atom or a fluorine atom; and R$^6$ represents a methyl group, an ethyl group, a cyclopropyl group, a chlorine atom, a bromine atom or a methoxy group.

[11] The tetrazolinone compound according to [3] wherein

R$^1$ represents a group of a formula (4):

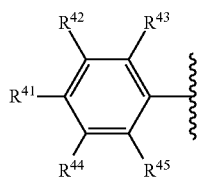

(4)

[wherein
R$^{43}$ represents a hydrogen atom, a halogen atom, a nitro group, a cyano group, a trimethylsilyl group, a trimethylsilylethynyl group, a pentafluorosulfanyl group, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C2-C6 alkenyloxy group, an C2-C6 alkynyloxy group, a C2-C6 haloalkenyloxy group, a C2-C6 haloalkynyloxy group, an C2-C6 alkynylthio group, an C2-C6 alkenylthio group, a C2-C6 haloalkenylthio group, a C2-C6 haloalkynylthio group, an amino group optionally substituted with an C1-C6 alkyl group, an C2-C6 acyl group, a C2-C6 haloacyl group, an C2-C6 acyloxy group, an C2-C6 acylthio group, an C1-C6 alkylsulfonyl group, a C1-C6 haloalkylsulfonyl group, an C1-C6 alkylsulfinyl group, a C1-C6 haloalkylsulfinyl group, a C2-C5 polyoxaalkyloxy group, or an C2-C5 oxacycloalkyloxy group;

R$^{41}$, R$^{42}$, R$^{44}$ and R$^{45}$ represent independently of each other a hydrogen atom or a halogen atom].

[12] The tetrazolinone compound according to [11] wherein
R$^{43}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group; and R$^6$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom.

[13] The tetrazolinone compound according to [11] wherein
R$^{43}$ represents a hydrogen atom, a fluorine atom, a chlorine atom, a bromine atom, an iodine atom, a methyl group, an ethyl group, a methoxy group, a methylthio group, a trifluoromethyl group or a trifluoromethoxy group;

R$^{41}$, R$^{42}$, R$^{44}$ and R$^{45}$ represent independently of each other a hydrogen atom or a fluorine atom; and R$^6$ represent a methyl group, an ethyl group, a cyclopropyl group, a chlorine atom, a bromine atom or a methoxy group.

[14] The tetrazolinone compound according to [3] wherein R$^1$ represents an C1-C12 alkyl group optionally substituted with one or more substituents selected from group P$^1$, a C3-C12 cycloalkyl group optionally substituted with one or more substituents selected from group P$^1$, or an adamantyl group optionally substituted with one or more substituents selected from group P$^1$ (with the proviso that when the C1-C12 alkyl group, the C3-C12 cycloalkyl group or the adamantyl group has two or more substituents, the substituents may be same or different to each other).

[15] The tetrazolinone compound according to [14] wherein R$^6$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom.

[16] The tetrazolinone compound according to [15] wherein R$^6$ represents a methyl group, an ethyl group, a cyclopropyl group, a chlorine atom, a bromine atom or a methoxy group.

[17] The tetrazolinone compound according to [1] wherein
X represents an oxygen atom;
R$^2$, R$^4$ and R$^5$ represent a hydrogen atom;
R$^{10}$ represent a methyl group; and
Y and Q represent an oxygen atom.

[18] The tetrazolinone compound according to claim 17 wherein
R$^1$ represents an C6-C12 aryl group optionally substituted with one or more substituents selected from group P$^1$, an C1-C12 alkyl group optionally substituted with one or more substituents selected from group P$^1$, a C3-C12 cycloalkyl group optionally substituted with one or more substituents selected from group P$^1$, or an adamantyl group optionally substituted with one or more substituents selected from group P$^1$ (with the proviso that when the C6-C16 aryl group, the C1-C12 alkyl group, the C3-C12 cycloalkyl group or the adamantyl group has two or more substituents, the substituents may be same or different to each other);

R$^6$ represents a hydroxycarbonyl group, a formyl group, a halogen atom, a nitro group, a cyano group, a hydroxyl group, a thiol group, a trimethylsilyl group, a trimethylsilylethynyl group, a pentafluorosulfanyl group, an C1-C4 alkyl group, a C1-C4 haloalkyl group, an C2-C4 alkenyl group, a C2-C4 haloalkenyl group, an C2-C4 alkynyl group, a C2-C4 haloalkynyl group, a C3-C4 cycloalkyl group, a C3-C4 halocycloalkyl group, an C1-C4 alkoxy group, a C1-C4 haloalkoxy group, an C1-C4 alkylthio group, a C1-C4 haloalkylthio group, a C3-C4 cycloalkyloxy group, a C3-C4 halocycloalkyloxy group, a C3-C4 cycloalkylthio group, a C2-C4 alkenyloxy group, an C2-C4 alkynyloxy group, a C2-C4 haloalkenyloxy group, a C2-C4 haloalkynyloxy group, an C2-C4 alkynylthio group, an C2-C4 alkenylthio group, a C2-C4 haloalkenylthio group, a C2-C4 haloalkynylthio group, an amino group optionally substituted with an C1-C4 alkyl group, an C2-C4 acyl group, a C2-C4 haloacyl group, an C2-C4 acyloxy group, an C2-C4 acylthio group, an C2-C4 alkoxycarbonyl group, an aminocarbonyl group optionally substituted with an C1-C3 alkyl group, an aminosulfonyl group optionally substituted with an C1-C3 alkyl group, an C1-C4 alkylsulfonyl group, a C1-C4 haloalkylsulfonyl group, an C1-C4 alkylsulfinyl group, or a C1-C4 haloalkylsulfinyl group; and R$^7$, R$^8$ and R$^9$ represent independently of each other a hydrogen atom or a fluorine atom.

[19] The tetrazolinone compound according to [18] wherein R$^1$ represents an C6-C12 aryl group optionally substituted with one or more substituents selected from group P$^1$ (with the proviso that when the C6-C16 aryl group has two or more substituents, the substituents may be same or different to each other).

[20] The tetrazolinone compound according to [3] wherein R$^1$ represents a group of a formula (2):

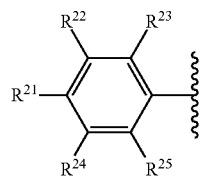

(2)

[wherein
R$^{21}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group; and R$^{22}$, R$^{23}$, R$^{24}$ and R$^{25}$ represent independently of each other a hydrogen atom or a halogen atom];

$R^7$, $R^8$ and $R^9$ represent a hydrogen atom; and $R^6$ represents a halogen atom, an C1-C3 alkyl group, C1-C3 haloalkyl group or an C1-C3 alkoxy group.

[21] The tetrazolinone compound according to [20] wherein
$R^1$ represents a halogen atom, a methyl group, a trifluoromethyl group or a methoxy group;
$R^{22}$, $R^{23}$, $R^{24}$ and $R^{25}$ represent independently of each other a hydrogen atom or a fluorine atom; and
$R^6$ represents a chlorine atom, a bromine atom, a methyl group, an ethyl group or a methoxy group.

[22] The tetrazolinone compound according to [3] wherein
$R^1$ represents a group of a formula (3):

$$(3)$$

[wherein
$R^{32}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group; and
$R^{31}$, $R^{33}$, $R^{34}$ and $R^{35}$ represent independently of each other a hydrogen atom or a halogen atom];
$R^7$, $R^8$ and $R^9$ represent a hydrogen atom; and
$R^6$ represents a halogen atom, an C1-C3 alkyl group, a C1-C3 haloalkyl group or an C1-C3 alkoxy group.

[23] The tetrazolinone compound according to [22] wherein
$R^{32}$ represents a halogen atom, a methyl group, trifluoromethyl group or a methoxy group; and
$R^{31}$, $R^{33}$, $R^{34}$ and $R^{35}$ represent independently of each other a hydrogen atom or a fluorine atom; and
$R^6$ represents a chlorine atom, a bromine atom, a methyl group, an ethyl group or a methoxy group.

[24] The tetrazolinone compound according to [3] wherein
$R^1$ represents a group of a formula (3):

$$(4)$$

[wherein
$R^{43}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group; and
$R^{41}$, $R^{42}$, $R^{44}$ and $R^{45}$ represent independently of each other a hydrogen atom or a halogen atom];
$R^7$, $R^8$ and $R^9$ represent a hydrogen atom; and
$R^6$ represents a halogen atom, an C1-C3 alkyl group, a C1-C3 haloalkyl group or an C1-C3 alkoxy group.

[25] The tetrazolinone compound according to [24] wherein
$R^{43}$ represents a halogen atom, a methyl group, a trifluoromethyl group or a methoxy group;
$R^{41}$, $R^{42}$, $R^{44}$ and $R^{45}$ represent independently of each other a hydrogen atom or a fluorine atom; and
$R^6$ represents a chlorine atom, a bromine atom, a methyl group, an ethyl group or a methoxy group.

[26] The tetrazolinone compound according to [3] wherein
$R^6$ represents a C3-C4 cycloalkyl group, a C3-C4 halocycloalkyl group, a C1-C3 haloalkoxy group, an C1-C4 alkylthio group, a C1-C4 haloalkylthio group, a nitro group, a cyano group, a hydroxyl group, a thiol group, trimethylsilyl group, a trimethylsilylethynyl group, a pentafluorosulfanyl group, an C2-C4 alkenyl group, a C2-C4 haloalkenyl group, an C2-C4 alkynyl group, a C2-C4 haloalkynyl group, a C3-C4 cycloalkyloxy group, a C3-C4 halocycloalkyloxy group, a C3-C4 cycloalkylthio group, a C2-C4 alkenyloxy group, an C2-C4 alkynyloxy group, a C2-C4 haloalkenyloxy group, a C2-C4 haloalkynyloxy group, an C2-C4 alkynylthio group, an C2-C4 alkenylthio group, a C2-C4 haloalkenylthio group, a C2-C4 haloalkynylthio group, an amino group optionally substituted with an C1-C4 alkyl group, an C2-C4 acyl group, a C2-C4 haloacyl group, an C2-C4 acyloxy group, an C2-C4 acylthio group, an C2-C4 alkoxycarbonyl group, an aminocarbonyl group optionally substituted with an C1-C3 alkyl group, an aminosulfonyl group optionally substituted with an C1-C3 alkyl group, an C1-C4 alkylsulfonyl group, a C1-C4 haloalkylsulfonyl group, an C1-C4 alkylsulfinyl group, a C1-C4 haloalkylsulfinyl group, a hydroxycarbonyl group, or a formyl group.

[27] An agent for controlling pests comprising the tetrazolinone compound according to any one of [1] to [26].

[28] A method for controlling pests comprising applying an effective amount of the tetrazolinone compound according to any one of [1] to [26] to plant or soil.

[29] Use of the tetrazolinone compound according to any one of [1] to [26] for controlling pests.

[30] A thiazole compound of a formula (5):

$$(5)$$

[wherein
$R^{51}$, $R^{52}$, $R^{53}$, $R^{54}$ and $R^{55}$ represent independently of each other a hydrogen atom, a halogen atom, a nitro group, a cyano group, a trimethylsilyl group, a trimethylsilylethynyl group, a pentafluorosulfanyl group, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C2-C6 alkenyloxy group, an C2-C6 alkynyloxy group, a C2-C6 haloalkenyloxy group, a C2-C6 haloalkynyloxy group, an C2-C6 alkynylthio group, an C2-C6 alkenylthio group, a C2-C6 haloalkenylthio group, a C2-C6 haloalkynylthio group, an amino group optionally substituted with an C1-C6 alkyl group, an C2-C6 acyl group, a C2-C6 haloacyl group, an C2-C6 acyloxy group, an C2-C6 acylthio group, an C1-C6 alkylsulfonyl group, a C1-C6 haloalkylsulfonyl group, an C1-C6 alkylsulfinyl group, a C1-C6 haloalkylsulfinyl group, a C2-C5 polyoxaalkyloxyl group, or an C2-C5 oxacycloalkyloxy group;

$R^{56}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group, or an C1-C4 alkylamino group; and $R^{57}$ represents a group of a formula (6):

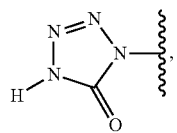
(6)

a formyl group, a C2-C6 halogenated acyl group, an C2-C6 alkoxycarbonyl group, a hydroxycarbonyl group, a hydroxymethyl group, an amino group, an isocyanate group, a nitro group, a halomethyl group, a halogen atom, NSO, $CON_3$, or aminocarbonyl group optionally substituted with a chlorine atom, a bromine atom, or hydroxyl group].

[31] The thiazole compound according to [30], wherein
$R^{51}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group;
$R^{56}$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom;
$R^{52}$, $R^{53}$, $R^{54}$ and $R^{55}$ represent independently of each other a hydrogen atom or a halogen atom.

[32] The thiazole compound according to [30], wherein
$R^{52}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group;
$R^{56}$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom; and
$R^{51}$, $R^{53}$, $R^{54}$ and $R^{55}$ represent independently of each other a hydrogen atom or a halogen atom.

[33] The thiazole compound according to [30], wherein
$R^{52}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group;
$R^{56}$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom; and
$R^{51}$, $R^{52}$, $R^{53}$ and $R^{54}$ represent independently of each other a hydrogen atom or a halogen atom.

[34] The thiazole compound according to [31], wherein
$R^{51}$ represents a halogen atom, a methyl group, an ethyl group or a methoxy group;
$R^{56}$ represents a chlorine atom, a bromine atom, a methyl group, an ethyl group, a cyclopropyl group or a methoxy group; and
$R^{52}$, $R^{53}$, $R^{54}$ and $R^{55}$ represent independently of each other a hydrogen atom or a fluorine atom.

[35] The thiazole compound according to [31], wherein
$R^{52}$ represents a halogen atom, a methyl group, an ethyl group or a methoxy group;
$R^{56}$ represents a chlorine atom, a bromine atom, a methyl group, an ethyl group, a cyclopropyl group or a methoxy group; and
$R^{51}$, $R^{53}$, $R^{54}$ and $R^{55}$ represent independently of each other a hydrogen atom or a fluorine atom.

[36] The thiazole compound according to [33], wherein
$R^{53}$ represents a halogen atom, a methyl group, an ethyl group or a methoxy group;
$R^{56}$ represents a chlorine atom, a bromine atom, a methyl group, an ethyl group, a cyclopropyl group or a methoxy group; and
$R^{51}$, $R^{52}$, $R^{53}$ and $R^{54}$ represent independently of each other a hydrogen atom or a fluorine atom.

The present invention can control pests.

DESCRIPTION OF EMBODIMENTS

The compound of the present invention (hereinafter, sometimes referred to as "the present compound") is a tetrazolinone compound of a formula (1):

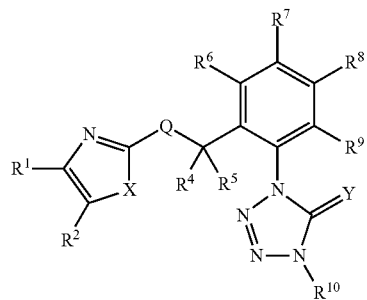
(1)

[wherein,
$R^1$ represents an C6-C16 aryl group optionally substituted with one or more substituents selected from the group $P^1$, an C7-C18 aralkyl group optionally substituted with one or more substituents selected from the group $P^1$, an C1-C12 alkyl group optionally substituted with one or more substituents selected from the group $P^1$, an C2-C12 alkenyl group optionally substituted with one or more substituents selected from the group $P^1$, an C2-C12 alkynyl group optionally substituted with one or more substituents selected from the group $P^1$, a C3-C12 cycloalkyl group optionally substituted with one or more substituents selected from the group $P^1$, an C2-C12 acyl group optionally substituted with one or more substituents selected from the group P1, an adamantyl group optionally substituted with one or more substituents selected from the group $P^1$, a C3-C12 trialkylsilyl group, a hydrogen atom or a halogen atom (with the proviso that when the C6-C16 aryl group, the C7-C18 aralkyl group, the C1-C12 alkyl group, the C2-C12 alkenyl group, the C2-C12 alkynyl group, the C3-C12 cycloalkyl group, the C2-C12 acyl group or the adamantyl group has two or more substituents, the substituents may be same or different to each other);

X represents a sulfur atom or an oxygen atom;

$R^2$ represents a hydrogen atom, an C1-C12 alkyl group, a C1-C12 haloalkyl group, an C2-C12 alkenyl group, a C2-C12 haloalkenyl group, an C2-C12 alkynyl group, a C2-C12 haloalkynyl group, an C2-C12 alkoxycarbonyl group, a hydroxycarbonyl group or a halogen atom;

$R^4$ and $R^5$ represent independently of each other a hydrogen atom, a halogen atom or an C1-C3 alkyl group, or $R^4$ and $R^5$ combine each other together with the carbon to which they are attached to form a C3-C6 cycloalkane ring;

$R^6$, $R^7$, $R^8$ and $R^9$ represent independently of each other an C1-C12 alkyl group, a halogen atom, a C1-C12 haloalkyl group, a C3-C12 cycloalkyl group, a C3-C12 halocycloalkyl group, an C1-C12 alkoxy group, a C1-C12 haloalkoxy group, an C1-C12 alkylthio group, a C1-C12 haloalkylthio group, a nitro group, a cyano group, a hydroxyl group, a thiol group, a pentafluorosulfanyl group, an C2-C12 alkenyl group, a C2-C12 haloalkenyl group, an C2-C12 alkynyl group, a C2-C12 haloalkynyl group, a C3-C12 cycloalkyloxy group, a C3-C12 halocycloalkyloxy group, a C3-C12 cycloalkylthio group, an C2-C12 alkenyloxy group, an C2-C12 alkynyloxy group, a C2-C12 haloalkenyloxy group, a C2-C12 haloalkynyloxy group, an C2-C12 alkynythio group, an C2-C12 alkenythio group, a C2-C12 haloalkenythio group, a C2-C12 haloalkynythio group, an C2-C12 acyl group, a C2-C12 haloacyl group, an C2-C12 acyloxy group, an C2-C12 acylthio group, an C2-C12 alkoxycarbonyl group, a C3-C12 trialkylsilyl group, a C5-C14 trialkylsilylethynyl group, an C1-C12 alkylsulfonyl group, a C1-C12 haloalkylsulfonyl group, an C1-C12 alkylsulfinyl group, a C1-C12 haloalkylsulfinyl group, an aminosulfonyl group optionally substituted with an C1-C12 alkyl group, an amino group optionally substituted with an C1-C12 alkyl group, an aminocarbonyl group optionally substituted with an C1-C12 alkyl group, a hydrogen atom, hydroxycarbonyl group, or a formyl group, or the adjacent $R^6$ and $R^7$, the adjacent $R^7$ and $R^8$, or the adjacent $R^8$ and $R^9$ may connect each other together with the carbon to which they are attached to form a C4-C6 cycloalkene ring, a C5-C6 cycloalkyldiene ring or a benzene ring;

$R^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group;

Y represents an oxygen atom or a sulfur atom;

Q represents an oxygen atom, a sulfur atom or a $NR^{11}$ group; and $R^{11}$ represents a halogen atom, an C1-C6 alkyl group or a C1-C6 haloalkyl group;

Group $P^1$: a group consisting of a halogen atom, an C1-C12 alkyl group, a C1-C12 haloalkyl group, an C1-C12 alkoxy group, a C1-C12 haloalkoxy group, an C1-C12 alkylthio group, a C1-C12 haloalkylthio group, a hydroxycarbonyl group, a formyl group, a nitro group, a cyano group, a hydroxyl group, a thiol group, a pentafluorosulfanyl group, an C2-C12 alkenyl group, a C2-C12 haloalkenyl group, an C2-C12 alkynyl group, a C2-C12 haloalkynyl group, a C3-C12 cycloalkyl group, a C3-C12 halocycloalkyl group, a C3-C12 cycloalkyloxy group, a C3-C12 halocycloalkyloxy group, a C3-C12 cycloalkylthio group, an C2-C12 alkenyloxy group, an C2-C12 alkynyloxy group, a C2-C12 haloalkenyloxy group, a C2-C12 haloalkynyloxy group, an C2-C12 alkynythio group, an C2-C12 alkenylthio group, a C2-C12 haloalkenythio group, a C2-C12 haloalkynythio group, an C2-C12 acyl group, a C2-C12 haloacyl group, an C2-C12 acyloxy group, an C2-C12 acylthio group, an C2-C12 alkoxycarbonyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a C3-C12 trialkylsilyl group, a C5-C14 trialkylsilylethynyl group, an C1-C12 alkylsulfonyl group, a C1-C12 haloalkylsulfonyl group, an C6-C16 arylsulfonyl group, a C6-C16 haloarylsulfonyl group, an C1-C12 alkylsulfinyl group, a C1-C12 haloalkylsulfinyl group, an C6-C16 arylsulfinyl group, a C6-C16 haloarylsulfinyl group, a C2-11 polyoxaalkyloxy group, an C2-C5 oxacycloalkyloxy group, an aminocarbonyl group optionally substituted with an C1-C12 alkyl group and/or an C6-C12 aryl group, an aminosulfonyl group optionally substituted with an C1-C12 alkyl group and/or an C6-C12 aryl group, and an amino group optionally substituted with an C1-C12 alkyl group].

The present invention provides also a thiazole compound (hereinafter, sometimes referred to as "the present thiazole compound Z") of a formula (5):

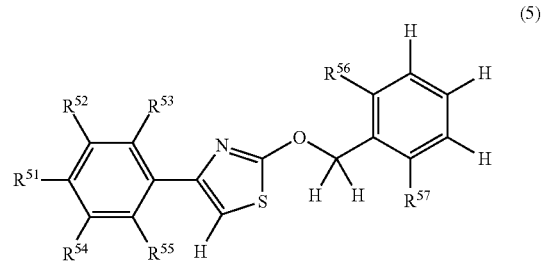

(5)

[wherein $R^{51}$, $R^{52}$, $R^{53}$, $R^{54}$ and $R^{55}$ represent independently of each other a hydrogen atom, a halogen atom, a nitro group, a cyano group, a trimethylsilyl group, a trimethylsilylethynyl group, a pentafluorosulfanyl group, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C2-C6 alkenyloxy group, an C2-C6 alkynyloxy group, a C2-C6 haloalkenyloxy group, a C2-C6 haloalkynyloxy group, an C2-C6 alkynylthio group, an C2-C6 alkenylthio group, a C2-C6 haloalkenylthio group, a C2-C6 haloalkynylthio group, an amino group optionally substituted with an C1-C6 alkyl group, an C2-C6 acyl group, a C2-C6 haloacyl group, an C2-C6 acyloxy group, an C2-C6 acylthio group, an C1-C6 alkylsulfonyl group, a C1-C6 haloalkylsulfonyl group, an C1-C6 alkylsulfinyl group, a C1-C6 haloalkylsulfinyl group, a C2-C5 polyoxaalkyloxyl group, or an C2-C5 oxacycloalkyloxy group;

$R^{56}$ represents a halogen atom, an C1-C3 alkyl group, C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group, or an C1-C4 alkylamino group; and $R^{57}$ represents a group of a formula (6):

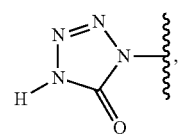

(6)

a formyl group, a halogenated acyl group, an C2-C6 alkoxycarbonyl group, a hydroxycarbonyl group, hydroxymethyl group, an amino group, an isocyanate group, a nitro group, a halomethyl group, a halogen atom, NSO, $CON_3$, $CONH_2$, CONHCl, CONHBr or CONHOH],
which is used in a preparation of the present compound.

Hereinafter, the present invention is explained in detail.

The substituent to be used herein is specifically described below.

The term "halogen atom" includes, for example, a fluorine atom, a chlorine atom, a bromine atom and an iodine atom.

The term "C1-C12 alkyl group" represents a straight or branched alkyl group, and includes, for example, a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, an undecyl group, and a dodecyl group.

The term "C1-C12 haloalkyl group" represents a group wherein at least one hydrogen atom of the straight or branched C1-C12 alkyl group is substituted with a halogen atom, and includes, for example, a monofluoromethyl group, a monochloromethyl group, a dichloromethyl group, difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 2-(fluoromethyl)-3-fluoropropyl group, a 4-fluorobutyl group, a 5-fluoropentyl group, a 2,2-difluorohexyl group, a perfluoro-n-heptyl group, a perfluoro-n-octyl group, a perfluoro-n-nonyl group, a perfluoro-n-decyl group, a perfluoro-n-undecyl group, and a perfluoro-n-dodecyl group. The halogen atom that can be substituted for a hydrogen atom includes a fluorine atom, a chlorine atom, a bromine atom and an iodine atom.

The term "C2-C12 alkenyl group" represents a straight or branched alkenyl group, and includes, for example, a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, a 5-hexenyl group, a 1-heptenyl group, a 6-heptenyl group, an 1-octenyl group, an 7-octenyl group, a 1-nonenyl group, a 8-nonenyl group, a 1-decenyl group, a 9-decenyl group, an 1-undecenyl group, an 10-undecenyl group, a 1-dodecenyl group, and a 11-dodecenyl group.

A term "C2-C12 haloalkenyl group" represents a group wherein at least one hydrogen atom of the straight or branched C2-C12 alkenyl group is substituted with a halogen atom, and includes, for example, a 2-chlorovinyl group, a 2-bromovinyl group, an 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 3,3-dichloro-2-propenyl group, a 3,3-dibromo-2-propenyl group, a 3-fluoro-3-chloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, a 3,4,4-trifluoro-1,3-butadienyl group, a 3,4-dibromo-1-pentenyl group, a 4,4-difluoro-3-methyl-3-butenyl group, a 3,3,4,4,5,5,5-heptafluoro-1-pentenyl group, a 5,5-difluoro-4-pentenyl group, a 4,5,5-trifluoro-4-pentenyl group, a 3,4,4,4-tetrafluoro-3-trifluoromethyl-1-butenyl group, a 4,4,4-trifluoro-3-methyl-2-butenyl group, a 3,5,5-trifluoro-2,4-pentadienyl group, a 4,4,5,5,5,6,6,6-heptafluoro-2-hexenyl group, a 3,4,4,5,5,5-hexafluoro-3-trifluoromethyl-1-pentenyl group, a 4,5,5,5-tetrafluoro-4-trifluoromethyl-2-pentenyl group, a 5-bromo-4,5,5-trifluoro-4-trifluoromethyl-2-pentenyl group, a perfluoro-1-butenyl group, a perfluoro-3-butenyl group, a perfluoro-1-pentenyl group, a perfluoro-4-pentenyl group, a perfluoro-1-hexenyl group, a perfluoro-5-hexenyl group, a perfluoro-1-heptenyl group, a perfluoro-6-heptenyl group, a perfluoro-1-octenyl group, a perfluoro-7-octenyl group, perfluoro-1-nonenyl group, a perfluoro-8-nonenyl group, a perfluoro-1-decenyl group, a perfluoro-9-decenyl group, a perfluoro-1-undecenyl group, a perfluoro-10-undecenyl group, a perfluoro-1-dodecenyl group, and a perfluoro-11-dodecenyl group. The halogen atom that can be substituted for a hydrogen atom includes a fluorine atom, a chlorine atom, a bromine atom and an iodine atom.

The term "C2-C12 alkynyl group" represents a straight or branched alkynyl group, and includes, for example, an ethynyl group, a propargyl group, a 1-butyne-3-yl group, a 3-methyl-1-butyne-3-yl group, a 2-butynyl group, a 3-butynyl group, a 2-pentynyl group, a 3-pentynyl group, a 4-pentynyl group, a 1-hexynyl group, a 5-hexynyl group, a 1-heptynyl group, a 6-heptynyl group, an 1-octynyl group, an 7-octynyl group, a 1-nonynyl group, a 8-nonynyl group, a 1-decynyl group, a 9-decynyl group, an 1-undecynyl group, an 10-undecynyl group, a 1-dodecynyl group and a 11-dodecynyl group.

The term "C2-C12 haloalkynyl group" represents a group wherein at least one hydrogen atom of the straight or branched C2-C12 alkynyl group is substituted with a halogen atom, and includes, for example, a fluoroethynyl group, a 3-chloro-2-propynyl group, a 3-bromo-2-propynyl group, an 3-iodo-2-propynyl group, an 3-chloro-1-propynyl group, a 5-chloro-4-pentynyl group, a 3,3,3-trifluoro-1-propynyl group, a 3,3,3-trifluoro-1-propynyl group, a perfluoro-2-butynyl group, a perfluoro-3-butynyl group, a perfluoro-2-pentynyl group, a perfluoro-3-pentynyl group, a perfluoro-4-pentynyl group, a perfluoro-1-hexynyl group, a perfluoro-5-hexynyl group, a perfluoro-1-heptynyl group, a perfluoro-6-heptynyl group, a perfluoro-1-octynyl group, a perfluoro-7-octynyl group, a perfluoro-1-nonynyl group, a perfluoro-8-nonynyl group, a perfluoro-1-decynyl group, a perfluoro-9-decynyl group, a perfluoro-1-undecynyl group, a perfluoro-10-undecynyl group, a perfluoro-1-dodecynyl group, and a perfluoro-11-dodecynyl group. The halogen atom that can be substituted for a hydrogen atom includes a fluorine atom, a chlorine atom, a bromine atom and an iodine atom.

The term "C3-C12 cycloalkyl group" includes, for example, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

The term "C3-C12 halocycloalkyl group" represents a group wherein at least one hydrogen atom of the C3-C12 cycloalkyl group is substituted with a halogen atom, and includes, for example a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 2-chlorocyclopentyl group, a 2-chlorocyclohexyl group, a 4,4-difluorocyclohexyl group, a 4-chlorocyclohexyl group, a 2-fluorocycloheptyl group, a 2-fluorocyclooctyl group, a 2-fluorocyclononyl group, a 2-fluorocyclodecyl group, a 2-fluorocycloundecyl group, and a 2-fluorocyclododecyl group. The halogen atom that can be substituted for a hydrogen atom includes a fluorine atom, a chlorine atom, a bromine atom and an iodine atom.

The term "C1-C12 alkoxy group" represents a straight or branched alkoxy group, and includes, for example, a methoxy group, an ethoxy group, a propyloxy group, an isopropyloxy group, a butyloxy group, an isobutyloxy group, a sec-butyloxy group, a tert-butyloxy group, a pentyloxy group, an isoamyloxy group, a neopentyloxy group, a 2-pentyloxy group, a 3-pentyloxy group, a 2-methylbutyloxy group, a hexyloxy group, an isohexyloxy group, a 3-methylpentyloxy group, a 4-methylpentyloxy group, a heptyloxy group, an octyloxy group, a nonyloxy group, a decyloxy group, an undecyloxy group, and a dodecyloxy group.

The term "C1-C12 haloalkoxy group" represents a group wherein at least one hydrogen atom of the straight or branched C1-C12 alkoxy group is substituted with a halogen atom, and includes, for example, a trifluoromethoxy group, a bromodifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 3,3,3-trifluoropropoxy group, a nonafluorobutoxy group, a nonachlorobutoxy group, a nonabromobutoxy group, a nonaiodobutoxy group, a perfluoropentyloxy group, a perchloropentyloxy group, a perbromopentyloxy group, a perfluorohexyloxy group, a perchlorohexyloxy group, a perbromohexyloxy group, a periodohexyloxy group, a perfluoroheptyloxy group, a perchloroheptyloxy group, a perbromoheptyloxy group, a perfluorooctyloxy group, a perchlorooctyloxy group, a perbromooctyloxy group, a perfluorononyloxy group, a perchlorononyloxy group, a perbromononyloxy group, a perfluorodecyloxy group, a perchlorodecyloxy group, a perbromodecyloxy group, a perfluoroundecyloxy group, and a perfluorododecyloxy group. The halogen atom that can be substituted for a hydrogen atom includes a fluorine atom, a chlorine atom, a bromine atom and an iodine atom.

The term "C1-C12 alkylthio group" represents a straight or branched alkylthio group, and includes, for example, a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, an isoamylthio group, a 2-pentylthio group, a 3-pentylthio group, a 2-methylbutylthio group, a hexylthio group, an isohexylthio group, a sec-hexylthio group, a 3-methylpentylthio group, a 4-methylpentylthio group, a heptylthio group, an isoheptylthio group, a sec-heptylthio group, an octylthio group, an 2-ethylhexylthio group, a nonylthio group, a decylthio group, an undecylthio group, and a dodecylthio group.

The term "C1-C12 haloalkylthio group" represents a group wherein at least one hydrogen atom of the straight or branched C1-C12 alkylthio group is substituted with a halogen atom, and includes, for example, a monofluoromethylthio group, a bromodifluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, a 2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2,2-difluoropropylthio group, a 3,3,3-trifluoropropylthio group, a nonafluorobutylthio group, a nonachlorobutylthio group, a nonabromobutylthio group, a nonaiodobutylthio group, a perfluoropentylthio group, a perchloropentylthio group, a perbromopentylthio group, a perfluorohexylthio group, a perchlorohexylthio group, a perbromohexylthio group, a periodohexylthio group, a perfluoroheptylthio group, a perchloroheptylthio group, a perbromoheptylthio group, a perfluoroctylthio group, a perchloroctylthio group, a perbromoctylthio group, a perfluorononylthio group, a perchlorononylthio group, a perbromononylthio group, a perfluorodecylthio group, a perchlorodecylthio group, a perbromodecylthio group, a perfluoroundecylthio group, and a perfluorododecylthio group. The halogen atom that can be substituted for a hydrogen atom includes a fluorine atom, a chlorine atom, a bromine atom and an iodine atom.

The term "C3-C12 cycloalkyloxy group" includes, for example, a cyclopropyloxy group, a cyclobutyloxy group, a cyclopentyloxy group, a cyclohexyloxy group, a cycloheptyloxy group, a cyclooctyloxy group, a cyclononyloxy group, a cyclodecyloxy group, a cycloundecyloxy group, and a cyclododecyloxy group.

The term "C3-C12 halocycloalkyloxy group" represents a group wherein at least one hydrogen atom of the C3-C12 cycloalkyloxy group is substituted with a halogen atom, and includes, for example, a 2-fluorocyclopropyloxy group, a 2,2-difluorocyclopropyloxy group, a 2-chloro-2-fluorocyclopropyloxy group, a 2,2-dichlorocyclopropyloxy group, a 2,2- dibromocyclopropyloxy group, a 2,2-difluoro-1-methylcyclopropyloxy group, a 2,2-dichloro-1-methylcyclopropyloxy group, a 2,2-dibromo-1-methylcyclopropyloxy group, a 1-(trifluoromethyl)cyclopropyloxy group, a 2,2,3,3-tetrafluorocyclobutyloxy group, a 2-chlorocyclohexyloxy group, a 4,4-difluorocyclohexyloxy group, a 4-chlorocyclohexyloxy group, a 2-fluorocycloheptyloxy group, a 2-fluorocyclooctyloxy group, a 2-fluorocyclononyloxy group, a 2-fluorocyclodecyloxy group, a 2-fluorocycloundecyloxy group, and a 2-fluorocyclododecyloxy group. The halogen atom that can be substituted for a hydrogen atom includes a fluorine atom, a chlorine atom, a bromine atom and an iodine atom.

The term "C3-C12 cycloalkylthio group" includes, for example, a cyclopropylthio group, a cyclobutylthio group, a cyclopentylthio group, a cyclohexylthio group, a cycloheptylthio group, a cyclooctylthio group, a cyclononylthio group, a cyclodecylthio group, a cycloundecylthio group, and a cyclododecylthio group.

The term "C2-C12 alkenyloxy group" represents a straight or branched alkenyloxy group, and includes, for example, a vinyloxy group, a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-3-butenyloxy group, a 1-vinyl-2-propenyloxy group, a 5-hexenyloxy group, a 6-heptenyloxy group, an 7-octenyloxy group, a 8-nonenyloxy group, a 9-decenyloxy group, an 10-undecenyloxy group, and a 11-dodecenyloxy group.

The term "C2-C12 haloalkenyloxy group" represents a group wherein at least one hydrogen atom of the straight or branched an C2-C12 alkenyloxy group is substituted with a halogen atom, and includes, for example, a 1-fluorovinyloxy group, a 2-fluorovinyloxy group, a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, a 2,3,3-trichloro-2-propenyloxy group, a 3,3-dichloro-2-propenyloxy group, a 3,3-dibromo-2-propenyloxy group, a 3-fluoro-3-chloro-2-propenyloxy group, a 4-bromo-3-chloro-3,4,4-trifluoro-1-butenyloxy group, a 1-bromomethyl-2-propenyloxy group, a 3-chloro-2-butenyloxy group, a 4,4,4-trifluoro-2-butenyloxy group, a 4-bromo-4,4-difluoro-2-butenyloxy group, a 3-bromo-3-butenyloxy group, a 3,4,4-trifluoro-3-butenyloxy group, a 3,4,4-tribromo-3-butenyloxy group, a 3-bromo-2-methyl-2-propenyloxy group, a 3,3-difluoro-2-methyl-2-propenyloxy group, a 3-chloro-4,4,4-trifluoro-2-butenyloxy group, a 4,4-difluoro-3-methyl-3-butenyloxy group, a 5,5-difluoro-4-pentenyloxy group, a 4,5,5-trifluoro-4-pentenyloxy group, a 4,4,4-trifluoro-3-methyl-2-butenyloxy group, a 3,5,5-trifluoro-2,4-pentadienyloxy group, a 4,4,5,5,6,6,6-heptafluoro-2-hexenyloxy group, a 4,5,5,5-tetrafluoro-4-trifluoromethyl-2-pentenyloxy group, a 5-bromo-4,5,5-trifluoro-4-trifluoromethyl-2-pentenyloxy group, a perfluoro-3-butenyloxy group, a perfluoro-4-pentenyloxy group, a perfluoro-5-hexenyloxy group, a perfluoro-6-heptenyloxy group, a perfluoro-7-octenyloxy group, a perfluoro-8-nonenyloxy group, a perfluoro-9-decenyloxy group, a perfluoro-10-undecenyloxy group, and a perfluoro-11-dodecenyloxy group. The halogen atom that can be substituted for a hydrogen atom includes a fluorine atom, a chlorine atom, a bromine atom and an iodine atom.

The term "C2-C12 alkynyloxy group" represents a straight or branched alkynyloxy group, and includes, for example, an ethynyloxy group, a propargyloxy group, a 1-butyne-3-yloxy group, a 3-methyl-1-butyne-3-yloxy group, a 2-butynyloxy group, a 3-butynyloxy group, a 2-pentynyloxy group, a 3-pentynyloxy group, a 4-pentynyloxy group, a 5-hexynyloxy group, a 6-heptynyloxy group, an 7-octynyloxy group, a 8-nonynyloxy group, a 9-decynyloxy group, an 10-undecynyloxy group, and a 11-dodecynyloxy group.

The term "C2-C12 haloalkynyloxy group" represents a group wherein at least one hydrogen atom of the straight or branched C2-C12 alkynyloxy group is substituted with a halogen atom, and includes, for example, a bromoethynyloxy group, a 3-chloro-2-propynyloxy group, a 3-bromo-2-propynyloxy group, an 3-iodo-2-propynyloxy group, a 5-chloro-4-pentynyloxy group, a 3,3,3-trifluoro-1-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, a perfluoro-5-hexynyloxy group, a perfluoro-6-heptynyloxy group, a perfluoro-7-octynyloxy group, a perfluoro-8-nonynyloxy group, a perfluoro-9-decynyloxy group, a perfluoro-10-undecynyloxy group, and a perfluoro-11-dodecynyloxy group. The halogen atom that can be substituted for a hydrogen atom includes a fluorine atom, a chlorine atom, a bromine atom and an iodine atom.

The term "C2-C12 alkenylthio group" represents a straight or branched alkenylthio group, and includes, for example, a vinylthio group, a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 11-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, a 5-hexenylthio group, a 6-heptenylthio group, an 7-octenylthio group, a 8-nonenylthio group, a 9-decenylthio group, an 10-undecenylthio group, and a 11-dodecenylthio group.

The term "C2-C12 haloalkenythio group" represents a group wherein at least one hydrogen atom is substituted with a halogen atom, and includes, for example, a 1-fluorovinylthio group, a 2-fluorovinylthio group, a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, a 3,3-dichloro-2-propenylthio group, a 3,3-dibromo-2-propenylthio group, a 3-fluoro-3-chloro-2-propenylthio group, a 4-bromo-3-chloro-3,4,4-trifluoro-1-butenylthio group, a 1-bromomethyl-2-propenylthio group, a 3-chloro-2-butenylthio group, a 4,4,4-trifluoro-2-butenylthio group, a 4-bromo-4,4-difluoro-2-butenylthio group, a 3-bromo-3-butenylthio group, a 3,4,4-trifluoro-3-butenylthio group, a 3,4,4-tribromo-3-butenylthio group, a 3-bromo-2-methyl-2-propenylthio group, a 3,3-difluoro-2-methyl-2-propenylthio group, a 3-chloro-4,4,4-trifluoro-2-butenylthio group, a 4,4-difluoro-3-methyl-3-butenylthio group, a 5,5-difluoro-4-pentenylthio group, a 4,5,5-trifluoro-4-pentenylthio group, a 4,4,4-trifluoro-3-methyl-2-butenylthio group, a 3,5,5-trifluoro-2,4-pentadienylthio group, a 4,4,5,5,6,6,6-heptafluoro-2-hexenylthio group, a 4,5,5,5-tetrafluoro-4-trifluoromethyl-2-pentenylthio group, a 5-bromo-4,5,5-trifluoro-4-trifluoromethyl-2-pentenylthio group, a perfluoro-3-butenylthio group, a perfluoro-4-pentenylthio group, a perfluoro-5-hexenylthio group, a perfluoro-6-heptenylthio group, a perfluoro-7-octenylthio group, a perfluoro-8-nonenylthio group, a perfluoro-9-decenylthio group, a perfluoro-10-undecenylthio group, and a perfluoro-11-dodecenylthio group. The halogen atom that can be substituted for a hydrogen atom includes a fluorine atom, a chlorine atom, a bromine atom and an iodine atom.

The term "C2-C12 alkynythio group" represents a straight or branched alkynylthio group, and includes, for example, an ethynylthio group, a propargylthio group, a 1-butyne-3-ylthio group, a 3-methyl-1-butyne-3-ylthio group, a 2-butynylthio group, a 3-butynylthio group, a 2-pentynylthio group, a 3-pentynylthio group, a 4-pentynylthio group, a 5-hexynylthio group, a 6-heptynylthio group, an 7-octynylthio group, a 8-nonynylthio group, a 9-decynylthio group, an 10-undecynylthio group, and a 11-dodecynylthio group.

The term of "C2-C12 haloalkynythio group" represents a group wherein at least one hydrogen atom of the straight or branched an C2-C12 alkynythio group is substituted with a halogen atom, and includes, for example, a bromoethynylthio group, a 3-chloro-2-propynylthio group, a 3-bromo-2-propynylthio group, an 3-iodo-2-propynylthio group, a 5-chloro-4-pentynylthio group, a 3,3,3-trifluoro-1-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, a perfluoro-5-hexynylthio group, a perfluoro-6-heptynylthio group, a perfluoro-7-octynylthio group, a perfluoro-8-nonynylthio group, a perfluoro-9-decynylthio group, a perfluoro-10-undecynylthio group, and a perfluoro-11-dodecynylthio group. The halogen atom that can be substituted for a hydrogen atom includes a fluorine atom, a chlorine atom, a bromine atom and an iodine atom.

The term "amino group optionally substituted with an C1-C12 alkyl group" represents an amino group wherein one or two hydrogen atom on the amino group may be optionally substituted with a straight or branched C1-C12 alkyl group, and the total number of carbon atoms of the alkyl group is one to twelve and the alkyl group may be same or different to each other. The amino group includes, for example, an amino group, a N-methylamino group, an N-ethylamino group, a N-propylamino group, an N-isopropylamino group, a N-butylamino group, a N-pentylamino group, a N-hexylamino group, a N-heptylamino group, an N-octylamino group, a N-nonylamino group, a N-decylamino group, an N-undecylamino group, a N-dodecylamino group, a N,N-dimethylamino group, a N,N-diethylamino group, a N,N-dipropylamino group, a N,N-diisopropylamino group, a N,N-dibutylamino group, an N-ethyl-N-methylamino group, a N-propyl-N-methylamino group, a N-butyl-N-methylamino group, a N-pentyl-N-methylamino group, a N-hexyl-N-methylamino group, a N-heptyl-N-methylamino group, an N-octyl-N-methylamino group, a N-nonyl-N-methylamino group, a N-decyl-N-methylamino group and an N-undecyl-N-methyl group.

The term "C2-C12 acyl group" represents either a straight or branched aliphatic acyl group or an aromatic acyl group, wherein each of the total number of carbon atoms including a carbon atom of a carbonyl group is two to twelve, and includes, for example, an acetyl group, a propionyl group, a butanoyl group, a pentanoyl group, hexanoyl group, a heptanoyl group, an octanoyl group, a nonanoyl group, a decanoyl group, an undecanoyl group, a dodecanoyl group, a benzoyl group, a 1-naphthoyl group, and a 2-naphthoyl group.

The term "C2-C12 haloacyl group" represents a group wherein at least one hydrogen atom of the C2-C12 straight or branched aliphatic acyl group or aromatic acyl group is substituted with a halogen atom, wherein each of the total number of carbon atoms including a carbon atom of a carbonyl group is two to twelve, and includes, for example, a trichloroacetyl group, a fluoroacetyl group, a difluoroacetyl group, a trifluoroacetyl group, a pentafluoropropionyl group, a pentachloropropionyl group, a pentabromopropionyl group, a pentaiodopropionyl group, a 3,3,3-trichloropropionyl group, a 3,3,3-trifluoropropionyl group, a 3,3,3-tribromopropionyl group, a 3,3,3-triiodopropionyl group, a heptafluorobutanoyl group, a heptachlorobutanoyl group, a heptabromobutanoyl group, a heptaiodobutanoyl group, a 4,4,4-trifluorobutanoyl group, a 4,4,4-trichlorobutanoyl group, a 4,4,4-tribromobutanoyl group, a 4,4,4-triiodobutanoyl group, a nonafluoropentanoyl group, a nonachloropentanoyl group, a nonabromopentanoyl group, a nonaiodopentanoyl group, a perfluorohexanoyl group, a perfluoroheptanoyl group, a perfluorooctanoyl group, a perfluorononanoyl group, a perfluorodecanoyl group, a perfluoroundecanoyl group, a perfluorododecanoyl group, a 4-fluorobenzoyl group, a 4-chlorobenzoyl group, a 4 bromobenzoyl group, a 2,3,4,5,6-pentafluorobenzoyl group, a 3,5-dichlorobenzoyl group, a 3,5-difluorobenzoyl group, a 4-chloro-1-naphthoyl group, a 6-chloro-2-naphthoyl group, a 4-fluoro-1-naphthoyl group, a 6-fluoro-2-naphthoyl group, a 4-bromo-1-naphthoyl group, and a 6-bromo-2-naphthoyl group. The halogen atom that can be substituted for a hydrogen atom includes a fluorine atom, a chlorine atom, bromine atom and an iodine atom.

The term "C2-C12 acyloxy group" represents either a straight or branched aliphatic acyloxy group or an aromatic acyloxy group, wherein each of the total number of carbon atoms including a carbon atom of a carbonyl group is two to twelve, and includes, for example, an acetoxy group, a propionyloxy group, a butanoyloxy group, a pentanoyloxy group, a hexanoyloxy group, a heptanoyloxy group, an octanoyloxy group, a nonanoyloxy group, a decanoyloxy group, an undecanoyloxy group, a dodecanoyloxy group, a benzoyloxy group, a 1-naphthoyloxy group, and a 2-naphthoyloxy group.

The term "C2-C12 acylthio group" represents either a straight or branched aliphatic acylthio group or an aromatic acylthio group, wherein each of the total number of carbon atoms including a carbon atom of a carbonyl group is two to twelve, and includes, for example, an acetylthio group, a propionylthio group, a butanoylthio group, a pentanoylthio group, a hexanoylthio group, a heptanoylthio group, an octanoylthio group, a nonanoylthio group, a decanoylthio group, an undecanoylthio group, a dodecanoylthio group, a benzoylthio group, a 1-naphthoylthio group, and a 2-naphthoylthio group.

The term "C2-C12 alkoxycarbonyl group" may be either straight or branched, wherein the total number of carbon atoms of the alkoxy moiety and the carbonyl group is two to twelve, and includes, for example, a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, tert-butyloxycarbonyl group, a pentyloxycarbonyl group, an isoamyloxycarbonyl group, a neopentyloxycarbonyl group, a 2-pentyloxycarbonyl group, a 3-pentyloxycarbonyl group, a 2-methylbutyloxycarbonyl group, a hexyloxycarbonyl group, an isohexyloxycarbonyl group, a 3-methylpentyloxycarbonyl group, a 4-methylpentyloxycarbonyl group, a heptyloxycarbonyl group, a 2-heptyloxycarbonyl group, an octyloxycarbonyl group, a nonyloxycarbonyl group, a decyloxycarbonyl group, and an undecyloxycarbonyl group.

The term "aminocarbonyl group optionally substituted with an C1-C12 alkyl group" represents a group wherein one or two hydrogen atom on the aminocarbonyl group is substituted with the straight or branched C1-C12 alkyl group, wherein the total number of carbon atoms including a carbon atom of a carbonyl group is one to twelve, and the C1-C12 alkyl group may be same or different from each other. The aminocarbonyl group includes, for example, an aminocarbonyl group, a N-methylaminocarbonyl group, an N-ethylaminocarbonyl group, a N-propylaminocarbonyl group, an N-isopropylaminocarbonyl group, a N-butylaminocarbonyl group, a N-pentylaminocarbonyl group, a N-hexylaminocarbonyl group, a N-heptylaminocarbonyl group, an N-octylaminocarbonyl group, a N-nonylaminocarbonyl group, a N-decylaminocarbonyl group, an N-undecylaminocarbonyl group, a N,N-dimethylaminocarbonyl group, a N,N-diethylaminocarbonyl group, a N,N-dipropylaminocarbonyl group, a N,N-diisopropylaminocarbonyl group, a N,N-dibutylaminocarbonyl group, an N-ethyl-N-methylaminocarbonyl group, a N-propyl-N-methylaminocarbonyl group, a N-butyl-N-methylaminocarbonyl group, a N-pentyl-N-methylaminocarbonyl group, a N-hexyl-N-methylaminocarbonyl group, a N-heptyl-N-methylaminocarbonyl group, an N-octyl-N-methylaminocarbonyl group, a N-nonyl-N-methylaminocarbonyl group and a N-decyl-N-methylaminocarbonyl group.

The term "aminosulfonyl group optionally substituted with an C1-C12 alkyl group" represents an amino group wherein one or two hydrogen atom on the aminosulfonyl group may be optionally substituted with the straight or branched C1-C12 alkyl group, wherein the total number of carbon atoms of the alkyl group is one to twelve and the alkyl group may be same or different from each other. The aminosulfonyl group includes, for example, an aminosulfonyl group, a N-methylaminosulfonyl group, an N-ethylaminosulfonyl group, a N-propylaminosulfonyl group, an N-isopropylaminosulfonyl group, a N-butylaminosulfonyl group, a N-pentylaminosulfonyl group, a N-hexylaminosulfonyl group, a N-heptylaminosulfonyl group, an N-octylaminosulfonyl group, a N-nonylaminosulfonyl group, a N-decylaminosulfonyl group, an N-undecylaminosulfonyl group, a N-dodecylaminosulfonyl group, a N,N-dimethylaminosulfonyl group, a N,N-diethylaminosulfonyl group, a N,N-dipropylaminosulfonyl group, a N,N-diisopropylaminosulfonyl group, a N,N-dibutylaminosulfonyl group, a N-ethyl-N-methylaminosulfonyl group, a N-propyl-N-methylaminosulfonyl group, a N-butyl-N-methylaminosulfonyl group, a N-pentyl-N-methylaminosulfonyl group, a N-hexyl-N-methylaminosulfonyl group, a N-heptyl-N-methylaminosulfonyl group, a N-octyl-N-methylaminosulfonyl group, a N-nonyl-N-methylaminosulfonyl group, a N-decyl-N-methylaminosulfonyl group and an N-undecyl-N-methylaminosulfonyl group.

The term "C3-C12 trialkylsilyl group" includes, for example, a trimethylsilyl group, a tert-butyldimethylsilyl group, a triethylsilyl group, an isopropyldimethylsilyl group, a triisopropylsilyl group, a tri(tert-butyl)silyl group, and a tri(n-butyl)silyl group.

The term "C5-C14 trialkylsilylethynyl group" represents an ethynyl group containing trialkylsilyl group wherein the total number of carbon atoms including carbon atoms of the ethynyl group and the alkyl group may be same or different from each other, and includes, for example, a trimethylsilylethynyl group, a tert-butyldimethylsilylethynyl group, a triethylsilylethynyl group, an isopropyldimethylsilylethynyl group, a triisopropylsilylethynyl group, a tri(tert-butyl)silylethynyl group, and a tri(n-butyl)silylethynyl group.

The term "C1-C12 alkylsulfonyl group" represents a straight or branched alkylsulfonyl group, and includes, for example, a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, an isopentylsulfonyl group, a neopentylsulfonyl group, an isoamylsulfonyl group, a 2-pentylsulfonyl group, a 3-pentylsulfonyl group, a 2-methylbutylsulfonyl group, a hexylsulfonyl group, an isohexylsulfonyl group, a sec-hexylsulfonyl group, a 3-methylpentylsulfonyl group, a 4-methylpentylsulfonyl group, a heptylsulfonyl group, an isoheptylsulfonyl group, a sec-heptylsulfonyl group, an octylsulfonyl group, an 2-ethylhexylsulfonyl group, a nonylsulfonyl group, a decylsulfonyl group, an undecylsulfonyl group, and a dodecylsulfonyl group.

The term "C1-C12 haloalkylsulfonyl group" represents a group wherein at least one hydrogen atom of the straight or branched an C1-C12 alkylsulfonyl group is substituted with a halogen atom, and includes, for example, a monofluoromethylsulfonyl group, a bromodifluoromethylsulfonyl group, a difluoromethylsulfonyl group, a trifluoromethylsulfonyl group, a trichloromethylsulfonyl group, a tribromomethylsulfonyl group, a triiodomethylsulfonyl group, a chlorofluoromethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-trifluoroethylsulfonyl group, a 2,2,2-tribromoethylsulfonyl group, a 2,2,2-triiodoethylsulfonyl group, a 2,2-difluoroethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a 2,2-difluoropropylsulfonyl group, a 3,3,3-trifluoropropylsulfonyl group, a nonafluorobutylsulfonyl group, a nonachlorobutylsulfonyl group, a nonabromobutylsulfonyl group, a nonaiodobutylsulfonyl group, a perfluoropentylsulfonyl group, a perchloropentylsulfonyl group, a perbromopentylsulfonyl group, a perfluorohexylsulfonyl group, a perchlorohexylsulfonyl group, a perbromohexylsulfonyl group, a periodohexylsulfonyl group, a perfluoroheptylsulfonyl group, a perchloroheptylsulfonyl group, a perbromoheptylsulfonyl group, a perfluorooctylsulfonyl group, a perchlorooctylsulfonyl group, a perbromooctylsulfonyl group, a perfluorononylsulfonyl group, a perchlorononylsulfonyl group, a perbromononylsulfonyl group, a perfluorodecylsulfonyl group, a perchlorodecylsulfonyl group, a perbromodecylsulfonyl group, a perfluoroundecylsulfonyl group, and a perfluorododecylsulfonyl group. The halogen atom that can be substituted for a hydrogen atom includes a fluorine atom, a chlorine atom, a bromine atom and an iodine atom.

The term "C1-C12 alkylsulfinyl group" represents a straight or branched alkylsulfinyl group, and includes, for example, a methylsulfinyl group, an ethylsulfinyl group, propylsulfinyl group, an isopropylsulfinyl group, a butylsulfinyl group, an isobutylsulfinyl group, a sec-butylsulfinyl group, a tert-butylsulfinyl group, a pentylsulfinyl group, an isopentylsulfinyl group, a neopentylsulfinyl group, an isoamylsulfinyl group, a 2-pentylsulfinyl group, a 3-pentylsulfinyl group, a 2-methylbutylsulfinyl group, a hexylsulfinyl group, an isohexylsulfinyl group, a sec-hexylsulfinyl group, a 3-methylpentylsulfinyl group, a 4-methylpentylsulfinyl group, a heptylsulfinyl group, an isoheptylsulfinyl group, a sec-heptylsulfinyl group, an octylsulfinyl group, an 2-ethylhexylsulfinyl group, a nonylsulfinyl group, a decylsulfinyl group, an undecylsulfinyl group, and a dodecylsulfinyl group.

The term "C1-C12 haloalkylsulfinyl group" represents a group wherein at least one hydrogen atom of the straight or branched an C1-C12 alkylsulfinyl group is substituted with a halogen atom, and includes, for example, a monofluoromethylsulfinyl group, a bromodifluoromethylsulfinyl group, a difluoromethylsulfinyl group, a trifluoromethylsulfinyl group, a trichloromethylsulfinyl group, a tribromomethylsulfinyl group, a triiodomethylsulfinyl group, a chlorofluoromethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, 2,2,2-trifluoroethylsulfinyl group, a 2,2,2-trifluoroethylsulfinyl group, a 2,2,2-tribromoethylsulfinyl group, a 2,2,2-triiodoethylsulfinyl group, a 2,2-difluoroethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 2,2,2-triiodopropylsulfinyl group, a 2,2-difluoropropylsulfinyl group, a 3,3,3-trifluoropropylsulfinyl group, a nonafluorobutylsulfinyl group, a nonachlorobutylsulfinyl group, a nonabromobutylsulfinyl group, a nonaiodobutylsulfinyl group, a perfluoropentylsulfinyl group, a perchloropentylsulfinyl group, a perbromopentylsulfinyl group, a perfluorohexylsulfinyl group, a perchlorohexylsulfinyl group, a perbromohexylsulfinyl group, a periodohexylsulfinyl group, a perfluoroheptylsulfinyl group, a perchloroheptylsulfinyl group, a perbromoheptylsulfinyl group, a perfluorooctylsulfinyl group, perchlorooctylsulfinyl group, a perbromooctylsulfinyl group, a perfluorononylsulfinyl group, a perchlorononylsulfinyl group, a perbromononylsulfinyl group, a perfluorodecylsulfinyl group, a perchlorodecylsulfinyl group, a perbromodecylsulfinyl group, a perfluoroundecylsulfinyl group, and a perfluorododecylsulfinyl group. The halogen atom that can be substituted for a hydrogen atom includes a fluorine atom, a chlorine atom, a bromine atom and an iodine atom.

The term "C6-C16 aryl group" includes, for example, a phenyl group, a 1-naphthyl group, a 2-naphthyl group, an 1-acenaphthyl group, a 1-phenanthryl group, an 9-anthryl group, and a 1-pyrenyl group.

The term "C6-C16 haloaryl group" represents a group wherein at least one hydrogen atom of the C6-C16 aryl group is substituted with a halogen atom, and includes, for example, 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, an 2-iodophenyl group, an 3-iodophenyl group, an 4-iodophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a 2,3,4-trifluorophenyl group, a 2,4,5-trifluorophenyl group, a 3,4,5-trifluorophenyl group, a 2,4,6-trichlorophenyl group, a 2,3,4-trichlorophenyl group, a 2,4,5-trichlorophenyl group, a 3,4,5-trichlorophenyl group, a pentafluorophenyl group, a pentachlorophenyl group, a 2-bromo-3-fluorophenyl group, a 2-bromo-4-fluorophenyl group, a 2-bromo-5-fluorophenyl group, a 2-bromo-6-fluorophenyl group, a 3-bromo-2-fluorophenyl group, a 3-bromo-4-fluorophenyl group, a 3-bromo-5-fluorophenyl group, a 3-bromo-6-fluorophenyl group, a 4-bromo-2-fluorophenyl group, a 4-bromo-3-fluorophenyl group, a 5-bromo-6-fluorophenyl group, a 2-chloro-3-fluorophenyl group, a 2-chloro-4-fluorophenyl group, a 2-chloro-5-fluorophenyl group, a 2-chloro-6-fluorophenyl group, a 3-chloro-2-fluorophenyl group, a 3-chloro-4-fluorophenyl group, a 3-chloro-5-fluorophenyl group, a 3-chloro-6-fluorophenyl group, a 4-chloro-2-fluorophenyl group, a 4-chloro-3-fluorophenyl group, a 5-chloro-6-fluorophenyl group, a 2-fluoro-1-naphthyl group, a 3-fluoro-1-naphthyl group, a 4-fluoro-1-naphthyl group, a 5-fluoro-1-naphthyl group, a 6-fluoro-1-naphthyl group, a 7-fluoro-1-naphthyl group, a 2-chloro-1-naphthyl group, a 3-chloro-1-naphthyl group, a 4-chloro-1-naphthyl group, a 5-chloro-1-naphthyl group, a 6-chloro-1-naphthyl group, a 7-chloro-1-naphthyl group, a 2-bromo-1-naphthyl group, a 3-bromo-1-naphthyl group, a 4-bromo-1-naphthyl group, a 5-bromo-1-naphthyl group, a 6-bromo-1-naphthyl group, a 7-bromo-1-naphthyl group, a heptachloro-1-naphthyl group, a heptafluoro-1-naphthyl group, a 1-fluoro-2-naphthyl group, a 3-fluoro-2-naphthyl group, a 4-fluoro-2-naphthyl group, a 5-fluoro-2-naphthyl group, a 6-fluoro-2-naphthyl group, a 7-fluoro-2-naphthyl group, a 1-chloro-2-naphthyl group, a 3-chloro-2-naphthyl group, a 4-chloro-2-naphthyl group, a 5-chloro-2-naphthyl group, a 6-chloro-2-naphthyl group, a 7-chloro-2-naphthyl group, a 1-bromo-2-naphthyl group, a 3-bromo-2-naphthyl group, a 4-bromo-2-naphthyl group, a 5-bromo-2-naphthyl group, a 6-bromo-2-naphthyl group, a 7-bromo-2-naphthyl group, a heptachloro-2-naphthyl group, a heptafluoro-2-naphthyl group, a 3-fluoro-1-acenaphthyl group, a 9-fluoro-1-phenanthryl group, a 10-fluoro-9-anthryl group, and a 6-fluoro-1-pyrenyl group. The halogen atom that can be substituted for a hydrogen atom includes a fluorine atom, a chlorine atom, a bromine atom and an iodine atom.

The term "C6-C16 aryloxy group" includes, for example, a phenyloxy group, a 1-naphthyloxy group, a 2-naphthyloxy group, an 1-acenaphthyloxy group, a 1-phenanthryloxy group, an 9-anthryloxy group, and a 1-pyrenyloxy group.

The term "C6-C16 haloaryloxy group" represents a group wherein at least one hydrogen atom of the C6-C16 aryloxy group is substituted with a halogen atom, and includes, for example, a 2-fluorophenyloxy group, a 3-fluorophenyloxy group, a 4-fluorophenyloxy group, a 2-chlorophenyloxy group, a 3-chlorophenyloxy group, a 4-chlorophenyloxy group, a 2-bromophenyloxy group, a 3-bromophenyloxy group, a 4-bromophenyloxy group, an 2-iodophenyloxy group, an 3-iodophenyloxy group, an 4-iodophenyloxy group, a 2,4-difluorophenyloxy group, a 2,5-difluorophenyloxy group, a 2,6-difluorophenyloxy group, a 3,5-difluorophenyloxy group, a 2,4-dichlorophenyloxy group, a 2,5-dichlorophenyloxy group, a 2,6-dichlorophenyloxy group, a 3,5-dichlorophenyloxy group, a 2,4,6-trifluorophenyloxy group, a 2,3,4-trifluorophenyloxy group, a 2,4,5-trifluorophenyloxy group, a 3,4,5-trifluorophenyloxy group, a 2,4,6-trichlorophenyloxy group, a 2,3,4-trichlorophenyloxy group, a 2,4,5-trichlorophenyloxy group, a 3,4,5-trichlorophenyloxy group, a pentafluorophenyloxy group, a pentachlorophenyloxy group, a 2-bromo-3-fluorophenyloxy group, a 2-bromo-4-fluorophenyloxy group, a 2-bromo-5-fluorophenyloxy group, a 2-bromo-6-fluorophenyloxy group, a 3-bromo-2-fluorophenyloxy group, a 3-bromo-4-fluorophenyloxy group, a 3-bromo-5-fluorophenyloxy group, a 3-bromo-6-fluorophenyloxy group, a 4-bromo-2-fluorophenyloxy group, a 4-bromo-3-fluorophenyloxy group, a 5-bromo-6-fluorophenyloxy group, a 2-chloro-3-fluorophenyloxy group, a 2-chloro-4-fluorophenyloxy group, a 2-chloro-5-fluorophenyloxy group, a 2-chloro-6-fluorophenyloxy group, a 3-chloro-2-fluorophenyloxy group, a 3-chloro-4-fluorophenyloxy group, a 3-chloro-5-fluorophenyloxy group, a 3-chloro-6-fluorophenyloxy group, a 4-chloro-2-fluorophenyloxy group, a 4-chloro-3-fluorophenyloxy group, a 5-chloro-6-fluorophenyloxy group, a 2-fluoro-1-naphthyloxy group, a 3-fluoro-1-naphthyloxy group, a 4-fluoro-1-naphthyloxy group, a 5-fluoro-1-naphthyloxy group, a 6-fluoro-1-naphthyloxy group, a 7-fluoro-1-naphthyloxy group, a 2-chloro-1-naphthyloxy group, a 3-chloro-1-naphthyloxy group, a 4-chloro-1-naphthyloxy group, a 5-chloro-1-naphthyloxy group, a 6-chloro-1-naphthyloxy group, a 7-chloro-1-naphthyloxy group, a 2-bromo-1-naphthyloxy group, a 3-bromo-1-naphthyloxy group, a 4-bromo-1-naphthyloxy group, a 5-bromo-1-naphthyloxy group, a 6-bromo-1-naphthyloxy group, a 7-bromo-1-naphthyloxy group, a heptachloro-1-naphthyloxy group, a heptafluoro-1-naphthyloxy group, a 1-fluoro-2-naphthyloxy group, a 3-fluoro-2-naphthyloxy group, a 4-fluoro-2-naphthyloxy group, a 5-fluoro-2-naphthyloxy group, a 6-fluoro-2-naphthyloxy group, a 7-fluoro-2-naphthyloxy group, a 1-chloro-2-naphthyloxy group, a 3-chloro-2-naphthyloxy group, a 4-chloro-2-naphthyloxy group, a 5-chloro-2-naphthyloxy group, a 6-chloro-2-naphthyloxy group, a 7-chloro-2-naphthyloxy group, a 1-bromo-2-naphthyloxy group, a 3-bromo-2-naphthyloxy group, a 4-bromo-2-naphthyloxy group, a 5-bromo-2-naphthyloxy group, a 6-bromo-2-naphthyloxy group, a 7-bromo-2-naphthyloxy group, a heptachloro-2-naphthyloxy group, a heptafluoro-2-naphthyloxy group, a 3-fluoro-1-acenaphthyloxy group, a 9-fluoro-1-phenanthryloxy group, a 10-fluoro-9-anthryloxy group, and a 6-fluoro-1-pyrenyloxy group. The halogen atom that can be substituted for a hydrogen atom includes a fluorine atom, a chlorine atom, a bromine atom and an iodine atom.

The term "C6-C16 arylthio group" includes, for example, a phenylthio group, a 1-naphthylthio group, a 2-naphthylthio group, an 1-acenaphthylthio group, a 1-phenanthrylthio group, an 9-anthrylthio group, and a 1-pyrenylthio group.

The term "C6-C16 haloarylthio group" represents a group wherein at least one hydrogen atom of the C6-C16 arylthio group is substituted with a halogen atom, and includes, for example, a 2-fluorophenylthio group, a 3-fluorophenylthio group, a 4-fluorophenylthio group, a 2-chlorophenylthio group, a 3-chlorophenylthio group, a 4-chlorophenylthio group, a 2-bromophenylthio group, a 3-bromophenylthio group, a 4-bromophenylthio group, an 2-iodophenylthio group, an 3-iodophenylthio group, an 4-iodophenylthio group, a 2,4-difluorophenylthio group, a 2,5-difluorophenylthio group, a 2,6-difluorophenylthio group, a 3,5-difluorophenylthio group, a 2,4-dichlorophenylthio group, a 2,5-dichlorophenylthio group, a 2,6-dichlorophenylthio group, a 3,5-dichlorophenylthio group, a 2,4,6-trifluorophenylthio group, a 2,3,4-trifluorophenylthio group, a 2,4,5-trifluorophenylthio group, a 3,4,5-trifluorophenylthio group, a 2,4,6-trichlorophenylthio group, a 2,3,4-trichlorophenylthio group, a 2,4,5-trichlorophenylthio group, a 3,4,5-trichlorophenylthio group, a pentafluorophenylthio group, a pentachlorophenylthio group, a 2-bromo-3-fluorophenylthio group, a 2-bromo-4-fluorophenylthio group, a 2-bromo-5-fluorophenylthio group, a 2-bromo-6-fluorophenylthio group, a 3-bromo-2-fluorophenylthio group, a 3-bromo-4-fluorophenylthio group, a 3-bromo-5-fluorophenylthio group, a 3-bromo-6-fluorophenylthio group, a 4-bromo-2-fluorophenylthio group, a 4-bromo-3-fluorophenylthio group, a 5-bromo-6-fluorophenylthio group, a 2-chloro-3-fluorophenylthio group, a 2-chloro-4-fluorophenylthio group, a 2-chloro-5-fluorophenylthio group, a 2-chloro-6-fluorophenylthio group, a 3-chloro-2-fluorophenylthio group, a 3-chloro-4-fluorophenylthio group, a 3-chloro-5-fluorophenylthio group, a 3-chloro-6-fluorophenylthio group, a 4-chloro-2-fluorophenylthio group, a 4-chloro-3-fluorophenylthio group, a 5-chloro-6-fluorophenylthio group, a 2-fluoro-1-naphthylthio group, a 3-fluoro-1-naphthylthio group, a 4-fluoro-1-naphthylthio group, a 5-fluoro-1-naphthylthio group, a 6-fluoro-1-naphthylthio group, a 7-fluoro-1-naphthylthio group, a 2-chloro-1-naphthylthio group, a 3-chloro-1-naphthylthio group, a 4-chloro-1-naphthylthio group, a 5-chloro-1-naphthylthio group, a 6-chloro-1-naphthylthio group, a 7-chloro-1-naphthylthio group, a 2-bromo-1-naphthylthio group, a 3-bromo-1-naphthylthio group, a 4-bromo-1-naphthylthio group, a 5-bromo-1-naphthylthio group, a 6-bromo-1-naphthylthio group, a 7-bromo-1-naphthylthio group, a heptachloro-1-naphthylthio group, a heptafluoro-1-naphthylthio group, a 1-fluoro-2-naphthylthio group, a 3-fluoro-2-naphthylthio group, a 4-fluoro-2-naphthylthio group, a 5-fluoro-2-naphthylthio group, a 6-fluoro-2-naphthylthio group, a 7-fluoro-2-naphthylthio group, a 1-chloro-2-naphthylthio group, a 3-chloro-2-naphthylthio group, a 4-chloro-2-naphthylthio group, a 5-chloro-2-naphthylthio group, a 6-chloro-2-naphthylthio group, a 7-chloro-2-naphthylthio group, a 1-bromo-2-naphthylthio group, a 3-bromo-2-naphthylthio group, a 4-bromo-2-naphthylthio group, a 5-bromo-2-naphthylthio group, a 6-bromo-2-naphthylthio group, a 7-bromo-2-naphthylthio group, a heptachloro-2-naphthylthio group, a heptafluoro-2-naphthylthio group, a 3-fluoro-1-acenaphthylthio group, a 9-fluoro-1-phenanthrylthio group, a 10-fluoro-9-anthrylthio group, and a 6-fluoro-1-pyrenylthio group. The halogen atom that can be substituted for a hydrogen atom includes a fluorine atom, a chlorine atom, a bromine atom and an iodine atom.

The term "C7-C18 aralkyl group" includes, for example, a benzyl group, a phenethyl group, a 3-phenylpropyl group, a 4-phenylbutyl group, a 5-phenylpentyl group, a 6-phenylhexyl group, a 7-phenylheptyl group, a 8-phenyloctyl group, a 9-phenylnonyl group, a 10-phenyldecyl group, a 11-phenylundecyl group, a 1,2-phenyldodecyl group, a 1-naphthylmethyl group, a 2-(1-naphthyl)ethyl group, a 3-(1-naphthyl)propyl group, a 4-(1-naphthyl)butyl group, a 5-(1-naphthyl)pentyl group, a 6-(1-naphthyl)hexyl group, a 7-(1-naphthyl)heptyl group, a 8-(1-naphthyl)octyl group, a 2-naphthylmethyl group, a 2-(2-naphthyl)ethyl group, a 3-(2-naphthyl)propyl group, a 4-(2-naphthyl)butyl group, a 5-(2-naphthyl)pentyl group, a 6-(2-naphthyl)hexyl group, a 7-(2-naphthyl)heptyl group, a 8-(2-naphthyl)octyl group, an 1-anthrylmethyl group, an 2-(1-anthryl)ethyl group, an 3-(1-anthryl)propyl group, an 4-(1-anthryl)butyl group, an 2-anthrylmethyl group, an 2-(2-anthryl)ethyl group, an 3-(2-anthryl)propyl group, an 4-(2-anthryl)butyl group, an 9-anthrylmethyl group, an 2-(9-anthryl)ethyl group, an 3-(9-anthryl)propyl group, an 4-(9-anthryl)butyl group, a 1-phenanthrylmethyl group, a 2-(1-phenanthryl)ethyl group, a 3-(1-phenanthryl)propyl group, a 4-(1-phenanthryl)butyl group, a 1-pyrenylthiomethyl group, and a 2-(1-pyrenylthio)ethyl group.

The term "C7-C18 haloaralkyl group" represents a group wherein at least one hydrogen atom on the alkyl or the aryl moiety of the C7-C18 aralkyl group is substituted with a halogen atom, and includes, for example, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, an 2-iodobenzyl group, an 3-iodobenzyl group, an 4-iodobenzyl group, a 2,4-difluorobenzyl group, a 2,5-difluorobenzyl group, a 2,6-difluorobenzyl group, a 3,5-difluorobenzyl group, a 2,4-dichlorobenzyl group, a 2,5-dichlorobenzyl group, a 2,6-dichlorobenzyl group, a 3,5-dichlorobenzyl group, a 2,4,6-trifluorobenzyl group, a 2,3,4-trifluorobenzyl group, a 2,4,5-trifluorobenzyl group, 3,4,5-trifluorobenzyl group, a 2,4,6-trichlorobenzyl group, a 2,3,4-trichlorobenzyl group, a 2,4,5-trichlorobenzyl group, a 3,4,5-trichlorobenzyl group, a pentafluorobenzyl group, a pentachloroobenzyl group, a 2-bromo-3-fluorobenzyl group, a 2-bromo-4-fluorobenzyl group, a 2-bromo-5-fluorobenzyl group, a 2-bromo-6-fluorobenzyl group, a 3-bromo-2-fluorobenzyl group, a 3-bromo-4-fluorobenzyl group, a 3-bromo-5-fluorobenzyl group, a 3-bromo-6-fluorobenzyl group, a 4-bromo-2-fluorobenzyl group, a 4-bromo-3-fluorobenzyl group, a 5-bromo-6-fluorobenzyl group, a 2-chloro-3-fluorobenzyl group, a 2-chloro-4-fluorobenzyl group, a 2-chloro-5-fluorobenzyl group, a 2-chloro-6-fluorobenzyl group, a 3-chloro-2-fluorobenzyl group, a 3-chloro-4-fluorobenzyl group, a 3-chloro-5-fluorobenzyl group, a 3-chloro-6-fluorobenzyl group, a 4-chloro-2-fluorobenzyl group, a 4-chloro-3-fluorobenzyl group a 5-chloro-6-fluorobenzyl group, a 2-(4-fluorophenyl)ethyl group, 2-(4-chlorophenyl)ethyl group, a 2-(4-bromophenyl) ethyl group, an 2-(4-iodophenyl)ethyl group, a 2-(3-fluorophenyl)ethyl group, a 2-(3-chlorophenyl)ethyl group, a 2-(3-bromophenyl)ethyl group, an 2-(3-iodophenyl)ethyl group, a 2-(2-fluorophenyl)ethyl group, a 2-(2-chlorophenyl) ethyl group, a 2-(2-bromophenyl)ethyl group, an 2-(2-iodophenyl)ethyl group, a 3-(4-fluorophenyl)propyl group, a 3-(4-chlorophenyl)propyl group, a 3-(4-bromophenyl)propyl group, an 3-(4-iodophenyl)propyl group, a 3-(3-fluorophenyl)propyl group, a 3-(3-chlorophenyl)propyl group, a 3-(3-bromophenyl)propyl group, an 3-(3-iodophenyl)propyl group, a 3-(2-fluorophenyl)propyl group, a 3-(2-chlorophenyl)propyl group, a 3-(2-bromophenyl)propyl group, an 3-(2-iodophenyl)propyl group, a 4-(4-fluorophenyl)butyl group, a 4-(4-chlorophenyl)butyl group, a 4-(4-bromophenyl)butyl group, an 4-(4-iodophenyl)butyl group, a 5-(4-fluorophenyl)pentyl group, a 5-(4-chlorophenyl)pentyl group, a 5-(4-bromophenyl)pentyl group, an 5-(4-iodophenyl)pentyl group, a 6-(4-fluorophenyl)hexyl group, a 6-(4-chlorophenyl)hexyl group, a 6-(4-bromophenyl)hexyl group, an 6-(4-iodophenyl) hexyl group, a 7-(4-fluorophenyl)heptyl group, a 7-(4-chlorophenyl)heptyl group, a 7-(4-bromophenyl)heptyl group, an 7-(4-iodophenyl)heptyl group, a 8-(4-fluorophenyl)octyl group, a 8-(4-chlorophenyl)octyl group, a 8-(4-bromophenyl)octyl group, an 8-(4-iodophenyl)octyl group, a 9-(4-fluorophenyl)nonyl group, a 9-(4-chlorophenyl)nonyl group, a 9-(4-bromophenyl) nonyl group, an 9-(4-iodophenyl)nonyl group, a 10-(4-fluorophenyl)decyl group, a 10-(4-chlorophenyl)decyl group, a 10-(4-bromophenyl)decyl group, an 10-(4-iodophenyl)decyl group, a 11-(4-fluorophenyl)undecyl group, a 11-(4-chlorophenyl)undecyl group, a 11-(4-bromophenyl)undecyl group, an 11-(4-iodophenyl)undecyl group, a 1,2-(4-fluorophenyl)dodecyl group, a 1,2-(4-chlorophenyl)dodecyl group, a 1,2-(4-bromophenyl)dodecyl group, an 1,2-(4-iodophenyl)dodecyl group, a 2-fluoro-1-naphthylmethyl group, a 3-fluoro-1-naphthylmethyl group, a 4-fluoro-1-naphthylmethyl group, a 5-fluoro-1-naphthylmethyl group, a 6-fluoro-naphthylmethyl group, a 7-fluoro-1-naphthylmethyl group, a 2-chloro-1-naphthylmethyl group, a 3-chloro-1-naphthylmethyl group, a 4-chloro-1-naphthylmethyl group, a 5-chloro-1-naphthylmethyl group, a 6-chloro-1-naphthylmethyl group, a 7-chloro-1-naphthylmethyl group, a 2-bromo-1-naphthylmethyl group, a 3-bromo-1-naphthylmethyl group, a 4-bromo-1-naphthylmethyl group, a 5-bromo-1-naphthylmethyl group, a 6-bromo-1-naphthylmethyl group, a 7-bromo-1-naphthylmethyl group, a heptachloro-1-naphthylmethyl group, a heptafluoro-1-naphthylmethyl group, a 1-fluoro-2-naphthylmethyl group, a 3-fluoro-2-naphthylmethyl group, a 4-fluoro-2-naphthylmethyl group, a 5-fluoro-2-naphthylmethyl group, a 6-fluoro-2-naphthylmethyl group, a 7-fluoro-2-naphthylmethyl group, a 1-chloro-2-naphthylmethyl group, a 3-chloro-2-naphthylmethyl group, a 4-chloro-2-naphthylmethyl group, a 5-chloro-2-naphthylmethyl group, a 6-chloro-2-naphthylmethyl group, a 7-chloro-2-naphthylmethyl group, a 1-bromo-2-naphthylmethyl group, a 3-bromo-2-naphthylmethyl group, a 4-bromo-2-naphthylmethyl group, a 5-bromo-2-naphthylmethyl group, a 6-bromo-2-naphthylmethyl group, a 7-bromo-2-naphthylmethyl group, a heptachloro-2-naphthylmethyl group, a heptafluoro-2-naphthylmethyl group, a 2-(5-fluoro-1-naphthyl)ethyl group, a 2-(5-chloro-1-naphthyl)ethyl group, a 2-(5-bromo-1-naphthyl)ethyl group, a 2-(6-fluoro-2-naphthyl)ethyl group, a 2-(6-chloro-2-naphthyl)ethyl group, a 2-(6-bromo-2-naphthyl)ethyl group, a 3-(5-fluoro-1-naphthyl)propyl group, a 3-(5-chloro-1-naphthyl)propyl group, a 3-(5-bromo-1-naphthyl)propyl group, a 3-(6-fluoro-2-naphthyl)propyl group, a 3-(6-chloro-2-naphthyl)propyl group, a 3-(6-bromo-2-naphthyl)propyl group, a 4-(5-fluoro-1-naphthyl)butyl group, a 4-(5-chloro-1-naphthyl)butyl group, a 4-(5-bromo-1-naphthyl)butyl group, a 4-(6-fluoro-2-naphthyl)butyl group, a 4-(6-chloro-2-naphthyl)butyl group, a 4-(6-bromo-2-naphthyl)butyl group, a 5-(5-fluoro-1-naphthyl)pentyl group, a 5-(5-chloro-1-naphthyl)pentyl group, a 5-(5-bromo-1-naphthyl)pentyl group, a 5-(6-fluoro-2-naphthyl)pentyl group, a 5-(6-chloro-2-naphthyl)pentyl group, a 5-(6-bromo-2-naphthyl)pentyl group, a 6-(5-fluoro-1-naphthyl)hexyl group, a 6-(5-chloro-1-naphthyl)hexyl group, a 6-(5-bromo-1-naphthyl)hexyl group, a 6-(6-fluoro-2-naphthyl)hexyl group, a 6-(6-chloro-2-naphthyl)hexyl group, a 6-(6-bromo-2-naphthyl)hexyl group, a 6-(5-fluoro-1-naphthyl)heptyl group, a 6-(5-chloro-1-naphthyl)heptyl group, a 6-(5-bromo-1-naphthyl)heptyl group, a 6-(6-fluoro-2-naphthyl)heptyl group, a 6-(6-chloro-2-naphthyl)heptyl group, a 6-(6-bromo-2-naphthyl)heptyl group, a 6-(5-fluoro-1-naphthyl)octyl group, a 6-(5-chloro-1-naphthyl)octyl group, a 6-(5-bromo-1-naphthyl)octyl group, a 6-(6-fluoro-2-naphthyl)octyl group, a 6-(6-chloro-2-naphthyl)octyl group, a 6-(6-bromo-2-naphthyl)octyl group, a 3-fluoro-1-acenaphthylmethyl group, a 9-fluoro-1-phenanthryla methyl group, a 10-fluoro-9-anthrylmethyl group, a 6-fluoro-1-pyrenylmethyl group, and a 11-difluoro(1-phenyl)methyl group. The halogen atom that can be substituted for a hydrogen atom includes a fluorine atom, a chlorine atom, a bromine atom and an iodine atom.

The term "C7-C18 arylalkoxy group" includes, for example, a benzyloxy group, a phenethyloxy group, a 3-phenylpropyloxy group, a 4-phenylbutyloxy group, a 5-phenylpentyloxy group, a 6-phenylhexyloxy group, a 7-phenylheptyloxy group, a 8-phenyloctyloxy group, a 9-phenylnonyloxy group, a 10-phenyldecyloxy group, a 11-phenylundecyloxyoxy group, a 1,2-phenyldodecyloxy group, 1-naphthylmethyloxy group, a 2-(1-naphthyl)ethyloxy group, a 3-(1-naphthyl) propyloxy group, a 4-(1-naphthyl)butyloxy group, a 5-(1-naphthyl)pentyloxy group, a 6-(1-naphthyl)hexyloxy group, a 7-(1-naphthyl)heptyloxy group, a 8-(1-naphthyl)octyloxy group, a 2-naphthylmethyloxy group, a 2-(2-naphthyl)ethyloxy group, a 3-(2-naphthyl)propyloxy group, a 4-(2-naphthyl)butyloxy group, a 5-(2-naphthyl)pentyloxy group, a 6-(2-naphthyl)hexyloxy group, a 7-(2-naphthyl)heptyloxy group, a 8-(2-naphthyl)octyloxy group, an 1-anthrylmethyloxy group, an 2-(1-anthryl)ethyloxy group, an 3-(1-anthryl) propyloxy group, an 4-(1-anthryl)butyloxy group, an 2-anthrylmethyloxy group, an 2-(2-anthryl)ethyloxy group, an 3-(2-anthryl)propyloxy group, an 4-(2-anthryl)butyloxy group, an 9-anthrylmethyloxy group, an 2-(9-anthryl)ethyloxy group, an 3-(9-anthryl)propyloxy group, an 4-(9-anthryl)butyloxy group, a 1-phenanthrylmethyloxy group, a 2-(1-phenanthryl)ethyloxy group, a 3-(1-phenanthryl)propyloxy group, a 4-(1-phenanthryl)butyloxy group, a 1-pyrenylmethyloxy group, and a 2-(1-pyrenyl)ethyloxy group.

The term "C7-C18 haloarylalkoxy group" represents a group wherein at least one hydrogen atom on the aryl or the alkyl moiety of the C7-C18 arylalkoxy group is substituted with a halogen atom, and includes, for example, a 2-fluorobenzyloxy group, a 3-fluorobenzyloxy group, a 4-fluorobenzyloxy group, a 2-chlorobenzyloxy group, a 3-chlorobenzyloxy group, a 4-chlorobenzyloxy group, a 2-bromobenzyloxy group, a 3-bromobenzyloxy group, a 4-bromobenzyloxy group, an 2-iodobenzyloxy group, an 3-iodobenzyloxy group, an 4-iodobenzyloxy group, a 2,4-difluorobenzyloxy group, a 2,5-difluorobenzyloxy group, a 2,6-difluorobenzyloxy group, a 3,5-difluorobenzyloxy group, a 2,4-dichlorobenzyloxy group, a 2,5-dichlorobenzyloxy group, a 2,6-dichlorobenzyloxy group, a 3,5-dichlorobenzyloxy group, a 2,4,6-trifluorobenzyloxy group, a 2,3,4-trifluorobenzyloxy group, a 2,4,5-trifluorobenzyloxy group, a 3,4,5-trifluorobenzyloxy group, a 2,4,6-trichlorobenzyloxy group, a 2,3,4-trichlorobenzyloxy group, a 2,4,5-trichlorobenzyloxy group, a 3,4,5-trichlorobenzyloxy group, a pentafluorobenzyloxy group, a pentachlorobenzyloxy group, a 2-bromo-3-fluorobenzyloxy group, a 2-bromo-4-fluorobenzyloxy group, a 2-bromo-5-fluorobenzyloxy group, a 2-bromo-6-fluorobenzyloxy group, a 3-bromo-2-fluorobenzyloxy group, a 3-bromo-4-fluorobenzyloxy group, a 3-bromo-5-fluorobenzyloxy group, a 3-bromo-6-fluorobenzyloxy group, a 4-bromo-2-fluorobenzyloxy group, a 4-bromo-3-fluorobenzyloxy group, a 5-bromo-6-fluorobenzyloxy group a 2-chloro-3-fluorobenzyloxy group, a 2-chloro-4-fluorobenzyloxy group, a 2-chloro-5-fluorobenzyloxy group, a 2-chloro-6-fluorobenzyloxy group, a 3-chloro-2-fluorobenzyloxy group, a 3-chloro-4-fluorobenzyloxy group, a 3-chloro-5-fluorobenzyloxy group, a 3-chloro-6-fluorobenzyloxy group, a 4-chloro-2-fluorobenzyloxy group, a 4-chloro-3-fluorobenzyloxy group, a 5-chloro-6-fluorobenzyloxy group, a 2-(4-fluorophenyl) ethyloxy group, a 2-(4-chlorophenyl)ethyloxy group, a 2-(4-bromophenyl)ethyloxy group, a 2-(4-iodophenyl)ethyloxy group, a 2-(3-fluorophenyl)ethyloxy group, a 2-(3-chlorophenyl)ethyloxy group, a 2-(3-bromophenyl)ethyloxy group, an 2-(3-iodophenyl)ethyloxy group, a 2-(2-fluorophenyl)ethyloxy group, a 2-(2-chlorophenyl)ethyloxy group, a 2-(2-bromophenyl)ethyloxy group, an 2-(2-iodophenyl)ethyloxy group, a 3-(4-fluorophenyl)propyloxy group, a 3-(4-chlorophenyl)propyloxy group, a 3-(4-bromophenyl)propyloxy group, an 3-(4-iodophenyl)propyloxy group, a 3-(3-fluorophenyl)propyloxy group, a 3-(3-chlorophenyl)propyloxy group, a 3-(3-bromophenyl)propyloxy group, an 3-(3-iodophenyl)propyloxy group, a 3-(2-fluorophenyl)propyloxy group, a 3-(2-chlorophenyl)propyloxy group, a 3-(2-bromophenyl)propyloxy group, an 3-(2-iodophenyl)propyloxy group, a 4-(4-fluorophenyl)butyloxy group, a 4-(4-chlorophenyl)butyloxy group, a 4-(4-bromophenyl)butyloxy group, an 4-(4-iodophenyl)butyloxy group, a 5-(4-fluorophenyl)pentyloxy group, a 5-(4-chlorophenyl)pentyloxy group, a 5-(4-bromophenyl)pentyloxy group, an 5-(4-iodophenyl)pentyloxy group, a 6-(4-fluorophenyl)hexyloxy group, a 6-(4-chlorophenyl)hexyloxy group, a 6-(4-bromophenyl)hexyloxy group, an 6-(4-iodophenyl)hexyloxy group, a 7-(4-fluorophenyl)heptyloxy group, a 7-(4-chlorophenyl)heptyloxy group, a 7-(4-bromophenyl)heptyloxy group, an 7-(4-iodophenyl)heptyloxy group, a 8-(4-fluorophenyl)octyloxy group, a 8-(4-chlorophenyl)octyloxy group, a 8-(4-bromophenyl)octyloxy group, an 8-(4-iodophenyl)octyloxy group, a 9-(4-fluorophenyl)nonyloxy group, a 9-(4-chlorophenyl)nonyloxy group, a 9-(4-bromophenyl)nonyloxy group, an 9-(4-iodophenyl)nonyloxy group, a 10-(4-fluorophenyl)decyloxy group, a 10-(4-chlorophenyl)decyloxy group, a 10-(4-bromophenyl)decyloxy group, an 10-(4-iodophenyl)decyloxy group, a 11-(4-fluorophenyl)undecyloxy group, a 11-(4-chlorophenyl)undecyloxy group, a 11-(4-bromophenyl)undecyloxy group, an 11-(4-iodophenyl)undecyloxy group, a 1,2-(4-fluorophenyl)dodecyloxy group, a 1,2-(4-chlorophenyl)dodecyloxy group, a 1,2-(4-bromophenyl)dodecyloxy group, an 1,2-(4-iodophenyl)dodecyloxy group, a 2-fluoro-1-naphthylmethyloxy group, a 3-fluoro-1-naphthylmethyloxy group, a 4-fluoro-1-naphthylmethyloxy group, a 5-fluoro-1-naphthylmethyloxy group, a 6-fluoro-1-naphthylmethyloxy group, a 7-fluoro-1-naphthylmethyloxy group, a 2-chloro-1-naphthylmethyloxy group, a 3-chloro-1-naphthylmethyloxy group, a 4-chloro-1-naphthylmethyloxy group, a 5-chloro-1-naphthylmethyloxy group, a 6-chloro-1-naphthylmethyloxy group, a 7-chloro-1-naphthylmethyloxy group, a 2-bromo-1-naphthylmethyloxy group, a 3-bromo-1-naphthylmethyloxy group, a 4-bromo-1-naphthylmethyloxy group, a 5-bromo-1-naphthylmethyloxy group, a 6-bromo-1-naphthylmethyloxy group, a 7-bromo-1-naphthylmethyloxy group, a heptachloro-1-naphthylmethyloxy group, a heptafluoro-1-naphthylmethyloxy group, a 1-fluoro-2-naphthylmethyloxy group, a 3-fluoro-2-naphthylmethyloxy group, a 4-fluoro-2-naphthylmethyloxy group, a 5-fluoro-2-naphthylmethyloxy group, a 6-fluoro-2-naphthylmethyloxy group, a 7-fluoro-2-naphthylmethyloxy group, a 1-chloro-2-naphthylmethyloxy group, a 3-chloro-2-naphthylmethyloxy group, a 4-chloro-2-naphthylmethyloxy group, a 5-chloro-2-naphthylmethyloxy group, a 6-chloro-2-naphthylmethyloxy group, a 7-chloro-2-naphthylmethyloxy group, a 1-bromo-2-naphthylmethyloxy group, a 3-bromo-2-naphthylmethyloxy group, a 4-bromo-2-naphthylmethyloxy group, a 5-bromo-2-naphthylmethyloxy group, a 6-bromo-2-naphthylmethyloxy group, a 7-bromo-2-naphthylmethyloxy group, a heptachloro-2-naphthylmethyloxy group, a heptafluoro-2-naphthylmethyloxy group, a 2-(5-fluoro-1-naphthyl)ethyloxy group, a 2-(5-chloro-1-naphthyl)ethyloxy group, a 2-(5-bromo-1-naphthyl)ethyloxy group, a 2-(6-fluoro-2-naphthyl)ethyloxy group, a 2-(6-chloro-2-naphthyl)ethyloxy group, a 2-(6-bromo-2-naphthyl)ethyloxy group, a 3-(5-fluoro-1-naphthyl)propyloxy group, a 3-(5-chloro-1-naphthyl)propyloxy group, a 3-(5-bromo-1-naphthyl)propyloxy group, a 3-(6-fluoro-2-naphthyl)propyloxy group, a 3-(6-chloro-2-naphthyl)propyloxy group, a 3-(6-bromo-2-naphthyl)propyloxy group, a 4-(5-fluoro-1-naphthyl)butyloxy group, a 4-(5-chloro-1-naphthyl)butyloxy group, a 4-(5-bromo-1-naphthyl)butyloxy group, a 4-(6-fluoro-2-naphthyl)butyloxy group, a 4-(6-chloro-2-naphthyl)butyloxy group, a 4-(6-bromo-2-naphthyl)butyloxy group, a 5-(5-fluoro-1-naphthyl)pentyloxy group, a 5-(5-chloro-1-naphthyl)pentyloxy group, a 5-(5-bromo-1-naphthyl)pentyloxy group, a 5-(6-fluoro-2-naphthyl)pentyloxy group, a 5-(6-chloro-2-naphthyl)pentyloxy group, a 5-(6-bromo-2-naphthyl)pentyloxy group, a 6-(5-fluoro-1-naphthyl)hexyloxy group, a 6-(5-chloro-1-naphthyl)hexyloxy group, a 6-(5-bromo-1-naphthyl)hexyloxy group, a 6-(6-fluoro-2-naphthyl)hexyloxy group, a 6-(6-chloro-2-naphthyl)hexyloxy group, a 6-(6-bromo-2-naphthyl)hexyloxy group, a 6-(5-fluoro-1-naphthyl)heptyloxy group, a 6-(5-chloro-1-naphthyl)heptyloxy group, a 6-(5-bromo-1-naphthyl)heptyloxy group, a 6-(6-fluoro-2-naphthyl)heptyloxy group, a 6-(6-chloro-2-naphthyl)heptyloxy group, a 6-(6-bromo-2-naphthyl)heptyloxy group, a 6-(5-fluoro-1-naphthyl)octyloxy group, a 6-(5-chloro-1-naphthyl)octyloxy group, a 6-(5-bromo-1-naphthyl)octyloxy group, a 6-(6-fluoro-2-naphthyl)octyloxy group, a 6-(6-chloro-2-naphthyl)octyloxy group, a 6-(6-bromo-2-naphthyl)octyloxy group, a 3-fluoro-1-acenaphthylmethyloxy group, a 9-fluoro-1-phenanthrylmethyloxy group, a 10-fluoro-9-anthrylmethyloxy group, a 6-fluoro-1-pyrenylmethyloxy group, and a 11-difluoro-1-phenylmethyloxy group.

The term "C3-C16 arylsulfonyl group" includes, for example, a phenylsulfonyl group, a 1-naphthylsulfonyl group, a 2-naphthylsulfonyl group, an 1-acenaphthylsulfonyl group, a 1-phenanthrylsulfonyl group, an 9-anthrylsulfonyl group, and a 1-pyrenylsulfonyl group.

The term "C3-C16 haloarylsulfonyl group" represents a group wherein at least one hydrogen atom of the C3-C16 arylsulfonyl group is substituted with a halogen atom, and includes, for example, a 2-fluorophenylsulfonyl group, a 3-fluorophenylsulfonyl group, a 4-fluorophenylsulfonyl group, a 2-chlorophenylsulfonyl group, a 3-chlorophenylsulfonyl group, a 4-chlorophenylsulfonyl group, a 2-bromophenylsulfonyl group, a 3-bromophenylsulfonyl group, a 4-bromophenylsulfonyl group, an 2-iodophenylsulfonyl group, an 3-iodophenylsulfonyl group, an 4-iodophenylsulfonyl group, a 2,4-difluorophenylsulfonyl group, a 2,5-difluorophenylsulfonyl group, a 2,6-difluorophenylsulfonyl group, a 3,5-difluorophenylsulfonyl group, a 2,4-dichlorophenylsulfonyl group, a 2,5-dichlorophenylsulfonyl group, a 2,6-dichlorophenylsulfonyl group, a 3,5-dichlorophenylsulfonyl group, a 2,4,6-trifluorophenylsulfonyl group, a 2,3,4-trifluorophenylsulfonyl group, a 2,4,5-trifluorophenylsulfonyl group, a 3,4,5-trifluorophenylsulfonyl group, a 2,4,6-trichlorophenylsulfonyl group, a 2,3,4-trichlorophenylsulfonyl group, a 2,4,5-trichlorophenylsulfonyl group, a 3,4,5-trichlorophenylsulfonyl group, a pentafluorophenylsulfonyl group, a pentachlorophenylsulfonyl group, a 2-bromo-3-fluorophenylsulfonyl group, a 2-bromo-4-fluorophenylsulfonyl group, a 2-bromo-5-fluorophenylsulfonyl group, a 2-bromo-6-fluorophenylsulfonyl group, a 3-bromo-2-fluorophenylsulfonyl group, a 3-bromo-4-fluorophenylsulfonyl group, a 3-bromo-5-fluorophenylsulfonyl group, a 3-bromo-6-fluorophenylsulfonyl group, a 4-bromo-2-fluorophenylsulfonyl group, a 4-bromo-3-fluorophenylsulfonyl group, a 5-bromo-6-fluorophenylsulfonyl group, a 2-chloro-3-fluorophenylsulfonyl group, a 2-chloro-4-fluorophenylsulfonyl group, a 2-chloro-5-fluorophenylsulfonyl group, a 2-chloro-6-fluorophenylsulfonyl group, a 3-chloro-2-fluorophenylsulfonyl group, a 3-chloro-4-fluorophenylsulfonyl group, a 3-chloro-5-fluorophenylsulfonyl group, a 3-chloro-6-fluorophenylsulfonyl group, a 4-chloro-2-fluorophenylsulfonyl group, a 4-chloro-3-fluorophenylsulfonyl group, a 5-chloro-6-fluorophenylsulfonyl group, a 2-fluoro-1-naphthylsulfonyl group, a 3-fluoro-1-naphthylsulfonyl group, a 4-fluoro-1-naphthylsulfonyl group, a 5-fluoro-1-naphthylsulfonyl group, a 6-fluoro-1-naphthylsulfonyl group, a 7-fluoro-1-naphthylsulfonyl group, a 2-chloro-1-naphthylsulfonyl group, a 3-chloro-1-naphthylsulfonyl group, a 4-chloro-1-naphthylsulfonyl group, a 5-chloro-1-naphthylsulfonyl group, a 6-chloro-1-naphthylsulfonyl group, a 7-chloro-1-naphthylsulfonyl group, a 2-bromo-1-naphthylsulfonyl group, a 3-bromo-1-naphthylsulfonyl group, a 4-bromo-1-naphthylsulfonyl group, a 5-bromo-1-naphthylsulfonyl group, a 6-bromo-1-naphthylsulfonyl group, a 7-bromo-1-naphthylsulfonyl group, a heptachloro-1-naphthylsulfonyl group, a heptafluoro-1-naphthylsulfonyl group, a 1-fluoro-2-naphthylsulfonyl group, a 3-fluoro-2-naphthylsulfonyl group, a 4-fluoro-2-naphthylsulfonyl group, a 5-fluoro-2-naphthylsulfonyl group, a 6-fluoro-2-naphthylsulfonyl group, a 7-fluoro-2-naphthylsulfonyl group, a 1-chloro-2-naphthylsulfonyl group, a 3-chloro-2-naphthylsulfonyl group, a 4-chloro-2-naphthylsulfonyl group, a 5-chloro-2-naphthylsulfonyl group, a 6-chloro-2-naphthylsulfonyl group, a 7-chloro-2-naphthylsulfonyl group, a 1-bromo-2-naphthylsulfonyl group, a 3-bromo-2-naphthylsulfonyl group, 4-bromo-2-naphthylsulfonyl group, a 5-bromo-2-naphthylsulfonyl group, a 6-bromo-2-naphthylsulfonyl group, a 7-bromo-2-naphthylsulfonyl group, a heptachloro-2-naphthylsulfonyl group, a heptafluoro-2-naphthylsulfonyl group, a 3-fluoro-1-acenaphthylsulfonyl group, a 9-fluoro-1-phenanthrylsulfonyl group, a 10-fluoro-9-anthrylsulfonyl group, and a 6-fluoro-1-pyrenylsulfonyl group. The halogen atom that can be substituted for a hydrogen atom includes a fluorine atom, a chlorine atom, a bromine atom and an iodine atom.

The term "C6-C16 arylsulfinyl group" includes, for example, a phenylsulfinyl group, a 1-naphthylsulfinyl group, a 2-naphthylsulfinyl group, an 1-acenaphthylsulfinyl group, a 1-phenanthrylsulfinyl group, an 9-anthrylsulfinyl group, and a 1-pyrenylsulfinyl group.

The term "C6-C16 haloarylsulfinyl group" represents a group wherein at least one hydrogen atom of the C6-C16 arylsulfinyl group is substituted with a halogen atom, and includes, for example, a 2-fluorophenylsulfinyl group, a 3-fluorophenylsulfinyl group, a 4-fluorophenylsulfinyl group, a 2-chlorophenylsulfinyl group, a 3-chlorophenylsulfinyl group, a 4-chlorophenylsulfinyl group, a 2-bromophenylsulfinyl group, a 3-bromophenylsulfinyl group, a 4-bromophenylsulfinyl group, an 2-iodophenylsulfinyl group, an 3-iodophenylsulfinyl group, an 4-iodophenylsulfinyl group, a 2,4-difluorophenylsulfinyl group, a 2,5-difluorophenylsulfinyl group, a 2,6-difluorophenylsulfinyl group, a 3,5-difluorophenylsulfinyl group, a 2,4-dichlorophenylsulfinyl group, a 2,5-dichlorophenylsulfinyl group, a 2,6-dichlorophenylsulfinyl group, a 3,5-dichlorophenylsulfinyl group, a 2,4,6-trifluorophenylsulfinyl group, a 2,3,4-trifluorophenylsulfinyl group, a 2,4,5-trifluorophenylsulfinyl group, a 3,4,5-trifluorophenylsulfinyl group, a 2,4,6-trichlorophenylsulfinyl group, a 2,3,4-trichlorophenylsulfinyl group, a 2,4,5-trichlorophenylsulfinyl group, a 3,4,5-trichlorophenylsulfinyl group, a pentafluorophenylsulfinyl group, a pentachlorophenylsulfinyl group, a 2-bromo-3-fluorophenylsulfinyl group, a 2-bromo-4-fluorophenylsulfinyl group, a 2-bromo-5-fluorophenylsulfinyl group, a 2-bromo-6-fluorophenylsulfinyl group, a 3-bromo-2-fluorophenylsulfinyl group, a 3-bromo-4-fluorophenylsulfinyl group, a 3-bromo-5-fluorophenylsulfinyl group, a 3-bromo-6-fluorophenylsulfinyl group, a 4-bromo-2-fluorophenylsulfinyl group, a 4-bromo-3-fluorophenylsulfinyl group, a 5-bromo-6-fluorophenylsulfinyl group, a 2-chloro-3-fluorophenylsulfinyl group, a 2-chloro-4-fluorophenylsulfinyl group, a 2-chloro-5-fluorophenylsulfinyl group, a 2-chloro-6-fluorophenylsulfinyl group, a 3-chloro-2-fluorophenylsulfinyl group, a 3-chloro-4-fluorophenylsulfinyl group, a 3-chloro-5-fluorophenylsulfinyl group, a 3-chloro-6-fluorophenylsulfinyl group, a 4-chloro-2-fluorophenylsulfinyl group, a 4-chloro-3-fluorophenylsulfinyl group, a 4-chloro-5-fluorophenylsulfinyl group, a 4-chloro-6-fluorophenylsulfinyl group, a 5-chloro-2-fluorophenylsulfinyl group, a 5-chloro-3-fluorophenylsulfinyl group, a 5-chloro-4-fluorophenylsulfinyl group, a 5-chloro-6-fluorophenylsulfinyl group, a 2-fluoro-1-naphthylsulfinyl group, a 3-fluoro-1-naphthylsulfinyl group, a 4-fluoro-1-naphthylsulfinyl group, a 5-fluoro-1-naphthylsulfinyl group, a 6-fluoro-1-naphthylsulfinyl group, a 7-fluoro-1-naphthylsulfinyl group, a 2-chloro-1-naphthylsulfinyl group, a 3-chloro-1-naphthylsulfinyl group, a 4-chloro-1-naphthylsulfinyl group, a 5-chloro-1-naphthylsulfinyl group, a 6-chloro-1-naphthylsulfinyl group, a 7-chloro-1-naphthylsulfinyl group, a 2-bromo-1-naphthylsulfinyl group, a 3-bromo-1-naphthylsulfinyl group, a 4-bromo-1-naphthylsulfinyl group, a 5-bromo-1-naphthylsulfinyl group, a 6-bromo-1-naphthylsulfinyl group, a 7-bromo-1-naphthylsulfinyl group, a heptachloro-1-naphthylsulfinyl group, a heptafluoro-1-naphthylsulfinyl group, a 1-fluoro-2-naphthylsulfinyl group, a 3-fluoro-2-naphthylsulfinyl group, a 4-fluoro-2-naphthylsulfinyl group, a 5-fluoro-2-naphthylsulfinyl group, a 6-fluoro-2-naphthylsulfinyl group, a 7-fluoro-2-naphthylsulfinyl group, a 1-chloro-2-naphthylsulfinyl group, a 3-chloro-2-naphthylsulfinyl group, a 4-chloro-2-naphthylsulfinyl group, a 5-chloro-2-naphthylsulfinyl group, a 6-chloro-2-naphthylsulfinyl group, a 7-chloro-2-naphthylsulfinyl group, a 1-bromo-2-naphthylsulfinyl group, a 3-bromo-2-naphthylsulfinyl group, a 4-bromo-2-naphthylsulfinyl group, a 5-bromo-2-naphthylsulfinyl group, a 6-bromo-2-naphthylsulfinyl group, a 7-bromo-2-naphthylsulfinyl group, a heptachloro-2-naphthylsulfinyl group, a heptafluoro-2-naphthylsulfinyl group, a 3-fluoro-1-acenaphthylsulfinyl group, a 9-fluoro-1-phenanthrylsulfinyl group, a 10-fluoro-9-anthrylsulfinyl group, and a 6-fluoro-1-pyrenylsulfinyl group. The halogen atom that can be substituted for a hydrogen atom includes a fluorine atom, a chlorine atom, a bromine atom and an iodine atom.

The term "aminocarbonyl group optionally substituted with an C1-C12 alkyl group and/or an C6-C12 aryl group" represents a group wherein one or two hydrogen atom of the aminocarbonyl group may be optionally substituted with a straight or branched C1-C12 alkyl group and/or an C6-C12 aryl group, wherein the substituents on the nitrogen atom are same or different from each other. The aminocarbonyl group includes, for example, an aminocarbonyl group, a N-methylaminocarbonyl group, an N-ethylaminocarbonyl group, a N-propylaminocarbonyl group, an N-isopropylaminocarbonyl group, a N-butylaminocarbonyl group, a N-pentylaminocarbonyl group, a N-hexylaminocarbonyl group, a N-heptylaminocarbonyl group, an N-octylaminocarbonyl group, a N-nonylaminocarbonyl group, a N-decylaminocarbonyl group, an N-undecylaminocarbonyl group, a N-dodecylaminocarbonyl group, a N,N-dimethylaminocarbonyl group, a N,N-diethylaminocarbonyl group, a N,N-dipropylaminocarbonyl group, a N,N-diisopropylaminocarbonyl group, a N,N-dibutylaminocarbonyl group, an N-ethyl-N-methylaminocarbonyl group, a N-propyl-N-methylaminocarbonyl group, a N-butyl-N-methylaminocarbonyl group, a N-pentyl-N-methylaminocarbonyl group, a N-hexyl-N-methylaminocarbonyl group, a N-heptyl-N-methylaminocarbonyl group, an N-octyl-N-methylaminocarbonyl group, a N-nonyl-N-methylaminocarbonyl group, a N-decyl-N-methylaminocarbonyl group, a N-undecyl-N-methylcarbonyl group, a N-dodecyl-N-methylaminocarbonyl group, a N-phenylaminocarbonyl group, a N,N-diphenylaminocarbonyl group, a N-methyl-N-phenylaminocarbonyl group, an N-ethyl-N-phenylaminocarbonyl group, a N-propyl-N-phenylaminocarbonyl group, a N-butyl-N-phenylaminocarbonyl group, a N-pentyl-N-phenylaminocarbonyl group, a N-hexyl-N-phenylaminocarbonyl group, a N-heptyl-N-phenylaminocarbonyl group, an N-octyl-N-phenylaminocarbonyl group, a N-nonyl-N-phenylaminocarbonyl group, a N-decyl-N-phenylaminocarbonyl group, an N-undecyl-N-phenylaminocarbonyl group, a N-dodecyl-N-phenylaminocarbonyl group, a N-(1-naphthyl)aminocarbonyl group, a N-(1-naphthyl)-N-methylaminocarbonyl group, a N-(2-naphthyl)aminocarbonyl group, and a N-(2-naphthyl)-N-methylaminocarbonyl group.

The term "aminosulfonyl group optionally substituted with an C1-C12 alkyl group and/or an C6-C12 aryl group" represents a group wherein one or two hydrogen atom of the aminosulfonyl group may be optionally substituted with a straight or branched an C1-C12 alkyl group and/or an C6-C12 aryl group, wherein the substituents on nitrogen atom may be same or different from each other, and includes, for example, an aminosulfonyl group, a N-methylaminosulfonyl group, an N-ethylaminosulfonyl group, a N-propylaminosulfonyl group, an N-isopropylaminosulfonyl group, a N-butylaminosulfonyl group, a N-pentylaminosulfonyl group, a N-hexylaminosulfonyl group, a N-heptylaminosulfonyl group, an N-octylaminosulfonyl group, a N-nonylaminosulfonyl group, a N-decylaminosulfonyl group, an N-undecylaminosulfonyl group, a N-dodecylaminosulfonyl group, a N,N-dimethylaminosulfonyl group, a N,N-diethylaminosulfonyl group, a N,N-dipropylaminosulfonyl group, a N,N-diisopropylaminosulfonyl group, a N,N-dibutylaminosulfonyl group, an N-ethyl-N-methylaminosulfonyl group, a N-propyl-N-methylaminosulfonyl group, a N-butyl-N-methylaminosulfonyl group, a N-pentyl-N-methylaminosulfonyl group, a N-hexyl-N-methylaminosulfonyl group, a N-heptyl-N-methylaminosulfonyl group, an N-octyl-N-methylaminosulfonyl group, a N-nonyl-N-methylaminosulfonyl group, a N-decyl-N-methylsulfonyl group, a N-undecyl-N-methylsulfonyl group, a N-dodecyl-N-methylaminosulfonyl group, a N-phenylaminosulfonyl group, a N,N-diphenylaminosulfonyl group, a N-methyl-N-phenylaminosulfonyl group, an N-ethyl-N-phenylaminosulfonyl group, a N-propyl-N-phenylaminosulfonyl group, a N-butyl-N-phenylaminosulfonyl group, a N-pentyl-N-phenylaminosulfonyl group, a N-hexyl-N-phenylaminosulfonyl group, a N-heptyl-N-phenylaminosulfonyl group, an N-octyl-N-phenylaminosulfonyl group, a N-nonyl-N-phenylaminosulfonyl group, a N-decyl-N-phenylaminosulfonyl group, an N-undecyl-N-phenylaminosulfonyl group, a N-dodecyl-N-phenylaminosulfonyl group, a N-(1-naphthyl)aminosulfonyl group, a N-(1-naphthyl)-N-methylaminosulfonyl group, a N-(2-naphthyl)aminosulfonyl group, and a N-(2-naphthyl)-N-methylaminosulfonyl group.

The term "C2-11 polyoxaalkyloxy group" represents a group wherein one methylene group of the straight C3 alkoxy group is replaced with an oxygen atom, or a group wherein one or two methylene group of the straight C4 alkoxy group is replaced with an oxygen atom, or a group wherein one, two or three methylene group of the straight C5-C12 alkoxy group is replaced with an oxygen atom, and the oxygen atoms do not adjoin each other. The C2-11 polyoxaalkyloxy group include, for example, a $CH_3$—O—$CH_2$—O group, a $CH_3$—$CH_2$—O—$CH_2$—O group, a $CH_3$—O—$(CH_2)_2$—O group, a $CH_3$—$CH_2$—O—$(CH_2)_2$—O group, a $CH_3$—$(CH_2)_2$—O—$CH_2$—O group, a $CH_3$—O—$(CH_2)_3$—O group, a $CH_3$—O—$CH_2$—O—$(CH_2)_2$—O group, a $CH_3$—$(CH_2)_2$—O—$(CH_2)_2$—O group, a $CH_3$—$(CH_2)_2$—O—$CH_2$—O group, a $CH_3$—$(CH_2)_3$—O—$CH_2$—O group, a $CH_3$—O—$(CH_2)_2$—$(CH_2)_2$—O group, a $CH_3$—O—$(CH_2)_2$—O—$CH_2$—O group, a $CH_3$—O—$(CH_2)_4$—O group, a $CH_3$—$(CH_2)_2$—O—$(CH_2)_3$—O group, a $CH_3$—$(CH_2)_3$—O—$(CH_2)_2$—O group, a $CH_3$—$CH_2$—O—$(CH_2)_2$—O—$(CH_2)_2$—O group, a $CH_3$—$CH_2$—O—$(CH_2)_4$—O group, a $CH_3$—O—$(CH_2)_2$—O—$(CH_2)_3$—O group, a $CH_3$—O—$(CH_2)_3$—O—$(CH_2)_2$—O group, a $CH_3$—O—$(CH_2)_5$—O group, a $CH_3$—$(CH_2)$—O—$(CH_2)_2$—$(CH_2)_2$—O group, a $CH_3$—$(CH_2)_2$—O—$(CH_2)_4$—O group, a $CH_3$—$(CH_2)_3$—O—$(CH_2)_3$—O group, a $CH_3$—$(CH_2)_4$—O—$(CH_2)_2$—O group, a $CH_3$—$CH_2$—O—$(CH_2)_2$—O—$(CH_2)_3$—O group, a $CH_3$—$CH_2$—O—$(CH_2)_3$—O—$(CH_2)_2$—O group, a $CH_3$—$CH_2$—O—$(CH_2)_5$—O group, a $CH_3$—O—$(CH_2)_2$—O—$(CH_2)_2$—O—$(CH_2)_2$—O group, a $CH_3$—O—$(CH_2)_2$—O—$(CH_2)_4$—O group, a $CH_3$—O—$(CH_2)_3$—O—$(CH_2)_3$—O group, a $CH_3$—O—$(CH_2)_4$—O—$(CH_2)_2$—O group, a $CH_3$—O—$(CH_2)_6$—O group, a $CH_3$—$(CH_2)_2$—

O—(CH$_2$)$_2$O—(CH$_2$)$_3$—O group, a CH$_3$—(CH$_2$)$_2$—O—(CH$_2$)$_3$—O—(CH$_2$)$_2$—O group, a CH$_3$—(CH$_2$)$_2$—O—(CH$_2$)$_4$—O—(CH$_2$)$_2$—O group, a CH$_3$—(CH$_2$)$_2$—O—(CH$_2$)$_5$—O group, a CH$_3$—(CH$_2$)$_3$—O—(CH$_2$)$_2$—O—(CH$_2$)$_2$—O group, a CH$_3$—(CH$_2$)$_3$—O—(CH$_2$)$_4$—O group, a CH$_3$—(CH$_2$)$_4$—O—(CH$_2$)$_3$—O group, a CH$_3$—(CH$_2$)$_5$—O—(CH$_2$)$_2$—O group, a CH$_3$—CH$_2$—O—(CH$_2$)$_2$—O—(CH$_2$)$_2$—O—(CH$_2$)$_2$—O group, a CH$_3$—CH$_2$—O—(CH$_2$)$_2$—O—(CH$_2$)$_4$—O group, a CH$_3$—CH$_2$—O—(CH$_2$)$_3$—O—(CH$_2$)$_3$—O group, a CH$_3$—CH$_2$—O—(CH$_2$)$_4$—O—(CH$_2$)$_2$—O group, a CH$_3$—CH$_2$—O—(CH$_2$)$_6$—O group, a CH$_3$—O—(CH$_2$)$_2$—O—(CH$_2$)$_2$—O—(CH$_2$)$_3$—O group, a CH$_3$—O—(CH$_2$)$_2$—O—(CH$_2$)$_5$—O group, a CH$_3$—O—(CH$_2$)$_3$—O—(CH$_2$)$_2$—O—(CH$_2$)$_2$—O group, a CH$_3$—O—(CH$_2$)$_3$—O—(CH$_2$)$_4$—O group, a CH$_3$—O—(CH$_2$)$_4$—O—(CH$_2$)$_3$—O group, a CH$_3$—O—(CH$_2$)$_5$—O—(CH$_2$)$_2$—O group, a CH$_3$—O—(CH$_2$)$_7$—O group, a CH$_3$—(CH$_2$)$_2$—O—(CH$_2$)$_2$—O—(CH$_2$)$_2$—O—(CH$_2$)$_2$—O group, a CH$_3$—(CH$_2$)$_2$—O—(CH$_2$)$_2$—O—(CH$_2$)$_4$—O group, a CH$_3$—(CH$_2$)$_2$—O—(CH$_2$)$_3$—O—(CH$_2$)$_3$—O group, a CH$_3$—(CH$_2$)$_2$—O—(CH$_2$)$_6$—O group, a CH$_3$—(CH$_2$)$_3$—O—(CH$_2$)$_2$—O—(CH$_2$)$_3$—O group, a CH$_3$—(CH$_2$)$_3$—O—(CH$_2$)$_3$—O—(CH$_2$)$_2$—O group, a CH$_3$—(CH$_2$)$_3$—O—(CH$_2$)$_5$—O group, a CH$_3$—(CH$_2$)$_4$—O—(CH$_2$)$_2$—O—(CH$_2$)$_2$—O group, a CH$_3$—(CH$_2$)$_4$—O—(CH$_2$)$_4$—O group, a CH$_3$—(CH$_2$)$_4$—O—(CH$_2$)$_3$—O group, a CH$_3$—(CH$_2$)$_5$—O—(CH$_2$)$_3$—O group, a CH$_3$—(CH$_2$)$_5$—O—(CH$_2$)$_4$—O group, a CH$_3$—(CH$_2$)$_6$—O—(CH$_2$)$_2$—O group, a CH$_3$—CH$_2$—O—(CH$_2$)$_2$—O—(CH$_2$)$_2$—O—(CH$_2$)$_3$—O group, a CH$_3$—CH$_2$—O—(CH$_2$)$_2$—O—(CH$_2$)$_3$—O—(CH$_2$)$_2$—O group, a CH$_3$—CH$_2$—O—(CH$_2$)$_2$—O—(CH$_2$)$_5$—O group, a CH$_3$—CH$_2$—O—(CH$_2$)$_3$—O—(CH$_2$)$_2$—O—(CH$_2$)$_2$—O group, a CH$_3$—CH$_2$—O—(CH$_2$)$_3$—O—(CH$_2$)$_4$—O group, a CH$_3$—CH$_2$—O—(CH$_2$)$_4$—O—(CH$_2$)$_3$—O group, a CH$_3$—CH$_2$—O—(CH$_2$)$_5$—O—(CH$_2$)$_2$—O group, a CH$_3$—CH$_2$—O—(CH$_2$)$_7$—O group, a CH$_3$—O—(CH$_2$)$_2$—O—(CH$_2$)$_2$—O—(CH$_2$)$_4$—O group, a CH$_3$—O—(CH$_2$)$_2$—O—(CH$_2$)$_3$—O—(CH$_2$)$_2$—O group, a CH$_3$—O—(CH$_2$)$_2$—O—(CH$_2$)$_3$—O—(CH$_2$)$_3$—O group, a CH$_3$—O—(CH$_2$)$_2$—O—(CH$_2$)$_4$—O—(CH$_2$)$_2$—O group, a CH$_3$—O—(CH$_2$)$_2$—O—(CH$_2$)$_6$—O group, a CH$_3$—O—(CH$_2$)$_3$—O—(CH$_2$)$_2$—O—(CH$_2$)$_3$—O group, a CH$_3$—O—(CH$_2$)$_3$—O—(CH$_2$)$_3$—O—(CH$_2$)$_2$—O group, a CH$_3$—O—(CH$_2$)$_3$—O—(CH$_2$)$_5$—O group, a CH$_3$—O—(CH$_2$)$_4$—O—(CH$_2$)$_2$—O—(CH$_2$)$_2$—O group, a CH$_3$—O—(CH$_2$)$_4$—O—(CH$_2$)$_4$—O group, a CH$_3$—O—(CH$_2$)$_5$—O—(CH$_2$)$_3$—O group, a CH$_3$—O—(CH$_2$)$_6$—O—(CH$_2$)$_2$—O group, a CH$_3$—(CH$_2$)$_2$—O—(CH$_2$)$_8$—O group, a CH$_3$—(CH$_2$)$_2$—O—(CH$_2$)$_2$—O—(CH$_2$)$_5$—O group, a CH$_3$—(CH$_2$)$_2$—O—(CH$_2$)$_3$—O—(CH$_2$)$_4$—O group, a CH$_3$—(CH$_2$)$_2$—O—(CH$_2$)$_4$—O—(CH$_2$)$_3$—O group, a CH$_3$—(CH$_2$)$_2$—O—(CH$_2$)$_5$—(CH$_2$)$_2$—O group, a CH$_3$—(CH$_2$)$_2$—(CH$_2$)$_7$—O group, a CH$_3$—(CH$_2$)$_3$—O—(CH$_2$)$_3$—O—(CH$_2$)$_3$—O group, a CH$_3$—(CH$_2$)$_3$—O—(CH$_2$)$_4$—O—(CH$_2$)$_2$—O group, a CH$_3$—(CH$_2$)$_3$—O—(CH$_2$)$_6$—O group, a CH$_3$—(CH$_2$)$_4$—O—(CH$_2$)$_2$—O—(CH$_2$)$_3$—O group, a CH$_3$—(CH$_2$)$_4$—O—(CH$_2$)$_3$—O—(CH$_2$)$_2$—O group, a CH$_3$—(CH$_2$)$_4$—O—(CH$_2$)$_5$—O group, a CH$_3$—(CH$_2$)$_5$—O—(CH$_2$)$_2$—O—(CH$_2$)$_2$—O group, a CH$_3$—(CH$_2$)$_6$—O—(CH$_2$)$_3$—O group, a CH$_3$—(CH$_2$)$_7$—O—(CH$_2$)$_2$—O group, a CH$_3$—CH$_2$—O—(CH$_2$)$_2$—O—(CH$_2$)$_6$—O group, a CH$_3$—CH$_2$—O—(CH$_2$)$_3$—O—(CH$_2$)$_5$—O group, a CH$_3$—CH$_2$—O—(CH$_2$)$_5$—O—(CH$_2$)$_4$—O group, a CH$_3$—CH$_2$—O—(CH$_2$)$_8$—O group, a CH$_3$—O—(CH$_2$)$_2$—O—(CH$_2$)$_7$—O group, a CH$_3$—O—(CH$_2$)$_3$—O—(CH$_2$)$_6$—O group, a CH$_3$—O—(CH$_2$)$_4$—O—(CH$_2$)$_5$—O—(CH$_2$)$_4$—O group, a CH$_3$—O—(CH$_2$)$_6$—O—(CH$_2$)$_3$—O group, a CH$_3$—O—(CH$_2$)$_9$—O group, a CH$_3$—(CH$_2$)$_2$—O—(CH$_2$)$_8$—O group, a CH$_3$—(CH$_2$)$_3$—O—(CH$_2$)$_2$—O—(CH$_2$)$_4$—O group, a CH$_3$—(CH$_2$)$_3$—O—(CH$_2$)$_7$—O group, a CH$_3$—(CH$_2$)$_4$—O—(CH$_2$)$_6$—O group, a CH$_3$—(CH$_2$)$_5$—O—(CH$_2$)$_5$—O group, a CH$_3$—(CH$_2$)$_6$—O—(CH$_2$)$_4$—O group, a CH$_3$—(CH$_2$)$_7$—O—(CH$_2$)$_3$—O group, a CH$_3$—(CH$_2$)$_8$—O—(CH$_2$)$_2$—O group, a CH$_3$—CH$_2$—O—(CH$_2$)$_9$—O group, and a CH$_3$—O—(CH$_2$)$_{10}$—O group.

The term "C2-C5 oxacycloalkyloxy group" represents a group wherein one methylene group in a ring of the C3-C6 cycloalkyloxy group is replaced with an oxygen atom, and includes, for example, an oxiranyloxy group, an oxetanyloxy group, a tetrahydrofuranyloxy group, and a tetrahydropyranyloxy group.

The term "C5-C6 cycloalkyldiene ring" includes specifically, cyclopentadiene ring and cyclohexadiene ring.

The term "C4-C6 cycloalkene ring" includes specifically, a cyclobutene ring, a cyclopentene ring and a cyclohexene ring.

The term "C3-C6 cycloalkane ring" includes, specifically, cyclopropane ring, a cyclobutane ring, a cyclopentane ring and a cyclohexane ring.

The term "C1-C6 alkyl group" represents a straight or branched alkyl group, and includes, for example, a methyl group, an ethyl group, a propyl group, an isopropyl group, a butyl group, an isobutyl group, a sec-butyl group, a tert-butyl group, a pentyl group, and a hexyl group.

The term "C1-C6 haloalkyl group" represents a group wherein at least one hydrogen atom of the straight or branched an C1-C6 alkyl group is substituted with a halogen atom, and includes, for example, a monofluoromethyl group, a monochloromethyl group, a dichloromethyl group, a difluoromethyl group, a trifluoromethyl group, a trichloromethyl group, a tribromomethyl group, a chlorofluoromethyl group, a dichlorofluoromethyl group, a 2,2,2-trifluoroethyl group, a 2,2,2-trichloroethyl group, a pentafluoroethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-3-fluoropropyl group, a 4-fluorobutyl group, a 5-fluoropentyl group, and a 2,2-difluorohexyl group. The halogen atom that can be substituted for a hydrogen atom includes a fluorine atom, a chlorine atom, a bromine atom and an iodine atom.

The term "C1-C6 alkenyl group" represents a straight or branched alkenyl group, and includes, for example, a vinyl group, a 1-propenyl group, an isopropenyl group, a 2 propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, an 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, and a 5-hexenyl group.

The term "C1-C6 haloalkenyl group" represents a group wherein at least one hydrogen atom of the C1-C6 alkenyl group is substituted with a halogen atom, and includes, for example, a 2-chlorovinyl group, a 2-bromovinyl group, an 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3, 3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-chloro-2-propenyl group, a 3,3-dichloro-2-propenyl group, a 3,3-dibromo-2-propenyl group, a 3-fluoro-3-chloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, a 3,4,4-trifluoro-1,3-butadienyl group, a perfluoro-1-butenyl group, a perfluoro-3-butenyl group, a 3,4-dibromo-1-pentenyl group, a 4,4-difluoro-3-methyl-3-butenyl group, a 3,3,4,4,5,5,5-heptafluoro-1-pentenyl group, a 5,5-difluoro-4-pentenyl group, a 4,5,5-trifluoro-4-pentenyl group, a 3,4,4,4-tetrafluoro-3-trifluoromethyl-1-butenyl group, a 4,4,4-trifluoro-3-methyl-2-butenyl group, a 3,5,5-trifluoro-2,4-pentadienyl group, a perfluoro-1-pentenyl group, a perfluoro-4-pentenyl group, a 4,4,5,5,6,6,6-heptafluoro-2-hexenyl group, a 3,4,4,5,5,5-hexafluoro-3-trifluoromethyl-1-pentenyl group, a 4,5,5,5-tetrafluoro-4-trifluoromethyl-2-pentenyl group, a 5-bromo-4,5,5-trifluoro-4-trifluoromethyl-2-pentenyl group, a perfluoro-1-hexenyl group, and a perfluoro-5-hexenyl group. The halogen atom that can be substituted for a hydrogen atom includes a fluorine atom, a chlorine atom, a bromine atom and an iodine atom.

The term "C2-C6 alkynyl group" represents a straight or branched alkynyl group, and includes, for example, an ethynyl group, a propargyl group, a 1-butyne-3-yl group, a 2-butynyl group, a 3-butynyl group, a 3-methyl-1-butyne-3-yl group, a 2-pentynyl group, a 3-pentynyl group, a 4-pentynyl group, a 1-hexynyl group, and a 5-hexynyl group.

The term "C2-C6 haloalkynyl group" represents a group wherein at least one hydrogen atom of the a straight or branched an C2-C6 alkynyl group is substituted with a halogen atom, and includes, for example, a fluoroethynyl group, a 3-chloro-2-propynyl group, a 3-bromo-2-propynyl group, an 3-iodo-2-propynyl group, a 3-chloro-1-propynyl group, a 5-chloro-4-pentynyl group, a 3,3,3-trifluoro-1-propynyl group, a 3,3,3-trifluoro-1-propynyl group, a perfluoro-2-butynyl group, a perfluoro-3-butynyl group, a perfluoro-2-pentynyl group, a perfluoro-3-pentynyl group, a perfluoro-4-pentynyl group, a perfluoro-1-hexynyl group, and a perfluoro-5-hexynyl group. The halogen atom that can be substituted for a hydrogen atom includes a fluorine atom, a chlorine atom, a bromine atom and an iodine atom.

The term "C2-C6 alkoxyalkyl group" may be either a straight or a branched group wherein the total number of carbon atoms of the alkoxy moiety and the alkyl moiety is two to six carbon atoms, and includes, for example, a methoxymethyl group, an ethoxymethyl group, a propyloxymethyl group, an isopropyloxymethyl group, a butyloxymethyl group, an isobutyloxymethyl group, a sec-butyloxymethyl group, a pentyloxymethyl group, a 1-methoxyethyl group, a 2-methoxyethyl group, an 2-ethoxyethyl group, a 2-propyloxyethyl group, an 2-isopropyloxyethyl group, a 2-butyloxyethyl group, a 3-methoxypropyl group, an 3-ethoxypropyl group, a 3-propyloxypropyl group, a 3-methoxybutyl group, an 3-ethoxybutyl group, a 4-methoxybutyl group, an 4-ethoxybutyl group, and a 5-methoxypentyl group.

The term "C3-C6 cycloalkyl group" includes, for example, a cyclopropyl group, a cyclobutyl group, a cyclopentyl group, and a cyclohexyl group.

The term "C3-C6 halocycloalkyl group" represents a group wherein at least one hydrogen atom of the C3-C6 cycloalkyl group is substituted with a halogen atom, and includes, for example, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 2-chlorocyclopentyl group, a 2-chlorocyclohexyl group, a 4,4-difluorocyclohexyl group, and a 4-chlorocyclohexyl group. The halogen atom that can be substituted for a hydrogen atom includes a fluorine atom, a chlorine atom, a bromine atom and an iodine atom.

The term "C1-C6 alkoxy group" represents a straight or branched alkoxy group, and includes, for example, a methoxy group, an ethoxy group, a propyloxy group, an isopropyloxy group, a butyloxy group, an isobutyloxy group, a sec-butyloxy group, a tert-butyloxy group, a pentyloxy group, an isoamyloxy group, a neopentyloxy group, a 2-pentyloxy group, a 3-pentyloxy group, a 2-methylbutyloxy group, a hexyloxy group, an isohexyloxy group, a 3-methylpentyloxy group, and a 4-methylpentyloxy group.

The term "C1-C6 haloalkoxy group" represents a group wherein at least one hydrogen atom of the straight or branched an C1-C6 alkoxy group is substituted with a halogen atom, and includes, for example, a trifluoromethoxy group, a bromodifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 3,3,3-trifluoropropoxy group, a nonafluorobutoxy group, a nonachlorobutoxy group, a nonabromobutoxy group, a nonaiodobutoxy group, a perfluoropentyloxy group, a perchloropentyloxy group, a perbromopentyloxy group, a perfluorohexyloxy group, a perchlorohexyloxy group, a perbromohexyloxy group, and a periodohexyloxy group. The halogen atom that can be substituted for a hydrogen atom includes a fluorine atom, a chlorine atom, a bromine atom and an iodine atom.

The term "C1-C6 alkylthio group" represents a straight or branched alkylthio group, and includes, for example, a methylthio group, an ethylthio group, propylthio group, an isopropylthio group, a butylthio group, an isobutylthio group, a sec-butylthio group, a tert-butylthio group, a pentylthio group, an isopentylthio group, a neopentylthio group, an isoamylthio group, a 2-pentylthio group, a 3-pentylthio group, a 2-methylbutylthio group, a hexylthio group, an isohexylthio group, a sec-hexylthio group, a 3-methylpentylthio group, and a 4-methylpentylthio group.

The term "C1-C6 haloalkylthio group" represents a group wherein at least one hydrogen atom of the straight or branched C1-C6 alkylthio group is substituted with a halogen atom, and includes, for example, a monofluoromethylthio group, a bromodifluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-trifluoroethylthio group, a 2,2,2-tribromoethylthio group, a 2,2,2-triiodoethylthio group, a 2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2,2-difluoropropylthio group, a 3,3,3-trifluoropropylthio group, a nonafluorobutylthio group, a nonachlorobutylthio group, a nonabromobutylthio group, a nonaiodobutylthio group, a perfluoropentylthio group, a perchloropentylthio group, a perbromopentylthio group, a perfluorohexylthio group, a perchlorohexylthio group, a perbromohexylthio group, and a periodohexylthio group. The halogen atom that can be substituted for a hydrogen atom includes a fluorine atom, a chlorine atom, a bromine atom and an iodine atom.

The term "C3-C6 cycloalkyloxy group" includes, for example, a cyclopropyloxy group, a cyclobutyloxy group, a cyclopentyloxy group, and a cyclohexyloxy group.

The term "C3-C6 halocycloalkyloxy group" represents a group wherein at least one hydrogen atom of the C3-C6 cycloalkyloxy group is substituted with a halogen atom, and includes, for example, a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 2,2-difluorol-methylcyclopropyloxy group, a 2,2-dichlorol-methylcyclopropyloxy group, a 2,2-dibromol-methylcyclopropyloxy group, a 1-(trifluoromethyl)cyclopropyloxy group, a 2,2,3,3-tetrafluorocyclobutyloxy group, a 2-chlorocyclohexyloxy group, a 4,4-difluorocyclohexyloxy group, and a 4-chlorocyclohexyloxy group. The halogen atom that can be substituted includes a fluorine atom, a chlorine atom, a bromine atom and an iodine atom.

The term "C3-C6 cycloalkylthio group" includes, for example, a cyclopropylthio group, a cyclobutylthio group, a cyclopentylthio group, and a cyclohexylthio group.

The term "C2-C6 alkenyloxy group" represents a straight or branched alkenyloxy group, and includes, for example, a vinyloxy group, a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-3-butenyloxy group, a 1-vinyl-2-propenyloxy group, and a 5-hexenyloxy group.

The term "C2-C6 haloalkenyloxy group" represents a group wherein at least one hydrogen atom of the straight or branched C2-C6 alkenyloxy group is substituted with a halogen atom, and includes, for example, a 1-fluorovinyloxy group, a 2-fluorovinyloxy group, a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, a 2,3,3-trichloro-2-propenyloxy group, a 3,3-dichloro-2-propenyloxy group, a 3,3-dibromo-2-propenyloxy group, a 3-fluoro-3-chloro-2-propenyloxy group, a 4-bromo-3-chloro-3,4,4-trifluoro-1-butenyloxy group, a 1-bromomethyl-2-propenyloxy group, a 3-chloro-2-butenyloxy group, a 4,4,4-trifluoro-2-butenyloxy group, a 4-bromo-4,4-difluoro-2-butenyloxy group, a 3-bromo-3-butenyloxy group, a 3,4,4-trifluoro-3-butenyloxy group, a 3,4,4-tribromo-3-butenyloxy group, a 3-bromo-2-methyl-2-propenyloxy group, a 3,3-difluoro-2-methyl-2-propenyloxy group, a 3-chloro-4,4,4-trifluoro-2-butenyloxy group, a perfluoro-3-butenyloxy group, a 4,4-difluoro-3-methyl-3-butenyloxy group, a 5,5-difluoro-4-pentenyloxy group, a 4,5,5-trifluoro-4-pentenyloxy group, a 4,4,4-trifluoro-3-methyl-2-butenyloxy group, a 3,5,5-trifluoro-2,4-pentadienyloxy group, a perfluoro-4-pentenyloxy group, a 4,4,5,5,6,6,6-heptafluoro-2-hexenyloxy group, a 4,5,5,5-tetrafluoro-4-trifluoromethyl-2-pentenyloxy group, a 5-bromo-4,5,5-trifluoro-4-trifluoromethyl-2-pentenyloxy group, and a perfluoro-5-hexenyloxy group. The halogen atom that can be substituted for a hydrogen atom includes a fluorine atom, a chlorine atom, a bromine atom and an iodine atom.

The term "C2-C6 alkynyloxy group" represents a straight or branched alkynyloxy group, and includes, for example, an ethynyloxy group, a propargyloxy group, a 1-butyne-3-yloxy group, a 2-butynyloxy group, a 3-butynyloxy group, a 3-methyl-1-butyne-3-yloxy group, a 2-pentynyloxy group, a 3-pentynyloxy group, a 4-pentynyloxy group, and a 5-hexynyloxy group.

The term "C2-C6 haloalkynyloxy group" represents a group wherein at least one hydrogen atom of the straight or branched C2-C6 alkynyloxy group is substituted with a halogen atom, and includes, for example, a bromoethynyloxy group, a 3-chloro-2-propynyloxy group, a 3-bromo-2-propynyloxy group, an 3-iodo-2-propynyloxy group, a 5-chloro-4-pentynyloxy group, a 3,3,3-trifluoro-1-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group. The halogen atom that can be substituted for a hydrogen atom includes a fluorine atom, a chlorine atom, a bromine atom and an iodine atom.

The term "C2-C6 alkenylthio group" represents a straight or branched alkenylthio group, and includes, for example, a vinylthio group, a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, and a 5-hexenylthio group.

The term "C2-C6 haloalkenylthio group" represents a group wherein at least one hydrogen atom of the straight or branched C2-C6 alkenylthio group is substituted with a halogen atom, and includes, for example, a 1-fluorovinylthio group, a 2-fluorovinylthio group, a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, a 3,3-dichloro-2-propenylthio group, a 3,3-dibromo- 2-propenylthio group, a 3-fluoro-3-chloro-2-propenylthio group, a 4-bromo-3-chloro-3,4,4-trifluoro-1-butenylthio group, a 1-bromomethyl-2-propenylthio group, a 3-chloro-2-butenylthio group, a 4,4,4-trifluoro-2-butenylthio group, a 4-bromo-4,4-difluoro-2-butenylthio group, a 3-bromo-3-butenylthio group, a 3,4,4-trifluoro-3-butenylthio group, a 3,4,4-tribromo-3-butenylthio group, a 3-bromo-2-methyl-2-propenylthio group, a 3,3-difluoro-2-methyl-2-propenylthio group, a 3-chloro-4,4,4-trifluoro-2-butenylthio group, a perfluoro-3-butenylthio group, a 4,4-difluoro-3-methyl-3-butenylthio group, a 5,5-difluoro-4-pentenylthio group, a 4,5,5-trifluoro-4-pentenylthio group, a 4,4,4-trifluoro-3-methyl-2-butenylthio group, a 3,5,5-trifluoro-2,4-pentadienylthio group, a perfluoro-4-pentenylthio group, a 4,4,5,5,6,6,6-heptafluoro-2-hexenylthio group, a 4,5,5,5-tetrafluoro-4-trifluoromethyl-2-pentenylthio group, a 5-bromo-4,5,5-trifluoro-4-trifluoromethyl-2-pentenylthio group, and a perfluoro-5-hexenylthio group. The halogen atom that can be substituted for a hydrogen atom includes a fluorine atom, a chlorine atom, a bromine atom and an iodine atom.

The term "C2-C6 alkynylthio group" represents a straight or branched alkynylthio group, and includes, for example, an ethynylthio group, a propargylthio group, a 1-butyne-3-ylthio group, a 2-butynylthio group, a 3-butynylthio group, a 3-methyl-1-butyne-3-ylthio group, a 2-pentynylthio group, a 3-pentynylthio group, a 4-pentynylthio group, and a 5-hexynylthio group.

The term "C2-C6 haloalkynylthio group" represents a group wherein at least one hydrogen atom of the straight or branched C2-C6 alkynylthio group is substituted with a halogen atom, and includes, for example, a bromoethynylthio group, a 3-chloro-2-propynylthio group, a 3-bromo-2-propynylthio group, an 3-iodo-2-propynylthio group, a 5-chloro-4-pentynylthio group, a 3,3,3-trifluoro-1-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, and a perfluoro-5-hexynylthio group. The halogen atom that can be substituted for a hydrogen atom includes a fluorine atom, a chlorine atom, a bromine atom and an iodine atom.

The term "amino group optionally substituted by an C1-C6 alkyl group" represents a group wherein one or two hydrogen atom of the amino group is substituted with a straight or branched C1-C6 alkyl group and the C1-C6 alkyl group may be same or different, and the total number of carbon atoms of the alkyl substituent(s) ranges from 1 to 6. The amino group includes, for example, an amino group, a N-methylamino group, a N,N-dimethylamino group, an N-ethylamino group, an N-ethyl-N-methylamino group, a N,N-diethylamino group, a N-propylamino group, an N-isopropylamino group, a N-propyl-N-methylamino group, a N,N-dipropylamino group, a N,N-diisopropylamino group, a N-butylamino group, a N-butyl-N-methylamino group, a N,N-dibutylamino group, a N-pentylamino group, a N-pentyl-N-methylamino group, a N-hexylamino group, and a N-hexyl-N-methylamino group.

The term "C2-C6 acyl group" represents a straight or branched aliphatic acyl group, and the total number of carbon atoms of the C2-C6 acyl group including the carbonyl group ranges from 2 to 6. The C2-C6 acyl group includes, for example, an acetyl group, a propionyl group, a butanoyl group, a pentanoyl group, and a hexanoyl group.

The term "C2-C6 haloacyl group" represents a group wherein at least one hydrogen of the straight or branched C2-C6 aliphatic acyl group is substituted with a halogen atom, and the total number of carbon atoms of the C2-C6 haloacyl group including the carbonyl group ranges from 2 to 6. The C2-C6 haloacyl group includes, for example, a trichloroacetyl group, a fluoroacetyl group, a difluoroacetyl group, a trifluoroacetyl group, a pentafluoropropionyl group, a pentachloropropionyl group, a pentabromopropionyl group, a pentaiodopropionyl group, a 3,3,3-trichloropropionyl group, a 3,3,3-trifluoropropionyl group, a 3,3,3-tribromopropionyl group, a 3,3,3-triiodopropionyl group, a heptafluorobutanoyl group, a heptachlorobutanoyl group, a heptabromobutanoyl group, a heptaiodobutanoyl group, a 4,4,4-trifluorobutanoyl group, a 4,4,4-trichlorobutanoyl group, a 4,4,4-tribromobutanoyl group, a 4,4,4-triiodobutanoyl group, a nonafluoropentanoyl group, a nonachloropentanoyl group, a nonabromopentanoyl group, a nonaiodopentanoyl group, and a perfluorohexanoyl group. The halogen atom that can be substituted for a hydrogen atom includes a fluorine atom, a chlorine atom, a bromine atom and an iodine atom.

The term "C2-C6 acyloxy group" represents a straight or branched aliphatic acyloxy group, and the total number of carbon atoms of the C2-C6 acyloxy group including the carbonyl group ranges from 2 to 6. The C2-C6 acyloxy group includes, for example, an acetoxy group, a propionyloxy group, a butanoyloxy group, a pentanoyloxy group, and a hexanoyloxy group.

The term "C2-C6 acylthio group" represents a straight or branched aliphatic acylthio group, and the total number of carbon atoms of the C2-C6 acylthio group including the carbonyl group ranges from 2 to 6. The C2-C6 acylthio group includes, for example, an acetylthio group, a propionylthio group, a butanoylthio group, a pentanoylthio group, and a hexanoylthio group.

The term "C1-C6 alkylsulfonyl group" represents a straight or branched alkylsulfonyl group, and includes, for example, a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, an isopentylsulfonyl group, a neopentylsulfonyl group, an isoamylsulfonyl group, a 2-pentylsulfonyl group, a 3-pentylsulfonyl group, a 2-methylbutylsulfonyl group, a hexylsulfonyl group, an isohexylsulfonyl group, a sec-hexylsulfonyl group, a 3-methylpentylsulfonyl group, and a 4-methylpentylsulfonyl group.

The term "C1-C6 haloalkylsulfonyl group" represents a group wherein at least one hydrogen atom of the straight or branched C1-C6 alkylsulfonyl group is substituted with a halogen atom, and includes, for example, a monofluoromethylsulfonyl group, a bromodifluoromethyl sulfonyl group, a difluoromethylsulfonyl group, a trifluoromethylsulfonyl group, a trichloromethylsulfonyl group, a tribromomethylsulfonyl group, a triiodomethylsulfonyl group, a chlorofluoromethylsulfonyl group, a pentafluoroethylsulfonyl group, a pentachlorooethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-trifluoroethylsulfonyl group, a 2,2,2-tribromoethylsulfonyl group, a 2,2,2-triiodoethylsulfonyl group, a 2,2-difluoroethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a 2,2-difluoropropylsulfonyl group, a 3,3,3-trifluoropropylsulfonyl group, a nonafluorobutylsulfonyl group, a nonachlorobutylsulfonyl group, a nonabromobutylsulfonyl group, a nonaiodobutylsulfonyl group, a perfluoropentylsulfonyl group, a perchloropentylsulfonyl group, a perbromopentylsulfonyl group, a perfluorohexylsulfonyl group, a perchlorohexylsulfonyl group, a perbromohexylsulfonyl group, and an periodohexylsulfonyl group. The halogen atom that can be substituted for a hydrogen atom includes a fluorine atom, a chlorine atom, a bromine atom and an iodine atom.

The term "C1-C6 alkylsulfinyl group" represents a straight or branched alkylsulfinyl group, and includes, for example, a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a pentylsulfinyl group, an isopentylsulfinyl group, a neopentylsulfinyl group, an isoamylsulfinyl group, a 2-pentylsulfinyl group, a 3-pentylsulfinyl group, a 2-methylbutylsulfinyl group, a hexylsulfinyl group, an isohexylsulfinyl group, a sec-hexylsulfinyl group, a 3-methylpentylsulfinyl group, and a 4-methylpentylsulfinyl group.

The term "C1-C6 haloalkylsulfinyl group" represents a group wherein at least one hydrogen atom of the straight or branched C1-C6 alkylsulfinyl group is substituted with a halogen atom, and includes, for example, a monofluoromethylsulfinyl group, a bromodifluoromethyl sulfinyl group, a difluoromethylsulfinyl group, a trifluoromethylsulfinyl group, a trichloromethylsulfinyl group, a tribromomethylsulfinyl group, a triiodomethylsulfinyl group, a chlorofluoromethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-trifluoroethylsulfinyl group, a 2,2,2-tribromoethylsulfinyl group, a 2,2,2-triiodoethylsulfinyl group, a 2,2-difluoroethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, a 2,2-difluoropropylsulfinyl group, a 3,3,3-trifluoropropylsulfinyl group, a nonafluorobutylsulfinyl group, a nonachlorobutylsulfinyl group, a nonabromobutylsulfinyl group, a nonaiodobutylsulfinyl group, a perfluoropentylsulfinyl group, a perchloropentylsulfinyl group, a perbromopentylsulfinyl group, a perfluorohexylsulfinyl group, a perchlorohexylsulfinyl group, a perbromohexylsulfinyl group, and a periodohexylsulfinyl group. The halogen atom that can be substituted for a hydrogen atom includes a fluorine atom, a chlorine atom, a bromine atom and an iodine atom.

The term "C2-C5 polyoxaalkyloxyl group" represents a group wherein one methylene group of the straight C3 alkoxy group is replaced with an oxygen atom, or a group wherein one or two methylene group of the straight C4 alkoxy group is replaced with an oxygen atom, or a group wherein one, two or three methylene group of the straight C5-C12 alkoxy group is replaced with an oxygen atom, and the oxygen atoms do not adjoin each other. The C2-C5 polyoxaalkyloxy group includes, for example, a $CH_3$—O—$CH_2$—O group, a $CH_3$—$CH_2$—O—$CH_2$—O group, a $CH_3$—O—$(CH_2)_2$—O group, a $CH_3$—$CH_2$—O—$(CH_2)_2$—O group, a $CH_3$—O—$(CH_2)_2$—O—$CH_2$—O group, a $CH_3$—O—$(CH_2)_3$—O group, a $CH_3CH_2$—O—$(CH_2)_2$—O group, a $CH_3$—$(CH_2)_2$—O—$(CH_2)_2$—O group, a $CH_3$—$(CH_2)_2$—O—$CH_2$—O group, a $CH_3$—$(CH_2)_3$—O—$CH_2$—O group, a $CH_3$—O—$(CH_2)_2$—O—$(CH_2)_2$—O group, a $CH_3$—O—$(CH_2)_2$—O—$CH_2$—O group, and a $CH_3$—O—$(CH_2)_4$—O group.

The term "C1-C4 alkyl group" represents a straight or branched alkyl group, and includes, for example, a methyl group, an ethyl group, a propyl group, an isopropyl group, a butyl group, an isobutyl group, a sec-butyl group, and a tert-butyl group.

The term "C1-C4 haloalkyl group" represents a group wherein at least one hydrogen atom of the straight or branched C1-C4 alkyl group is substituted with a halogen atom, and includes, for example, a monofluoromethyl group, a monochloromethyl group, a dichloromethyl group, a difluoromethyl group, a trifluoromethyl group, a trichloromethyl group, a tribromomethyl group, a chlorofluoromethyl group, a dichlorofluoromethyl group, a 2,2,2-trifluoroethyl group, a 2,2,2-trichloroethyl group, a pentafluoroethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, 2-(fluoromethyl)-3-fluoroethyl group, and a 4-fluorobutyl. The halogen atom that can be substituted for a hydrogen atom includes a fluorine atom, a chlorine atom, a bromine atom and an iodine atom.

The term "C2-C4 alkenyl group" represents a straight or branched alkenyl, and includes, for example, a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, and a 1,3-butadienyl group.

The term "C2-C4 haloalkenyl group" represents a group wherein at least one hydrogen atom of the straight or branched C2-C4 alkenyl group is substituted with a halogen atom, and includes, for example, a 2-chlorovinyl group, a 2-bromovinyl group, an 2-iodovinyl group, a 3-chloro-2-propenyl group, a 3-bromo-2-propenyl group, a 1-chloro methylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 3,3-dichloro-2-propenyl group, a 3,3-dibromo-2-propenyl group, a 3-fluoro-3-chloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, a 3,4,4-trifluoro-1,3-butadienyl group, a perfluoro-1-butenyl group, and a perfluoro-3-butenyl group. The halogen atom that can be substituted for a hydrogen atom includes a fluorine atom, a chlorine atom, a bromine atom and an iodine atom.

The term "C2-C4 alkynyl group" represents a straight or branched alkynyl group, and includes, for example, an ethynyl group, a propargyl group, a 1-butyne-3-yl group, a 2-butynyl group, and a 3-butynyl group.

The term "C2-C4 haloalkynyl group" represents a group wherein at least one hydrogen atom of the straight or branched C2-C4 alkynyl group is substituted with a halogen atom, and includes, for example, a fluoroethynyl, group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3,3,3-trifluoro-1-propynyl group, a perfluoro-2-butynyl group, and a perfluoro-3-butynyl group. The halogen atom that can be substituted for a hydrogen atom includes a fluorine atom, a chlorine atom, a bromine atom and an iodine atom.

The term "C3-C4 cycloalkyl group" includes, for example, a cyclopropyl group, and a cyclobutyl group.

The term "C3-C4 halocycloalkyl group" represents a group wherein at least one hydrogen atom of the C3-C4 cycloalkyl group is substituted with a halogen atom, and includes, for example, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, and a 2,2,3,3-tetrafluorocyclobutyl group. The halogen atom that can be substituted for a hydrogen atom includes a fluorine atom, a chlorine atom, a bromine atom and an iodine atom.

The term "C1-C4 alkoxy group" represents a straight or branched alkoxy group, and includes, for example, a methoxy group, an ethoxy group, a propyloxy group, an isopropyloxy group, a butyloxy group, an isobutyloxy group, a sec-butyloxy group, and a tert-butyloxy group.

The term "C1-C4 haloalkoxy group" represents a group wherein at least one hydrogen atom of the straight or branched C1-C4 alkoxy group is substituted with a halogen atom, and includes, for example, a trifluoromethoxy group, a bromodifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 3,3,3-trifluoropropoxy group, a nonafluorobutoxy group, a nonachlorobutoxy group, a nonabromobutoxy group, and a nonaiodobutoxy group. The halogen atom that can be substituted for a hydrogen atom includes a fluorine atom, a chlorine atom, a bromine atom and an iodine atom.

The term "C1-C4 alkylthio group" represents a straight or branched alkylthio group, and includes, for example, a methylthio group, an ethylthio group, a propylthio group, an isopropylthio group, a butylthio group, an isobutylthio group, a sec-butylthio group, and a tert-butylthio group.

The term "C1-C4 haloalkylthio group" represents a group wherein at least one hydrogen atom of the straight or branched C1-C4 alkylthio group is substituted with a halogen atom, and includes, for example, a monofluoromethylthio group, a bromodifluoromethylthio group, a difluoromethylthio group, a trifluoromethylthio group, trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, a 2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2,2-difluoropropylthio group, a 3,3,3-trifluoropropylthio group, a nonafluorobutylthio group, a nonachlorobutylthio group, a nonabromobutylthio group, and a nonaiodobutylthio group. The halogen atom that can be substituted for a hydrogen atom includes a fluorine atom, a chlorine atom, a bromine atom and an iodine atom.

The term "C3-C4 cycloalkyloxy group" includes, for example, a cyclopropyloxy group, and a cyclobutyloxy group.

The term "C3-C4 halocycloalkyloxy group" represents a group wherein at least one hydrogen atom of the C3-C4 cycloalkyloxy group is substituted with a halogen atom, and includes, for example, a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 2,2-difluoro-1-methylcyclopropyloxy group, a 2,2-dichloro-1-methylcyclopropyloxy group, a 2,2-dibromo-1-methylcyclopropyloxy group, a 1-(a trifluoromethyl)cyclopropyloxy group, and a 2,2,3,3-tetrafluorocyclobutyloxy group. The halogen atom that can be substituted for a hydrogen atom includes a fluorine atom, a chlorine atom, a bromine atom and an iodine atom.

The term "C3-C4 cycloalkylthio group" includes, for example, a cyclopropylthio group, and a cyclobutylthio group.

The term "C2-C4 alkenyloxy group" represents a straight or branched alkenyloxy group, and includes, for example, a vinyloxy group, a 2-propenyloxy group, a 2-butenyloxy group, a 1-methyl-2-propenyloxy group, a 3-butenyloxy group, and a 2-methyl-2-propenyloxy group.

The term "C2-C4 haloalkenyloxy group" represents a group wherein at least one hydrogen atom of the straight or branched C2-C4 alkenyloxy group is substituted with a halogen atom, and includes, for example, a 1-fluorovinyloxy group, a 2-fluorovinyloxy group, a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, a 2,3,3-trichloro-2-propenyloxy group, a 3,3-dichloro-2-propenyloxy group, a 3,3-dibromo-2-propenyloxy group, a 3-fluoro-3-chloro-2-propenyloxy group, a 4-bromo-3-chloro-3,4,4-trifluoro-1-butenyloxy group, a 1-bromomethyl-2-propenyloxy group, a 3-chloro-2-butenyloxy group, a 4,4,4-trifluoro-2-butenyloxy group, a 4-bromo-4,4-difluoro-2-butenyloxy group, a 3-bromo-3-butenyloxy group, a 3,4,4-trifluoro-3-butenyloxy group, a 3,4,4-tribromo-3-butenyloxy group, a 3-bromo-2-methyl-2-propenyloxy group, a 3,3-difluoro-2-methyl-2-propenyloxy group, a 3-chloro-4,4,4-trifluoro-2-butenyloxy group, a perfluoro-3-butenyloxy group, and a 4,4-difluoro-3-methyl-3-butenyloxy group. The halogen atom that can be substituted for a hydrogen atom includes a fluorine atom, a chlorine atom, a bromine atom and an iodine atom.

The term "C2-C4 alkynyloxy group" represents a straight or branched alkynyloxy group, and includes, for example, an ethynyloxy group, a propargyloxy group, a 1-butyne-3-yloxy group, a 2-butynyloxy group, and a 3-butynyloxy group.

The term "C2-C4 haloalkynyloxy group" represents a group wherein at least one of hydrogen atom the straight or branched C2-C4 alkynyloxy group is substituted with a halogen atom, and includes, for example, a bromoethynyloxy group, a 3-chloro-2-propynyloxy group, a 3-bromo-2-propynyloxy group, a 3-iodo-2-propynyloxy group, a 3,3,3-trifluoro-1-propynyloxy group, a perfluoro-2-butynyloxy group, and a perfluoro-3-butynyloxy group. The halogen atom that can be substituted for a hydrogen atom includes a fluorine atom, a chlorine atom, a bromine atom and an iodine atom.

The term "C2-C4 alkenylthio group" represents a straight or branched alkenylthio group, and includes, for example, a vinylthio group, a 2-propenylthio group, a 2-butenylthio group, a 1-methyl-2-propenylthio group, a 3-butenylthio group, and a 2-methyl-2-propenylthio group.

The term "C2-C4 haloalkenylthio group" represents a group wherein at least one hydrogen atom of the straight or branched C2-C4 alkenylthio group is substituted with a halogen atom, and includes, for example, a 1-fluorovinylthio group, a 2-fluorovinylthio group, a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, a 3,3-dichloro-2-propenylthio group, a 3,3-dibromo-2-propenylthio group, a 3-fluoro-3-chloro-2-propenylthio group, a 4-bromo-3-chloro-3,4,4-trifluoro-1-butenylthio group, a 1-bromomethyl-2-propenylthio group, a 3-chloro-2-butenylthio group, a 4,4,4-trifluoro-2-butenylthio group, a 4-bromo-4,4-difluoro-2-butenylthio group, a 3-bromo-3-butenylthio group, a 3,4,4-trifluoro-3-butenylthio group, a 3,4,4-tribromo-3-butenylthio group, a 3-bromo-2-methyl-2-propenylthio group, a 3,3-difluoro-2-methyl-2-propenylthio group, a 3-chloro-4,4,4-trifluoro-2-butenylthio group, and a perfluoro-3-butenylthio group. The halogen atom that can be substituted for a hydrogen atom includes a fluorine atom, a chlorine atom, a bromine atom and an iodine atom.

The term "C2-C4 alkynylthio group" represents a straight or branched alkynylthio group, and includes, for example, an ethynylthio group, a propargylthio group, a 1-butyne-3-ylthio group, a 2-butynylthio group, and a 3-butynylthio group.

The term "C2-C4 haloalkynylthio group" represents a group wherein at least one hydrogen atom of the straight or branched C2-C4 alkynylthio group is substituted with a halogen atom, and includes, for example, a bromoethynylthio group, a 3-chloro-2-propynylthio group, a 3-bromo-2-propynylthio group, an 3-iodo-2-propynylthio group, a 3,3,3-trifluoro-1-propynylthio group, a perfluoro-2-butynylthio group, and a perfluoro-3-butynylthio group. The halogen atom that can be substituted for a hydrogen atom includes a fluorine atom, a chlorine atom, a bromine atom and an iodine atom.

The term "amino group optionally substituted with an C1-C4 alkyl group" represents a group wherein one or two hydrogen atom of the amino group is substituted with a straight or branched C1-C4 alkyl group and the C1-C4 alkyl group may be same or different from each other. The amino group includes, for example, an amino group, a N-methylamino group, a N,N-dimethylamino group, an N-ethylamino group, an N-ethyl-N-methylamino group, a N,N-diethylamino group, a N-propylamino group, an N-isopropylamino group, a N-propyl-N-methylamino group, a N,N-dipropylamino group, a N,N-diisopropylamino group, a N-butylamino group, a N-butyl-N-methylamino group, and a N,N-dibutylamino group.

The term "C2-C4 acyl group" represents a straight or branched aliphatic acyl group, and includes, for example, an acetyl group, a propionyl group, and a butanoyl group.

The term "C2-C4 haloacyl group" represents a group wherein at least one hydrogen atom of the straight or branched aliphatic C2-C4 acyl group is substituted with a halogen atom, and includes, for example, a trichloroacetyl group, a fluoroacetyl group, a difluoroacetyl group, a trifluoroacetyl group, a pentafluoropropionyl group, a pentachloropropionyl group, a pentabromopropionyl group, a pentaiodopropionyl group, a 3,3,3-trichloropropionyl group, a 3,3,3-trifluoropropionyl group, a 3,3,3-tribromopropionyl group, a 3,3,3-triiodopropionyl group, a heptafluorobutanoyl group, a heptachlorobutanoyl group, a heptabromobutanoyl group, a heptaiodobutanoyl group, a 4,4,4-trifluorobutanoyl group, a 4,4,4-trichlorobutanoyl group, a 4,4,4-tribromobutanoyl group, and a 4,4,4-triiodobutanoyl group. The halogen atom that can be substituted for a hydrogen atom includes a fluorine atom, a chlorine atom, a bromine atom and an iodine atom.

The term "C2-C4 acyloxy group" represents a straight or branched aliphatic acyloxy group, and includes, for example, an acetoxy group, a propionyloxy group, and a butanoyloxy group.

The term "C2-C4 acylthio group" represents a straight or branched aliphatic acylthio group, and includes, for example, an acetylthio group, a propionylthio group, and a butanoylthio group.

The term "C2-C4 alkoxycarbonyl group" may be either straight or branched and the total number of carbon atoms of the alkoxy moiety and the carbonyl group is two to four, and includes, for example, a methoxycarbonyl group, an ethoxycarbonyl group, a propyloxycarbonyl group, and an isopropyloxycarbonyl group.

The term "C1-C4 alkylsulfonyl group" represents a straight or branched alkylsulfonyl group, and includes, for example, a methylsulfonyl group, an ethylsulfonyl group, a propylsulfonyl group, an isopropylsulfonyl group, butylsulfonyl group, an isobutylsulfonyl group, a sec-butylsulfonyl group, and a tert-butylsulfonyl group.

The term "C1-C4 haloalkylsulfonyl group" represents a group wherein at least one hydrogen atom of the straight or branched C1-C4 alkylsulfonyl group is substituted with a halogen atom, and includes, for example, a monofluoromethylsulfonyl group, a bromodifluoromethylsulfonyl group, a difluoromethylsulfonyl group, a trifluoromethylsulfonyl group, a trichloromethylsulfonyl group, a tribromomethylsulfonyl group, a triiodomethylsulfonyl group, a chlorofluoromethylsulfonyl group, a pentafluoroethylsulfonyl group, a pentachlorooethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-trifluoroethylsulfonyl group, a 2,2,2-tribromoethylsulfonyl group, a 2,2,2-triiodoethylsulfonyl group, a 2,2-difluoroethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a 2,2-difluoropropylsulfonyl group, a 3,3,3-trifluoropropylsulfonyl group, a nonafluorobutylsulfonyl group, a nonachlorobutylsulfonyl group, a nonabromobutylsulfonyl group, and a nonaiodobutylsulfonyl group. The halogen atom that can be substituted for a hydrogen atom includes a fluorine atom, a chlorine atom, a bromine atom and an iodine atom.

The term "C1-C4 alkylsulfinyl group" includes, for example, a methylsulfinyl group, an ethylsulfinyl group, a propylsulfinyl group, an isopropylsulfinyl group, a butylsulfinyl group, an isobutylsulfinyl group, a sec-butylsulfinyl group, and a tert-butylsulfinyl group.

The term "C1-C4 haloalkylsulfinyl group" represents a group wherein at least one hydrogen atom of the straight or branched C1-C4 alkylsulfinyl group is substituted with a halogen atom, and includes, for example, a monofluoromethylsulfinyl group, a bromodifluoromethylsulfinyl group, a difluoromethylsulfinyl group, a trifluoromethylsulfinyl group, a trichloromethylsulfinyl group, a tribromomethylsulfinyl group, a triiodomethylsulfinyl group, a chlorofluoromethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-trifluoroethylsulfinyl group, a 2,2,2-tribromoethylsulfinyl group, a 2,2,2-triiodoethylsulfinyl group, a 2,2-difluoroethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, a 2,2-difluoropropylsulfinyl group, a 3,3,3-trifluoropropylsulfinyl group, a nonafluorobutylsulfinyl group, a nonachlorobutylsulfinyl group, a nonabromobutylsulfinyl group, and a nonaiodobutylsulfinyl group. The halogen atom that can be substituted for a hydrogen atom includes a fluorine atom, a chlorine atom, a bromine atom and an iodine atom.

The term "C1-C3 alkyl group" represents a straight or branched alkyl group, and includes, for example, a methyl group, an ethyl group, a propyl group, and an isopropyl group.

The term "C1-C3 haloalkyl group" represents a group wherein at least one hydrogen atom of the straight or branched C1-C3 alkyl group is substituted with a halogen atom, and includes, for example, a monofluoromethyl group, a monochloromethyl group, a dichloromethyl group, a difluoromethyl group, a trifluoromethyl group, a trichloromethyl group, a tribromomethyl group, a chlorofluoromethyl group, a dichlorofluoromethyl group, a 2,2,2-trifluoroethyl group, a 2,2,2-trichloroethyl group, a pentafluoroethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group and a 3,3,3-trifluoropropyl group. The halogen atom that can be substituted for a hydrogen atom includes a fluorine atom, a chlorine atom, a bromine atom and an iodine atom.

The term "C2-C3 alkenyl group" represents a straight or branched alkenyl group, and includes, for example, a vinyl group, a 1-propenyl group, an isopropenyl group, and a 2-propenyl group.

The term "C2-C3 alkynyl group" represents a straight or branched alkynyl group, and includes, for example, an ethynyl group, and a propargyl group.

The term "C3-C4 cycloalkyl group" includes, for example, a cyclopropyl group, and a cyclobutyl group.

The term "C1-C3 alkoxy group" represents a straight or branched alkoxy group, and includes, for example, a methoxy group, an ethoxy group, a propyloxy group, and an isopropyloxy group.

The term "C1-C3 haloalkoxy group" represents a group wherein at least one hydrogen atom of the straight or branched C1-C3 alkoxy group is substituted with a halogen atom, and includes, for example, a trifluoromethoxy group, a bromodifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, and a 3,3,3-trifluoropropoxy group. The halogen atom that can be substituted for a hydrogen atom includes a fluorine atom, a chlorine atom, a bromine atom and an iodine atom.

The term "amino group optionally substituted with an C1-C3 alkyl group" represents a group wherein one, two or three hydrogen atom of the amino group is substituted with the straight or branched C1-C3 alkyl group and the C1-C3 alkyl group may be same or different from each other, and the total number of carbon atoms of the alkyl substituent(s) ranges from 1 to 3. The amino group includes, for example, an amino group, a N-methylamino group, a N,N-dimethylamino group, an N-ethylamino group, an N-ethyl-N-methylamino group, a N-propylamino group and an N-isopropylamino group.

The term "aminocarbonyl group optionally substituted with an C1-C3 alkyl group" represents a group wherein one or two hydrogen atom of the aminocarbonyl group is substituted with the straight or branched C1-C3 alkyl group and the C1-C3 alkyl group may be same or different from each other, and the total number of carbon atoms of the aminocarbony group including the carbonyl group ranges from 1 to 3. The aminocarbonyl group includes, for example, an aminocarbonyl group, a N-methylaminocarbonyl group, a N,N-dimethylaminocarbonyl group and an N-ethylaminocarbonyl group.

The term "aminosulfonyl group optionally substituted with an C1-C3 alkyl group" represents a group wherein one or two hydrogen atom(s) of the aminosulfonyl group is substituted with the straight or branched C1-C3 alkyl group, and the C1-C3 alkyl group may be same or different from each other, and the total number of carbon atoms of the alkyl substituent(s) ranges from 1 to 3. The aminosulfonyl group includes, for example, an aminosulfonyl group, a N-methylaminosulfonyl group, a N,N-dimethylaminosulfonyl group, an N-ethylaminosulfonyl group, an N-ethyl N-methylaminosulfonyl group, a N-propylaminosulfonyl group and an N-isopropylaminosulfonyl group.

The term "C2-C6 alkoxycarbonyl group" may be either straight or branched and the total number of carbon atoms of the alkoxy moiety and the carbonyl group is two to six, and includes, for example, a methoxycarbonyl group; an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutyloxycarbonyl group.

The term "halomethyl group" includes, for example, a chloromethyl group, a dichloromethyl group, a trichloromethyl group, a bromomethyl group, a dibromomethyl group, a tribromomethyl group, an iodomethyl group, a diiodomethyl group, and a triiodomethyl group.

The term "aminocarbonyl group optionally substituted with a chlorine atom, a bromine atom, or a hydroxyl group" represents a group wherein one or two hydrogen atom(s) of the aminocarbonyl group is substituted with a chlorine atom, a bromine atom, or a hydroxyl group, and includes, for example, an aminocarbonyl group, a N-chloroaminocarbonyl group, a N-bromoaminocarbonyl group, a N,N-dicholoroaminocarbonyl group, a N,N-dibromoaminocarbonyl group, a N-chloro-N-bromoaminocarbanyl group and a N-hydroxyaminocarbonyl group.

Examples of an embodiment of the present compound include the compounds of the formula (1) wherein the substituent represents the following ones.

a compound wherein $R^1$ represents a haloaryl group;
a compound wherein $R^1$ represents an aryl group substituted with an C1-C3 alkyl group;
a compound wherein $R^1$ represents an aryl group substituted with an C1-C3 alkoxy group;
a compound wherein $R^1$ represents an aryl group substituted with a C1-C3 haloalkoxy group;
a compound wherein $R^1$ represents a 4-chlorophenyl group;
a compound wherein $R^1$ represents a 4-fluorophenyl group;
a compound wherein $R^1$ represents a 4-bromophenyl group;
a compound wherein $R^1$ represents a 4-methoxyphenyl group;
a compound wherein $R^1$ represents a 4-methylphenyl group;
a compound wherein $R^1$ represents a 4-trifluoromethoxyphenyl group;
a compound wherein $R^1$ represents a 4-methylthiophenyl group;
a compound wherein $R^1$ represents a tert-butyl group;
a compound wherein $R^1$ represents an adamantyl group;
a compound wherein X represents a sulfur atom;
a compound wherein X represents an oxygen atom;
a compound wherein $R^2$ represents a halogen atom;
a compound wherein $R^4$ represents a halogen atom;
a compound wherein $R^5$ represents a halogen atom;
a compound wherein $R^6$ represents a halogen atom;
a compound wherein $R^6$ represents a methyl group;
a compound wherein $R^6$ represents an ethyl group;
a compound wherein $R^6$ represents a propyl group;
a compound wherein $R^6$ represents a cyclopropyl group;
a compound wherein $R^6$ represents a trifluoromethyl group;
a compound wherein $R^6$ represents a difluoromethyl group;
a compound wherein $R^6$ represents a 2-propenyl group;
a compound wherein $R^6$ represents a chlorine atom;
a compound wherein $R^6$ represents a bromine atom;
a compound wherein $R^6$ represents a fluorine atom;
a compound wherein $R^6$ represents a vinyl group;
a compound wherein $R^6$ represents a methoxy group;
a compound wherein $R^6$ represents a methoxy group;
a compound wherein $R^6$ represents an C1-C4 alkyl group;
a compound wherein $R^6$ represents a halogen atom;
a compound wherein $R^6$ represents a C1-C4 haloalkyl group;
a compound wherein $R^6$ represents a C3-C4 cycloalkyl group;
a compound wherein $R^6$ represents a C3-C4 halocycloalkyl group;
a compound wherein $R^6$ represents an C1-C4 alkoxy group;
a compound wherein $R^6$ represents a C1-C4 haloalkoxy group;
a compound wherein $R^6$ represents an C1-C4 alkylthio group;
a compound wherein $R^6$ represents a C1-C4 haloalkylthio group;
a compound wherein $R^7$ represents a hydrogen atom;
a compound wherein $R^8$ represents a hydrogen atom;
a compound wherein $R^9$ represents a hydrogen atom;
a compound wherein $R^{10}$ represents a methyl group;
a compound wherein Y represents an oxygen atom;
a compound wherein Q represents an oxygen atom;
a compound wherein $R^1$ represents a haloaryl group, and $R^6$ represents an C1-C4 alkyl group;
a compound wherein $R^1$ represents a haloaryl group, and $R^6$ represents a halogen atom;
a compound wherein $R^1$ represents a haloaryl group, and represents a C1-C4 haloalkyl group;
a compound wherein $R^1$ represents a haloaryl group, and represents a C3-C4 cycloalkyl group;
a compound wherein $R^1$ represents a haloaryl group, and $R^6$ represents a C3-C4 halocycloalkyl group;
a compound wherein $R^1$ represents a haloaryl group, and $R^6$ represents an C1-C4 alkoxy group;
a compound wherein $R^1$ represents a haloaryl group, and $R^6$ represents a C1-C4 haloalkoxy group;
a compound wherein $R^1$ represents a haloaryl group, and $R^6$ represents an C1-C4 alkylthio group;
a compound wherein $R^1$ represents a haloaryl group, and $R^6$ represents a C1-C4 haloalkylthio group;
a compound wherein $R^1$ represents a haloaryl group, and $R^6$ represents a halogen atom;
a compound wherein $R^1$ represents a haloaryl group, and $R^6$ represents a methyl group;
a compound wherein $R^1$ represents a haloaryl group, and $R^6$ represents an ethyl group;
a compound wherein $R^1$ represents a haloaryl group, and $R^6$ represents a propyl group;
a compound wherein $R^1$ represents a haloaryl group, and $R^6$ represents a cyclopropyl group;
a compound wherein $R^1$ represents a haloaryl group, and $R^6$ represents a trifluoromethyl group;
a compound wherein $R^1$ represents a haloaryl group, and $R^6$ represents a difluoromethyl group;
a compound wherein $R^1$ represents a haloaryl group, and $R^6$ represents a 2-propenyl group;
a compound wherein $R^1$ represents a haloaryl group, and $R^6$ represents a chlorine atom;
a compound wherein $R^1$ represents a haloaryl group, and $R^6$ represents a bromine atom;
a compound wherein $R^1$ represents a haloaryl group, and $R^6$ represents a fluorine atom;
a compound wherein $R^1$ represents a haloaryl group, and $R^6$ represents a vinyl group;
a compound wherein $R^1$ represents a haloaryl group, and $R^6$ represents a methoxy group;
a compound wherein $R^1$ represents an aryl group optionally substituted with an C1-C3 alkyl group, and $R^6$ represents an C1-C4 alkyl group;
a compound wherein $R^1$ represents an aryl group optionally substituted with an C1-C3 alkyl group, and $R^6$ represents a halogen atom;
a compound wherein $R^1$ represents an aryl group optionally substituted with an C1-C3 alkyl group, and $R^6$ represents a C1-C4 haloalkyl group;
a compound wherein $R^1$ represents an aryl group optionally substituted with an C1-C3 alkyl group, and $R^6$ represents a C3-C4 cycloalkyl group;
a compound wherein $R^1$ represents an aryl group optionally substituted with an C1-C3 alkyl group, and $R^6$ represents a C3-C4 halocycloalkyl group;
a compound wherein $R^1$ represents an aryl group optionally substituted with an C1-C3 alkyl group, and $R^6$ represents an C1-C4 alkoxy group;

a compound wherein $R^1$ represents an aryl group optionally substituted with an C1-C3 alkyl group, and $R^6$ represents a C1-C4 haloalkoxy group;

a compound wherein $R^1$ represents an aryl group optionally substituted with an C1-C3 alkyl group, and $R^6$ represents an C1-C4 alkylthio group;

a compound wherein $R^1$ represents an aryl group optionally substituted with an C1-C3 alkyl group, and $R^6$ represents a C1-C4 haloalkylthio group;

a compound wherein $R^1$ represents an aryl group optionally substituted with an C1-C3 alkyl group, and $R^6$ represents a hydrogen atom;

a compound wherein $R^1$ represents an aryl group optionally substituted with an C1-C3 alkyl group, and $R^6$ represents a methyl group;

a compound wherein $R^1$ represents an aryl group optionally substituted with an C1-C3 alkyl group, and $R^6$ represents an ethyl group;

a compound wherein $R^1$ represents an aryl group optionally substituted with an C1-C3 alkyl group, and $R^6$ represents a propyl group;

a compound wherein $R^1$ represents an aryl group optionally substituted with an C1-C3 alkyl group, and $R^6$ represents a cyclopropyl group;

a compound wherein $R^1$ represents an aryl group optionally substituted with an C1-C3 alkyl group, and $R^6$ represents a trifluoromethyl group;

a compound wherein $R^1$ represents an aryl group optionally substituted with an C1-C3 alkyl group, and $R^6$ represents a difluoromethyl group;

a compound wherein $R^1$ represents an aryl group optionally substituted with an C1-C3 alkyl group, and $R^6$ represents a 2-propenyl group;

a compound wherein $R^1$ represents an aryl group optionally substituted with an C1-C3 alkyl group, and $R^6$ represents a chlorine atom;

a compound wherein $R^1$ represents an aryl group optionally substituted with an C1-C3 alkyl group, and $R^6$ represents a bromine atom;

a compound wherein $R^1$ represents an aryl group optionally substituted with an C1-C3 alkyl group, and $R^6$ represents a fluorine atom;

a compound wherein $R^1$ represents an aryl group optionally substituted with an C1-C3 alkyl group, and $R^6$ represents a vinyl group;

a compound wherein $R^1$ represents an aryl group optionally substituted with an C1-C3 alkyl group, and $R^6$ represents a methoxy group;

a compound wherein $R^1$ represents an aryl group optionally substituted with an C1-C3 alkoxy group, and $R^6$ represents an C1-C4 alkyl group;

a compound wherein $R^1$ represents an aryl group optionally substituted with an C1-C3 alkoxy group, and $R^6$ represents a halogen atom;

a compound wherein $R^1$ represents an aryl group optionally substituted with an C1-C3 alkoxy group, and $R^6$ represents a C1-C4 haloalkyl group;

a compound wherein $R^1$ represents an aryl group optionally substituted with an C1-C3 alkoxy group, and $R^6$ represents a C3-C4 cycloalkyl group;

a compound wherein $R^1$ represents an aryl group optionally substituted with an C1-C3 alkoxy group, and $R^6$ represents a C3-C4 halocycloalkyl group;

a compound wherein $R^1$ represents an aryl group optionally substituted with an C1-C3 alkoxy group, and $R^6$ represents an C1-C4 alkoxy group;

a compound wherein $R^1$ represents an aryl group optionally substituted with an C1-C3 alkoxy group, and $R^6$ represents a C1-C4 haloalkoxy group;

a compound wherein $R^1$ represents an aryl group optionally substituted with an C1-C3 alkoxy group, and $R^6$ represents an C1-C4 alkylthio group;

a compound wherein $R^1$ represents an aryl group optionally substituted with an C1-C3 alkoxy group, and $R^6$ represents a C1-C4 haloalkylthio group;

a compound wherein $R^1$ represents an aryl group optionally substituted with an C1-C3 alkoxy group, and $R^6$ represents a C1-C4 haloalkylthio group;

a compound wherein $R^1$ represents an aryl group optionally substituted with an C1-C3 alkoxy group, and $R^6$ represents a halogen atom;

a compound wherein $R^1$ represents an aryl group optionally substituted with an C1-C3 alkoxy group, and $R^6$ represents a methyl group;

a compound wherein $R^1$ represents an aryl group optionally substituted with an C1-C3 alkoxy group, and $R^6$ represents an ethyl group;

a compound wherein $R^1$ represents an aryl group optionally substituted with an C1-C3 alkoxy group, and $R^6$ represents a propyl group;

a compound wherein $R^1$ represents an aryl group optionally substituted with an C1-C3 alkoxy group, and $R^6$ represents a cyclopropyl group;

a compound wherein $R^1$ represents an aryl group optionally substituted with an C1-C3 alkoxy group, and $R^6$ represents a trifluoromethyl group;

a compound wherein $R^1$ represents an aryl group optionally substituted with an C1-C3 alkoxy group, and $R^6$ represents a difluoromethyl group;

a compound wherein $R^1$ represents an aryl group optionally substituted with an C1-C3 alkoxy group, and $R^6$ represents a 2-propenyl group;

a compound wherein $R^1$ represents an aryl group optionally substituted with an C1-C3 alkoxy group, and $R^6$ represents a chlorine atom;

a compound wherein $R^1$ represents an aryl group optionally substituted with an C1-C3 alkoxy group, and $R^6$ represents a bromine atom;

a compound wherein $R^1$ represents an aryl group optionally substituted with an C1-C3 alkoxy group, and $R^6$ represents a fluorine atom;

a compound wherein $R^1$ represents an aryl group optionally substituted with an C1-C3 alkoxy group, and $R^6$ represents a vinyl group;

a compound wherein $R^1$ represents an aryl group optionally substituted with an C1-C3 alkoxy group, and $R^6$ represents a methoxy group;

a compound wherein $R^1$ represents an aryl group optionally substituted with a C1-C3 haloalkoxy group, and $R^6$ represents an C1-C4 alkyl group;

a compound wherein $R^1$ represents an aryl group optionally substituted with a C1-C3 haloalkoxy group, and $R^6$ represents a halogen atom;

a compound wherein $R^1$ represents an aryl group optionally substituted with a C1-C3 haloalkoxy group, and $R^6$ represents a C1-C4 haloalkyl group;

a compound wherein $R^1$ represents an aryl group optionally substituted with a C1-C3 haloalkoxy group, and $R^6$ represents a C3-C4 cycloalkyl group;

a compound wherein $R^1$ represents an aryl group optionally substituted with a C1-C3 haloalkoxy group, and $R^6$ represents a C3-C4 halocycloalkyl group;

a compound wherein $R^1$ represents an aryl group optionally substituted with a C1-C3 haloalkoxy group, and $R^6$ represents an C1-C4 alkoxy group;

a compound wherein $R^1$ represents an aryl group optionally substituted with a C1-C3 haloalkoxy group, and $R^6$ represents an C1-C4 alkoxy group;

a compound wherein $R^1$ represents an aryl group optionally substituted with a C1-C3 haloalkoxy group, and $R^6$ represents a C1-C4 haloalkoxy group;

a compound wherein $R^1$ represents an aryl group optionally substituted with a C1-C3 haloalkoxy group, and $R^6$ represents an C1-C4 alkylthio group;

a compound wherein $R^1$ represents an aryl group optionally substituted with a C1-C3 haloalkoxy group, and $R^6$ represents a C1-C4 haloalkylthio group;

a compound wherein $R^1$ represents an aryl group optionally substituted with a C1-C3 haloalkoxy group, and $R^6$ represents a hydrogen atom;

a compound wherein $R^1$ represents an aryl group optionally substituted with a C1-C3 haloalkoxy group, and $R^6$ represents a methyl group;

a compound wherein $R^1$ represents an aryl group optionally substituted with a C1-C3 haloalkoxy group, and $R^6$ represents an ethyl group;

a compound wherein $R^1$ represents an aryl group optionally substituted with a C1-C3 haloalkoxy group, and $R^6$ represents a propyl group;

a compound wherein $R^1$ represents an aryl group optionally substituted with a C1-C3 haloalkoxy group, and $R^6$ represents a cyclopropyl group;

a compound wherein $R^1$ represents an aryl group optionally substituted with a C1-C3 haloalkoxy group, and $R^6$ represents a trifluoromethyl group;

a compound wherein $R^1$ represents an aryl group optionally substituted with a C1-C3 haloalkoxy group, and $R^6$ represents a difluoromethyl group;

a compound wherein $R^1$ represents an aryl group optionally substituted with a C1-C3 haloalkoxy group, and $R^6$ represents a 2-propenyl group;

a compound wherein $R^1$ represents an aryl group optionally substituted with a C1-C3 haloalkoxy group, and $R^6$ represents a chlorine atom;

a compound wherein $R^1$ represents an aryl group optionally substituted with a C1-C3 haloalkoxy group, and $R^6$ represents a bromine atom;

a compound wherein $R^1$ represents an aryl group optionally substituted with a C1-C3 haloalkoxy group, and $R^6$ represents a fluorine atom;

a compound wherein $R^1$ represents an aryl group optionally substituted with a C1-C3 haloalkoxy group, and $R^6$ represents a vinyl group;

a compound wherein $R^1$ represents an aryl group optionally substituted with a C1-C3 haloalkoxy group, and $R^6$ represents a methoxy group;

a compound wherein $R^1$ represents a 4-chlorophenyl group, and $R^6$ represents an C1-C4 alkyl group;

a compound wherein $R^1$ represents a 4-chlorophenyl group, and $R^6$ represents a halogen atom;

a compound wherein $R^1$ represents a 4-chlorophenyl group, and $R^6$ represents a C1-C4 haloalkyl group;

a compound wherein $R^1$ represents a 4-chlorophenyl group, and $R^6$ represents a C3-C4 cycloalkyl group;

a compound wherein $R^1$ represents a 4-chlorophenyl group, and $R^6$ represents a C3-C4 halocycloalkyl group;

a compound wherein $R^1$ represents a 4-chlorophenyl group, and $R^6$ represents an C1-C4 alkoxy group;

a compound wherein $R^1$ represents a 4-chlorophenyl group, and $R^6$ represents a C1-C4 haloalkoxy group;

a compound wherein $R^1$ represents a 4-chlorophenyl group, and $R^6$ represents an C1-C4 alkylthio group;

a compound wherein $R^1$ represents a 4-chlorophenyl group, and $R^6$ represents a C1-C4 haloalkylthio group;

a compound wherein $R^1$ represents a 4-chlorophenyl group, and $R^6$ represents a hydrogen atom;

a compound wherein $R^1$ represents a 4-chlorophenyl group, and $R^6$ represents a methyl group;

a compound wherein $R^1$ represents a 4-chlorophenyl group, and $R^6$ represents an ethyl group;

a compound wherein $R^1$ represents a 4-chlorophenyl group, and $R^6$ represents a propyl group;

a compound wherein $R^1$ represents a 4-chlorophenyl group, and $R^6$ represents a cyclopropyl group;

a compound wherein $R^1$ represents a 4-chlorophenyl group, and $R^6$ represents a trifluoromethyl group;

a compound wherein $R^1$ represents a 4-chlorophenyl group, and $R^6$ represents a difluoromethyl group;

a compound wherein $R^1$ represents a 4-chlorophenyl group, and $R^6$ represents a 2-propenyl group;

a compound wherein $R^1$ represents a 4-chlorophenyl group, and $R^6$ represents a chlorine atom;

a compound wherein $R^1$ represents a 4-chlorophenyl group, and $R^6$ represents a bromine atom;

a compound wherein $R^1$ represents a 4-chlorophenyl group, and $R^6$ represents a fluorine atom;

a compound wherein $R^1$ represents a 4-chlorophenyl group, and $R^6$ represents a vinyl group;

a compound wherein $R^1$ represents a 4-chlorophenyl group, and $R^6$ represents a methoxy group;

a compound wherein $R^1$ represents a 4-fluorophenyl group, and $R^6$ represents a halogen atom;

a compound wherein $R^1$ represents a 4-fluorophenyl group, and $R^6$ represents a C1-C4 haloalkyl group;

a compound wherein $R^1$ represents a 4-fluorophenyl group, and $R^6$ represents a C3-C4 cycloalkyl group;

a compound wherein $R^1$ represents a 4-fluorophenyl group, and $R^6$ represents a C3-C4 halocycloalkyl group;

a compound wherein $R^1$ represents a 4-fluorophenyl group, and $R^6$ represents an C1-C4 alkoxy group;

a compound wherein $R^1$ represents a 4-fluorophenyl group, and $R^6$ represents a C1-C4 haloalkoxy group;

a compound wherein $R^1$ represents a 4-fluorophenyl group, and $R^6$ represents an C1-C4 alkylthio group;

a compound wherein $R^1$ represents a 4-fluorophenyl group, and $R^6$ represents a C1-C4 haloalkylthio group;

a compound wherein $R^1$ represents a 4-fluorophenyl group, and $R^6$ represents a hydrogen atom;

a compound wherein $R^1$ represents a 4-fluorophenyl group, and $R^6$ represents a methyl group;

a compound wherein $R^1$ represents a 4-fluorophenyl group, and $R^6$ represents an ethyl group;

a compound wherein $R^1$ represents a 4-fluorophenyl group, and $R^6$ represents a propyl group;

a compound wherein $R^1$ represents a 4-fluorophenyl group, and $R^6$ represents a cyclopropyl group;

a compound wherein $R^1$ represents a 4-fluorophenyl group, and $R^6$ represents a trifluoromethyl group;

a compound wherein $R^1$ represents a 4-fluorophenyl group, and $R^6$ represents a difluoromethyl group;

a compound wherein $R^1$ represents a 4-fluorophenyl group, and $R^6$ represents a 2-propenyl group;

a compound wherein $R^1$ represents a 4-fluorophenyl group, and $R^6$ represents a chlorine atom;

a compound wherein $R^1$ represents a 4-fluorophenyl group, and $R^6$ represents a bromine atom;

a compound wherein $R^1$ represents a 4-fluorophenyl group, and $R^6$ represents a fluorine atom;

a compound wherein $R^1$ represents a 4-fluorophenyl group, and $R^6$ represents a vinyl group;

a compound wherein $R^1$ represents a 4-fluorophenyl group, and $R^6$ represents a methoxy group;

a compound wherein $R^1$ represents a 4-bromophenyl group, and $R^6$ represents an C1-C4 alkyl group;

a compound wherein $R^1$ represents a 4-bromophenyl group, and $R^6$ represents a halogen atom;

a compound wherein $R^1$ represents a 4-bromophenyl group, and $R^6$ represents a C1-C4 haloalkyl group;

a compound wherein $R^1$ represents a 4-bromophenyl group, and $R^6$ represents a C3-C4 cycloalkyl group;

a compound wherein $R^1$ represents a 4-bromophenyl group, and $R^6$ represents a C3-C4 halocycloalkyl group;

a compound wherein $R^1$ represents a 4-bromophenyl group, and $R^6$ represents an C1-C4 alkoxy group;

a compound wherein $R^1$ represents a 4-bromophenyl group, and $R^6$ represents a C1-C4 haloalkoxy group;

a compound wherein $R^1$ represents a 4-bromophenyl group, and $R^6$ represents an C1-C4 alkylthio group;

a compound wherein $R^1$ represents a 4-bromophenyl group, and $R^6$ represents a C1-C4 haloalkylthio group;

a compound wherein $R^1$ represents a 4-bromophenyl group, and $R^6$ represents a hydrogen atom;

a compound wherein $R^1$ represents a 4-bromophenyl group, and $R^6$ represents a methyl group;

a compound wherein $R^1$ represents a 4-bromophenyl group, and $R^6$ represents an ethyl group;

a compound wherein $R^1$ represents a 4-bromophenyl group, and $R^6$ represents a propyl group;

a compound wherein $R^1$ represents a 4-bromophenyl group, and $R^6$ represents a cyclopropyl group;

a compound wherein $R^1$ represents a 4-bromophenyl group, and $R^6$ represents a trifluoromethyl group;

a compound wherein $R^1$ represents a 4-bromophenyl group, and $R^6$ represents a difluoromethyl group;

a compound wherein $R^1$ represents a 4-bromophenyl group, and $R^6$ represents a 2-propenyl group;

a compound wherein $R^1$ represents a 4-bromophenyl group, and $R^6$ represents a chlorine atom;

a compound wherein $R^1$ represents a 4-bromophenyl group, and $R^6$ represents a bromine atom;

a compound wherein $R^1$ represents a 4-bromophenyl group, and $R^6$ represents a fluorine atom;

a compound wherein $R^1$ represents a 4-bromophenyl group, and $R^6$ represents a vinyl group;

a compound wherein $R^1$ represents a 4-bromophenyl group, and $R^6$ represents a methoxy group;

a compound wherein $R^1$ represents a 4-methoxyphenyl group, and $R^6$ represents an C1-C4 alkyl group;

a compound wherein $R^1$ represents a 4-methoxyphenyl group, and $R^6$ represents a halogen atom;

a compound wherein $R^1$ represents a 4-methoxyphenyl group, and $R^6$ represents a C1-C4 haloalkyl group;

a compound wherein $R^1$ represents a 4-methoxyphenyl group, and $R^6$ represents a C3-C4 cycloalkyl group;

a compound wherein $R^1$ represents a 4-methoxyphenyl group, and $R^6$ represents a C3-C4 halocycloalkyl group;

a compound wherein $R^1$ represents a 4-methoxyphenyl group, and $R^6$ represents an C1-C4 alkoxy group;

a compound wherein $R^1$ represents a 4-methoxyphenyl group, and $R^6$ represents an C1-C4 alkoxy group;

a compound wherein $R^1$ represents a 4-methoxyphenyl group, and $R^6$ represents a C1-C4 haloalkoxy group;

a compound wherein $R^1$ represents a 4-methoxyphenyl group, and $R^6$ represents an C1-C4 alkylthio group;

a compound wherein $R^1$ represents a 4-methoxyphenyl group, and $R^6$ represents an C1-C4 alkylthio group;

a compound wherein $R^1$ represents a 4-methoxyphenyl group, and $R^6$ represents a C1-C4 haloalkylthio group;

a compound wherein $R^1$ represents a 4-methoxyphenyl group, and $R^6$ represents a hydrogen atom;

a compound wherein $R^1$ represents a 4-methoxyphenyl group, and $R^6$ represents a methyl group;

a compound wherein $R^1$ represents a 4-methoxyphenyl group, and $R^6$ represents an ethyl group;

a compound wherein $R^1$ represents a 4-methoxyphenyl group, and $R^6$ represents a propyl group;

a compound wherein $R^1$ represents a 4-methoxyphenyl group, and $R^6$ represents a cyclopropyl group;

a compound wherein $R^1$ represents a 4-methoxyphenyl group, and $R^6$ represents a trifluoromethyl group;

a compound wherein $R^1$ represents a 4-methoxyphenyl group, and $R^6$ represents a difluoromethyl group;

a compound wherein $R^1$ represents a 4-methoxyphenyl group, and $R^6$ represents a 2-propenyl group;

a compound wherein $R^1$ represents a 4-methoxyphenyl group, and $R^6$ represents a chlorine atom;

a compound wherein $R^1$ represents a 4-methoxyphenyl group, and $R^6$ represents a bromine atom;

a compound wherein $R^1$ represents a 4-methoxyphenyl group, and $R^6$ represents a fluorine atom;

a compound wherein $R^1$ represents a 4-methoxyphenyl group, and $R^6$ represents a vinyl group;

a compound wherein $R^1$ represents a 4-methoxyphenyl group, and $R^6$ represents a methoxy group;

a compound wherein $R^1$ represents a 4-methylphenyl group, and $R^6$ represents an C1-C4 alkyl group;

a compound wherein $R^1$ represents a 4-methylphenyl group, and $R^6$ represents a halogen atom;

a compound wherein $R^1$ represents a 4-methylphenyl group, and $R^6$ represents a C1-C4 haloalkyl group;

a compound wherein $R^1$ represents a 4-methylphenyl group, and $R^6$ represents a C3-C4 cycloalkyl group;

a compound wherein $R^1$ represents a 4-methylphenyl group, and $R^6$ represents a C3-C4 halocycloalkyl group;

a compound wherein $R^1$ represents a 4-methylphenyl group, and $R^6$ represents an C1-C4 alkoxy group;

a compound wherein $R^1$ represents a 4-methylphenyl group, and $R^6$ represents a C1-C4 haloalkoxy group;

a compound wherein $R^1$ represents a 4-methylphenyl group, and $R^6$ represents an C1-C4 alkylthio group;

a compound wherein $R^1$ represents a 4-methylphenyl group, and $R^6$ represents a C1-C4 haloalkylthio group;

a compound wherein $R^1$ represents a 4-methylphenyl group, and $R^6$ represents a hydrogen atom;

a compound wherein $R^1$ represents a 4-methylphenyl group, and $R^6$ represents a methyl group;

a compound wherein $R^1$ represents a 4-methylphenyl group, and $R^6$ represents an ethyl group;

a compound wherein $R^1$ represents a 4-methylphenyl group, and $R^6$ represents a propyl group;

a compound wherein $R^1$ represents a 4-methylphenyl group, and $R^6$ represents a cyclopropyl group;

a compound wherein $R^1$ represents a 4-methylphenyl group, and $R^6$ represents a trifluoromethyl group;

a compound wherein $R^1$ represents a 4-methylphenyl group, and $R^6$ represents a difluoromethyl group;

a compound wherein $R^1$ represents a 4-methylphenyl group, and $R^6$ represents a 2-propenyl group;
a compound wherein $R^1$ represents a 4-methylphenyl group, and $R^6$ represents a chlorine atom;
a compound wherein $R^1$ represents a 4-methylphenyl group, and $R^6$ represents a bromine atom;
a compound wherein $R^1$ represents a 4-methylphenyl group, and $R^6$ represents a fluorine atom;
a compound wherein $R^1$ represents a 4-methylphenyl group, and $R^6$ represents a vinyl group;
a compound wherein $R^1$ represents a 4-methylphenyl group, and $R^6$ represents a methoxy group;
a compound wherein $R^1$ represents a 4-trifluoromethoxyphenyl group, and $R^6$ represents an C1-C4 alkyl group;
a compound wherein $R^1$ represents a 4-trifluoromethoxyphenyl group, and $R^6$ represents a halogen atom;
a compound wherein $R^1$ represents a 4-trifluoromethoxyphenyl group, and $R^6$ represents a C1-C4 haloalkyl group;
a compound wherein $R^1$ represents a 4-trifluoromethoxyphenyl group, and $R^6$ represents a C3-C4 cycloalkyl group;
a compound wherein $R^1$ represents a 4-trifluoromethoxyphenyl group, and $R^6$ represents a C3-C4 cycloalkyl group;
a compound wherein $R^1$ represents a 4-trifluoromethoxyphenyl group, and $R^6$ represents a C3-C4 halocycloalkyl group;
a compound wherein $R^1$ represents a 4-trifluoromethoxyphenyl group, and $R^6$ represents an C1-C4 alkoxy group;
a compound wherein $R^1$ represents a 4-trifluoromethoxyphenyl group, and $R^6$ represents a C1-C4 haloalkoxy group;
a compound wherein $R^1$ represents a 4-trifluoromethoxyphenyl group, and $R^6$ represents an C1-C4 alkylthio group;
a compound wherein $R^1$ represents a 4-trifluoromethoxyphenyl group, and $R^6$ represents a C1-C4 haloalkylthio group;
a compound wherein $R^1$ represents a 4-trifluoromethoxyphenyl group, and $R^6$ represents a hydrogen atom;
a compound wherein $R^1$ represents a 4-trifluoromethoxyphenyl group, and $R^6$ represents a methyl group;
a compound wherein $R^1$ represents a 4-trifluoromethoxyphenyl group, and $R^6$ represents an ethyl group;
a compound wherein $R^1$ represents a 4-trifluoromethoxyphenyl group, and $R^6$ represents a propyl group;
a compound wherein $R^1$ represents a 4-trifluoromethoxyphenyl group, and $R^6$ represents a cyclopropyl group;
a compound wherein $R^1$ represents a 4-trifluoromethoxyphenyl group, and $R^6$ represents a trifluoromethyl group;
a compound wherein $R^1$ represents a 4-trifluoromethoxyphenyl group, and $R^6$ represents a difluoromethyl group;
a compound wherein $R^1$ represents a 4-trifluoromethoxyphenyl group, and $R^6$ represents a 2-propenyl group;
a compound wherein $R^1$ represents a 4-trifluoromethoxyphenyl group, and $R^6$ represents a chlorine atom;
a compound wherein $R^1$ represents a 4-trifluoromethoxyphenyl group, and $R^6$ represents a bromine atom;
a compound wherein $R^1$ represents a 4-trifluoromethoxyphenyl group, and $R^6$ represents a fluorine atom;
a compound wherein $R^1$ represents a 4-trifluoromethoxyphenyl group, and $R^6$ represents a vinyl group;
a compound wherein $R^1$ represents a 4-trifluoromethoxyphenyl group, and $R^6$ represents a methoxy group;
a compound wherein $R^1$ represents a 4-methylthiophenyl group, and $R^6$ represents an C1-C4 alkyl group;
a compound wherein $R^1$ represents a 4-methylthiophenyl group, and $R^6$ represents a halogen atom;
a compound wherein $R^1$ represents a 4-methylthiophenyl group, and $R^6$ represents a C1-C4 haloalkyl group;
a compound wherein $R^1$ represents a 4-methylthiophenyl group, and $R^6$ represents a C3-C4 cycloalkyl group;
a compound wherein $R^1$ represents a 4-methylthiophenyl group, and $R^6$ represents a C3-C4 halocycloalkyl group;
a compound wherein $R^1$ represents a 4-methylthiophenyl group, and $R^6$ represents an C1-C4 alkoxy group;
a compound wherein $R^1$ represents a 4-methylthiophenyl group, and $R^6$ represents a C1-C4 haloalkoxy group;
a compound wherein $R^1$ represents a 4-methylthiophenyl group, and $R^6$ represents an C1-C4 alkylthio group;
a compound wherein $R^1$ represents a 4-methylthiophenyl group, and $R^6$ represents a C1-C4 haloalkylthio group;
a compound wherein $R^1$ represents a 4-methylthiophenyl group, and $R^6$ represents a hydrogen atom;
a compound wherein $R^1$ represents a 4-methylthiophenyl group, and $R^6$ represents a methyl group;
a compound wherein $R^1$ represents a 4-methylthiophenyl group, and $R^6$ represents an ethyl group;
a compound wherein $R^1$ represents a 4-methylthiophenyl group, and $R^6$ represents a propyl group;
a compound wherein $R^1$ represents a 4-methylthiophenyl group, and $R^6$ represents a cyclopropyl group;
a compound wherein $R^1$ represents a 4-methylthiophenyl group, and $R^6$ represents a trifluoromethyl group;
a compound wherein $R^1$ represents a 4-methylthiophenyl group, and $R^6$ represents a difluoromethyl group;
a compound wherein $R^1$ represents a 4-methylthiophenyl group, and $R^6$ represents a 2-propenyl group;
a compound wherein $R^1$ represents a 4-methylthiophenyl group, and $R^6$ represents a chlorine atom;
a compound wherein $R^1$ represents a 4-methylthiophenyl group, and $R^6$ represents a bromine atom;
a compound wherein $R^1$ represents a 4-methylthiophenyl group, and $R^6$ represents a fluorine atom;
a compound wherein $R^1$ represents a 4-methylthiophenyl group, and $R^6$ represents a vinyl group;
a compound wherein $R^1$ represents a 4-methylthiophenyl group, and $R^6$ represents a methoxy group;
a compound wherein $R^1$ represents a tert-butyl group, and $R^6$ represents an C1-C4 alkyl group;
a compound wherein $R^1$ represents a tert-butyl group, and $R^6$ represents a halogen atom;
a compound wherein $R^1$ represents a tert-butyl group, and $R^6$ represents a C1-C4 haloalkyl group;
a compound wherein $R^1$ represents a tert-butyl group, and $R^6$ represents a C3-C4 cycloalkyl group;
a compound wherein $R^1$ represents a tert-butyl group, and $R^6$ represents a C3-C4 halocycloalkyl group;
a compound wherein $R^1$ represents a tert-butyl group, and $R^6$ represents an C1-C4 alkoxy group;
a compound wherein $R^1$ represents a tert-butyl group, and $R^6$ represents a C1-C4 haloalkoxy group;
a compound wherein $R^1$ represents a tert-butyl group, and $R^6$ represents an C1-C4 alkylthio group;
a compound wherein $R^1$ represents a tert-butyl group, and $R^6$ represents a C1-C4 haloalkylthio group;
a compound wherein $R^1$ represents a tert-butyl group, and $R^6$ represents a hydrogen atom;
a compound wherein $R^1$ represents a tert-butyl group, and $R^6$ represents a methyl group;
a compound wherein $R^1$ represents a tert-butyl group, and $R^6$ represents an ethyl group;
a compound wherein $R^1$ represents a tert-butyl group, and $R^6$ represents a propyl group;
a compound wherein $R^1$ represents a tert-butyl group, and $R^6$ represents a cyclopropyl group;

a compound wherein $R^1$ represents a tert-butyl group, and $R^6$ represents a trifluoromethyl group;

a compound wherein $R^1$ represents a tert-butyl group, and $R^6$ represents a difluoromethyl group;

a compound wherein $R^1$ represents a tert-butyl group, and $R^6$ represents a 2-propenyl group;

a compound wherein $R^1$ represents a tert-butyl group, and $R^6$ represents a chlorine atom;

a compound wherein $R^1$ represents a tert-butyl group, and $R^6$ represents a bromine atom;

a compound wherein $R^1$ represents a tert-butyl group, and $R^6$ represents a fluorine atom;

a compound wherein $R^1$ represents a tert-butyl group, and $R^6$ represents a vinyl group;

a compound wherein $R^1$ represents a tert-butyl group, and $R^6$ represents a methoxy group;

a compound wherein $R^1$ represents an adamantyl group, and $R^6$ represents an C1-C4 alkyl group;

a compound wherein $R^1$ represents an adamantyl group, and $R^6$ represents a halogen atom;

a compound wherein $R^1$ represents an adamantyl group, and $R^6$ represents a C1-C4 haloalkyl group;

a compound wherein $R^1$ represents an adamantyl group, and $R^6$ represents a C3-C4 cycloalkyl group;

a compound wherein $R^1$ represents an adamantyl group, and $R^6$ represents a C3-C4 halocycloalkyl group;

a compound wherein $R^1$ represents an adamantyl group, and $R^6$ represents an C1-C4 alkoxy group;

a compound wherein $R^1$ represents an adamantyl group, and $R^6$ represents a C1-C4 haloalkoxy group;

a compound wherein $R^1$ represents an adamantyl group, and $R^6$ represents an C1-C4 alkylthio group;

a compound wherein $R^1$ represents an adamantyl group, and $R^6$ represents a C1-C4 haloalkylthio group;

a compound wherein $R^1$ represents an adamantyl group, and $R^6$ represents a hydrogen atom;

a compound wherein $R^1$ represents an adamantyl group, and $R^6$ represents a methyl group;

a compound wherein $R^1$ represents an adamantyl group, and $R^6$ represents an ethyl group;

a compound wherein $R^1$ represents an adamantyl group, and $R^6$ represents a propyl group;

a compound wherein $R^1$ represents an adamantyl group, and $R^6$ represents a cyclopropyl group;

a compound wherein $R^1$ represents an adamantyl group, and $R^6$ represents a trifluoromethyl group;

a compound wherein $R^1$ represents an adamantyl group, and $R^6$ represents a difluoromethyl group;

a compound wherein $R^1$ represents an adamantyl group, and $R^6$ represents a 2-propenyl group;

a compound wherein $R^1$ represents an adamantyl group, and $R^6$ represents a chlorine atom;

a compound wherein $R^1$ represents an adamantyl group, and $R^6$ represents a bromine atom;

a compound wherein $R^1$ represents an adamantyl group, and $R^6$ represents a fluorine atom;

a compound wherein $R^1$ represents an adamantyl group, and $R^6$ represents a vinyl group;

a compound wherein $R^1$ represents an adamantyl group, and $R^6$ represents a methoxy group;

a compound wherein X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents hydrogen atom, $R^6$ represents a cyclopropyl group, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom; a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 4 trifluoromethoxyphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents hydrogen atom, $R^6$ represents a fluorine atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents an ethyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a propyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a propyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a propyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a propyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a propyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a propyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a propyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a propyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a propyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a propyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-trifluoromethoxyphenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^7$ represents, a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a haloaryl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents, a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a difluoromethyl group, $R^1$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with an C1-C3 alkoxy group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an aryl group optionally substituted with a C1-C3 haloalkoxy group, X represents a sulfur atom, $R^2$ represents a hydrogen atom, represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-chlorophenyl group, X represents a sulfur atom, $R^2$ represents a hydrogen atom, R$^4$ represents a hydrogen atom, R$^5$ represents a hydrogen atom, R$^6$ represents an ethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a propyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a cyclopropyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a trifluoromethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a difluoromethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a 2-propenyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a chlorine atom, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a bromine atom, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a fluorine atom, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a vinyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-chlorophenyl group, X represents a sulfur atom, R$^2$ represents a hydrogen atom, R$^4$ represents a hydrogen atom, R$^5$ represents a hydrogen atom, R$^6$ represents a methoxy group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-fluorophenyl group, X represents a sulfur atom, R$^2$ represents a hydrogen atom, R$^4$ represents a hydrogen atom, R$^5$ represents a hydrogen atom, R$^6$ represents a hydrogen atom, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-fluorophenyl group, X represents a sulfur atom, R$^2$ represents a hydrogen atom, R$^4$ represents a hydrogen atom, R$^5$ represents a hydrogen atom, R$^6$ represents a methyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-fluorophenyl group, X represents a sulfur atom, R$^2$ represents a hydrogen atom, R$^4$ represents a hydrogen atom, R$^5$ represents a hydrogen atom, R$^6$ represents an ethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-fluorophenyl group, X represents a sulfur atom, R$^2$ represents a hydrogen atom, R$^4$ represents a hydrogen atom, R$^5$ represents a hydrogen atom, R$^6$ represents a propyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-fluorophenyl group, X represents a sulfur atom, R$^2$ represents a hydrogen atom, R$^4$ represents a hydrogen atom, R$^5$ represents a hydrogen atom, R$^6$ represents a cyclopropyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-fluorophenyl group, X represents a sulfur atom, R$^2$ represents a hydrogen atom, R$^4$ represents a hydrogen atom, R$^5$ represents a hydrogen atom, R$^6$ represents a trifluoromethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-fluorophenyl group, X represents a sulfur atom, R$^2$ represents a hydrogen atom, R$^4$ represents a hydrogen atom, R$^5$ represents a hydrogen atom, R$^6$ represents a difluoromethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-fluorophenyl group, X represents a sulfur atom, R$^2$ represents a hydrogen atom, R$^4$ represents a hydrogen atom, R$^5$ represents a hydrogen atom, R$^6$ represents a 2-propenyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a 4-fluorophenyl group, X represents a sulfur atom, R$^2$ represents a hydrogen atom, R$^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-fluorophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a propyl group, $R^1$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a cyclopropyl group, $R^1$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^1$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a difluoromethyl group, $R^1$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-bromophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^1$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^1$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methoxyphenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylphenyl group, X represents a sulfur atom, $R^2$ represents a hydrogen atom, R⁴ represents a hydrogen atom, R⁵ represents a hydrogen atom, R⁶ represents a difluoromethyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-methylphenyl group, X represents a sulfur atom, R² represents a hydrogen atom, R⁴ represents a hydrogen atom, R⁵ represents a hydrogen atom, R⁶ represents a 2-propenyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-methylphenyl group, X represents a sulfur atom, R² represents a hydrogen atom, R⁴ represents a hydrogen atom, R⁵ represents a hydrogen atom, R⁶ represents a chlorine atom, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-methylphenyl group, X represents a sulfur atom, R² represents a hydrogen atom, R⁴ represents a hydrogen atom, R⁵ represents a hydrogen atom, R⁶ represents a bromine atom, R⁷ represents a hydrogen atom, R⁸ represents a hydrogen atom, represents a hydrogen atom, R¹⁰ represents a methyl group, Q represents an oxygen atom, and Y represents an oxygen atom;

a compound wherein R¹ represents a 4-methylphenyl group, X represents a sulfur atom, R² represents a hydrogen atom, R⁴ represents a hydrogen atom, R⁵ represents a hydrogen atom, R⁶ represents a fluorine atom, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-methylphenyl group, X represents a sulfur atom, R² represents a hydrogen atom, R⁴ represents a hydrogen atom, R⁵ represents a hydrogen atom, R⁶ represents a vinyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-methylphenyl group, X represents a sulfur atom, R² represents a hydrogen atom, R⁴ represents a hydrogen atom, R⁵ represents a hydrogen atom, R⁶ represents a methoxy group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a hydrogen atom, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a methyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents an ethyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a propyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a cyclopropyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a trifluoromethyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a difluoromethyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4 trifluoromethoxyphenyl group, X represents a sulfur atom, R² represents a hydrogen atom, R⁴ represents a hydrogen atom, R⁵ represents a hydrogen atom, R⁶ represents a 2-propenyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a chlorine atom, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a bromine atom, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a fluorine atom, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein R¹ represents a 4-trifluoromethoxyphenyl group, X represents a sulfur atom, R² represents a hydrogen atom, R⁴ represents a hydrogen atom, R⁵ represents a hydrogen atom, R⁶ represents a vinyl group, R⁷ represents a hydrogen atom, R⁸ represents a hydrogen atom, R⁹ represents a hydrogen atom, R¹⁰ represents a methyl group, Q represents an oxygen atom, and Y represents an oxygen atom;

a compound wherein $R^1$ represents a 4 trifluoromethoxyphenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 4-methylthiophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a tert-butyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$ represents a hydrogen atom, R$^5$ represents a hydrogen atom, R$^6$ represents a propyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$ represents a hydrogen atom, R$^5$ represents a hydrogen atom, R$^6$ represents a cyclopropyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a tert-butyl group, represents a sulfur atom, R$^2$ represents a hydrogen atom, R$^4$ represents a hydrogen atom, R$^5$ represents a hydrogen atom, R$^6$ represents a cyclopropyl group, R$^7$ represents a hydrogen atom, R$^8$ represents a hydrogen atom, R$^9$ represents hydrogen atom, R$^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$ represents a hydrogen atom, R$^5$ represents a hydrogen atom, R$^6$ represents a trifluoromethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$ represents a hydrogen atom, R$^5$ represents a hydrogen atom, R$^6$ represents a difluoromethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$ represents a hydrogen atom, R$^5$ represents a hydrogen atom, R$^6$ represents a 2-propenyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$ represents a hydrogen atom, R$^5$ represents a hydrogen atom, R$^6$ represents a chlorine atom, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$-represents a hydrogen atom, R$^5$ represents a hydrogen atom, R$^6$ represents a bromine atom, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$ represents a hydrogen atom, R$^5$ represents a hydrogen atom, R$^6$ represents a fluorine atom, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$ represents a hydrogen atom, R$^5$ represents a hydrogen atom, R$^6$ represents a vinyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents a tert-butyl group, X represents a sulfur atom, R$^2$ represents a hydrogen atom, R$^4$ represents a hydrogen atom, R$^5$ represents a hydrogen atom, R$^6$ represents a methoxy group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents an adamantyl group, X represents a sulfur atom, R$^2$ represents a hydrogen atom, R$^4$ represents a hydrogen atom, R$^5$ represents a hydrogen atom, Fe represents a hydrogen atom, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents an adamantyl group, X represents a sulfur atom, R$^2$ represents a hydrogen atom, R$^4$ represents a hydrogen atom, R$^5$ represents a hydrogen atom, R$^6$ represents a methyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents an adamantyl group, X represents a sulfur atom, R$^2$ represents a hydrogen atom, R$^4$ represents a hydrogen atom, R$^5$ represents a hydrogen atom, R$^6$ represents an ethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents an adamantyl group, X represents a sulfur atom, R$^2$ represents a hydrogen atom, R$^4$ represents a hydrogen atom, R$^5$ represents a hydrogen atom, R$^6$ represents a propyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents an adamantyl group, X represents a sulfur atom, R$^2$ represents a hydrogen atom, R$^4$ represents a hydrogen atom, R$^5$ represents a hydrogen atom, R$^6$ represents a cyclopropyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents an adamantyl group, X represents a sulfur atom, R$^2$ represents a hydrogen atom, R$^4$ represents a hydrogen atom, R$^5$ represents a hydrogen atom, R$^6$ represents a trifluoromethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents an adamantyl group, X represents a sulfur atom, R$^2$ represents a hydrogen atom, R$^4$ represents a hydrogen atom, R$^5$ represents a hydrogen atom, R$^6$ represents a difluoromethyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein R$^1$ represents an adamantyl group, X represents a sulfur atom, R$^2$ represents a hydrogen atom, R$^4$ represents a hydrogen atom, R$^5$ represents a hydrogen atom, R$^6$ represents a 2-propenyl group, R$^7$ represents a hydrogen atom, R$^8$ represents a hydrogen atom, R$^9$ represents a hydrogen atom, R$^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents hydrogen atom, $R^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents an adamantyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group;

a compound wherein $R^1$ represents a 3-fluorophenyl group;

a compound wherein $R^1$ represents a 3-bromophenyl group;

a compound wherein $R^1$ represents a 3-methoxyphenyl group;

a compound wherein $R^1$ represents a 3-methylphenyl group;

a compound wherein $R^1$ represents a 3-trifluoromethoxyphenyl group;

a compound wherein $R^1$ represents a 3-methylthiophenyl group;

a compound wherein $R^1$ represents a 3-chlorophenyl group, and $R^6$ represents an C1-C4 alkyl group;

a compound wherein $R^1$ represents a 3-chlorophenyl group, and $R^6$ represents a halogen atom;

a compound wherein $R^1$ represents a 3-chlorophenyl group, and $R^6$ represents a C1-C4 haloalkyl group;

a compound wherein $R^1$ represents a 3-chlorophenyl group, and $R^6$ represents a C3-C4 cycloalkyl group;

a compound wherein $R^1$ represents a 3-chlorophenyl group, and $R^6$ represents a C3-C4 halocycloalkyl group;

a compound wherein $R^1$ represents a 3-chlorophenyl group, and $R^6$ represents an C1-C4 alkoxy group;

a compound wherein $R^1$ represents a 3-chlorophenyl group, and $R^6$ represents a C1-C4 haloalkoxy group;

a compound wherein $R^1$ represents a 3-chlorophenyl group, and $R^6$ represents an C1-C4 alkylthio group;

a compound wherein $R^1$ represents a 3-chlorophenyl group, and $R^6$ represents a C1-C4 haloalkylthio group;

a compound wherein $R^1$ represents a 3-chlorophenyl group, and $R^6$ represents a hydrogen atom;

a compound wherein $R^1$ represents a 3-chlorophenyl group, and $R^6$ represents a methyl group;

a compound wherein $R^1$ represents a 3-chlorophenyl group, and $R^6$ represents an ethyl group;

a compound wherein $R^1$ represents a 3-chlorophenyl group, and $R^6$ represents a propyl group;

a compound wherein $R^1$ represents a 3-chlorophenyl group, and $R^6$ represents a cyclopropyl group;

a compound wherein $R^1$ represents a 3-chlorophenyl group, and $R^6$ represents a trifluoromethyl group;

a compound wherein $R^1$ represents a 3-chlorophenyl group, and $R^6$ represents a difluoromethyl group;

a compound wherein $R^1$ represents a 3-chlorophenyl group, and $R^6$ represents a 2-propenyl group;

a compound wherein $R^1$ represents a 3-chlorophenyl group, and $R^6$ represents a chlorine atom;

a compound wherein $R^1$ represents a 3-chlorophenyl group, and $R^6$ represents a bromine atom;

a compound wherein $R^1$ represents a 3-chlorophenyl group, and $R^6$ represents a fluorine atom;

a compound wherein $R^1$ represents a 3-chlorophenyl group, and $R^6$ represents a vinyl group;

a compound wherein $R^1$ represents a 3-chlorophenyl group, and $R^6$ represents a methoxy group;

a compound wherein $R^1$ represents a 3-fluorophenyl group, and $R^6$ represents an C1-C4 alkyl group;

a compound wherein $R^1$ represents a 3-fluorophenyl group, and $R^6$ represents a halogen atom;

a compound wherein $R^1$ represents a 3-fluorophenyl group, and $R^6$ represents a C1-C4 haloalkyl group;

a compound wherein $R^1$ represents a 3-fluorophenyl group, and $R^6$ represents a C3-C4 cycloalkyl group;

a compound wherein $R^1$ represents a 3-fluorophenyl group, and $R^6$ represents a C3-C4 halocycloalkyl group;

a compound wherein $R^1$ represents a 3-fluorophenyl group, and $R^6$ represents an C1-C4 alkoxy group;

a compound wherein $R^1$ represents a 3-fluorophenyl group, and $R^6$ represents a C1-C4 haloalkoxy group;

a compound wherein $R^1$ represents a 3-fluorophenyl group, and $R^6$ represents an C1-C4 alkylthio group;

a compound wherein $R^1$ represents a 3-fluorophenyl group, and $R^6$ represents a C1-C4 haloalkylthio group;

a compound wherein $R^1$ represents a 3-fluorophenyl group, and $R^6$ represents a hydrogen atom;

a compound wherein $R^1$ represents a 3-fluorophenyl group, and $R^6$ represents a methyl group;

a compound wherein $R^1$ represents a 3-fluorophenyl group, and $R^6$ represents an ethyl group;

a compound wherein $R^1$ represents a 3-fluorophenyl group, and $R^6$ represents a propyl group;

a compound wherein $R^1$ represents a 3-fluorophenyl group, and $R^6$ represents a cyclopropyl group;

a compound wherein $R^1$ represents a 3-fluorophenyl group, and $R^6$ represents a trifluoromethyl group;

a compound wherein $R^1$ represents a 3-fluorophenyl group, and $R^6$ represents a difluoromethyl group;

a compound wherein $R^1$ represents a 3-fluorophenyl group, and $R^6$ represents a 2-propenyl group;

a compound wherein $R^1$ represents a 3-fluorophenyl group, and $R^6$ represents a chlorine atom;

a compound wherein $R^1$ represents a 3-fluorophenyl group, and $R^6$ represents a bromine atom;

a compound wherein $R^1$ represents a 3-fluorophenyl group, and $R^6$ represents a fluorine atom;

a compound wherein $R^1$ represents a 3-fluorophenyl group, and $R^6$ represents a vinyl group;

a compound wherein $R^1$ represents a 3-fluorophenyl group, and $R^6$ represents a methoxy group;

a compound wherein $R^1$ represents a 3-bromophenyl group, and $R^6$ represents an C1-C4 alkyl group;

a compound wherein $R^1$ represents a 3-bromophenyl group, and $R^6$ represents a halogen atom;

a compound wherein $R^1$ represents a 3-bromophenyl group, and $R^6$ represents a C1-C4 haloalkyl group;

a compound wherein $R^1$ represents a 3-bromophenyl group, and $R^6$ represents a C3-C4 cycloalkyl group;

a compound wherein $R^1$ represents a 3-bromophenyl group, and $R^6$ represents a C3-C4 halocycloalkyl group;

a compound wherein $R^1$ represents a 3-bromophenyl group, and $R^6$ represents an C1-C4 alkoxy group;

a compound wherein $R^1$ represents a 3-bromophenyl group, and $R^6$ represents a C1-C4 haloalkoxy group;

a compound wherein $R^1$ represents a 3-bromophenyl group, and $R^6$ represents an C1-C4 alkylthio group;

a compound wherein $R^1$ represents a 3-bromophenyl group, and $R^6$ represents a C1-C4 haloalkylthio group;

a compound wherein $R^1$ represents a 3-bromophenyl group, and $R^6$ represents a hydrogen atom;

a compound wherein $R^1$ represents a 3-bromophenyl group, and $R^6$ represents a methyl group;

a compound wherein $R^1$ represents a 3-bromophenyl group, and $R^6$ represents an ethyl group;

a compound wherein $R^1$ represents a 3-bromophenyl group, and $R^6$ represents a propyl group;

a compound wherein $R^1$ represents a 3-bromophenyl group, and $R^6$ represents a cyclopropyl group;

a compound wherein $R^1$ represents a 3-bromophenyl group, and $R^6$ represents a trifluoromethyl group;

a compound wherein $R^1$ represents a 3-bromophenyl group, and $R^6$ represents a difluoromethyl group;

a compound wherein $R^1$ represents a 3-bromophenyl group, and $R^6$ represents a 2-propenyl group;

a compound wherein $R^1$ represents a 3-bromophenyl group, and $R^6$ represents a chlorine atom;

a compound wherein $R^1$ represents a 3-bromophenyl group, and $R^6$ represents a bromine atom;

a compound wherein $R^1$ represents a 3-bromophenyl group, and $R^6$ represents a fluorine atom;

a compound wherein $R^1$ represents a 3-bromophenyl group, and $R^6$ represents a vinyl group;

a compound wherein $R^1$ represents a 3-bromophenyl group, and $R^6$ represents a methoxy group;

a compound wherein $R^1$ represents a 3-methoxyphenyl group, and $R^6$ represents an C1-C4 alkyl group;

a compound wherein $R^1$ represents a 3-methoxyphenyl group, and $R^6$ represents a halogen atom;

a compound wherein $R^1$ represents a 3-methoxyphenyl group, and $R^6$ represents a C1-C4 haloalkyl group;

a compound wherein $R^1$ represents a 3-methoxyphenyl group, and $R^6$ represents a C3-C4 cycloalkyl group;

a compound wherein $R^1$ represents a 3-methoxyphenyl group, and $R^6$ represents a C3-C4 halocycloalkyl group;

a compound wherein $R^1$ represents a 3-methoxyphenyl group, and $R^6$ represents an C1-C4 alkoxy group;

a compound wherein $R^1$ represents a 3-methoxyphenyl group, and $R^6$ represents a C1-C4 haloalkoxy group;

a compound wherein $R^1$ represents a 3-methoxyphenyl group, and $R^6$ represents an C1-C4 alkylthio group;

a compound wherein $R^1$ represents a 3-methoxyphenyl group, and $R^6$ represents a C1-C4 haloalkylthio group;

a compound wherein $R^1$ represents a 3-methoxyphenyl group, and $R^6$ represents a hydrogen atom;

a compound wherein $R^1$ represents a 3-methoxyphenyl group, and $R^6$ represents a methyl group;

a compound wherein $R^1$ represents a 3-methoxyphenyl group, and $R^6$ represents an ethyl group;

a compound wherein $R^1$ represents a 3-methoxyphenyl group, and $R^6$ represents a propyl group;

a compound wherein $R^1$ represents a 3-methoxyphenyl group, and $R^6$ represents a cyclopropyl group;

a compound wherein $R^1$ represents a 3-methoxyphenyl group, and $R^6$ represents a trifluoromethyl group;

a compound wherein $R^1$ represents a 3-methoxyphenyl group, and $R^6$ represents a difluoromethyl group;

a compound wherein $R^1$ represents a 3-methoxyphenyl group, and $R^6$ represents a 2-propenyl group;

a compound wherein $R^1$ represents a 3-methoxyphenyl group, and $R^6$ represents a chlorine atom;

a compound wherein $R^1$ represents a 3-methoxyphenyl group, and $R^6$ represents a bromine atom;

a compound wherein $R^1$ represents a 3-methoxyphenyl group, and $R^6$ represents a fluorine atom;

a compound wherein $R^1$ represents a 3-methoxyphenyl group, and $R^6$ represents a vinyl group;

a compound wherein. $R^1$ represents a 3-methoxyphenyl group, and $R^6$ represents a methoxy group;

a compound wherein $R^1$ represents a 3-methylphenyl group, and $R^6$ represents an C1-C4 alkyl group;

a compound wherein $R^1$ represents a 3-methylphenyl group, and $R^6$ represents a halogen atom;

a compound wherein $R^1$ represents a 3-methylphenyl group, and $R^6$ represents a C1-C4 haloalkyl group;

a compound wherein $R^1$ represents a 3-methylphenyl group, and $R^6$ represents a C3-C4 cycloalkyl group;

a compound wherein $R^1$ represents a 3-methylphenyl group, and $R^6$ represents a C3-C4 halocycloalkyl group;

a compound wherein $R^1$ represents a 3-methylphenyl group, and $R^6$ represents an C1-C4 alkoxy group;

a compound wherein $R^1$ represents a 3-methylphenyl group, and $R^6$ represents a C1-C4 haloalkoxy group;

a compound wherein $R^1$ represents a 3-methylphenyl group, and $R^6$ represents an C1-C4 alkylthio group;

a compound wherein $R^1$ represents a 3-methylphenyl group, and $R^6$ represents a C1-C4 haloalkylthio group;

a compound wherein $R^1$ represents a 3-methylphenyl group, and $R^6$ represents a hydrogen atom;

a compound wherein $R^1$ represents a 3-methylphenyl group, and $R^6$ represents a methyl group;

a compound wherein $R^1$ represents a 3-methylphenyl group, and $R^6$ represents an ethyl group;

a compound wherein $R^1$ represents a 3-methylphenyl group, and $R^6$ represents a propyl group;

a compound wherein $R^1$ represents a 3-methylphenyl group, and $R^6$ represents a cyclopropyl group;

a compound wherein $R^1$ represents a 3-methylphenyl group, and $R^6$ represents a trifluoromethyl group;

a compound wherein $R^1$ represents a 3-methylphenyl group, and $R^6$ represents a difluoromethyl group;

a compound wherein $R^1$ represents a 3-methylphenyl group, and $R^6$ represents a 2-propenyl group;

a compound wherein $R^1$ represents a 3-methylphenyl group, and $R^6$ represents a chlorine atom;

a compound wherein $R^1$ represents a 3-methylphenyl group, and $R^6$ represents a bromine atom;

a compound wherein. $R^1$ represents a 3-methylphenyl group, and $R^6$ represents a fluorine atom;

a compound wherein $R^1$ represents a 3-methylphenyl group, and $R^6$ represents a vinyl group;

a compound wherein $R^1$ represents a 3-methylphenyl group, and $R^6$ represents a methoxy group;

a compound wherein $R^1$ represents a 3-trifluoromethoxyphenyl group, and $R^6$ represents an C1-C4 alkyl group;

a compound wherein $R^1$ represents a 3-trifluoromethoxyphenyl group, and $R^6$ represents a halogen atom;

a compound wherein $R^1$ represents a 3-trifluoromethoxyphenyl group, and $R^6$ represents a C1-C4 haloalkyl group;

a compound wherein $R^1$ represents a 3 trifluoromethoxyphenyl group, and $R^6$ represents a C3-C4 cycloalkyl group;

a compound wherein $R^1$ represents a 3-trifluoromethoxyphenyl group, and $R^6$ represents a C3-C4 halocycloalkyl group;

a compound wherein $R^1$ represents a 3-trifluoromethoxyphenyl group, and $R^6$ represents an C1-C4 alkoxy group;

a compound wherein $R^1$ represents a 3-trifluoromethoxyphenyl group, and $R^6$ represents a C1-C4 haloalkoxy group;

a compound wherein $R^1$ represents a 3-trifluoromethoxyphenyl group, and $R^6$ represents an C1-C4 alkylthio group;

a compound wherein $R^1$ represents a 3-trifluoromethoxyphenyl group, and $R^6$ represents a C1-C4 haloalkylthio group;

a compound wherein $R^1$ represents a 3-trifluoromethoxyphenyl group, and $R^6$ represents a hydrogen atom;

a compound wherein $R^1$ represents a 3-trifluoromethoxyphenyl group, and $R^6$ represents a methyl group;

a compound wherein. $R^1$ represents a 3-trifluoromethoxyphenyl group, and $R^6$ represents an ethyl group;

a compound wherein $R^1$ represents a 3-trifluoromethoxyphenyl group, and $R^6$ represents a propyl group;

a compound wherein $R^1$ represents a 3-trifluoromethoxyphenyl group, and $R^6$ represents a cyclopropyl group;

a compound wherein $R^1$ represents a 3-trifluoromethoxyphenyl group, and $R^6$ represents a trifluoromethyl group;

a compound wherein $R^1$ represents a 3-trifluoromethoxyphenyl group, and $R^6$ represents a difluoromethyl group;

a compound wherein $R^1$ represents a 3-trifluoromethoxyphenyl group, and $R^6$ represents a 2-propenyl group;

a compound wherein $R^1$ represents a 3-trifluoromethoxyphenyl group, and $R^6$ represents a chlorine atom;

a compound wherein $R^1$ represents a 3-trifluoromethoxyphenyl group, and $R^6$ represents a bromine atom;

a compound wherein $R^1$ represents a 3-trifluoromethoxyphenyl group, and $R^6$ represents a fluorine atom;

a compound wherein $R^1$ represents a 3-trifluoromethoxyphenyl group, and $R^6$ represents a vinyl group;

a compound wherein $R^1$ represents a 3-trifluoromethoxyphenyl group, and $R^6$ represents a methoxy group;

a compound wherein $R^1$ represents a 3-methylthiophenyl group, and $R^6$ represents an C1-C4 alkyl group;

a compound wherein $R^1$ represents a 3-methylthiophenyl group, and $R^6$ represents a halogen atom;

a compound wherein $R^1$ represents a 3-methylthiophenyl group, and $R^6$ represents a C1-C4 haloalkyl group;

a compound wherein $R^1$ represents a 3-methylthiophenyl group, and $R^6$ represents a C3-C4 cycloalkyl group;

a compound wherein $R^1$ represents a 3-methylthiophenyl group, and $R^6$ represents a C3-C4 halocycloalkyl group;

a compound wherein $R^1$ represents a 3-methylthiophenyl group, and $R^6$ represents an C1-C4 alkoxy group;

a compound wherein $R^1$ represents a 3-methylthiophenyl group, and $R^6$ represents a C1-C4 haloalkoxy group;

a compound wherein $R^1$ represents a 3-methylthiophenyl group, and $R^6$ represents an C1-C4 alkylthio group;

a compound wherein $R^1$ represents a 3-methylthiophenyl group, and $R^6$ represents a C1-C4 haloalkylthio group;

a compound wherein $R^1$ represents a 3-methylthiophenyl group, and $R^6$ represents a hydrogen atom;

a compound wherein $R^1$ represents a 3-methylthiophenyl group, and $R^6$ represents a methyl group;

a compound wherein $R^1$ represents a 3-methylthiophenyl group, and $R^6$ represents an ethyl group;

a compound wherein $R^1$ represents a 3-methylthiophenyl group, and $R^6$ represents a propyl group;

a compound wherein $R^1$ represents a 3-methylthiophenyl group, and $R^6$ represents a cyclopropyl group;

a compound wherein $R^1$ represents a 3-methylthiophenyl group, and $R^6$ represents a trifluoromethyl group;

a compound wherein $R^1$ represents a 3-methylthiophenyl group, and $R^6$ represents a difluoromethyl group;

a compound wherein $R^1$ represents a 3-methylthiophenyl group, and $R^6$ represents a 2-propenyl group;

a compound wherein $R^1$ represents a 3-methylthiophenyl group, and $R^6$ represents a chlorine atom;

a compound wherein $R^1$ represents a 3-methylthiophenyl group, and $R^6$ represents a bromine atom;

a compound wherein $R^1$ represents a 3-methylthiophenyl group, and $R^6$ represents a fluorine atom;

a compound wherein $R^1$ represents a 3-methylthiophenyl group, and $R^6$ represents a vinyl group;

a compound wherein $R^1$ represents a 3-methylthiophenyl group, and $R^6$ represents a methoxy group;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents hydrogen atom, $R^6$ represents a fluorine atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein R represents a 3-bromophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-chlorophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-fluorophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a bromine atom, R represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-bromophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methoxyphenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylphenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-trifluoromethoxyphenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3 trifluoromethoxyphenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 3-methylthiophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group;

a compound wherein $R^1$ represents a 2-fluorophenyl group;

a compound wherein $R^1$ represents a 2-bromophenyl group;

a compound wherein $R^1$ represents a 2-methoxyphenyl group;

a compound wherein $R^1$ represents a 2-methylphenyl group;

a compound wherein $R^1$ represents a 2 trifluoromethoxyphenyl group;

a compound wherein $R^1$ represents a 2-methylphenyl group;

a compound wherein $R^1$ represents a 2-chlorophenyl group, and $R^6$ represents an C1-C4 alkyl group;

a compound wherein $R^1$ represents a 2-chlorophenyl group, and $R^6$ represents a halogen atom;

a compound wherein $R^1$ represents a 2-chlorophenyl group, and $R^6$ represents a C1-C4 haloalkyl group;

a compound wherein $R^1$ represents a 2-chlorophenyl group, and $R^6$ represents a C3-C4 cycloalkyl group;

a compound wherein $R^1$ represents a 2-chlorophenyl group, and $R^6$ represents a C3-C4 halocycloalkyl group;

a compound wherein $R^1$ represents a 2-chlorophenyl group, and $R^6$ represents an C1-C4 alkoxy group;

a compound wherein $R^1$ represents a 2-chlorophenyl group, and $R^6$ represents a C1-C4 haloalkoxy group;

a compound wherein $R^1$ represents a 2-chlorophenyl group, and $R^6$ represents an C1-C4 alkylthio group;

a compound wherein $R^1$ represents a 2-chlorophenyl group, and $R^6$ represents a C1-C4 haloalkylthio group;

a compound wherein $R^1$ represents a 2-chlorophenyl group, and $R^6$ represents a hydrogen atom;

a compound wherein $R^1$ represents a 2-chlorophenyl group, and $R^6$ represents a methyl group;

a compound wherein $R^1$ represents a 2-chlorophenyl group, and $R^6$ represents an ethyl group;

a compound wherein $R^1$ represents a 2-chlorophenyl group, and $R^6$ represents a propyl group;

a compound wherein $R^1$ represents a 2-chlorophenyl group, and $R^6$ represents a cyclopropyl group;

a compound wherein $R^1$ represents a 2-chlorophenyl group, and $R^6$ represents a trifluoromethyl group;

a compound wherein $R^1$ represents a 2-chlorophenyl group, and $R^6$ represents a difluoromethyl group;

a compound wherein $R^1$ represents a 2-chlorophenyl group, and $R^6$ represents a 2-propenyl group;

a compound wherein $R^1$ represents a 2-chlorophenyl group, and $R^6$ represents a chlorine atom;

a compound wherein $R^1$ represents a 2-chlorophenyl group, and $R^6$ represents a bromine atom;

a compound wherein $R^1$ represents a 2-chlorophenyl group, and $R^6$ represents a fluorine atom;

a compound wherein $R^1$ represents a 2-chlorophenyl group, and $R^6$ represents a vinyl group;

a compound wherein $R^1$ represents a 2-chlorophenyl group, and $R^6$ represents a methoxy group;

a compound wherein $R^1$ represents a 2-fluorophenyl group, and $R^6$ represents an C1-C4 alkyl group;

a compound wherein $R^1$ represents a 2-fluorophenyl group, and $R^6$ represents a halogen atom;

a compound wherein $R^1$ represents a 2-fluorophenyl group, and $R^6$ represents a C1-C4 haloalkyl group;

a compound wherein $R^1$ represents a 2-fluorophenyl group, and $R^6$ represents a C3-C4 cycloalkyl group;

a compound wherein $R^1$ represents a 2-fluorophenyl group, and $R^6$ represents a C3-C4 halocycloalkyl group;

a compound wherein $R^1$ represents a 2-fluorophenyl group, and $R^6$ represents an C1-C4 alkoxy group;

a compound wherein $R^1$ represents a 2-fluorophenyl group, and $R^6$ represents a C1-C4 haloalkoxy group;

a compound wherein $R^1$ represents a 2-fluorophenyl group, and $R^6$ represents an C1-C4 alkylthio group;

a compound wherein $R^1$ represents a 2-fluorophenyl group, and $R^6$ represents a C1-C4 haloalkylthio group;

a compound wherein $R^1$ represents a 2-fluorophenyl group, and $R^6$ represents a hydrogen atom;

a compound wherein $R^1$ represents a 2-fluorophenyl group, and $R^6$ represents a methyl group;

a compound wherein $R^1$ represents a 2-fluorophenyl group, and $R^6$ represents an ethyl group;
a compound wherein $R^1$ represents a 2-fluorophenyl group, and $R^6$ represents a propyl group;
a compound wherein $R^1$ represents a 2-fluorophenyl group, and $R^6$ represents a cyclopropyl group;
a compound wherein $R^1$ represents a 2-fluorophenyl group, and $R^6$ represents a trifluoromethyl group;
a compound wherein $R^1$ represents a 2-fluorophenyl group, and $R^6$ represents a difluoromethyl group;
a compound wherein $R^1$ represents a 2-fluorophenyl group, and $R^6$ represents a 2-propenyl group;
a compound wherein $R^1$ represents a 2-fluorophenyl group, and $R^6$ represents a chlorine atom;
a compound wherein $R^1$ represents a 2-fluorophenyl group, and $R^6$ represents a bromine atom;
a compound wherein $R^1$ represents a 2-fluorophenyl group, and $R^6$ represents a fluorine atom;
a compound wherein $R^1$ represents a 2-fluorophenyl group, and $R^6$ represents a vinyl group;
a compound wherein $R^1$ represents a 2-fluorophenyl group, and $R^6$ represents a methoxy group;
a compound wherein $R^1$ represents a 2-bromophenyl group, and $R^6$ represents an C1-C4 alkyl group;
a compound wherein $R^1$ represents a 2-bromophenyl group, and $R^6$ represents a halogen atom;
a compound wherein $R^1$ represents a 2-bromophenyl group, and $R^6$ represents a C1-C4 haloalkyl group;
a compound wherein $R^1$ represents a 2-bromophenyl group, and $R^6$ represents a C3-C4 cycloalkyl group;
a compound wherein $R^1$ represents a 2-bromophenyl group, and $R^6$ represents a C3-C4 halocycloalkyl group;
a compound wherein $R^1$ represents a 2-bromophenyl group, and $R^6$ represents an C1-C4 alkoxy group;
a compound wherein $R^1$ represents a 2-bromophenyl group, and $R^6$ represents a C1-C4 haloalkoxy group;
a compound wherein $R^1$ represents a 2-bromophenyl group, and $R^6$ represents an C1-C4 alkylthio group;
a compound wherein $R^1$ represents a 2-bromophenyl group, and $R^6$ represents a C1-C4 haloalkylthio group;
a compound wherein $R^1$ represents a 2-bromophenyl group, and $R^6$ represents a hydrogen atom;
a compound wherein $R^1$ represents a 2-bromophenyl group, and $R^6$ represents a methyl group;
a compound wherein $R^1$ represents a 2-bromophenyl group, and $R^6$ represents an ethyl group;
a compound wherein $R^1$ represents a 2-bromophenyl group, and $R^6$ represents a propyl group;
a compound wherein $R^1$ represents a 2-bromophenyl group, and $R^6$ represents a cyclopropyl group;
a compound wherein $R^1$ represents a 2-bromophenyl group, and $R^6$ represents a trifluoromethyl group;
a compound wherein $R^1$ represents a 2-bromophenyl group, and $R^6$ represents a difluoromethyl group;
a compound wherein $R^1$ represents a 2-bromophenyl group, and $R^6$ represents a 2-propenyl group;
a compound wherein $R^1$ represents a 2-bromophenyl group, and $R^6$ represents a chlorine atom;
a compound wherein $R^1$ represents a 2-bromophenyl group, and $R^6$ represents a bromine atom;
a compound wherein $R^1$ represents a 2-bromophenyl group, and $R^6$ represents a fluorine atom;
a compound wherein $R^1$ represents a 2-bromophenyl group, and $R^6$ represents a vinyl group;
a compound wherein $R^1$ represents a 2-bromophenyl group, and $R^6$ represents a methoxy group;
a compound wherein $R^1$ represents a 2-methoxyphenyl group, and $R^6$ represents an C1-C4 alkyl group;
a compound wherein $R^1$ represents a 2-methoxyphenyl group, and $R^6$ represents a halogen atom;
a compound wherein $R^1$ represents a 2-methoxyphenyl group, and $R^6$ represents a C1-C4 haloalkyl group;
a compound wherein $R^1$ represents a 2-methoxyphenyl group, and $R^6$ represents a C3-C4 cycloalkyl group;
a compound wherein $R^1$ represents a 2-methoxyphenyl group, and $R^6$ represents a C3-C4 halocycloalkyl group;
a compound wherein $R^1$ represents a 2-methoxyphenyl group, and $R^6$ represents an C1-C4 alkoxy group;
a compound wherein $R^1$ represents a 2-methoxyphenyl group, and $R^6$ represents a C1-C4 haloalkoxy group;
a compound wherein $R^1$ represents a 2-methoxyphenyl group, and $R^6$ represents an C1-C4 alkylthio group;
a compound wherein $R^1$ represents a 2-methoxyphenyl group, and $R^6$ represents a C1-C4 haloalkylthio group;
a compound wherein $R^1$ represents a 2-methoxyphenyl group, and $R^6$ represents a hydrogen atom;
a compound wherein $R^1$ represents a 2-methoxyphenyl group, and $R^6$ represents a methyl group;
a compound wherein $R^1$ represents a 2-methoxyphenyl group, and $R^6$ represents an ethyl group;
a compound wherein $R^1$ represents a 2-methoxyphenyl group, and $R^6$ represents a propyl group;
a compound wherein $R^1$ represents a 2-methoxyphenyl group, and $R^6$ represents a cyclopropyl group;
a compound wherein $R^1$ represents a 2-methoxyphenyl group, and $R^6$ represents a trifluoromethyl group;
a compound wherein $R^1$ represents a 2-methoxyphenyl group, and $R^6$ represents a difluoromethyl group;
a compound wherein $R^1$ represents a 2-methoxyphenyl group, and $R^6$ represents a 2-propenyl group;
a compound wherein $R^1$ represents a 2-methoxyphenyl group, and $R^6$ represents a chlorine atom;
a compound wherein $R^1$ represents a 2-methoxyphenyl group, and $R^6$ represents a bromine atom;
a compound wherein $R^1$ represents a 2-methoxyphenyl group, and $R^6$ represents a fluorine atom;
a compound wherein $R^1$ represents a 2-methoxyphenyl group, and $R^6$ represents a vinyl group;
a compound wherein $R^1$ represents a 2-methoxyphenyl group, and $R^6$ represents a methoxy group;
a compound wherein $R^1$ represents a 2-methylphenyl group, and $R^6$ represents an C1-C4 alkyl group;
a compound wherein $R^1$ represents a 2-methylphenyl group, and $R^6$ represents a halogen atom;
a compound wherein $R^1$ represents a 2-methylphenyl group, and $R^6$ represents a C1-C4 haloalkyl group;
a compound wherein $R^1$ represents a 2-methylphenyl group, and $R^6$ represents a C3-C4 cycloalkyl group;
a compound wherein $R^1$ represents a 2-methylphenyl group, and $R^6$ represents a C3-C4 halocycloalkyl group;
a compound wherein $R^1$ represents a 2-methylphenyl group, and $R^6$ represents an C1-C4 alkoxy group;
a compound wherein $R^1$ represents a 2-methylphenyl group, and $R^6$ represents an C1-C4 alkoxy group;
a compound wherein $R^1$ represents a 2-methylphenyl group, and $R^6$ represents a C1-C4 haloalkoxy group;
a compound wherein $R^1$ represents a 2-methylphenyl group, and $R^6$ represents an C1-C4 alkylthio group;
a compound wherein $R^1$ represents a 2-methylphenyl group, and $R^6$ represents a C1-C4 haloalkylthio group;
a compound wherein $R^1$ represents a 2-methylphenyl group, and $R^6$ represents a hydrogen atom;

a compound wherein $R^1$ represents a 2-methylphenyl group, and $R^6$ represents a methyl group;

a compound wherein $R^1$ represents a 2-methylphenyl group, and $R^6$ represents an ethyl group;

a compound wherein $R^1$ represents a 2-methylphenyl group, and $R^6$ represents a propyl group;

a compound wherein $R^1$ represents a 2-methylphenyl group, and $R^6$ represents a cyclopropyl group;

a compound wherein $R^1$ represents a 2-methylphenyl group, and $R^6$ represents a trifluoromethyl group;

a compound wherein $R^1$ represents a 2-methylphenyl group, and $R^6$ represents a difluoromethyl group;

a compound wherein $R^1$ represents a 2-methylphenyl group, and $R^6$ represents a 2-propenyl group;

a compound wherein $R^1$ represents a 2-methylphenyl group, and $R^6$ represents a chlorine atom;

a compound wherein $R^1$ represents a 2-methylphenyl group, and $R^6$ represents a bromine atom;

a compound wherein $R^1$ represents a 2-methylphenyl group, and $R^6$ represents a vinyl group;

a compound wherein $R^1$ represents a 2-methylphenyl group, and $R^6$ represents a methoxy group;

a compound wherein $R^1$ represents a 2-trifluoromethoxyphenyl group, and $R^6$ represents an C1-C4 alkyl group;

a compound wherein $R^1$ represents a 2-trifluoromethoxyphenyl group, and $R^6$ represents a halogen atom;

a compound wherein $R^1$ represents a 2-trifluoromethoxyphenyl group, and $R^6$ represents a C1-C4 haloalkyl group;

a compound wherein $R^1$ represents a 2-trifluoromethoxyphenyl group, and $R^6$ represents a C3-C4 cycloalkyl group;

a compound wherein $R^1$ represents a 2-trifluoromethoxyphenyl group, and $R^6$ represents a C3-C4 halocycloalkyl group;

a compound wherein $R^1$ represents a 2-trifluoromethoxyphenyl group, and $R^6$ represents an C1-C4 alkoxy group;

a compound wherein $R^1$ represents a 2-trifluoromethoxyphenyl group, and $R^6$ represents a C1-C4 haloalkoxy group;

a compound wherein $R^1$ represents a 2-trifluoromethoxyphenyl group, and $R^6$ represents an C1-C4 alkylthio group;

a compound wherein $R^1$ represents a 2-trifluoromethoxyphenyl group, and $R^6$ represents a C1-C4 haloalkylthio group;

a compound wherein $R^1$ represents a 2-trifluoromethoxyphenyl group, and $R^6$ represents a hydrogen atom;

a compound wherein $R^1$ represents a 2-trifluoromethoxyphenyl group, and $R^6$ represents a methyl group;

a compound wherein $R^1$ represents a 2-trifluoromethoxyphenyl group, and $R^6$ represents an ethyl group;

a compound wherein $R^1$ represents a 2-trifluoromethoxyphenyl group, and $R^6$ represents a propyl group;

a compound wherein $R^1$ represents a 2-trifluoromethoxyphenyl group, and $R^6$ represents a cyclopropyl group;

a compound wherein $R^1$ represents a 2-trifluoromethoxyphenyl group, and $R^6$ represents a trifluoromethyl group;

a compound wherein $R^1$ represents a 2-trifluoromethoxyphenyl group, and $R^6$ represents a difluoromethyl group;

a compound wherein $R^1$ represents a 2-trifluoromethoxyphenyl group, and $R^6$ represents a 2-propenyl group;

a compound wherein $R^1$ represents a 2-trifluoromethoxyphenyl group, and $R^6$ represents a chlorine atom;

a compound wherein $R^1$ represents a 2-trifluoromethoxyphenyl group, and $R^6$ represents a bromine atom;

a compound wherein $R^1$ represents a 2-trifluoromethoxyphenyl group, and $R^6$ represents a fluorine atom;

a compound wherein $R^1$ represents a 2-trifluoromethoxyphenyl group, and $R^6$ represents a vinyl group;

a compound wherein $R^1$ represents a 2-trifluoromethoxyphenyl group, and $R^6$ represents a methoxy group;

a compound wherein $R^1$ represents a 2-methylphenyl group, and $R^6$ represents an C1-C4 alkyl group;

a compound wherein $R^1$ represents a 2-methylphenyl group, and $R^6$ represents a halogen atom;

a compound wherein $R^1$ represents a 2-methylphenyl group, and $R^6$ represents a C1-C4 haloalkyl group;

a compound wherein $R^1$ represents a 2-methylphenyl group, and $R^6$ represents a C3-C4 cycloalkyl group;

a compound wherein $R^1$ represents a 2-methylphenyl group, and $R^6$ represents a C3-C4 halocycloalkyl group;

a compound wherein $R^1$ represents a 2-methylphenyl group, and $R^6$ represents an C1-C4 alkoxy group;

a compound wherein $R^1$ represents a 2-methylphenyl group, and $R^6$ represents a C1-C4 haloalkoxy group;

a compound wherein $R^1$ represents a 2-methylphenyl group, and $R^6$ represents an C1-C4 alkylthio group;

a compound wherein $R^1$ represents a 2-methylphenyl group, and $R^6$ represents a C1-C4 haloalkylthio group;

a compound wherein $R^1$ represents a 2-methylphenyl group, and $R^6$ represents a hydrogen atom;

a compound wherein $R^1$ represents a 2-methylphenyl group, and $R^6$ represents a methyl group;

a compound wherein $R^1$ represents a 2-methylphenyl group, and $R^6$ represents an ethyl group;

a compound wherein $R^1$ represents a 2-methylphenyl group, and $R^6$ represents an ethyl group;

a compound wherein $R^1$ represents a 2-methylphenyl group, and $R^6$ represents a propyl group;

a compound wherein $R^1$ represents a 2-methylphenyl group, and $R^6$ represents a cyclopropyl group;

a compound wherein $R^1$ represents a 2-methylphenyl group, and $R^6$ represents a trifluoromethyl group;

a compound wherein $R^1$ represents a 2-methylphenyl group, and $R^6$ represents a difluoromethyl group;

a compound wherein $R^1$ represents a 2-methylphenyl group, and $R^6$ represents a 2-propenyl group;

a compound wherein $R^1$ represents a 2-methylphenyl group, and $R^6$ represents a chlorine atom;

a compound wherein $R^1$ represents a 2-methylphenyl group, and $R^6$ represents a bromine atom;

a compound wherein $R^1$ represents a 2-methylphenyl group, and $R^6$ represents a fluorine atom;

a compound wherein $R^1$ represents a 2-methylphenyl group, and $R^6$ represents a vinyl group;

a compound wherein $R^1$ represents a 2-methylphenyl group, and $R^6$ represents a methoxy group;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents hydrogen atom, $R^6$ represents a 2-propenyl group, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 2 trifluoromethoxyphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a methyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents an ethyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a propyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a cyclopropyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a difluoromethyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a 2-propenyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a chlorine atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a bromine atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a fluorine atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a vinyl group, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a methoxy group, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-chlorophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-fluorophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-bromophenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methoxyphenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents hydrogen atom, $R^6$ represents a cyclopropyl group, represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a trifluoromethyl group, represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, represents a hydrogen atom, $R^9$ represents a hydrogen atom, $R^{10}$ represents a methyl group, Q represents an oxygen atom, and Y represents an oxygen atom;

a compound wherein $R^1$ represents a 2 trifluoromethoxyphenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-trifluoromethoxyphenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a hydrogen atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a propyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound wherein $R^1$ represents a 2-methylphenyl group, X represents a sulfur atom, $R^2$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, Q represents an oxygen atom, and Y represents an oxygen atom;

a compound of the formula (a) wherein $R^1$ represents a butyl group, a tert-butyl group, a cyclopropyl group, 1-adamantyl group, a 2-propenyl group, an isopropenyl group or a trifluoromethyl group, $R^2$, $R^4$, $R^5$, $R^7$, $R^8$ and $R^9$ represent independently of each other a halogen atom, $R^6$ represents an hydrogen atom, a bromo group, a methyl group, an ethyl group, a methoxy group or a cyclopropyl group, $R^{10}$ represents a methyl group, X represents a sulfur atom, and Q and Y represent an oxygen atom;

a compound of the formula (1) wherein $R^1$ represents an C1-C12 alkyl group, $R^2$, $R^4$, $R^5$, $R^7$, $R^8$ and $R^9$ represent independently of each other a halogen atom, $R^6$ represents a hydrogen atom, a halogen atom, an C1-C4 alkyl group, an C1-C4 alkoxy group, a C3-C4 cycloalkyl group or a C1-C4 haloalkyl group, $R^{10}$ represents a methyl group, X represents a sulfur atom, and Q and Y represent an oxygen atom;

a compound of the formula (2) wherein $R^{21}$ represents a hydrogen atom, a halogen atom, an C1-C6 alkyl group, a C1-C6 haloalkyl group, an C1-C6 alkoxy group, a C1-C6 haloalkoxy group, an C1-C6 alkylthio group, a C1-C5 haloalkylthio group, a nitro group or a cyano group, $R^{23}$ and $R^{25}$ represent independently of each other a hydrogen atom, a halogen atom, $R^{22}$ and $R^{24}$ represent independently of each other a hydrogen atom, a halogen atom, $R^2$ represents a hydrogen atom, a halogen atom or an C1-C6 alkyl group, $R^4$ and $R^5$ represent a hydrogen atom, $R^6$ represents a hydrogen atom, an C1-C4 alkyl group, a C3-C4 cycloalkyl group, a C1-C4 haloalkyl group, a halogen atom or an C1-C4 alkoxy group, $R^7$, $R^8$ and $R^9$ represent independently of each other a hydrogen atom or a halogen atom, $R^{10}$ represents a methyl group, X represents a sulfur atom or an oxygen atom, Q represents an oxygen atom, and Y represents a sulfur atom or an oxygen atom;

a compound of the formula (2) wherein R21 represents a hydrogen atom, a fluorine atom, a chlorine atom, a bromine atom, an iodine atom, a methyl group, an ethyl group, a butyl group, a tert-butyl group, a trifluoromethyl group, a methoxy group, an ethoxy group, an isopropyloxy group, trifluoromethoxy group, a methylthio group, a trifluoromethylthio group, a nitro group or a cyano group, $R^{23}$ and $R^{25}$ represent independently of each other a hydrogen atom, a fluorine atom, a chlorine atom or a bromine atom, $R^{22}$ and $R^{24}$ represent independently of each other a hydrogen atom, a fluorine atom or a chlorine atom, $R^2$ represents a hydrogen atom, a bromine atom or a methyl group, $R^4$ and $R^5$ represent a hydrogen atom, $R^6$ represents a hydrogen atom, a methyl group, an ethyl group, a vinyl group, an isopropenyl group, an ethynyl group, a propargyl group, a propynyl group, a cyclopropyl group, a trifluoromethyl group, a fluorine atom, a chlorine atom, a bromine atom, a methoxy group, a nitro group or an amino group, $R^7$, $R^8$ and $R^9$ represent independently of each other a hydrogen atom or a fluorine atom, $R^{10}$ represents a methyl group, X represents a sulfur atom or an oxygen atom, Q represents an oxygen atom, and Y represents an oxygen atom;

a compound wherein $R^1$ represents a group of the formula (3), $R^{32}$ represents a hydrogen atom, an C1-C6 alkyl group, an C1-C6 alkoxy group, a C1-C6 haloalkyl group, a C1-C6 haloalkoxy group, an C1-C6 alkylthio group or a cyano group, $R^{31}$, $R^{33}$, $R^{34}$ and $R^{35}$ represent a hydrogen atom, $R^2$, $R^4$, $R^5$, $R^7$, $R^8$ and $R^9$ represent a hydrogen atom, $R^6$ represents a methyl group, $R^{10}$ represents a methyl group, X represents a sulfur atom, Q represents an oxygen atom and Y represents an oxygen atom;

a compound wherein $R^1$ represents a group of the formula (3), $R^{32}$ represents a hydrogen atom, a methyl group, an ethyl group, a butyl group, a heptyl group, a methoxy group, an ethoxy group, an isopropyloxy group, a trifluoromethyl group, a trifluoromethoxy group, a methylthio group or a cyano group, $R^{31}$, $R^{33}$, $R^{34}$ and $R^{35}$ represent a hydrogen atom, $R^2$, $R^4$, $R^5$, $R^7$, $R^8$ and $R^9$ represent a hydrogen atom, $R^6$ represents a methyl group, $R^{10}$ represents a methyl group, X represents a sulfur atom, Q represents an oxygen atom and Y represents an oxygen atom;

a compound wherein $R^1$ represents a group of the formula (4), $R^{43}$ represents a hydrogen atom, a halogen atom, an C1-C6 alkyl group, an C1-C6 alkoxy group, a C1-C6 haloalkyl group, a C1-C6 haloalkoxy group, an C1-C6 alkylthio group, a cyano group or a hydroxy group, $R^{41}$ represents a hydrogen atom or a halogen atom, $R^{42}$, $R^{44}$ and $R^{45}$ represent a hydrogen atom, $R^2$, $R^4$, $R^5$, $R^7$, $R^8$ and $R^9$ represent a hydrogen atom, $R^6$ represents a hydrogen atom, an C1-C4 alkyl group, a C3-C4 cycloalkyl group, a C1-C4 haloalkyl group, a halogen atom, an C1-C4 alkoxy group, $R^{10}$ represents a methyl group, X represents a sulfur atom, Q represents an oxygen atom or a sulfur atom, and Y represents an oxygen atom;

a compound wherein $R^1$ represents a group of the formula (4), $R^{43}$ represents a hydrogen atom, a fluorine atom, a methyl group, an ethyl group, a butyl group, a heptyl group, a methoxy group, an ethoxy group, an isopropyloxy group, a trifluoromethyl group, trifluoromethoxy group, a methylthio group, a cyano group or a hydroxy group, $R^{41}$ represents a hydrogen atom, a fluorine atom or a chlorine atom, $R^{42}$, $R^{44}$ and $R^{45}$ represent a hydrogen atom, $R^2$, $R^4$, $R^5$, $R^7$, $R^8$ and $R^9$ represent a hydrogen atom, $R^6$ represents a hydrogen atom, a methyl group, an ethyl group, a cyclopropyl group, trifluoromethyl group, a fluorine atom, a chlorine atom, a bromine atom, iodine atom, a methoxy group or an ethoxy group, $R^{10}$ represents a methyl group, X represents a sulfur atom, Q represents an oxygen atom or a sulfur atom, and Y represents an oxygen atom;

a tetrazolinone compound represented by a formula (X):

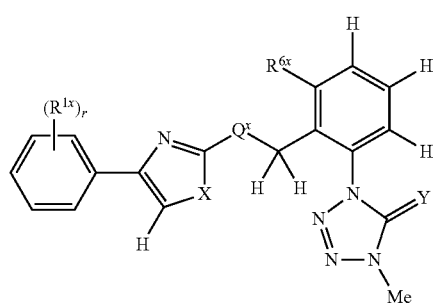

[wherein
$R^{1x}$ represents a hydrogen atom, an C1-C6 alkyl group, a C1-C6 haloalkyl group, an C1-C6 alkoxy group, a C1-C6 haloalkoxy group, an C1-C6 alkylthio group, an C2-C6 acyl group or a halogen atom;
r is an integer of any one of 0 to 5 (with the proviso that when r is an integer of any one of 2 to 5, a plural of said $R^{1x}$s may be same or different from each other);

X represents a sulfur atom or an oxygen atom;

Y represents an oxygen atom or a sulfur atom;

$Q^x$ represents an oxygen atom or a sulfur atom;

$R^{6x}$ represents a hydrogen atom, a halogen atom, an C1-C6 alkyl group, a C1-C6 haloalkyl group, a C3-C6 cycloalkyl group or an C1-C6 alkoxy group];

a tetrazolinone compound represented by a formula (Y):

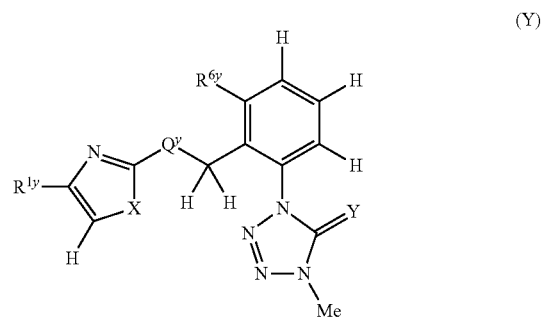

[wherein
$R^{1y}$ represents a halogen atom, an C1-C6 alkyl group, a C1-C6 haloalkyl group, an C1-C6 alkenyl group, a C3-C6 cycloalkyl group, an C2-C6 acyl group, a naphthyl group or an adamantyl group;

X represents a sulfur atom or an oxygen atom;

Y represents a sulfur atom or an oxygen atom;

$Q^x$ represents an oxygen atom or a sulfur atom;

$R^{6y}$ represents a hydrogen atom, a halogen atom, an C1-C6 alkyl group, a C1-C6 haloalkyl group, a C3-C6 cycloalkyl group or an C1-C6 alkoxy group].

Herein, although a structural formula of a compound represents a definite isomeric form for convenience, the compound of the present invention is not limited to the expediential description of the structure formula, and encompasses all isomeric forms including active geometric isomers, optical isomers, stereoisomers, and tautomers which each may be arisen due to the structure of the compound and isomeric mixtures thereof, and may be either one of the isomeric forms or mixtures thereof. For example, although the compound of the present invention has an asymmetric carbon atom and may thus include optically active substances and racemates, the compound of the present invention is not specifically limited thereto, and may encompass any ones.

The present compound can be prepared, for example, according to the below-mentioned process.

(Process A)

The present compound of the formula (1) can be prepared by reacting a compound of a formula (A1) (hereinafter, described as Compound (A1)) with compound of either a formula (A21), a formula (A22) or a formula (A23) (hereinafter, each described as Compound (A21), Compound (A22) or Compound (A23)) in the presence of a base.

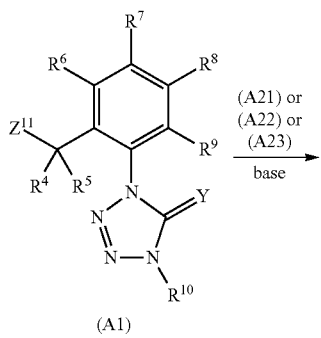

(A1)

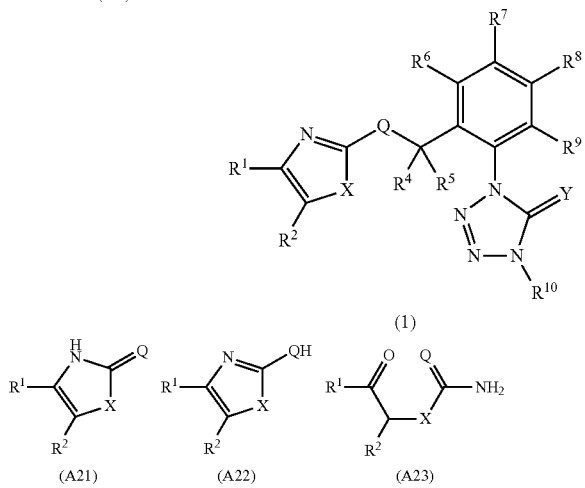

(1)

(A21)   (A22)   (A23)

[wherein
$R^1, R^2, R^4, R^5, R^6, R^7, R^8, R^9, R^{10}$, X, Y and Q are the same as defined above, $Z^{11}$ represents a leaving group such as a chlorine atom, a bromine atom, an iodine atom, a methanesulfonyloxy group, a trifluoromethanesulfonyloxy group, or a p-toluenesulfonyloxy group.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone: esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (A21), Compound (A22) or Compound (A23) is each used usually within a range of 1 to 10 molar ratio(s), and the base is used usually within a range of 1 to 10 molar ratio(s), as opposed to 1 mole of Compound (A1).

The reaction temperature is usually within a range of −20 to 150° C. The reaction period of the reaction is usually within a range of 0.1 to 24 hours. If necessary, sodium iodide, tetrabutylammonium iodide and the others may be added to the reaction and these compounds are used usually within a range of 0.001 to 5 molar ratios as opposed to 1 mole of Compound (A1).

When the reaction is completed, the reaction mixtures are extracted with organic solvent(s), and the resulting organic layers are worked up (for example, drying and concentration) to isolate the present compound of the formula (1). The isolated present compound may be further purified, for example, by chromatography and recrystallization.

(Process B)

The present compound of the formula (1) wherein Q is an oxygen atom, i.e., the compound of a formula (1-10) (hereinafter, described as Compound (1-10)), can be prepared by reacting a compound of a formula (B1) (hereinafter, described as Compound (B1)) with compound of a formula (B2) (hereinafter, described as Compound (B2)) in the presence of a base.

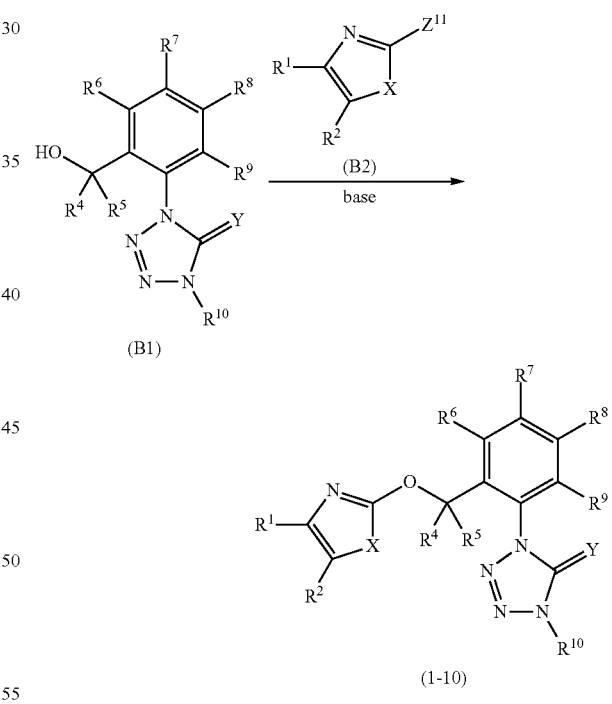

(B1)

(1-10)

[wherein
$R^1, R^2, R^4, R^5, R^6, R^7, R^8, R^9, R^{10}$, X, Y and $Z^{11}$ are the same as defined above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone: esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as cesium fluoride; alkali metal hydrides such as lithium hydride, sodium hydride, potassium hydride; and alkali metal alkoxides such as sodium tert-butoxide, potassium tert-butoxide.

In the reaction, Compound (B2) is used usually within a range of 1 to 10 molar ratio(s), and the base is used usually within a range of 1 to 10 molar ratio(s), as opposed to 1 mole of Compound (B1).

The reaction temperature is usually within a range of −20 to 150° C. The reaction period of the reaction is usually within a range of 0.1 to 24 hours. If necessary, sodium iodide, tetrabutylammonium iodide and the others may be added to the reaction and these compounds are used usually within a range of 0.001 to 5 molar ratios as opposed to 1 mole of Compound (B1).

When the reaction is completed, the reaction mixtures are extracted with organic solvent(s), and the resulting organic layers are worked up (for example, drying and concentration) to isolate the present compound of the formula (1). The isolated present compound may be further purified, for example, by chromatography and recrystallization.

(Process C)

The present compound of the formula (1) wherein Y represents a sulfur atom (hereinafter, described as Compound (1-S)) can be prepared by sulfurating a compound of the formula (1) wherein Y represents an oxygen atom (hereinafter, described as Compound (1-O)).

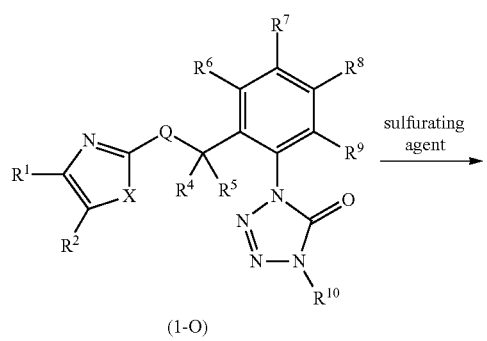

(1-O)

-continued

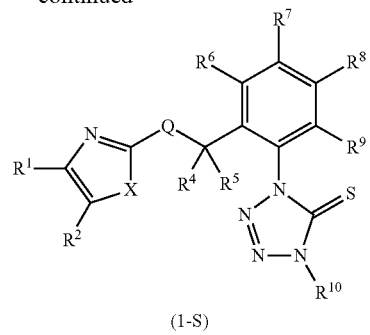

(1-S)

[wherein $R^1$, $R^2$, $R^4$, $R^5$, $R^6$, $R^7$, $R^8$, $R^9$, $R^{10}$, X and Q are the same as defined above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as acetonitrile, propionitrile; and mixed solvents thereof.

Examples of the sulfurating agent to be used in the reaction include phosphorus pentasulfide, Lawesson's reagent (2,4-bis(4-methoxyphenyl)-1,3,2,4-dithiadiphosphetane 2,4-disulfide). In the reaction, the sulfurating agent is used within a range of 0.5 to 1.5 molar ratios as opposed to 1 mole of Compound (1-0).

The reaction temperature is usually within a range of −20 to 150° C. The reaction period of the reaction is usually within a range of 0.1 to 24 hours. If necessary, organic bases such as pyridine and triethylamine and inorganic bases such as alkali metal hydroxides and alkali metal carbonates and the others may be added to the reaction and these compounds are used usually within a range of 0.5 to 1.5 molar ratios as opposed to 1 mole of Compound (1-0).

When the reaction is completed, the reaction mixtures are extracted with organic solvent(s), and the resulting organic layers are worked up (for example, drying and concentration) to isolate the present compound of the formula (1-S). The isolated present compound may be further purified, for example, by chromatography and recrystallization.

(Process D)

The present compound of the formula (1) can be prepared by reacting a compound of a formula (D1) (hereinafter, described as Compound (D1)) with a compound of a formula (D2) (hereinafter, described as Compound (D2)) in the presence of a base.

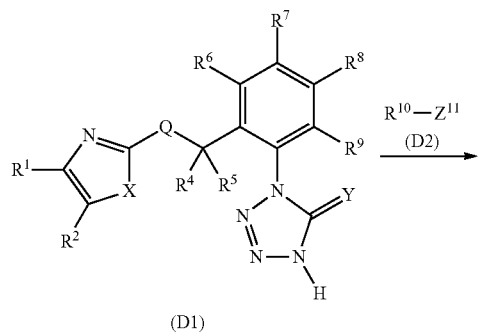

(D1)

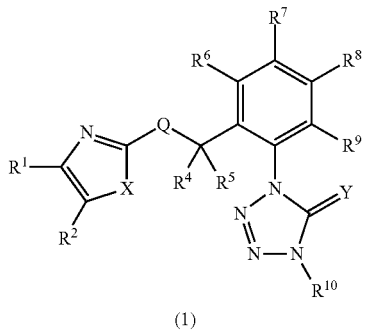

(1)

[wherein
$R^1, R^2, R^4, R^5, R^6, R^7, R^8, R^9, R^{10}, X, Y, Q$ and $Z^{11}$ are the same as defined above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone: esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (D2) to be used in the reaction can be usually used as a commercially available product. Specific examples include alkyl halides such as chlorodifluoromethane, methyl bromide, ethyl bromide, n-propyl bromide, methyl iodide, ethyl iodide, n-propyl bromide, aryl bromide, cyclopropyl bromide, benzyl bromide, 1,1-difluoro-2-iodoethane; dialkyl sulfates such as dimethyl sulfate, diethyl sulfate and di-n-propyl sulfate; alkyl or aryl sulfates such as methyl p-toluenesulfonate, ethyl methanesulfonate and n-propyl methanesulfonate; and halogenated alkoxyalkyls such as chloromethoxymethane; and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide. In the reaction, Compound (D2) is used usually within a range of 1 to 10 molar ratio(s), and the base is used usually within a range of 0.5 to 10 molar ratios, as opposed to 1 mole of Compound (D1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1). The isolated present compound may be further purified, for example, by chromatography and recrystallization.

(Process F)

The present compound of the formula (1) wherein $R^6$ represents $R^{71}$, i.e., the compound of a formula (1-1) (hereinafter, described as Compound (1-1)), can be prepared by coupling a compound of a formula (F11) (hereinafter, described as Compound (F11)) with a compound of a formula (F21) (hereinafter, described as Compound (F21)) in the presence of a base and a catalyst.

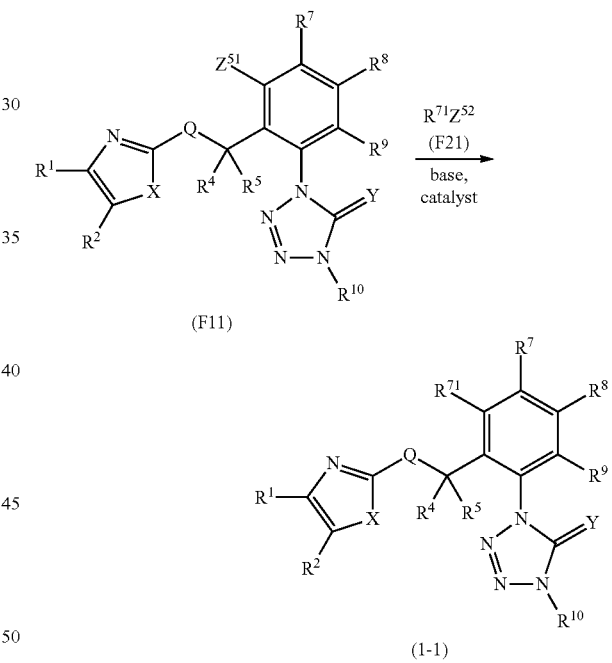

[wherein,
$R^1, R^2, R^4, R^5, R^7, R^8, R^9, R^{10}, Q, X$ and $Y$ are the same as defined above, $Z^{51}$ represents a chlorine atom, a bromine atom or a trifluoromethanesulfonyloxy group, $R^{71}$ represents an C1-C12 alkyl group, a C1-C12 haloalkyl group, a C2-C12 alkenyl group, a C2-C12 haloalkenyl group, an C2-C12 alkynyl group, a C2-C12 haloalkynyl group or a C3-C12 cycloalkyl group, and $Z^{52}$ represents a B(OH)$_2$, an alkoxyboryl group or a trifluoroborate (BF$_3^-$K$^+$).]

The reaction is performed according to the methods described in J. Am. Chem. Soc. 1989, 111, 314 or Chem. Rev. 1995, 95, 2457.

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone: esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Examples of Compound (F21) to be used in the reaction include boronic acid derivatives, boronate ester derivatives and trifluoroborate salts, and these compounds are used as a commercially available product, or may be prepared according to a method described in a review article of N. Miyaura and A. Suzuki, Chem. Rev. 1995, 95, 2457 and the others.

The boronate ester derivatives can be prepared, for example, by reacting an iodo compound ($R^{71}$—I) or a bromo compound ($R^{71}$—Br) with an alkyl lithium (such as butyl lithium), followed by reacting the resulting mixtures with boronate esters such as trimethyl borate. The resulting boronate ester derivatives can be hydrolyzed to the corresponding boronic acid derivatives as needed. Further, according to a method described in a review article of Molander et al. Acc. Chem. Res. 2007, 40, 275 and the others, the above-mentioned boronate ester derivatives can be fluorinated with potassium bifluoride and the like to obtain the trifluoroborate salts.

Examples of the catalyst to be used in the reaction include dichlorobis(triphenylphosphine)palladium, tetrakistriphenylphosphinepalladium(0), palladium(II) acetate/triscyclohexylphosphine, bis(diphenylphoshine ferrocenyl)palladium (II) dichloride, 1,3-bis(2,6-diisopropylphenyl)imidazole-2-ylidene (1,4-naphthoquinone)palladium dimer, aryl(chloro) (1,3-dimethyl-1,3-dihydro-2H-imidazole-2-ylidene) palladium or palladium(II) acetate/dicyclohexyl(2',4',6'-triisopropylbiphenyl-2-yl)phosphine, and tris(dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; and alkali metal alkoxides such as sodium methoxide, sodium ethoxide, sodium tert-butoxide, potassium tert-butoxide.

In the reaction, Compound (F21) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (F11).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-1). The isolated present compound may be further purified, for example, by chromatography and recrystallization.

According to Process F, the present compound of the formula (1) wherein $R^7$ represents $R^{71}$, i.e., compound of a below-mentioned formula (1-2) (hereinafter, described as Compound (1-2)), can be prepared by coupling compound of a formula (F12) (hereinafter, describes as Compound (F12)) with Compound (F12) in the presence of a base and the catalyst.

According to the process for preparing the above-mentioned Compound (1-1), the present compound of the formula (1) wherein $R^8$ represents $R^{71}$, i.e., a compound of a below-mentioned formula (1-3) (hereinafter, described as Compound (1-3)), can be prepared by coupling a compound of a below-mentioned formula (F13) (hereinafter, described as Compound (F13)) with Compound (F21) in the presence of a base and a catalyst.

According to the process for preparing the above-mentioned Compound (1-1), the present compound of the formula (1) wherein $R^9$ represents $R^{71}$, i.e., a compound of a below-mentioned formula (1-4) (hereinafter, described as Compound (1-4)), can be prepared by coupling compound of a below-mentioned formula (F14) (hereinafter, described as Compound (F14)) with Compound (F21) in the presence of a base and a catalyst.

According to the process for preparing the above-mentioned Compound (1-1), the present compound of the formula (1) wherein $R^1$ represents $R^{81}$, i.e., a compound of a below-mentioned formula (1-5) (hereinafter, described as Compound (1-5)), can be prepared by coupling compound of below-mentioned formula (F15) (hereinafter, described as Compound (F15)) with Compound (F31) in the presence of a base and a catalyst.

According to the process for preparing the above-mentioned Compound (1-1), the present compound of the formula (1) wherein $R^2$ represents $R^{91}$, i.e., a compound of a below-mentioned formula (1-6) (hereinafter, described as Compound (1-6)), can be prepared by coupling a compound of a below-mentioned formula (F16) (hereinafter, described as Compound (F16)) with Compound (F41) in the presence of a base and a catalyst.

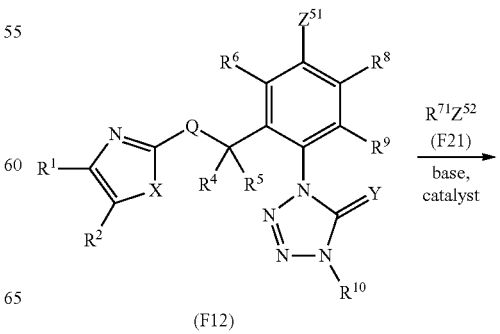

(F12)

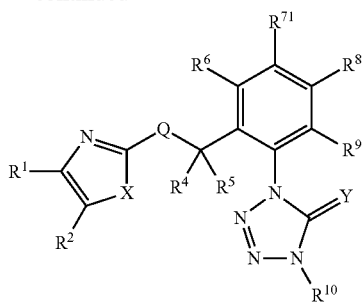

(1-2)

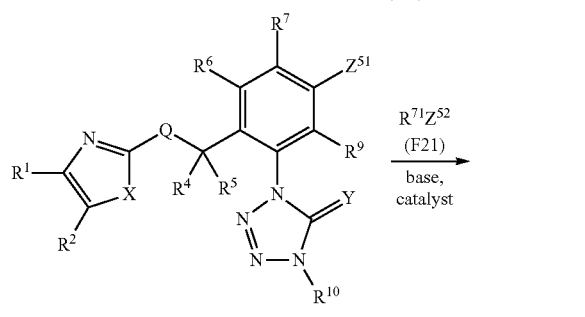

(F13)

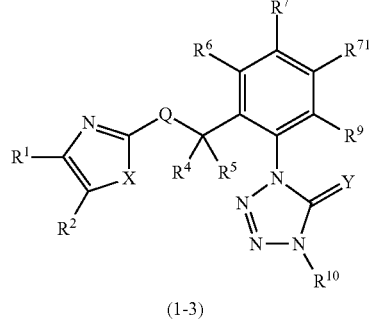

(1-3)

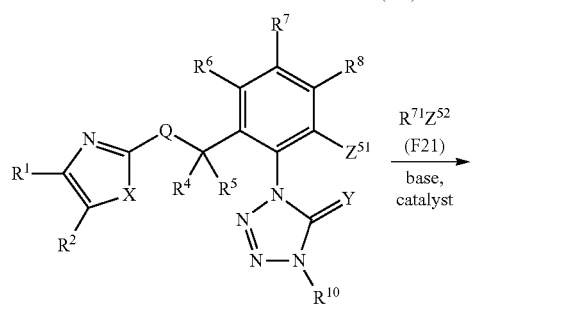

(F14)

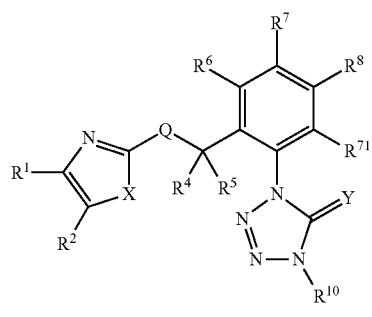

(1-4)

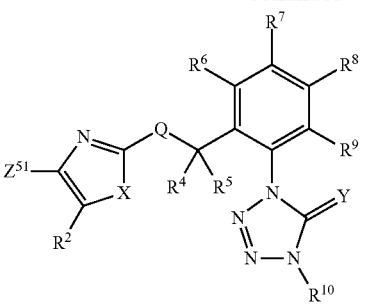

(F15)

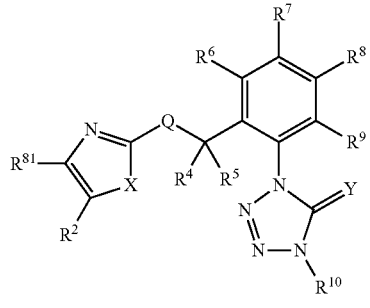

(1-5)

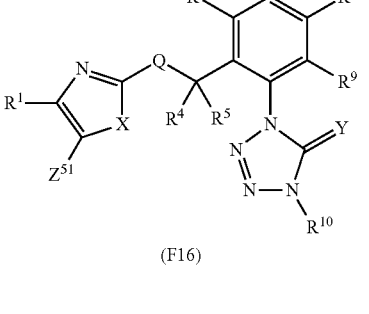

(F16)

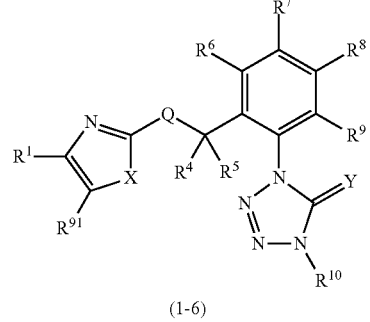

(1-6)

[wherein $R^1, R^2, R^4, R^5, R^6, R^7, R^8, R^9, R^{10}, Z^{51}, Z^{52}, R^{71}$, X and Y are the same as described above;

$R^{81}$ represents an C6-C16 aryl group optionally substituted with one or more substituents selected from group $P^1$ which may be same or different from each other when the number of the selected substituents is two or more, an C7-C18 aralkyl group optionally substituted with one or more substituents selected from group $P^1$ which may be same or different from each other when the number of the selected substituents is two or more, an C1-C12 alkyl group optionally substituted with one or more substituents selected from group $P^1$ which may be same or different from each other when the number of the selected substituents is two or more, an C2-C12 alkenyl group optionally substituted with one or more substituents selected from group $P^1$ which may be same or different from each other when the number of the selected substituents is two or more, or an C3C1-C2 cycloalkyl group optionally substituted with one or more substituents selected from group $P^1$ which may be same or different from each other when the number of the selected substituents is two or more; and $R^{91}$ represents an C1-C12 alkyl group, a C1-C12 haloalkyl group, an C1-C12 alkenyl group, a C1-C12 haloalkenyl group, an C1-C12 alkynyl group or a C1-C12 haloalkynyl group.]

According to the above-mentioned Process F, the compound of the formula (1) wherein two or more substituents selected from $R^1$, $R^2$, $R^6$, $R^7$, $R^8$ or $R^9$ represents either $R^{71}$, $R^{81}$ or $R^{91}$ can be prepared.

The present compound of the formula (1) can be prepared as needed, by using the other known coupling methods instead of the above-mentioned Process F.

Hereinafter, a process for preparing the present thiazole compound Z is described in detail.

The present thiazole compound can be prepared, for example, by the below-mentioned process.

(Synthesis Z1)

The present thiazole compound Z of the above-mentioned formula wherein $R^{57}$ represents a nitro group, i.e., a compound of a below-mentioned formula (H3) (hereinafter, described as Compound (H3)), can be prepared by reacting a compound of a below-mentioned formula (H1) (hereinafter, described as Compound (H1)) with compound of a below-mentioned formula (H2) (hereinafter, described as Compound (H2)) in the presence of a base.

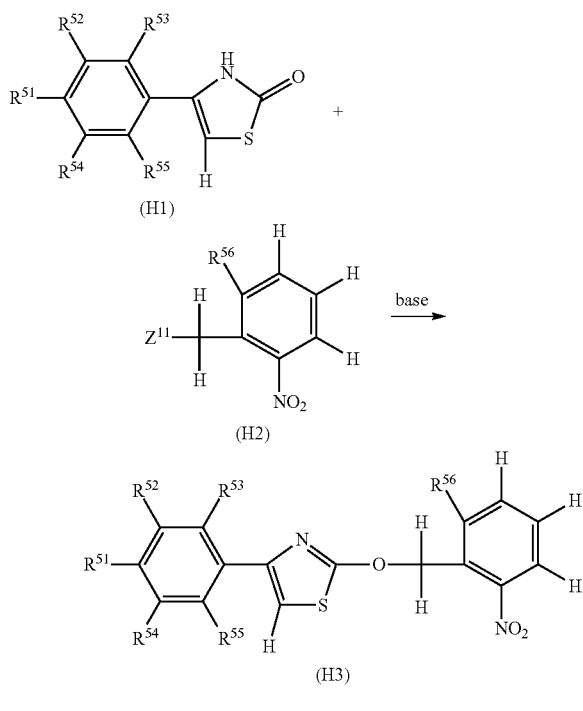

[wherein
$R^{51}$, $R^{52}$, $R^{53}$, $R^{54}$, $R^{55}$, $R^{56}$ and $Z^{11}$ are the same as described above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone: esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (H2) is used usually within a range of 1 to 10 molar ratio(s), and the base is used usually within a range of 0.5 to 5 molar ratio(s), as opposed to 1 mole of Compound (H2).

The reaction temperature is usually within a range of −20 to 150° C. The reaction period of the reaction is usually within a range of 0.1 to 24 hours. If necessary, sodium iodide, tetrabutylammonium iodide and the others may be added to the reaction and these compounds are used usually within a range of 0.001 to 1.2 molar ratios as opposed to 1 mole of Compound (H1).

When the reaction is completed, the reaction mixtures are extracted with organic solvent(s), and the resulting organic layers are worked up (for example, drying and concentration) to isolate Compound (H3). Compound (H3) may be further purified, for example, by chromatography and recrystallization.

(Synthesis Z2)

The present thiazole compound Z of the above-mentioned formula (5) wherein $R^{57}$ represents an amino group, i.e., a compound of a below-mentioned formula (H4) (hereinafter, described as Compound (H4)), can be prepared by reacting a compound of the above-mentioned Compound (H3)) with hydrogen gas in the presence of a catalyst.

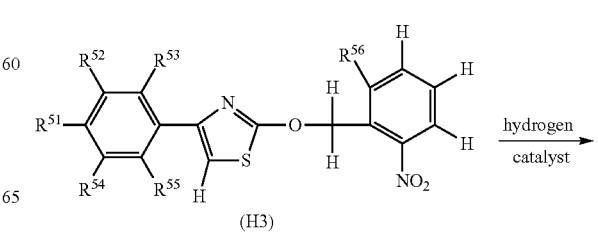

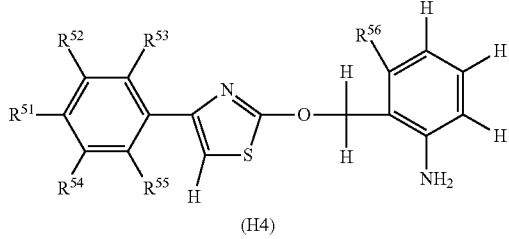

(H4)

[wherein
R$^{51}$, R$^{52}$, R$^{53}$, R$^{54}$, R$^{55}$ and R$^{56}$ are the same as described above.]

This reaction is usually carried out in a solvent.

Examples of the solvent to be used in the reaction include alcohols such as methanol, ethanol, propanol, butanol; esters such as ethyl acetate, butyl acetate; halogenated hydrocarbons such as carbon tetrachloride, chloroform, dichloromethane, 1,2-dichloroethane, tetrachloroethane, chlorobenzene; ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; acetic acid; water; and mixed solvents thereof.

Examples of the catalyst to be used in the reaction include palladium on carbon (Pd/C), osmium on carbon (Os/C), ruthenium on carbon (Ru/C), rhodium on carbon (Rh/C) and Raney nickel.

The reaction temperature is usually within a range of −20 to 150° C. The reaction period of the reaction is usually within a range of 0.1 to 24 hours.

When the reaction is completed, the catalyst is filtered off, and the resulting organic layers are worked up (for example, concentration) to isolate Compound (H4). The isolated Compound (H4) may be further purified, for example, by distillation, chromatography and recrystallization.

(Synthesis Z3)

Compound (4) can be prepared also by reacting the above-mentioned Compound (H3) with a reducing agent in an acid.

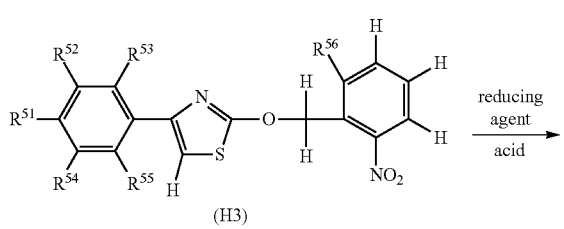

(H3)

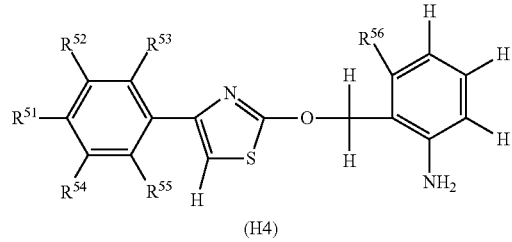

(H4)

[wherein
R$^{51}$, R$^{52}$, R$^{53}$, R$^{54}$, R$^{55}$ and R$^{56}$ are the same as described above.]

This reaction is usually carried out in a solvent.

Examples of the solvent to be used in the reaction include aliphatic carboxylic acids such as acetic acid; alcohols such as methanol, ethanol; water and mixed solvents thereof.

Examples of the reducing agent to be used in the reaction include iron, tin and zinc.

Examples of the acid to be used in the reaction include hydrochloric acid, sulfuric acid, acetic acid, aqueous ammonium chloride solution.

In the reaction, the reducing agent is used usually within a range of 1 to 30 molar ratio(s), as opposed to 1 mole of Compound (H3).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (H4). Compound (H4) may be further purified, for example, by distillation, chromatography and recrystallization.

(Synthesis Z4)

The present thiazole compound Z of the above-mentioned formula (5) wherein R$^{57}$ represents an isocyanate group, i.e., a compound of a below-mentioned formula (H5) (hereinafter, described as Compound (H5)), can be prepared by reacting Compound (H4) with phosgenes.

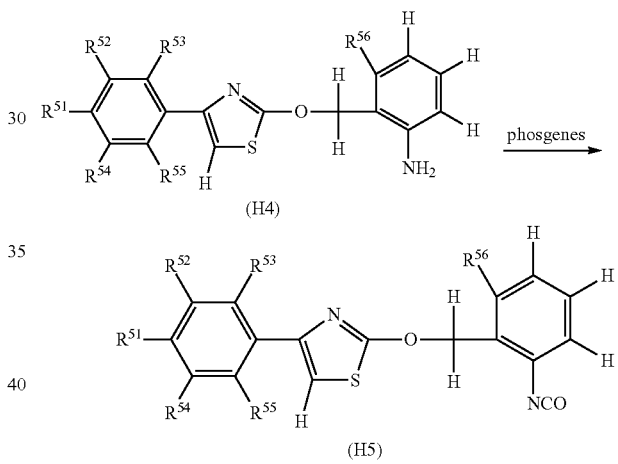

[wherein
R$^{51}$, R$^{52}$, R$^{53}$, R$^{54}$, R$^{55}$ and R$^{56}$ are the same as described above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the phosgenes to be used in the reaction include phosgene, diphosgene and triphosgene.

In the reaction, phosgenes are used usually within a range of 0.3 to 10 molar ratios, as opposed to 1 mole of Compound (H4).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonates and the others may be added to the reaction, and these compounds are used usually within a range of 0.05 to 5 molar ratios as opposed to 1 mole of Compound (H4).

When the reaction is completed, the reaction mixtures are extracted with organic solvent(s), and the resulting organic layers are worked up (for example, drying and concentration) to isolate Compound (H5). The isolated Compound (H5) may be further purified, for example, by chromatography and recrystallization.

(Synthesis Z5)

The present thiazole compound Z of the above-mentioned formula (5) wherein $R^{57}$ represents a NSO group, i.e., a compound of a below-mentioned formula (H6) (hereinafter, described as Compound (H6)), can be prepared by reacting Compound (H6) with a thionyl chloride.

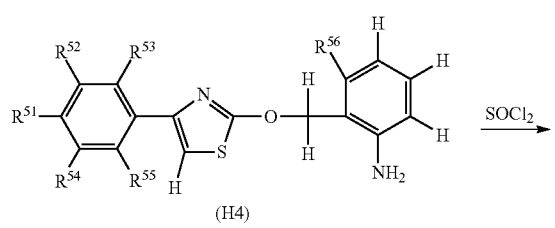

[wherein
$R^{51}$, $R^{52}$, $R^{53}$, $R^{54}$, $R^{55}$ and $R^{56}$ are the same as described above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

In the reaction, thionyl chloride is used usually within a range of 1 to 10 molar ratio(s) as opposed to 1 mole of Compound (H4).

The reaction temperature is usually within a range of –20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (H6). The isolated Compound (H6) may be further purified, for example, by chromatography and recrystallization.

(Synthesis Z6)

The compound of the below-mentioned formula (H5) can be prepared also by reacting Compound (H6) with phosgenes.

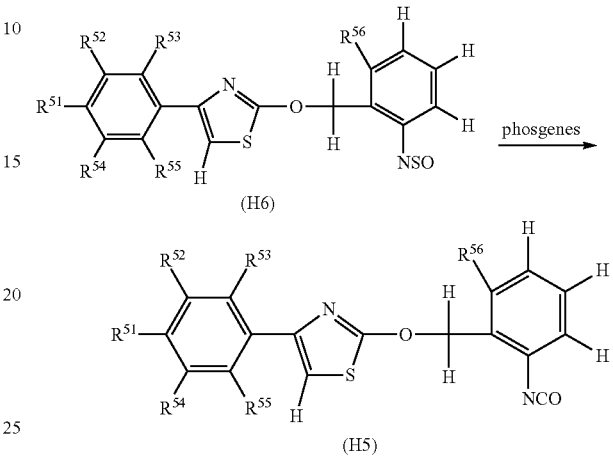

[wherein
$R^{51}$, $R^{52}$, $R^{53}$, $R^{54}$, $R^{55}$ and $R^{56}$ are the same as described above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the phosgenes to be used in the reaction include phosgene, diphosgene and triphosgene.

In the reaction, phosgenes are used usually within a range of 0.3 to 10 molar ratios as opposed to 1 mole of Compound (H6).

The reaction temperature is usually within a range of –20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonates and the others may be added to the reaction, and these compounds are used usually within a range of 0.05 to 5 molar ratios as opposed to 1 mole of Compound (H6).

When the reaction is completed, the reaction mixtures are extracted with organic solvent(s), and the resulting organic layers are worked up (for example, drying and concentration) to isolate Compound (H5). The isolated Compound (H5) may be further purified, for example, by distillation, chromatography and recrystallization.

(Synthesis Z7)

The present thiazole compound Z of the above-mentioned formula (5) wherein $R^{57}$ represents an C2-C6 alkoxycarbonyl group, i.e., a compound of a below-mentioned formula (H8) (hereinafter, described as Compound (H8)), can be prepared by reacting Compound (H1) with a below-mentioned formula (H7) (hereinafter, described as Compound (H7)) in the presence of a base.

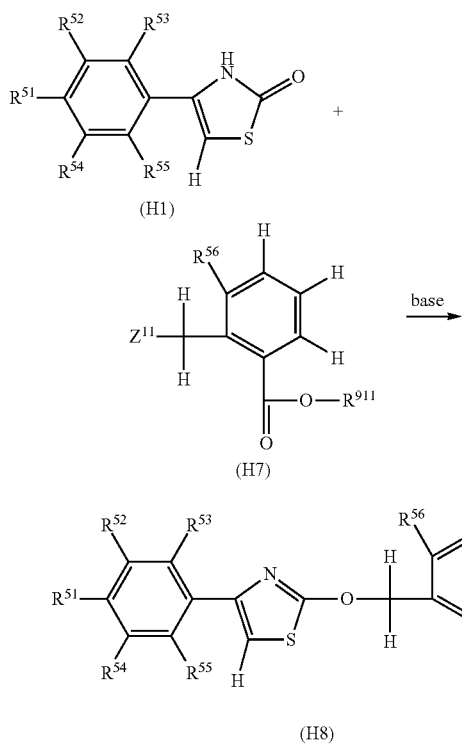

[wherein,
$R^{51}$, $R^{52}$, $R^{53}$, $R^{54}$, $R^{55}$, $R^{56}$ and $Z^{11}$ are the same as described above; and $R^{911}$ represents an C1-C5 alkyl group.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (H7) is used usually within a range of 1 to 10 molar ratio(s), and the base is used usually within a range of 0.5 to 50 molar ratios, as opposed to 1 mole of Compound (H1).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction, and these compounds are used usually within a range of 0.001 to 1.2 molar ratios as opposed to 1 mole of Compound (H1).

When the reaction is completed, the reaction mixtures are extracted with organic solvent(s), and the resulting organic layers are worked up (for example, drying and concentration) to isolate Compound (H8). The isolated Compound (H8) may be further purified, for example, by chromatography and recrystallization.

(Synthesis Z8)

The present thiazole compound Z of the above-mentioned formula (5) wherein $R^{57}$ represents a carbonyl group, i.e., a compound of a below-mentioned formula (H9) (hereinafter, described as Compound (H9)), can be prepared by reacting Compound (H8) with a hydrolytic agent.

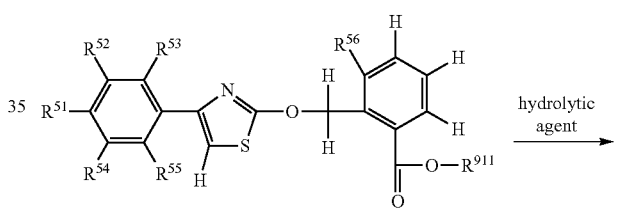

[wherein
$R^{51}$, $R^{52}$, $R^{53}$, $R^{54}$, $R^{55}$, $R^{56}$, and $R^{911}$ are the same as described above.]

This reaction is usually carried out in a solvent.

Examples of the solvent to be used in the reaction include water; alcohols such as methanol, ethanol, propanol, butanol; hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; ketones such as acetone, methyl ethyl ketone, methyl isobutyl ketone; and mixed solvents thereof.

Examples of the hydrolytic agent to be used in the reaction include bases such as aqueous potassium hydroxide solution and aqueous sodium hydroxide solution; and acids such as hydrochloric acid and sulfuric acid.

In the reaction, the hydrolytic agent is used usually within a range of 0.5 to 20 molar ratios as opposed to 1 mole of Compound (H8).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (H9). The isolated Compound (H9) may be further purified, for example, by distillation, chromatography and recrystallization.

(Synthesis Z9)

The present thiazole compound Z of the above-mentioned formula (5) wherein $R^{57}$ represents a halogenated acyl group, i.e., a compound of a below-mentioned formula (H10) (hereinafter, described as Compound (H10)), can be prepared by reacting Compound (H9) with a halogenating agent.

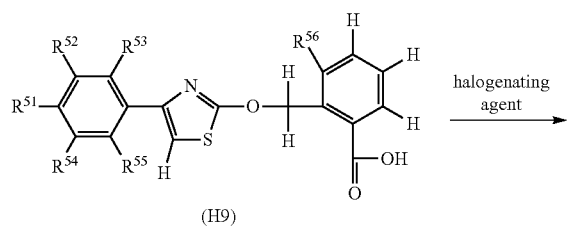

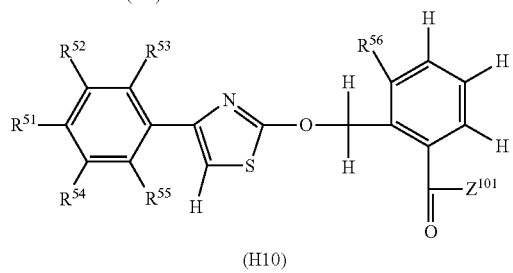

[wherein
$R^{51}$, $R^{52}$, $R^{53}$, $R^{54}$, $R^{55}$, $R^{56}$, and $Z^{101}$ are the same as described above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include phosphorous oxychloride, phosphorous trichloride, phosphorous pentachloride, thionyl chloride, phosphorous oxybromide, phosphorus tribromide, phosphorous pentabromide, phosphorus triiodide, oxalyl dichloride, oxalyl dibromide, triphosgene, diphosgene, phosgene and sulfuryl chloride.

In the reaction, the halogenating agent is used usually within a range of 1 to 10 molar ratio(s) as opposed to 1 mole of Compound (H9).

The reaction temperature is usually within a range of −20 to 150° C. The reaction period of the reaction is usually within a range of 0.1 to 24 hours.

A catalyst may be added to the reaction, and includes, for example, dimethylformamide. The catalyst is used usually within a range of 0.001 to 1 molar ratio(s) as opposed to 1 mole of Compound (H9).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene; alkali metal carbonate such as lithium carbonate, sodium carbonate, potassium carbonate and cesium carbonate; alkali metal bicarbonate such as lithium bicarbonate, sodium bicarbonate, potassium bicarbonate and cesium bicarbonate and the other may be added to the reaction, and these compounds are used usually within a range of 0.05 to 5 molar ratios as opposed to 1 mole of Compound (H9).

When the reaction is completed, the reaction mixtures are extracted with organic solvent(s), and the resulting organic layers are worked up (for example, drying and concentration) to isolate Compound (H10). The isolated Compound (H10) may be further purified, for example, by distillation, chromatography and recrystallization.

(Synthesis Z10)

The present thiazole compound Z of the above-mentioned formula (5) wherein $R^{57}$ represents a $CON_3$ group, i.e., compound of a below-mentioned formula (H11) (hereinafter, described as Compound (H11)), can be prepared by reacting Compound (H10) with sodium azide.

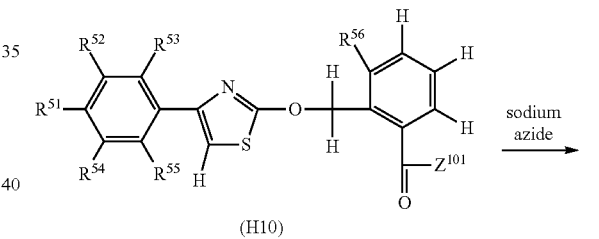

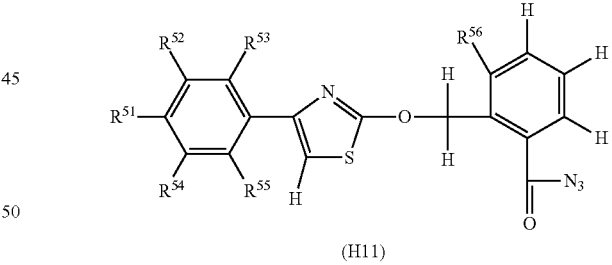

[wherein
$R^{51}$, $R^{52}$, $R^{53}$, $R^{54}$, $R^{55}$, $R^{56}$, and $Z^{101}$ are the same as described above.]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

In the reaction, sodium azide is used usually within a range of 1 to 10 molar ratio(s) as opposed to 1 mole of Compound (H10).

The reaction temperature is usually within a range of −20 to 50° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (H11). The isolated Compound (H11) may be further purified, for example, by chromatography and recrystallization.

(Synthesis Z11)

Compound (H5) can be prepared also by heating Compound (H11).

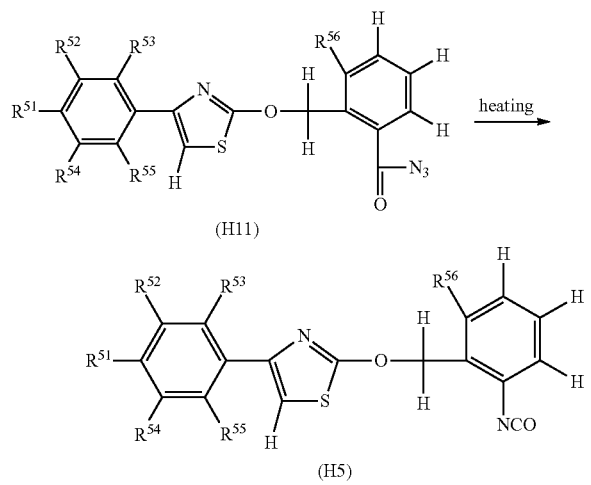

[wherein
$R^{51}$, $R^{52}$, $R^{53}$, $R^{54}$, $R^{55}$ and $R^{56}$ are the same as described above.]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (H5). The isolated Compound (H5) may be further purified, for example, by distillation, chromatography and recrystallization.

(Synthesis Z12)

The present thiazole compound Z of the above-mentioned formula (5) wherein $R^{57}$ represents a $CONH_2$ group, i.e., a compound of a below-mentioned formula (H13) (hereinafter, described as Compound (H13)), can be prepared by reacting Compound (H10) with an ammonia.

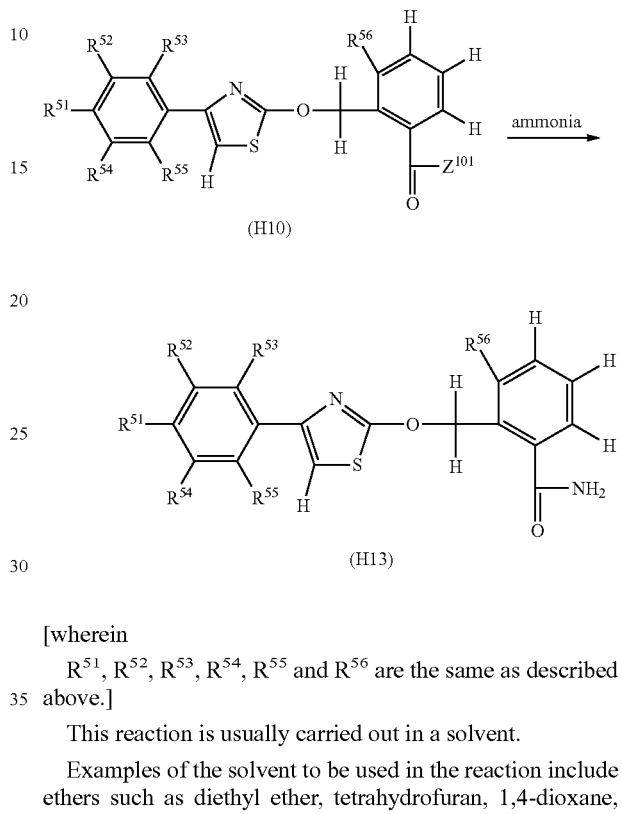

[wherein
$R^{51}$, $R^{52}$, $R^{53}$, $R^{54}$, $R^{55}$ and $R^{56}$ are the same as described above.]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of the ammonia to be used in the reaction include aqueous ammonia, ammonia gas, ammonia methanol solution and ammonia ethanol solution.

In the reaction, ammonia is used usually within a range of 1 to a large excess molar ratio(s) as opposed to 1 mole of Compound (H10).

The reaction temperature is usually within a range of −20 to 50° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (H13). The isolated Compound (H13) may be further purified, for example, by chromatography and recrystallization.

(Synthesis Z13)

Compound (H5) can be also prepared by reacting Compound (H13) with hypohalous acid salts.

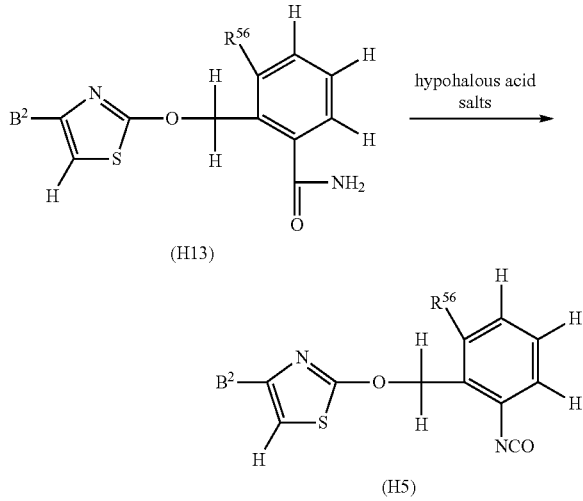

[wherein $R^{51}$, $R^{52}$, $R^{53}$, $R^{54}$, $R^{55}$ and $R^{56}$ are the same as described above.]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of the hypohalous acid salts to be used in the reaction include sodium hypobromite, sodium hypochlorite, potassium hypobromite, potassium hypochlorite, barium hypobromite, barium hypochlorite, calcium hypobromite and calcium hypochlorite.

Also chlorine or bromine is mixed with sodium hydroxide, potassium hydroxide, barium hydroxide, calcium hydroxide and the others to form a hypochlorite or a hypobromite, which also can be used.

The reaction temperature is usually within a range of 0 to 150° C. The reaction period of the reaction is usually within a range of 0.1 to 24 hours.

In the reaction, the hypohalous acid salts are used usually within a range of 1 to 10 molar ratio(s) as opposed to 1 mole of Compound (H13).

When the reaction is completed, the reaction mixtures are extracted with organic solvent(s), and the resulting organic layers are worked up (for example, drying and concentration) to isolate Compound (H5). The isolated Compound (H5) may be further purified, for example, by distillation, chromatography and recrystallization.

(Synthesis Z14)

The present thiazole compound Z of the above-mentioned formula (5) wherein $R^{57}$ represents a CONHOH group, i.e., a compound of a below-mentioned formula (H14) (hereinafter, described as Compound (H14)), can be prepared by reacting Compound (H10) with hydroxylamine.

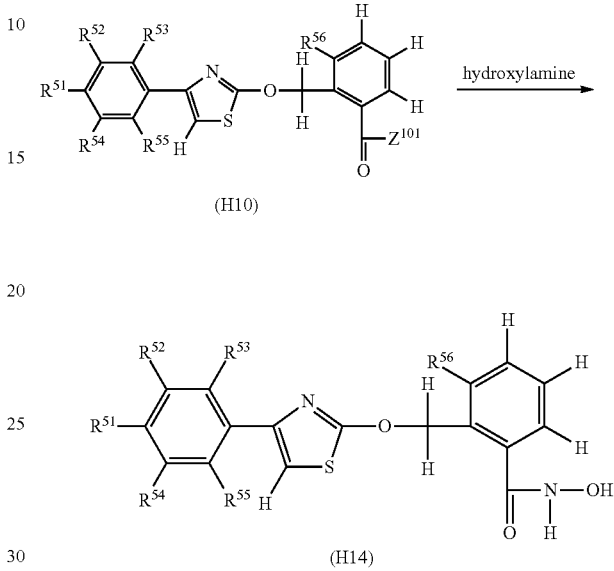

[wherein $R^{51}$, $R^{52}$, $R^{53}$, $R^{54}$, $R^{55}$, $R^{56}$ and $Z^{101}$ are the same as described above.]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

In the reaction, hydroxylamine is used usually within a range of 1 to 10 molar ratio(s) as opposed to 1 mole of Compound (H10).

The reaction temperature is usually within a range of −20 to 50° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (H14). The isolated Compound (H14) may be further purified, for example, by chromatography and recrystallization.

(Synthesis Z15)

Compound (H5) can be prepared also by reacting Compound (H14) with an acylating agent.

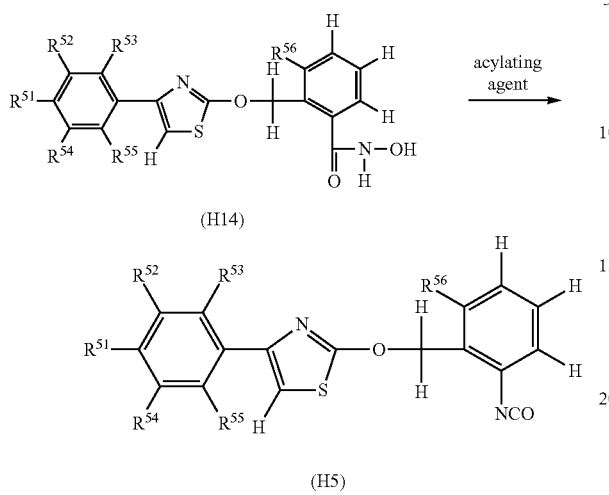

[wherein
$R^{51}$, $R^{52}$, $R^{53}$, $R^{54}$, $R^{55}$ and $R^{56}$ are the same as described above.]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Example of the acylating agent to be used in the reaction include acid anhydride such as acetic anhydride, propionic anhydride; acyl halides such as acetyl chloride, acetyl bromide, benzolyl chloride; sulfonyl chlorides such as p-toluenesulfonyl chloride, methanesulfonyl chloride; sulfur trioxide-pyridine complex and thionyl chloride.

If necessary, a base such as pyridine, triethylamine, tributylamine, diazabicycloundecene, sodium hydroxide, potassium hydroxide may be added to the reaction, and these compounds are used usually within a range of 1 to 10 molar ratio(s) as opposed to 1 mole of Compound (H14).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (H5). The isolated Compound (H5) may be further purified, for example, by distillation, chromatography and recrystallization.

(Synthesis Z16)

The present thiazole compound Z of the above-mentioned formula (5) wherein $R^{57}$ represents a CONHCl group or a CONHBr group, i.e., a compound of a below-mentioned formula (H15) (hereinafter, described as Compound (H15)), can be prepared by reacting Compound (H13) with a halogenating agent.

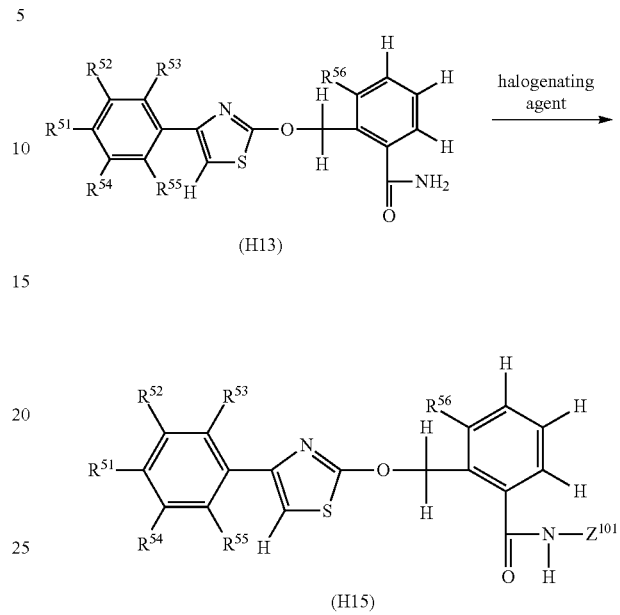

[wherein
$R^{51}$, $R^{52}$, $R^{53}$, $R^{54}$, $R^{55}$, $R^{56}$ and $Z^{101}$ are the same as described above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include sodium hypochlorite, tert-butyl hypochlorite, isocyanuric acid, chlorine and sulfuryl chloride.

In the reaction, a halogenating agent is used usually within a range of 1 to 10 molar ratio(s) as opposed to 1 mole of Compound (H13).

The reaction temperature is usually within a range of −20 to 150° C. The reaction period of the reaction is usually within a range of 0.1 to 24 hours.

A catalyst may be added to the reaction, and includes, for example, dimethylformamide. The catalyst is used usually within a range of 0.001 to 1 molar ratio(s) as opposed to 1 mole of Compound (H13).

When the reaction is completed, the reaction mixtures are extracted with organic solvent(s), and the resulting organic layers are worked up (for example, drying and concentration) to isolate Compound (H15). The isolated Compound (H15) may be further purified, for example, by distillation, chromatography and recrystallization.

(Synthesis Z17)

Compound (H5) can be prepared also by reacting Compound (H15) with a base.

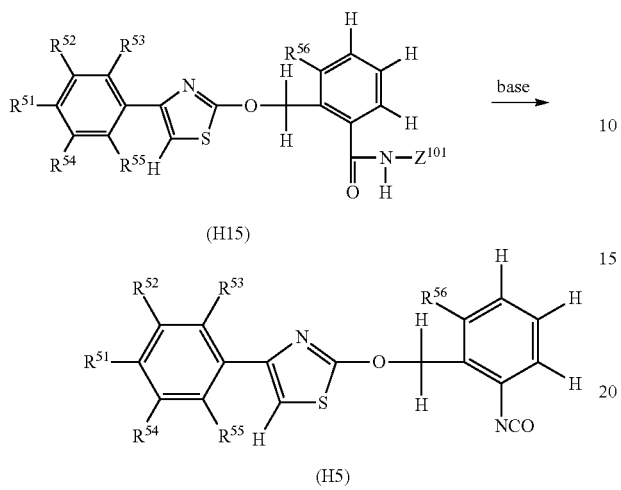

[wherein
$R^{51}$, $R^{52}$, $R^{53}$, $R^{54}$, $R^{55}$, $R^{56}$ and $Z^{101}$ are the same as described above.]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; water; and mixed solvents thereof.

Examples of the base to be used in the reaction include pyridine, triethylamine, tributylamine, diazabicycloundecene, sodium hydroxide, potassium hydroxide. In the reaction, the base is used usually within a range of 1 to 10 molar ratio(s) as opposed to 1 mole of Compound (H15).

The reaction temperature is usually within a range of −20 to 150° C. The reaction period of the reaction is usually within a range of 0.1 to 24 hours.

When the reaction is completed, the reaction mixtures are extracted with organic solvent(s) and the resulting organic layers are worked up (for example, drying and concentration) to isolate Compound (H5). The isolated Compound (H5) may be further purified, for example, by distillation, chromatography and recrystallization.

(Synthesis Z18)

The present thiazole compound Z of the above-mentioned formula (5) wherein $R^{57}$ represents a halogen atom, i.e., a compound of a below-mentioned formula (H17) (hereinafter, described as Compound (H17)), can be prepared by reacting Compound (H1) with a compound of the below-mentioned formula (H16) (hereinafter, described as Compound (H16)) in the presence of a base.

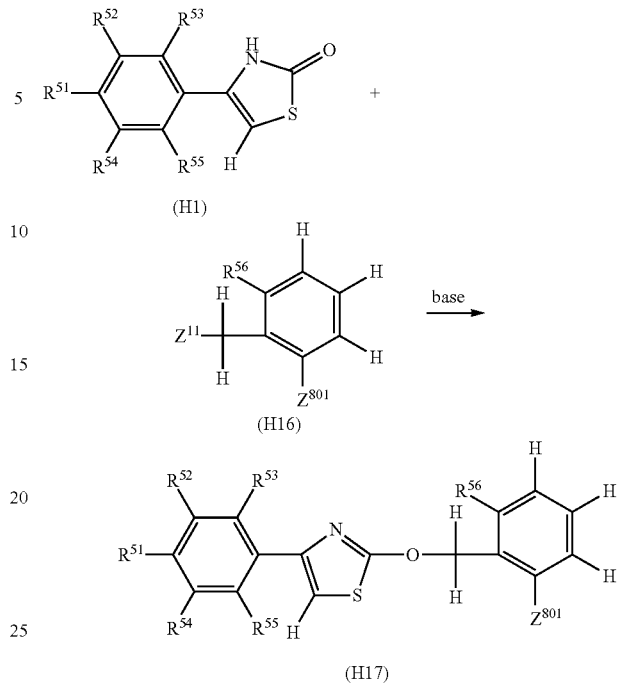

[wherein
$R^{51}$, $R^{52}$, $R^{53}$, $R^{54}$, $R^{55}$, $R^{56}$, $Z^{11}$ and $Z^{801}$ are the same as described above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali-metal carbonates such as lithium carbonate, sodium carbonate, potassium carbonate, cesium carbonate; alkali-metal bicarbonates such as lithium bicarbonate, sodium bicarbonate, potassium bicarbonate, cesium bicarbonate; alkali-metal hydroxides such as lithium hydroxide, sodium hydroxide, potassium hydroxide, cesium hydroxide; alkali-metal halides such as sodium fluoride, potassium fluoride, cesium fluoride; alkali-metal hydrides such as lithium hydride, sodium hydride, potassium hydride; alkali metal alkoxides such as sodium tert-butoxide, potassium tert-butoxide; and the others.

In the reaction, Compound (H16) is used usually within a range of 1 to 10 molar ratio(s), and the base is used usually within a range of 0.5 to 5 molar ratio(s), as opposed to 1 mole of Compound (H1).

The reaction temperature is usually within a range of −20 to 150° C. The reaction period of the reaction is usually within a range of 0.1 to 24 hours.

If necessary, sodium iodide, tetrabutylammonium iodide or the others may be added to the reaction, and these compounds is used usually within a range of 0.001 to 1.2 molar ratio(s) as opposed to 1 mole of Compound (H1).

When the reaction is completed, the reaction mixtures are extracted with organic solvent(s), and the resulting organic layers are worked up (for example, drying and concentration) to isolate Compound (H17). The isolated Compound (H17) may be further purified, for example, by chromatography and recrystallization.

(Synthesis Z19)

Compound (H9) can be also prepared by reacting Compound (H17) with a carbonylating agent.

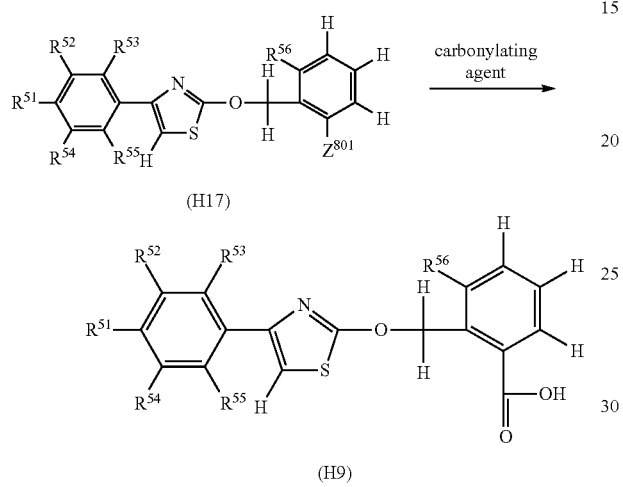

[wherein
$R^{51}$, $R^{52}$, $R^{53}$, $R^{54}$, $R^{55}$, $R^{56}$, and $Z^{801}$ are the same as described above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; and mixed solvents thereof.

Examples of the carbonylating agent to be used in the reaction include a combination of metal or metallic compound and carbon homologation agent, such as that of magnesium and carbon dioxide, that of isopropylmagnesium bromide and carbon dioxide, and that of n-butyllitium and carbon dioxide.

In the reaction, the metal or metallic compound is used usually within a range of 1 to 20 molar ratio(s), and the carbon homologation agent is used usually within a range of 1 to a large excess molar ratio(s), as opposed to 1 mole of Compound (17).

When carbon dioxide is used as carbon homologation agent, examples of the carbon dioxide include carbonic acid gas and dry ice.

The reaction temperature is usually within a range of −80 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (H9). The isolated Compound (H9) may be further purified, for example, by distillation, chromatography and recrystallization.

(Synthesis Z20)

A compound of the below-mentioned formula (H18) (hereinafter, described as Compound (H18)) can be prepared by reacting a compound of the below-mentioned formula (H5) (hereinafter, described as Compound (H5)) with an azidation agent.

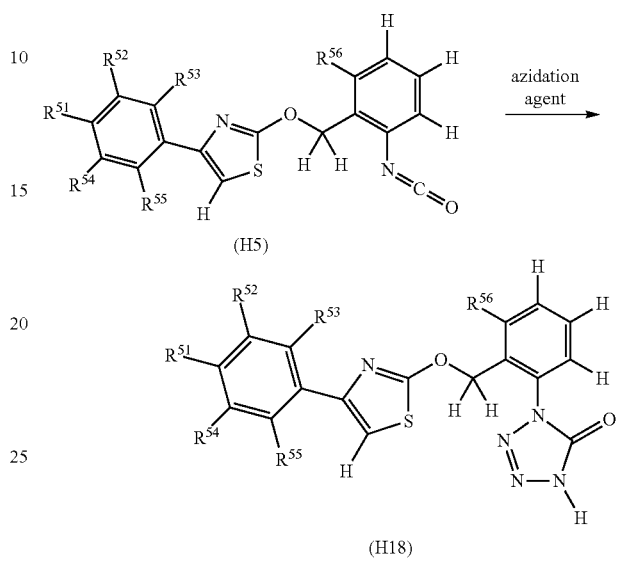

[wherein
$R^{51}$, $R^{52}$, $R^{53}$, $R^{54}$, $R^{55}$ and $R^{56}$ are the same as described above.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Examples of the azidation agent to be used in the reaction include inorganic azides such as sodium azide, barium azide and lithium azide; and organic azides such as trimethylsilyl azide and diphenylphosphoryl azide.

In the reaction, the azidation agent is used usually within a range of 1 to 10 molar ratio(s) as opposed to 1 mole of Compound (H5).

The reaction temperature is usually within a range of −20 to 150° C. The reaction period of the reaction is usually within a range of 0.1 to 24 hours.

If necessary, a Lewis acid such as aluminium chloride and zinc chloride may be added to the reaction, and these compounds are used usually within a range of 0.05 to 5 molar ratio(s) as opposed to 1 mole of Compound (H5).

When the reaction is completed, the reaction mixtures are extracted with organic solvent(s), and the resulting organic layers are worked up (for example, drying and concentration) to isolate Compound (H18). The isolated Compound (H18) may be further purified, for example, by chromatography and recrystallization.

Hereinafter, a process for preparing an intermediate compound is described in detail.

(Reference Process A)

A compound of a formula (XA3) (hereinafter, described as Compound (XA3)) can be prepared by reacting a compound of a formula (XA1) (hereinafter, described as Compound (XA1)) or a compound of a formula (XA2) (hereinafter, described as Compound (XA2)) with an azidation agent.

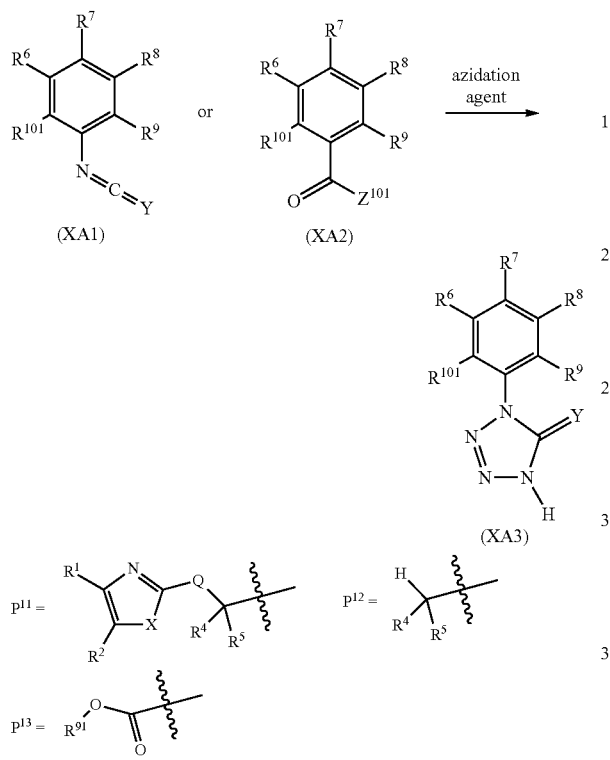

[wherein
$R^1$, $R^2$, $R^4$, $R^5$, $R^6$, $R^7$, $R^8$, $R^9$, X and Y are the same as described above; $R^{101}$ represents $P^{11}$, $P^{12}$ or $P^{13}$; $R^{91}$ represents an C1-C12 alkyl group; $Z^{101}$ represents a chlorine atom or a bromine atom; and a wavy line represents a binding site.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Examples of the azidation agent to be used in the reaction include inorganic azides such as sodium azide, barium azide and lithium azide; and organic azides such as trimethylsilyl azide and diphenylphosphoryl azide.

In the reaction, the azidation agent is used usually within a range of 1 to 10 molar ratio(s) as opposed to 1 mole of Compound (XA1) or Compound (XA2).

The reaction temperature is usually within a range of −20 to 150° C. The reaction period of the reaction is usually within a range of 0.1 to 24 hours.

If necessary, a Lewis acid such as aluminium chloride and zinc chloride may be added to the reaction, and these compounds are used usually within a range of 0.001 to 5 molar ratio(s) as opposed to 1 mole of Compound (XA1) or Compound (XA2).

When the reaction is completed, the reaction mixtures are extracted with organic solvent(s), and the resulting organic layers are worked up (for example, drying and concentration) to isolate Compound (XA3). The isolated Compound (XA3) may be further purified, for example, by chromatography and recrystallization.

(Reference Process B)

Compound (XA1) can be prepared by reacting a compound of a formula (XB1) (hereinafter, described as Compound (XB1)) with phosgenes.

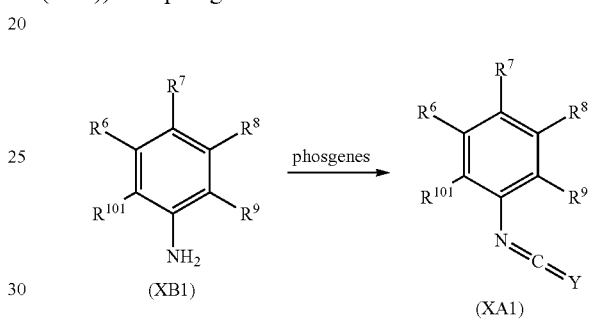

[wherein
$R^6$, $R^7$, $R^8$, $R^9$, $R^{101}$ and Y are the same as described above; $R^{101}$ represents $P^{11}$, $P^{12}$ or $P^{13}$; $R^{91}$ represents an C1-C12 alkyl group; $Z^{101}$ represents a chlorine atom or a bromine atom; and a wavy line represents a binding site.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the phosgenes to be used in the reaction include phosgene, diphosgene, triphosgene, and thiophosgene.

In the reaction, the phosgenes are used usually within a range of 0.3 to 10 molar ratios as opposed to 1 mole of Compound (XB1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali-metal carbonates such as lithium carbonate, sodium carbonate, potassium carbonate, cesium carbonate; alkali-metal bicarbonates such as lithium bicarbonate, sodium bicarbonate, potassium bicarbonate, cesium bicarbonate may be added to the reaction, and these compounds are used usually within a range of 0.001 to 5 molar ratios as opposed to 1 mole of Compound (XB1).

When the reaction is completed, the reaction mixtures are extracted with organic solvent(s), and the resulting organic layers are worked up (for example, drying and concentration) to isolate Compound (XA1). The isolated Compound (XA1) may be further purified, for example, by distillation, chromatography and recrystallization.

(Reference Process C)

Compound (XA2) can be prepared by reacting a compound of a formula (XC1) (hereinafter, described as Compound (XC1)) with a halogenating agent.

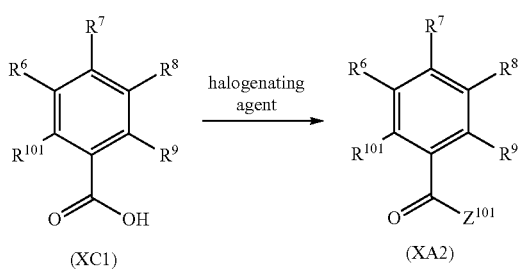

[wherein
$R^6$, $R^7$, $R^8$, $R^9$, $R^{101}$ and $Z^{101}$ are the same as described above.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include phosphorous oxychloride, phosphorous trichloride, phosphorous pentachloride, thionyl chloride, phosphorous oxybromide, phosphorus tribromide, phosphorous pentabromide, phosphorus triiodide, oxalyl dichloride, oxalyl dibromide, triphosgene, diphosgene, phosgene and sulfuryl chloride.

In the reaction, the halogenating agent is used usually within a range of 1 to 10 molar ratio(s) as opposed to 1 mole of Compound (XC1).

The reaction temperature is usually within a range of −20 to 150° C. The reaction period of the reaction is usually within a range of 0.1 to 24 hours.

A catalyst may be added to the reaction, and includes, for example, dimethylformamide. The catalyst is used usually within a range of 0.001 to 1 molar ratio(s) as opposed to 1 mole of Compound (XC1).

If necessary, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali-metal carbonates such as lithium carbonate, sodium carbonate, potassium carbonate, cesium carbonate; alkali-metal bicarbonates such as lithium bicarbonate, sodium bicarbonate, potassium bicarbonate, cesium bicarbonate may be added to the reaction, and these compounds are used usually within a range of 0.001 to 5 molar ratio(s) as opposed to 1 mole of Compound (XC1).

When the reaction is completed, the reaction mixtures are extracted with organic solvent(s), and the resulting organic layers are worked up (for example, drying and concentration) to isolate Compound (XA2). The isolated Compound (XA2) may be further purified, for example, by distillation, chromatography and recrystallization.

(Reference Process D)

Compound (XA1) can be prepared by reacting Compound (XB1) with a carbamating agent to form a compound of the below-mentioned formula (XD1) (hereinafter, described as Compound (XD1)), followed by reacting the resulting Compound (XD1) with Compound (XD2).

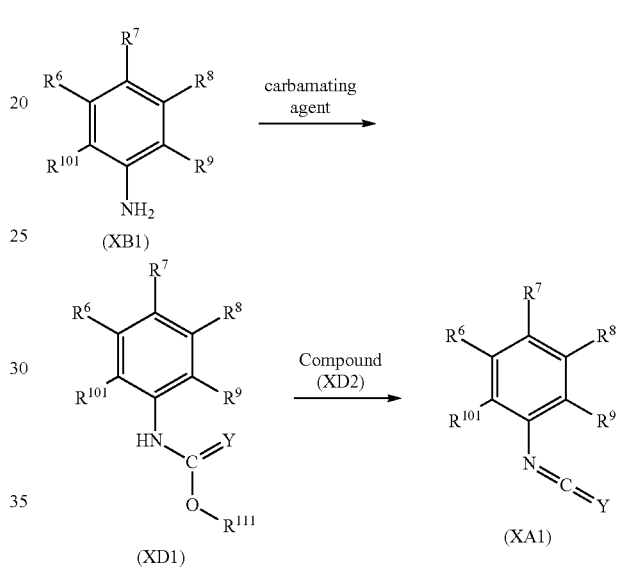

[wherein
$R^6$, $R^7$, $R^8$, $R^9$, $R^{101}$ and Y are the same as described above;
$R^{111}$ represents an C1-C12 alkyl group or an optionally substituted phenyl group.]

Hereinafter, the process for preparing Compound (XD1) from Compound (XB1) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the carbamating agent to be used in the reaction include phenyl chloroformate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate and O-ethyl chlorothioformate.

In the reaction, the carbamating agent is used usually within a range of 1 to 10 molar ratio(s) as opposed to 1 mole of Compound (XB1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali-metal carbonates such as lithium carbonate, sodium carbonate, potassium carbonate, cesium carbonate; alkali-metal bicarbonates such as lithium bicarbonate, sodium bicarbonate, potassium bicarbonate, cesium bicarbonate may be added to the reaction, and these compounds are used usually within a range of 0.001 to 5 molar ratios as opposed to 1 mole of Compound (XB1).

When the reaction is completed, the reaction mixtures are extracted with organic solvent(s), and the resulting organic layers are worked up (for example, drying and concentration) to isolate Compound (XD1). The isolated Compound (XD1) may be further purified, for example, by distillation, chromatography and recrystallization.

Hereinafter, the process for preparing Compound (XA1) from Compound (XD1) is explained.

This reaction is usually carried out in a solvent.

Examples of the solvent that can be used in the reaction include ethers such as tetrahydrofuran, dioxane, ethyleneglycol dimethyl ether, methyl tert-butyl ether; hydrocarbons such as toluene, xylene; halogenated hydrocarbons such as carbon tetrachloride, chloroform, 1,2-dichloroethane, chlorobenzene; nitriles such as acetonitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; and mixed solvents thereof.

Examples of Compound (XD2) include phosphorous pentachloride, phosphorous oxychloride, diphosphorus pentoxide, trichlorosilane, dichlorosilane, monochlorosilane, boron trichloride, 2-chloro-1,3,2-benzodioxaborole, diiodosilane, methyl trichlorosilane, montmorillonite K-10, dimethyl dichlorosilane, chlorotrimethylsilane.

In the reaction, Compound (XD2) is used usually within a range of 1 to 10 molar ratio(s) as opposed to 1 mole of Compound (XD1).

The reaction temperature is usually within a range of −20 to 250° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali-metal carbonates such as lithium carbonate, sodium carbonate, potassium carbonate, cesium carbonate; alkali-metal bicarbonates such as lithium bicarbonate, sodium bicarbonate, potassium bicarbonate, cesium bicarbonate may be added to the reaction, and these compounds are used usually within a range of 0.001 to 5 molar ratios as opposed to 1 mole of Compound (XD1).

When the reaction is completed, the reaction mixtures are extracted with organic solvent(s), and the resulting organic layers are worked up (for example, drying and concentration) to isolate Compound (XA1). The isolated Compound (XA1) may be further purified, for example, by distillation, chromatography and recrystallization.

(Reference Process E)

A compound of a formula (XE2) (hereinafter, described as Compound (XE2)) can be prepared by reacting a compound of a formula (XE1) (hereinafter, described as Compound (XE1)) with a hydrogen gas in the presence of a catalyst.

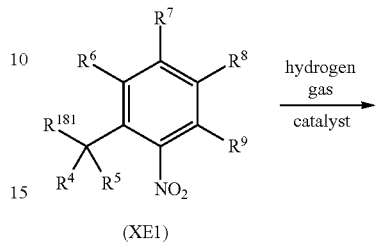

(XE1)

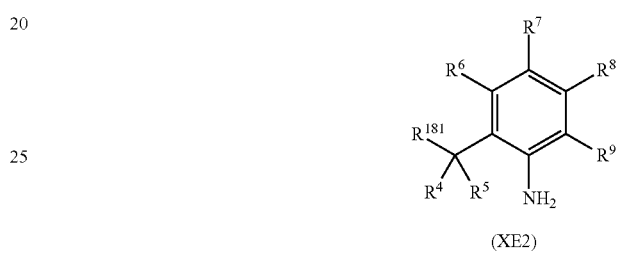

(XE2)

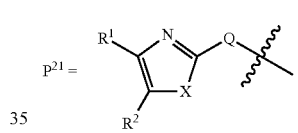

[wherein $R^1$, $R^2$, $R^4$, $R^5$, $R^6$, $R^7$, $R^8$, $R^9$, X and Q are the same as described above; $R^{181}$ represents a hydrogen atom or $P^{21}$; and a wavy bond represents a binding site.]

This reaction is usually carried out in a solvent.

Examples of the solvent that can be used in the reaction include alcohols such as methanol, ethanol, propanol, butanol: esters such as ethyl acetate, butyl acetate; halogenated hydrocarbons such as carbon tetrachloride, chloroform, dichloromethane, 1,2-dichloroethane, tetrachloroethane, chlorobenzene; ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; acetic acid; water; and mixed solvents thereof.

Examples of the catalyst to be used in the reaction includes palladium on carbon (Pd/C), platinum on carbon (Pt/C), osmium on carbon (Os/C), ruthenium on carbon (Ru/C), rhodium on carbon (Rh/C) and Raney nickel.

The reaction temperature is usually within a range of −20 to 150° C. The reaction period of the reaction is usually within a range of 0.1 to 24 hours.

When the reaction is completed, the catalyst is filtered off, and the resulting organic layers are worked up (for example, concentration) to isolate Compound (XE2). The isolated Compound (XE2) may be further purified, for example, by distillation, chromatography and recrystallization.

(Reference Process F)
Compound (XE2) can be prepared by reducing Compound (XE1) with a reducing agent in the presence of an acid.

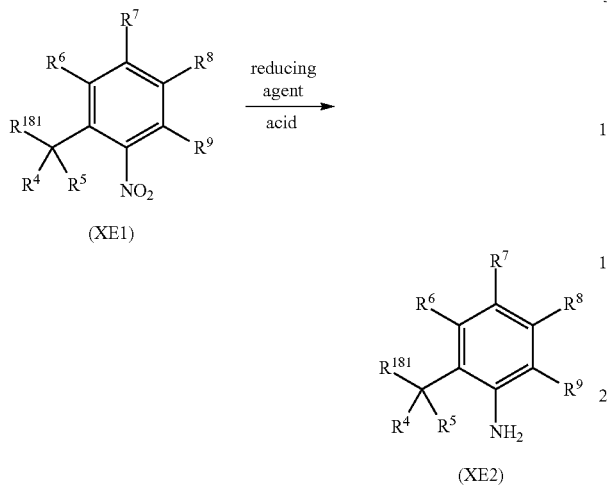

(XE1)

(XE2)

[wherein
$R^4$, $R^5$, $R^6$, $R^7$, $R^8$, $R^9$ and $R^{181}$ are the same as described above.]

This reaction is usually carried out in a solvent.

Examples of the solvent that can be used in the reaction include aliphatic carboxylic acid such as acetic acid; alcohols such as methanol, ethanol; water; and mixed solvents thereof.

Examples of the reducing agent to be used in the reaction include iron, tin and zinc.

Examples of the acid to be used in the reaction include hydrochloric acid, sulfuric acid, acetic acid, aqueous ammonium chloride solution.

In the reaction, the reducing agent is used usually within a range of 1 to 30 molar ratio(s) as opposed to 1 mole of Compound (XE1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XE2). Compound (XE2) may be further purified, for example, by distillation, chromatography and recrystallization.

(Reference Process G)
A compound of a formula (XG2) (hereinafter, described as Compound (XG2)) can be prepared by reacting a compound of a formula (XG1) (hereinafter, described as Compound (XG1)) and Compound (D2) in the presence of a base.

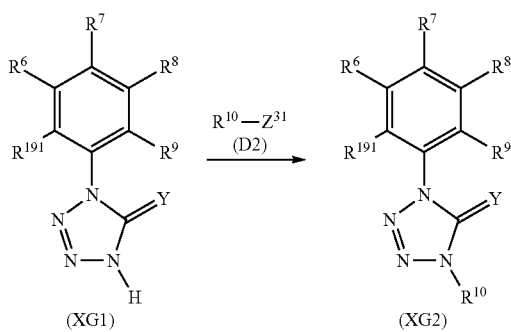

(XG1)    (XG2)

[wherein
$R^6$, $R^7$, $R^8$, $R^9$, $R^{10}$, Y and $Z^{31}$ are the same as described above; and $R^{191}$ represents $P^{12}$ or $P^{13}$.]

The reaction can be carried out according to the above-mentioned process D.

(Reference Process H)
A compound of a formula (XH2) (hereinafter, described as Compound (XH2)) can be prepared by reacting a compound of a formula (XH1) (hereinafter, described as Compound (XH1)) with a halogenating agent and a radical initiator.

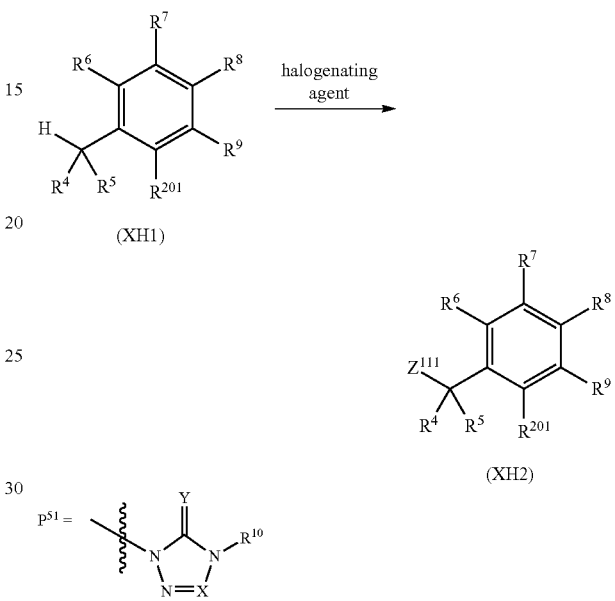

(XH1)

(XH2)

[wherein
$R^4$, $R^5$, $R^6$, $R^7$, $R^8$, $R^9$, $R^{10}$ and Y are the same as described above; $Z^{111}$ represents a chlorine atom, a bromine atom or an iodine atom; $R^{201}$ represents a $P^{51}$ group or a nitro group, and a wavy bond represents a binding site.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, α,α,α-trichlorotoluene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include a chlorinating agent, a brominating agent or iodinating agent such as chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-pbromoglutarimide, N-chloro-N-cyclohexyl-benzenesulfonamide and N-bromophthalimide.

Examples of the radical initiator to be used in the reaction include benzoyl peroxide, azobisisobutyronitrile (AIBN), diacylperoxide, dialkyl peroxydicarbonate, tert-alkyl peroxyester, monoperoxy carbonate, di(tert-alkylperoxy)ketal and ketone peroxide.

In the reaction, the halogenating agent is used usually within a range of 1 to 10 molar ratio(s), and the radical initiator is used usually within a range of 0.001 to 5 equivalents, as opposed to 1 mole of Compound (XH1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). Compound (XH2) may be further purified, for example, by distillation, chromatography and recrystallization.

(Reference Process J)

A compound of a formula (XJ2) (hereinafter, described as Compound (XJ2)) can be prepared by reacting Compound (XH2) with a compound of a formula (XJ1) (hereinafter, described as Compound (XJ1)).

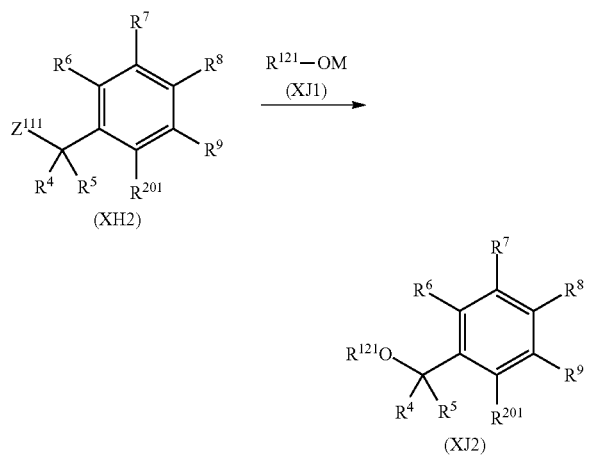

[wherein
$R^4$, $R^5$, $R^6$, $R^7$, $R^6$, $R^9$, $R^{201}$ and $Z^{111}$ are the same as described above; $R^{121}$ represents an C1-C12 alkyl group or a phenyl group, and M represents sodium, potassium and lithium.]

This reaction is usually carried out in a solvent.

Examples of the solvent that can be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of Compound (XJ1) include sodium methoxide, sodium ethoxide, sodium n-propoxide, sodium n-butoxide, sodium isopropoxide, sodium sec-butoxide, sodium tert-butoxide, potassium methoxide, potassium ethoxide, potassium n-propoxide, potassium n-butoxide, potassium isopropoxide, potassium sec-butoxide, potassium tert-butoxide and sodium phenoxide.

In the reaction, Compound (XJ1) is used usually within a range of 1 to 10 molar ratio(s) as opposed to 1 mole of Compound (XH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XJ2). Compound (XJ2) may be further purified, for example, by distillation, chromatography and recrystallization.

(Reference Process K)

A compound of a formula (XK1) (hereinafter, described as Compound (XK1)) can be prepared by reacting Compound (XH2) and water in the presence of a base.

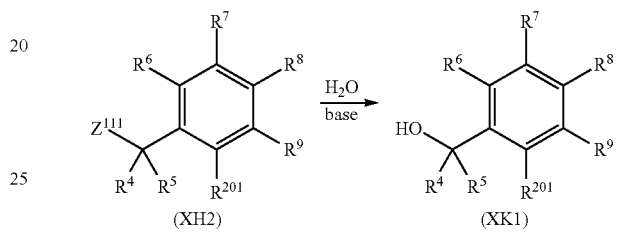

[wherein
$R^4$, $R^5$, $R^6$, $R^7$, $R^8$, $R^9$, $R^{201}$ and $Z^{111}$ are the same as described above.]

This reaction is usually carried out in water or a solvent containing water.

Examples of the solvent that can be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; metallic organic acid salts such as lithium formate, lithium acetate, sodium formate, sodium acetate, potassium formate, potassium acetate; metallic nitrates such as silver nitrate, sodium nitrate; alkali-metal bicarbonates such as lithium bicarbonate, sodium bicarbonate, potassium bicarbonate, cesium bibicarbonate; alkali-metal hydroxides such as lithium hydroxide, sodium hydroxide, potassium hydroxide, cesium hydroxide; alkali metal alkoxides such as sodium methoxide, sodium ethoxide, sodium tert-butoxide, potassium tert-butoxide.

In the reaction, the base is used usually within a range of 1 to 50 molar ratio(s) as opposed to 1 mole of Compound (XH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate. Compound (XK1). Compound (XK1) may be further purified, for example, by distillation, chromatography and recrystallization.

(Reference Process L)

Compound (XH2) can be prepared by reacting Compound (XJ2) and a halogenating agent.

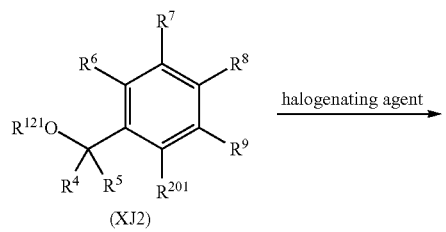

[wherein
$R^4$, $R^5$, $R^6$, $R^7$, $R^8$, $R^9$, $R^{121}$, $R^{201}$ and $Z^{111}$ are the same as described above.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent include hydrochloric acid, hydrobromic acid and hydroiodic acid.

In the reaction, the halogenating agent is used usually within a range of 1 to 100 molar ratio(s) as opposed to 1 mole of Compound (XJ2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). Compound (XH2) may be further purified, for example, by distillation, chromatography and recrystallization.

(Reference Process Q)

Compound (XH2) can be prepared by reacting Compound (XK1) and a halogenating agent.

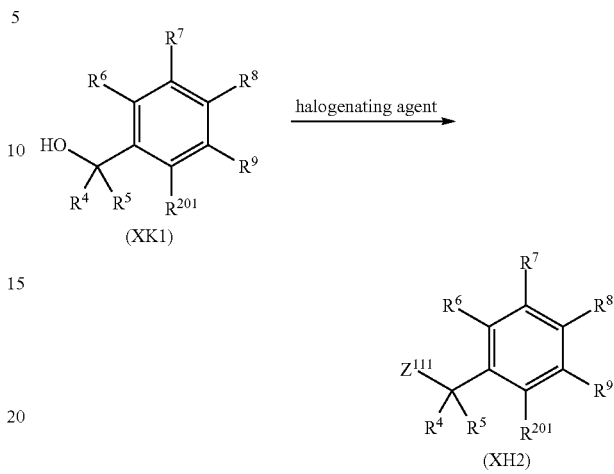

[wherein
$R^4$, $R^5$, $R^6$, $R^7$, $R^8$, $R^9$, $R^{201}$ and $Z^{111}$ are the same as described above.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorous oxychloride, phosphorous trichloride, phosphorous pentachloride, thionyl chloride, phosphorous oxybromide, phosphorous pentabromide, phosphorus triiodide, oxalyl dichloride, oxalyl dibromide, acetyl chloride, carbon tetrabromide, N-bromosuccinimide, lithium chloride, sodium iodide and acetyl bromide.

In the reaction, the halogenating agent is used usually within a range of 1 to 10 molar ratio(s) as opposed to 1 mole of Compound (XK1).

To promote the reaction, an additive agent may be added depending on the halogenating agent used, and specifically includes zinc chloride for acetyl chloride; triphenylphosphine for carbon tetrabromide; dimethyl sulfide for N-bromosuccinimide; boron trifluoride diethyl etherate complex for sodium iodide; boron trifluoride diethyl etherate complex for acetyl bromide; triethylamine and methanesulfonyl chloride for lithium chloride; aluminium chloride for sodium iodide; and trimethylsilyl chloride for sodium iodide. The amount of the additive agent is used usually within a range of 0.001 to 5 molar ratio(s) as opposed to 1 mole of Compound (XK1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). Compound (XH2) may be further purified, for example, by distillation, chromatography and recrystallization.

(Reference Process M)

A compound of a formula (XM3) (hereinafter, described as Compound (XM3)) can be prepared by reacting a compound of a formula (XM1) (hereinafter, described as Compound (XM1)) with a compound of a formula (XM2) (hereinafter, described as Compound (XM2)) in the presence of a base.

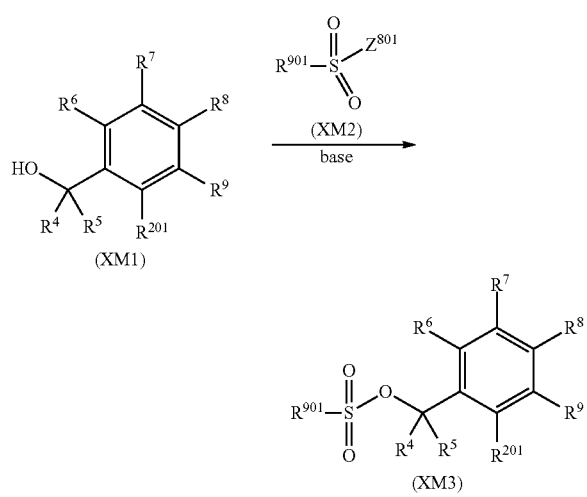

[wherein $R^4$, $R^5$, $R^6$, $R^7$, $R^8$, $R^9$ and $R^{201}$ are the same as described above; $R^{901}$ represents a p-methylphenyl group, a methyl group or a trifluoromethyl group, and $R^{801}$ represents a fluorine atom, a chlorine atom or a bromine atom.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; water; and mixed solvents thereof.

Examples of the based to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal hydrides such as lithium hydride, sodium hydride, potassium hydride; alkali metal alkoxides such as sodium methoxide, sodium ethoxide, sodium tert-butoxide, potassium tert-butoxide.

In the reaction, Compound (XM2) is used usually within a range of 1 to 10 molar ratio(s), and the base is used usually within a range of 1 to 5 molar ratio(s), as opposed to 1 mole of Compound (XM1).

The reaction temperature is usually within a range of −20 to 150° C. The reaction period of the reaction is usually within a range of 0.1 to 24 hours.

If necessary, sodium iodide and tetrabutylammonium iodide and the like may be added to the reaction, and these compounds are used usually within a range of 0.001 to 5 molar ratio(s) as opposed to 1 mole of Compound (XM1).

When the reaction is completed, the reaction mixtures are extracted with organic solvent(s), and the resulting organic layers are worked up (for example, drying and concentration) to isolate Compound (XM3). Compound (XH2) may be further purified, for example, by chromatography and recrystallization.

(Reference Process N)

A compound of a formula (XN12) (hereinafter, described as Compound (XN12)) can be prepared by coupling a compound of a formula (XN11) (hereinafter, described as Compound (XN11)) with Compound (F21) in the presence of a base and a catalyst.

A compound of a formula (XN22) (hereinafter, described as Compound (XN22)) can be prepared by coupling a compound of a formula (XN21) (hereinafter, described as Compound (XN21)) with Compound (F21) in the presence of a base and a catalyst.

A compound of a formula (XN32) (hereinafter, described as Compound (XN32)) can be prepared by coupling a compound of a formula (XN31) (hereinafter, described as Compound (XN31)) with Compound (F21) in the presence of a base and a catalyst.

A compound of a formula (XN42) (hereinafter, described as Compound (XN42)) can be prepared by coupling a compound of a formula (XN41) (hereinafter, described as Compound (XN41)) with Compound (F21) in the presence of a base and a catalyst.

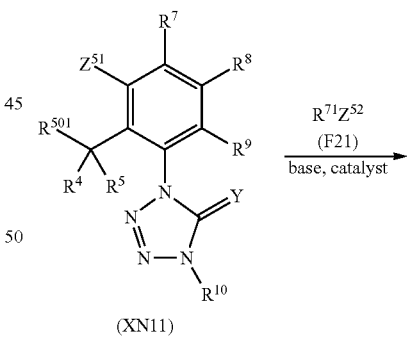

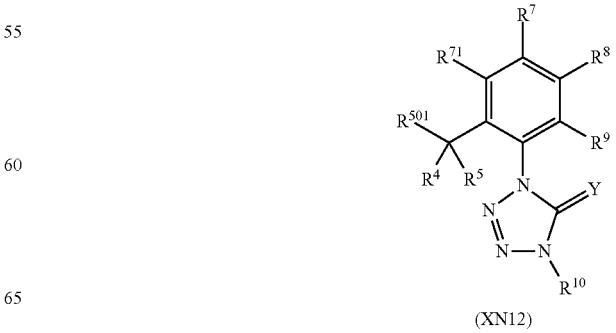

-continued

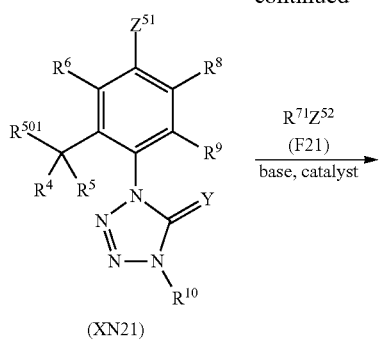

(XN21)

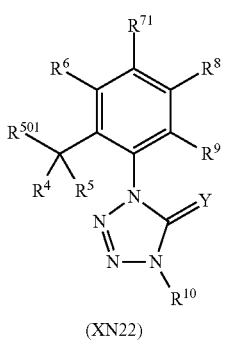

(XN22)

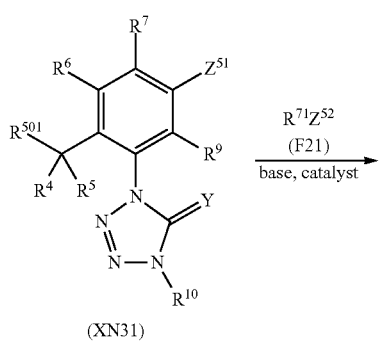

(XN31)

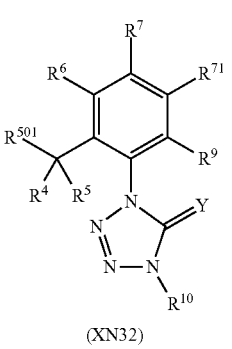

(XN32)

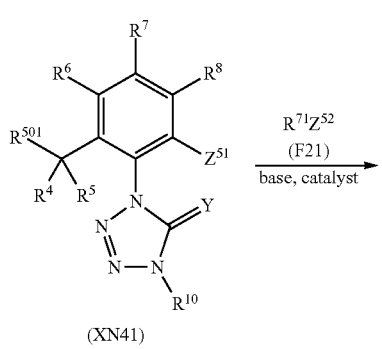

(XN41)

-continued (XN42)

[wherein $R^{501}$ represents a hydrogen atom or an $OR^{121}$ group; $R^{121}$, $R^4$, $R^5$, $R^6$, $R^7$, $R^8$, $R^9$, $R^{10}$, Y, $Z^{51}$, $Z^{52}$ and $R^{71}$ are the same as described above.]

The reaction can be carried out according to the above-mentioned Process F.

Also, among a compound of a formula (XN50):

(XN50)

[wherein $R^4$, $R^5$, $R^6$, $R^7$, $R^8$, $R^9$, $R^{10}$, $R^{501}$ and Y are the same as described above], a compound wherein two or more substituents selected from $R^6$, $R^7$, $R^8$ and $R^9$ represent a $R^{71}$ group can be prepared according to the above-mentioned Process F.

Further, Compound (XN50) can be prepared according to a known coupling method described in Process F.

(Reference Process W)

A compound of a formula (XW2) (hereinafter, described as Compound (XW2)) can be prepared by reacting a compound of a formula (XW1) (hereinafter, described as Compound (XW1)) with an alcohol in the presence of a reaction accelerator.

(XW1)

-continued

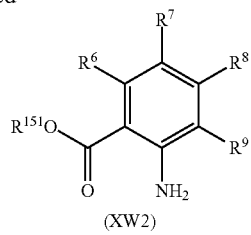

[wherein
R⁶, R⁷, R⁸ and R⁹ are the same as described above; and R151 represents an C1-C12 alkyl group.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof, and the alcohol to be reacted with Compound (XW2) may be used as solvent.

Examples of the alcohols include methanol, ethanol, propanol, butanol, pentanol.

Examples of the reaction accelerator include mineral acids such as hydrochloric acid, sulfuric acid; carbodiimides such as dicyclohexylcarbodiimide, diisopropylcarbodiimide, N'-(3-dimethylaminopropyl)-N-ethylcarbodiimide; organic acids such as methanesulfonic acid, toluenesulfonic acid; Mitsunobu reagents such as triphenylphosphine/diethyl azodicarboxylate; thionyl chloride; boron trifluoride-ethyl ether complex.

In the reaction, the reaction accelerator is used usually within a range of 0.001 to 10 molar ratios, and the alcohol is used usually in a large excess amount, as opposed to 1 mole of Compound (XW1).

If necessary, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate may be added to the reaction, and these compounds are used usually within a range of 0.001 to 5 molar ratio(s) as opposed to 1 mole of Compound (XW1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XW2). Compound (XW2) may be further purified, for example, by distillation, chromatography and recrystallization.

(Reference Process V)

Compound (XW2) can be prepared by reacting Compound (XW1) with a halogenating agent to form a compound of a formula (XV1) (hereinafter, described as Compound (XV1)), followed by reacting the resulting Compound (XV1) with an alcohol.

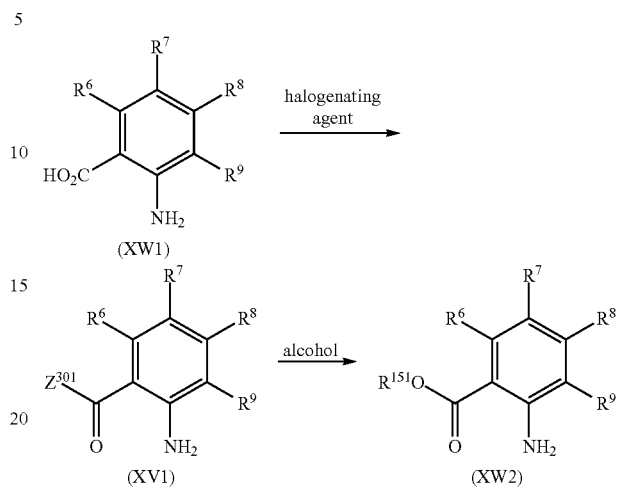

[wherein
R⁶, R⁷, R⁸, R⁹ and R¹⁵¹ are the same as described above; and R³⁰¹ represents a chlorine atom, a bromine atom or an iodine atom.]

The process for preparing Compound (XV1) by reacting Compound (XW1) and a halogenating agent can be carried out according to Reference Process C.

Hereinafter, a process for preparing Compound (XW2) from Compound (XV1) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof, and the alcohol to be reacted with Compound (XV1) may be used as solvent.

Examples of the alcohols include methanol, ethanol, propanol, n-butanol, sec-butanol, tert-butanol and n-pentanol.

In the reaction, the alcohol is used usually within a range of 1 to 50 molar ratio(s) as opposed to 1 mole of Compound (XV1), and may be reacted as solvent in a large excess amounts.

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XW2). Compound (XW2) may be further purified, for example, by distillation, chromatography and recrystallization.

(Reference Process Y)

A compound of a formula (XY2) (hereinafter, described as Compound (XY2)) can be prepared by reacting a compound of a formula (XY1) (hereinafter, described as Compound (XY1)) with an alkylating agent.

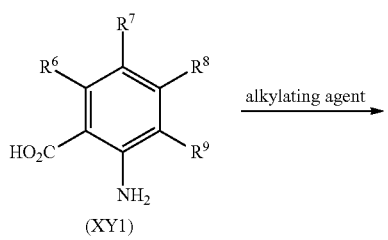

(XY1)

alkylating agent

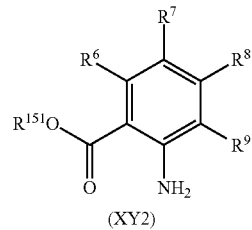

(XY2)

[wherein $R^6$, $R^7$, $R^8$, $R^9$ and $R^{151}$ are the same as described above.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the alkylating agent to be used in the reaction include diazoalkyls such as diazomethane, trimethylsilyldiazomethane; halogenated alkyls such as chlorodifluoromethane, methyl bromide, ethyl bromide, n-propyl bromide, methyl iodide, ethyl iodide, n-propyl bromide, aryl bromide, cyclopropyl bromide, benzyl bromide, 1,1-difluoro-2-iodomethane; dialkyl sulfates such as dimethyl sulfates, diethyl sulfates, di-n-propyl sulfates; alkyl or aryl sulfonates such as methyl p-toluenesulfonate, ethyl p-toluenesulfonate, n-propyl p-toluenesulfonate, methyl methanesulfonate, ethyl methanesulfonate, n-propyl methanesulfonate.

In the reaction, the alkylating agent is used usually within a range of 1 to 10 molar ratios as opposed to 1 mole of Compound (XY1).

If necessary, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; or quaternary ammonium salts such as tetra(n-butyl)ammonium hydroxide may be added to the reaction, and these compounds are used usually within a range of 0.001 to 5 molar ratios as opposed to 1 mole of Compound (XY1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XY2). Compound (XY2) may be further purified, for example, by distillation, chromatography and recrystallization.

(Reference Process X)

A compound of a formula (XX2) (hereinafter, described as Compound (XX2)) can be prepared by reacting a compound of a formula (XX1) (hereinafter, described as Compound (XX1)) with a reducing agent.

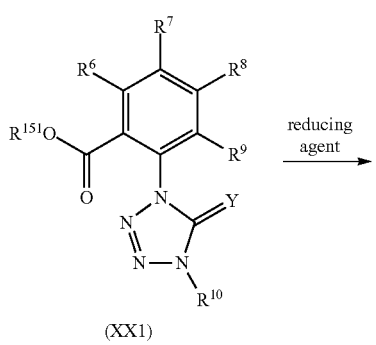

(XX1)

reducing agent

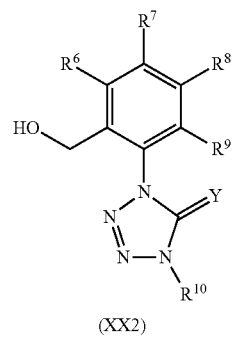

(XX2)

[wherein, $R^6$, $R^7$, $R^8$, $R^9$, $R^{10}$, $R^{151}$ and Y are the same as described above.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; alcohols such as methanol, ethanol, propanol, butanol; water; and mixed solvents thereof.

Examples of the reducing agent to be used in the reaction include lithium triethylborohydride, diisobutylaluminium hydride, lithium aminoborohydride, lithium borohydride, sodium borohydride, borane, borane-dimethyl sulfide complex and borane-tetrahydrofuran complex.

In the reaction, the reducing agent is used usually within a range of 1 to 10 molar ratio(s) as opposed to 1 mole of Compound (XX1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XX2). Compound (XX2) may be further purified, for example, by distillation, chromatography and recrystallization.

(Reference Process Z)

A compound of a formula (XZ2) (hereinafter, described as Compound (XZ2)) can be prepared by reacting a compound of a formula (XZ1) (hereinafter, described as Compound (XZ1)) with a reducing agent.

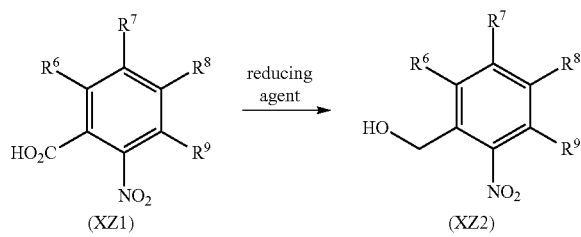

[wherein, $R^6$, $R^7$, $R^8$ and $R^9$ are the same as described above.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; water; and mixed solvents thereof.

Examples of the reducing agent to be used in the reaction include, borane, borane-tetrahydrofuran complex, borane-dimethyl sulfide complex. Also, borohydrides such as sodium borohydride and potassium borohydride are mixed with acids such as sulfuric acid, hydrochloric acid, methanesulfonic acid and boron trifluoride diethyl etherate complex to develop a borane, which also can be used.

In the reaction, the reducing agent is used usually within a range of 1 to 10 molar ratio(s) as opposed as 1 mole of Compound (XZ1).

The reaction temperature is usually within a range of −20 to 100° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (XZ2). Compound (XZ2) may be further purified, for example, by distillation, chromatography and recrystallization.

(Reference Process P)

A compound of a formula (XP3) (hereinafter, described as Compound (XP3)) can be prepared by reacting a compound of a formula (XP1) (hereinafter, described as Compound (XP1)) with a thiocyanating agent to form a compound of a formula (XP2) (hereinafter, described as Compound (XP2)), followed by reacting Compound (XP2) with an acid.

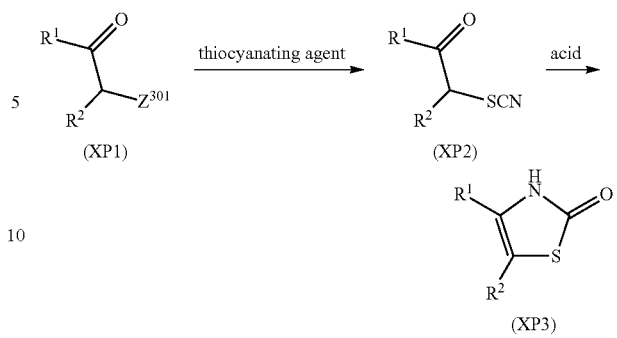

[wherein, $R^1$, $R^2$ and $Z^{301}$ are the same as defined above.]

Hereinafter, a process for preparing Compound (XP2) from Compound (XP1) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Examples of the thiocyanating agent to be used in the reaction include ammonium thiocyanate, potassium thiocyanate, sodium thiocyanate, lead thiocyanate, 6-methyl 4-oxo-2-thioxo-3,4-dihydro-2H-1,3-oxadine, 1-n-butyl-3-methylimidazolium thiocyanate, 2-hydroxy-N,N,N-tributylethaneaminium thiocyanate, copper(II) thiocyanate and copper(I) thiocyanate.

In the reaction, the thiocyanating agent is used usually within a range of 1 to 10 molar ratio(s) as opposed to 1 mole of Compound (XP1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XP2). Compound (XP2) may be further purified, for example, by distillation, chromatography and recrystallization.

Hereinafter, a process for preparing Compound (XP2) from Compound (XP3) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; organic acids such as formic acid, acetic acid, trifluoroacetic acid; water; and mixed solvents thereof.

Examples of the acid to be used in the reaction include concentrated hydrochloric acid, concentrated sulfuric acid, trifluoroacetic acid, methanesulfonic acid, trifluoromethanesulfonic acid, p-toluenesulfonic acid and nitric acid.

In the reaction, the acid is used usually within a range of 0.1 to 10 molar ratios as opposed to 1 mole of Compound (XP2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XP3). Compound (XP3) may be further purified, for example, by distillation, chromatography and recrystallization.

(Reference Process Q-2)

A compound of a formula (XQ3) (hereinafter, described as Compound (XQ3)) or a compound of a formula (XQ4) (hereinafter, described as Compound (XQ4)) can be prepared by reacting a compound of a formula (XQ1) (hereinafter, described as Compound (XQ1)) with a compound of a formula (XQ2) (hereinafter, described as Compound (XQ2)).

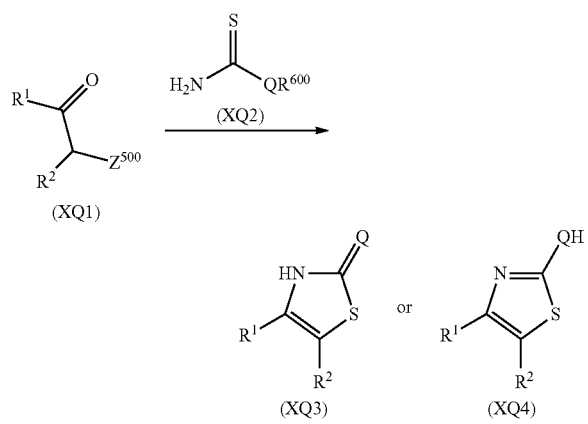

[wherein,
$R^1$, $R^2$, $Z^{500}$ and Q are the same as defined above; and $R^{600}$ represents an C1-C12 alkyl group or a hydrogen atom.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Examples of Compound (XQ2) include O-methyl thiocarbamate, O-ethyl thiocarbamate, thiourea, dithiocarbamate; and sodium salts and ammonium salts thereof.

In the reaction, Compound (XQ2) is used usually within a range of 1 to 10 molar ratio(s) as opposed to 1 mole of Compound (XQ1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XQ3) or Compound (XQ4). Compound (XQ3) or Compound (XQ4) may be further purified, for example, by distillation, chromatography and recrystallization.

(Reference Process R)

A compound of a formula (XP3) (hereinafter, described as Compound (XR3)) or a compound of a formula (XR4) (hereinafter, described as Compound (XR4)) can be prepared by reacting a compound of a formula (XR1) (hereinafter, described as Compound (XR1)) with water in the presence of a base to form a compound of a formula (XR2) (hereinafter, described as Compound (XR2)), followed by reacting Compound (XR2) with phosgenes, consecutively with ammonia, and further with an acid.

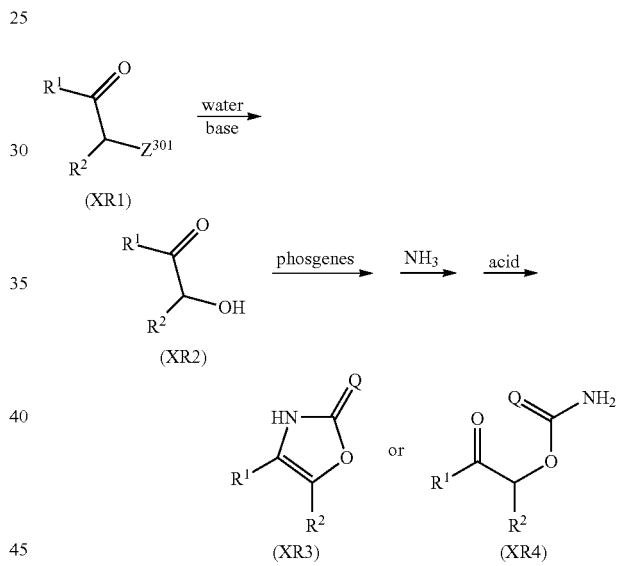

[wherein,
$R^1$, $R^2$ and $R^{301}$ are the same as defined above.]

Hereinafter, a process for preparing Compound (XR2) from Compound (XR1) is explained.

This reaction is usually carried out in water or a solvent containing water.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; metallic organic acid salts such as lithium formate, lithium acetate, sodium formate, sodium acetate, potassium formate, potassium acetate; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; and alkali metal hydroxides such as lithium hydroxide, sodium hydroxide, potassium hydroxide, cesium hydroxide.

In the reaction, the base is used usually within a range of 1 to 10 molar ratio(s) as opposed to 1 mole of Compound (XR1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XR2). Compound (XR2) may be further purified, for example, by distillation, chromatography and recrystallization.

Hereinafter, a process for preparing Compound (XR3) or Compound (XR4) from Compound (XR2) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Examples of the phosgenes to be used in the reaction include phosgene, diphosgene, triphosgene and thiophosgene.

In the reaction, the phosgenes are used usually within a range of 0.3 to 10 molar ratios as opposed to 1 mole of Compound (XR2).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; quaternary ammonium salts such as tetra(n-butyl)ammonium hydroxide may be added to the reaction, and these compound are used usually within a range of 0.001 to 5 molar ratios as opposed to 1 mole of Compound (XR2).

After a reaction of Compound (XR2) and phosgenes, to the resulting mixture is added aqueous ammonia, followed by addition of an acid to obtain Compound (XR3) or Compound (XR4).

Examples of the acid include hydrochloric acid, sulfuric acid, acetic acid, trifluoroacetic acid, toluenesulfonic acid, and trifluoromethanesulfonic acid.

When the reaction is completed, the reaction mixtures are extracted with organic solvent(s), and the resulting organic layers are worked up (for example, drying and concentration) to isolate Compound (XR3) or Compound (XR4). Compound (XR3) or Compound (XR4) may be further purified, for example, by distillation, chromatography and recrystallization.

(Reference Process S)

Compound (B2) can be prepared by reacting Compound (A21) or Compound (A22) and a halogenating agent.

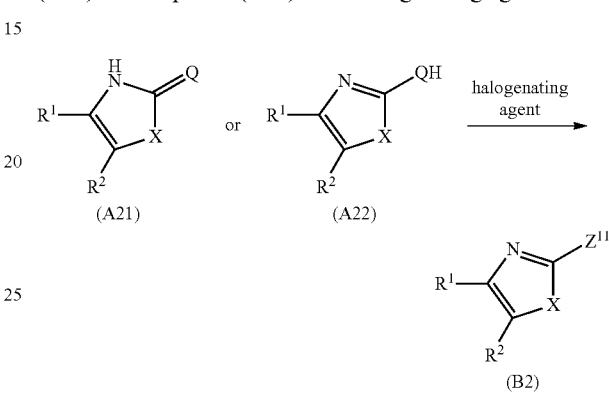

wherein, $R^1$, $R^2$, X, Q and $Z^{11}$ are the same as defined above.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; organic acids such as formic acid, acetic acid, trifluoroacetic acid; water; and mixed solvents thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorous oxychloride, phosphorous trichloride, phosphorous pentachloride, thionyl chloride, phosphorous oxybromide, phosphorous pentabromide, phosphorus triiodide, oxalyl dichloride, oxalyl dibromide, acetyl chloride, carbon tetrabromide, N-bromosuccinimide, sodium iodide and acetyl bromide.

In the reaction, the halogenating agent is used usually within a range of 1 to 10 molar ratio(s) as opposed to 1 mole of Compound (A21) or Compound (A22).

In the reaction, an additive agent may be added depending on the halogenating agent used, and specifically, includes zinc chloride when acetyl chloride is used; triphenylphosphine when carbon tetrabromide is used; dimethyl sulfide when N-bromosuccinimide is used; boron trifluoride diethyl etherate complex when sodium iodide is used; boron trifluoride diethyl etherate complex when acetyl bromide is used; aluminium chloride when sodium iodide is used; and trimethylsilyl chloride when sodium iodide is used. The amount of the additive agent is used usually within a range of 0.01 to 5 molar ratios as opposed to 1 mole of Compound (A21) or Compound (A22).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (B2). Compound (B2) may be further purified, for example, by distillation, chromatography and recrystallization.

Although a form used for the present compound may be the present compound as itself, the present compound is usually prepared by mixing the present compound with solid carriers, liquid carriers, gas carriers, surfactants and the others, and if necessary, adding stickers, dispersers and stabilizers, to formulate into wettable powders, water dispersible granules, flowables, granules, dry flowables, emulsifiable concentrates, aqueous solutions, oil solutions, smoking agents, aerosols, microcapsules and the others, In these formulations, the present compound is contained in a range of usually 0.1 to 99%, preferably 0.2 to 90% by weight.

Examples of the solid carrier include clays (for example, kaolin, diatomaceous earth, synthetic hydrated silicon dioxide, Fubasami clay, bentonite and acid clay), talcs or the other inorganic minerals (for example, sericite, quartz powder, sulfur powder, activated charcoal, calcium carbonate and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene and methyl naphthalene), aliphatic hydrocarbons (for example, n-hexane, cyclohexane and kerosene), esters (for example, ethyl acetate and butyl acetate), nitriles (for example, acetonitrile and isobutyronitrile), ethers (for example, dioxane and diisopropylether), acid amides (for example, N,N-dimethyl formamide (DMF) and dimethylacetamide), halogenated hydrocarbons (for example, dichloroethane, trichloro ethylene and carbon tetrachloride) and the others.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of other auxiliary agents for formulation include stickers, dispersers and stabilizers, specifically casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof and the others.

The method for applying the present compound is not particularly limited, as far as the applying form is a form by which the present compound may be applied substantially, and includes, for example, an application to plants such as a foliage application; an application to area for cultivating plants such as a submerged treatment; and an application to soil such as seed disinfection.

The application dose varies depending on weather conditions, dosage forms, timing of application, methods of application, areas to be applied, target diseases and target crops etc., but is in the range of usually from 1 to 500 g, and preferably from 2 to 200 g per 1,000 m$^2$ of the area to be applied. The emulsifiable concentrate, the wettable powder or the suspension concentrate, etc., is usually applied by diluting it with water. In this case, the concentration of the present compound after dilution is in the range of usually 0.0005 to 2% by weight, and preferably 0.005 to 1% by weight. The dust formulation or the granular formulation etc., is usually applied as itself without diluting it. In the application to seeds, the amount of the present compound is in the range of usually from 0.001 to 100 g, and preferably from 0.01 to 50 g per 1 kg of the seeds.

Herein, examples of the place where the pests live include paddy fields, fields, tea gardens, orchards, non-agricultural lands, houses, nursery trays, nursery boxes, nursery soils and nursery bed.

Also, in another embodiment, for example, the present compound can be administered to the inside (inside of the body) or the outside (body surface) of the below-mentioned vertebrate to exterminate systemically or unsystemically the living things or parasites which are parasitic on the vertebrate. Examples of a method of the internal medication include an oral administration, an anal administration, a transplanation, an administration via injection subcutaneously, intramuscularly or intravenously. Examples of a method of outside medication include a transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., but it is desirable in general to administer the present compound so that a dose of the active ingredient (the present compound or salts thereof) is in the range of generally from 0.1 mg to 2,000 mg and preferably 0.5 mg to 1,000 mg per 1 kg of body weight of the animal.

The present compound can be used as agent for controlling plant disease in agricultural lands such as fields, paddy fields, lawns, orchards. The compound of the present invention can control diseases occurred in the agricultural lands or the others for cultivating the following "plant".

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli, cauliflower),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (for example, spinach and Swiss chard),
lamiaceous vegetables (for example, *Perilla frutescens*, mint and basil), strawberry, sweet potato, *Dioscorea japonica*, colocasia and the others;

Flowers:
Ornamental Foliage Plants:
Fruits:
pomaceous fruits (for example, apple, pear, Japanese pear, Chinese quince and quince),
stone fruits (for example, peach, plum, nectarine, *Prunus mume*, cherry fruit, apricot and prune),
citrus fruits (for example, *Citrus unshiu*, orange, lemon, lime and grapefruit),
nuts (for example, chestnut, walnuts, hazelnuts, almond, pistachio, cashew nuts and *macadamia* nuts),
berry fruits (for example, blueberry, cranberry, blackberry and raspberry),
grape, kaki persimmon, olive, Japanese plum, banana, coffee, date palm, coconuts, and the others;

Trees Other than Fruit Trees:
tea, mulberry, flowering plant,
roadside trees (for example, ash, birch, dogwood, Eucalyptus, *Ginkgo biloba*, lilac, maple, *Quercus*, poplar, *Judas* tree, *Liquidambar formosana*, plane tree, zelkova, Japanese arborvitae, fir wood, hemlock, juniper, *Pinus, Picea,* and *Taxus cuspidate*);
and the others.

The above-mentioned "plant" includes genetically modified crops.

The pests on which the present compound has a control efficacy include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), rhizoctonia seeding blight (*Rhizoctonia solani*), and take-all disease (*Gaeumannomyces graminis*);

Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and rhizoctonia seeding blight (*Rhizoctonia solani*);

Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum gfaminicola*), gray leaf spot (*Cercospora zeae-maydis*), eyespot (*Kabatiella zeae*), and phaeosphaeria leaf spot (*Phaeosphaeria maydis*);

Cotton diseases: anthracnose (*Colletotrichum gossypii*), grey mildew (*Ramuraria areola*), alternaria leaf spot (*Alternaria macrospora, A. gossypii*);

Coffee diseases: rust (*Hemileia vastatrix*);

Rape seed diseases: sclerotinia rot (*Sclerotinia sclerotiorum*), black spot (*Alternaria brassicae*), and black leg (*Phoma lingam*);

Citrus diseases: melanose (*Diaporthe citri*), scab (*Elsinoe fawcetti*), and fruit rot (*Penicillium digitatum, P. italicum*);

Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Colletotrichum acutatum*);

Pear diseases: scab (*Venturia nashicola, V. pirina*), black spot (*Alternaria alternata* Japanese pear pathotype) and rust (*Gymnosporangium haraeanum*);

Peach diseases: brown rot (*Monilinia fructicola*), scab (*Cladosporium carpophilum*) and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.) and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*);

Eggplant disease: brown spot (*Phomopsis vexans*) and powdery mildew (*Erysiphe cichoracearum*);

Diseases of Cruciferous Vegetables: alternaria leaf spot (*Alternaria japonica*), white spot (*Cercosporella brassicae*), clubroot (*Plasmodiophora parasitica*), downy mildew (*Peronospora parasitica*);

Welsh onion diseases: rust (*Puccinia allii*);

Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrichum glycines, C. truncatum*), Rhizoctonia aerial blight (*Rhizoctonia solani*), septoria brown spot (*Septoria glycines*), and frog eye leaf spot (*Cercospora sojina*);

Kidney bean diseases: anthracnose (*Colletotrichum lindemthianum*);

Peanut diseases: early leaf spot (*Cercospora personata*), late leaf spot (*Cercospora arachidicola*) and southern blight (*Sclerotium rolfsii*);

Garden pea diseases: powdery mildew (*Erysiphe pisi*);

Potato diseases: early blight (*Alternaria solani*), late blight (*Phytophthora infestans*), and verticillium wilt (*verticillium albo-atrum, V. dahliae, V. nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*);

Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: *cercospora* leaf spot (*Cercospora beticola*), leaf blight (*Thanatephorus cucumeris*), root rot (*Thanatephorus cucumeris*) and *aphanomyces* root rot (*Aphanomyces sochlioides*);

Rose diseases: black spot (*Diplocarpon rosae*) and powdery mildew (*Sphaerotheca pannosa*);

Diseases of Chrysanthemum: leaf blight (*Septoria chrysanthemi-indici*) and white rust (*Puccinia horiana*);

Onion diseases: *botrytis* leaf blight (*Botrytis cinerea, B. byssoidea, B. squamosa*), gray-mold neck rot (*Botrytis slli*), and small sclerotial rot (*Botrytis squamosa*);

Various crops diseases: gray mold (*Botrytis cinerea*), and *sclerotinia* rot (*Sclerotinia sclerotiorum*);

Diseases of Japanese radish: *alternaria* leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola*).

Hemiptera:
*Delphacidae* (for example, *Laodelphax striatellus, Nilaparvata lugens,* or *Sogatella furcifera*);
*Deltocephalidae* (for example, *Nephotettix cincticeps,* or *Nephotettix virescens*);
*Aphididae* (for example, *Aphis gossypii, Myzus persicae, Brevicoryne brassicae, Macrosiphum euphorbiae, Aulacorthum solani, Rhopalosiphum padi, Toxoptera citricidus*);
*Pentatomidae* (for example, *Nezara antennata, Riptortus clavetus, Leptocorisa chinensis, Eysarcoris parvus, Halyomorpha mista,* or *Lygus lineolaris*);
*Aleyrodidae* (for example, *Trialeurodes vaporariorum,* or *Bemisia argentifolii*);
*Coccoidea* (for example, *Aonidiella aurantii, Comstockaspis perniciosa, Unaspis citri, Ceroplastes rubens,* or *Icerya purchasi*);
*Tingidae*;
*Psyllidae*; and the others;
Lepidoptera:
*Pyralidae* (for example, *Chilo suppressalis, Tryporyza incertulas, Cnaphalocrocis medinalis, Notarcha derogata, Plodia interpunctella, Ostrinia furnacalis, Hellula undalis, Pediasia teterrellus*);
*Noctuidae* (for example, *Spodoptera litura, Spodoptera exigua, Pseudaletia separata, Mamestra brassicae, Agrotis ipsilon, Plusia nigrisigna, Trichoplusia* spp., *Heliothis* spp, or *Helicoverpa* spp.;
*Pieridae* (for example, *Pieris rapae*);
*Tortricidae* (for example, *Adoxophyes* spp., *Grapholita molesta, Cydia pomonella, Leguminivora glycinivorella, Matsumuraeses azukivora, Adophyes orana fasciata, Adoxophyes* sp., *Homona magnanima, Archips fuscocupreanus, Cydia pomonella*);
*Gracillariidae* (for example, *Caloptilia theivora, Phyllonorycter ringoneella*);
*Carposinidae* (for example, *Carposina niponensis*);
*Lyonetiidae* (for example, *Lyonetia* spp.);
*Lymantriidae* (for example, *Lymantria* spp., or *Euproctis* spp.);
*Yponomeutidae* (for example, *Plutella xylostella*);
*Gelechiidae* (for example, *Pectinophora gossypiella* or *Phthorimaea operculella*);
*Arctiidae* (for example, *Hyphantria cunea*);
*Tineidae* (for example, *Tinea translucens,* or *Tineola bisselliella*); and the others;

Thysanoptera:
Thysanoptera (for example, *Frankliniella occidentalis, Thrips palmi, Scirtothrips dorsalis, Thrips tabaci, Frankliniella intonsa, Frankliniella fusca*);
Diptera:
*Musca domestica, Culex popiens pallens, Tabanus trigonus, Hylemya antiqua, Hylemya platura, Anopheles sinensis, Agromyza oryzae, Hydrellia griseola, Chlorops oryzae, Dacus cucurbitae, Ceratitis capitata, Liriomyza trifolii,* and the others;
Coleoptera:
*Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda*), and the others;
Orthoptera:
*Locusta migratoria, Gryllotalpa africana, Oxya yezoensis, Oxya japonica,* and the others;
Hymenoptera:
*Athalia rosae, Acromyrmex* spp., *Solenopsis* spp., and the others;
Nematodes:
*Aphelenchoides besseyi, Nothotylenchus acris, Heterodera glycines, Meloidogyne incognita, Pratylenchus, Nacobbus aberrans,* and the others;
Blattariae:
*Blattella germanica, Periplaneta fuliginosa, Periplaneta americana, Periplaneta brunnea, Blatta orientalis,* and the others;
Acarina:
*Tetranychidae* (for example, *Tetranychus urticae, Panonychus citri,* or *Oligonychus* spp.);
*Eriophyidae* (for example, *Aculops pelekassi*);
*Tarsonemidae* (for example, *Polyphagotarsonemus latus*);
*Tenuipalpidae*;
*Tuckerellidae*;
*Acaridae* (for example, *Tyrophagus putrescentiae*);
*Pyroglyphidae* (for example, *Dermatophagoides farinae,* or *Dermatophagoides ptrenyssnus*);
*Cheyletidae* (for example, *Cheyletus eruditus, Cheyletus malaccensis,* or *Cheyletus moorei*);
*Dermanyssidae*;
and the others.

Also the formulation comprising the present compound or salts thereof can be used in the field relating to a treatment of livestock diseases or livestock industry, and for example, can exterminate the living things or parasites which are parasitic on the inside and/or the outside of a vertebrate such as human being, cow, sheep, pig, poultry, dog, cat and fish, so as to maintain public health. Examples of the pests include *Isodes* spp. (for example, *Isodes scapularis*), *Boophilus* spp. (for example, *Boophilus microplus*), *Amblyomma* spp., *Hyalomma* spp., *Rhipicephalus* spp. (for example, *Rhipicephalus sanguineus*), *Haemaphysalis* spp. (for example, *Haemaphysalis longicornis*), *dermacentor* spp., *Ornithodoros* spp. (for example, *Ornithodoros moubata*), *Dermahyssus gallinae, Ornithonyssus sylviarum, Sarcoptes* spp. (for example, *Sarcoptes scabiei*), *Psoroptes* spp., *Chorioptes* spp., *Demodex* spp., *Eutrombicula* spp., *Ades* spp. (for example, *Aedes albopictus*), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., *Phthiraptera* (for example, *Damalinia* spp.), *Linognathus* spp., *Haematopinus* spp., *Ctenocephalides* spp.

(for example, *Ctenocephalides felis*) *Xenosylla* spp., *monomorium pharaonis* and nematodes [for example, hairworm (for example, *Nippostrongylus brasiliensis*, *Trichostrongylus axei*, *Trichostrongylus colubriformis*), *Trichinella* spp. (for example, *Trichinella spiriralis*), *Haemonchus contortus*, *Nematodirus* spp. (for example, *Nematodirus battus*), *Ostertagia circumcincta*, *Cooperia* spp., *Hymenolepis nana*, and the others.

EXAMPLES

The following Examples including Preparation examples, Formulation examples and Test examples, serve to illustrate the present invention in more detail, which should not intend to limit the present invention.

The Preparation examples are shown below. $^1$H NMR means a proton nuclear magnetic resonance, spectrum and Tetramethyl silane is used as an internal standard and chemical shift (δ) is expressed in ppm.

Preparation Example 1

A mixture of 1-(2-bromomethylphenyl)-4-methyl-1,4-dihydrotetrazole-5-one (hereinafter, referred to as "Intermediate (PRH)") 1.18 g, 4-phenyl-2-oxo-thiazole (hereinafter, referred to as "Intermediate (PR01)") 0.71 g, potassium carbonate 0.61 g and acetonitrile 20 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-phenylthiazole (hereinafter, referred to as "Present compound (T001)") 0.08 g.

Present Compound (T001)

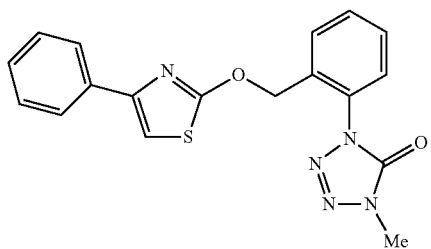 [SMILES: Cn1nnn(-c2ccccc2COc2nc(-c3ccccc3)cs2)c1=O]

$^1$H NMR (CDCl$_3$) δ: 3.64 (3H, s), 5.64 (2H, s), 6.85 (1H, s), 7.30 (1H, t, J=7.3 Hz), 7.39 (2H, t, J=7.3 Hz), 7.47-7.57 (3H, m), 7.72-7.74 (1H, m), 7.77-7.79 (2H, m).

Preparation Example 2

A mixture of Intermediate (PRH) 0.81 g, 4-(4-fluorophenyl)-2-oxo-thiazole (hereinafter, referred to as "Intermediate (PR02)") 0.59 g, potassium carbonate 0.42 g and acetonitrile 15 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-fluorophenyl)thiazole (hereinafter, referred to as "Present compound (T002)") 0.19 g.

Present Compound (T002)

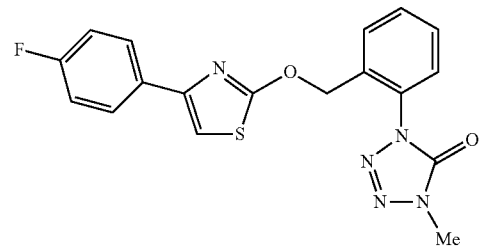

$^1$H NMR (CDCl$_3$) δ: 3.65 (3H, s), 5.62 (2H, s), 6.77 (1H, s), 7.07 (2H, t, J=8.5 Hz), 7.47-7.56 (3H, m), 7.71-7.64 (3H, m).

Preparation Example 3

A mixture of Intermediate (PRH) 3.23 g, 4-(4-chlorophenyl)-2-oxo-thiazole (hereinafter, referred to as "Intermediate (PR03)") 2.54 g, potassium carbonate 1.60 g and acetonitrile 50 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-chlorophenyl)thiazole (hereinafter, referred to as "Present compound (T003)") 1.20 g.

Present Compound (T003)

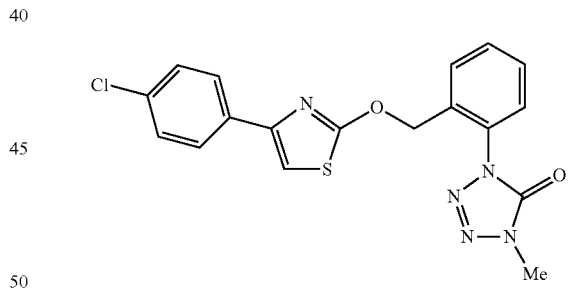

$^1$H NMR (CDCl$_3$) δ: 3.65 (3H, s), 5.62 (2H, s), 6.83 (1H, s), 7.35 (2H, dt, J=2.4, 8.5 Hz), 7.47-7.57 (3H, m), 7.69-7.72 (3H, m).

Preparation Example 4

A mixture of Intermediate (PRH) 2.05 g, 4-(4-bromophenyl)-2-oxo-thiazole (hereinafter, referred to as "Intermediate (PR04)") 2.05 g, potassium carbonate 1.33 g and N,N-dimethylformamide 30 mL was stirred at 80° C. for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-bromophenyl)thiazole (hereinafter, referred to as "Present compound (T004)") 0.70 g.

Present Compound (T004)

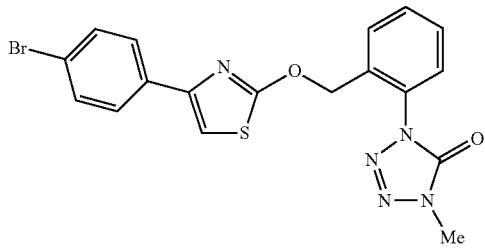 [SMILES: Cn1nnn(-c2ccccc2COc2nc(-c3ccc(Cl)cc3)cs2)c1=O]

$^1$H NMR (CDCl$_3$) δ: 3.65 (3H, s), 5.62 (2H, s), 6.85 (1H, s), 7.47-7.57 (5H, m), 7.65 (2H, dt, J=2.2, 8.7), 7.70-7.73 (1H, m).

Preparation Example 5

Under ice-cooling, to a mixture of Intermediate (PRH) 1.25 g, 4-(4-iodophenyl)-2-oxo-thiazole (hereinafter, referred to as "Intermediate (PR05)") 1.21 g and N,N-dimethylformamide 15 mL was added sodium hydride 0.21 g (dispersion in paraffin liquid, 55% contents) and the resulting mixtures were stirred at room temperature for one hour. To the resulting mixtures were added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-iodophenyl)thiazole (hereinafter, referred to as "Present compound (T005)") 0.39 g.

Present Compound (T005)

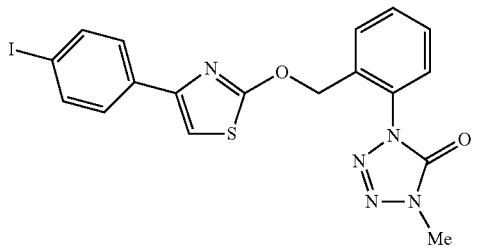 [SMILES: Cn1nnn(-c2ccccc2COc2nc(-c3ccc(I)cc3)cs2)c1=O]

$^1$H NMR (CDCl$_3$) δ: 3.65 (3H, s), 5.61 (2H, s), 6.86 (1H, s), 7.47-7.56 (5H, m), 7.69-7.72 (3H, m).

Preparation Example 6

A mixture of Intermediate (PRH) 1.08 g, 4-(4-bromo-2-fluorophenyl)-2-oxo-tiazole (hereinafter, referred to as "Intermediate (PR06)") 1.10 g, potassium carbonate 0.66 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-bromo-2-fluorophenyl)thiazole (hereinafter, referred to as "Present compound (T006)") 0.36 g.

Present Compound (T006)

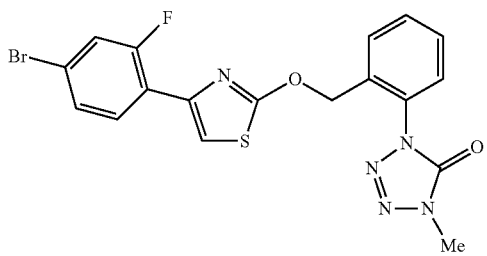 [SMILES: Cn1nnn(-c2ccccc2COc2nc(-c3ccc(Br)cc3F)cs2)c1=O]

$^1$H NMR (CDCl$_3$) δ: 3.67 (3H, s), 5.61 (2H, s), 7.14 (1H, d, J=1.5 Hz), 7.29 (1H, dd, J=1.7, 10.9), 7.35 (1H, dd, J=1.9, 8.5 Hz), 7.47-7.57 (3H, m), 7.70-7.71 (1H, m), 7.92 (1H, t, J=8.5 Hz).

Preparation Example 7

A mixture of Intermediate (PRH) 1.08 g, 4-(4-bromo-2,5-difluorophenyl)-2-oxo-thiazole (hereinafter, referred to as "Intermediate (PR07)") 1.17 g, potassium carbonate 0.66 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-bromo-2,5-difluorophenyl)thiazole (hereinafter, referred to as "Present compound (T007)") 0.09 g.

Present Compound (T007)

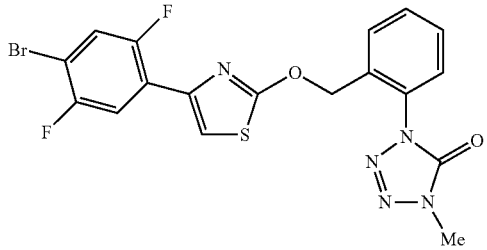 [SMILES: Cn1nnn(-c2ccccc2COc2nc(-c3cc(F)c(Br)cc3F)cs2)c1=O]

$^1$H NMR (CDCl$_3$) δ: 3.70 (3H, s), 5.61 (2H, s), 7.19 (1H, J=2.2 Hz), 7.32 (1H, dd, J=5.6, J=10.2 Hz), 7.48-7.57 (3H, m), 7.70-7.72 (1H, m), 7.81 (1H, dd, J=6.6, 9.3 Hz).

Preparation Example 8

A mixture of Intermediate (PRH) 1.08 g, 4-(4-bromo-3-fluorophenyl)-2-oxo-thiazole (hereinafter, referred to as "Intermediate (PR08)") 1.10 g, cesium carbonate 1.56 g and N,N-dimethylformamide 15 mL was stirred at 80° C. for two and a half hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-bromo-3-fluorophenyl)thiazole (hereinafter, referred to as "Present compound (T008)") 0.52 g.

Present Compound (T008)

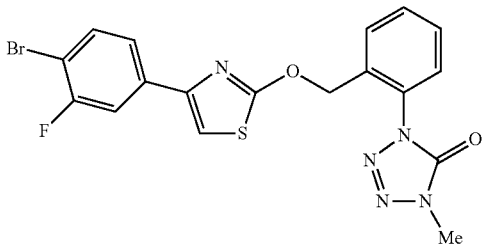 [SMILES: Cn1nnn(-c2ccccc2COc2nc(-c3ccc(Br)c(F)c3)cs2)c1=O]

$^1$H NMR (CDCl$_3$) δ: 3.68 (3H, s), 5.62 (2H, s), 6.89 (1H, s), 7.42 (1H, ddd, J=0.5, 1.9, 8.5 Hz), 7.48-7.57 (5H, m), 7.70-7.73 (1H, m).

Preparation Example 9

A mixture of Intermediate (PRH) 1.08 g, 4-(2,3,4,5,6-pentafluorophenyl)-2-oxo-thiazole (hereinafter, referred to as "Intermediate (PR09)") 1.07 g, cesium carbonate 1.56 g and N,N-dimethylformamide 15 mL was stirred at 80° C. for two and a half hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(2,3,4,5,6-pentafluorophenyl)thiazole (hereinafter, referred to as "Present compound (T009)") 0.09 g.

Present Compound (T009)

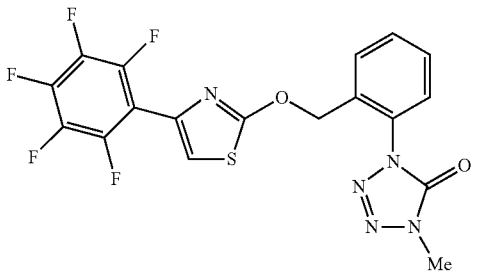 [SMILES: Cn1nnn(-c2ccccc2COc2nc(-c3c(F)c(F)c(F)c(F)c3F)cs2)c1=O]

$^1$H NMR (CDCl$_3$) δ: 3.71 (3H, s), 5.57 (2H, s), 6.96 (1H, s), 7.46-7.56 (3H, m), 7.71-7.73 (1H, m).

Preparation Example 10

A mixture of Intermediate (PRH) 1.08 g, 4-(4-trifluoromethylphenyl)-2-oxo-thiazole (hereinafter, referred to as "Intermediate (PR10)") 0.98 g, potassium carbonate 0.66 g and acetonitrile 15 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-trifluoromethylphenyl)thiazole (hereinafter, referred to as "Present compound (T010)") 0.41 g.

Present Compound (T010)

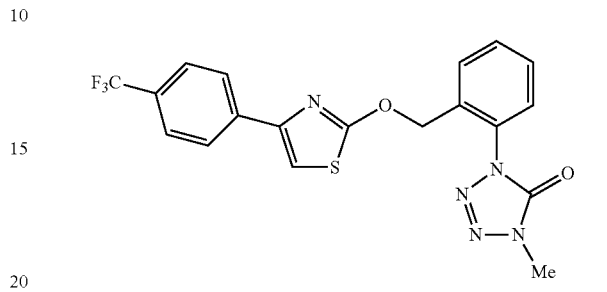

$^1$H NMR (CDCl$_3$) δ: 3.66 (3H, s), 5.64 (2H, s), 6.96 (1H, s), 7.48-7.57 (3H, m), 7.63 (2H, d, J=8.3 Hz), 7.71-7.73 (1H, m), 7.87 (2H, d, J=8.1 Hz).

Preparation Example 11

Under ice-cooling, to a mixture of Intermediate (PRH) 1.08 g, 4-(4-trifluoromethoxyphenyl)-2-oxo-thiazole (hereinafter, referred to as "Intermediate (PR11)") 1.04 g and N,N-dimethylformamide 15 mL was added sodium hydride 0.18 g (dispersion in paraffin liquid, 55% contents) and the resulting mixtures were stirred at room temperature for one hour. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-trifluoromethoxyphenyl)thiazole (hereinafter, referred to as "Present compound (T011)") 0.25 g.

Present Compound (T011)

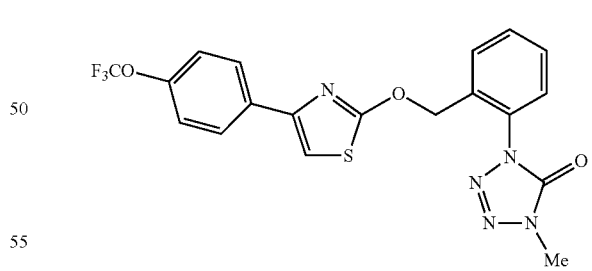

$^1$H NMR (CDCl$_3$) δ: 3.65 (3H, s), 5.63 (2H, s), 6.84 (1H, s), 7.23 (2H, d, J=8.7 Hz), 7.47-7.57 (3H, m), 7.71-7.73 (1H, m), 7.79 (2H, dt, J=1.7, 8.5 Hz).

Preparation Example 12

A mixture of Intermediate (PRH) 0.76 g, 4-(4-methylphenyl)-2-oxo-thiazole (hereinafter, referred to as "Intermediate (PR12)") 0.54 g, potassium carbonate 0.39 g and acetonitrile 5 mL was stirred with heating under reflux for two and a half hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-methylphenyl)thiazole (hereinafter, referred to as "Present compound (T012)") 0.09 g.

Present Compound (T012)

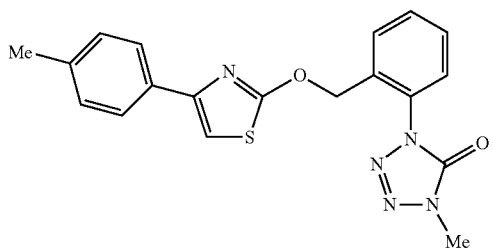

$^1$H NMR (CDCl$_3$) δ: 2.37 (3H, s), 3.64 (3H, s), 5.63 (2H, s), 6.78 (1H, s), 7.19 (2H, d, J=7.8 Hz), 7.46-7.56 (3H, m), 7.67 (2H, d, J=8.0 Hz), 7.71-7.34 (1H, m).

Preparation Example 13

A mixture of Intermediate (PRH) 1.08 g, 4-(4-methoxyphenyl)-2-oxo-thiazole (hereinafter, referred to as "Intermediate (PR13)") 0.99 g, potassium carbonate 0.66 g and acetonitrile 15 mL was stirred with heating under reflux for thirteen hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-methoxyphenyl)thiazole (hereinafter, referred to as "Present compound (T013)") 0.15 g.

Present Compound (T013)

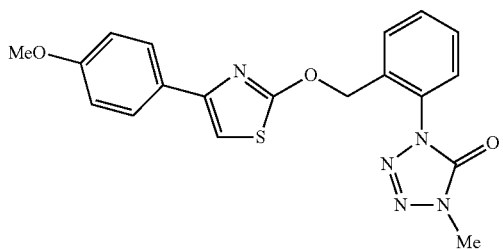

$^1$H NMR (CDCl$_3$) δ: 3.64 (3H, s), 3.84 (3H, s), 5.62 (2H, s), 6.70 (1H, s), 6.92 (2H, dt, J=2.9, 8.8 Hz), 7.46-7.57 (3H, m), 7.69-7.73 (3H, m).

Preparation Example 14

A mixture of Intermediate (PRH) 1.08 g, 4-(4-butylphenyl)-2-oxo-thiazole (hereinafter, referred to as "Intermediate (PR14)") 0.93 g, potassium carbonate 0.66 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-butylphenyl)thiazole (hereinafter, referred to as "Present compound (T014)") 0.35 g.

Present Compound (T014)

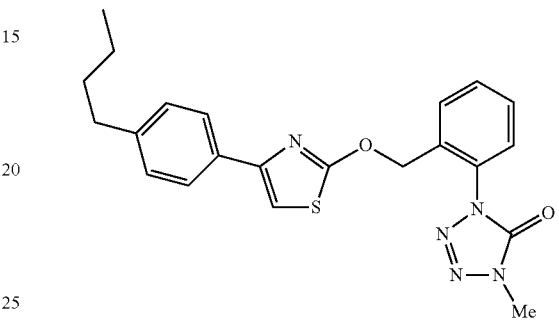

$^1$H NMR (CDCl$_3$) δ: 0.93 (3H, t, J=7.2 Hz), 1.31-1.42 (2H, m), 1.57-1.66 (2H, m), 2.62 (2H, t, J=7.7 Hz), 3.63 (3H, s), 5.63 (2H, s), 6.78 (1H, s), 7.18-7.22 (2H, m), 7.46-7.55 (3H, m), 7.67-7.73 (3H, m).

Preparation Example 15

A mixture of Intermediate (PRH) 1.08 g, 4-[4-(1,1-dimethylethyl)phenyl]-2-oxo-thiazole (hereinafter, referred to as "Intermediate (PR15)") 0.93 g, potassium carbonate 0.66 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-[4-(1,1-dimethylethyl)phenyl]thiazole (hereinafter, referred to as "Present compound (T015)") 0.54 g.

Present Compound (T015)

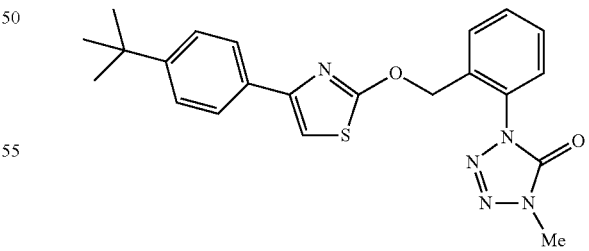

$^1$H NMR (CDCl$_3$) δ: 1.34 (9H, s), 3.63 (3H, s), 5.63 (2H, s), 6.79 (1H, s), 7.41 (2H, dt, J=2.2, 8.2 Hz), 7.46-7.55 (3H, m), 7.69-7.73 (3H, m).

Preparation Example 16

A mixture of Intermediate (PRH) 1.08 g, 4-(4-nitrophenyl)-2-oxo-thiazole (hereinafter, referred to as "Intermediate (PR16)") 0.89 g, potassium carbonate 0.66 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-nitrophenyl)thiazole (hereinafter, referred to as "Present compound (T016)") 0.19 g.

Present Compound (T016)

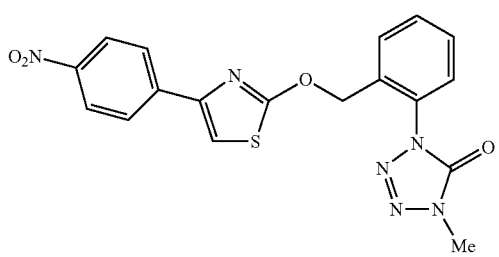 [SMILES: Cn1nnn(-c2ccccc2COc2nc(-c3ccc([N+](=O)[O-])cc3)cs2)c1=O]

$^1$H NMR (CDCl$_3$) δ: 3.68 (3H, s), 5.64 (2H, s), 7.08 (1H, s), 7.49-7.58 (3H, m), 7.71-7.73 (1H, m), 7.92 (2H, dt, J=2.4, 9.0 Hz), 8.24 (2H, dt, 2.0, 9.0 Hz).

Preparation Example 17

A mixture of Intermediate (PRH) 2.15 g, 4-([1,1'-biphenyl]-4-yl)-2-oxo-thiazole (hereinafter, referred to as "Intermediate (PR17)") 2.03 g, potassium carbonate 1.33 g and N,N-dimethylformamide 30 mL was stirred at 80° C. for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-([1,1'-biphenyl]-4-yl)thiazole (hereinafter, referred to as "Present compound (T017)") 0.50 g.

Present Compound (T017)

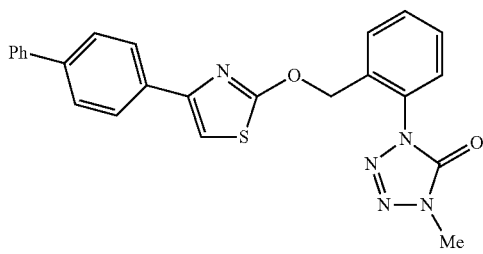

$^1$H NMR (CDCl$_3$) δ: 3.64 (3H, s), 5.65 (2H, s), 6.88 (1H, s), 7.35 (1H, t, J=7.5 Hz), 7.43-7.56 (5H, m), 7.63 (4H, d, J=8.0 Hz), 7.72-7.74 (1H, m), 7.85 (2H, d, J=8.2 Hz).

Preparation Example 18

A mixture of Intermediate (PRH) 2.33 g, 4-[4-(tetrahydropyran-2-yloxy)phenyl]-2-oxo-thiazole (hereinafter, referred to as "Intermediate (PR18)") 2.40 g, potassium carbonate 1.44 g and N,N-dimethylformamide 30 mL was stirred at 80° C. for two and a half hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-[4-(tetrahydropyran-2-yloxy)phenyl]thiazole (hereinafter, referred to as "Present compound (T018)") 2.03 g.

Present Compound (T018)

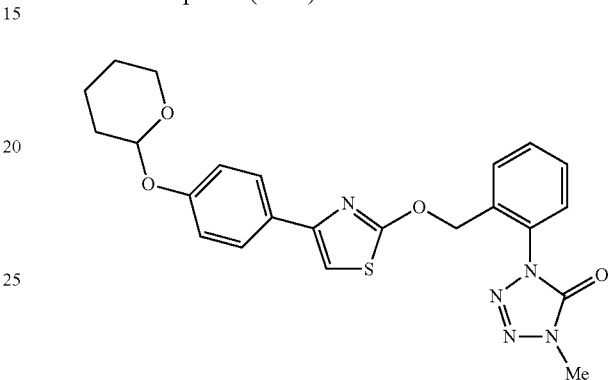

$^1$H NMR (CDCl$_3$) δ: 1.59-2.08 (6H, m), 3.59-3.64 (1H, m), 3.64 (3H, s), 3.91 (1H, ddd, J=3.2, 9.4, 11.7 Hz), 5.45 (1H, t, J=3.2 Hz), 5.62 (2H, s), 6.71 (1H, s), 7.06 (2H, dt, J=2.9, 8.8 Hz), 7.46-7.56 (3H, m), 7.68-7.73 (3H, m).

Preparation Example 19

A mixture of the above-mentioned Present compound (T018) 1.70 g, iodine 0.10 g and methanol 50 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-hydroxyphenyl)thiazole (hereinafter, referred to as "Present compound (T019)") 0.66 g.

Present Compound (T019)

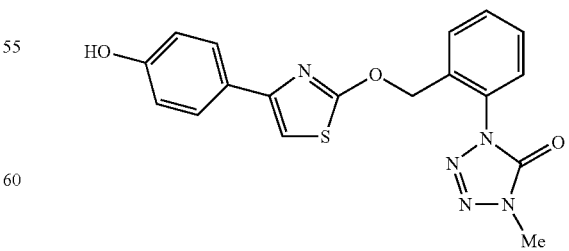

$^1$H NMR (DMSO-d$_6$) δ: 3.54 (3H, s), 5.58 (2H, s), 6.79 (2H, d, J=8.5 Hz), 7.17 (1H, s), 7.56-7.67 (5H, m), 7.78-7.80 (1H, m), 9.62 (1H, s).

Preparation Example 20

A mixture of Intermediate (PRH) 1.08 g, [4-(N,N-dimethylaminosulfonyl)phenyl]-2-oxo-thiazole (hereinafter, referred to as "Intermediate (PR20)") 1.14 g, potassium carbonate 0.66 g and N,N-dimethylformamide 15 mL was stirred at 80° C. for two and a half hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-[4-(N,N-dimethylaminosulfonyl)phenyl]thiazole (hereinafter, referred to as "Present compound (T020)") 0.56 g.

Present Compound (T020)

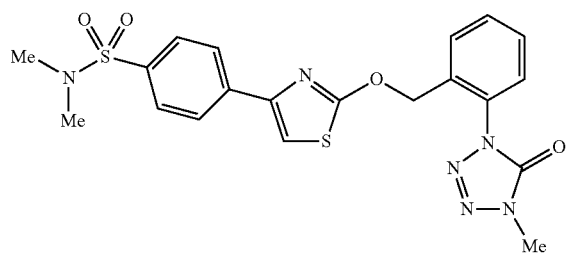 [SMILES: CN(C)S(=O)(=O)c1ccc(-c2csc(OCc3ccccc3-n3nnn(C)c3=O)n2)cc1]

$^1$H NMR (CDCl$_3$) δ: 2.72 (6H, s), 3.68 (3H, s), 5.64 (2H, s), 7.03 (1H, s), 7.49-7.58 (3H, m), 7.72-7.74 (1H, m), 7.79 (2H, d, J=8.2 Hz), 7.94 (2H, d, J=8.2 Hz).

Preparation Example 21

A mixture of Intermediate (PRH) 1.08 g, 4-{4-[2-(2-methoxyethoxy)ethoxy]phenyl}-2-oxo-thiazole (hereinafter, referred to as "Intermediate (PR21)") 1.18 g, potassium carbonate 0.66 g and acetonitrile 15 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-{4-[2-(2-methoxyethoxy)ethoxy]phenyl}thiazole (hereinafter, referred to as "Present compound (T021)") 0.30 g.

Present Compound (T021)

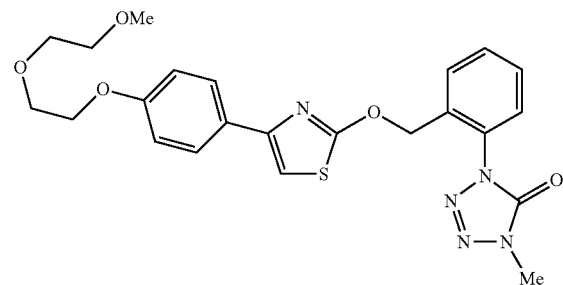 [SMILES: COCCOCCOc1ccc(-c2csc(OCc3ccccc3-n3nnn(C)c3=O)n2)cc1]

$^1$H NMR (CDCl$_3$) δ: 3.40 (3H, s), 3.58-3.60 (2H, m), 3.63 (3H, s), 3.72-3.75 (2H, m), 3.88 (2H, t, J=4.8 Hz), 4.17 (2H, t, J=5.3 Hz), 5.62 (2H, s), 6.70 (1H, s), 6.93 (2H, dt, J=2.9, 8.9 Hz), 7.46-7.56 (3H, m), 7.68-7.73 (3H, m).

Preparation Example 22

A mixture of Intermediate (PRH) 1.08 g, 4-(2-naphthyl)-2-oxo-thiazole (hereinafter, referred to as "Intermediate (PR22)") 0.91 g, potassium carbonate 0.66 g and acetonitrile 15 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(2-naphthyl)thiazole (hereinafter, referred to as "Present compound (T022)") 0.32 g.

Present Compound (T022)

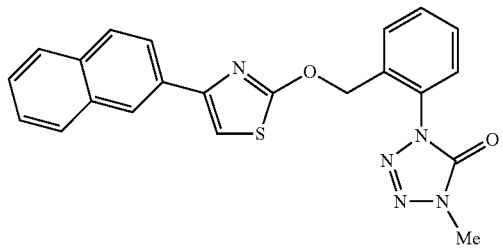 [SMILES: Cn1nnn(-c2ccccc2COc2nc(-c3ccc4ccccc4c3)cs2)c1=O]

$^1$H NMR (CDCl$_3$) δ: 3.63 (3H, s), 5.69 (2H, s), 6.97 (1H, s), 7.44-7.58 (5H, m), 7.75-7.67 (1H, m), 7.81-7.84 (3H, m), 7.92-7.94 (1H, m), 8.31 (1H, s).

Preparation Example 23

A mixture of the above-mentioned Present compound (T019) 0.41 g, acetic anhydride 0.12 g, potassium carbonate 0.19 g and acetonitrile 30 mL was stirred at room temperature for three hours. After cooling the reaction solution, thereto were added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-acetoxyphenyl)thiazole (hereinafter, referred to as "Present compound (T023)") 0.30 g.

Present Compound (T023)

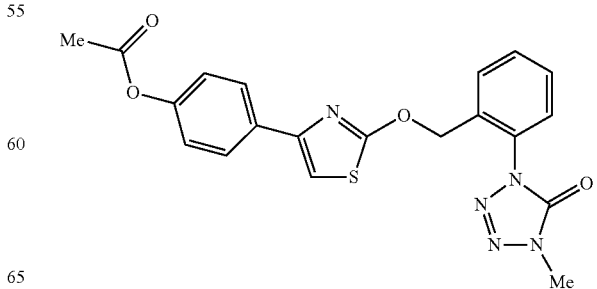

¹H NMR (CDCl₃) δ: 2.32 (3H, s), 3.64 (3H, s), 5.62 (2H, s), 6.81 (1H, s), 7.11 (2H, dt, J=2.7, 8.5 Hz), 7.47-7.57 (3H, m), 7.71-7.73 (1H, m), 7.78 (2H, dt, J=2.7, 8.5).

Preparation Example 24

A mixture of Intermediate (PRH) 1.08 g, 4-trifluoromethyl-2-oxo-thiazole (hereinafter, referred to as "Intermediate (PR24)") 0.68 g, potassium carbonate 0.66 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-trifluoromethylthiazole (hereinafter, referred to as "Present compound (T024)") 0.19 g.

Present Compound (T024)

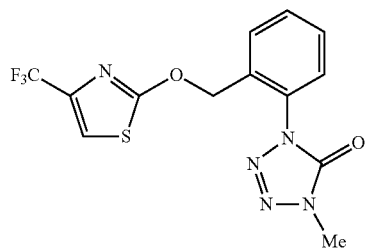 [SMILES: Cn1nnn(-c2ccccc2COc2nc(C(F)(F)F)cs2)c1=O]

¹H NMR (CDCl₃) δ: 3.72 (3H, s), 5.58 (2H, s), 7.12 (1H, s), 7.48-7.57 (3H, m), 7.68-7.70 (1H, m).

Preparation Example 25

A mixture of Intermediate (PRH) 1.08 g, 4-(1,1-dimethylethyl)-2-oxo-thiazole (hereinafter, referred to as "Intermediate (PR25)") 0.63 g, cesium carbonate 1.56 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(1,1-dimethylethyl)thiazole (hereinafter, referred to as "Present compound (T025)") 0.71 g.

Present Compound (T025)

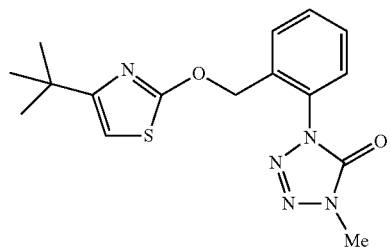 [SMILES: Cn1nnn(-c2ccccc2COc2nc(C(C)(C)C)cs2)c1=O]

¹H NMR (CDCl₃) δ: 1.22 (9H, s), 3.71 (3H, s), 5.49 (2H, s), 6.18 (1H, s), 7.45-7.53 (3H, m), 7.69-7.73 (1H, m).

Preparation Example 26

A mixture of Intermediate (PRH) 1.08 g, 4-(1,1-dimethylethyl)-2-oxo-thiazole (hereinafter, referred to as "Intermediate (PR25)") 0.63 g, cesium carbonate 1.56 g and N,N-dimethylformamide 15 mL was stirred at 80° C. for six hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(1-adamantyl)thiazole (hereinafter, referred to as "Present compound (T026)") 0.65 g.

Present Compound (T026)

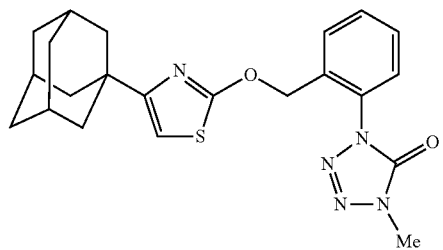 [SMILES: Cn1nnn(-c2ccccc2COc2nc(C34CC5CC(CC(C5)C3)C4)cs2)c1=O]

¹H NMR (CDCl₃) δ: 1.74 (6H, m), 1.84 (6H, d, J=2.9 Hz), 2.04 (3H, m), 3.71 (3H, s), 5.49 (2H, s), 6.14 (1H, s), 7.53-7.45 (3H, m), 7.72-7.69 (1H, m).

Preparation Example 27

A mixture of 1-(2-bromomethyl-3-methylphenyl)-4-methyl-1,4-dihydrotetrazole-5-one (hereinafter, referred to as "Intermediate (PRM)") 0.60 g, Intermediate (PR01) 0.39 g, cesium carbonate 0.90 g and acetonitrile 10 mL was stirred with heating under reflux for two and a half hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-phenylthiazole (hereinafter, referred to as "Present compound (T029)") 0.33 g.

Present Compound (T029)

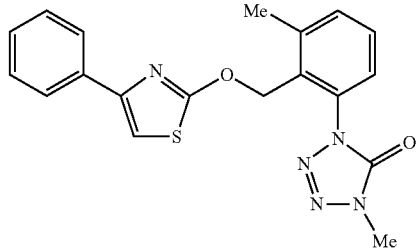 [SMILES: Cc1cccc(-n2nnn(C)c2=O)c1COc1nc(-c2ccccc2)cs1]

¹H NMR (CDCl₃) δ: 2.58 (3H, s), 3.57 (3H, s), 5.61 (2H, s), 6.84 (1H, s), 7.25-7.32 (2H, m), 7.38-7.45 (4H, m), 7.77-7.80 (2H, m).

Preparation Example 28

A mixture of Intermediate (PRM) 0.60 g, Intermediate (PR02) 0.44 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-fluorophenyl)thiazole (hereinafter, referred to as "Present compound (T030)") 0.37 g.

Present Compound (T030)

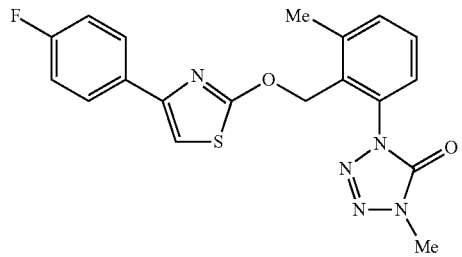

¹H NMR (CDCl₃) δ: 2.57 (3H, s), 3.58 (3H, s), 5.58 (2H, s), 6.76 (1H, s), 7.08 (2H, tt, J=2.0, 8.8 Hz), 7.26 (1H, dd, J=2.2, 6.7 Hz), 7.40 (1H, dd, J=2.2, 7.8 Hz), 7.42 (1H, t, J=7.6 Hz), 7.75 (2H, ddt, J=2.9, 5.4, 9.0 Hz).

Preparation Example 29

A mixture of Intermediate (PRM) 0.60 g, Intermediate (PR03) 0.47 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-chlorophenyl)thiazole (hereinafter, referred to as "Present compound (T031)") 0.36 g.

Present Compound (T031)

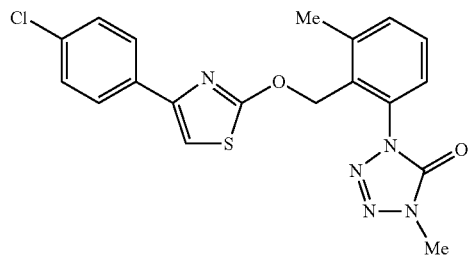

¹H NMR (CDCl₃) δ: 2.57 (3H, s), 3.59 (3H, s), 5.58 (2H, s), 6.83 (1H, s), 7.27 (1H, dd, J=2.2, 6.7 Hz), 7.36 (2H, dt, J=2.2, 8.8 Hz), 7.40 (1H, dd, J=2.4, 8.0 Hz), 7.43 (1H, t, J=7.6 Hz), 7.71 (2H, dt, J=2.2, 8.8 Hz).

Preparation Example 30

A mixture of Intermediate (PRM) 1.13 g, Intermediate (PR04) 1.02 g, cesium carbonate 1.56 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-bromophenyl)thiazole (hereinafter, referred to as "Present compound (T032)") 0.80 g.

Present Compound (T032)

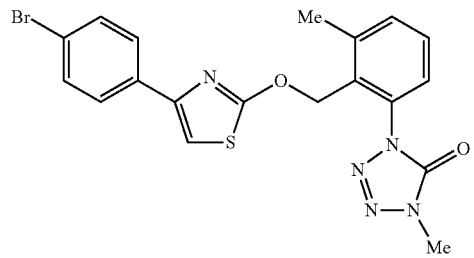 [SMILES: Cc1cccc(-n2nnn(C)c2=O)c1COc1nc(-c2ccc(Cl)cc2)cs1]

¹H NMR (CDCl₃) δ: 2.56 (3H, s), 3.58 (3H, s), 5.58 (2H, s), 6.83 (1H, s), 7.26 (1H, dd, J=2.2, 7.0 Hz), 7.39 (1H, dd, 1.9, 7.7 Hz), 7.42 (1H, t, J=7.7 Hz), 7.50 (2H, dt, J=1.9, 8.7 Hz), 7.64 (2H, dt, J=2.2, 8.5 Hz).

Preparation Example 31

A mixture of Intermediate (PRM) 0.60 g, Intermediate (PR05) 0.68 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-iodophenyl)thiazole (hereinafter, referred to as "Present compound (T033)") 0.25 g.

Present Compound (T033)

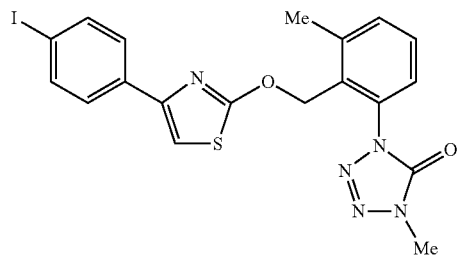 [SMILES: Cc1cccc(-n2nnn(C)c2=O)c1COc1nc(-c2ccc(I)cc2)cs1]

¹H NMR (CDCl₃) δ: 2.57 (3H, s), 3.59 (3H, s), 5.58 (2H, s), 6.85 (1H, s), 7.26-7.28 (1H, m), 7.39-7.45 (2H, m), 7.52 (2H, d, J=8.5 Hz), 7.72 (2H, d, J=8.5 Hz).

Preparation Example 32

A mixture of Intermediate (PRM) 0.60 g, Intermediate (PR06) 0.61 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-bromo-2-fluorophenyl)thiazole (hereinafter, referred to as "Present compound (T034)") 0.18 g.

Present Compound (T034)

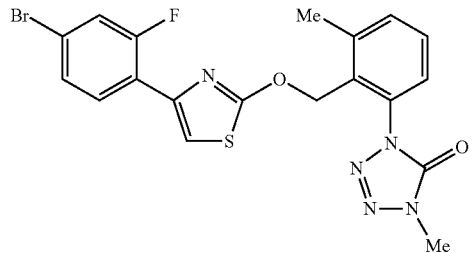 [SMILES: Cc1cccc(-n2nnn(C)c2=O)c1COc1nc(-c2ccc(Br)cc2F)cs1]

¹H NMR (CDCl₃) δ: 2.56 (3H, s), 3.62 (3H, s), 5.57 (2H, s), 7.13 (1H, d, J=2.2 Hz), 7.26-7.31 (2H, m), 7.35 (1H, ddd, J=0.5, 1.7, 8.4 Hz), 7.40 (1H, dd, J=1.9, 8.0 Hz), 7.43 (1H, t, J=7.5 Hz), 7.93 (1H, t, J=8.5 Hz).

Preparation Example 33

A mixture of Intermediate (PRM) 0.60 g, Intermediate (PR08) 0.61 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-bromo-3-fluorophenyl)thiazole (hereinafter, referred to as "Present compound (T035)") 0.25 g.

Present Compound (T035)

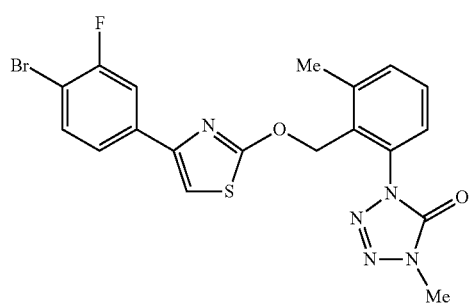 [SMILES: Cc1cccc(-n2nnn(C)c2=O)c1COc1nc(-c2ccc(Br)c(F)c2)cs1]

¹H NMR (CDCl₃) δ: 2.57 (3H, s), 3.63 (3H, s), 5.58 (2H, s), 6.88 (1H, s), 7.26-7.29 (1H, m), 7.40-7.45 (3H, m), 7.52-7.56 (2H, m).

Preparation Example 34

A mixture of Intermediate (PRM) 0.60 g, Intermediate (PR09) 0.60 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2,3,4,5,6-pentafluorophenyl)thiazole (hereinafter, referred to as "Present compound (T036)") 0.10 g.

Present Compound (T036)

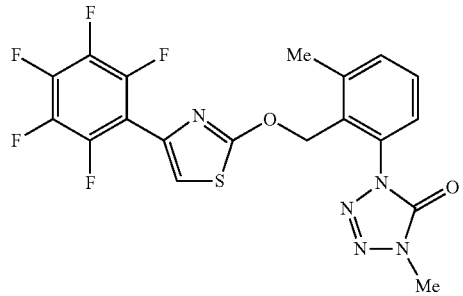 [SMILES: Cc1cccc(-n2nnn(C)c2=O)c1COc1nc(-c2c(F)c(F)c(F)c(F)c2F)cs1]

¹H NMR (CDCl₃) δ: 2.56 (3H, s), 3.69 (3H, s), 5.54 (2H, s), 6.93 (1H, s), 7.25 (1H, dd, J=1.7, 7.0), 7.39 (1H, dd, J=2.4, 8.0 Hz), 7.42 (1H, t, J=7.5 Hz).

Preparation Example 35

A mixture of Intermediate (PRM) 0.60 g, Intermediate (PR10) 0.55 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-trifluoromethylphenyl)thiazole (hereinafter, referred to as "Present compound (T037)") 0.22 g.

Present Compound (T037)

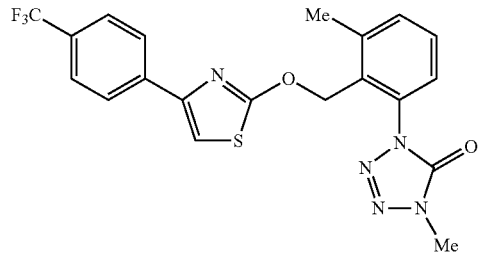 [SMILES: Cc1cccc(-n2nnn(C)c2=O)c1COc1nc(-c2ccc(C(F)(F)F)cc2)cs1]

¹H NMR (CDCl₃) δ: 2.58 (3H, s), 3.60 (3H, s), 5.60 (2H, s), 6.96 (1H, s), 7.28 (1H, dd, J=2.2, 7.2 Hz), 7.40 (1H, dd, J=2.2, 7.7 Hz), 7.44 (1H, t, J=7.7 Hz), 7.64 (2H, d, J=8.2 Hz), 7.88 (2H, d, J=8.0 Hz).

Preparation Example 36

A mixture of Intermediate (PRM) 0.60 g, Intermediate (PR11) 0.58 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-trifluoromethoxyphenyl)thiazole (hereinafter, referred to as "Present compound (T038)") 0.20 g.

Present Compound (T038)

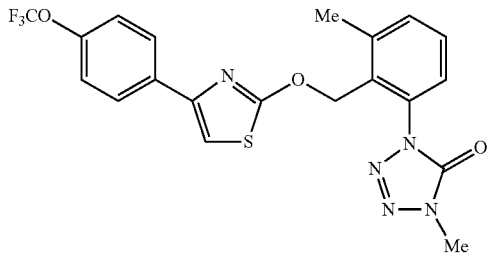 [SMILES: Cc1cccc(-n2nnn(C)c2=O)c1COc1nc(-c2ccc(OC(F)(F)F)cc2)cs1]

¹H NMR (CDCl₃) δ: 2.57 (3H, s), 3.59 (3H, s), 5.59 (2H, s), 6.83 (1H, s), 7.24 (2H, d, J=8.9 Hz), 7.27 (1H, dd, J=2.2, 7.0 Hz), 7.40 (1H, dd, J=2.4, 8.0 Hz), 7.43 (1H, t, 7.7 Hz), 7.80 (2H, dt, J=2.2, 8.9 Hz).

Preparation Example 37

A mixture of Intermediate (PRM) 0.60 g, Intermediate (PR12) 0.43 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-methylphenyl)thiazole (hereinafter, referred to as "Present compound (T039)") 0.20 g.

Present Compound (T039)

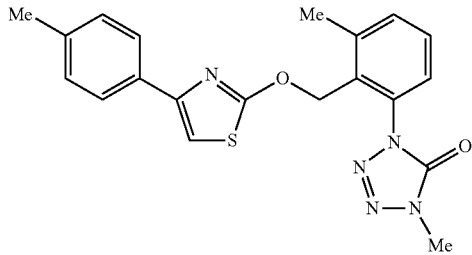

¹H NMR (CDCl₃) δ: 2.37 (3H, s), 2.57 (3H, s), 3.58 (3H, s), 5.60 (2H, s), 6.80 (1H, s), 7.20 (2H, d, J=8.5 Hz), 7.26 (1H, dd, J=2.4, 6.8 Hz), 7.39-7.44 (2H, m), 7.67 (2H, d, J=8.2 Hz).

Preparation Example 38

A mixture of Intermediate (PRM) 0.60 g, Intermediate (PR13) 0.46 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-methoxyphenyl)thiazole (hereinafter, referred to as "Present compound (T040)") 0.27 g.

Present Compound (T040)

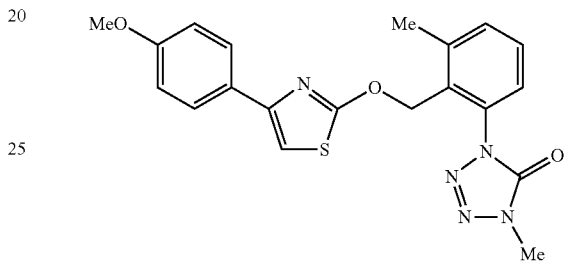

¹H NMR (CDCl₃) δ: 2.57 (3H, s), 3.58 (3H, s), 3.85 (3H, s), 5.59 (2H, s), 6.69 (1H, s), 6.93 (2H, dt, J=2.2, 8.9 Hz), 7.26 (1H, dd, 2.4, 6.8 Hz), 7.39-7.45 (2H, m), 7.72 (2H, dt, J=2.2, 8.9 Hz).

Preparation Example 39

A mixture of Intermediate (PRM) 0.60 g, Intermediate (PR14) 0.52 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-butylphenyl)thiazole (hereinafter, referred to as "Present compound (T041)") 0.37 g.

Present Compound (T041)

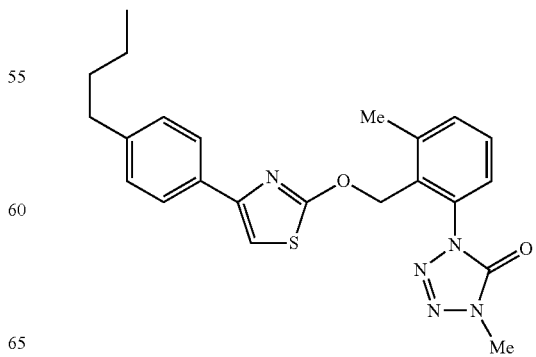

¹H NMR (CDCl₃) δ: 0.93 (3H, t, J=7.5 Hz), 1.32-1.41 (2H, m), 1.57-1.65 (2H, m), 2.57 (3H, s), 2.63 (2H, t, J=7.7 Hz), 3.57 (3H, s), 5.60 (2H, s), 6.77 (1H, s), 7.20 (2H, d, J=8.0 Hz), 7.26 (1H, dd, J=2.6, 6.5 Hz), 7.39-7.44 (2H, m), 7.69 (2H, d, J=8.2 Hz).

Preparation Example 40

A mixture of Intermediate (PRM) 0.60 g, Intermediate (PR15) 0.52 g, cesium carbonate 0.90 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-[4-(1,1-dimethylethyl)phenyl]thiazole (hereinafter, referred to as "Present compound (T042)") 0.23 g.

Present Compound (T042)

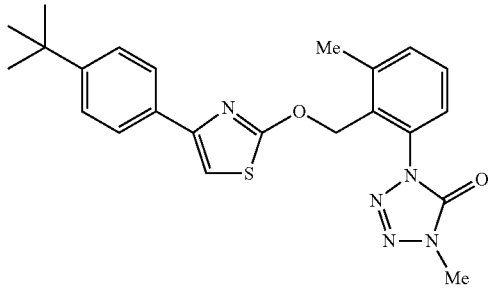 [SMILES: Cc1cccc(-n2nnn(C)c2=O)c1COc1nc(-c2ccc(C(C)(C)C)cc2)cs1]

¹H NMR (CDCl₃) δ: 1.34 (9H, s), 2.57 (3H, s), 3.57 (3H, s), 5.60 (2H, s), 6.78 (1H, s), 7.24-7.27 (1H, m), 7.38-7.44 (4H, m), 7.70 (2H, d, J=8.5 Hz).

Preparation Example 41

A mixture of Intermediate (PRM) 0.60 g, Intermediate (PR16) 0.50 g, cesium carbonate 0.90 g and N,N-dimethylformamide 10 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-nitrophenyl)thiazole (hereinafter, referred to as "Present compound (T043)") 0.14 g.

Present Compound (T043)

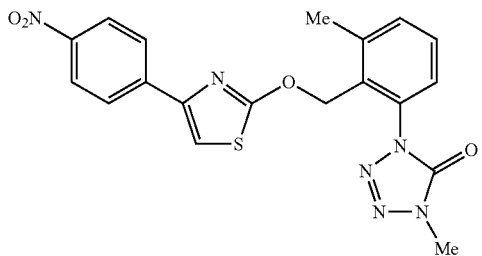 [SMILES: Cc1cccc(-n2nnn(C)c2=O)c1COc1nc(-c2ccc([N+](=O)[O-])cc2)cs1]

¹H NMR (CDCl₃) δ: 2.58 (3H, s), 3.63 (3H, s), 5.61 (2H, s), 7.07 (1H, s), 7.29 (1H, dd, J=1.9, 7.2 Hz), 7.43 (1H, dd, J=2.2, 8.0 Hz), 7.45 (1H, t, J=7.5 Hz), 7.93 (2H, dt, J=1.9, 8.9 Hz), 8.26 (2H, dt, J=2.2, 9.2 Hz).

Preparation Example 42

A mixture of Intermediate (PRM) 0.60 g, Intermediate (PR17) 0.57 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-([1,1'-biphenyl]-4-yl)thiazole (hereinafter, referred to as "Present compound (T044)") 0.37 g.

Present Compound (T044)

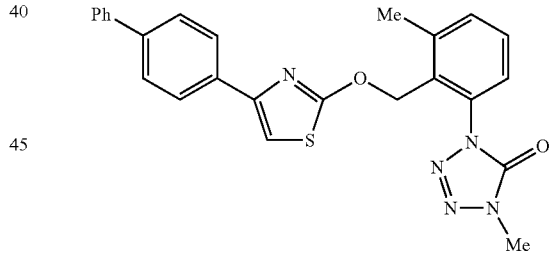

¹H NMR (CDCl₃) δ: 2.59 (3H, s), 3.59 (3H, s), 5.62 (2H, s), 6.88 (1H, s), 7.27 (1H, dd, J=2.4, 6.8 Hz), 7.36 (1H, t, J=7.5 Hz), 7.40-7.48 (4H, m), 7.64 (4H, d, J=8.5 Hz), 7.86 (2H, d, J=8.5 Hz).

Preparation Example 43

A mixture of Intermediate (PRM) 0.60 g, Intermediate (PR21) 0.66 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-{4-[2-(2-methoxyethoxy)-ethoxy]phenyl}thiazole (hereinafter, referred to as "Present compound (T045)") 0.34 g.

Present Compound (T045)

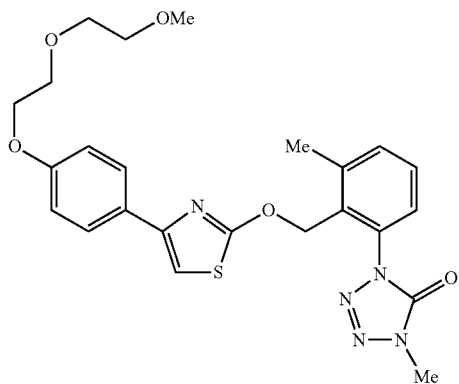 [SMILES: COCCOCCOc1ccc(-c2csc(OCc3c(C)cccc3-n3nnn(C)c3=O)n2)cc1]

$^1$H NMR (CDCl$_3$) δ: 2.57 (3H, s), 3.40 (3H, s), 3.58 (3H, s), 3.58-3.60 (2H, m), 3.74 (2H, t, J=4.9 Hz), 3.88 (2H, t, J=4.6 Hz), 4.18 (2H, t, J=4.4 Hz), 5.58 (2H, s), 6.69 (1H, s), 6.92-6.97 (2H, m), 7.26-7.31 (1H, m), 7.34-7.44 (2H, m), 7.69 (2H, d, J=8.5 Hz).

Preparation Example 44

A mixture of Intermediate (PRM) 0.60 g, Intermediate (PR22) 0.51 g, cesium carbonate 0.90 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-naphthyl)thiazole (hereinafter, referred to as "Present compound (T046)") 0.10 g.

Present Compound (T046)

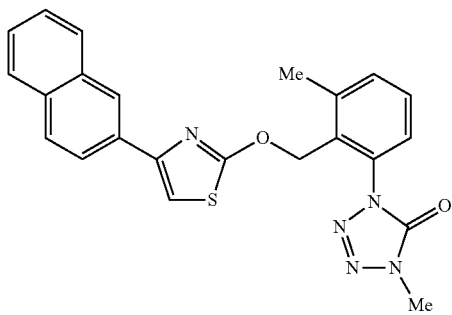 [SMILES: Cc1cccc(-n2nnn(C)c2=O)c1COc1nc(-c2ccc3ccccc3c2)cs1]

$^1$H NMR (CDCl$_3$) δ: 2.61 (3H, s), 3.56 (3H, s), 5.66 (2H, s), 6.97 (1H, s), 7.28 (1H, dd, J=2.7, 6.0 Hz), 7.41-7.52 (4H, m), 7.82-7.85 (3H, m), 7.92-7.94 (1H, m), 8.31 (1H, s).

Preparation Example 45

A mixture of Intermediate (PRM) 0.60 g, Intermediate (PR25) 0.35 g, cesium carbonate 0.90 g and acetonitrile 10 mL was stirred with heating under reflux for two and a half hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(1,1-dimethylethyl)thiazole (hereinafter, referred to as "Present compound (T047)") 0.57 g.

Present Compound (T047)

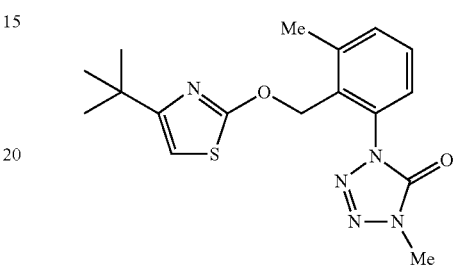

$^1$H NMR (CDCl$_3$) δ: 1.22 (9H, s), 2.56 (3H, s), 3.69 (3H, s), 5.48 (2H, s), 6.17 (1H, s), 7.25 (1H, dd, J=2.0, 8.0 Hz), 7.37 (1H, dd, J=2.0, 7.8 Hz), 7.40 (1H, t, J=7.6 Hz).

Preparation Example 46

A mixture of Intermediate (PRM) 1.13 g, Intermediate (PR26) 0.94 g, cesium carbonate 1.56 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(1-adamantyl)thiazole (hereinafter, referred to as "Present compound (T048)") 1.10 g.

Present Compound (T048)

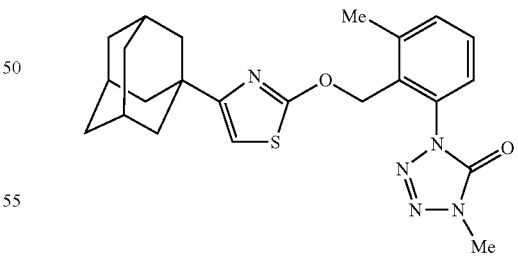

$^1$H NMR (CDCl$_3$) δ: 1.71-1.78 (6H, m), 1.84 (6H, d, J=2.9 Hz), 2.04 (3H, s), 2.56 (3H, s), 3.69 (3H, s), 5.47 (2H, s), 6.12 (1H, s), 7.25 (1H, dd, J=1.7, 7.1 Hz), 7.37 (1H, dd, J=2.4, 8.1 Hz), 7.40 (1H, t, J=7.8 Hz).

Preparation Example 47

A mixture of 1-(2-bromomethyl-3-fluorophenyl)-4-methyl-1,4-dihydrotetrazole-5-one (hereinafter, referred to as "Intermediate (PRF)") 1.19 g, Intermediate (PR04) 1.07 g, cesium carbonate 1.63 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-fluorophenyl-2-yl]methyloxy}-4-(4-bromophenyl)thiazole (hereinafter, referred to as "Present compound (T049)") 0.67 g.

Present Compound (T049)

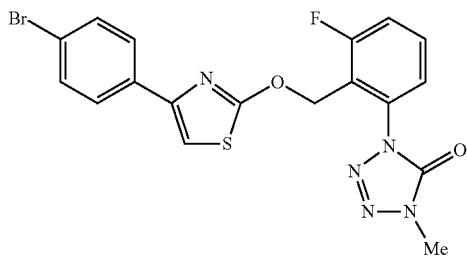

$^1$H NMR (CDCl$_3$) δ: 3.58 (3H, s), 5.72 (2H, s), 6.84 (1H, s), 7.28-7.33 (2H, m), 7.49-7.55 (3H, m), 7.65 (2H, dt, J=2.4, 8.5 Hz).

Preparation Example 48

A mixture of 1-(2-bromomethyl-3-chlorophenyl)-4-methyl-1,4-dihydrotetrazole-5-one (hereinafter, referred to as "Intermediate (PRC)") 0.73 g, Intermediate (PR04) 0.62 g, cesium carbonate 0.94 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-chlorophenyl-2-yl]methyloxy}-4-(4-bromophenyl)thiazole (hereinafter, referred to as "Present compound (T050)") 0.43 g.

Present Compound (T050)

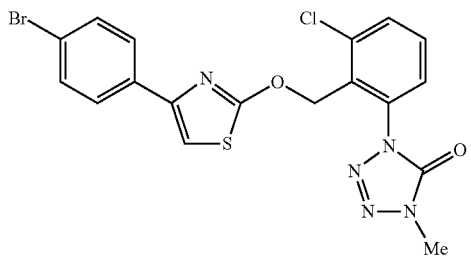

$^1$H NMR (CDCl$_3$) δ: 3.57 (3H, s), 5.77 (2H, s), 6.85 (1H, s), 7.39 (1H, d, J=8.0 Hz), 7.48 (1H, d, J=8.0 Hz), 7.52 (2H, dt, J=2.2, 8.5 Hz), 7.63 (1H, d, J=8.2 Hz), 7.67 (2H, dt, J=2.2, 8.5 Hz).

Preparation Example 49

A mixture of 1-(2-bromomethyl-3-bromophenyl)-4-methyl-1,4-dihydrotetrazole-5-one (hereinafter, referred to as "Intermediate (PRB)") 1.00 g, Intermediate (PR04) 0.66 g, cesium carbonate 1.01 g and N,N-dimethylformamide 10 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-bromophenyl-2-yl]methyloxy}-4-(4-bromophenyl)thiazole (hereinafter, referred to as "Present compound (T051)") 0.44 g.

Present Compound (T051)

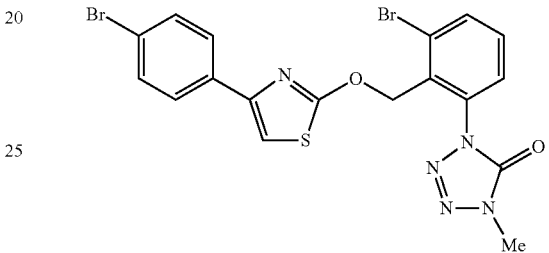

$^1$H NMR (CDCl$_3$) δ: 3.56 (3H, s), 5.77 (2H, s), 6.85 (1H, s), 7.38-7.43 (2H, m), 7.52 (2H, dt, J=2.4, 8.5 Hz), 7.67 (2H, dt, J=2.4, 8.5 Hz), 7.82 (1H, dd, J=2.7, 6.8 Hz).

Preparation Example 50

A mixture of 1-(2-bromomethyl-3-iodophenyl)-4-methyl-1,4-dihydrotetrazole-5-one (hereinafter, referred to as "Intermediate (PRI)") 1.76 g, Intermediate (PR04) 1.02 g, cesium carbonate 1.56 g and N,N-dimethylformamide 15 mL was stirred at 80° C. for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-iodophenyl-2-yl]methyloxy}-4-(4-bromophenyl)thiazole (hereinafter, referred to as "Present compound (T052)") 1.01 g.

Present Compound (T052)

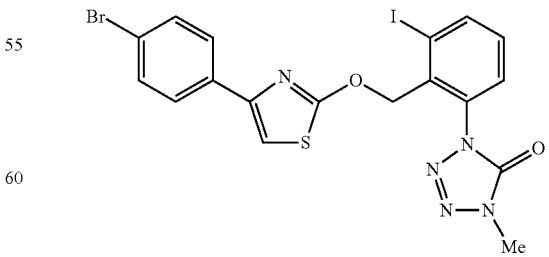

$^1$H NMR (DMSO-d$_6$) δ: 3.51 (3H, s), 5.59 (2H, s), 7.40 (1H, t, J=8.0 Hz), 7.56 (1H, s), 7.59-7.64 (3H, m), 7.78-7.82 (2H, m), 8.20 (1H, d, J=8.0 Hz).

Preparation Example 51

A mixture of 1-(2-bromomethyl-3-methoxyphenyl)-4-methyl-1,4-dihydrotetrazole-5-one (hereinafter, referred to as "Intermediate (PRMT)") 1.20 g, Intermediate (PR04) 1.02 g, cesium carbonate 1.56 g and N,N-dimethylformamide 15 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methoxyphenyl-2-yl]methyloxy}-4-(4-bromophenyl)thiazole (hereinafter, referred to as "Present compound (T053)") 0.49 g.

Present Compound (T053)

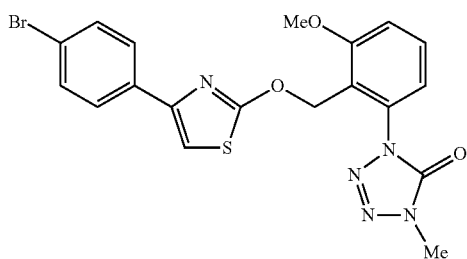

$^1$H NMR (CDCl$_3$) δ: 3.53 (3H, s), 3.93 (3H, s), 5.67 (2H, s), 6.82 (1H, s), 7.05 (1H, d, J=8.0 Hz), 7.10 (1H, d, J=8.2 Hz), 7.47-7.52 (3H, m), 7.67 (2H, dt, J=2.2, 8.2 Hz).

Preparation Example 52

A mixture of Intermediate (PRH) 1.08 g, 4-(4-bromophenyl)-5-methyl-2-oxo-thiazole (hereinafter, referred to as "Intermediate (PRM04)") 1.08 g, potassium carbonate 0.66 g and N,N-dimethylformamide 15 mL was stirred at 80° C. for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-bromophenyl)-5-methylthiazole (hereinafter, referred to as "Present compound (T054)") 0.27 g.

Present Compound (T054)

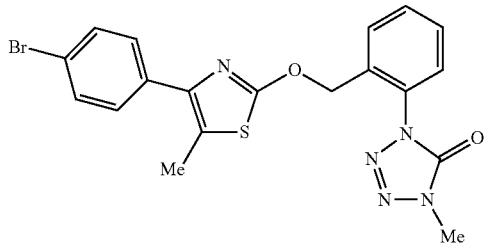 [SMILES: Cc1sc(OCc2ccccc2-n2nnn(C)c2=O)nc1-c1ccc(Br)cc1]

$^1$H NMR (CDCl$_3$) δ: 2.38 (3H, s), 3.64 (3H, s), 5.53 (2H, s), 7.42-7.56 (7H, m), 7.69-7.71 (1H, m).

Preparation Example 53

A mixture of Intermediate (PRH) 1.08 g, 4-butyl-5-methyl-2-oxo-thiazole (hereinafter, referred to as "Intermediate (PRM27)") 0.69 g, cesium carbonate 1.56 g and N,N-dimethylformamide 15 mL was stirred at 80° C. for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-butyl-5-methylthiazole (hereinafter, referred to as "Present compound (T055)") 0.14 g.

Present Compound (T055)

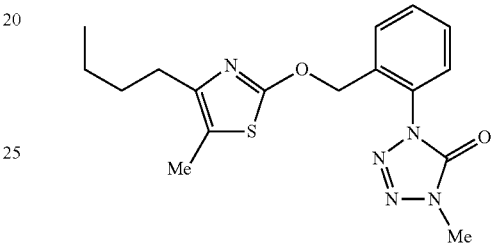

$^1$H NMR (CDCl$_3$) δ: 0.91 (3H, t, J=7.2 Hz), 1.30-1.39 (2H, m), 1.46-1.54 (2H, m), 2.11 (3H, s), 2.54 (2H, t, J=7.2 Hz), 3.71 (3H, s), 5.44 (2H, s), 7.45-7.54 (3H, m), 7.66-7.69 (1H, m).

Preparation Example 54

A mixture of 1-(2-hydroxymethylphenyl)-4-methyl-1,4-dihydrotetrazole-5-one (hereinafter, referred to as "Intermediate (PRHO)") 0.50 g, sodium tert-butoxide 0.21 g and tetrahydrofuran 50 mL was stirred at 25° C. for five minutes, and to the resulting mixtures were then added 2,4-dibromo-thiazole 0.45 g and the resulting mixtures were stirred with heating under reflux for one hour. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure to give 2-{[1-(4,5-dihydro-4-methyl-5-oxo-1H-tetrazole-1-yl)phenyl-2-yl]methyloxy}-4-bromothiazole (hereinafter, referred to as "Present compound (T028)") 0.46 g.

Present Compound (T028)

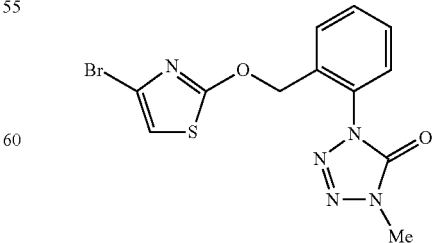

$^1$H NMR (CDCl$_3$) δ: 3.73 (3H, s), 5.54 (2H, s), 6.58 (1H, s), 7.48-7.56 (3H, m), 7.65-7.68 (1H, m).

Preparation Example 55

A mixture of Present compound (T028) 0.35 g, 4-ethylthiophenylboronic acid 0.32 g, cesium fluoride 0.51 g, [1,1'-bis(diphenylphosphino)ferrocene]palladium(II) dichloride dichloromethane adduct 0.08 g and dioxane 100 mL was stirred at 90° C. for five and a half hours. After cooling the reaction mixtures, the mixtures, the mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-methylthiophenyl)thiazole (hereinafter, referred to as "Present compound (T027)") 0.26 g.

Present Compound (T027)

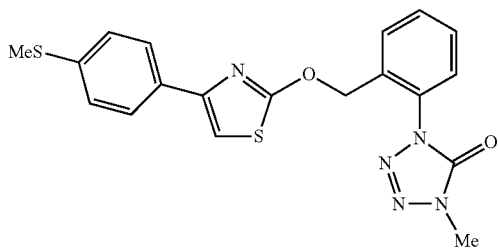 [SMILES: CSc1ccc(-c2csc(OCc3ccccc3-n3nnn(C)c3=O)n2)cc1]

$^1$H NMR (CDCl$_3$) δ: 2.51 (3H, s), 3.64 (3H, s), 5.62 (2H, s), 6.80 (1H, s), 2.26-2.28 (2H, m), 7.47-7.57 (3H, m), 7.69-7.73 (3H, m).

Preparation Example 56

A mixture of Intermediate (PRH) 1.08 g, 2-(4-chlorophenyl)-2-oxoethylcarbamate (hereinafter, referred to as "Intermediate (PRX03)") 0.78 g, cesium carbonate 1.56 g and N,N-dimethylformamide 15 mL was stirred at 80° C. for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(4-chlorophenyl)oxazole (hereinafter, referred to as "Present compound (T056)") 0.10 g.

Present Compound (T056)

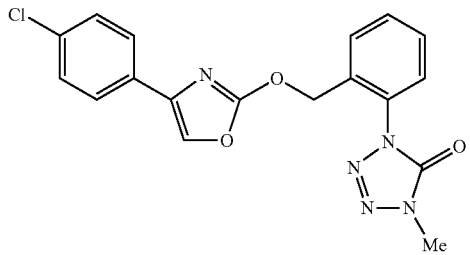 [SMILES: Cn1nnn(-c2ccccc2COc2nc(-c3ccc(Cl)cc3)co2)c1=O]

$^1$H NMR (CDCl$_3$) δ: 3.69 (3H, s), 5.57 (2H, s), 7.35 (2H, dt, J=1.4, 8.2 Hz), 7.46 (1H, s), 7.48-7.58 (5H, m), 7.73-7.75 (1H, m).

Preparation Example 57

A mixture of 1-(2-hydroxymethyl-3-methylphenyl)-4-methyl-1,4-dihydrotetrazole-5-one (hereinafter, referred to as "Intermediate (PRMO)") 8.7 g, sodium tert-butoxide 4.6 g and tetrahydrofuran 250 mL was stirred at 25° C. for fifteen minutes and to the resulting mixtures were added 2,4-dibromo-thiazole 9.6 g and the resulting mixtures were heated under reflux for thirty minutes. To the reaction mixtures after standing to cool was added water and the resulting mixtures were extracted with ethyl acetate. The organic layers were washed with aqueous saturated sodium bicarbonate solution and saturated saline, and were dried over anhydrous magnesium sulfate and were then concentrated under reduced pressure to give 2-{[1-(4,5-dihydro-4-methyl-5-oxo-1H-tetrazole-1-yl)-3-methylphenyl-2-yl]methyloxy}-4-bromothiazole (hereinafter, referred to as "Present compound (T057)") 12 g.

Present Compound (T057)

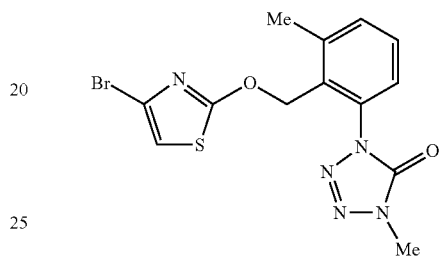

$^1$H NMR (CDCl$_3$) δ: 2.53 (3H, s), 3.73 (3H, s), 5.49 (2H, s), 6.56 (1H, s), 7.28 (1H, dd, J=7.8, 1.4 Hz), 7.40 (1H, dd, J=7.8, 1.4 Hz), 7.44 (1H, t, J=7.8 Hz).

Preparation Example 58

A mixture of Present compound (T057) 0.35 g, 4-methylthiophenylboronic acid 0.31 g, cesium fluoride 0.49 g, [1,1'-bis(diphenylphosphino)ferrocene]palladium(II) dichloride dichloromethane adduct 0.08 g and dioxane 6 mL was stirred at 90° C. for three and a half hours. After cooling the reaction mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-methylthiophenyl)thiazole (hereinafter, referred to as "Present compound (T058)") 0.37 g.

Present Compound (T058)

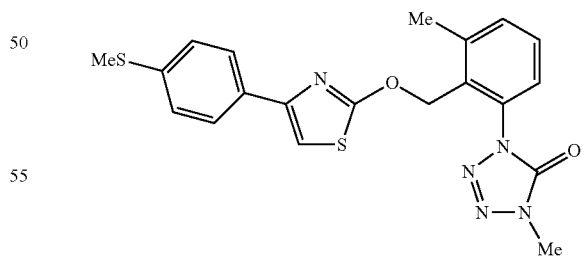

$^1$H NMR (CDCl$_3$) δ: 2.52 (3H, s), 2.57 (3H, s), 3.58 (3H, s), 5.59 (2H, s), 6.79 (1H, s), 7.27-7.28 (3H, m), 7.39-7.45 (2H, m), 7.69-7.72 (2H, m).

Preparation Example 59

A mixture of Present compound (T057) 0.30 g, 3-methylthiophenylboronic acid 0.26 g, cesium fluoride 0.42 g, [1,1'- bis(diphenylphosphino)ferrocene]palladium(II) dichloride dichloromethane adduct 0.06 g and dioxane 6 mL was stirred at 90° C. for three and a half hours. After cooling the reaction mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-methylthiophenyl)thiazole (hereinafter, referred to as "Present compound (T059)") 0.33 g.

Present Compound (T059)

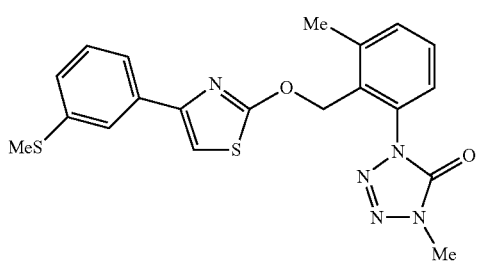 [SMILES: CSc1cccc(-c2csc(OCc3c(C)cccc3-n3nnn(C)c3=O)n2)c1]

$^1$H NMR (CDCl$_3$) δ: 2.54 (3H, s), 2.58 (3H, s), 3.58 (3H, s), 5.61 (2H, s), 6.84 (1H, s), 7.19-7.21 (1H, m), 7.25-7.28 (1H, m), 7.31 (1H, t, J=7.7 Hz), 7.40-7.45 (2H, m), 7.52-7.54 (1H, m), 7.70 (1H, t, J=1.7 Hz).

Preparation Example 60

A mixture of Present compound (T057) 0.30 g, 2-methylthiophenylboronic acid 0.26 g, cesium fluoride 0.42 g, [1,1'-bis(diphenylphosphino)ferrocene]palladium(II) dichloride dichloromethane adduct 0.06 g and dioxane 6 mL was stirred at 90° C. for three and a half hours. After cooling the reaction mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-methylthiophenyl)thiazole (hereinafter, referred to as "Present compound (T060)") 0.12 g.

Present Compound (T060)

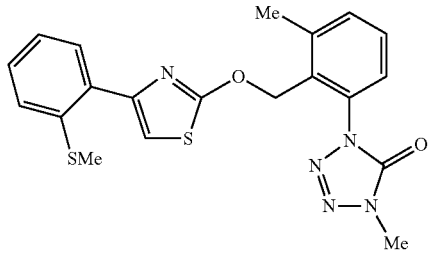 [SMILES: CSc1ccccc1-c1csc(OCc2c(C)cccc2-n2nnn(C)c2=O)n1]

$^1$H NMR (CDCl$_3$) δ: 2.46 (3H, s), 2.56 (3H, s), 3.58 (3H, s), 5.56 (2H, s), 6.97 (1H, s), 7.20 (1H, ddd, J=8.0, 7.0, 1.9 Hz), 7.25-7.34 (3H, m), 7.38-7.44 (2H, m), 7.61 (1H, dd, J=8.0, 1.5 Hz).

Preparation Example 61

A mixture of Present compound (T057) 0.35 g, 3-chlorophenylboronic acid 0.29 g, cesium fluoride 0.49 g, [1,1'-bis(diphenylphosphino)ferrocene]palladium(II) dichloride dichloromethane adduct 0.08 g and dioxane 6 mL was stirred at 90° C. for four and a half hours. After cooling the reaction mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-chlorophenyl)thiazole (hereinafter, referred to as "Present compound (T061)") 0.24 g.

Present Compound (T061)

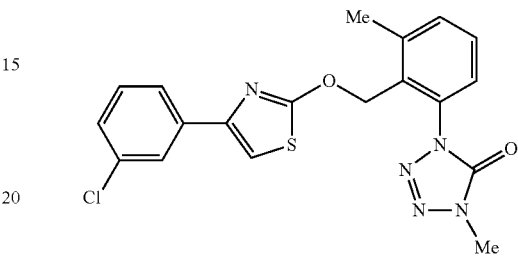

$^1$H NMR (CDCl$_3$) δ: 2.58 (3H, s), 3.62 (3H, s), 5.59 (2H, s), 6.87 (1H, s), 7.26-7.29 (2H, m), 7.32 (1H, t, J=7.6 Hz), 7.39-7.47 (2H, m), 7.65 (1H, dt, J=7.56, 1.8 Hz), 7.77 (1H, t, J=1.8 Hz).

Preparation Example 62

A mixture of Present compound (T057) 0.35 g, 2-chlorophenylboronic acid 0.29 g, cesium fluoride 0.49 g, [1,1'-bis(diphenylphosphino)ferrocene]palladium(II) dichloride dichloromethane adduct 0.08 g and dioxane 6 mL was stirred at 90° C. for four and a half hours. After cooling the reaction mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-chlorophenyl)thiazole (hereinafter, referred to as "Present compound (T062)") 0.37 g.

Present Compound (T062)

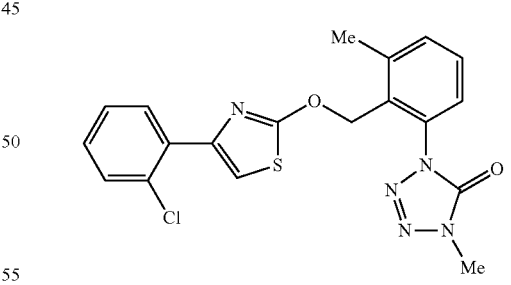

$^1$H NMR (CDCl$_3$) δ: 2.56 (3H, s), 3.59 (3H, s), 5.57 (2H, s), 7.22-7.29 (3H, m), 7.32 (1H, td, J=7.6, 1.0 Hz), 7.38-7.46 (3H, m), 7.86 (1H, dd, J=7.8, 1.0 Hz).

Preparation Example 63

A mixture of Present compound (T057) 0.35 g, 3-methylphenylboronic acid 0.25 g, cesium fluoride 0.49 g, [1,1'-bis(diphenylphosphino)ferrocene]palladium(II) dichloride dichloromethane adduct 0.08 g and dioxane 6 mL was stirred at 90° C. for three and a half hours. After cooling the reaction mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-methylphenyl)thiazole (hereinafter, referred to as "Present compound (T063)") 0.32 g.

Present Compound (T063)

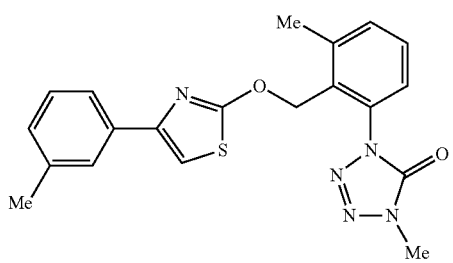 [SMILES: Cc1cccc(-c2csc(OCc3c(C)cccc3-n3nnn(C)c3=O)n2)c1]

$^1$H NMR (CDCl$_3$) δ: 2.41 (3H, s), 2.58 (3H, s), 3.58 (3H, s), 5.59 (2H, s), 6.82 (1H, s), 7.12 (1H, d, J=7.6 Hz), 7.27-7.31 (2H, m), 7.46-7.38 (2H, m), 7.57 (1H, d, J=7.6 Hz), 7.61 (1H, s).

Preparation Example 64

A mixture of Present compound (T057) 0.35 g, 2-methylphenylboronic acid 0.25 g, cesium fluoride 0.49 g, [1,1'-bis(diphenylphosphino)ferrocene]palladium(II) dichloride dichloromethane adduct 0.08 g and dioxane 6 mL was stirred at 90° C. for three hours. After cooling the reaction mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-methylphenyl)thiazole (hereinafter, referred to as "Present compound (T064)") 0.17 g.

Present Compound (T064)

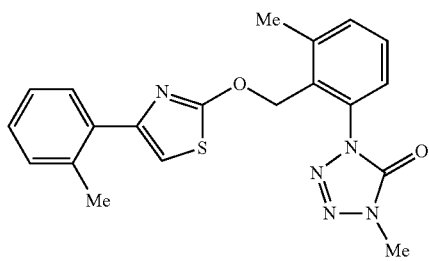 [SMILES: Cc1ccccc1-c1csc(OCc2c(C)cccc2-n2nnn(C)c2=O)n1]

$^1$H NMR (CDCl$_3$) δ: 2.43 (3H, s), 2.56 (3H, s), 3.51 (3H, s), 5.56 (2H, s), 6.59 (1H, s), 7.23-7.28 (4H, m), 7.38-7.45 (2H, m), 7.50-7.56 (1H, m)

Preparation Example 65

A mixture of Present compound (T057) 0.30 g, 3-methoxyphenylboronic acid 0.24 g, cesium fluoride 0.42 g, [1,1'-bis(diphenylphosphino)ferrocene]palladium(II) dichloride dichloromethane adduct 0.06 g and dioxane 6 mL was stirred at 90° C. for three and a half hours. After cooling the reaction mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-methoxyphenyl)thiazole (hereinafter, referred to as "Present compound (T065)") 0.28 g.

Present Compound (T065)

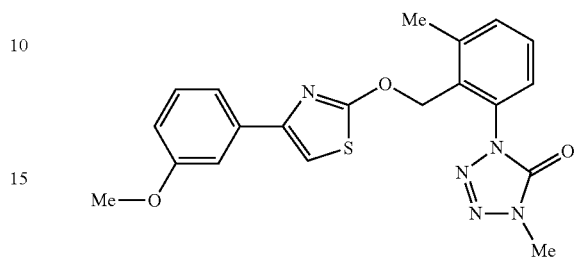

$^1$H NMR (CDCl$_3$) δ: 2.58 (3H, s), 3.58 (3H, s), 3.87 (3H, s), 5.60 (2H, s), 6.84 (1H, s), 6.86 (1H, ddd, J=8.3, 2.9, 1.0 Hz), 7.27-7.29 (1H, m), 7.31 (1H, d, J=8.1 Hz), 7.33-7.38 (2H, m), 7.39-7.45 (2H, m).

Preparation Example 66

A mixture of Present compound (T057) 0.30 g, 2-methoxyphenylboronic acid 0.24 g, cesium fluoride 0.42 g [1,1'-bis(diphenylphosphino)ferrocene]palladium(II) dichloride dichloromethane adduct 0.06 g and dioxane 6 mL was stirred at 90° C. for three and a half hours. After cooling the reaction mixtures, the mixtures were filtered off and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-methoxyphenyl)thiazole (hereinafter, referred to as "Present compound (T066)") 0.19 g.

Present Compound (T066)

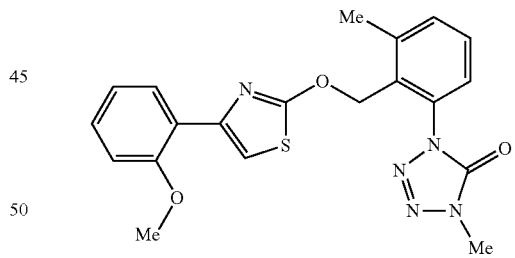

$^1$H NMR (CDCl$_3$) δ: 2.57 (3H, s), 3.59 (3H, s), 3.93 (3H, s), 5.58 (2H, s), 6.96 (1H, d, J=8.3 Hz), 7.05 (1H, t, J=7.7 Hz), 7.27 (2H, td, J=7.7, 1.9 Hz), 7.34 (1H, s), 7.38-7.45 (2H, m), 8.10 (1H, dd, J=7.7, 1.9 Hz).

Preparation Example 67

A mixture of Present compound (T004) 0.37 g, Lawesson's reagent (2,4-Bis(4-methoxyphenyl)-1,3,2,4-dithiadiphoshetane-2,4-disulfide) 0.20 g, triethylamine 0.08 g and toluene 8 mL was stirred at 100° C. for eight hours and the resulting mixtures were then concentrated under reduced pressure. The resulting residues were subjected to a silica gel column chromatography to give 2-{[1-(4,5-dihydro-4-methyl-5-thioxo-1H-tetrazole-1-yl)phenyl-2-yl]methyloxy}-4-(4-bromophenyl)thiazole (hereinafter, referred to as "Present compound (T067)") 0.04 g.

Present Compound (T067)

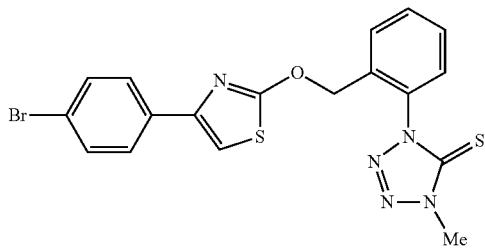 [SMILES: Cn1nnn(-c2ccccc2COc2nc(-c3ccc(Br)cc3)cs2)c1=S]

$^1$H NMR (CDCl$_3$) δ: 3.87 (3H, s), 5.56 (2H, s), 6.84 (1H, s), 7.48-7.50 (3H, m), 7.56-7.59 (2H, m), 7.64 (2H, dt, J=8.7, 2.0 Hz), 7.75 (1H, dd, J=7.6, 1.6 Hz).

Preparation Example 68

A mixture of 1-(2-bromomethyl-5-fluorophenyl)-4-methyl-1,4-dihydrotetrazole-5-one (hereinafter, referred to as "Intermediate (PRF5)") 0.86 g, Intermediate (PR04) 0.85 g, cesium carbonate 1.17 g and N,N-dimethylformamide 20 mL was stirred at 80° C. for ten hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-5-fluorophenyl-2-yl]methyloxy}-4-(4-bromophenyl)thiazole (hereinafter, referred to as "Present compound (T068)") 0.21 g.

Present Compound (T068)

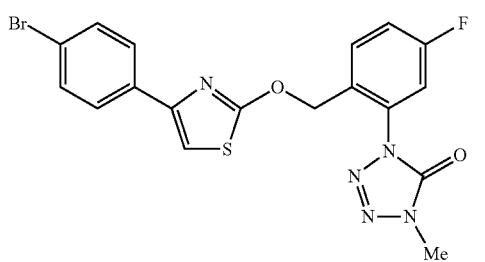 [SMILES: Cn1nnn(-c2cc(F)ccc2COc2nc(-c3ccc(Br)cc3)cs2)c1=O]

$^1$H NMR (CDCl$_3$) δ: 3.66 (3H, s), 5.59 (2H, s), 6.85 (1H, s), 7.24-7.26 (2H, m), 7.51 (2H, dt, J=8.9, 2.2 Hz), 7.63 (2H, dt, J=8.9, 2.2 Hz), 7.70 (1H, dd, J=8.5, 6.0 Hz).

Preparation Example 69

A mixture of 1-(2-bromomethyl-6-fluorophenyl)-4-methyl-1,4-dihydrotetrazole-5-one (hereinafter, referred to as "Intermediate (PRF6)") 0.86 g, Intermediate (PR04) 0.85 g, cesium carbonate 1.17 g and N,N-dimethylformamide 20 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-6-fluorophenyl-2-yl]methyloxy}-4-(4-bromophenyl)thiazole (hereinafter, referred to as "Present compound (T069)") 0.30 g.

Present Compound (T069)

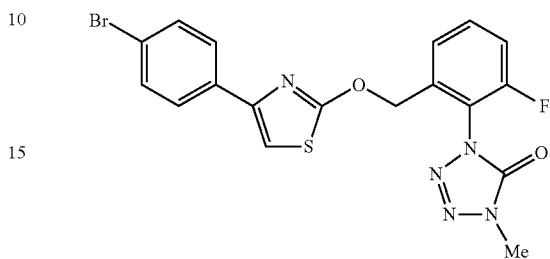

$^1$H NMR (CDCl$_3$) δ: 3.63 (3H, s), 5.56 (2H, s), 6.87 (1H, s), 7.27-7.32 (1H, m), 7.49-7.59 (4H, m), 7.65 (2H, dt, J=8.9, 2.1 Hz).

Preparation Example 70

A mixture of Intermediate (PRMT) 0.50 g, Intermediate (PR26) 0.39 g, cesium carbonate 0.65 g and N,N-dimethylformamide 15 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methoxyphenyl-2-yl]methyloxy}-4-(1-adamantyl)thiazole (hereinafter, referred to as "Present compound (T070)") 0.43 g.

Present Compound (T070)

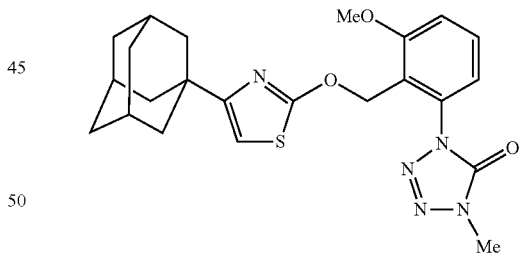

$^1$H NMR (CDCl$_3$) δ: 1.71-1.78 (6H, m), 1.86-1.86 (6H, m), 2.04 (3H, s), 3.66 (3H, s), 3.91 (3H, s), 5.53 (2H, s), 6.11 (1H, s), 7.06 (2H, t, J=7.8 Hz), 7.46 (1H, t, J=8.3 Hz).

Preparation Example 71

A mixture of 1-(2-bromomethyl-3-cyclopropylphenyl)-4-methyl-1,4-dihydrotetrazole-5-one (hereinafter, referred to as "Intermediate (PRCP)") 0.50 g, Intermediate (PR26) 0.38 g, cesium carbonate 0.63 g and N,N-dimethylformamide 15 mL was stirred at 80° C. for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-cyclopropylphenyl-2-yl]methyloxy}-4-(1-adamantyl)thiazole (hereinafter, referred to as "Present compound (T071)") 0.50 g.

Present Compound (T071)

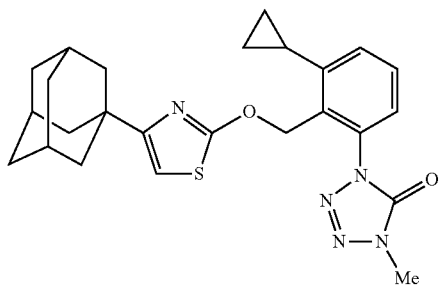 [SMILES: Cn1nnn(-c2cccc(C3CC3)c2COc2nc(C34CC5CC(CC(C5)C3)C4)cs2)c1=O]

$^1$H NMR (CDCl$_3$) δ: 0.75-0.77 (2H, m), 0.99-1.04 (2H, m), 1.72-1.77 (6H, m), 1.86-1.89 (6H, m), 2.05 (3H, s), 2.23-2.28 (1H, m), 3.68 (3H, s), 5.67 (2H, s), 6.12 (1H, s), 7.24-7.26 (2H, m), 7.41 (1H, t, J=8.0 Hz).

Preparation Example 72

A mixture of 1-(2-bromomethyl-3-ethylphenyl)-4-methyl-1,4-dihydrotetrazole-5-one (hereinafter, referred to as "Intermediate (PRE)") 0.50 g, Intermediate (PR26) 0.40 g, cesium carbonate 0.66 g and N,N-dimethylformamide 15 mL was stirred at 80° C. for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-ethylphenyl-2-yl]methyloxy}-4-(1-adamantyl)thiazole (hereinafter, referred to as "Present compound (T072)") 0.60 g.

Present Compound (T072)

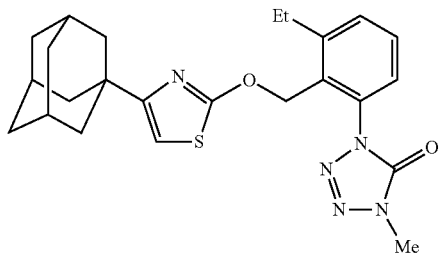 [SMILES: CCc1cccc(-n2nnn(C)c2=O)c1COc1nc(C23CC4CC(CC(C4)C2)C3)cs1]

$^1$H NMR (CDCl$_3$) δ: 1.29 (3H, t, J=7.6 Hz), 1.71-1.78 (6H, m), 1.84-1.85 (6H, m), 2.05 (3H, s), 2.91 (2H, q, J=7.6 Hz), 3.67 (3H, s), 5.49 (2H, s), 6.12 (1H, s), 7.26 (1H, dd, J=7.2, 1.9 Hz), 7.40-7.47 (2H, m).

Preparation Example 73

A mixture of Intermediate (PRE) 0.50 g, Intermediate (PR04) 0.43 g, cesium carbonate 0.66 g and N,N-dimethylformamide 15 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-ethylphenyl-2-yl]methyloxy}-4-(4-bromophenyl)thiazole (hereinafter, referred to as "Present compound (T073)") 0.36 g.

Present Compound (T073)

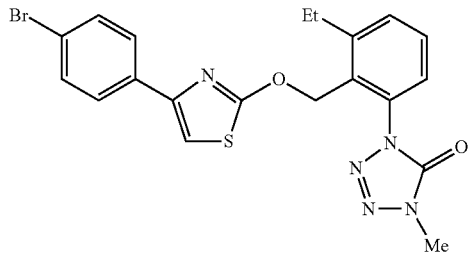

$^1$H NMR (CDCl$_3$) δ: 1.32 (3H, t, J=7.6 Hz), 2.91 (2H, q, J=7.6 Hz), 3.56 (3H, s), 5.61 (2H, s), 6.85 (1H, s), 7.27 (1H, t, J=4.1 Hz), 7.45-7.47 (2H, m), 7.52 (2H, dt, J=8.8, 2.1 Hz), 7.66 (2H, dt, J=8.9, 2.1 Hz).

Preparation Example 74

A mixture of Intermediate (PRCP) 0.50 g, Intermediate (PR04) 0.41 g, cesium carbonate 0.63 g and N,N-dimethylformamide 10 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-cyclopropylphenyl-2-yl]methyloxy}-4-(4-bromophenyl)thiazole (hereinafter, referred to as "Present compound (T074)") 0.42 g.

Present Compound (T074)

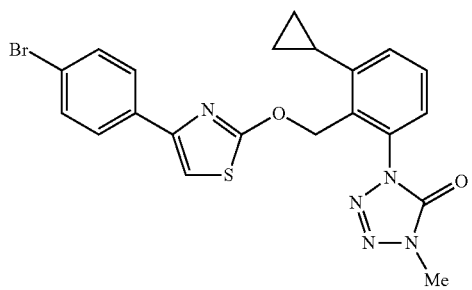 [SMILES: Cn1nnn(-c2cccc(C3CC3)c2COc2nc(-c3ccc(Br)cc3)cs2)c1=O]

$^1$H NMR (CDCl$_3$) δ: 0.77-0.81 (2H, m), 1.02-1.07 (2H, m), 2.18-2.25 (1H, m), 3.57 (3H, s), 5.79 (2H, s), 6.84 (1H, s), 7.27 (2H, dd, J=7.8, 4.7 Hz), 7.44 (1H, t, J=8.0 Hz), 7.51 (2H, d, J=8.5 Hz), 7.66 (2H, d, J=8.2 Hz).

Preparation Example 75

A mixture of Present compound (T057) 0.35 g, 3-fluoro-4-methylphenylboronic acid 0.28 g, cesium fluoride 0.49 g,

[1,1'-bis(diphenylphosphino)ferrocene]palladium(II) dichloride dichloromethane adduct 0.08 g and dioxane 6 mL was stirred at 90° C. for three hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-fluoro-4-methylphenyl)thiazole (hereinafter, referred to as "Present compound (T075)") 0.35 g.

Present Compound (T075)

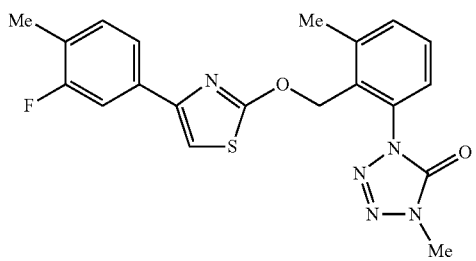 [SMILES: Cc1ccc(-c2csc(OCc3c(C)cccc3-n3nnn(C)c3=O)n2)cc1F]

$^1$H NMR (CDCl$_3$) δ: 2.29 (3H, d, J=1.69 Hz), 2.58 (3H, s), 3.62 (3H, s), 5.59 (2H, s), 6.80 (1H, s), 7.18 (1H, t, J=7.73 Hz), 7.29-7.26 (1H, m), 7.39-7.45 (4H, m).

Preparation Example 76

A mixture of Present compound (T057) 0.35 g, 2-fluoro-4-methylphenylboronic acid 0.28 g, cesium fluoride 0.49 g, [1,1'-bis(diphenylphosphino)ferrocene]palladium(II) dichloride dichloromethane adduct 0.06 g and dioxane 6 mL was stirred at 90° C. for three hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-fluoro-4-methylphenyl)thiazole (hereinafter, referred to as "Present compound (T076)") 0.35 g.

Present Compound (T076)

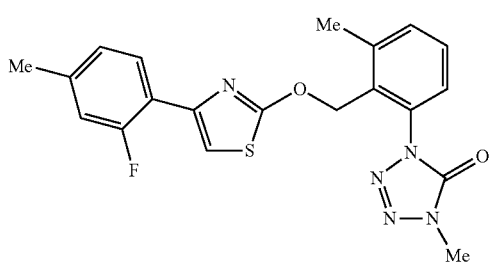 [SMILES: Cc1ccc(-c2csc(OCc3c(C)cccc3-n3nnn(C)c3=O)n2)c(F)c1]

$^1$H NMR (CDCl$_3$) δ: 2.36 (3H, s), 2.56 (3H, s), 3.60 (3H, s), 5.58 (2H, s), 6.92 (1H, d, J=12.8 Hz), 7.01 (1H, d, J=8.2 Hz), 7.07 (1H, d, J=1.9 Hz), 7.26-7.29 (1H, m), 7.39-7.44 (2H, m), 7.91 (1H, t, J=8.2 Hz).

Preparation Example 77

A mixture of Present compound (T057) 0.35 g, 2-fluoro-4-methoxyphenylboronic acid 0.31 g, cesium fluoride 0.49 g, [1,1'-bis(diphenylphosphino)ferrocene]palladium(II) dichloride dichloromethane adduct 0.08 g and dioxane 6 mL was stirred at 90° C. for five hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-fluoro-4-methoxyphenyl)thiazole (hereinafter, referred to as "Present compound (T077)") 0.31 g.

Present Compound (T077)

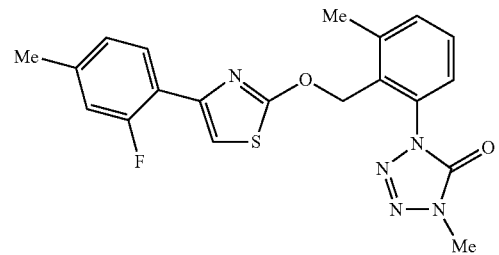 [SMILES: Cc1ccc(-c2csc(OCc3c(C)cccc3-n3nnn(C)c3=O)n2)c(F)c1]

$^1$H NMR (CDCl$_3$) δ: 2.56 (3H, s), 3.60 (3H, s), 3.83 (3H, s), 5.57 (2H, s), 6.67 (1H, dd, J=13.3, 2.4 Hz), 6.76 (1H, dd, J=8.8, 2.4 Hz), 6.98 (1H, d, J=2.2 Hz), 7.26-7.28 (1H, m), 7.38-7.45 (2H, m), 7.96 (1H, t, J=8.8 Hz).

Preparation Example 78

A mixture of Present compound (T057) 0.35 g, 3-fluoro-4-methoxyphenylboronic acid 0.31 g, cesium fluoride 0.49 g, [1,1'-bis(diphenylphosphino)ferrocene]palladium(II) dichloride dichloromethane adduct 0.08 g and dioxane 6 mL was stirred at 90° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-fluoro-4-methoxyphenyl)thiazole (hereinafter, referred to as "Present compound (T078)") 0.14 g.

Present Compound (T078)

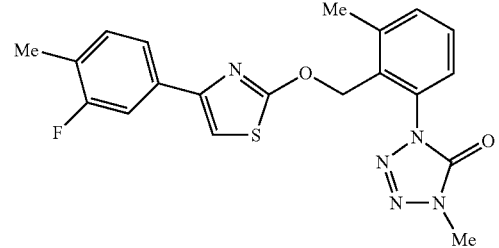 [SMILES: Cc1ccc(-c2csc(OCc3c(C)cccc3-n3nnn(C)c3=O)n2)cc1F]

$^1$H NMR (CDCl$_3$) δ: 2.57 (3H, s), 3.62 (3H, s), 3.93 (3H, s), 5.58 (2H, s), 6.72 (1H, s), 6.97 (1H, t, J=9.2 Hz), 7.25-7.29 (1H, m), 7.38-7.45 (2H, m), 7.50 (2H, d, J=9.2 Hz).

Preparation Example 79

A mixture of Intermediate (PRB) 0.40 g, Intermediate (PR26) 0.27 g, cesium carbonate 0.45 g and N,N-dimethylformamide 10 mL was stirred at 80° C. for a half hour. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-bromophenyl-2-yl]methyloxy}-4-(1-adamantyl)thiazole (hereinafter, referred to as "Present compound (T079)") 0.47 g.

Present Compound (T079)

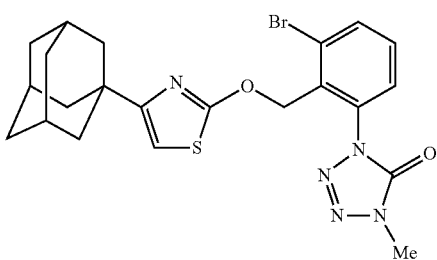

$^1$H NMR (CDCl$_3$) δ: 1.74 (6H, d, J=2.4 Hz), 1.84 (6H, d, J=2.9 Hz), 2.04 (3H, s), 3.67 (3H, s), 5.64 (2H, s), 6.12 (1H, s), 7.37 (1H, t, J=7.7 Hz), 7.41 (1H, dd, J=1.7, 7.7 Hz), 7.78 (1H, dd, J=7.7, 1.7 Hz).

Preparation Example 80

A mixture of Present compound (T057) 0.30 g, 4-chloro-2-fluorophenylboronic acid 0.27 g, cesium fluoride 0.42 g, [1,1'-bis(diphenylphosphino)ferrocene]palladium(II) dichloride dichloromethane adduct 0.06 g and dioxane 6 mL was stirred at 90° C. for two hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-chloro-2-fluorophenyl)thiazole (hereinafter, referred to as "Present compound (T080)") 0.30 g.

Present Compound (T080)

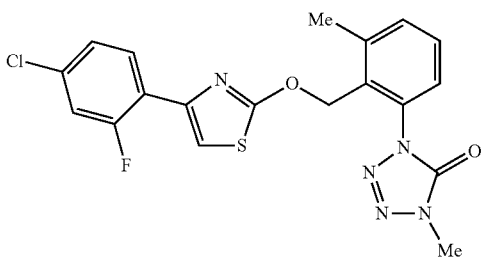 [SMILES: Cc1cccc(-n2nnn(C)c2=O)c1COc1nc(-c2ccc(Cl)cc2F)cs1]

$^1$H NMR (CDCl$_3$) δ: 2.55 (3H, s), 3.61 (3H, s), 5.57 (2H, s), 7.10-7.15 (2H, m), 7.19 (1H, dd, J=8.5, 2.0 Hz), 7.27 (1H, dd, J=8.5, 2.0 Hz), 7.38-7.44 (2H, m), 7.99 (1H, t, J=8.5 Hz).

Preparation Example 81

A mixture of Present compound (T057) 0.30 g, 4-chloro-3-fluorophenylboronic acid 0.27 g, cesium fluoride 0.42 g, [1,1'-bis(diphenylphosphino)ferrocene]palladium(II) dichloride dichloromethane adduct 0.06 g and dioxane 6 mL was stirred at 90° C. for two hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-chloro-3-fluorophenyl)thiazole (hereinafter, referred to as "Present compound (T081)") 0.30 g.

Present Compound (T081)

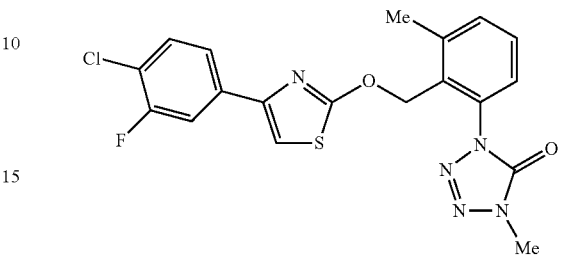

$^1$H NMR (CDCl$_3$) δ: 2.57 (3H, s), 3.63 (3H, s), 5.58 (2H, s), 6.86 (1H, s), 7.29-7.26 (1H, m), 7.38-7.44 (3H, m), 7.49 (1H, dd, J=8.5, 1.5 Hz), 7.57 (1H, dd, J=10.3, 1.8 Hz).

Preparation Example 82

A mixture of Present compound (T057) 0.25 g, 3-fluoro-4-nitrophenylboronic acid 0.26 g, cesium fluoride 0.34 g, [1,1'-bis(diphenylphosphino)ferrocene]palladium(II) dichloride dichloromethane adduct 0.05 g and dioxane 6 mL was stirred at 90° C. for six hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-fluoro-4-nitrophenyl)thiazole (hereinafter, referred to as "Present compound (T082)") 0.06 g.

Present Compound (T082)

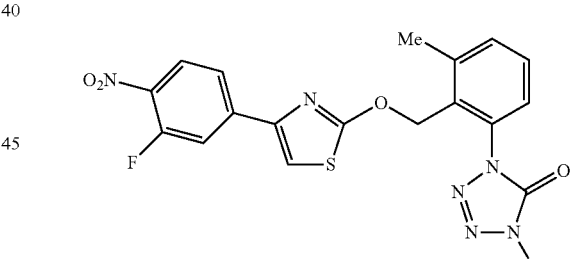

$^1$H NMR (CDCl$_3$) δ: 2.58 (3H, s), 3.66 (3H, s), 5.60 (2H, s), 7.09 (1H, s), 7.29 (1H, dd, J=7.1, 2.0 Hz), 7.41-7.47 (2H, m), 7.65 (1H, d, J=8.8 Hz), 7.69 (1H, d, J=12.2 Hz), 8.11 (1H, t, J=8.1 Hz).

Preparation Example 83

A mixture of 1-(2-bromomethyl-3-cyanophenyl)-4-methyl-1,4-dihydrotetrazole-5-one (hereinafter, referred to as "Intermediate (PRCN)") 0.14 g, Intermediate (PR04) 0.14 g, cesium carbonate 0.18 g and N,N-dimethylformamide 10 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-cyanophenyl-2-yl]methyloxy}-4-(4-bromophenyl)thiazole (hereinafter, referred to as "Present compound (T083)") 0.13 g.

Present Compound (T083)

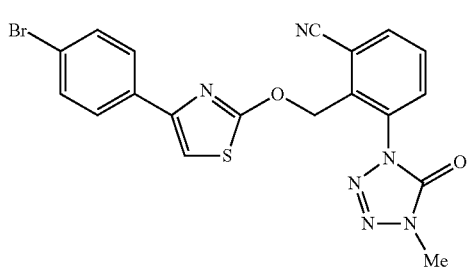

$^1$H NMR (CDCl$_3$) δ: 3.63 (3H, s), 5.87 (2H, s), 6.85 (1H, s), 7.51 (2H, d, J=8.5 Hz), 7.63-7.68 (3H, m), 7.73 (1H, d, J=8.2 Hz), 7.88 (1H, d, J=8.2 Hz).

Preparation Example 84

A mixture of Present compound (T057) 0.35 g, 3,4,5-trifluorophenylboronic acid 0.32 g, cesium fluoride 0.49 g, [1,1'-bis(diphenylphosphino)ferrocene]palladium(II) dichloride dichloromethane adduct 0.08 g and dioxane 10 mL was stirred at 90° C. for twenty-four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3,4,5-trifluorophenyl)thiazole (hereinafter, referred to as "Present compound (T084)") 0.18 g.

Present Compound (T084)

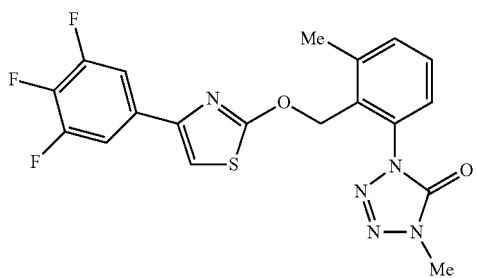 [SMILES: Cc1cccc(-n2nnn(C)c2=O)c1COc1nc(-c2cc(F)c(F)c(F)c2)cs1]

$^1$H NMR (CDCl$_3$) δ: 2.57 (3H, s), 3.66 (3H, s), 5.57 (2H, s), 6.82 (1H, s), 7.27-7.31 (1H, m), 7.35-7.47 (4H, m).

Preparation Example 85

A mixture of Present compound (T057) 0.35 g, 3,4-difluorophenylboronic acid 0.29 g, cesium fluoride 0.49 g, [1,1'-bis(diphenylphosphino)ferrocene]palladium(II) dichloride dichloromethane adduct 0.08 g and dioxane 10 mL was stirred at 90° C. for six hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3,4-difluorophenyl)thiazole (hereinafter, referred to as "Present compound (T085)") 0.15 g.

Present Compound (T085)

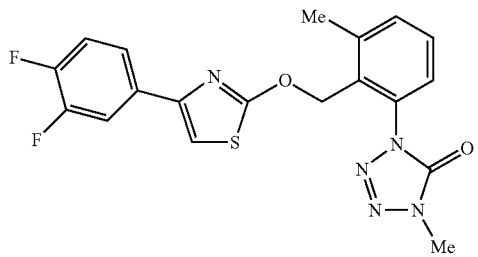 [SMILES: Cc1cccc(-n2nnn(C)c2=O)c1COc1nc(-c2ccc(F)c(F)c2)cs1]

$^1$H NMR (CDCl$_3$) δ: 2.57 (3H, s), 3.63 (3H, s), 5.58 (2H, s), 6.79 (1H, s), 7.17 (1H, q, J=9.2 Hz), 7.28 (1H, s), 7.39-7.46 (2H, m), 7.46-7.52 (1H, m), 7.55-7.64 (1H, m).

Preparation Example 86

A mixture of Present compound (T057) 0.35 g, 2,4-difluorophenylboronic acid 0.29 g, cesium fluoride 0.49 g, [1,1'-bis(diphenylphosphino)ferrocene]palladium(II) dichloride dichloromethane adduct 0.08 g and dioxane 10 mL was stirred at 90° C. for six hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2,4-difluorophenyl)thiazole (hereinafter, referred to as "Present compound (T086)") 0.22 g.

Present Compound (T086)

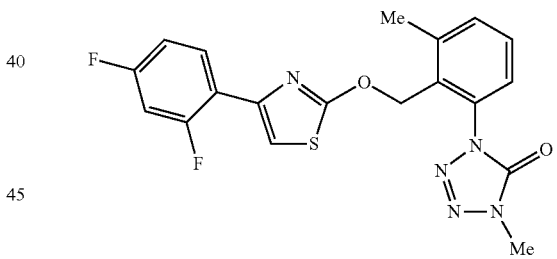

$^1$H NMR (CDCl$_3$) δ: 2.56 (3H, s), 3.62 (3H, s), 5.57 (2H, s), 6.87 (1H, ddd, J=11.7, 9.1, 2.6 Hz), 6.99-6.92 (1H, m), 7.07 (1H, d, J=2.2 Hz), 7.26-7.30 (1H, m), 7.40-7.46 (2H, m), 8.04 (1H, td, J=8.8, 6.8 Hz).

Preparation Example 87

A mixture of Present compound (T057) 0.30 g, 2-fluorophenylboronic acid 0.22 g, cesium fluoride 0.42 g, [1,1'-bis(diphenylphosphino)ferrocene]palladium(II) dichloride dichloromethane adduct 0.06 g and dioxane 6 mL was stirred at 90° C. for four and a half hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-fluorophenyl)thiazole (hereinafter, referred to as "Present compound (T087)") 0.13 g.

Present Compound (T087)

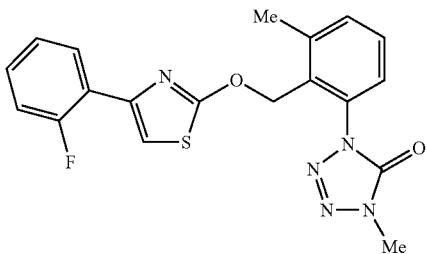

¹H NMR (CDCl₃) δ: 2.57 (3H, s), 3.60 (3H, s), 5.59 (2H, s), 7.11 (1H, ddd, J=11.8, 7.7, 1.7 Hz), 7.15 (1H, d, J=2.2 Hz), 7.19-7.23 (1H, m), 7.25-7.29 (2H, m), 7.41-7.46 (2H, m), 8.05 (1H, td, J=7.7, 1.9 Hz).

Preparation Example 88

A mixture of Present compound (T057) 0.30 g, 3-fluorophenylboronic acid 0.22 g, cesium fluoride 0.42 g, [1,1'-bis(diphenylphosphino)ferrocene]palladium(II) dichloride dichloromethane adduct 0.06 g and dioxane 6 mL was stirred at 90° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-fluorophenyl)thiazole (hereinafter, referred to as "Present compound (T088)") 0.25 g.

Present Compound (T088)

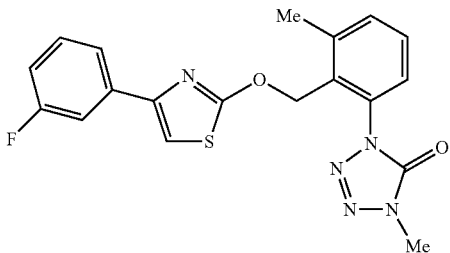 [SMILES: Cc1cccc(-n2nnn(C)c2=O)c1COc1nc(-c2cccc(F)c2)cs1]

¹H NMR (CDCl₃) δ: 2.57 (3H, s), 3.60 (3H, s), 5.60 (2H, s), 6.86 (1H, s), 6.99 (1H, tdd, J=8.5, 2.5, 0.7 Hz), 7.27 (1H, dd, J=7.3, 2.3 Hz), 7.34 (1H, td, J=7.9, 6.0 Hz), 7.39-7.45 (2H, m), 7.46-7.50 (1H, m), 7.54 (1H, dt, J=7.9, 1.3 Hz).

Preparation Example 89

A mixture of Present compound (T057) 0.30 g, 2-nitrophenylboronic acid 0.26 g, cesium fluoride 0.42 g, [1,1'-bis(diphenylphosphino)ferrocene]palladium(II) dichloride dichloromethane adduct 0.06 g and dioxane 6 mL was stirred at 90° C. for five hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-nitrophenyl)thiazole (hereinafter, referred to as "Present compound (T089)") 0.27 g.

Present Compound (T089)

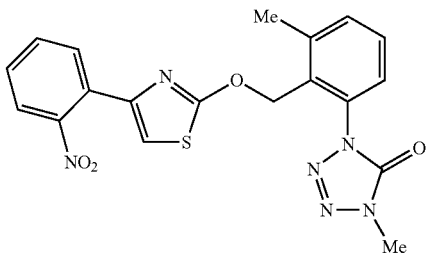

¹H NMR (CDCl₃) δ: 2.52 (3H, s), 3.65 (3H, s), 5.44 (2H, s), 6.81 (1H, s), 7.25 (1H, dd, J=7.1, 2.3 Hz), 7.37-7.44 (2H, m), 7.46 (1H, td, J=7.6, 1.8 Hz), 7.58 (1H, t, J=7.6 Hz), 7.63 (1H, dd, J=7.6, 1.8 Hz), 7.73 (1H, d, J=8.0 Hz).

Preparation Example 90

A mixture of Present compound (T057) 0.30 g, 2,6-dimethylphenylboronic acid 0.24 g, cesium fluoride 0.42 g, [1,1'-bis(diphenylphosphino)ferrocene]palladium(II) dichloride dichloromethane adduct 0.06 g and dioxane 6 mL was stirred at 90° C. for five hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2,6-dimethylphenyl)thiazole (hereinafter, referred to as "Present compound (T090)") 0.29 g.

Present Compound (T090)

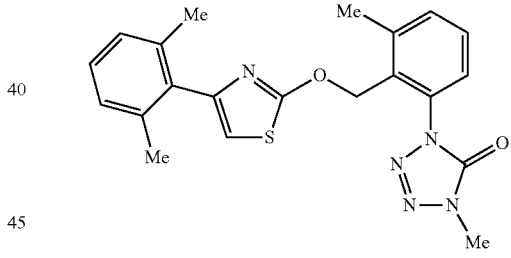

¹H NMR (CDCl₃) δ: 2.15 (6H, s), 2.54 (3H, s), 3.44 (3H, d, J=0.7 Hz), 5.53 (2H, s), 6.39 (1H, d, J=0.7 Hz), 7.08 (2H, d, J=7.3 Hz), 7.16 (1H, dd, J=8.2, 6.6 Hz), 7.26 (1H, dd, J=7.3, 2.1 Hz), 7.38 (1H, d, J=6.6 Hz), 7.41 (1H, t, J=7.3 Hz).

Preparation Example 91

A mixture of Intermediate (PRM) 0.35 g, Intermediate (PR28) 0.35 g, cesium carbonate 0.39 g and N,N-dimethylformamide 10 mL was stirred at 80° C. for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-bromophenyl-2-yl]methyloxy}-4-(2-methylphenyl)thiazole (hereinafter, referred to as "Present compound (T091)") 0.26 g.

Present Compound (T091)

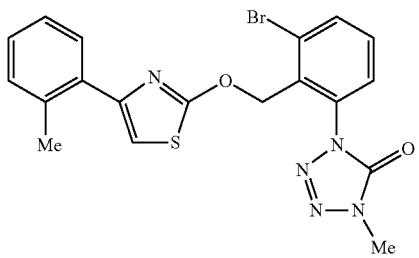

$^1$H NMR (CDCl$_3$) δ: 2.43 (3H, s), 3.44 (3H, s), 5.75 (2H, s), 6.60 (1H, s), 7.24-7.26 (3H, m), 7.37-7.42 (2H, m), 7.55-7.51 (1H, m), 7.81 (1H, dd, J=6.3, 3.1 Hz).

Preparation Example 92

A mixture of Present compound (T057) 0.30 g, 2-trifluoromethylphenylboronic acid 0.30 g, cesium fluoride 0.42 g, [1,1'-bis(diphenylphosphino)ferrocene]palladium(II) dichloride dichloromethane adduct 0.06 g and dioxane 6 mL was stirred at 90° C. for eight and a half hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-trifluoromethylphenyl)thiazole (hereinafter, referred to as "Present compound (T092)") 0.28 g.

Present Compound (T092)

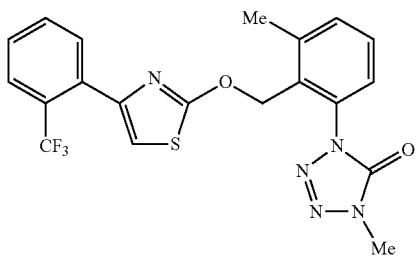

$^1$H NMR (CDCl$_3$) δ: 2.54 (3H, s), 3.58 (3H, s), 5.52 (2H, s), 6.71 (1H, s), 7.27 (1H, d, J=5.3 Hz), 7.39-7.44 (2H, m), 7.47 (1H, t, J=7.7 Hz), 7.55-7.62 (2H, m), 7.74 (1H, d, J=7.7 Hz).

Preparation Example 93

A mixture of Present compound (T057) 0.30 g, 3-trifluoromethylphenylboronic acid 0.30 g, cesium fluoride 0.42 g, [1,1'-bis(diphenylphosphino)ferrocene]palladium(II) dichloride dichloromethane adduct 0.06 g and dioxane 6 mL was stirred at 90° C. for six hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-trifluoromethylphenyl)thiazole (hereinafter, referred to as "Present compound (T093)") 0.27 g.

Present Compound (T093)

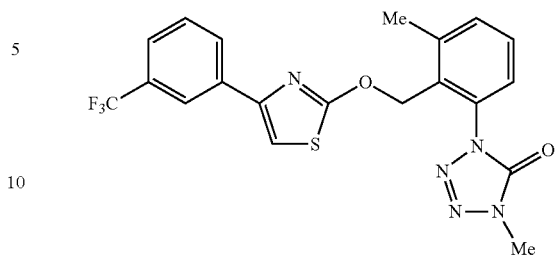

$^1$H NMR (CDCl$_3$) δ: 2.59 (3H, s), 3.61 (3H, s), 5.60 (2H, s), 6.93 (1H, s), 7.28 (1H, dd, J=7.1, 2.5 Hz), 7.40-7.46 (2H, m), 7.51 (1H, t, J=7.6 Hz), 7.56 (1H, d, J=7.6 Hz), 7.95 (1H, d, J=7.6 Hz), 8.03 (1H, s).

Preparation Example 94

A mixture of Intermediate (PRMT) 0.30 g, 4-(2-methylphenyl)-2-oxo-thiazole (hereinafter, referred to as "Intermediate (PR28)") 0.21 g, cesium carbonate 0.30 g and N,N-dimethylformamide 10 mL was stirred at 80° C. for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methoxyphenyl-2-yl]methyloxy}-4-(2-methylphenyl)thiazole (hereinafter, referred to as "Present compound (T094)") 0.19 g.

Present Compound (T094)

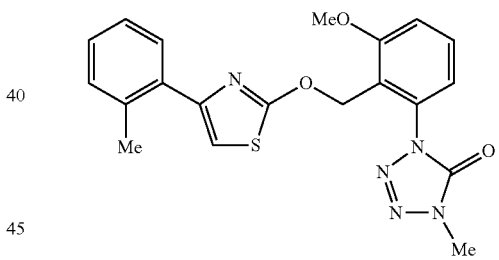

$^1$H NMR (CDCl$_3$) δ: 2.44 (3H, s), 3.44 (3H, s), 3.94 (3H, s), 5.67 (2H, s), 6.58 (1H, s), 7.04 (1H, d, J=8.1 Hz), 7.09 (1H, d, J=8.1 Hz), 7.23-7.25 (3H, m), 7.49 (1H, t, J=8.1 Hz), 7.52-7.57 (1H, m].

Preparation Example 95

A mixture of 1-(2-bromomethyl-3-ethoxyphenyl)-4-methyl-1,4-dihydrotetrazole-5-one (hereinafter, referred to as "Intermediate (PREO)") 0.31 g, Intermediate (PR28) 0.21 g, cesium carbonate 0.39 g and N,N-dimethylformamide 10 mL was stirred at 80° C. for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-ethoxyphenyl-2-yl]methyloxy}-4-(2-methylphenyl)thiazole (hereinafter, referred to as "Present compound (T095)") 0.22 g.

Present Compound (T095)

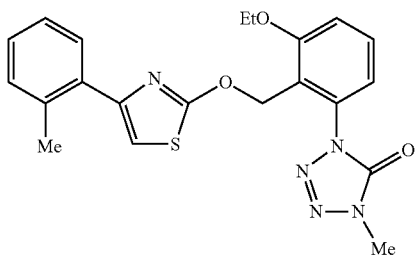 [SMILES: Cc1ccccc1-c1csc(OCc2c(Br)cccc2-n2nnn(C)c2=O)n1]

$^1$H NMR (CDCl$_3$) δ: 1.43 (3H, t, J=7 Hz), 2.45 (3H, s), 3.46 (3H, s), 4.14 (2H, q, J=7.0 Hz), 5.68 (2H, s), 6.58 (1H, s), 7.03 (1H, d, J=8.0 Hz), 7.07 (1H, d, J=8.2 Hz), 7.22-7.26 (3H, m), 7.46 (1H, t, J=8.2 Hz), 7.54 (1H, t, J=4.8 Hz).

Preparation Example 96

A mixture of Intermediate (PRCP) 0.31 g, Intermediate (PR28) 0.21 g, cesium carbonate 0.39 g and N,N-dimethylformamide 10 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-cyclopropylphenyl-2-yl]methyloxy}-4-(2-methylphenyl)thiazole (hereinafter, referred to as "Present compound (T096)") 0.19 g.

Present Compound (T096)

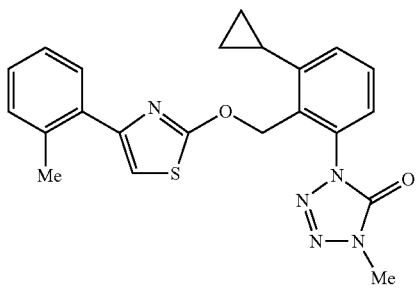 [SMILES: Cc1ccccc1-c1csc(OCc2c(C3CC3)cccc2-n2nnn(C)c2=O)n1]

$^1$H NMR (CDCl$_3$) δ: 0.76-0.82 (2H, m), 1.01-1.07 (2H, m), 2.18-2.25 (1H, m), 2.44 (3H, s), 3.51 (3H, s), 5.77 (2H, s), 6.60 (1H, s), 7.23-7.30 (5H, m), 7.44 (1H, t, J=7.80 Hz), 7.52-7.56 (1H, m).

Preparation Example 97

A mixture of Intermediate (PRE) 0.50 g, Intermediate (PR28) 0.31 g, cesium carbonate 0.66 g and N,N-dimethylformamide 15 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-ethylphenyl-2-yl]methyloxy}-4-(2-methylphenyl)thiazole (hereinafter, referred to as "Present compound (T097)") 0.22 g.

Present Compound (T097)

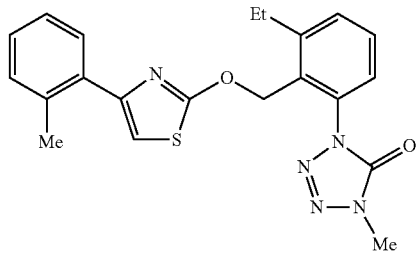

$^1$H NMR (CDCl$_3$) δ: 1.31 (3H, t, J=7.6 Hz), 2.44 (3H, s), 2.90 (2H, q, J=7.6 Hz), 3.49 (3H, s), 5.58 (2H, s), 6.60 (1H, s), 7.22-7.28 (4H, m), 7.44 (1H, dd, J=7.9, 2.0 Hz), 7.48 (1H, t, J=7.6 Hz), 7.51-7.55 (1H, m).

Preparation Example 98

A mixture of Intermediate (PRF) 0.50 g, Intermediate (PR28) 0.36 g, cesium carbonate 0.68 g and N,N-dimethylformamide 15 mL was stirred at 80° C. for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-fluorophenyl-2-yl]methyloxy}-4-(2-methylphenyl)thiazole (hereinafter, referred to as "Present compound (T098)") 0.08 g.

Present Compound (T098)

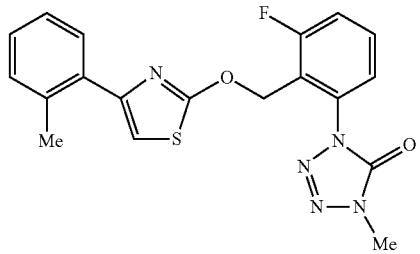

$^1$H NMR (CDCl$_3$) δ: 2.40 (3H, s), 3.45 (3H, s), 5.69 (2H, d, J=1.4 Hz), 6.57 (1H, s), 7.21-7.24 (3H, m), 7.26-7.31 (2H, m), 7.47-7.53 (2H, m).

Preparation Example 99

A mixture of 1-(2-bromomethyl-3-trifluoromethylphenyl)-4-methyl-1,4-dihydrotetrazole-5-one (hereinafter, referred to as "Intermediate (PRTF)") 0.34 g, Intermediate (PR28) 0.21 g, cesium carbonate 0.39 g and N,N-dimethylformamide 10 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-trifluoromethylphenyl-2-yl]methyloxy}-4-(2-methylphenyl)thiazole (hereinafter, referred to as "Present compound (T099)") 0.06 g.

Present Compound (T099)

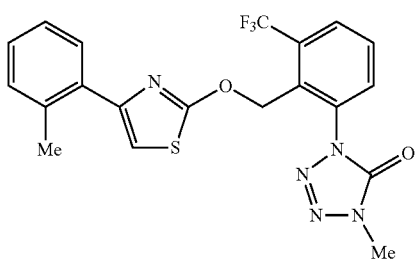 [SMILES: Cc1ccccc1-c1csc(OCc2c(-n3nnn(C)c3=O)cccc2C(F)(F)F)n1]

$^1$H NMR (CDCl$_3$) δ: 2.44 (3H, s), 3.41 (3H, s), 5.77 (2H, s), 6.61 (1H, s), 7.24-7.26 (3H, m), 7.52-7.56 (1H, m), 7.65 (1H, dd, J=8.0, 1.6 Hz), 7.68 (1H, t, J=8.0 Hz), 7.92 (1H, dd, J=7.4, 1.7 Hz).

Preparation Example 100

A mixture of Intermediate (PRH) 0.27 g, Intermediate (PR28) 0.21 g, cesium carbonate 0.39 g and N,N-dimethylformamide 10 mL was stirred at 80° C. for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(2-methylphenyl)thiazole (hereinafter, referred to as "Present compound (T100)") 0.08 g.

Present Compound (T100)

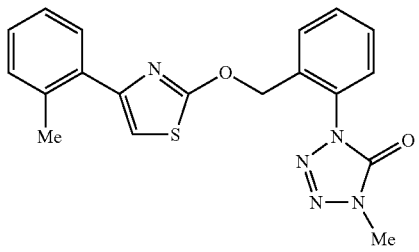 [SMILES: Cc1ccccc1-c1csc(OCc2ccccc2-n2nnn(C)c2=O)n1]

$^1$H NMR (CDCl$_3$) δ: 2.39 (3H, s), 3.60 (3H, s), 5.60 (2H, s), 6.61 (1H, s), 7.21-7.25 (2H, m), 7.32-7.38 (1H, m), 7.46-7.56 (4H, m), 7.71 (1H, dd, J=7.3, 1.8 Hz).

Preparation Example 101

A mixture of Intermediate (PRC) 0.50 g, Intermediate (PR28) 0.32 g, cesium carbonate 0.65 g and N,N-dimethylformamide 15 mL was stirred at 80° C. for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-chlorophenyl-2-yl]methyloxy}-4-(2-methylphenyl)thiazole (hereinafter, referred to as "Present compound (T101)") 0.30 g.

Present Compound (T101)

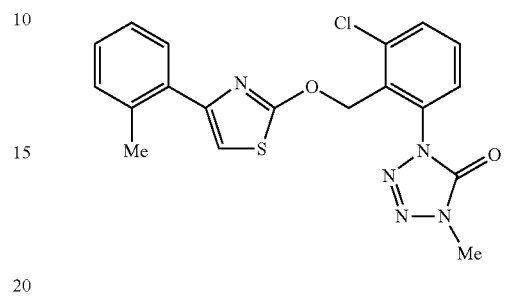

$^1$H NMR (CDCl$_3$) δ: 2.43 (3H, s), 3.45 (3H, s), 5.75 (2H, s), 6.60 (1H, s), 7.24-7.26 (3H, m), 7.37 (1H, dd, J=8.0, 1.1 Hz), 7.48 (1H, t, J=8.0 Hz), 7.52-7.53 (1H, m), 7.62 (1H, dd, J=8.1, 1.3 Hz).

Preparation Example 102

A mixture of Intermediate (PRB) 0.50 g, 4-(2-methoxyphenyl)-2-oxo-thiazole (hereinafter, referred to as "Intermediate (PR29)") 0.30 g, cesium carbonate 0.56 g and N,N-dimethylformamide 15 mL was stirred at 80° C. for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-bromophenyl-2-yl]methyloxy}-4-(2-methoxyphenyl)thiazole (hereinafter, referred to as "Present compound (T102)") 0.38 g.

Present Compound (T102)

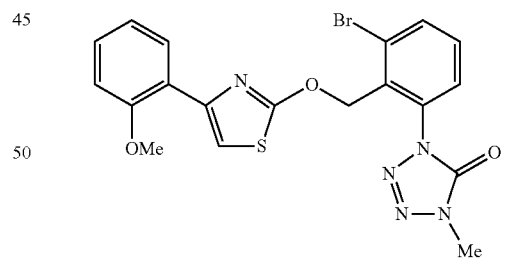

$^1$H NMR (CDCl$_3$) δ: 3.54 (3H, s), 3.93 (3H, s), 5.78 (2H, s), 6.96 (1H, dd, J=8.2, 0.7 Hz), 7.05 (1H, td, J=7.7, 1.1 Hz), 7.25-7.30 (1H, m), 7.35 (1H, s), 7.38-7.43 (2H, m), 7.81 (1H, dd, J=6.9, 2.5 Hz), 8.14 (1H, dd, J=7.7, 1.8 Hz).

Preparation Example 103

A mixture of Intermediate (PREO) 0.50 g, Intermediate (PR29) 0.33 g, cesium carbonate 0.63 g and N,N-dimethylformamide 15 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-ethoxyphenyl-2-yl]methyloxy}-4-(2-methoxyphenyl)thiazole (hereinafter, referred to as "Present compound (T103)") 0.22 g.

Present Compound (T103)

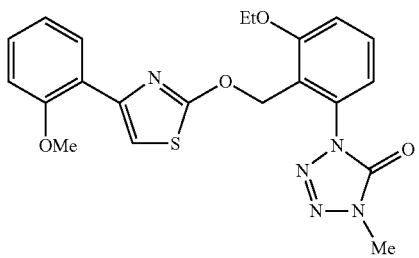 [SMILES: CCOc1cccc(-n2nnn(C)c2=O)c1COc1nc(-c2ccccc2OC)cs1]

¹H NMR (CDCl₃) δ: 1.43 (3H, t, J=7.1 Hz), 3.53 (3H, s), 3.94 (3H, s), 4.16 (2H, t, J=7.1 Hz), 5.70 (2H, s), 6.96 (1H, dd, J=8.4, 0.8 Hz), 7.01-7.09 (3H, m), 7.27 (1H, td, J=7.8, 1.9 Hz), 7.33 (1H, s), 7.45 (1H, t, J=8.1 Hz), 8.15 (1H, dd, J=7.8, 1.9 Hz).

Preparation Example 104

A mixture of Intermediate (PRTF) 0.50 g, Intermediate (PR29) 0.31 g, cesium carbonate 0.58 g and N,N-dimethylformamide 10 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-trifluoromethylphenyl-2-yl]methyloxy}-4-(2-methoxyphenyl)thiazole (hereinafter, referred to as "Present compound (T104)") 0.40 g.

Present Compound (T104)

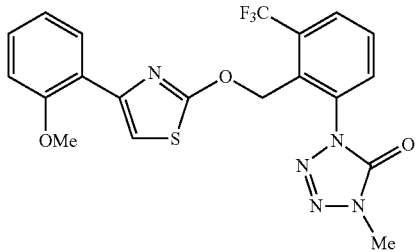 [SMILES: COc1ccccc1-c1csc(OCc2c(-n3nnn(C)c3=O)cccc2C(F)(F)F)n1]

¹H NMR (CDCl₃) δ: 3.46 (3H, s), 3.94 (3H, s), 5.81 (2H, s), 6.97 (1H, dd, J=8.2, 0.9 Hz), 7.06 (1H, td, J=7.6, 1.1 Hz), 7.28 (1H, ddd, J=8.5, 7.3, 1.6 Hz), 7.35 (1H, s), 7.71-7.63 (2H, m), 7.93 (1H, dd, J=7.4, 2.0 Hz), 8.12 (1H, dd, J=7.8, 1.8 Hz).

Preparation Example 105

A mixture of Intermediate (PRI) 0.50 g, Intermediate (PR29) 0.26 g, cesium carbonate 0.50 g and N,N-dimethylformamide 15 mL was stirred at 80° C. for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-iodophenyl-2-yl]methyloxy}-4-(2-methoxyphenyl)thiazole (hereinafter, referred to as "Present compound (T105)") 0.35 g.

Present Compound (T105)

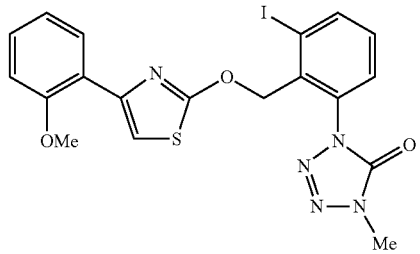 [SMILES: COc1ccccc1-c1csc(OCc2c(I)cccc2-n2nnn(C)c2=O)n1]

¹H NMR (CDCl₃) δ: 3.54 (3H, s), 3.94 (3H, s), 5.73 (2H, s), 6.96 (1H, dd, J=8.2, 0.7 Hz), 7.05 (1H, td, J=7.6, 1.1 Hz), 7.22 (1H, t, J=8.0 Hz), 7.28 (1H, ddd, J=8.2, 7.6, 1.8 Hz), 7.36 (1H, s), 7.43 (1H, dd, J=8.0, 1.1 Hz), 8.09 (1H, dd, J=8.0, 1.1 Hz), 8.16 (1H, dd, J=7.8, 1.8 Hz).

Preparation Example 106

A mixture of Intermediate (PRE) 0.50 g, Intermediate (PR29) 0.35 g, cesium carbonate 0.66 g and N,N-dimethylformamide 10 mL was stirred at 80° C. for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-ethoxyphenyl-2-yl]methyloxy}-4-(2-methoxyphenyl)thiazole (hereinafter, referred to as "Present compound (T106)") 0.48 g.

Present Compound (T106)

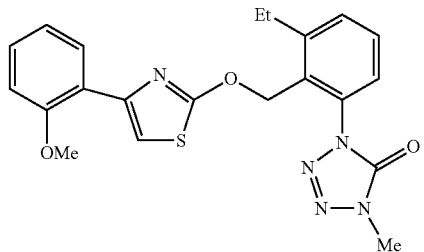 [SMILES: CCc1cccc(-n2nnn(C)c2=O)c1COc1nc(-c2ccccc2OC)cs1]

¹H NMR (CDCl₃) δ: 1.31 (3H, t, J=7.6 Hz), 2.91 (2H, q, J=7.6 Hz), 3.56 (3H, s), 3.94 (3H, s), 5.61 (2H, s), 6.97 (1H, dd, J=8.4, 0.8 Hz), 7.05 (1H, td, J=7.6, 1.1 Hz), 7.25-7.30 (2H, m), 7.34 (1H, s), 7.44 (1H, dd, J=7.8, 1.8 Hz), 7.48 (1H, t, J=7.3 Hz), 8.12 (1H, dd, J=7.8, 1.8 Hz).

Preparation Example 107

A mixture of Intermediate (PRF) 0.50 g, Intermediate (PR29) 0.50 g, cesium carbonate 0.68 g and N,N-dimethylformamide 10 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-fluorophenyl-2-yl]methyloxy}-4-(2-methoxyphenyl)thiazole (hereinafter, referred to as "Present compound (T107)") 0.28 g.

Present Compound (T107)

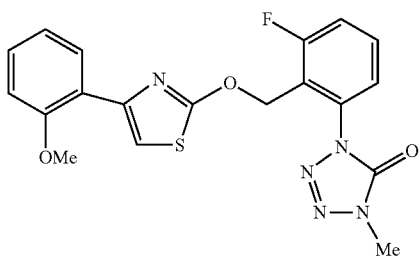 [SMILES: COc1ccccc1-c1csc(OCc2c(F)cccc2-n2nnn(C)c2=O)n1]

$^1$H NMR (CDCl$_3$) δ: 3.57 (3H, s), 3.93 (3H, s), 5.73 (2H, d, J=1.1 Hz), 6.96 (1H, dd, J=8.2, 1.1 Hz), 7.05 (1H, td, J=7.5, 1.1 Hz), 7.24-7.33 (3H, m), 7.33 (1H, s), 7.51 (1H, ddd, J=8.2, 8.2, 5.7 Hz), 8.11 (1H, dd, J=7.8, 1.8 Hz).

Preparation Example 108

A mixture of Intermediate (PRC) 0.50 g, Intermediate (PR29) 0.34 g, cesium carbonate 0.65 g and N,N-dimethylformamide 10 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-chlorophenyl-2-yl]methyloxy}-4-(2-methoxyphenyl)thiazole (hereinafter, referred to as "Present compound (T108)") 0.25 g.

Present Compound (T108)

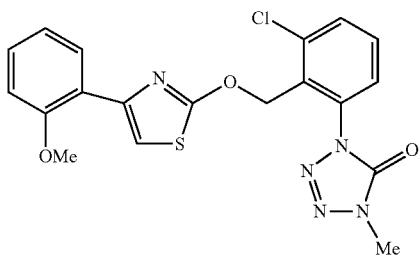

$^1$H NMR (CDCl$_3$) δ: 3.55 (3H, s), 3.93 (3H, s), 5.78 (2H, s), 6.96 (1H, dd, J=8.4, 0.8 Hz), 7.05 (1H, td, J=7.5, 1.0 Hz), 7.27 (1H, ddd, J=8.4, 7.3, 1.8 Hz), 7.34 (1H, s), 7.37 (1H, dd, J=8.0, 1.4 Hz), 7.47 (1H, t, J=8.0 Hz), 7.62 (1H, dd, J=8.1, 1.3 Hz), 8.13 (1H, dd, J=7.8, 1.8 Hz).

Preparation Example 109

A mixture of Present compound (T057) 0.30 g, 4-fluoro-2-methylphenylboronic acid 0.24 g, cesium fluoride 0.42 g, [1,1'-bis(diphenylphosphino)ferrocene]palladium(II) dichloride dichloromethane adduct 0.06 g and dioxane 6 mL was stirred at 90° C. for three hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-fluoro-2-methylphenyl)thiazole (hereinafter, referred to as "Present compound (T109)") 0.19 g.

Present Compound (T109)

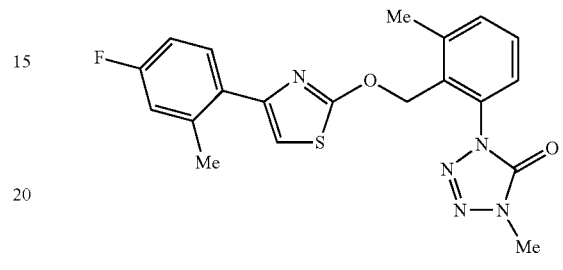

$^1$H NMR (CDCl$_3$) δ: 2.40 (3H, s), 2.55 (3H, s), 3.54 (3H, s), 5.54 (2H, s), 6.55 (1H, s), 6.89-6.98 (2H, m), 7.26 (1H, dd, J=7.1, 2.0 Hz), 7.39 (1H, dd, J=7.8, 2.1 Hz), 7.42 (1H, t, J=7.4 Hz), 7.48 (1H, dd, J=8.4, 6.1 Hz).

Preparation Example 110

A mixture of Intermediate (PRM) 0.30 g, 4-(2-bromophenyl)-2-oxo-thiazole (hereinafter, referred to as "Intermediate (PR30)") 0.27 g, cesium carbonate 0.41 g and N,N-dimethylformamide 10 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-bromophenyl)thiazole (hereinafter, referred to as "Present compound (T110)") 0.28 g.

Present Compound (T110)

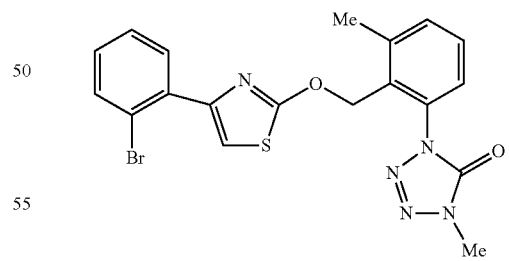

$^1$H NMR (CDCl$_3$) δ: 2.56 (3H, s), 3.58 (3H, s), 5.56 (2H, s), 7.12 (1H, s), 7.17 (1H, td, J=7.7, 1.8 Hz), 7.27 (1H, dd, J=6.8, 2.2 Hz), 7.34-7.44 (3H, m), 7.64 (1H, dd, J=8.0, 1.2 Hz), 7.72 (1H, dd, J=7.9, 1.8 Hz).

Preparation Example 111

A mixture of Intermediate (PRH) 0.50 g, Intermediate (PR29) 0.39 g, cesium carbonate 0.73 g and N,N-dimethylformamide 15 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methyloxy}-4-(2-methoxyphenyl)thiazole (hereinafter, referred to as "Present compound (T111)") 0.12 g.

Present Compound (T111)

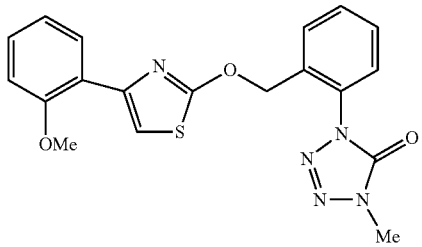 [SMILES: COc1ccccc1-c1csc(OCc2ccccc2-n2nnn(C)c2=O)n1]

$^1$H NMR (CDCl$_3$) δ: 3.64 (3H, s), 3.93 (3H, s), 5.62 (2H, s), 6.96 (1H, d, J=8.2 Hz), 7.04 (1H, td, J=7.6, 1.1 Hz), 7.24-7.29 (1H, m), 7.34 (1H, s), 7.46-7.57 (3H, m), 7.73 (1H, dd, J=6.9, 1.8 Hz), 8.09 (1H, dd, J=7.8, 1.6 Hz).

Preparation Example 112

A mixture of Intermediate (PRMT) 0.50 g, Intermediate (PR29) 0.35 g, cesium carbonate 0.65 g and N,N-dimethylformamide 10 mL was stirred at 80° C. for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methoxyphenyl-2-yl]methyloxy}-4-(2-methoxyphenyl)thiazole (hereinafter, referred to as "Present compound (T112)") 0.07 g.

Present Compound (T112)

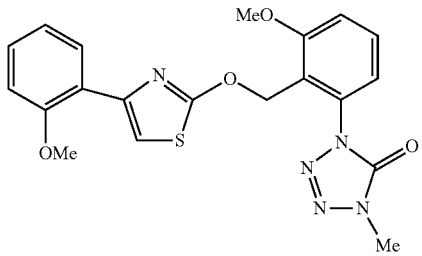 [SMILES: COc1ccccc1-c1csc(OCc2c(OC)cccc2-n2nnn(C)c2=O)n1]

$^1$H NMR (CDCl$_3$) δ: 3.53 (3H, s), 3.93 (3H, s), 3.94 (3H, s), 5.68 (2H, s), 6.96 (1H, dd, J=8.4, 0.8 Hz), 7.02-7.07 (2H, m), 7.31-7.22 (1H, m), 7.10 (1H, d, J=8.7 Hz), 7.32 (1H, s), 7.49 (1H, t, J=8.1 Hz), 8.13 (1H, dd, J=7.7, 1.7 Hz).

Preparation Example 113

A mixture of Intermediate (PRCP) 0.50 g, Intermediate (PR29) 0.34 g, cesium carbonate 0.63 g and N,N-dimethylformamide 10 mL was stirred at 80° C. for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-cyclopropylphenyl-2-yl]methyloxy}-4-(2-methoxyphenyl)thiazole (hereinafter, referred to as "Present compound (T113)") 0.30 g.

Present Compound (T113)

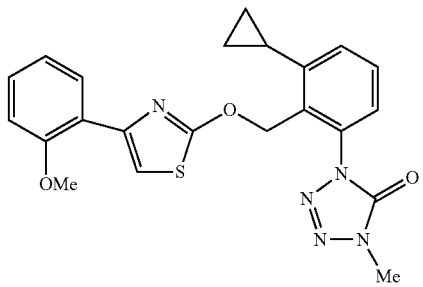 [SMILES: COc1ccccc1-c1csc(OCc2c(C3CC3)cccc2-n2nnn(C)c2=O)n1]

$^1$H NMR (CDCl$_3$) δ: 0.79 (2H, dt, J=6.2, 5.3 Hz), 1.01-1.07 (2H, m), 2.17-2.26 (1H, m), 3.56 (3H, s), 3.94 (3H, s), 5.79 (2H, s), 6.97 (1H, d, J=8.2 Hz), 7.05 (1H, td, J=7.6, 1 Hz), 7.30-7.24 (3H, m), 7.34 (1H, s), 7.43 (1H, t, J=7.9 Hz), 8.12 (1H, dd, J=7.8, 1.8 Hz).

Preparation Example 114

A mixture of Present compound (T057) 0.30 g, 4-fluoro-2-methoxyphenylboronic acid 0.27 g, cesium fluoride 0.42 g, [1,1'-bis(diphenylphosphino)ferrocene]palladium(II) dichloride dichloromethane adduct 0.06 g and dioxane 6 mL was stirred at 90° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-fluoro-2-methoxyphenyl)thiazole (hereinafter, referred to as "Present compound (T114)") 0.30 g.

Present Compound (T114)

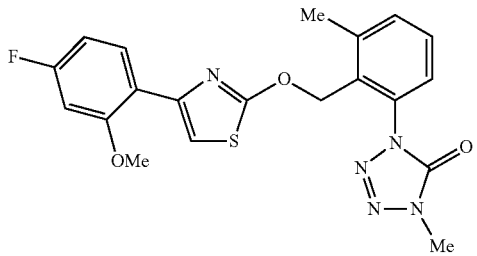 [SMILES: COc1cc(F)ccc1-c1csc(OCc2c(C)cccc2-n2nnn(C)c2=O)n1]

$^1$H NMR (CDCl$_3$) δ: 2.56 (3H, s), 3.60 (3H, s), 3.92 (3H, s), 5.57 (2H, s), 6.69 (1H, dd, J=10.9, 2.4 Hz), 6.75 (1H, ddd, J=8.6, 7.1, 2.4 Hz), 7.25 (1H, s), 7.27 (1H, dd, J=6.8, 2.4 Hz), 7.39-7.45 (2H, m), 8.07 (1H, dd, J=8.6, 7.1 Hz).

Preparation Example 115

A mixture of Present compound (T057) 0.30 g, 1-naphthylboronic acid 0.27 g, cesium fluoride 0.42 g, [1,1'-bis(diphenylphosphino)ferrocene]palladium(II) dichloride dichloromethane adduct 0.06 g and dioxane 6 mL was stirred at 90° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(1-naphthyl)thiazole (hereinafter, referred to as "Present compound (T115)") 0.10 g.

Present Compound (T115)

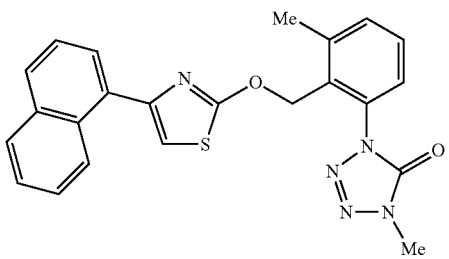 [SMILES: Cc1cccc(-n2nnn(C)c2=O)c1COc1nc(-c2cccc3ccccc23)cs1]

¹H NMR (CDCl₃) δ: 2.55 (3H, s), 3.37 (3H, s), 5.62 (2H, s), 6.74 (1H, s), 7.25 (1H, dd, J=7.7, 2.1 Hz), 7.36-7.43 (2H, m), 7.46-7.52 (3H, m), 7.61 (1H, dd, J=7.2, 1.0 Hz), 7.84-7.88 (2H, m), 8.24 (1H, dd, J=4.7, 3.7 Hz).

Preparation Example 116

A mixture of Present compound (T057) 0.30 g, 2-isopropyloxyphenylboronic acid 0.28 g, cesium fluoride 0.42 g, [1,1'-bis(diphenylphosphino)ferrocene]palladium(II) dichloride dichloromethane adduct 0.06 g and dioxane 6 mL was stirred at 90° C. for three hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-isopropyloxyphenyl)thiazole (hereinafter, referred to as "Present compound (T116)") 0.29 g.

Present Compound (T116)

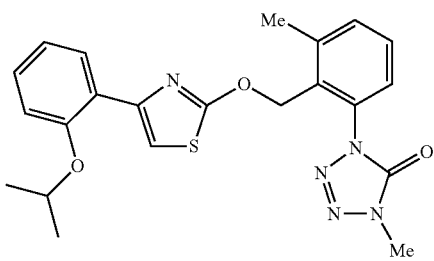 [SMILES: Cc1cccc(-n2nnn(C)c2=O)c1COc1nc(-c2ccccc2OC(C)C)cs1]

¹H NMR (CDCl₃) δ: 1.41 (6H, d, J=6 Hz), 2.57 (3H, s), 3.59 (3H, s), 4.66-4.75 (1H, m), 5.58 (2H, s), 6.95 (1H, d, J=8.2 Hz), 7.00 (1H, t, J=7.7 Hz), 7.20-7.31 (2H, m), 7.45-7.39 (3H, m), 8.12 (1H, dd, 1.7 Hz).

Preparation Example 117

A mixture of Present compound (T057) 0.30 g, 3-isopropyloxyphenylboronic acid 0.28 g, cesium fluoride 0.42 g, [1,1'-bis(diphenylphosphino)ferrocene]palladium(II) dichloride dichloromethane adduct 0.06 g and dioxane 6 mL was stirred at 90° C. for three hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-isopropyloxyphenyl)thiazole (hereinafter, referred to as "Present compound (T117)") 0.31 g.

Present Compound (T117)

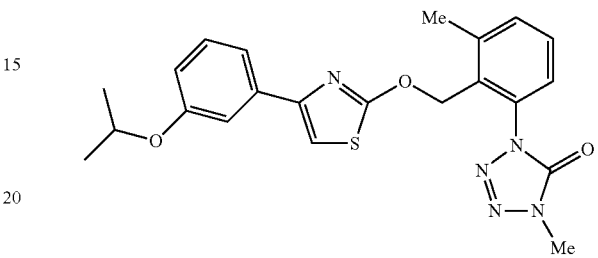

¹H NMR (CDCl₃) δ: 1.36 (6H, d, J=6.0 Hz), 2.57 (3H, s), 3.58 (3H, s), 4.57-4.68 (1H, m), 5.59 (2H, s), 6.81 (1H, s), 6.82-6.86 (1H, m), 7.24-7.30 (2H, m), 7.33-7.35 (2H, m), 7.37-7.44 (2H, m)

Preparation Example 118

A mixture of Present compound (T057) 0.30 g, 3-ethoxyphenylboronic acid 0.26 g, cesium fluoride 0.42 g, [1,1'-bis(diphenylphosphino)ferrocene]palladium(II) dichloride dichloromethane adduct 0.06 g and dioxane 5 mL was stirred at 100° C. for five hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-ethoxyphenyl)thiazole (hereinafter, referred to as "Present compound (T118)") 0.22 g.

Present Compound (T118)

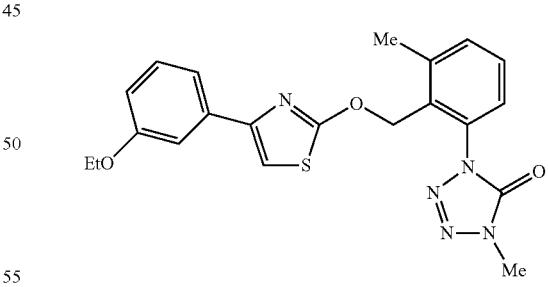

¹H NMR (CDCl₃) δ: 1.45 (3H, t, J=7.0 Hz), 2.58 (3H, s), 3.58 (3H, s), 4.10 (2H, q, J=7.0 Hz), 5.60 (2H, s), 6.83 (1H, s), 6.83-6.87 (1H, m), 7.26 (1H, dd, J=7.1, 2.1 Hz), 7.30 (1H, d, J=8.2 Hz), 7.34-7.37 (2H, m), 7.41 (1H, s), 7.43 (1H, t, J=7.8 Hz).

Preparation Example 119

A mixture of Intermediate (PRM) 0.40 g, 3-[3-(2-tetrahydropyranyloxy)phenyl]-2-oxo-thiazole (hereinafter, referred to as "Intermediate (PR31)") 0.39 g, cesium carbonate 0.55 g and N,N-dimethylformamide 5 mL was stirred at 80° C. for one hour. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-[3-(2-tetrahydropyranyloxy)phenyl]thiazole (hereinafter, referred to as "Present compound (T119)") 0.40 g.

Present Compound (T119)

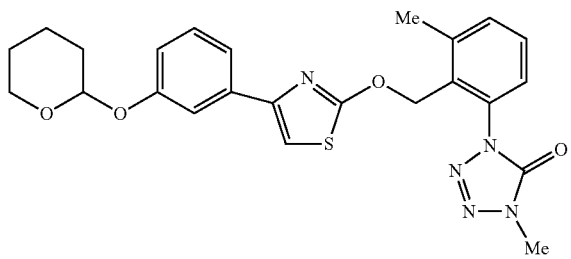 [SMILES: Cc1cccc(-n2nnn(C)c2=O)c1COc1nc(-c2cccc(OC3CCCCO3)c2)cs1]

¹H NMR (CDCl₃) δ: 1.57-1.75 (3H, m), 1.86-1.91 (2H, m), 1.98-2.09 (1H, m), 2.57 (3H, s), 3.57 (3H, s), 3.59-3.66 (1H, m), 3.94 (1H, ddd, J=12.8, 8.9, 2.9 Hz), 5.49 (1H, t, J=3 Hz), 5.59 (2H, s), 6.83 (1H, s), 7.01 (1H, ddd, J=8.2, 2.7, 1.0 Hz), 7.24-7.28 (1H, m), 7.30 (1H, d, J=8.2 Hz), 7.38-7.43 (3H, m), 7.46-7.49 (1H, m).

Preparation Example 120

A mixture of Present compound (T057) 0.30 g, 5-fluoro-2-methoxyphenylboronic acid 0.27 g, cesium fluoride 0.42 g, [1,1'-bis(diphenylphosphino)ferrocene]palladium(II) dichloride dichloromethane adduct 0.06 g and dioxane 6 mL was stirred at 90° C. for one and a half hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(5-fluoro-2-methoxyphenyl)thiazole (hereinafter, referred to as "Present compound (T120)") 0.28 g.

Present Compound (T120)

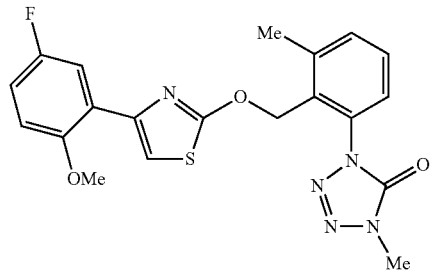 [SMILES: COc1ccc(F)cc1-c1csc(OCc2c(C)cccc2-n2nnn(C)c2=O)n1]

¹H NMR (CDCl₃) δ: 2.56 (3H, s), 3.62 (3H, s), 3.89 (3H, s), 5.58 (2H, s), 6.86 (1H, dd, J=9.7, 3.5 Hz), 6.93 (1H, td, J=9.6, 3.5 Hz), 7.26 (1H, dd, J=6.6, 2.3 Hz), 7.36-7.44 (3H, m), 7.80 (1H, dd, J=9.6, 3.5 Hz).

Preparation Example 121

A mixture of Intermediate (PRM) 0.29 g, 4-(2-methoxyphenyl)thiazole-2(1H)-thione (hereinafter, referred to as "Intermediate (PR29S)") 0.23 g, cesium carbonate 0.40 g and N,N-dimethylformamide 10 mL was stirred at 80° C. for one and a half hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)phenyl-2-yl]methy,sulfide}-4-(2-methoxyphenyl)thiazole (hereinafter, referred to as "Present compound (T121)") 0.36 g.

Present Compound (T121)

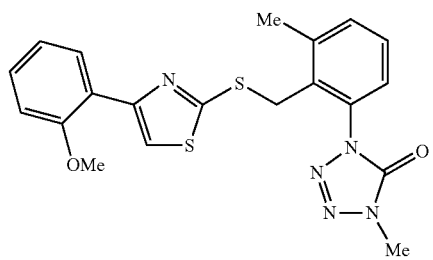 [SMILES: COc1ccccc1-c1csc(SCc2c(C)cccc2-n2nnn(C)c2=O)n1]

¹H NMR (CDCl₃) δ: 2.50 (3H, s), 3.48 (3H, s), 3.94 (3H, s), 4.65 (2H, s), 6.99 (1H, d, J=8.5 Hz), 7.07 (1H, td, J=7.7, 1.0 Hz), 7.19 (1H, dd, J=7.0, 2.2 Hz), 7.29-7.34 (3H, m), 7.83 (1H, s), 8.25 (1H, dd, J=8.0, 1.7 Hz).

Preparation Example 122

A mixture of Present compound (T057) 0.30 g, isopropenylboronic acid pinacol ester 0.26 g, cesium fluoride 0.42 g, [1,1'-bis(diphenylphosphino)ferrocene]palladium(II) dichloride dichloromethane adduct 0.06 g and dioxane 6 mL was stirred at 90° C. for one hour. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-isopropenylthiazole (hereinafter, referred to as "Present compound (T122)") 0.21 g.

Present Compound (T122)

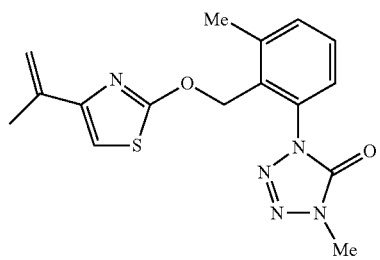 [SMILES: C=C(C)c1csc(OCc2c(C)cccc2-n2nnn(C)c2=O)n1]

¹H NMR (CDCl₃) δ: 2.02 (3H, s), 2.54 (3H, s), 3.66 (3H, s), 5.12 (1H, s), 5.52 (2H, s), 5.78 (1H, d, J=1.8 Hz), 6.48 (1H, s), 7.25 (1H, dd, J=7.5, 2.0 Hz), 7.38 (1H, dd, J=7.5, 2.0 Hz), 7.41 (1H, t, J=7.5 Hz).

Preparation Example 123

A mixture of Present compound (T057) 0.30 g, arylboronic acid pinacol ester 0.26 g, cesium fluoride 0.42 g, [1,1'-bis (diphenylphosphino)ferrocene]palladium(II) dichloride dichloromethane adduct 0.06 g and dioxane 6 mL was stirred at 90° C. for a half hour. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-arylthiazole (hereinafter, referred to as "Present compound (T123)") 0.10 g.

Present Compound (T123)

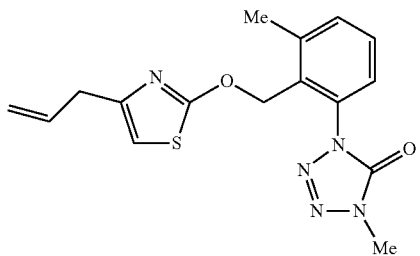 [SMILES: C=CCc1csc(OCc2c(C)cccc2-n2nnn(C)c2=O)n1]

$^1$H NMR (CDCl$_3$) δ: 2.53 (3H, s), 3.30 (2H, dq, J=6.8, 1.3 Hz), 3.68 (3H, s), 5.09-5.15 (2H, m), 5.45 (2H, s), 5.90-6.01 (1H, m), 6.21 (1H, t, J=1.1 Hz), 7.25 (1H, dd, J=7.5, 1.5 Hz), 7.36 (1H, dd, J=7.5, 1.5 Hz), 7.40 (1H, t, J=7.5 Hz).

Preparation Example 124

A mixture of Present compound (T057) 0.30 g, 1-ethoxyvinyltributyltin 0.31 g, lithium chloride 0.07 g, tetrakis(triphenylphosphine)palladium(0) 0.19 g and toluene 10 mL was stirred at 90° C. for one hour. After cooling the reaction mixtures, to the mixtures were added aqueous saturated potassium fluoride solution and the mixtures were stirred for two days. The reaction mixtures were filtered and extracted with ethyl acetate. The organic layers were washed with water and saturated saline, and were dried over anhydrous magnesium sulfate and were then concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-acetylthiazole (hereinafter, referred to as "Present compound (T124)") 0.16 g.

Present Compound (T124)

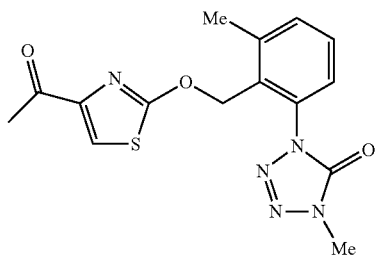 [SMILES: CC(=O)c1csc(OCc2c(C)cccc2-n2nnn(C)c2=O)n1]

$^1$H NMR (CDCl$_3$) δ: 2.51 (3H, s), 2.56 (3H, s), 3.69 (3H, s), 5.56 (2H, s), 7.28 (1H, dd, J=7.0, 1.2 Hz), 7.36-7.47 (2H, m), 7.52 (1H, s).

Preparation Example 125

A mixture of Present compound (T057) 0.30 g, 2-ethylphenylboronic acid 0.24 g, cesium fluoride 0.42 g, [1,1'-bis(diphenylphosphino)ferrocene]palladium(II) dichloride dichloromethane adduct 0.06 g and dioxane 5 mL was stirred at 80° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-ethylphenyl)thiazole (hereinafter, referred to as "Present compound (T125)") 0.26 g.

Present Compound (T125)

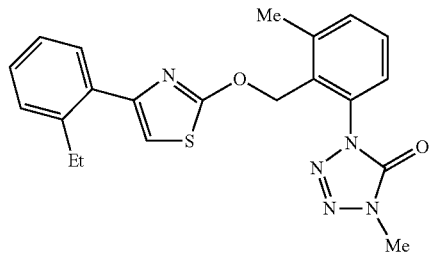 [SMILES: CCc1ccccc1-c1csc(OCc2c(C)cccc2-n2nnn(C)c2=O)n1]

$^1$H NMR (CDCl$_3$) δ: 1.18 (3H, t, J=7.5 Hz), 2.55 (3H, s), 2.78 (2H, q, J=7.5 Hz), 3.51 (3H, s), 5.55 (2H, s), 6.57 (1H, s), 7.34-7.20 (4H, m), 7.45-7.39 (3H, m).

Preparation Example 126

A mixture of Present compound (T057) 0.30 g, 4-cyanophenylboronic acid 0.23 g, cesium fluoride 0.42 g, [1,1'-bis(diphenylphosphino)ferrocene]palladium(II) dichloride dichloromethane adduct 0.06 g and dioxane 5 mL was stirred at 80° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-cyanophenyl)thiazole (hereinafter, referred to as "Present compound (T126)") 0.17 g.

Present Compound (T126)

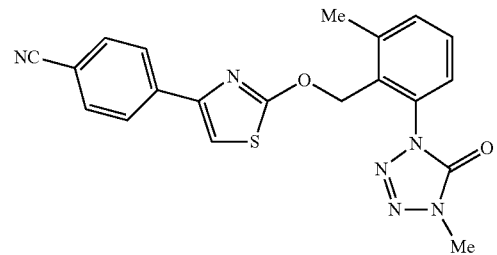 [SMILES: Cc1cccc(-n2nnn(C)c2=O)c1COc1nc(-c2ccc(C#N)cc2)cs1]

$^1$H NMR (CDCl$_3$) δ: 2.57 (3H, s), 3.62 (3H, s), 5.59 (2H, s), 7.01 (1H, d, J=0.5 Hz), 7.26-7.29 (1H, m), 7.40-7.47 (2H, m), 7.68 (2H, d, J=8.2 Hz), 7.88 (2H, d, J=8.2 Hz).

Preparation Example 127

A mixture of Present compound (T057) 0.30 g, 3-ethylphenylboronic acid 0.24 g, cesium fluoride 0.42 g, [1,1'-bis(diphenylphosphino)ferrocene]palladium(II) dichloride dichloromethane adduct 0.06 g and dioxane 5 mL was stirred at 100° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-ethylphenyl)thiazole (hereinafter, referred to as "Present compound (T127)") 0.27 g.

Present Compound (T127)

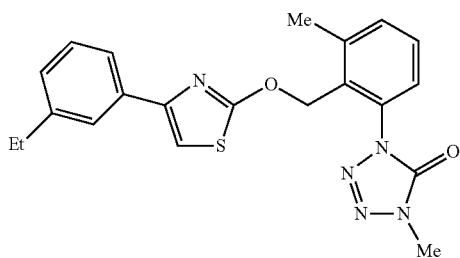 [SMILES: CCc1cccc(-c2csc(OCc3c(C)cccc3-n3nnn(C)c3=O)n2)c1]

$^1$H NMR (CDCl$_3$) δ: 1.29 (3H, t, J=7.6 Hz), 2.58 (3H, s), 2.71 (2H, q, J=7.6 Hz), 3.57 (3H, s), 5.61 (2H, s), 6.83 (1H, s), 7.15 (1H, d, J=7.6 Hz), 7.27 (1H, dd, J=6.6, 2.5 Hz), 7.31 (1H, t, J=7.6 Hz), 7.40-7.45 (2H, m), 7.59 (1H, dt, J=7.6, 1.4 Hz), 7.63 (1H, s).

Preparation Example 128

A mixture of Present compound (T057) 0.30 g, 3-cyanophenylboronic acid 0.23 g, cesium fluoride 0.42 g, [1,1'-bis(diphenylphosphino)ferrocene]palladium(II) dichloride dichloromethane adduct 0.06 g and dioxane 5 mL was stirred at 100° C. for five hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-cyanophenyl)thiazole (hereinafter, referred to as "Present compound (T128)") 0.12 g.

Present Compound (T128)

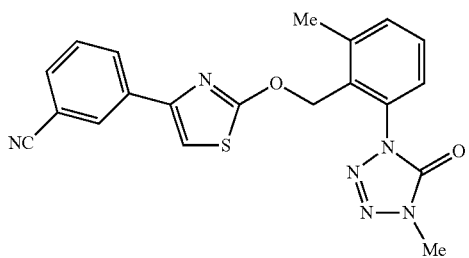 [SMILES: Cc1cccc(-n2nnn(C)c2=O)c1COc1nc(-c2cccc(C#N)c2)cs1]

$^1$H NMR (CDCl$_3$) δ: 2.58 (3H, s), 3.64 (3H, s), 5.59 (2H, s), 6.93 (1H, s), 7.28 (1H, dd, J=7.0, 2.2 Hz), 7.40-7.46 (2H, m), 7.49 (1H, t, J=7.7 Hz), 7.58 (1H, d, J=7.7 Hz), 7.98 (1H, d, J=8.0 Hz), 8.07 (1H, s).

Preparation Example 129

A mixture of Present compound (T057) 0.30 g, 2-trifluoromethoxyphenylboronic acid 0.32 g, cesium fluoride 0.42 g, [1,1'-bis(diphenylphosphino)ferrocene]palladium(II) dichloride dichloromethane adduct 0.06 g and dioxane 5 mL was stirred at 100° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-trifluoromethoxyphenyl)thiazole (hereinafter, referred to as "Present compound (T129)") 0.15 g.

Present Compound (T129)

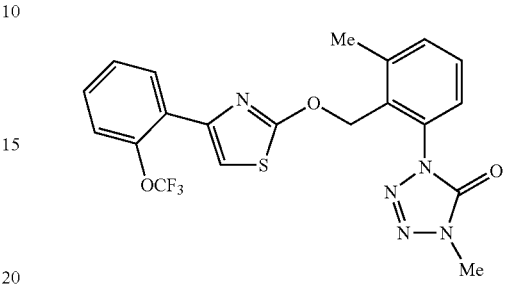

$^1$H NMR (CDCl$_3$) δ: 2.56 (3H, s), 3.60 (3H, s), 5.57 (2H, s), 7.13 (1H, s), 7.28 (1H, dd, J=7.1, 2.3 Hz), 7.30-7.39 (3H, m), 7.46-7.39 (2H, m), 8.06-8.09 (1H, m).

Preparation Example 130

A mixture of Present compound (T057) 0.30 g, 3-trifluoromethoxyphenylboronic acid 0.32 g, cesium fluoride 0.42 g, [1,1'-bis(diphenylphosphino)ferrocene]palladium(II) dichloride dichloromethane adduct 0.06 g and dioxane 5 mL was stirred at 100° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-trifluoromethoxyphenyl)thiazole (hereinafter, referred to as "Present compound (T130)") 0.15 g.

Present Compound (T130)

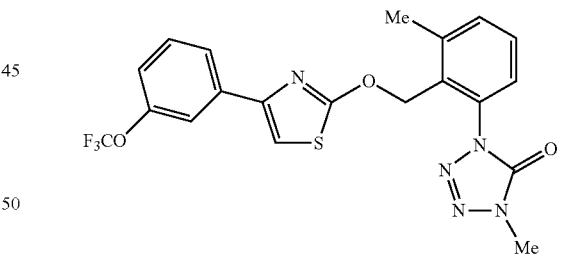

$^1$H NMR (CDCl$_3$) δ: 2.58 (3H, s), 3.61 (3H, s), 5.60 (2H, s), 6.89 (1H, s), 7.14-7.17 (1H, m), 7.27 (1H, dd, J=7.3, 2.3 Hz), 7.39-7.45 (3H, m), 7.63 (1H, s), 7.69 (1H, ddd, J=7.8, 1.6, 0.9 Hz).

Preparation Example 131

A mixture of Present compound (T057) 0.30 g, 2-cyanophenylboronic acid 0.23 g, cesium fluoride 0.42 g, [1,1'-bis(diphenylphosphino)ferrocene]palladium(II) dichloride dichloromethane adduct 0.06 g and dioxane 5 mL was stirred at 100° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-cyanophenyl)thiazole (hereinafter, referred to as "Present compound (T131)") 0.22 g.

Present Compound (T131)

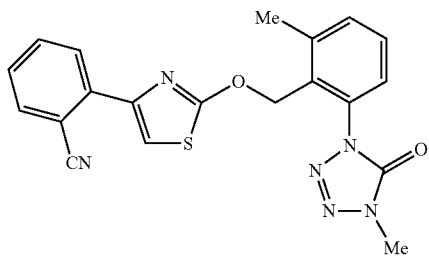 [SMILES: Cc1cccc(-n2nnn(C)c2=O)c1COc1nc(-c2ccccc2C#N)cs1]

¹H NMR (CDCl₃) δ: 2.57 (3H, s), 3.64 (3H, s), 5.59 (2H, s), 7.28 (1H, dd, J=7.3, 1.8 Hz), 7.37 (1H, s), 7.37-7.46 (3H, m), 7.63 (1H, td, J=8.0, 1.4 Hz), 7.72 (1H, dd, J=8.2, 0.8 Hz), 7.94 (1H, dd, J=8.0, 0.8 Hz).

Preparation Example 132

A mixture of Present compound (T057) 0.30 g, 2-ethoxyphenylboronic acid 0.26 g, cesium fluoride 0.42 g, [1,1'-bis(diphenylphosphino)ferrocene]palladium(II) dichloride dichloromethane adduct 0.06 g and dioxane 5 mL was stirred at 100° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-ethoxyphenyl)thiazole (hereinafter, referred to as "Present compound (T132)") 0.23 g.

Present Compound (T132)

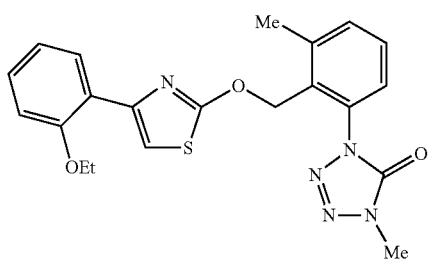

¹H NMR (CDCl₃) δ: 1.51 (3H, t, J=7.0 Hz), 2.57 (3H, s), 3.59 (3H, s), 4.16 (2H, q, J=7.0 Hz), 5.59 (2H, s), 6.94 (1H, d, J=7.7 Hz), 7.03 (1H, td, J=7.4, 1.0 Hz), 7.22-7.28 (2H, m), 7.39-7.44 (3H, m), 8.12 (1H, dd, J=7.8, 1.8 Hz).

Preparation Example 133

A mixture of Present compound (T057) 0.30 g, 4-acetylphenylboronic acid 0.26 g, cesium fluoride 0.42 g, [1,1'-bis(diphenylphosphino)ferrocene]palladium(II) dichloride dichloromethane adduct 0.06 g and dioxane 5 mL was stirred with heating under reflux for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-acetylphenyl)thiazole (hereinafter, referred to as "Present compound (T133)") 0.26 g.

Present Compound (T133)

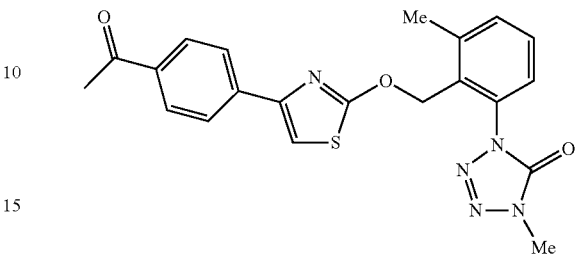

¹H NMR (CDCl₃) δ: 2.58 (3H, s), 2.63 (3H, s), 3.60 (3H, s), 5.61 (2H, s), 7.00 (1H, s), 7.27 (1H, dd, J=7.1, 2.3 Hz), 7.40-7.46 (2H, m), 7.87 (2H, d, J=8.6 Hz), 7.99 (2H, d, J=8.6 Hz).

Preparation Example 134

A mixture of Present compound (T057) 0.30 g, 4-ethoxyphenylboronic acid 0.26 g, cesium fluoride 0.42 g, [1,1'-bis(diphenylphosphino)ferrocene]palladium(II) dichloride dichloromethane adduct 0.06 g and dioxane 5 mL was stirred with heating under reflux for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-ethoxyphenyl)thiazole (hereinafter, referred to as "Present compound (T134)") 0.26 g.

Present Compound (T134)

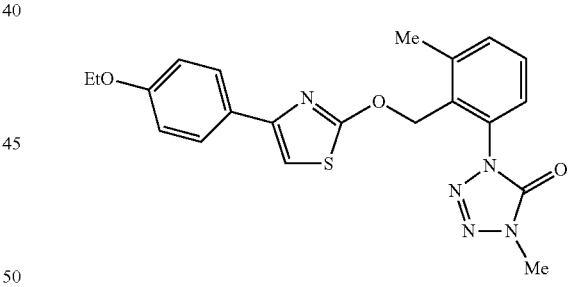

¹H NMR (CDCl₃) δ: 1.43 (3H, t, J=6.9 Hz), 2.57 (3H, s), 3.57 (3H, s), 4.06 (2H, q, J=6.9 Hz), 5.58 (2H, s), 6.68 (1H, s), 6.91 (2H, d, J=8.6 Hz), 7.24-7.28 (1H, m), 7.39-7.44 (2H, m), 7.70 (2H, d, J=8.6 Hz).

Preparation Example 135

A mixture of Present compound (T057) 0.30 g, cyclopropylboronic acid 0.14 g, cesium fluoride 0.42 g, [1,1'-bis(diphenylphosphino)ferrocene]palladium(II) dichloride dichloromethane adduct 0.06 g and dioxane 5 mL was stirred with heating under reflux for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-

3-methylphenyl-2-yl]methyloxy}-4-cyclopropylthiazole (hereinafter, referred to as "Present compound (T135)") 0.15 g.

Present Compound (T135)

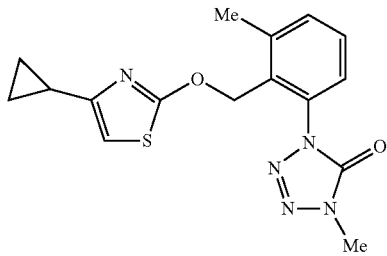 [SMILES: Cc1cccc(-n2nnn(C)c2=O)c1COc1nc(C2CC2)cs1]

$^1$H NMR (CDCl$_3$) δ: 0.73-0.86 (4H, m), 1.77-1.85 (1H, m), 2.52 (3H, s), 3.70 (3H, s), 5.42 (2H, s), 6.16 (1H, s), 7.26 (1H, d, J=6.6 Hz), 7.37 (1H, d, J=6.6 Hz), 7.41 (1H, t, J=6.6 Hz).

Preparation Example 136

A mixture of Present compound (T057) 0.30 g, 3-acetylboronic acid 0.26 g, cesium fluoride 0.42 g, [1,1'-bis(diphenylphosphino)ferrocene]palladium(II) dichloride dichloromethane adduct 0.06 g and dioxane 5 mL was stirred with heating under reflux for two hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-acetylphenyl)thiazole (hereinafter, referred to as "Present compound (T136)") 0.30 g.

Present Compound (T136)

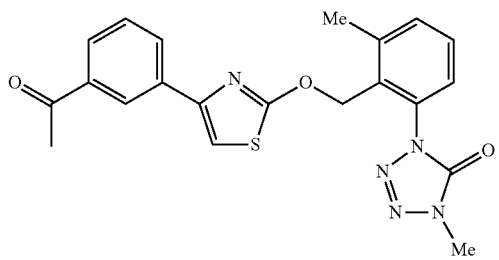 [SMILES: CC(=O)c1cccc(-c2csc(OCc3c(C)cccc3-n3nnn(C)c3=O)n2)c1]

$^1$H NMR (CDCl$_3$) δ: 2.59 (3H, s), 2.67 (3H, s), 3.60 (3H, s), 5.61 (2H, s), 6.95 (1H, s), 7.28 (1H, dd, J=6.8, 2.7 Hz), 7.41-7.46 (2H, m), 7.50 (1H, t, J=7.7 Hz), 7.89 (1H, d, J=7.7 Hz), 7.99 (1H, d, J=8.0 Hz), 8.35 (1H, t, J=1.7 Hz).

Preparation Example 137

A mixture of Present compound (T057) 0.30 g, 4-isopropoxyphenylboronic acid 0.26 g, cesium fluoride 0.42 g, [1,1'-bis(diphenylphosphino)ferrocene]palladium(II) dichloride dichloromethane adduct 0.06 g and dioxane 5 mL was stirred with heating under reflux for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-isopropoxyphenyl)thiazole (hereinafter, referred to as "Present compound (T137)") 0.23 g.

Present Compound (T137)

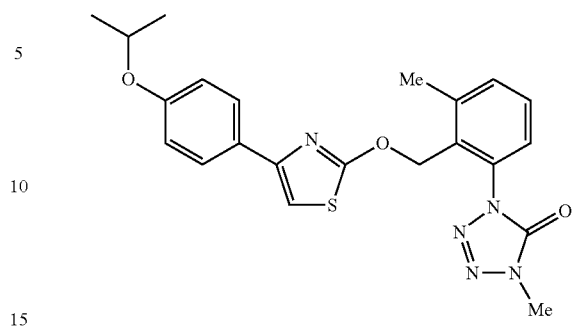

$^1$H NMR (CDCl$_3$) δ: 1.36 (6H, d, J=6.2 Hz), 2.57 (3H, s), 3.58 (3H, s), 4.54-4.65 (1H, m), 5.59 (2H, s), 6.68 (1H, s), 6.91 (2H, d, J=9.2 Hz), 7.26 (1H, dd, J=6.5, 2.7 Hz), 7.39-7.45 (2H, m), 7.70 (2H, d, J=9.2 Hz).

Preparation Example 138

A mixture of Present compound (T057) 0.30 g, 2-acetylphenylboronic acid 0.26 g, cesium fluoride 0.42 g, [1,1'-bis(diphenylphosphino)ferrocene]palladium(II) dichloride dichloromethane adduct 0.06 g and dioxane 5 mL was stirred with heating under reflux for three hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-acetylphenyl)thiazole (hereinafter, referred to as "Present compound (T138)") 0.11 g.

Present Compound (T138)

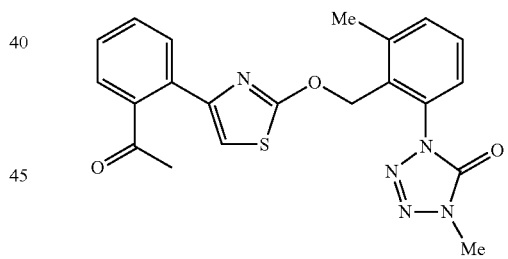

$^1$H NMR (CDCl$_3$) δ: 2.29 (3H, s), 2.53 (3H, s), 3.61 (3H, s), 5.48 (2H, s), 6.75 (1H, d, J=0.7 Hz), 7.25-7.28 (1H, m), 7.38-7.48 (5H, m), 7.57 (1H, d, J=7.5 Hz).

Preparation Example 139

A mixture of Present compound (T110) 0.35 g, butylboronic acid 0.16 g, cesium fluoride 0.41 g, [1,1'-bis(diphenylphosphino)ferrocene]palladium(II) dichloride dichloromethane adduct 0.06 g and dioxane 5 mL was stirred at 90° C. for a half hour. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-butylphenyl)thiazole (hereinafter, referred to as "Present compound (T139)") 0.08 g.

Present Compound (T139)

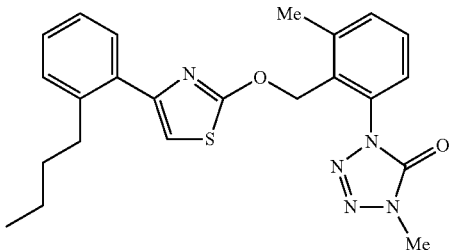 [SMILES: CCCCc1ccccc1-c1csc(OCc2c(C)cccc2-n2nnn(C)c2=O)n1]

¹H NMR (CDCl₃) δ: 0.87 (3H, t, J=7.6 Hz), 1.26-1.36 (2H, m), 1.47-1.56 (2H, m), 2.54 (3H, s), 2.75 (2H, dd, J=8.7, 7.6 Hz), 3.51 (3H, s), 5.53 (2H, s), 6.55 (1H, s), 7.19-7.31 (4H, m), 7.38-7.45 (3H, m).

Preparation Example 140

A mixture of Present compound (T057) 0.30 g, 4-ethylphenylboronic acid 0.28 g, cesium fluoride 0.42 g [1,1'-bis(diphenylphosphino)ferrocene]palladium(II)-dichloride dichloromethane adduct 0.06 g and dioxane 5 mL was stirred at 90° C. for two hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-ethylphenyl)thiazole (hereinafter, referred to as "Present compound (T140)") 0.34 g.

Present Compound (T140)

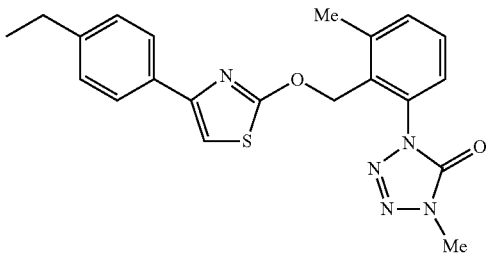 [SMILES: CCc1ccc(-c2csc(OCc3c(C)cccc3-n3nnn(C)c3=O)n2)cc1]

¹H NMR (CDCl₃) δ: 1.25 (3H, t, J=7.6 Hz), 2.57 (3H, s), 2.67 (2H, q, J=7.6 Hz), 3.57 (3H, s), 5.60 (2H, s), 6.77 (1H, s), 7.22 (2H, d, J=8.2 Hz), 7.26 (1H, dd, J=6.4, 2.5 Hz), 7.38-7.45 (2H, m), 7.69 (2H, d, J=8.2 Hz).

Preparation Example 141

A mixture of Present compound (T057) 0.30 g, 2-hydroxyphenylboronic acid 0.22 g, cesium fluoride 0.42 g, [1,1'-bis(diphenylphosphino)ferrocene]palladium(II) dichloride dichloromethane adduct 0.06 g and dioxane 6 mL was stirred at 90° C. for three hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-hydroxyphenyl)thiazole (hereinafter, referred to as "Present compound (T141)") 0.09 g.

Present Compound (T141)

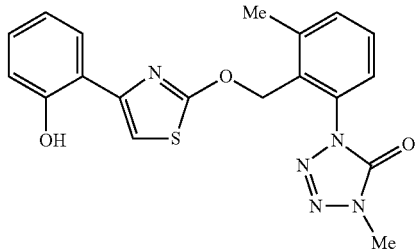 [SMILES: Cc1cccc(-n2nnn(C)c2=O)c1COc1nc(-c2ccccc2O)cs1]

¹H NMR (CDCl₃) δ: 2.53 (3H, s), 3.63 (3H, s), 5.52 (2H, s), 6.85 (1H, d, J=7.7 Hz), 6.88 (1H, s), 6.96 (1H, d, J=8.2 Hz), 7.19-7.24 (1H, m), 7.29 (1H, dd, J=7.5, 1.5 Hz), 7.46-7.38 (2H, m), 7.51 (1H, dd, J=8.0, 1.7 Hz), 10.64 (1H, s).

Preparation Example 142

A mixture of Present compound (T145) 0.35 g, butylboronic acid 0.16 g, cesium fluoride 0.41 g, [1,1'-bis(diphenylphosphino)ferrocene]palladium(II) dichloride dichloromethane adduct 0.06 g and dioxane 5 mL was stirred at 90° C. for eight hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-butylphenyl)thiazole (hereinafter, referred to as "Present compound (T142)") 0.28 g.

Present Compound (T142)

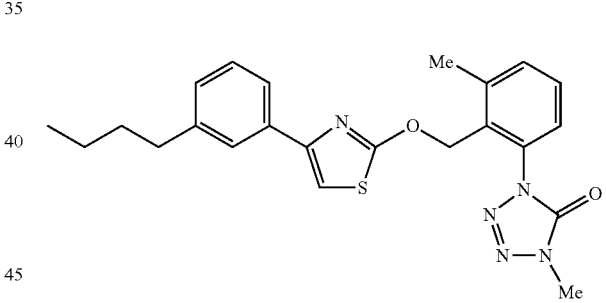

¹H NMR (CDCl₃) δ: 0.94 (3H, t, J=7.4 Hz), 1.33-1.44 (2H, m), 1.64 (2H, tt, J=7.4, 7.4 Hz), 2.57 (3H, s), 2.66 (2H, t, J=7.7 Hz), 3.56 (3H, s), 5.60 (2H, s), 6.81 (1H, s), 7.12 (1H, d, J=7.6 Hz), 7.25 (1H, d, J=5.8 Hz), 7.29 (1H, t, J=7.6 Hz), 7.38-7.43 (2H, m), 7.58 (1H, d, J=8.0 Hz), 7.60 (1H, s).

Preparation Example 143

A mixture of Present compound (T057) 0.30 g, 4-chloro-2-methoxyphenylboronic acid 0.29 g, cesium fluoride 0.42 g, [1,1'-bis(diphenylphosphino)ferrocene]palladium(II) dichloride dichloromethane adduct 0.06 g and dioxane 6 mL was stirred at 90° C. for three hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(4-chloro-2-methoxyphenyl)thiazole (hereinafter, referred to as "Present compound (T143)") 0.30 g.

Present Compound (T143)

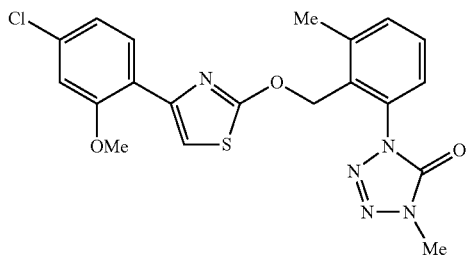 [SMILES: COc1cc(Cl)ccc1-c1csc(OCc2c(C)cccc2-n2nnn(C)c2=O)n1]

¹H NMR (CDCl₃) δ: 2.56 (3H, s), 3.60 (3H, s), 3.93 (3H, s), 5.57 (2H, s), 6.94 (1H, d, J=2.0 Hz), 7.03 (1H, dd, J=8.4, 2.0 Hz), 7.27 (1H, dd, J=6.8, 2.4 Hz), 7.30 (1H, s), 7.39-7.45 (2H, m), 8.03 (1H, d, J=8.4 Hz).

Preparation Example 144

A mixture of Present compound (T110) 0.35 g, heptylphenylboronic acid 0.16 g, cesium fluoride 0.41 g, [1,1'-bis(diphenylphosphino)ferrocene]palladium(II) dichloride dichloromethane adduct 0.06 g and dioxane 6 mL was stirred at 90° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(2-heptylphenyl)thiazole (hereinafter, referred to as "Present compound (T144)") 0.18 g.

Present Compound (T144)

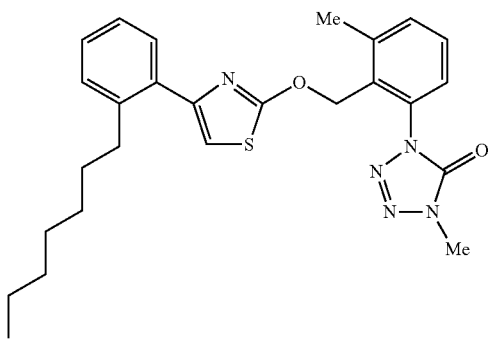 [SMILES: CCCCCCCc1ccccc1-c1csc(OCc2c(C)cccc2-n2nnn(C)c2=O)n1]

¹H NMR (CDCl₃) δ: 0.85 (3H, t, J=6.6 Hz), 1.18-1.32 (8H, brm), 1.47-1.57 (2H, brm), 2.54 (3H, s), 2.75 (2H, t, J=8.0 Hz), 3.49 (3H, s), 5.54 (2H, s), 6.54 (1H, s), 7.19-7.30 (4H, m), 7.37-7.43 (3H, m).

Preparation Example 145

A mixture of Intermediate (PRMO) 1.6 g, sodium tert-butoxide 0.84 g and tetrahydrofuran 40 mL was stirred at 25° C. for fifteen minutes and then to the resulting mixtures was added 2-chloro-4-(3-bromophenyl)thiazole (hereinafter, referred to as "Intermediate (PR32C)") 2.0 g and the mixtures were heated under reflux for one hour. To the reaction mixtures after standing to cool was added water and the resulting mixtures were extracted with ethyl acetate. The organic layers were washed with aqueous saturated sodium bicarbonate solution and saturated saline, and were then concentrated under reduced pressure to give 2-{[1-(4,5-dihydro-4-methyl-5-oxo-1H-tetrazole-1-yl)-3-methylphenyl-2-yl]methyloxy}-4-(3-bromophenyl)thiazole (hereinafter, referred to as "Present compound (T145)") 2.62 g.

Present Compound (T145)

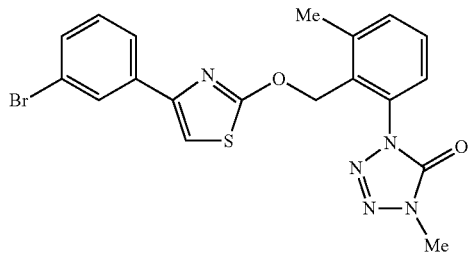 [SMILES: Cc1cccc(-n2nnn(C)c2=O)c1COc1nc(-c2cccc(Br)c2)cs1]

¹H NMR (CDCl₃) δ: 2.58 (3H, s), 3.62 (3H, s), 5.59 (2H, s), 6.86 (1H, s), 7.24-7.28 (2H, m), 7.46-7.40 (3H, m), 7.69 (1H, d, J=7.7 Hz), 7.93 (1H, s).

Preparation Example 146

A mixture of Present compound (T145) 0.35 g, heptylphenylboronic acid 0.15 g, cesium fluoride 0.41 g, [1,1'-bis(diphenylphosphino)ferrocene]palladium(II) dichloride dichloromethane adduct 0.06 g and dioxane 6 mL was stirred at 90° C. for four hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(3-heptylphenyl)thiazole (hereinafter, referred to as "Present compound (T146)") 0.29 g.

Present Compound (T146)

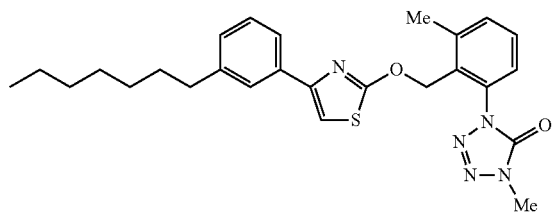 [SMILES: CCCCCCCc1cccc(-c2csc(OCc3c(C)cccc3-n3nnn(C)c3=O)n2)c1]

¹H NMR (CDCl₃) δ: 0.88 (3H, t, J=6.8 Hz), 1.23-1.41 (8H, m), 1.65 (2H, tt, J=7.9, 7.9 Hz), 2.57 (3H, s), 2.65 (2H, t, J=7.9 Hz), 3.55 (3H, s), 5.60 (2H, s), 6.81 (1H, s), 7.12 (1H, d, J=7.5 Hz), 7.23-7.32 (2H, m), 7.37-7.43 (2H, m), 7.58 (1H, d, J=8.2 Hz), 7.60 (1H, s).

Preparation Example 147

A mixture of 1-(2-bromomethyl-4-fluorophenyl)-4-methyl-1,4-dihydrotetrazole-5-one (hereinafter, referred to as "Intermediate (PRF4)") 0.86 g, Intermediate (PR04) 0.85 g, cesium carbonate 1.17 g and N,N-dimethylformamide 20 mL was stirred at 80° C. for ten hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-{

[1-(4,5-dihydro-4-methyl-5-oxo-1H-tetrazole-1-yl)-4-fluorophenyl-2-yl]methyloxy}-4-(4-bromophenyl)thiazole (hereinafter, referred to as "Present compound (T147)") 0.54 g.

Present, compound (T147)

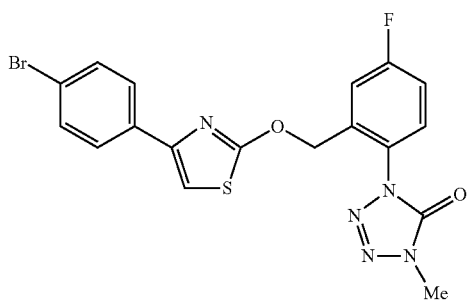 [SMILES: Cn1nnn(-c2ccc(F)cc2COc2nc(-c3ccc(Br)cc3)cs2)c1=O]

¹H NMR (CDCl₃) δ: 3.67 (3H, s), 5.57 (2H, s), 6.87 (1H, s), 7.20 (1H, ddd, J=9.7, 6.7, 2.0 Hz), 7.42-7.48 (2H, m), 7.51 (2H, dt, J=8.9, 2.2 Hz), 7.63 (2H, dt, J=8.9, 2.2 Hz).

Preparation Example 148

A mixture of Present compound (T057) 0.30 g, 5-methyl-2-methoxyphenylboronic acid 0.26 g, cesium fluoride 0.42 g, [1,1'-bis(diphenylphosphino)ferrocene]palladium(II) dichloride dichloromethane adduct 0.06 g and dioxane 6 mL was stirred with heating under reflux for five hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(5-methyl-2-methoxyphenyl)thiazole (hereinafter, referred to as "Present compound (T148)") 0.29 g.

Present Compound (T148)

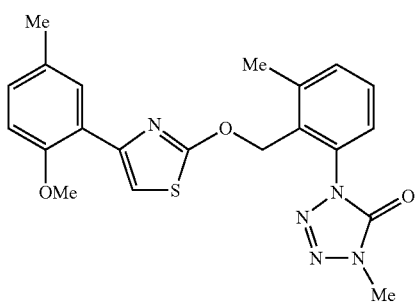 [SMILES: COc1ccc(Cl)cc1-c1csc(OCc2c(C)cccc2-n2nnn(C)c2=O)n1]

¹H NMR (CDCl₃) δ: 2.36 (3H, s), 2.55 (3H, s), 3.56 (3H, s), 3.87 (3H, s), 5.58 (2H, s), 6.83 (1H, d, J=8.2 Hz), 7.05 (1H, ddd, J=8.2, 1.6, 0.7 Hz), 7.25 (1H, dd, J=6.9, 2.3 Hz), 7.32 (1H, s), 7.36-7.42 (2H, m), 7.91 (1H, d, J=2.3 Hz).

Preparation Example 149

A mixture of Present compound (T057) 0.30 g, 5-chloro-2-methoxyphenylboronic acid 0.29 g, cesium fluoride 0.42 g, [1,1'-bis(diphenylphosphino)ferrocene]palladium(II) dichloride dichloromethane adduct 0.06 g and dioxane 6 mL was stirred with heating under reflux for twelve hours. After cooling the reaction mixtures, the mixtures were filtered and the filtrates were concentrated under reduced pressure. The resulting residues were subjected to a silica gel column chromatography to give 2-{[1-(4,5-dihydro-4-methyl-5-oxo-1H-tetrazole-1-yl)-3-methylphenyl-2-yl]methyloxy}-4-(5-chloro-2-methoxyphenyl)thiazole (hereinafter, referred to as "Present compound (T149)") 0.29 g.

Present Compound (T149)

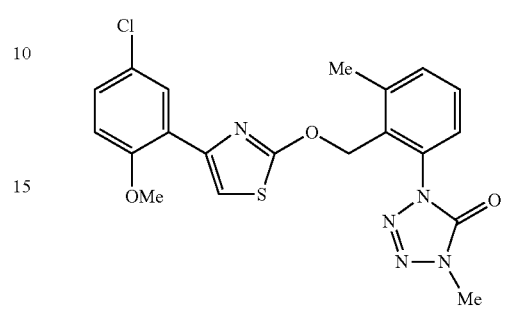

¹H-NMR (CDCl₃) δ: 2.57 (3H, s), 3.63 (3H, s), 3.90 (3H, s), 5.58 (2H, s), 6.87 (1H, d, J=8.7 Hz), 7.20 (1H, dd, J=8.7, 2.7 Hz), 7.27 (1H, dd, J=6.5, 2.9 Hz), 7.36 (1H, s), 7.39-7.45 (2H, m), 8.06 (1H, d, J=2.7 Hz).

Reference Preparation Example 1

Intermediate (PRH) was prepared according to the following steps (1) to (3).
<Step (1)>
Under ice-cooling, to N,N-dimethylformamide 500 mL was added anhydrous aluminum chloride 55.1 g and the resulting mixtures were stirred for fifteen minutes. Thereto was added sodium azide 26.9 g and the resulting mixtures were stirred for fifteen minutes and thereto was then added 1-isocyanato-2-methylbenzene 50.6 g and the resulting mixtures were heated at 70° C. for four hours. After cooling, to a mixture of sodium nitrite 51.8 g, water 2 L and ice 500 g was added the reaction solutions with stirring. The mixtures were acidified with 10% hydrochloric acid and were extracted with ethyl acetate. The organic layers were washed with water and saturated saline, and were dried over anhydrous magnesium sulfate and were then concentrated under reduced pressure to give 1-(2-methylphenyl)-1,4-dihydrotetrazole-5-one 69.8 g.

1-(2-methylphenyl)-1,4-dihydrotetrazole-5-one

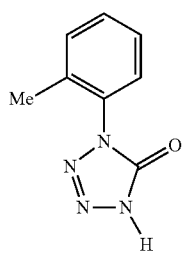 [SMILES: Cc1ccccc1-n1nn[nH]c1=O]

¹H NMR (CDCl₃) δ: 2.32 (3H, s), 7.37-7.47 (4H, m), 13.55 (1H, s).
<Step (2)>
To a mixture of the above-mentioned 1-(2-methylphenyl)-1,4-dihydrotetrazole-5-one 69.8 g and N,N-dimethylformamide 380 mL was added 55% sodium hydride 18.2 g under ice-cooling. After stirring the resulting mixture for twenty minutes, thereto was added methyl iodide 59.4 g. The mixtures were raised to room temperature and were stirred for two and a half hours. To the reaction mixtures was added water and the mixtures were extracted with methyl tert-butyl ether. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methylphenyl)-4-methyl-1,4-dihydrotetrazole-5-one 52.5 g.

1-(2-methylphenyl)-4-methyl-1,4-dihydrotetrazole-5-one

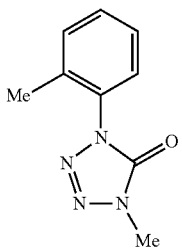 [SMILES: Cc1ccccc1-n1nnn(C)c1=O]

$^1$H NMR (CDCl$_3$) δ: 2.29 (3H, s), 3.72 (3H, s), 7.32-7.44 (4H, m).

<Step (3)>

A mixture of the above-mentioned 1-(2-methylphenyl)-4-methyl-1,4-dihydrotetrazole-5-one 18.0 g, N-bromosuccinimide 19.4 g and chlorobenzene 166 mL was made 96° C. and then thereto was added 1,1'-azobis(cyclohexane-1-carbonitrile) 2.57 g and the mixtures were stirred at 100° C. for three hours. After cooling the reaction solutions, thereto was added water and the resulting mixtures were extracted with methyl tert-butyl ether. The organic layers were washed with water and saturated saline, and were dried over anhydrous magnesium sulfate and were then concentrated under reduced pressure to give the residues 30.4 g. The residues were combined with the residues derived from similar preparation and the total residues 68.0 g were subjected to a silica gel column chromatography to give Intermediate (PRH) 33.8 g.

Intermediate (PRH)

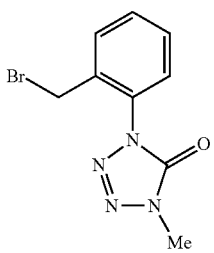 [SMILES: Cn1nnn(-c2ccccc2CBr)c1=O]

$^1$H NMR (CDCl$_3$) δ: 3.75 (3H, s), 4.59 (2H, s), 7.43-7.51 (3H, m) 7.53-7.56 (1H, m).

Reference Preparation Example 2

Intermediate (PRF) was prepared according to the following steps (1) to (3).
<Step (1)>
Under ice-cooling, to N,N-dimethylformamide 250 mL was added anhydrous aluminum chloride 21.9 g and the resulting mixtures were stirred for fifteen minutes. Thereto was added sodium azide 10.7 g and the resulting mixtures were stirred for fifteen minutes and thereto was then added 1-fluoro-3-isocyanato-2-methylbenzene 22.5 g and the resulting mixtures were heated at 80° C. for three and a half hours. After cooling the mixtures, to a mixture of sodium nitrite 34 g, water 2 L and ice 500 g was added the reaction solutions with stirring. The mixtures were acidified with 10% hydrochloric acid and were extracted with ethyl acetate. The organic layers were washed with water and saturated saline, and were dried over anhydrous magnesium sulfate and were then concentrated under reduced pressure to give 1-(2-methyl-3-fluorophenyl)-1,4-dihydrotetrazole-5-one 27.5 g.

1-(2-methyl-3-fluorophenyl)-1,4-dihydrotetrazole-5-one

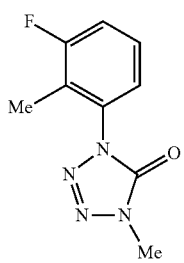 [SMILES: Cc1c(F)cccc1-n1nnn(C)c1=O]

$^1$H NMR (CDCl$_3$) δ: 2.21 (3H, s), 7.07-7.36 (3H, m), 12.93 (1H, s).

<Step (2)>
To a mixture of the above-mentioned 1-(2-methyl-3-fluorophenyl)-1,4-dihydrotetrazole-5-one 10.00 g and N,N-dimethylformamide 100 mL was added 55% sodium hydride 2.47 g under ice-cooling. The mixtures were raised to room temperature and were stirred for one hour. To the reaction mixtures was added methyl iodide 3.5 mL under ice-cooling. The mixtures were raised to room temperature and were stirred for fourteen hours. To the reaction mixtures was added water and the mixtures were extracted with ethyl acetate. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methyl-3-fluorophenyl)-4-methyl-1,4-dihydrotetrazole-5-one 2.19 g.

1-(2-methyl-3-fluorophenyl)-4-methyl-1,4-dihydrotetrazole-5-one

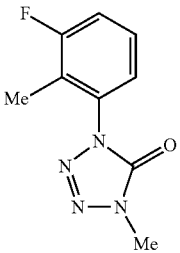 [SMILES: Cc1c(F)cccc1-n1nnn(C)c1=O]

$^1$H NMR (CDCl$_3$) δ: 2.19 (3H, s), 3.70 (3H, s), 7.16-7.20 (2H, m), 7.29 (1H, dt, J=5.9, 8.3 Hz).

<Step (3)>

A mixture of the above-mentioned 1-(2-methyl-3-fluorophenyl)-4-methyl-1,4-dihydrotetrazole-5-one 2.19 g, 1,1'-azobis(cyclohexane-1-carbonitrile) 0.52 g, N-bromosuccinimide 2.16 g and chlorobenzene 40 mL was stirred with heating under reflux for five hours. After cooling the reaction solutions, thereto was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give Intermediate (PRF) 2.36 g.

Intermediate (PRF)

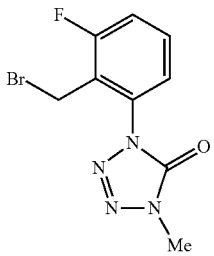 [SMILES: Cn1nnn(-c2cccc(F)c2CBr)c1=O]

$^1$H NMR (CDCl$_3$) δ: 3.75 (3H, s), 4.64 (2H, s), 7.23-7.30 (2H, m), 7.47 (1H, dt, J=5.9, 8.0 Hz).

Reference Preparation Example 3

Intermediate (PRC) was prepared according to the following steps (1) to (3).

<Step (1)>

Under ice-cooling, to N,N-dimethylformamide 250 mL was added anhydrous aluminum chloride 21.9 g and the resulting mixtures were stirred for fifteen minutes. Thereto was added sodium azide 10.7 g and the resulting mixtures were stirred for fifteen minutes and thereto was then added 1-chloro-3-isocyanato-2-methylbenzene 25.0 g and the resulting mixtures were heated at 80° C. for five hours. After cooling the mixtures, to a mixture of sodium nitrite g, water 2 L and ice 500 g was added the reaction solutions with stirring. The mixtures were acidified with 10% hydrochloric acid and were extracted with ethyl acetate. The organic layers were washed with water and saturated saline, and were dried over anhydrous magnesium sulfate and were then concentrated under reduced pressure to give 1-(2-methyl-3-chlorophenyl)-1,4-dihydrotetrazole-5-one 17.0 g.

1-(2-methyl-3-chlorophenyl)-1,4-dihydrotetrazole-5-one

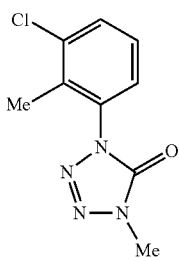

$^1$H NMR (CDCl$_3$) δ: 2.32 (3H, s), 7.28-7.36 (2H, m), 7.57 (1H, dd, J=6.8, 2.2 Hz), 13.08 (1H, s).

<Step (2)>

To a mixture of the above-mentioned 1-(2-methyl-3-chlorophenyl)-1,4-dihydrotetrazole-5-one 10.00 g and N,N-dimethylformamide 100 mL was added 55% sodium hydride 2.30 g under ice-cooling. The mixtures were raised to room temperature and were stirred for one hour. To the reaction mixtures was added methyl iodide 3.2 mL under ice-cooling. The mixtures were raised to room temperature and were stirred for fourteen hours. To the reaction mixtures was added water and the mixtures were extracted with ethyl acetate. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methyl-3-chlorophenyl)-4-methyl-1,4-dihydrotetrazole-5-one (hereinafter, referred to as "Intermediate (PRC-P)") 1.56 g.

Intermediate (PRC-P)

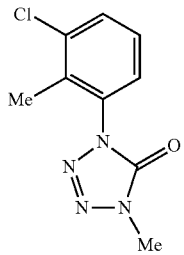

$^1$H NMR (CDCl$_3$) δ: 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).

<Step (3)>

A mixture of the above-mentioned Intermediate (PRC-P) 1.56 g, 1,1'-azobis(cyclohexane-1-carbonitrile) 0.34 g, N-bromosuccinimide 1.42 g and chlorobenzene 30 mL was stirred with heating under reflux for five hours. After cooling the reaction solutions, thereto was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give Intermediate (PRC) 1.94 g.

Intermediate (PRC)

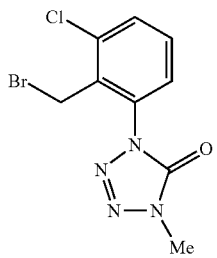 [SMILES: Cn1nnn(-c2cccc(Cl)c2CBr)c1=O]

$^1$H NMR (CDCl$_3$) δ: 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Reference Preparation Example 4

A mixture of 3-chloro-2-methy benzoate 21.5 g, oxalyl dichloride 17.6 g, N,N-dimethylformamide about 50 mL and tetrahydrofuran 300 mL was stirred at 25° C. for one hour. The reaction mixtures were concentrated under reduced pressure to give 3-chloro-2-methylbenzoic acid chloride.

A mixture of aluminium chloride 33.6 g, sodium azide 49.2 g and tetrahydrofuran 100 mL was stirred with heating under reflux for two hours. After the reaction mixtures were cooled under ice-cooling, and thereto was added a mixture of the above-mentioned 3-chloro-2-methylbenzoic acid chloride and tetrahydrofuran 100 mL and the resulting mixtures were stirred with heating under reflux for ten hours. After cooling the mixtures, to a mixture of sodium nitrite 75.6 g and water 500 mL was added the reaction mixtures with stirring. The mixtures were acidified with concentrated hydrochloric acid and were then extracted with ethyl acetate. The organic layers were dried over anhydrous sodium sulfate and were then concentrated under reduced pressure to give 1-(2-methyl-3-chlorophenyl)-1,4-dihydrotetrazole-5-one.

A mixture of the above-mentioned 1-(2-methyl-3-chlorophenyl)-1,4-dihydrotetrazole-5-one, potassium carbonate 57.5 g, dimethyl sulfate 19.1 g and N,N-dimethylformamide 150 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give Intermediate (PRC-P) 21.6 g.

Reference Preparation Example 5

Under cooling, to a mixture of methyl chloroformate 30 mL and tetrahydrofuran 50 mL was added dropwise 1-chloro-2-methyl-3-aminobenzene 5.00 g and the mixtures were stirred at 25° C. for a half hour. To the reaction mixtures was added water and the resulting mixtures were extracted with ethyl acetate. The organic layers were washed with aqueous saturated sodium bicarbonate solution and were dried over anhydrous sodium sulfate. The mixtures were concentrated under reduced pressure to give 1-chloro-2-methyl-3-methoxycarbonylaminobenzene 5.80 g.

A mixture of the above-mentioned 1-chloro-2-methyl-3-methoxycarbonylaminobenzene 5.80 g, phosphorus pentachloride 7.53 g and chlorobenzene 50 mL was stirred with heating under reflux for one hour. The reaction mixtures were concentrated under reduced pressure to give 1-chloro-3-isocyanato-2-methylbenzene.

A mixture of aluminium chloride 4.71 g, sodium azide 6.89 g and tetrahydrofuran 100 mL was stirred with heating under reflux for one hour. After the reaction mixtures were cooled under ice-cooling, thereto were added a mixture of the above-mentioned 1-chloro-3-isocyanato-2-methylbenzene and tetrahydrofuran 10 mL and the resulting mixtures were stirred with heating under reflux for five hours. After cooling the mixtures, to a mixture of sodium nitrite 10.59 g and water 300 mL was added the reaction mixtures with stirring. The mixtures were acidified with concentrated hydrochloric acid and were extracted with ethyl acetate. The organic layers were dried over anhydrous sodium sulfate and were then concentrated under reduced pressure to give 1-(2-methyl-3-chlorophenyl)-1,4-dihydrotetrazole-5-one.

A mixture of the above-mentioned 1-(2-methyl-3-chlorophenyl)-1,4-dihydrotetrazole-5-one, potassium carbonate 16.11 g, dimethyl sulfate 5.34 g and N,N-dimethylformamide 150 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The mixtures were concentrated under reduced pressure to give Intermediate (PRC-P) 4.80 g.

Reference Preparation Example 6

Intermediate (PRE) was prepared according to the following steps (1) to (4).

<Step (1)>

A mixture of 1-bromo-2-methyl-3-aminobenzene 25.0 g, triphosgene 60.0 g and toluene 400 mL was stirred with heating under reflux for three hours. The reaction mixtures after standing to cool were concentrated under reduced pressure to give 1-bromo-3-isocyanato-2-methylbenzene 30.3 g.

1-bromo-3-isocyanato-2-methylbenzene

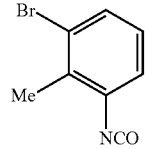

$^1$H NMR (CDCl$_3$) δ: 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

<Step (2)>

Under ice-cooling, to N,N-dimethylformamide 220 mL was added anhydrous aluminum chloride 19.7 g and the resulting mixtures were stirred for fifteen minutes. Thereto was added sodium azide 9.6 g and the resulting mixtures were stirred for fifteen minutes and thereto was then added 1-bromo-3-isocyanato-2-methylbenzene 30.3 g and the resulting mixtures were heated at 80° C. for five hours. After cooling the mixtures, to a mixture of sodium nitrite 33 g, water 2 L and ice 500 g was added the reaction solutions with stirring. The mixtures were acidified with 10% hydrochloric acid and were extracted with ethyl acetate. The organic layers were washed with water and saturated saline, and were dried over anhydrous magnesium sulfate and were then concentrated under reduced pressure to give 1-(2-methyl-3-bromophenyl)-1,4-dihydrotetrazole-5-one 31.4 g.

1-(2-methyl-3-bromophenyl)-1,4-dihydrotetrazole-5-one

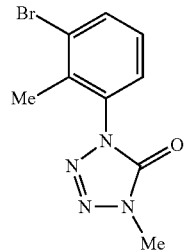 [SMILES: Cc1c(Br)cccc1-n1nnn(C)c1=O]

$^1$H NMR (DMSO-d$_6$) δ: 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

<Step (3)>

To a mixture of the above-mentioned 1-(2-methyl-3-bromophenyl)-1,4-dihydrotetrazole-5-one 31.40 g and N,N-dimethylformamide 250 mL was added 60% sodium hydride 5.90 g under ice-cooling. The mixtures were raised to room temperature and were stirred for one hour. To the reaction mixtures was added methyl iodide 8.4 mL under ice-cooling. The mixtures were raised to room temperature and were stirred for fourteen hours. To the reaction mixtures was added water and the mixtures were extracted with ethyl acetate. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methyl-3-bromophenyl)-4-methyl-1,4-dihydrotetrazole-5-one (hereinafter, referred to as "Intermediate (PRB-P)") 8.47 g.

Intermediate (PRB-P)

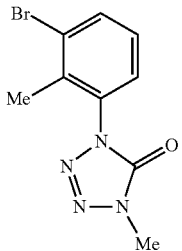 [SMILES: Cc1c(Br)cccc1-n1nnn(C)c1=O]

$^1$H NMR (CDCl$_3$) δ: 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

<Step (4)>

A mixture of the above-mentioned Intermediate (PRB-P) 8.47 g, 1,1'-azobis(cyclohexane-1-carbonitrile) 1.54 g, N-bromosuccinimide 6.44 g and chlorobenzene 125 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give Intermediate (PRB) 7.52 g.

Intermediate (PRB)

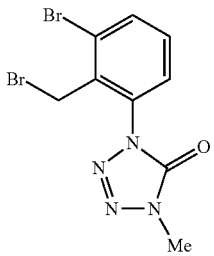 [SMILES: Cn1nnn(-c2cccc(Br)c2CBr)c1=O]

$^1$H NMR (CDCl$_3$) δ: 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Preparation Example 7

A mixture of 3-bromo-2-methy benzoate 146.0 g, oxalyl dichloride 94.8 g, N,N-dimethylformamide about 15 mg and tetrahydrofuran 500 mL was stirred at 25° C. for one hour. The reaction mixtures were concentrated under reduced pressure to give 3-bromo-2-methylbenzoic acid chloride.

A mixture of aluminium chloride 181.0 g, sodium azide 265.0 g and tetrahydrofuran 30.0 mL was stirred with heating under reflux for two hours. After the reaction mixtures were cooled under ice-cooling, and thereto was added a mixture of the above-mentioned 3-bromo-2-methylbenzoic acid chloride and tetrahydrofuran 200 mL and the resulting mixtures were stirred with heating under reflux for ten hours. After cooling the mixtures, to a mixture of sodium nitrite 407 g and water 1,500 mL was added the reaction mixtures with stirring. The mixtures were acidified with concentrated hydrochloric acid and were then extracted with ethyl acetate. The organic layers were dried over anhydrous sodium sulfate and were then concentrated under reduced pressure to give 1-(2-methyl-3-bromophenyl)-1,4-dihydrotetrazole-5-one.

A mixture of the above-mentioned 1-(2-methyl-3-bromophenyl)-1,4-dihydrotetrazole-5-one, potassium carbonate 310.0 g, dimethyl sulfate 103.0 g and N,N-dimethylformamide 500 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give Intermediate (PRB-P) 142.0 g.

Reference Preparation Example 8

A mixture of 3-iodo-2-methy benzoate 10.00 g, oxalyl dichloride 5.33 g, N,N-dimethylformamide about 15 mg and tetrahydrofuran 200 mL was stirred at 25° C. for one hour. The reaction mixtures were concentrated under reduced pressure to give 3-iodo-2-methylbenzoic acid chloride.

A mixture of aluminium chloride 10.20 g, sodium azide 14.90 g and tetrahydrofuran 100 mL was stirred with heating under reflux for two hours. After the reaction mixtures were cooled under ice-cooling, and thereto was added a mixture of the above-mentioned 3-iodo-2-methylbenzoic acid chloride and tetrahydrofuran 100 mL and the resulting mixtures were stirred with heating under reflux for ten hours. After cooling the mixtures, to a mixture of sodium nitrite 22.90 g and water 200 mL was added the reaction mixtures with stirring. The mixtures were acidified with concentrated hydrochloric acid and were then extracted with ethyl acetate. The organic layers were dried over anhydrous sodium sulfate and were then concentrated under reduced pressure to give 1-(2-methyl-3-iodophenyl)-1,4-dihydrotetrazole-5-one.

A mixture of the above-mentioned 1-(2-methyl-3-iodophenyl)-1,4-dihydrotetrazole-5-one, potassium carbonate 17.40 g, dimethyl sulfate 5.78 g and N,N-dimethylformamide 150 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give 1-(2-methyl-3-iodophenyl)-4- methyl-1,4-dihydrotetrazole-5-one (hereinafter, referred to as "Intermediate (PRI-P)") 8.10 g.

Intermediate (PRI-P)

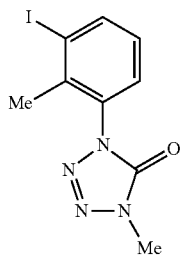

$^1$H NMR (CDCl$_3$) δ: 2.37 (3H, s), 3.72 (3H, s), 7.04 (1H, t, J=8.0 Hz), 7.32 (1H, d, J=7.7 Hz), 7.99 (1H, d, 8.0 Hz).

Reference Preparation Example 9

A mixture of Intermediate (PRI-P) 8.10 g, 1,1'-azobis(cyclohexane-1-carbonitrile) 1.25 g, N-bromosuccinimide 5.24 g and chlorobenzene 100 mL was stirred with heating under reflux for five hours. After cooling the reaction solutions, thereto was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give Intermediate (PRI) 3.11 g.

Intermediate (PRI)

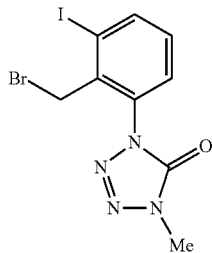

$^1$H NMR (CDCl$_3$) δ: 3.75 (3H, s), 4.71 (2H, s), 7.17 (1H, t, J=8.0 Hz), 7.39 (1H, d, J=8.0 Hz), 8.04 (1H, d, J=8.0 Hz).

Reference Preparation Example 10

Intermediate (PRMT) was prepared according to the following steps (1) to (4).
<Step (1)>

A mixture of 1-methoxy-2-methyl-3-aminobenzene 15.0 g, triphosgene 48.7 g and toluene 350 mL was stirred with heating under reflux for three hours. The reaction mixtures after standing to cool were concentrated under reduced pressure to give 1-methoxy-3-isocyanato-2-methylbenzene 17.0 g.

1-methoxy-3-isocyanato-2-methylbenzene

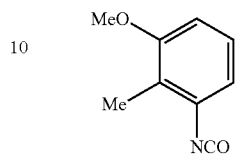

$^1$H NMR (CDCl$_3$) δ: 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).
<Step (2)>

Under ice-cooling, to N,N-dimethylformamide 180 mL was added anhydrous aluminum chloride 16.0 g and the resulting mixtures were stirred for fifteen minutes. Thereto was added sodium azide 7.8 g and the resulting mixtures were stirred for fifteen minutes and thereto was then added 1-methoxy-3-isocyanato-2-methylbenzene 17.0 g and the resulting mixtures were heated at 80° C. for four and a half hours. After cooling the mixtures, to a mixture of sodium nitrite 25 g, water 2 L and ice 500 g was added the reaction solutions with stirring. The mixtures were acidified with 10% hydrochloric acid and were extracted with ethyl acetate. The organic layers were washed with water and saturated saline, and were dried over anhydrous magnesium sulfate and were then concentrated under reduced pressure to give 1-(2-methyl-3-methoxyphenyl)-1,4-dihydrotetrazole-5-one 16.2 g.

1-(2-methyl-3-methoxyphenyl)-1,4-dihydrotetrazole-5-one

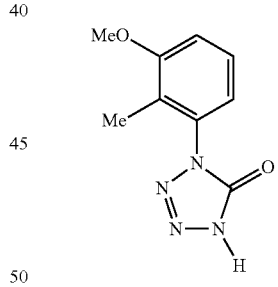

$^1$H NMR (DMSO-d$_6$) δ: 1.99 (3H, s), 3.87 (3H, s), 7.01 (1H, d, J=8.1 Hz), 7.17 (1H, d, J=8.1 Hz), 7.36 (1H, t, J=8.3 Hz), 14.63 (1H, s).
<Step (3)>

To a mixture of the above-mentioned 1-(2-methyl-3-methoxyphenyl)-1,4-dihydrotetrazole-5-one 10.00 g and N,N-dimethylformamide 100 mL was added 55% sodium hydride 2.47 g under ice-cooling. The mixtures were raised to room temperature and were stirred for one hour. To the reaction mixtures was added methyl iodide 3.5 mL under ice-cooling. The mixtures were raised to room temperature and were stirred for fourteen hours. To the reaction mixtures was added water and the mixtures were extracted with ethyl acetate. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methyl-3-methoxyphenyl)-4-methyl-1,4-dihydrotetrazole-5-one 2.19 g.

1-(2-methyl-3-methoxyphenyl)-4-methyl-1,4-dihydrotetrazole-5-one

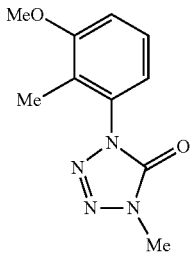 [SMILES: COc1cccc(-n2nnn(C)c2=O)c1C]

$^1$H NMR (CDCl$_3$) δ: 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz).
<Step (4)>
A mixture of the above-mentioned 1-(2-methyl-3-methoxyphenyl)-4-methyl-1,4-dihydrotetrazole-5-one 2.19 g, 1,1'-azobis(cyclohexane-1-carbonitrile) 0.52 g, N-bromosuccinimide 2.16 g and chlorobenzene 40 mL was stirred with heating under reflux for five hours. After cooling the reaction solutions, thereto was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give Intermediate (PRMT) 2.36 g.

Intermediate (PRMT)

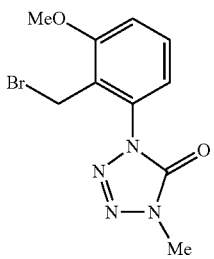 [SMILES: COc1cccc(-n2nnn(C)c2=O)c1CBr]

$^1$H NMR (CDCl$_3$) δ: 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Preparation Example 11

A mixture of the above-mentioned Intermediate (PRB) 45.0 g, sodium methoxide 37.4 g and tetrahydrofuran 60 mL was stirred at 25° C. for three hours. To the reaction mixtures was added aqueous saturated sodium bicarbonate solution and the resulting mixtures were extracted with ethyl acetate. The organic layers were washed with aqueous saturated sodium bicarbonate solution and were dried over anhydrous sodium sulfate. The resulting mixtures were concentrated under reduced pressure to give 1-(2-methoxymethyl-3-bromophenyl)-4-methyl-1,4-dihydrotetrazole-5-one (hereinafter, referred to as "Intermediate (PRB-M)").

Intermediate (PRB-M)

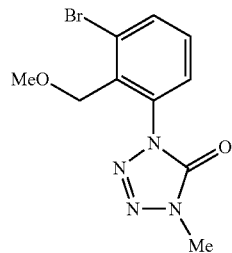

$^1$H NMR (CDCl$_3$) δ: 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).
A mixture of the above-mentioned Intermediate (PRB-M), methylboronic acid 23.2 g, cesium fluoride 66.7 g, [1,1'-bis(diphenylphosphino)ferrocene]palladium(II) dichloride dichloromethane adduct 10.6 g and dioxane 50 mL was stirred at 90° C. for five and a half hours. After cooling the reaction mixtures, the mixtures were filtered and the filtrates were concentrated under reduced pressure. The resulting residues were subjected to a silica gel column chromatography to give 1-(2-methoxymethyl-3-methylphenyl)-4-methyl-1,4-dihydrotetrazole-5-one (hereianfter, referred to as "Intermediate (PRM-M)").

Intermediate (PRM-M)

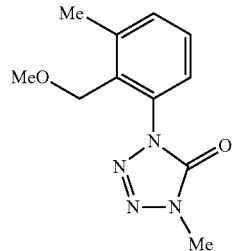 [SMILES: COCc1c(C)cccc1-n1nnn(C)c1=O]

$^1$H NMR (CDCl$_3$) δ: 2.48 (3H, s), 3.23 (3H, s), 3.72 (3H, s), 4.42 (2H, s), 7.21 (1H, t, J=5.1 Hz), 7.35 (2H, d, J=4.8 Hz).
A mixture of the above-mentioned Intermediate (PRM-M), acetic acid 50 mL and 25% hydrogen bromide-acetic acid solution 50 mL was stirred at 65° C. for one hour. To the reaction mixtures was added saturated saline, and the mixtures were extracted with ethyl acetate. The organic layers were washed with aqueous saturated sodium bicarbonate solution and were dried over anhydrous sodium sulfate. The mixtures were concentrated under reduced pressure to give Intermediate (PRM) 27.9 g.

Intermediate (PRM)

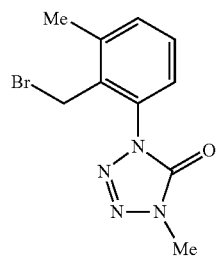 [SMILES: Cc1cccc(-n2nnn(C)c2=O)c1CBr]

¹H NMR (CDCl₃) δ: 2.51 (3H, s), 3.75 (3H, s), 4.51 (2H, s), 7.22-7.24 (1H, m), 7.36-7.39 (2H, m).

Reference Preparation Example 12

A mixture of Intermediate (PRH) 10.00 g, sodium formate 6.32 g, ethanol 400 mL and water 100 mL was stirred with heating under reflux for sixteen hours.

Thereto was added concentrated aqueous ammonia 100 mL and the resulting mixtures were stirred at 25° C. for twenty hours. After standing the reaction solutions to cool, thereto was added water and the resulting mixtures were extracted with ethyl acetate. The organic layers were washed with water and aqueous saturated sodium bicarbonate solution and were dried over anhydrous magnesium sulfate and were then concentrated under reduced pressure. The resulting residues were subjected to a silica gel column chromatography to give Intermediate (PRHO) 3.30 g.

Intermediate (PRHO)

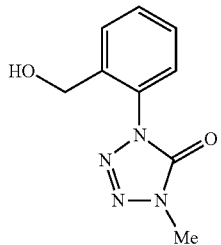 [SMILES: Cn1nnn(-c2ccccc2CO)c1=O]

¹H NMR (CDCl₃) δ: 3.51 (1H, t, J=7.0 Hz), 3.74 (3H, s), 4.53 (2H, d, J=7.0 Hz), 7.42 (1H, d, J=8.0 Hz), 7.48 (1H, t, J=8.0 Hz), 7.53 (1H, t, J=7.5 Hz), 7.64 (1H, d, J=7.5 Hz).

Reference Preparation Example 13

A mixture of potassium ethylxanthate 192.4 g, sodium chloroacetate 139.8 g, water 1.1 L was stirred at 25° C. for eight hours and thereto was then added concentrated aqueous ammonia 100 mL and the resulting mixtures were stirred at 25° C. for twenty hours. The reaction mixtures were extracted with methyl tert-butyl ether and the organic layers were then washed with saturated saline, and were dried over anhydrous sodium sulfate. The resulting mixtures were concentrated under reduced pressure to give O-ethyl thiocarbamates 58.7 g.

O-ethyl thiocarbamates

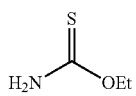

¹H NMR (CDCl₃) δ: 1.34 (3H, t, J=7.0 Hz), 4.49 (2H, q, J=7.0 Hz), 6.01 (1H, s), 6.40 (1H, s).

Reference Preparation Example 14

A mixture of 1-(4-chlorophenyl)-2-bromo-1-ethanone 10.00 g, the above-mentioned O-ethyl thiocarbamates 4.50 g and ethanol 40 mL was stirred with heating under reflux for eleven hours. To the reaction mixtures was added water and the precipitated solids were filtered and were washed with water to give Intermediate (PR03) 8.44 g.

Intermediate (PR03)

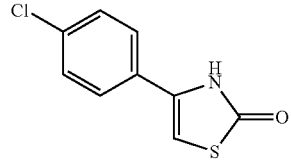

¹H NMR (DMSO-d₆) δ: 6.88 (1H, d, J=1.7 Hz), 7.50 (2H, dt, J=2.0, 8.8 Hz), 7.68 (2H, dt, J=2.2, 8.8 Hz), 11.84 (1H, s).

The following Intermediates (PR02), (PR04) and (PR26) were obtained by a procedure similar to the Reference Preparation example 14.

The physical properties are shown below.

Intermediate (PR02)

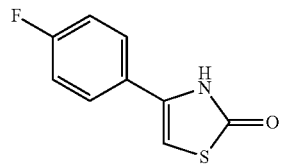

¹H NMR (DMSO-d₆) δ: 6.76 (1H, s), 7.27 (2H, t, J=8.7 Hz), 7.68 (2H, dd, J=5.3, 8.0 Hz), 11.77 (1H, s).

Intermediate (PR04)

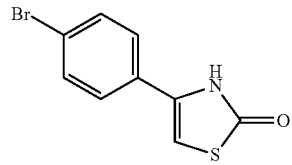

¹H NMR (DMSO-d₆) δ: 6.89 (1H, s), 7.61 (2H, d, J=8.5 Hz), 7.64 (2H, d, J=9.2 Hz), 11.85 (1H, s).

Intermediate (PR26)

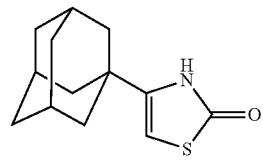 [SMILES: O=c1[nH]c(C23CC4CC(CC(C4)C2)C3)cs1]

¹H NMR (CDCl₃) δ: 1.71-1.79 (6H, m), 1.83 (6H, d, J=2.7 Hz), 2.07 (3H, s), 5.62 (1H, d, J=2.2 Hz), 10.01 (1H, s).

Reference Preparation Example 15

A mixture of 1-(2,3,4,5,6-pentafluorophenyl)-2-bromo-1-ethanone 5.00 g, ammonium thiocyanate 1.58 g and acetonitrile 100 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give 1-(2,3,4,5,6-pentafluorophenyl)-2-thiocyanato-1-ethanone.

The above-mentioned 1-(2,3,4,5,6-pentafluorophenyl)-2-thiocyanato-1-ethanone, 50% sulfuric acid 2 mL and acetic acid 50 mL was stirred with heating under reflux for one hour. After standing the reaction mixtures to cool, the mixtures were concentrated under reduced pressure. The resulting residues were subjected to a silica gel column chromatography to give Intermediate (PR06) 2.50 g.

Intermediate (PR06)

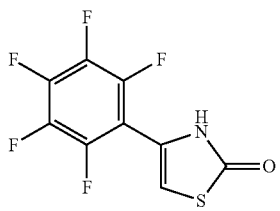 [SMILES: O=c1[nH]c(-c2c(F)c(F)c(F)c(F)c2F)cs1]

$^1$H NMR (DMSO-$d_6$) δ: 6.84 (1H, s), 11.92 (1H, s).

The following Intermediates (PR01), (PR10), (PR11), (PR12), (PR13), (PR16), (PR17), (PR24), (PR25), (PRM04) and (PRM27) were obtained by a procedure similar to the Reference Preparation example 15.

The physical properties are shown below.

Intermediate (PR01)

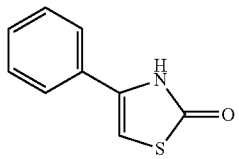 [SMILES: O=c1[nH]c(-c2ccccc2)cs1]

$^1$H NMR (DMSO-$d_6$) δ: 6.80 (1H, d, J=1.7 Hz), 7.35 (1H, tt, J=2.4, 7.3 Hz), 7.42 (2H, t, J=8.0 Hz), 7.64 (2H, d, J=8.5 Hz), 11.77 (1H, s).

Intermediate (PR10)

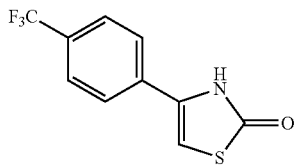

$^1$H NMR (DMSO-$d_6$) δ: 7.00 (1H, s), 7.76 (2H, d, J=8.7 Hz), 7.83 (2H, d, J=8.9 Hz), 11.94 (1H, s).

Intermediate (PR11)

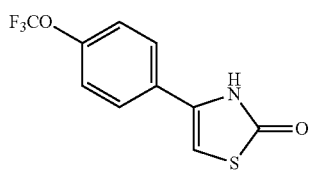 [SMILES: O=c1[nH]c(-c2ccc(OC(F)(F)F)cc2)cs1]

$^1$H NMR (DMSO-$d_6$) δ: 6.89 (1H, s), 7.44 (2H, d, J=8.5 Hz), 7.79 (2H, d, J=8.7 Hz), 11.89 (1H, s).

Intermediate (PR12)

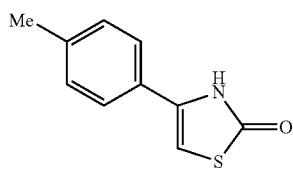 [SMILES: Cc1ccc(-c2csc(=O)[nH]2)cc1]

$^1$H NMR (DMSO-$d_6$) δ: 2.30 (3H, s), 6.69 (1H, s), 7.21 (2H, d, J=8.5 Hz), 7.52 (2H, d, J=8.0 Hz), 11.70 (1H, s).

Intermediate (PR13)

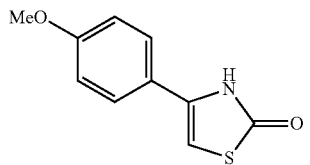 [SMILES: COc1ccc(-c2csc(=O)[nH]2)cc1]

$^1$H NMR (DMSO-$d_6$) δ: 3.76 (3H, s), 6.57 (1H, d, J=1.2 Hz), 6.96 (2H, dt, J=2.2, 8.9 Hz), 7.57 (2H, dt, J=1.9, 8.7 Hz), 11.67 (1H, s).

Intermediate (PR16)

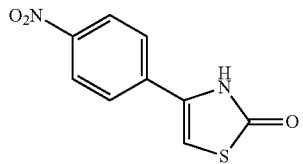 [SMILES: O=c1[nH]c(-c2ccc([N+](=O)[O-])cc2)cs1]

$^1$H NMR (DMSO-$d_6$) δ:
7.23 (1H, d, J=1.9 Hz), 7.93 (2H, dt, J=1.9, 8.7 Hz), 8.28 (2H, dt, J=1.7, 8.7 Hz), 12.06 (1H, s).

Intermediate (PR17)

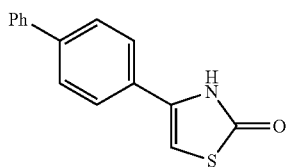

¹H NMR (DMSO-d₆) δ: 6.89 (1H, d, J=1.9 Hz), 7.39 (1H, dt, J=1.0, 7.3 Hz), 7.48 (2H, t, J=8.0 Hz), 7.73 (2H, d, J=8.7 Hz), 7.74 (2H, d, J=7.7 Hz), 7.77 (2H, d, 8.9 Hz), 11.85 (1H, s).

Intermediate (PR24)

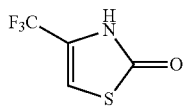

¹H NMR (DMSO-d₆) δ: 6.72 (1H, d, J=1.5 Hz), 10.83 (1H, s).

Intermediate (PR25)

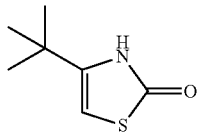

¹H NMR (DMSO-d₆) δ: 1.16 (9H, s), 5.88 (1H, s), 11.18 (1H, s).

Intermediate (PRM04)

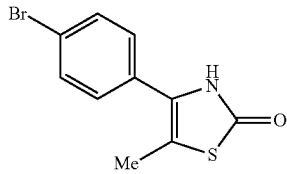 [SMILES: Cc1sc(=O)[nH]c1-c1ccc(Br)cc1]

¹H NMR (DMSO-d₆) δ: 2.11 (3H, s), 7.36 (2H, d, J=8.0 Hz), 7.63 (2H, d, J=7.7 Hz), 11.34 (1H, s).

Intermediate (PRM27)

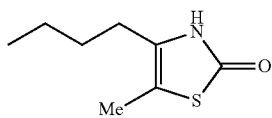

¹H NMR (CDCl₃) δ: 0.92 (3H, t, J=7.2 Hz), 1.32-1.39 (2H, m), 1.42-1.56 (2H, m), 2.01 (3H, s), 2.42 (2H, t, J=7.5 Hz), 9.65 (1H, s).

Reference Preparation Example 16

A mixture of 1-(4-bromo-2-fluorophenyl)ethanone 5.12 g, copper(II) bromide 11.06 g and ethyl acetate 100 mL was stirred with heating under reflux for four hours. After standing the reaction mixtures to cool, the mixtures were filtered and the resulting filtrates were concentrated to give 1-(4-bromo-2-fluorophenyl)-2-bromo-1-ethanone.

A mixture of the above-mentioned 1-(4-bromo-2-fluorophenyl)-2-bromo-1-ethanone, ammonium thiocyanate 2.15 g and acetonitrile 100 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give 1-(4-bromo-2-fluorophenyl)-2-thiocyanato-1-ethanone.

A mixture of the above-mentioned 1-(4-bromo-2-fluorophenyl)-2-thiocyanato-1-ethanone, 50% sulfuric acid 1 mL and acetic acid 100 mL was stirred with heating reflux for one hour. After standing the reaction mixtures to cool, thereto was added water and the precipitated solids were filtered and were washed with water to give Intermediate (PR06) 4.00 g.

Intermediate (PR06)

¹H NMR (DMSO-d₆) δ: 6.77 (1H, s), 7.52 (1H, dd, J=1.9, 8.5 Hz), 7.58 (1H, t, J=8.0 Hz), 7.71 (1H, dd, J=1.7, 10.9 Hz), 11.76 (1H, s).

The following Intermediates (PR05), (PR07), (PR08), (PR14), (PR15), (PR20), (PR21), (PR22) and 4-(4-hydroxyphenyl)-2-oxo-thiazole (hereinafter, referred to as "Intermediate (PR19)") were obtained by a procedure similar to the Reference Preparation example 16.

The physical properties are shown below.

Intermediate (PR05)

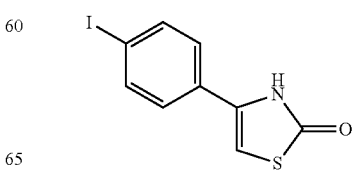

¹H NMR (DMSO-d₆) δ: 6.87 (1H, s), 7.46 (2H, J=8.0 Hz), 7.80 (2H, d, J=7.7 Hz), 11.82 (1H, s).

Intermediate (PR07)

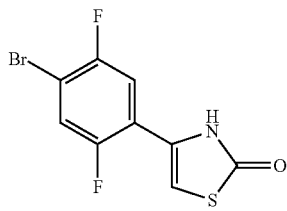 [SMILES: O=c1[nH]c(-c2cc(F)c(Br)cc2F)cs1]

¹H NMR (DMSO-d₆) δ: 6.89 (1H, s), 7.71 (1H, dd, J=6.8, 9.7 Hz), 7.90 (1H, dd, J=6.0, 10.6 Hz), 11.78 (1H, s).

Intermediate (PR08)

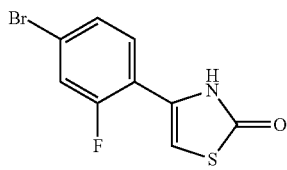 [SMILES: O=c1[nH]c(-c2ccc(Br)cc2F)cs1]

¹H NMR (DMSO-d₆) δ: 7.06 (1H, s), 7.49 (1H, d, J=8.5 Hz), 7.72 (1H, d, J=10.4 Hz), 7.83 (1H, t, J=8.2 Hz), 12.06 (1H, s).

Intermediate (PR14)

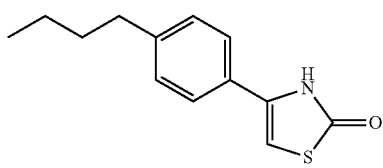 [SMILES: CCCCc1ccc(-c2csc(=O)[nH]2)cc1]

¹H NMR (CDCl₃) δ: 0.93 (3H, t, J=7.3 Hz), 1.31-1.41 (2H, m), 1.57-1.64 (2H, m), 2.63 (2H, t, J=7.8 Hz), 6.25 (1H, d, J=1.7 Hz), 7.25 (2H, d, J=7.8 Hz), 7.46 (2H, d, J=8.1 Hz), 10.95 (1H, s).

Intermediate (PR15)

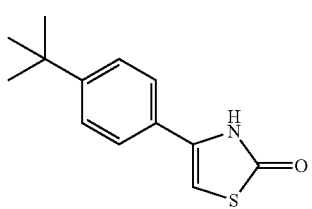 [SMILES: CC(C)(C)c1ccc(-c2csc(=O)[nH]2)cc1]

¹H NMR (DMSO-d₆) δ: 1.28 (9H, s), 6.72 (1H, s), 7.43 (2H, d, J=8.0 Hz), 7.58 (2H, d, J=8.0 Hz), 11.75 (1H, s).

Intermediate (PR20)

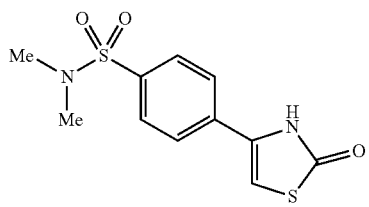 [SMILES: CN(C)S(=O)(=O)c1ccc(-c2csc(=O)[nH]2)cc1]

¹H NMR (DMSO-d₆) δ: 6.23 (6H, s), 7.12 (1H, s), 7.78 (2H, d, J=8.2 Hz), 7.92 (2H, d, J=8.2 Hz), 11.99 (1H, s).

Intermediate (PR21)

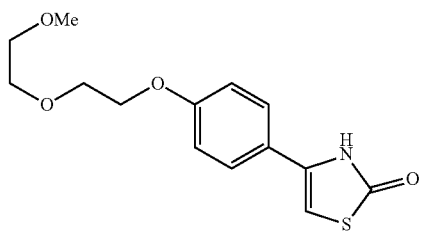 [SMILES: COCCOCCOc1ccc(-c2csc(=O)[nH]2)cc1]

¹H NMR (DMSO-d₆) δ: 3.25 (3H, s), 3.46 (2H, t, J=5.1 Hz), 3.58 (2H, t, J=5.1 Hz), 3.74 (2H, t, J=4.6 Hz), 4.12 (2H, t, J=4.6 Hz), 6.63 (1H, s), 6.99 (2H, d, J=8.5 Hz), 7.58 (2H, d, J=8.7 Hz), 11.68 (1H, s).

Intermediate (PR22)

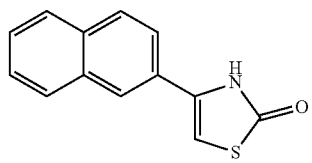 [SMILES: O=c1[nH]c(-c2ccc3ccccc3c2)cs1]

¹H NMR (DMSO-d₆) δ: 6.99 (1H, d, J=1.0 Hz), 7.53-7.59 (2H, m), 7.82 (1H, dd, J=1.2, 8.7 Hz), 7.87-7.94 (2H, m), 7.97 (1H, d, J=8.7 Hz), 8.21 (1H, s), 11.94 (1H, s).

Intermediate (PR19)

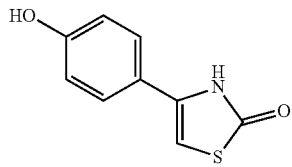 [SMILES: O=c1[nH]c(-c2ccc(O)cc2)cs1]

¹H NMR (DMSO-d₆) δ: 6.51 (1H, s), 6.79 (2H, d, J=8.2 Hz), 7.47 (2H, d, J=8.2 Hz), 9.76 (1H, s), 11.60 (1H, s).

Reference Preparation Example 17

A mixture of Intermediate (PR19) 3.00 g, p-toluenesulfonic acid monohydrate 0.03 g, 3,4-dihydro-2H-pyran 10 mL and dioxane 10 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give Intermediate (PR18) 3.50 g.

Intermediate (PR18)

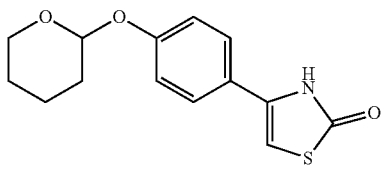 [SMILES: O=c1[nH]c(-c2ccc(OC3CCCCO3)cc2)cs1]

$^1$H NMR (DMSO-d$_6$) δ: 1.54-1.65 (3H, m), 1.70-1.92 (3H, m), 3.54-3.59 (1H, m), 3.71-3.77 (1H, m), 5.23 (1H, t, J=3.4 Hz), 6.63 (1H, d, J=1.0 Hz), 7.06 (2H, d, J=8.2 Hz), 7.58 (2H, d, J=8.2 Hz), 11.69 (1H, s).

Reference Preparation Example 18

To a mixture of 1-(4-chlorophenyl)-2-hydroxy-1-ethanone 6.00 g, N,N-dimethylamide 10 mL and toluene 50 mL was added triphosgene 3.93 g under ice-cooling. After the resulting mixtures were stirred at 0° C. for a half hour, thereto was added concentrated aqueous ammonia 40 mL and the reaction solutions were acidified with concentrated hydrochloric acid. To the reaction mixtures was added saturated saline, and the mixtures were extracted with ethyl acetate. The organic layers were washed with saturated saline, and were dried over anhydrous sodium sulfate. The resulting mixtures were concentrated under reduced pressure to give Intermediate (PRX03) 3.00 g.

Intermediate (PRX03)

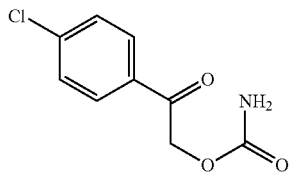 [SMILES: NC(=O)OCC(=O)c1ccc(Cl)cc1]

$^1$H NMR (DMSO-d$_6$) δ: 5.28 (2H, s), 6.64 (1H, s), 6.92 (1H, s), 7.63 (2H, dd, J=0.7, 8.5 Hz), 7.97 (2H, dd, J=1.0, 8.7 Hz).

Reference Preparation Example 19

A mixture of Intermediate (PRM) 28 g, calcium carbonate 40 g, dioxane 300 mL and water 300 mL was stirred with heating under reflux for five hours. After standing the reaction solutions to cool, thereto was added water and the mixtures were extracted with ethyl acetate. The organic layers were washed with water and saturated saline, and were dried over anhydrous sodium sulfate and were then concentrated under reduced pressure to give solids. The resulting solids were washed with hexane to give Intermediate (PRMO) 19 g.

Intermediate (PRMO)

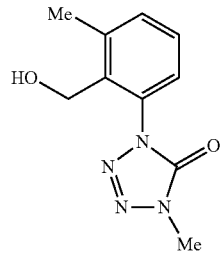 [SMILES: Cc1cccc(-n2nnn(C)c2=O)c1CO]

$^1$H NMR (CDCl$_3$) δ: 2.56 (3H, s), 3.75 (3H, s), 3.76 (1H, t, J=7.10 Hz), 4.48 (2H, d, J=7.10 Hz), 7.19-7.23 (1H, m), 7.34-7.40 (2H, m).

Reference Preparation Example 20

A mixture of Intermediate (PRM-M) described in Reference Preparation example 11 30.1 g, cyclopropylboronic acid 12.9 g, cesium fluoride 46.2 g, [1,1'-bis(diphenylphosphino)ferrocene]palladium(II) dichloride dichloromethane adduct 8.2 g and dioxane 680 mL was stirred at 90° C. for four hours. After cooling the reaction mixtures, the mixtures were filtered and the filtrates were concentrated under reduced pressure. The resulting residues were subjected to a silica gel column chromatography to give 1-(2-methoxymethyl-3-cyclopropylphenyl)-4-methyl-1,4-dihydrotetrazole-5-one 26.0 g.

1-(2-methoxymethyl-3-cyclopropylphenyl)-4-methyl-1,4-dihydrotetrazole-5-one

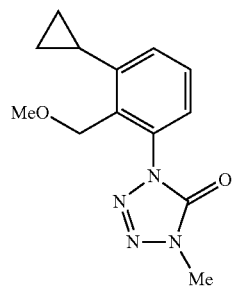 [SMILES: COCc1c(C2CC2)cccc1-n1nnn(C)c1=O]

$^1$H NMR (CDCl$_3$) δ(ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Preparation Example 21

A mixture of 1-(2-methoxymethyl-3-cyclopropylphenyl)-4-methyl-1,4-dihydrotetrazole-5-one described in Reference Preparation example 20 26.0 g, acetic acid 40 mL and 25% hydrogen bromide-acetic acid solution 40 mL was stirred at 65° C. for two hours. To the reaction mixtures was added saturated saline, and the mixtures were extracted with ethyl acetate. The organic layers were washed with aqueous saturated sodium bicarbonate solution and were dried over anhydrous sodium sulfate. The resulting mixtures were concentrated under reduced pressure to give Intermediate (PRCP) 30.8 g.

Intermediate (PRCP)

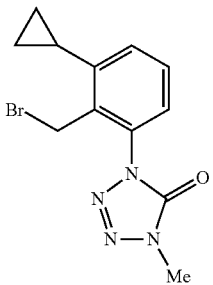

$^1$H NMR (CDCl$_3$) δ(ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Preparation Example 22

A mixture of Intermediate (PRM-M) described in Reference Preparation example 11 29.8 g, tributyl vinyl tin 35.2 g, tetrakistriphenylphosphine palladium 11.6 g and toluene 500 mL was stirred with heating under reflux for fourteen hours. After cooling the reaction solutions, thereto was added saturated aqueous ammonium chloride solution and the resulting mixtures were extracted with ethyl acetate. The organic layers were washed with water and saturated saline, and dried over anhydrous magnesium sulfate and were then concentrated under reduced pressure. The resulting residues were subjected to a silica gel column chromatography to give 1-(2-methoxymethyl-3-ethenylphenyl)-4-methyl-1,4-dihydrotetrazole-5-one 19.7 g.

1-(2-methoxymethyl-3-ethenylphenyl)-4-methyl-1,4-dihydrotetrazole-5-one

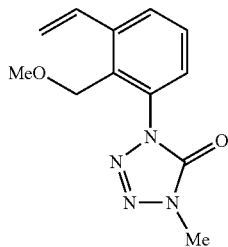 [SMILES: C=Cc1cccc(-n2nnn(C)c2=O)c1COC]

$^1$H NMR (CDCl$_3$) δ(ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

Reference Preparation Example 23

A mixture of 1-(2-methoxymethyl-3-ethenylphenyl)-4-methyl-1,4-dihydrotetrazole-5-one described in Reference Preparation example 22 19.7 g, palladium fibroin complex 3.02 g and methanol 1 L was stirred at room temperature under hydrogen atmosphere for eleven hours. The reaction mixtures were filtered and the filtrates were concentrated under reduced pressure. The resulting residues were subjected to a silica gel column chromatography to give 1-(2-methoxymethyl-3-ethylphenyl)-4-methyl-1,4-dihydrotetrazole-5-one 19.3 g.

1-(2-methoxymethyl-3-ethylphenyl)-4-methyl-1,4-dihydrotetrazole-5-one

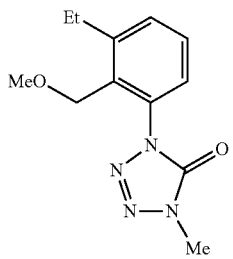 [SMILES: CCc1cccc(-n2nnn(C)c2=O)c1COC]

$^1$H NMR (CDCl$_3$) δ(ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

Reference Preparation Example 24

A mixture of 1-(2-methoxymethyl-3-ethylphenyl)-4-methyl-1,4-dihydrotetrazole-5-one described in Reference Preparation example 23 19.3 g, acetic acid 40 mL and 25% hydrogen bromide-acetic acid solution 40 mL was stirred at 65° C. for one and a half hours. To the reaction mixtures was added saturated saline, and the mixtures were extracted with ethyl acetate. The organic layers were washed with aqueous saturated sodium bicarbonate solution and were dried over anhydrous sodium sulfate. The resulting mixtures were concentrated under reduced pressure to give Intermediate (PRE) 23.3 g.

Intermediate (PRE)

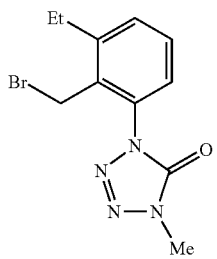 [SMILES: CCc1cccc(-n2nnn(C)c2=O)c1CBr]

$^1$H NMR (CDCl$_3$) δ(ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Preparation Example 25

A mixture of 2-methyl-3-nitrophenol 33.5 g, iodoethane 41 g and potassium carbonate 90 g in acetone 400 mL was stirred with heating under reflux for ten hours. The mixtures were cooled to room temperature and filtered and the resulting filtrates were concentrated. The resulting mixtures were extracted with ethyl acetate and the organic layers were washed with water and saturated saline, and were dried over anhydrous magnesium sulfate and were then concentrated under reduced pressure. The resulting residues were subjected to a silica gel column chromatography to give 1-ethoxy-2-methyl-3-nitrobenzene 39.9 g.

1-ethoxy-2-methyl-3-nitrobenzene

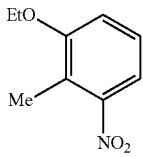

¹H NMR (CDCl₃) δ (ppm): 7.39 (1H, dd, J=8.2, 1.0 Hz), 7.24 (1H, t, J=8.3 Hz), 7.02 (1H, d, J=8.2 Hz), 4.08 (2H, q, J=7.0 Hz), 2.37 (3H, s), 1.50-1.42 (3H, m).

Reference Preparation Example 26

A mixture of 1-ethoxy-2-methyl-3-nitrobenzene described in Reference Preparation example 2539.9 g, palladium-carbon (palladium 5%) 4 g and ethanol 200 mL was stirred at room temperature under hydrogen atmosphere for eighteen hours. The mixtures were filtered and the filtrates were concentrated to give 3-ethoxy-2-methylaniline 33.0 g.

3-ethoxy-2-methylaniline

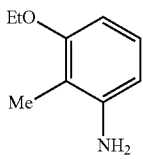

¹H NMR (CDCl₃) δ(ppm): 6.95 (1H, t, J=8.1 Hz), 6.35 (1H, d, J=2.9 Hz), 6.33 (1H, d, J=3.1 Hz), 4.02-3.97 (2H, m), 3.61 (2H, brs), 2.05 (3H, s), 1.40 (3H, t, J=7.1 Hz).

Reference Preparation Example 27

At room temperature, to a mixture of 3-ethoxy-2-methylaniline 33.0 g and toluene 400 mL was added triphosgene 25 g, and the resulting mixtures were stirred with heating reflux for four hours. The mixtures were concentrated under reduced pressure to give 1-ethoxy-3-isocyanato-2-methylbenzene 37.2 g.

1-ethoxy-3-isocyanato-2-methylbenzene

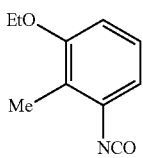

¹H NMR (CDCl₃) δ(ppm): 7.07 (1H, t, J=8.2 Hz), 6.70 (1H, d, J=7.7 Hz), 6.68 (1H, d, J=8.2 Hz), 4.02 (2H, q, J=7.0 Hz), 2.20 (3H, s), 1.42 (3H, t, J=7.0 Hz).

Reference Preparation Example 28

Under ice-cooling, to a mixture of N,N-dimethylformamide 350 mL and anhydrous aluminum chloride 33.6 g was added sodium azide 15 g, and the resulting mixtures were stirred for one hour. Thereto was thereafter added 1-ethoxy-3-isocyanato-2-methylbenzene described in Reference Preparation example 2737.2 g and the resulting mixtures were heated to 75° C. and were stirred for five hours. The mixtures were cooled and under ice-cooling, to the reaction mixtures was added ice water 100 mL, followed by addition of a mixture of sodium nitrite 23 g and water 150 mL, and the mixtures were acidified with concentrated hydrochloric acid to pH about 4. The mixtures were extracted with ethyl acetate and the organic layers were washed with water and saturated saline, and were dried over anhydrous magnesium sulfate and were then concentrated under reduced pressure. The resulting residues were subjected to a silica gel column chromatography to give 1-(2-methyl-3-ethoxyphenyl)-1,4-dihydrotetrazole-5-one 39.0 g.

1-(2-methyl-3-ethoxyphenyl)-1,4-dihydrotetrazole-5-one

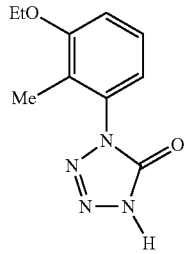 [SMILES: CCOc1cccc(-n2nn[nH]c2=O)c1C]

¹H NMR (CDCl₃) δ(ppm): 7.30 (1H, t, J=8.1 Hz), 6.99 (1H, d, J=8.5 Hz), 6.96 (1H, d, J=8.0 Hz), 4.10 (2H, q, J=6.9 Hz), 2.13 (3H, s), 1.46 (3H, t, J=7.0 Hz).

Reference Preparation Example 29

Under ice-cooling, to a mixture of 1-(2-methyl-3-ethoxyphenyl)-1,4-dihydrotetrazole-5-one 39.0 g, potassium carbonate 36.7 g and N,N-dimethylformamide 400 mL was added dimethyl sulfate 44.7 g and the resulting mixtures were raised to room temperature and were stirred for seven hours. Thereto was added water and the mixtures were extracted with ethyl acetate and the organic layers were washed with water and saturated saline, and were dried over anhydrous magnesium sulfate and were then concentrated under reduced pressure. The resulting residues were subjected to a silica gel column chromatography to give 1-(2-methyl-3-ethoxyphenyl)-4-methyl-1,4-dihydrotetrazole-5-one 38.2 g.

1-(2-methyl-3-ethoxyphenyl)-4-methyl-1,4-dihydrotetrazole-5-one

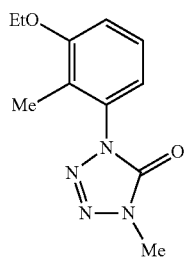 [SMILES: CCOc1cccc(-n2nnn(C)c2=O)c1C]

$^1$H NMR (CDCl$_3$) δ(ppm): 7.29-7.23 (1H, m), 6.96 (1H, d, J=8.2 Hz), 6.93 (1H, d, J=8.2 Hz), 4.08 (2H, q, J=6.9 Hz), 3.72 (3H, s), 2.11 (3H, s), 1.45 (3H, t, J=7.1 Hz).

Reference Preparation Example 30

A mixture of 1-(2-methyl-3-ethoxyphenyl)-4-methyl-1,4-dihydrotetrazole-5-one described in Reference Preparation example 29 38.2 g, 1,1'-azobis(cyclohexane-1-carbonitrile) 7.95 g, N-bromosuccinimide 33.4 g and chlorobenzene 380 mL was stirred with heating under reflux for five hours. After cooling the reaction solutions, thereto was added water and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give Intermediate (PREO) 38.2 g.

Intermediate (PREO)

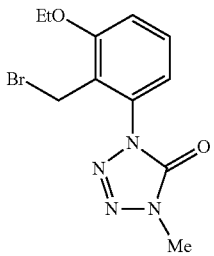 [SMILES: CCOc1cccc(-n2nnn(C)c2=O)c1CBr]

$^1$H NMR (CDCl$_3$) δ(ppm): 7.40 (1H, t, J=8.2 Hz), 7.01 (2H, t, J=8.3 Hz), 4.64 (2H, s), 4.17 (2H, q, J=7.0 Hz), 3.74 (3H, s), 1.49 (3H, t, J=6.9 Hz).

Reference Preparation Example 31

A mixture of 3-trifluoromethyl-2-methylbenzoic acid 5.00 g, oxalyl dichloride 3.42 g, N,N-dimethylformamide about 50 mg and tetrahydrofuran 200 mL was stirred at 25° C. for one hour. The reaction mixtures were concentrated under reduced pressure to give 3-trifluoromethyl-2-methylbenzoic acid chloride.

A mixture of aluminium chloride 6.53 g, sodium azide 9.55 g and tetrahydrofuran 100 mL was stirred with heating under reflux for two hours. The reaction mixtures were cooled under ice-cooling and thereto were added 3-trifluoromethyl-2-methylbenzoic acid chloride and tetrahydrofuran 100 mL and the mixtures were stirred with heating under reflux for ten hours. After cooling the mixtures, to a mixture of sodium nitrite 14.7 g and water 200 mL was added the reaction mixtures with stirring. The mixtures were acidified with concentrated hydrochloric acid and were then extracted with ethyl acetate. The organic layers were dried over anhydrous sodium sulfate and the resulting mixtures were then concentrated under reduced pressure to give 1-(2-methyl-3-trifluoromethylphenyl)-1,4-dihydrotetrazole-5-one.

A mixture of 1-(2-methyl-3-trifluoromethylphenyl)-1,4-dihydrotetrazole-5-one, potassium carbonate 11.20 g, dimethyl sulfate 3.71 g and N,N-dimethylformamide 150 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give 1-(2-methyl-3-trifluoromethylphenyl)-4-methyl-1,4-dihydrotetrazole-5-one 5.13 g.

1-(2-methyl-3-trifluoromethylphenyl)-4-methyl-1,4-dihydrotetrazole-5-one

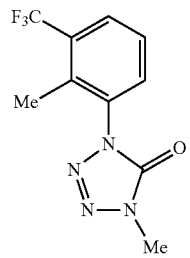

$^1$H NMR (CDCl$_3$) δ(ppm): 2.42 (3H, s), 3.75 (3H, s), 7.52 (1H, t, J=8.2 Hz), 7.62 (1H, dd, J=1.2, 7.7 Hz), 8.02 (1H, dd, J=1.2, 8.2 Hz).

Reference Preparation Example 32

A mixture of 1-(2-methyl-3-trifluoromethylphenyl)-4-methyl-1,4-dihydrotetrazole-5-one 1.00 g, 1,1'-azobis(cyclohexane-1-carbonitrile) 0.38 g, N-bromosuccinimide 0.79 g and chlorobenzene 30 mL was stirred with heating under reflux for five hours. After cooling the reaction solutions, thereto was added water, and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give Intermediate (PRTF) 1.21 g.

Intermediate (PRTF)

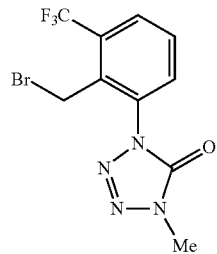 [SMILES: Cn1nnn(-c2cccc(C(F)(F)F)c2CBr)c1=O]

$^1$H NMR (CDCl$_3$) δ(ppm): 3.77 (3H, s), 4.75 (2H, s), 7.62 (1H, d, J=5.5 Hz), 7.63 (1H, d, J=3.4 Hz), 7.85 (1H, dd, J=3.6, 5.8 Hz).

Reference Preparation Example 33

A mixture of 2'-bromoacetophenone 1.99 toluenesulfonic acid monohydrate 0.19 g and N-bromosuccinimide 1.87 g was stirred at room temperature for four hours. To the reaction solutions was added water and the mixtures were extracted with methyl tert-butyl ether. The organic layers were washed with aqueous saturated sodium bicarbonate solution and saturated saline, and were dried over anhydrous magnesium sulfate and were then concentrated under reduced pressure. A mixture of the resulting residues, O-ethyl thiocarbamates 1.05 g and ethanol 20 mL was stirred with heating under reflux for four hours. After standing the mixtures to cool, thereto was added water. The precipitated solids were filtered off and the solids were washed with water and hexane to give Intermediate (PR30) 1.86 g.

Intermediate (PR30)

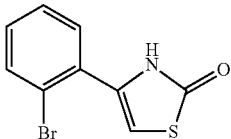 [SMILES: O=c1[nH]c(-c2ccccc2Br)cs1]

¹H NMR (CDCl₃) δ(ppm): 6.27 (1H, d, J=1.8 Hz), 7.25-7.31 (1H, m), 7.36-7.44 (2H, m), 7.66 (1H, dd, J=8.0, 0.9 Hz), 9.09 (1H, brs).

The following Intermediates (PR28), Intermediates (PR29) and 3-(3-bromophenyl)-2-oxo-thiazole were obtained by a procedure similar to Reference Preparation example 33.

The physical properties are shown below.

Intermediate (PR28)

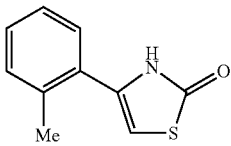

¹H NMR (CDCl₃) δ(ppm): 2.42 (3H, s), 6.01 (1H, d, J=1.8 Hz), 7.24-7.34 (4H, m), 10.03 (1H, brs).

Intermediate (PR29)

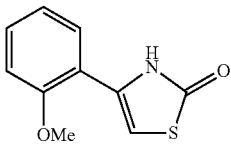 [SMILES: COc1ccccc1-c1csc(=O)[nH]1]

¹H NMR (CDCl₃) δ(ppm): 3.93 (3H, s), 6.35 (1H, d, J=2.1 Hz), 6.99 (1H, d, J=8.5 Hz), 7.03 (1H, td, J=7.6, 1.0 Hz), 7.35 (1H, ddd, J=8.5, 7.7, 1.8 Hz), 7.50 (1H, dd, J=7.7, 1.8 Hz), 9.42 (1H, brs).

3-(3-bromophenyl)-2-oxo-thiazole

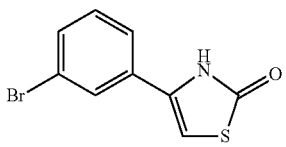

¹H NMR (CDCl₃) δ(ppm): 6.35 (1H, d, J=1.5 Hz), 7.33 (1H, t, J=8.0 Hz), 7.47 (1H, d, J=8.0 Hz), 7.50 (1H, dt, J=8.0, 0.7 Hz), 7.68 (1H, d, J=1.2 Hz), 10.52 (1H, brs).

Reference Preparation Example 34

A mixture of 3-(3-bromophenyl)-2-oxo-thiazole 7.68 g and phosphoryl chloride 20 mL was stirred with heating under reflux for three hours. After standing the mixtures to cool, the mixtures were added to water with stirring. The mixtures were extracted with t-butyl methyl ether. The organic layers were washed with water and saturated saline, and were dried over anhydrous magnesium sulfate and were then concentrated under reduced pressure to give Intermediate (PR32C) 7.84 g.

Intermediate (PR32C)

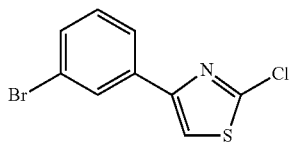

¹H NMR (CDCl₃) δ(ppm): 7.29 (1H, t, J=7.9 Hz), 7.39 (1H, s), 7.48 (1H, ddd, J=7.9, 1.9, 1.0 Hz), 7.78-7.75 (1H, m), 8.02 (1H, t, J=1.8 Hz).

Reference Preparation Example 35

A mixture of 3'-hydroxyacetophenone 6.1 g, copper(II) bromide 17.0 g and ethyl acetate 40 mL was stirred with heating under reflux for five hours. After standing the reaction solutions to cool, the solutions were subjected to a short path silica gel column chromatography. The solvents were distilled away from the resulting solutions to give the residues. A mixture of the resulting residues, O-ethyl thioncarbamates 4.71 g and ethanol 50 mL was stirred with heating under reflux for four hours. After standing the mixtures to cool, thereto was added water. The precipitated solids were filtered off and the solids were washed with a mixed solvent of methyl tert-butyl ether and hexane to give 3-(3-hydroxyphenyl)-2-oxo-thiazole 5.32 g.

3-(3-hydroxyphenyl)-2-oxo-thiazole

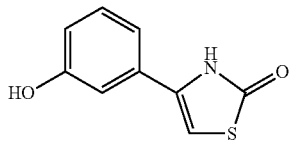 [SMILES: O=c1[nH]c(-c2cccc(Br)c2)cs1]

¹H NMR (DMSO-d₆) δ(ppm): 6.69 (1H, d, J=1.9 Hz), 6.77 (1H, ddd, J=8.0, 1.9, 0.9 Hz), 7.01 (1H, brs), 7.06 (1H, dd, J=8.0, 0.9 Hz), 7.21 (1H, t, J=8.0 Hz), 9.61 (1H, s), 11.67 (1H, s).

Reference Preparation Example 36

A mixture of the above-mentioned 3-(3-hydroxyphenyl)-2-oxo-thiazole 1.00 g, p-toluenesulfonic acid monohydrate 0.1 g, 3,4-dihydro-2H-pyran 5 mL and dioxane 5 mL was stirred at 25° C. for two hours. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure and the resulting residues were subjected to a silica gel column chromatography. The resulting residues were recrystallized from a mixed solvent of hexane and t-butyl methyl ether to give Intermediate (PR31) 0.75 g.

Intermediate (PR31)

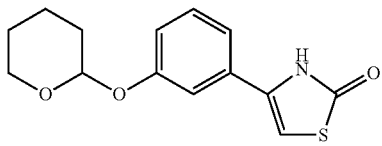 [SMILES: O=c1[nH]c(-c2cccc(OC3CCCCO3)c2)cs1]

$^1$H NMR (CDCl$_3$) δ(ppm):
1.50-1.76 (4H, brm), 1.86-1.91 (2H, m), 3.62-3.68 (1H, m), 3.88-3.94 (1H, m), 5.50 (1H, t, J=3.2 Hz), 6.29 (1H, d, J=1.8 Hz), 7.06 (1H, ddd, J=8.3, 2.4, 0.7 Hz), 7.14 (1H, ddd, J=7.8, 1.6, 0.9 Hz), 7.22 (1H, t, J=2.0 Hz), 7.34 (1H, t, J=8.0 Hz), 10.42 (1H, brs).

Reference Preparation Example 37

A mixture of Intermediate (PR29) 0.40 g, Lawesson's reagent (2,4-Bis(4-methoxyphenyl)-1,3,4-dithiadiphoshetane-2,4-disulfide) 2.34 g and toluene 20 mL were stirred with heating under reflux for twelve hours and were concentrated under reduced pressure. The resulting residues were subjected to a silica gel column chromatography to give Intermediate (PR29S) 0.23 g.

Intermediate (PR29S)

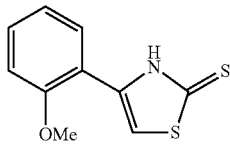 [SMILES: COc1ccccc1-c1csc(=S)[nH]1]

$^1$H NMR (CDCl$_3$) δ(ppm): 3.98 (3H, s), 6.77 (1H, s), 7.03 (1H, d, J=8.2 Hz), 7.06 (1H, t, J=7.6 Hz), 7.40 (1H, ddd, J=8.2, 7.6, 1.5 Hz), 7.51 (1H, dd, J=7.6, 1.5 Hz), 10.86 (1H, brs).

Reference Preparation Example 38

A mixture of Intermediate (PRB-P) 1.0 g, potassium ferrocyanide 0.34 g, [1,1'-bis(diphenylphosphino)ferrocene]palladium(II) dichloride dichloromethane adduct 0.15 g, sodium carbonate 0.39 g and N,N-dimethylformamide 5 mL was stirred at 130° C. for fifteen hours. To the reaction mixtures after standing to cool was added water and the mixtures were extracted with ethyl acetate. The organic layers were washed with aqueous saturated sodium bicarbonate solution and saturated saline, and were dried over anhydrous magnesium sulfate and were then concentrated under reduced pressure. The resulting residues were subjected to a silica gel column chromatography to give 1-(3-cyano-2-methylphenyl)-4-methyl-1,4-dihydrotetrazole-5-one 0.35 g.

1-(3-cyano-2-methylphenyl)-4-methyl-1,4-dihydrotetrazole-5-one

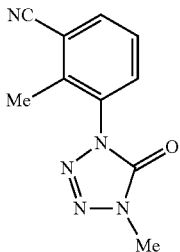 [SMILES: Cc1c(C#N)cccc1-n1nnn(C)c1=O]

$^1$H NMR (CDCl$_3$) δ(ppm): 2.52 (3H, s), 3.74 (3H, s), 7.47 (1H, t, J=7.8 Hz), 7.61 (1H, d, J=8.0 Hz), 7.78 (1H, d, J=7.7 Hz).

Reference Preparation Example 39

A mixture of 1-(3-cyano-2-methylphenyl)-4-methyl-1,4-dihydrotetrazole-5-one described in Reference Preparation example 380.25 g, N-bromosuccinimide 0.24 g, 1,1'-azobis(cyclohexane-1-carbonitrile) 0.11 g. and chlorobenzene 10 mL was stirred at 20° C. for three hours.

After cooling the reaction solutions, thereto was added water and the mixtures were extracted with ethyl acetate. The organic layers were washed with water and saturated saline, and dried over anhydrous magnesium sulfate and were then concentrated under reduced pressure to give residues. The resulting residues were subjected to a silica gel column chromatography to give Intermediate (PRCN) 0.14 g.

Intermediate (PRCN)

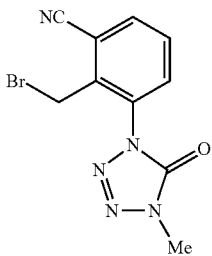 [SMILES: Cn1nnn(-c2cccc(C#N)c2CBr)c1=O]

$^1$H NMR (CDCl$_3$) δ(ppm): 3.76 (3H, s), 4.81 (2H, s), 7.62 (1H, t, J=7.9 Hz), 7.72 (1H, dd, J=7.9, 1.3 Hz), 7.83 (1H, dd, J=7.9, 1.3 Hz).

Reference Preparation Example 40

In Reference Preparation example 2,1-fluoro-3-isocyanato-4-methylbenzene was used instead of 1-fluoro-3-isocyanato-2-methylbenzene of the <step (1)> to give 1-(5-fluoro-2-methylphenyl)-1,4-dihydrotetrazole-5-one, and further, in Reference Preparation example 2,1-(5-fluoro-2-methylphenyl)-1,4-dihydrotetrazole-5-one was used instead of 1-(2-methyl-3-fluorophenyl)-1,4-dihydrotetrazole-5-one of the <step (2)> to give 1-(5-fluoro-2-methylphenyl)-4-methyl-1,4-dihydrotetrazole-5-one.

The physical properties are shown below.

1-(5-fluoro-2-methylphenyl)-4-methyl-1,4-dihydrotetrazole-5-one

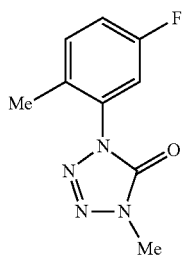 [SMILES: Cc1ccc(F)cc1-n1nnn(C)c1=O]

$^1$H NMR (DMSO-d$_6$) δ(ppm): 2.19 (3H, s), 3.63 (3H, s), 7.34-7.42 (2H, m), 7.51 (1H, dd, J=8.4, 6.2 Hz).

Reference Preparation Example 41

In Reference Preparation example 2,1-(5-fluoro-2-methylphenyl)-4-methyl-1,4-dihydrotetrazole-5-one described in Reference Preparation example 40 was used instead of 1-(2-methyl-3-fluorophenyl)-4-methyl-1,4-dihydrotetrazole-5-one of the <step (3)> to give Intermediate (PRF5).

The physical properties are shown below.

Intermediate (PRF5)

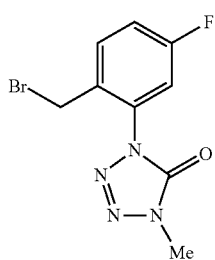 [SMILES: Cn1nnn(-c2cc(F)ccc2CBr)c1=O]

$^1$H NMR (CDCl$_3$) δ(ppm): 3.75 (3H, s), 4.59 (2H, s), 7.28-7.10 (2H, m), 7.53 (1H, dd, J=8.7, 5.7 Hz).

Reference Preparation Example 42

In Reference Preparation example 6,4-fluoro-2-methyl-1-aminobenzene was used instead of 1-bromo-2-methyl-3-aminobenzene of the <step (1)> to give 1-fluoro-4-isocyanato-3-methylbenzene and further, in Reference Preparation example 2,1-fluoro-4-isocyanato-3-methylbenzene was used instead of 1-fluoro-3-isocyanato-2-methylbenzene of the <step (1)> to give 1-(4-fluoro-2-methylphenyl)-1,4-dihydrotetrazole-5-one and furthermore, in Reference Preparation example 2,1-(4-fluoro-2-methylphenyl)-1,4-dihydrotetrazole-5-one was used instead of 1-(2-methyl-3-fluorophenyl)-1,4-dihydrotetrazole-5-one of the <step (2)> to give 1-(4-fluoro-2-methylphenyl)-4-methyl-1,4-dihydrotetrazole-5-one.

The physical properties are shown below.

Intermediate (PRF5)

1-(4-fluoro-2-methylphenyl)-4-methyl-1,4-dihydrotetrazole-5-one

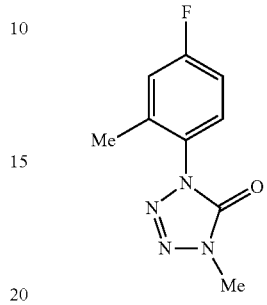

$^1$H NMR (CDCl$_3$) δ(ppm): 2.27 (3H, s), 3.72 (3H, s), 7.15-7.10 (2H, m), 7.34-7.30 (1H, m).

Reference Preparation Example 43

In Reference Preparation example 2, 1-(4-fluoro-2-methylphenyl)-4-methyl-1,4-dihydrotetrazole-5-one described in Reference Preparation example 42 was used instead of 1-(2-methyl-3-fluorophenyl)-4-methyl-1,4-dihydrotetrazole-5-one of the <step (3)> to give Intermediate (PRF4).

The physical properties are shown below.

Intermediate (PRF4)

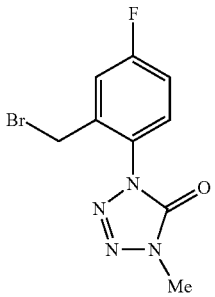 [SMILES: Cn1nnn(-c2ccc(F)cc2CBr)c1=O]

$^1$H NMR (CDCl$_3$) δ(ppm): 3.74 (3H, s), 4.51 (2H, s), 7.08-7.02 (1H, m), 7.45-7.41 (1H, m), 7.20-7.15 (1H, m).

Reference Preparation Example 44

In Reference Preparation example 6,2-fluoro-6-methyl-1-aminobenzene was used instead of 1-bromo-2-methyl-3-aminobenzene of <step (1)> to give 1-fluoro-2-isocyanato-3-methylbenzene and further, in Reference Preparation example 2,1-fluoro-2-isocyanato-3-methylbenzene was used instead of 1-fluoro-3-isocyanato-2-methylbenzene of the <step (1)> to give 1-(2-fluoro-6-methylphenyl)-1,4-dihydrotetrazole-5-one, and furthermore, in Reference Preparation example 2,1-(2-fluoro-6-methylphenyl)-1,4-dihydrotetrazole-5-one was used instead of 1-(2-methyl-3-fluorophenyl)-1,4-dihydrotetrazole-5-one of the <step (2)> to give 1-(2-fluoro-6-methylphenyl)-4-methyl-1,4-dihydrotetrazole-5-one.

The physical properties are shown below.

1-(2-fluoro-6-methylphenyl)-4-methyl-1,4-dihydrotetrazole-5-one

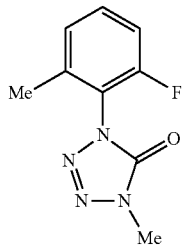 [SMILES: Cc1cccc(F)c1-n1nnn(C)c1=O]

$^1$H NMR (CDCl$_3$) δ(ppm): 2.26 (3H, s), 3.73 (3H, s), 7.10 (1H, t, J=8.8 Hz), 7.15 (1H, d, J=8.0 Hz), 7.40 (1H, td, J=8.0, 5.6 Hz).

Reference Preparation Example 45

In Reference Preparation example 2,1-(2-fluoro-6-methylphenyl)-4-methyl-1,4-dihydrotetrazole-5-one described in Reference Preparation example 44 was used instead of 1-(2-methyl-3-fluorophenyl)-4-methyl-1,4-dihydrotetrazole-5-one of the <step (3)> to give Intermediate (PRF6).

The physical properties are shown below.

Intermediate (PRF6)

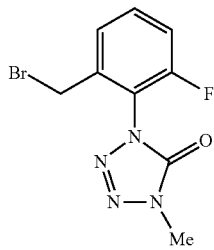 [SMILES: Cn1nnn(-c2c(F)cccc2CBr)c1=O]

$^1$H NMR (CDCl$_3$) δ(ppm): 3.76 (3H, s), 4.46 (2H, s), 7.23-7.29 (1H, m), 7.35 (1H, d, J=7.8 Hz), 7.50 (1H, td, J=7.8, 5.3 Hz).

According to the above-mentioned processes, the following compounds can be prepared:
Compounds AA-001~AA-379, AC-001~AC-379, AD-001~AD-379, AE-001~AE-379, AF-001~AF-379, AG-001~AG-379, AH-001~AH-379, AI-001~AI-379, AJ-001~AJ-379, AK-001~AK-379, AL-001~AL-379, AM-001~AM-379, AN-001~AN-379, AO-001~AO-379, AP-001~AP-379, AQ-001~AQ-379, AR-001~AR-379, AS-001~AS-379, AT-001~AT-379, AU-001~AU-379, AV-001~AV-379, AW-001~AW-379, AX-001~AX-379, AY-001~AY-379, AZ-001~AZ-379, AAA-001~AAA-379, AAB-001~AAB-379, AAC-001~AAC-379, AAD-001~AAD-379, AAE-001~AAE-379, AAF-001~AAF-379, AAG-001~AAG-379, AAH-001~AAH-379, AAI-001~AAI-379, AAJ-001~AAJ-379, AAK-001~AAK-379, AAL-001~AAL-379, AAM-001~AAM-379, AAN-001~AAN-379, AAO-001~AAO-379, AAP-001~AAP-379, AAQ-001~AAQ-379, AAR-001~AAR-379, AAS-001~AAS-379, AAT-001~AAT-379, AAU-001~AAU-379, AAV-001~AAV-379, AAW-001~AAW-379, AAX-001~AAX-379, AAY-001~AAY-379, AAZ-001~AAZ-379, ABA-001~ABA-379, ABB-001~ABB-379, ABC-001~ABC-379, ABD-001~ABD-379, ABE-001~ABE-379, ABF-001~ABF-379, ABG-001~ABG-379, ABH-001~ABH-379, ABI-001~ABI-379, ABJ-001~ABJ-379, ABK-001~ABK-379, ABL-001~ABL-379, ABM-001~ABM-379, ABN-001~ABN-379, ABO-001~ABO-379, ABP-001~ABP-379, ABQ-001~ABQ-379, ABR-001~ABR-379, ABS-001~ABS-379, ABT-001~ABT-379, ABU-001~ABU-379, ABW-001~ABW-379, ABX-001~ABX-379, ABY-001~ABY-379, ABZ-001~ABZ-379, ACA-001~ACA-379, ACB-001~ACB-379, ACC-001~ACC-379, ACD-001~ACD-379, ACE-001~ACE-379, ACF-001~ACF-379, ACG-001~ACG-379, ACH-001~ACH-379, ACJ-001~ACJ-379, ACK-001~ACK-379, ACL-001~ACL-379, ACM-001~ACM-379, ACN-001~ACN-379, ACO-001~ACO-379, ACP-001~ACP-379, ACQ-001~ACQ-379, ACR-001~ACR-379, ACS-001~ACS-379, ACT-001~ACT-379, ACU-001~ACU-379, ACW-001~ACW-379, ACX-001~ACX-379, ACY-001~ACY-379, ACZ-001~ACZ-379, ADA-001~ADA-379, ADB-001~ADB-379, ADC-001~ADC-379, ADD-001~ADD-379, ADE-001~ADE-379, ADF-001~ADF-379, ADG-001~ADG-379, ADH-001~ADH-379, ADI-001~ADI-379, ADJ-001~ADJ-379, ADK-001~ADK-379, ADL-001~ADL-379, ADM-001~ADM-379, ADN-001~ADN-379, ADO-001~ADO-379, ADP-001~ADP-379, ADQ-001~ADQ-379, ADR-001~ADR-379 and ADS-001~ADS-379.

Compounds AA-001~AA-379 represent tetrazolinone Compounds represented by a formula:

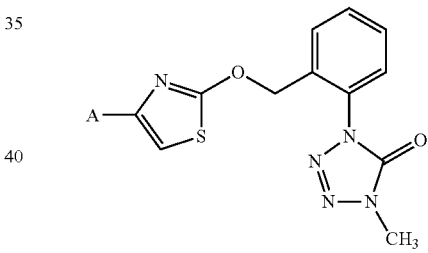

[wherein A represents a substituent corresponding to each of substituents Nos. 1 to 379 indicated in Table 1 to Table 16 as below-mentioned];

Compounds AB-001~AB-379 represent tetrazolinone Compounds represented by a formula:

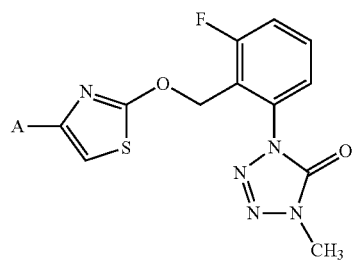

[wherein A represents a substituent corresponding to each of substituents Nos. 1 to 379 indicated in Table 1 to Table 16 as below-mentioned];

Compounds AC-001~AC-379 represent tetrazolinone Compounds represented by a formula:

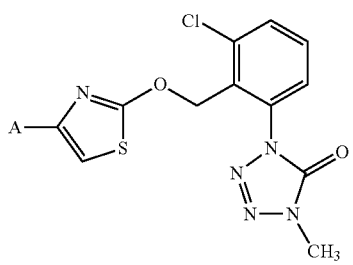

[wherein A represents a substituent corresponding to each of substituents Nos. 1 to 379 indicated in Table 1 to Table 16 as below-mentioned];

Compounds AD-001~AD-379 represent tetrazolinone Compounds represented by a formula:

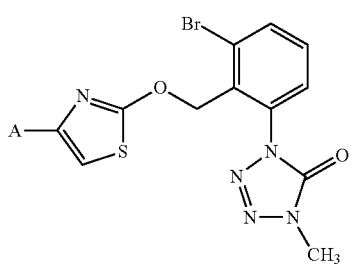

[wherein A represents a substituent corresponding to each of substituents Nos. 1 to 379 indicated in Table 1 to Table 16 as below-mentioned];

Compounds AE-001~AE-379 represent tetrazolinone Compounds represented by a formula:

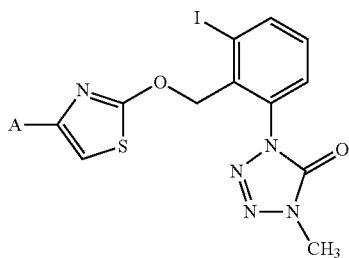

[wherein A represents a substituent corresponding to each of substituents Nos. 1 to 379 indicated in Table 1 to Table 16 as below-mentioned];

Compounds AF-001~AF-379 represent tetrazolinone Compounds represented by a formula:

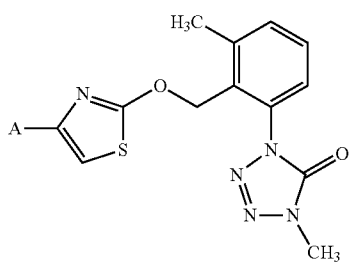

[wherein A represents a substituent corresponding to each of substituents Nos. 1 to 379 indicated in Table 1 to Table 16 as below-mentioned];

Compounds AG-001~AG-379 represent tetrazolinone Compounds represented by a formula:

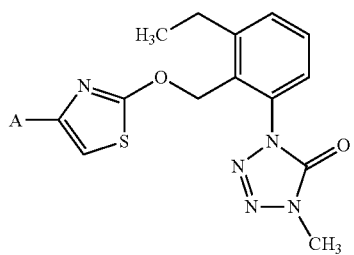

[wherein A represents a substituent corresponding to each of substituents Nos. 1 to 379 indicated in Table 1 to Table 16 as below-mentioned];

Compounds AH-001~AH-379 represent tetrazolinone Compounds represented by a formula:

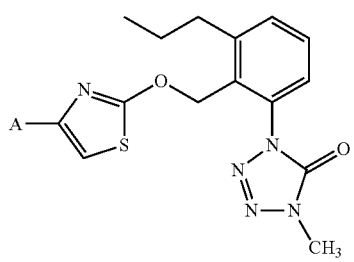

[wherein A represents a substituent corresponding to each of substituents Nos. 1 to 379 indicated in Table 1 to Table 16 as below-mentioned];

Compounds AI-001~AI-379 represent tetrazolinone Compounds represented by a formula:

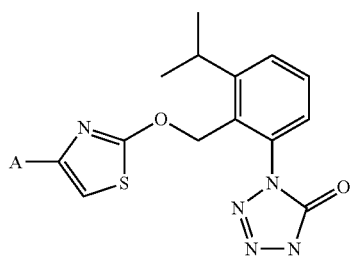

[wherein A represents a substituent corresponding to each of substituents Nos. 1 to 379 indicated in Table 1 to Table 16 as below-mentioned];

Compounds AJ-001~AJ-379 represent tetrazolinone Compounds represented by a formula:

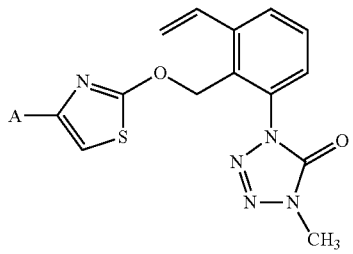

[wherein A represents a substituent corresponding to each of substituents Nos. 1 to 379 indicated in Table 1 to Table 16 as below-mentioned];

Compounds AK-001~AK-379 represent tetrazolinone Compounds represented by a formula:

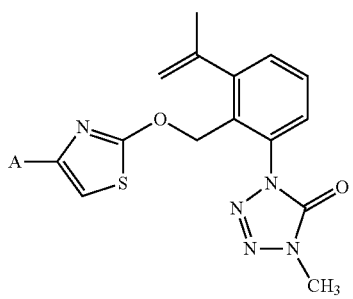

[wherein A represents a substituent corresponding to each of substituents Nos. 1 to 379 indicated in Table 1 to Table 16 as below-mentioned];

Compounds AL-001~AL-379 represent tetrazolinone Compounds represented by a formula:

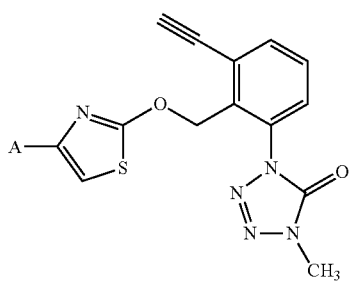

[wherein A represents a substituent corresponding to each of substituents Nos. 1 to 379 indicated in Table 1 to Table 16 as below-mentioned];

Compounds AM-001~AM-379 represent tetrazolinone Compounds represented by a formula:

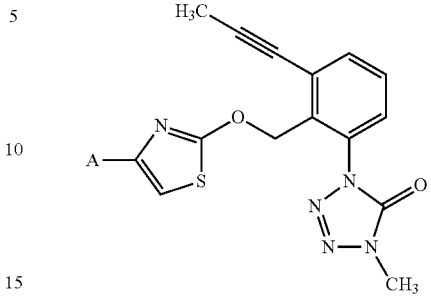

[wherein A represents a substituent corresponding to each of substituents Nos. 1 to 379 indicated in Table 1 to Table 16 as below-mentioned];

Compounds AN-001~AN-379 represent tetrazolinone Compounds represented by a formula:

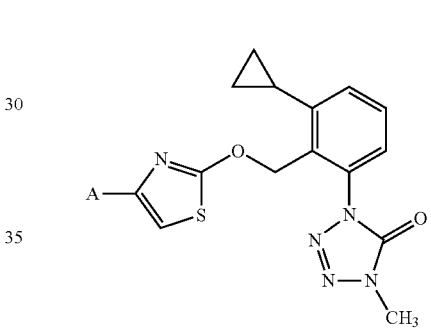

[wherein A represents a substituent corresponding to each of substituents Nos. 1 to 379 indicated in Table 1 to Table 16 as below-mentioned];

Compounds AO-001~AO-379 represent tetrazolinone Compounds represented by a formula:

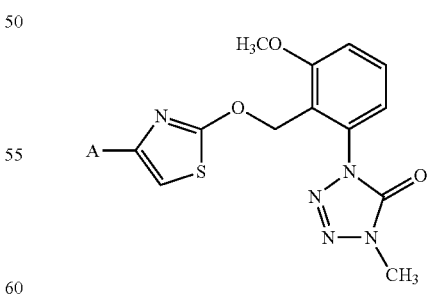

[wherein A represents a substituent corresponding to each of substituents Nos. 1 to 379 indicated in Table 1 to Table 16 as below-mentioned];

Compounds AP-001~AP-379 represent tetrazolinone Compounds represented by a formula:

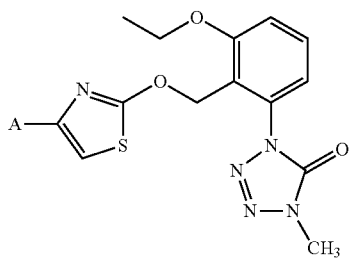

[wherein A represents a substituent corresponding to each of substituents Nos. 1 to 379 indicated in Table 1 to Table 16 as below-mentioned];

Compounds AQ-001~AQ-379 represent tetrazolinone Compounds represented by a formula:

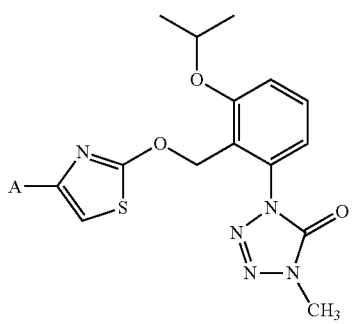

[wherein A represents a substituent corresponding to each of substituents Nos. 1 to 379 indicated in Table 1 to Table 16 as below-mentioned];

Compounds AR-001~AR-379 represent tetrazolinone Compounds represented by a formula:

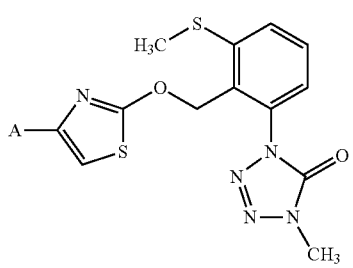

[wherein A represents a substituent corresponding to each of substituents Nos. 1 to 379 indicated in Table 1 to Table 16 as below-mentioned];

Compounds AS-001~AS-379 represent tetrazolinone Compounds represented by a formula:

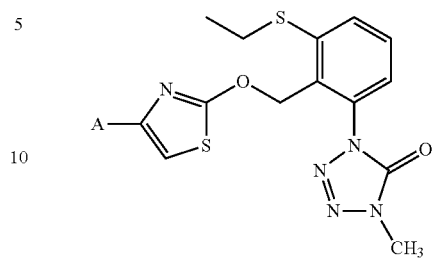

[wherein A represents a substituent corresponding to each of substituents Nos. 1 to 379 indicated in Table 1 to Table 16 as below-mentioned];

Compounds AT-001~AT-379 represent tetrazolinone Compounds represented by a formula:

[wherein A represents a substituent corresponding to each of substituents Nos. 1 to 379 indicated in Table 1 to Table 16 as below-mentioned];

Compounds AU-001~AU-379 represent tetrazolinone Compounds represented by a formula:

[wherein A represents a substituent corresponding to each of substituents Nos. 1 to 379 indicated in Table 1 to Table 16 as below-mentioned];

Compounds AV-001~AV-379 represent tetrazolinone Compounds represented by a formula:

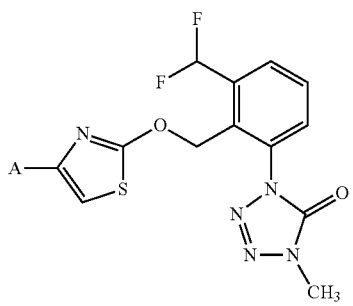

[wherein A represents a substituent corresponding to each of substituents Nos. 1 to 379 indicated in Table 1 to Table 16 as below-mentioned];

Compounds AW-001~AW-379 represent tetrazolinone Compounds represented by a formula:

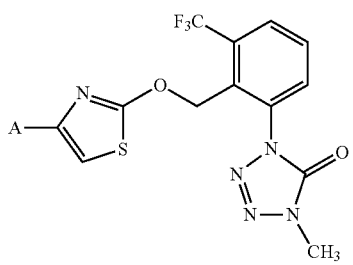

[wherein A represents a substituent corresponding to each of substituents Nos. 1 to 379 indicated in Table 1 to Table 16 as below-mentioned];

Compounds AX-001~AX-379 represent tetrazolinone Compounds represented by a formula:

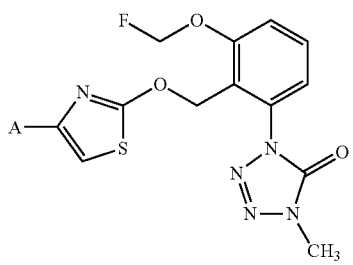

[wherein A represents a substituent corresponding to each of substituents Nos. 1 to 379 indicated in Table 1 to Table 16 as below-mentioned];

Compounds AY-001~AY-379 represent tetrazolinone Compounds represented by a formula:

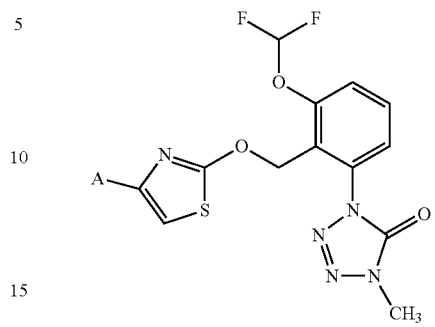

[wherein A represents a substituent corresponding to each of substituents Nos. 1 to 379 indicated in Table 1 to Table 16 as below-mentioned];

Compounds AZ-001~AZ-379 represent tetrazolinone Compounds represented by a formula:

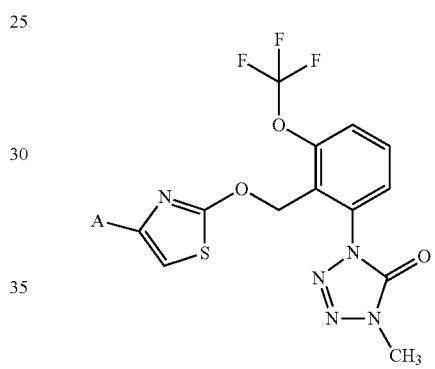

[wherein A represents a substituent corresponding to each of substituents Nos. 1 to 379 indicated in Table 1 to Table 16 as below-mentioned];

Compounds AAA-001~AAA-379 represent tetrazolinone Compounds represented by a formula:

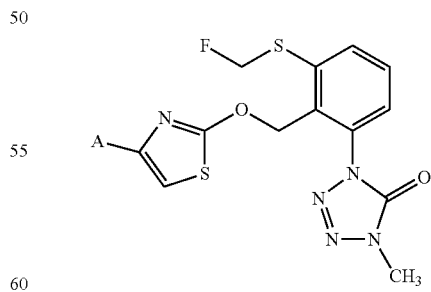

[wherein A represents a substituent corresponding to each of substituents Nos. 1 to 379 indicated in Table 1 to Table 16 as below-mentioned];

Compounds AAB-001~AAB-379 represent tetrazolinone Compounds represented by a formula:

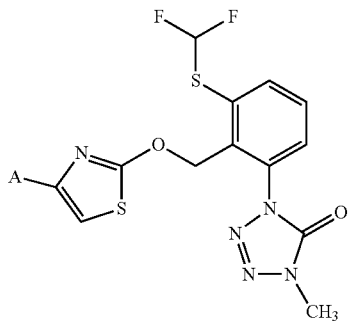

[wherein A represents a substituent corresponding to each of substituents Nos. 1 to 379 indicated in Table 1 to Table 16 as below-mentioned];

Compounds AAC-001~AAC-379 represent tetrazolinone Compounds represented by a formula:

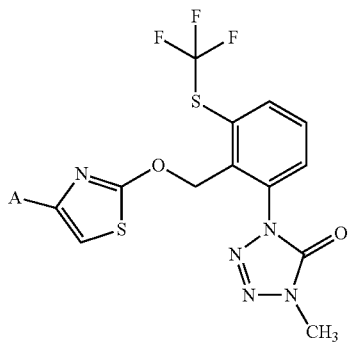

[wherein A represents a substituent corresponding to each of substituents Nos. 1 to 379 indicated in Table 1 to Table 16 as below-mentioned];

Compounds AAD-001~AAD-379 represent tetrazolinone Compounds represented by a formula:

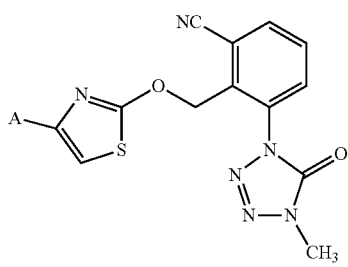

[wherein A represents a substituent corresponding to each of substituents Nos. 1 to 379 indicated in Table 1 to Table 16 as below-mentioned];

Compounds AAE-001~AAE-379 represent tetrazolinone Compounds represented by a formula:

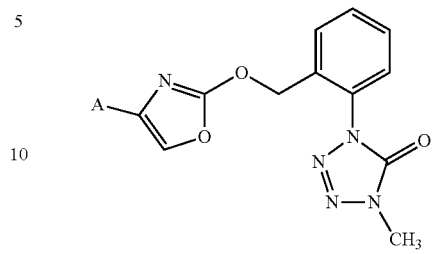

[wherein A represents a substituent corresponding to each of substituents Nos. 1 to 379 indicated in Table 1 to Table 16 as below-mentioned];

Compounds AAF-001~AAF-379 represent tetrazolinone Compounds represented by a formula:

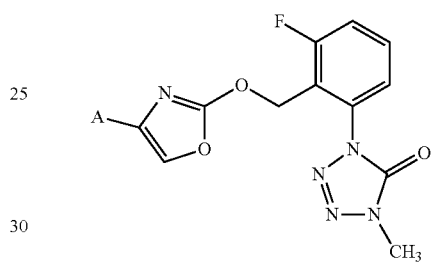

[wherein A represents a substituent corresponding to each of substituents Nos. 1 to 379 indicated in Table 1 to Table 16 as below-mentioned];

Compounds AAG-001~AAG-379 represent tetrazolinone Compounds represented by a formula:

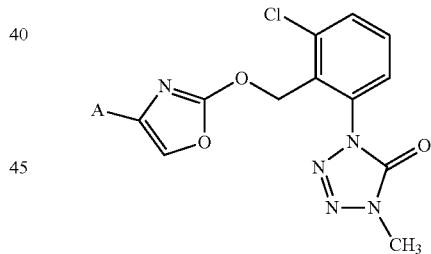

[wherein A represents a substituent corresponding to each of substituents Nos. 1 to 379 indicated in Table 1 to Table 16 as below-mentioned];

Compounds AAH-001~AAH-379 represent tetrazolinone Compounds represented by a formula:

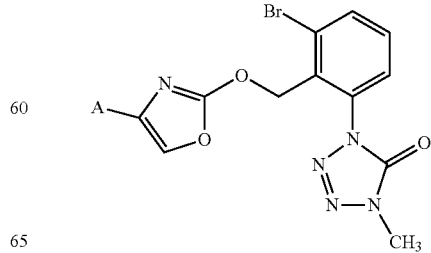

[wherein A represents a substituent corresponding to each of substituents Nos. 1 to 379 indicated in Table 1 to Table 16 as below-mentioned];

Compounds AAI-001~AAI-379 represent tetrazolinone Compounds represented by a formula:

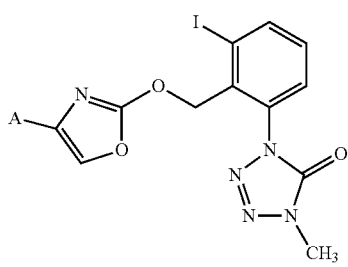

[wherein A represents a substituent corresponding to each of substituents Nos. 1 to 379 indicated in Table 1 to Table 16 as below-mentioned];

Compounds AAJ-001~AAJ-379 represent tetrazolinone Compounds represented by a formula:

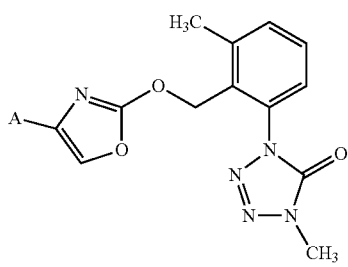

[wherein A represents a substituent corresponding to each of substituents Nos. 1 to 379 indicated in Table 1 to Table 16 as below-mentioned];

Compounds AAK-001~AAK-379 represent tetrazolinone Compounds represented by a formula:

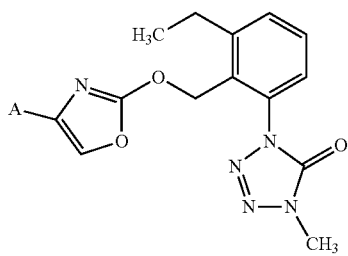

[wherein A represents a substituent corresponding to each of substituents Nos. 1 to 379 indicated in Table 1 to Table 16 as below-mentioned];

Compounds AAL-001~AAL-379 represent tetrazolinone Compounds represented by a formula:

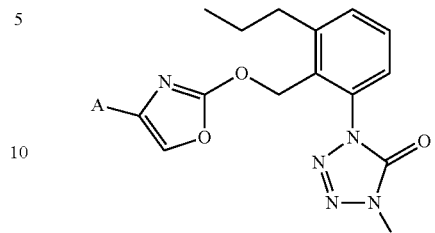

[wherein A represents a substituent corresponding to each of substituents Nos. 1 to 379 indicated in Table 1 to Table 16 as below-mentioned];

Compounds AAM-001~AAM-379 represent tetrazolinone Compounds represented by a formula:

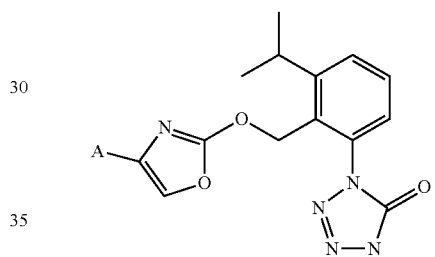

[wherein A represents a substituent corresponding to each of substituents Nos. 1 to 379 indicated in Table 1 to Table 16 as below-mentioned];

Compounds AAN-001~AAN-379 represent tetrazolinone Compounds represented by a formula:

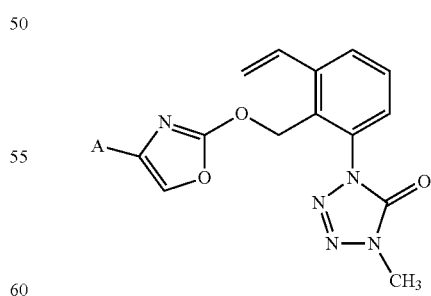

[wherein A represents a substituent corresponding to each of substituents Nos. 1 to 379 indicated in Table 1 to Table 16 as below-mentioned];

Compounds AAO-001~AAO-379 represent tetrazolinone Compounds represented by a formula:

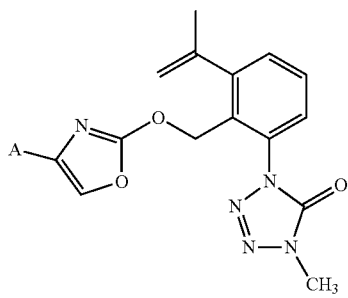

[wherein A represents a substituent corresponding to each of substituents Nos. 1 to 379 indicated in Table 1 to Table 16 as below-mentioned];

Compounds AAP-001~AAP-379 represent tetrazolinone Compounds represented by a formula:

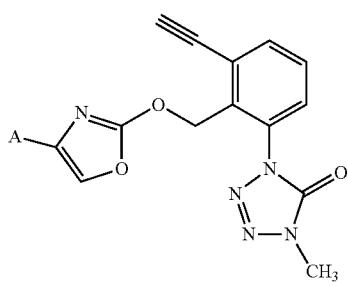

[wherein A represents a substituent corresponding to each of substituents Nos. 1 to 379 indicated in Table 1 to Table 16 as below-mentioned];

Compounds AAQ-001~AAQ-379 represent tetrazolinone Compounds represented by a formula:

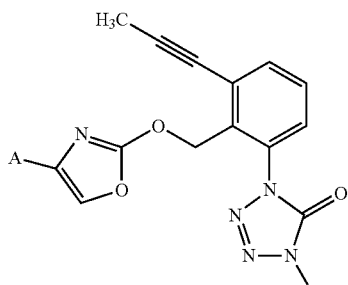

[wherein A represents a substituent corresponding to each of substituents Nos. 1 to 379 indicated in Table 1 to Table 16 as below-mentioned];

Compounds AAR-001~AAR-379 represent tetrazolinone Compounds represented by a formula:

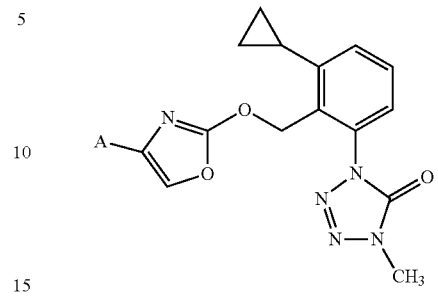

[wherein A represents a substituent corresponding to each of substituents Nos. 1 to 379 indicated in Table 1 to Table 16 as below-mentioned];

Compounds AA, S-001~AA, S-379 represent tetrazolinone Compounds represented by a formula:

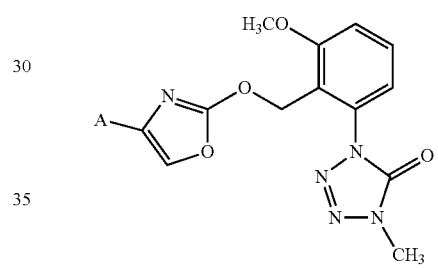

[wherein A represents a substituent corresponding to each of substituents Nos. 1 to 379 indicated in Table 1 to Table 16 as below-mentioned];

Compounds AAT-001~AAT-379 represent tetrazolinone Compounds represented by a formula:

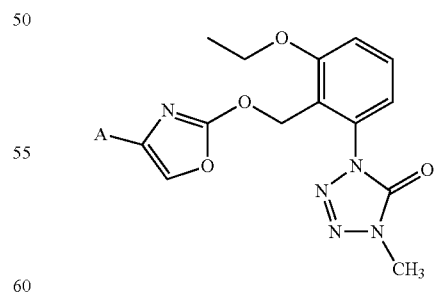

[wherein A represents a substituent corresponding to each of substituents Nos. 1 to 379 indicated in Table 1 to Table 16 as below-mentioned];

Compounds AAU-001~AAU-379 represent tetrazolinone Compounds represented by a formula:

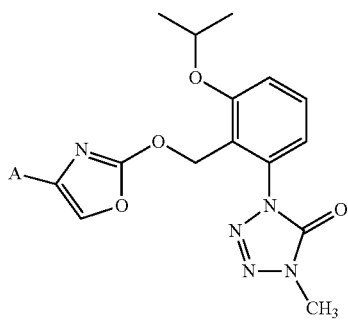

[wherein A represents a substituent corresponding to each of substituents Nos. 1 to 379 indicated in Table 1 to Table 16 as below-mentioned];

Compounds AAV-001~AAV-379 represent tetrazolinone Compounds represented by a formula:

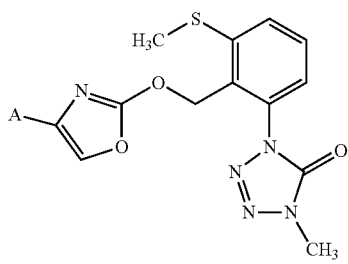

[wherein A represents a substituent corresponding to each of substituents Nos. 1 to 379 indicated in Table 1 to Table 16 as below-mentioned];

Compounds AAW-001~AAW-379 represent tetrazolinone Compounds represented by a formula:

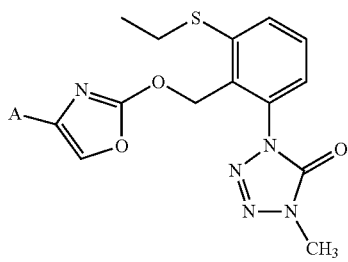

[wherein A represents a substituent corresponding to each of substituents Nos. 1 to 379 indicated in Table 1 to Table 16 as below-mentioned];

Compounds AAX-001~AAX-379 represent tetrazolinone Compounds represented by a formula:

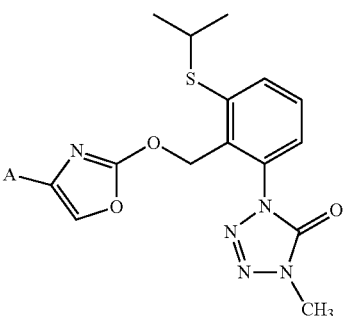

[wherein A represents a substituent corresponding to each of substituents Nos. 1 to 379 indicated in Table 1 to Table 16 as below-mentioned];

Compounds AAX-001~AAX-379 represent tetrazolinone Compounds represented by a formula:

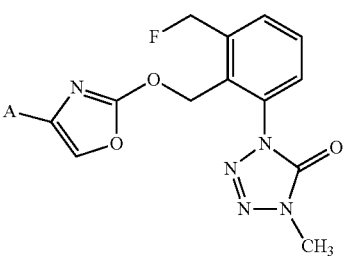

[wherein A represents a substituent corresponding to each of substituents Nos. 1 to 379 indicated in Table 1 to Table 16 as below-mentioned];

Compounds AAZ-001~AAZ-379 represent tetrazolinone Compounds represented by a formula:

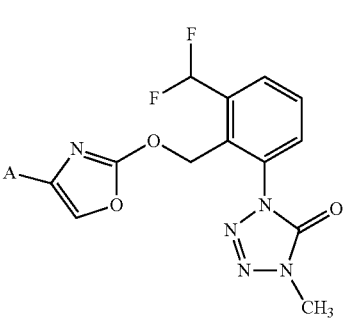

[wherein A represents a substituent corresponding to each of substituents Nos. 1 to 379 indicated in Table 1 to Table 16 as below-mentioned];

Compounds ABA-001~ABA-379 represent tetrazolinone Compounds represented by a formula:

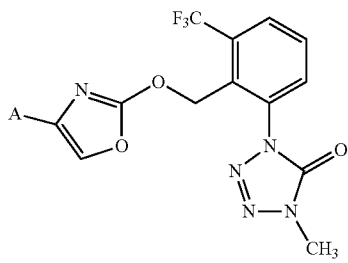

[wherein A represents a substituent corresponding to each of substituents Nos. 1 to 379 indicated in Table 1 to Table 16 as below-mentioned];

Compounds ABC-001~ABC-379 represent tetrazolinone Compounds represented by a formula:

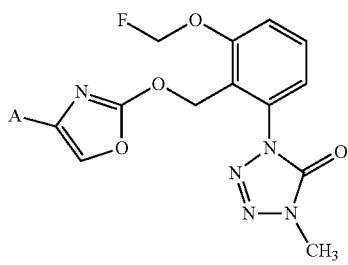

[wherein A represents a substituent corresponding to each of substituents Nos. 1 to 379 indicated in Table 1 to Table 16 as below-mentioned];

Compounds ABD-001~ABD-379 represent tetrazolinone Compounds represented by a formula:

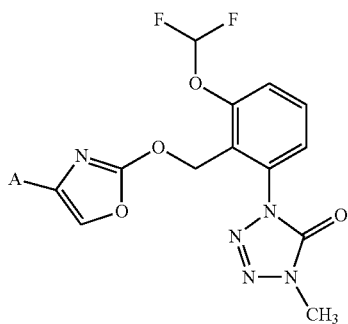

[wherein A represents a substituent corresponding to each of substituents Nos. 1 to 379 indicated in Table 1 to Table 16 as below-mentioned];

Compounds ABE-001~ABE-379 represent tetrazolinone Compounds represented by a formula:

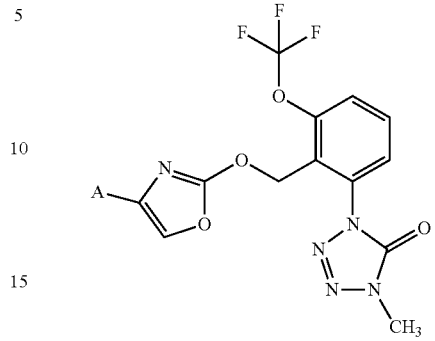

[wherein A represents a substituent corresponding to each of substituents Nos. 1 to 379 indicated in Table 1 to Table 16 as below-mentioned];

Compounds ABF-001~ABF-379 represent tetrazolinone Compounds represented by a formula:

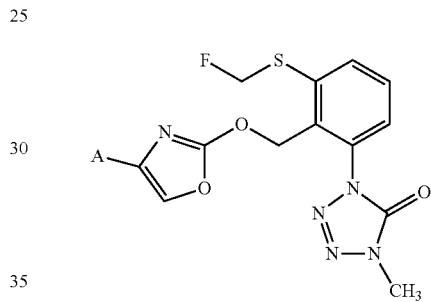

[wherein A represents a substituent corresponding to each of substituents Nos. 1 to 379 indicated in Table 1 to Table 16 as below-mentioned];

Compounds ABG-001~ABG-379 represent tetrazolinone Compounds represented by a formula:

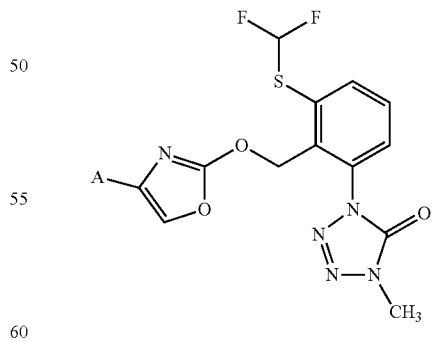

[wherein A represents a substituent corresponding to each of substituents Nos. 1 to 379 indicated in Table 1 to Table 16 as below-mentioned];

Compounds ABH-001~ABH-379 represent tetrazolinone Compounds represented by a formula:

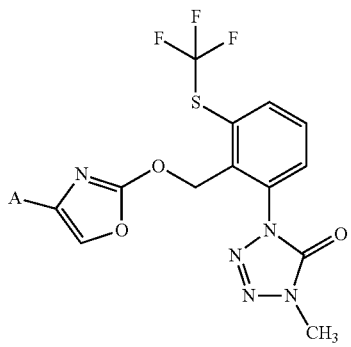

[wherein A represents a substituent corresponding to each of substituents Nos. 1 to 379 indicated in Table 1 to Table 16 as below-mentioned];

Compounds ABI-001~ABI-379 represent tetrazolinone Compounds represented by a formula:

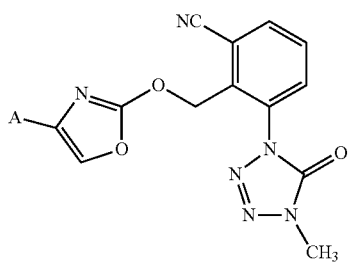

[wherein A represents a substituent corresponding to each of substituents Nos. 1 to 379 indicated in Table 1 to Table 16 as below-mentioned];

Compounds ABJ-001~ABJ-379 represent tetrazolinone Compounds represented by a formula:

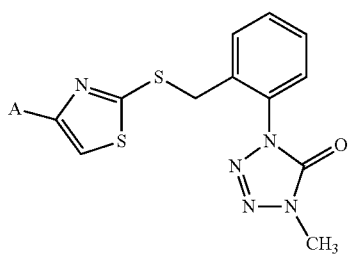

[wherein A represents a substituent corresponding to each of substituents Nos. 1 to 379 indicated in Table 1 to Table 16 as below-mentioned];

Compounds ABK-001~ABK-379 represent tetrazolinone Compounds represented by a formula:

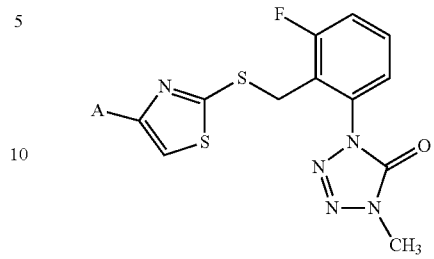

[wherein A represents a substituent corresponding to each of substituents Nos. 1 to 379 indicated in Table 1 to Table 16 as below-mentioned];

Compounds ABL-001~ABL-379 represent tetrazolinone Compounds represented by a formula:

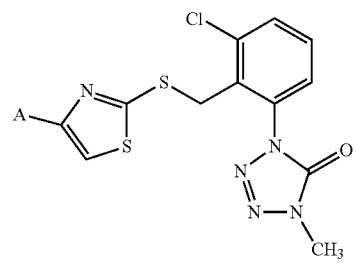

[wherein A represents a substituent corresponding to each of substituents Nos. 1 to 379 indicated in Table 1 to Table 16 as below-mentioned];

Compounds ABM-001~ABM-379 represent tetrazolinone Compounds represented by a formula:

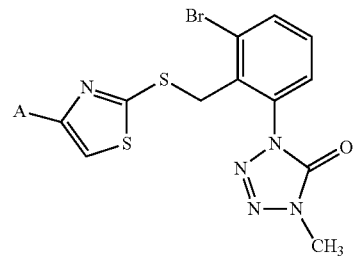

[wherein A represents a substituent corresponding to each of substituents Nos. 1 to 379 indicated in Table 1 to Table 16 as below-mentioned];

Compounds ABN-001~ABN-379 represent tetrazolinone Compounds represented by a formula:

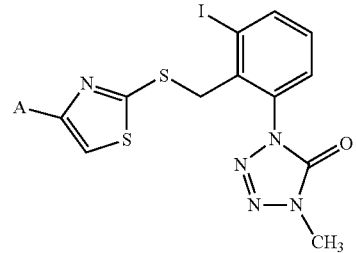

[wherein A represents a substituent corresponding to each of substituents Nos. 1 to 379 indicated in Table 1 to Table 16 as below-mentioned];

Compounds ABO-001~ABO-379 represent tetrazolinone Compounds represented by a formula:

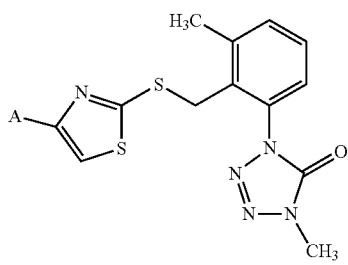

[wherein A represents a substituent corresponding to each of substituents Nos. 1 to 379 indicated in Table 1 to Table 16 as below-mentioned];

Compounds ABP-001~ABP-379 represent tetrazolinone Compounds represented by a formula:

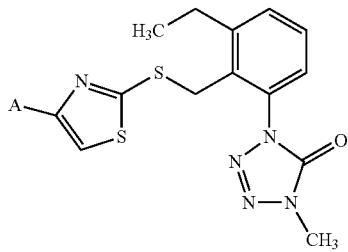

[wherein A represents a substituent corresponding to each of substituents Nos. 1 to 379 indicated in Table 1 to Table 16 as below-mentioned];

Compounds ABQ-001~ABQ-379 represent tetrazolinone Compounds represented by a formula:

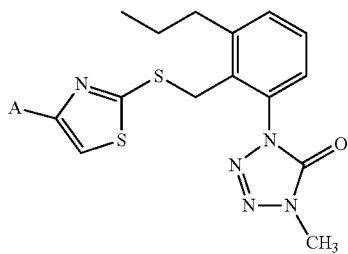

[wherein A represents a substituent corresponding to each of substituents Nos. 1 to 379 indicated in Table 1 to Table 16 as below-mentioned];

Compounds ABR-001~ABR-379 represent tetrazolinone Compounds represented by a formula:

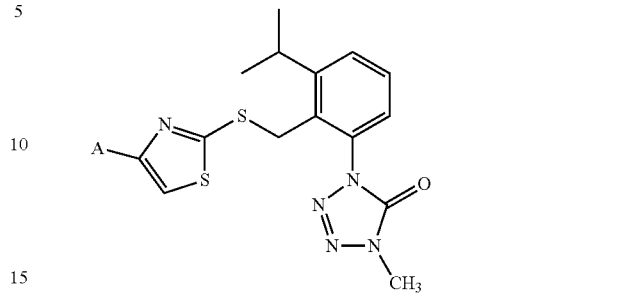

[wherein A represents a substituent corresponding to each of substituents Nos. 1 to 379 indicated in Table 1 to Table 16 as below-mentioned];

Compounds ABS-001~ABS-379 represent tetrazolinone Compounds represented by a formula:

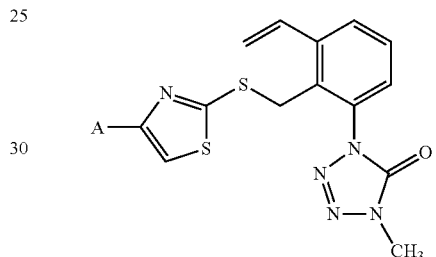

[wherein A represents a substituent corresponding to each of substituents Nos. 1 to 379 indicated in Table 1 to Table 16 as below-mentioned];

Compounds ABT-001~ABT-379 represent tetrazolinone Compounds represented by a formula:

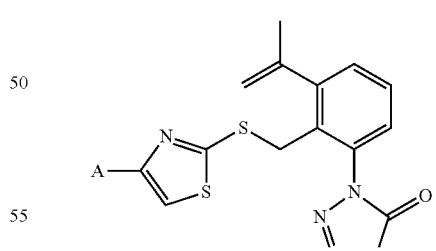

[wherein A represents a substituent corresponding to each of substituents Nos. 1 to 379 indicated in Table 1 to Table 16 as below-mentioned];

Compounds ABU-001~ABU-379 represent tetrazolinone Compounds represented by a formula:

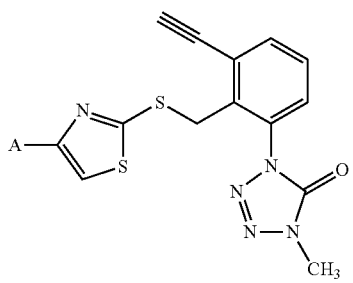

[wherein A represents a substituent corresponding to each of substituents Nos. 1 to 379 indicated in Table 1 to Table 16 as below-mentioned];

Compounds ABW-001~ABW-379 represent tetrazolinone Compounds represented by a formula:

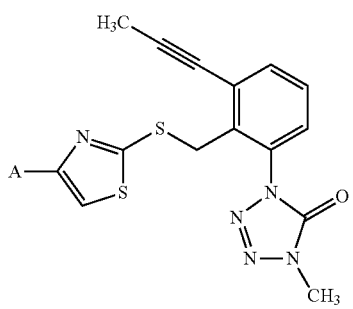

[wherein A represents a substituent corresponding to each of substituents Nos. 1 to 379 indicated in Table 1 to Table 16 as below-mentioned];

Compounds ABX-001~ABX-379 represent tetrazolinone Compounds represented by a formula:

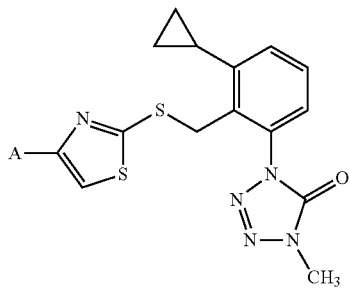

[wherein A represents a substituent corresponding to each of substituents Nos. 1 to 379 indicated in Table 1 to Table 16 as below-mentioned];

Compounds ABY-001~ABY-379 represent tetrazolinone Compounds represented by a formula:

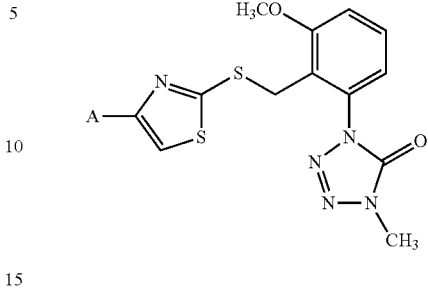

[wherein A represents a substituent corresponding to each of substituents Nos. 1 to 379 indicated in Table 1 to Table 16 as below-mentioned];

Compounds ABZ-001~ABZ-379 represent tetrazolinone Compounds represented by a formula:

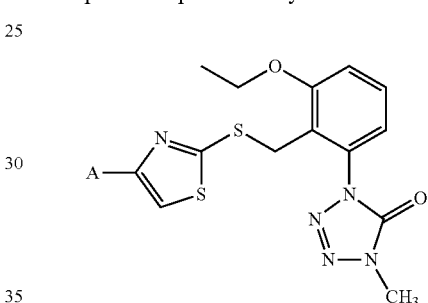

[wherein A represents a substituent corresponding to each of substituents Nos. 1 to 379 indicated in Table 1 to Table 16 as below-mentioned];

Compounds ACA-001~ACA-379 represent tetrazolinone Compounds represented by a formula:

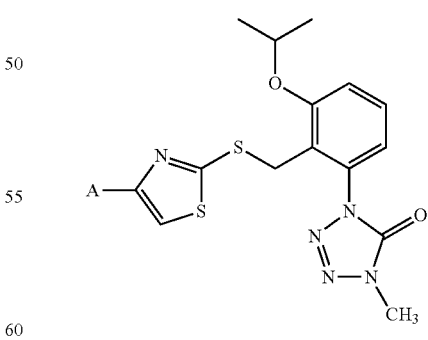

[wherein A represents a substituent corresponding to each of substituents Nos. 1 to 379 indicated in Table 1 to Table 16 as below-mentioned];

Compounds ACB-001~ACB-379 represent tetrazolinone Compounds represented by a formula:

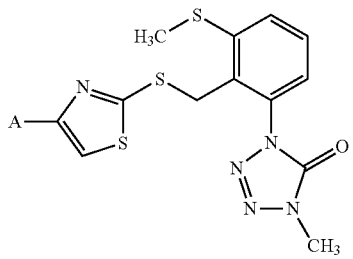

[wherein A represents a substituent corresponding to each of substituents Nos. 1 to 379 indicated in Table 1 to Table 16 as below-mentioned];

Compounds ACC-001~ACC-379 represent tetrazolinone Compounds represented by a formula:

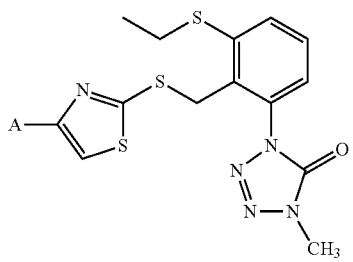

[wherein A represents a substituent corresponding to each of substituents Nos. 1 to 379 indicated in Table 1 to Table 16 as below-mentioned];

Compounds ACD-001~ACD-379 represent tetrazolinone Compounds represented by a formula:

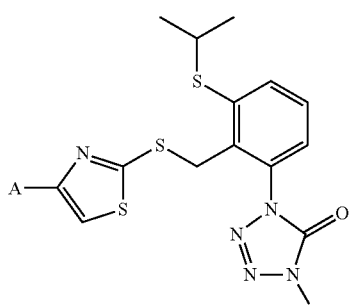

[wherein A represents a substituent corresponding to each of substituents Nos. 1 to 379 indicated in Table 1 to Table 16 as below-mentioned];

Compounds ACE-001~ACE-379 represent tetrazolinone Compounds represented by a formula:

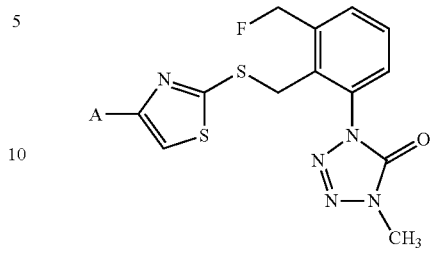

[wherein A represents a substituent corresponding to each of substituents Nos. 1 to 379 indicated in Table 1 to Table 16 as below-mentioned];

Compounds ACF-001~ACF-379 represent tetrazolinone Compounds represented by a formula:

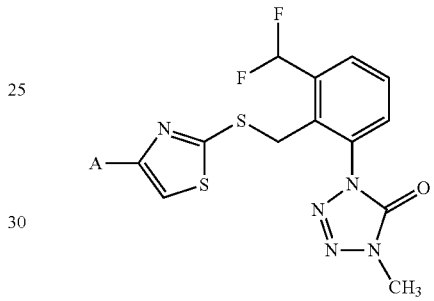

[wherein A represents a substituent corresponding to each of substituents Nos. 1 to 379 indicated in Table 1 to Table 16 as below-mentioned];

Compounds ACG-001~ACG-379 represent tetrazolinone Compounds represented by a formula:

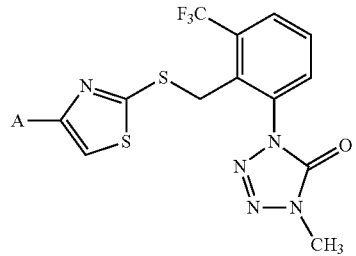

[wherein A represents a substituent corresponding to each of substituents Nos. 1 to 379 indicated in Table 1 to Table 16 as below-mentioned];

Compounds ACH-001~ACH-379 represent tetrazolinone Compounds represented by a formula:

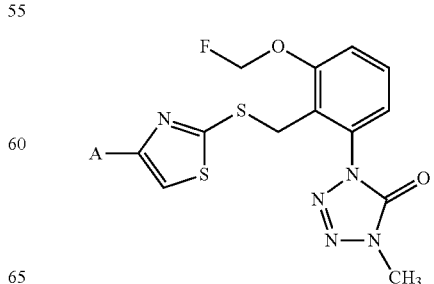

Compounds ACI-001~ACI-379 represent tetrazolinone Compounds represented by a formula:

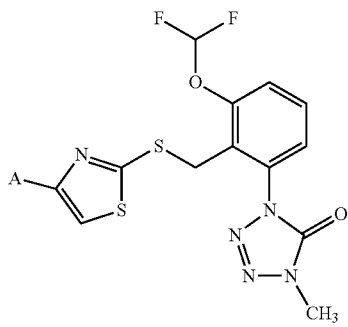

[wherein A represents a substituent corresponding to each of substituents Nos. 1 to 379 indicated in Table 1 to Table 16 as below-mentioned];

Compounds ACJ-001~ACJ-379 represent tetrazolinone Compounds represented by a formula:

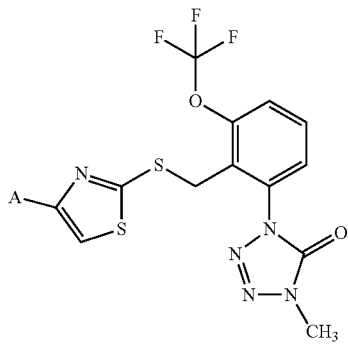

[wherein A represents a substituent corresponding to each of substituents Nos. 1 to 379 indicated in Table 1 to Table 16 as below-mentioned];

Compounds ACK-001~ACK-379 represent tetrazolinone Compounds represented by a formula:

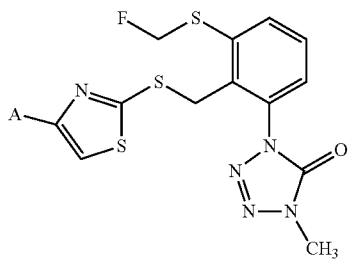

[wherein A represents a substituent corresponding to each of substituents Nos. 1 to 379 indicated in Table 1 to Table 16 as below-mentioned];

Compounds ACL-001~ACL-379 represent tetrazolinone Compounds represented by a formula:

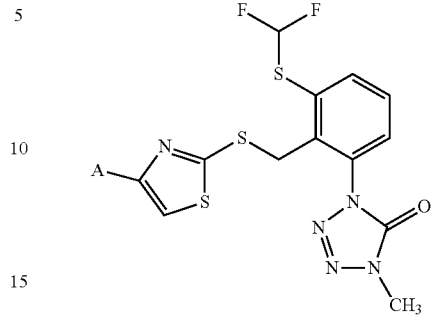

[wherein A represents a substituent corresponding to each of substituents Nos. 1 to 379 indicated in Table 1 to Table 16 as below-mentioned];

Compounds ACM-001~ACM-379 represent tetrazolinone Compounds represented by a formula:

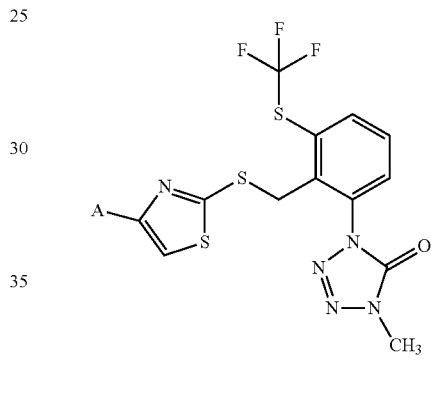

[wherein A represents a substituent corresponding to each of substituents Nos. 1 to 379 indicated in Table 1 to Table 16 as below-mentioned];

Compounds ACN-001~ACN-379 represent tetrazolinone Compounds represented by a formula:

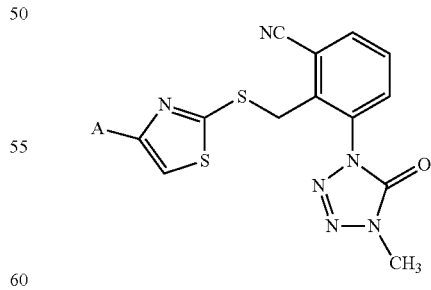

[wherein A represents a substituent corresponding to each of substituents Nos. 1 to 379 indicated in Table 1 to Table 16 as below-mentioned];

Compounds ACO-001~ACO-379 represent tetrazolinone Compounds represented by a formula:

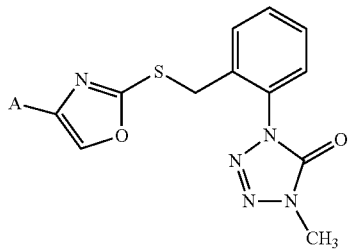

[wherein A represents a substituent corresponding to each of substituents Nos. 1 to 379 indicated in Table 1 to Table 16 as below-mentioned];

Compounds ACP-001~ACP-379 represent tetrazolinone Compounds represented by a formula:

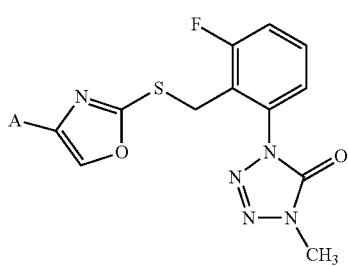

[wherein A represents a substituent corresponding to each of substituents Nos. 1 to 379 indicated in Table 1 to Table 16 as below-mentioned];

Compounds ACQ-001~ACQ-379 represent tetrazolinone Compounds represented by a formula:

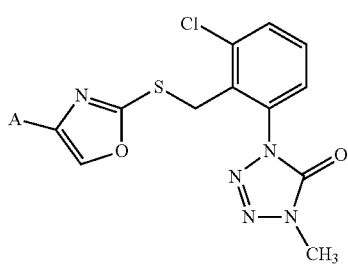

[wherein A represents a substituent corresponding to each of substituents Nos. 1 to 379 indicated in Table 1 to Table 16 as below-mentioned];

Compounds ACR-001~ACR-379 represent tetrazolinone Compounds represented by a formula:

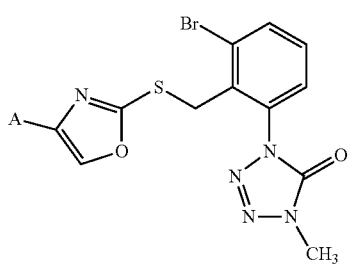

[wherein A represents a substituent corresponding to each of substituents Nos. 1 to 379 indicated in Table 1 to Table 16 as below-mentioned];

Compounds ACS-001~ACS-379 represent tetrazolinone Compounds represented by a formula:

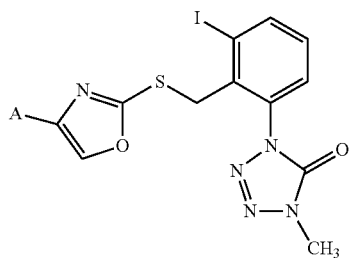

[wherein A represents a substituent corresponding to each of substituents Nos. 1 to 379 indicated in Table 1 to Table 16 as below-mentioned];

Compounds ACT-001~ACT-379 represent tetrazolinone Compounds represented by a formula:

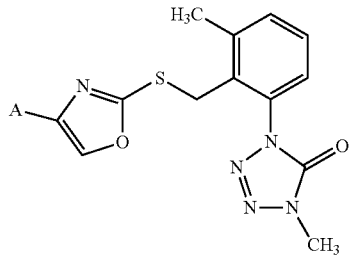

[wherein A represents a substituent corresponding to each of substituents Nos. 1 to 379 indicated in Table 1 to Table 16 as below-mentioned];

Compounds ACU-001~ACU-379 represent tetrazolinone Compounds represented by a formula:

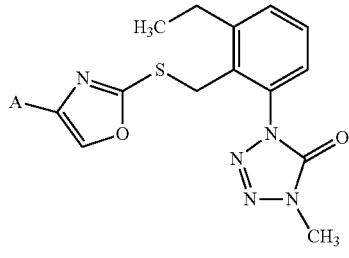

[wherein A represents a substituent corresponding to each of substituents Nos. 1 to 379 indicated in Table 1 to Table 16 as below-mentioned];

Compounds ACW-001~ACW-379 represent tetrazolinone Compounds represented by a formula:

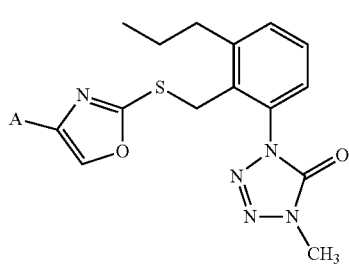

[wherein A represents a substituent corresponding to each of substituents Nos. 1 to 379 indicated in Table 1 to Table 16 as below-mentioned];

Compounds ACX-001~ACX-379 represent tetrazolinone Compounds represented by a formula:

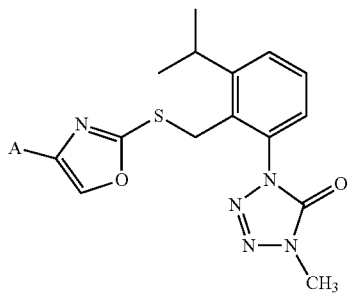

[wherein A represents a substituent corresponding to each of substituents Nos. 1 to 379 indicated in Table 1 to Table 16 as below-mentioned];

Compounds ACY-001~ACY-379 represent tetrazolinone Compounds represented by a formula:

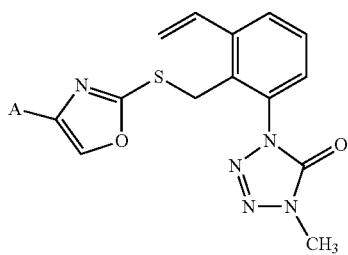

[wherein A represents a substituent corresponding to each of substituents Nos. 1 to 379 indicated in Table 1 to Table 16 as below-mentioned];

Compounds ACZ-001~ACZ-379 represent tetrazolinone Compounds represented by a formula:

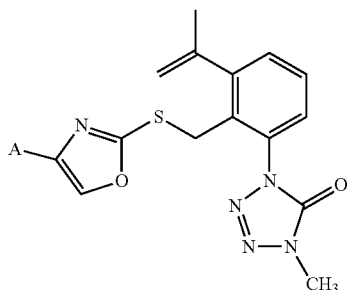

[wherein A represents a substituent corresponding to each of substituents Nos. 1 to 379 indicated in Table 1 to Table 16 as below-mentioned];

Compounds ADA-001~ADA-379 represent tetrazolinone Compounds represented by a formula:

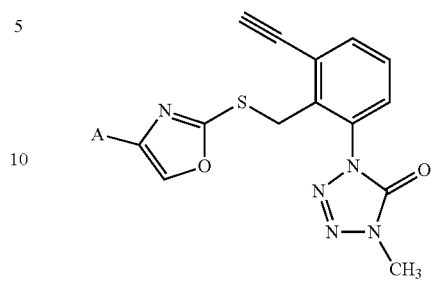

[wherein A represents a substituent corresponding to each of substituents Nos. 1 to 379 indicated in Table 1 to Table 16 as below-mentioned];

Compounds ADB-001~ADB-379 represent tetrazolinone Compounds represented by a formula:

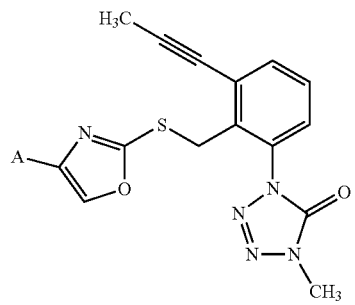

[wherein A represents a substituent corresponding to each of substituents Nos. 1 to 379 indicated in Table 1 to Table 16 as below-mentioned];

Compounds ADB-001~ADB-379 represent tetrazolinone Compounds represented by a formula:

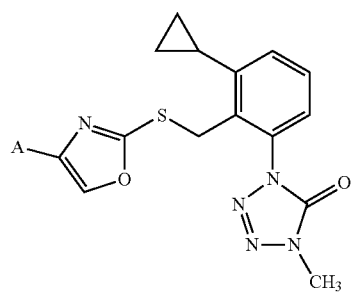

[wherein A represents a substituent corresponding to each of substituents Nos. 1 to 379 indicated in Table 1 to Table 16 as below-mentioned];

Compounds ADD-001~ADD-379 represent tetrazolinone Compounds represented by a formula:

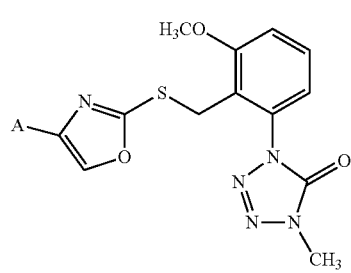

[wherein A represents a substituent corresponding to each of substituents Nos. 1 to 379 indicated in Table 1 to Table 16 as below-mentioned];

Compounds ADE-001~ADE-379 represent tetrazolinone Compounds represented by a formula:

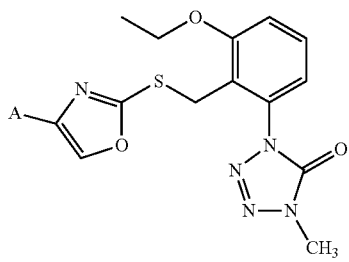

[wherein A represents a substituent corresponding to each of substituents Nos. 1 to 379 indicated in Table 1 to Table 16 as below-mentioned];

Compounds ADF-001~ADF-379 represent tetrazolinone Compounds represented by a formula:

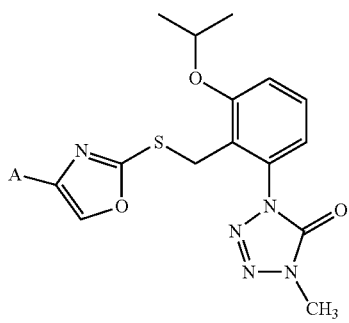

[wherein A represents a substituent corresponding to each of substituents Nos. 1 to 379 indicated in Table 1 to Table 16 as below-mentioned];

Compounds ADG-001~ADG-379 represent tetrazolinone Compounds represented by a formula:

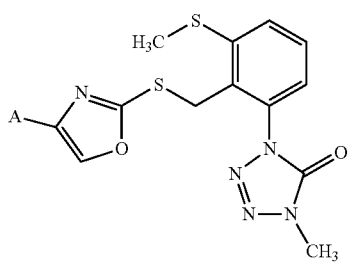

[wherein A represents a substituent corresponding to each of substituents Nos. 1 to 379 indicated in Table 1 to Table 16 as below-mentioned];

Compounds ADH-001~ADH-379 represent tetrazolinone Compounds represented by a formula:

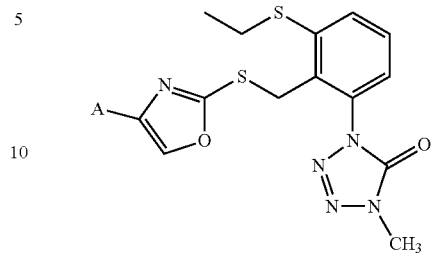

[wherein A represents a substituent corresponding to each of substituents Nos. 1 to 379 indicated in Table 1 to Table 16 as below-mentioned];

Compounds ADI-001~ADI-379 represent tetrazolinone Compounds represented by a formula:

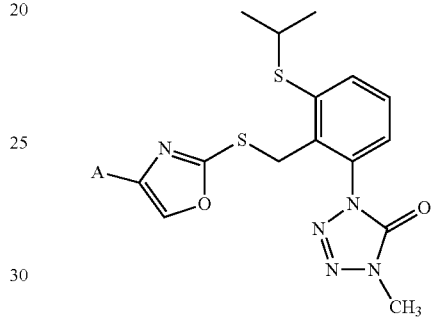

[wherein A represents a substituent corresponding to each of substituents Nos. 1 to 379 indicated in Table 1 to Table 16 as below-mentioned];

Compounds ADJ-001~ADJ-379 represent tetrazolinone Compounds represented by a formula:

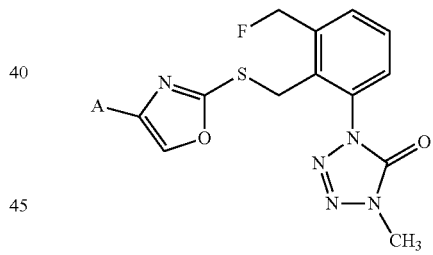

[wherein A represents a substituent corresponding to each of substituents Nos. 1 to 379 indicated in Table 1 to Table 16 as below-mentioned];

Compounds ADK-001~ADK-379 represent tetrazolinone Compounds represented by a formula:

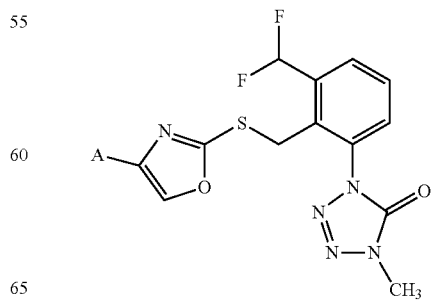

Compounds ADL-001~ADL-379 represent tetrazolinone Compounds represented by a formula:

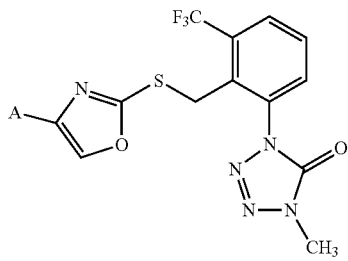

[wherein A represents a substituent corresponding to each of substituents Nos. 1 to 379 indicated in Table 1 to Table 16 as below-mentioned];

Compounds ADM-001~ADM-379 represent tetrazolinone Compounds represented by a formula:

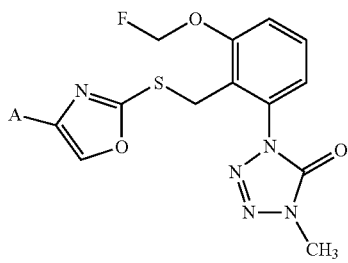

[wherein A represents a substituent corresponding to each of substituents Nos. 1 to 379 indicated in Table 1 to Table 16 as below-mentioned];

Compounds ADN-001~ADN-379 represent tetrazolinone Compounds represented by a formula:

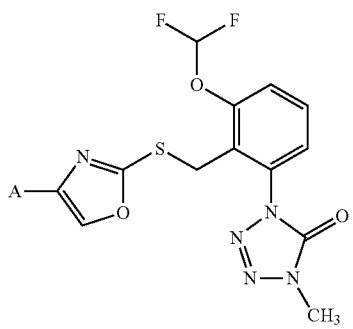

[wherein A represents a substituent corresponding to each of substituents Nos. 1 to 379 indicated in Table 1 to Table 16 as below-mentioned];

Compounds ADO-001~ADO-379 represent tetrazolinone Compounds represented by a formula:

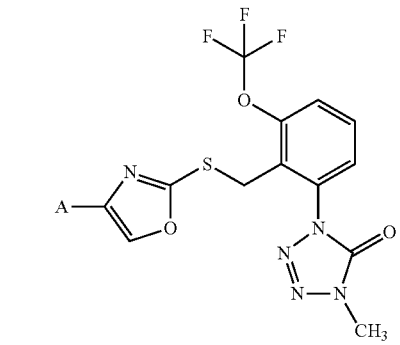

[wherein A represents a substituent corresponding to each of substituents Nos. 1 to 379 indicated in Table 1 to Table 16 as below-mentioned];

Compounds ADP-001~ADP-379 represent tetrazolinone Compounds represented by a formula:

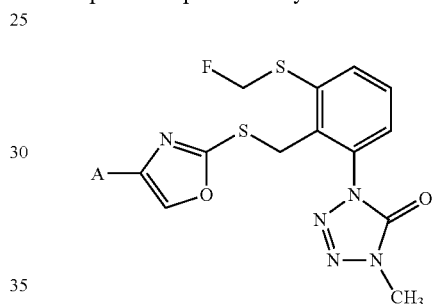

[wherein A represents a substituent corresponding to each of substituents Nos. 1 to 379 indicated in Table 1 to Table 16 as below-mentioned];

Compounds ADQ-001~ADQ-379 represent tetrazolinone Compounds represented by a formula:

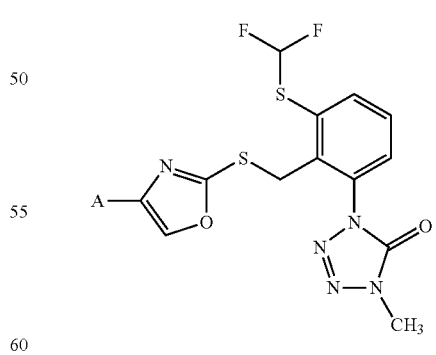

[wherein A represents a substituent corresponding to each of substituents Nos. 1 to 379 indicated in Table 1 to Table 16 as below-mentioned];

Compounds ADR-001~ADR-379 represent tetrazolinone Compounds represented by a formula:

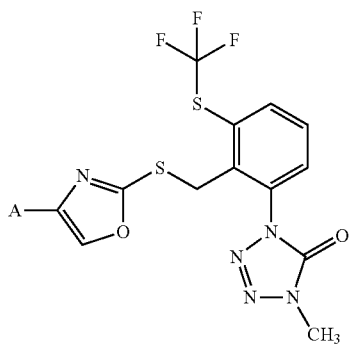

[wherein A represents a substituent corresponding to each of substituents Nos. 1 to 379 indicated in Table 1 to Table 16 as below-mentioned];

Compounds ADS-001~ADS-379 represent tetrazolinone Compounds represented by a formula:

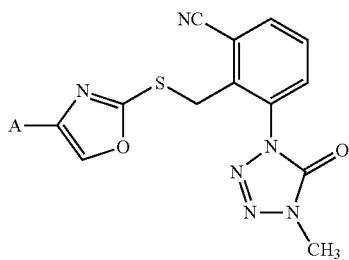

[wherein A represents a substituent corresponding to each of substituents Nos. 1 to 379 indicated in Table 1 to Table 16 as below-mentioned].

TABLE 1

| substituents Nos. | A |
|---|---|
| 1 | phenyl group |
| 2 | 2-fluorophenyl group |
| 3 | 3-fluorophenyl group |
| 4 | 4-fluorophenyl group |
| 5 | 2,4-difluorophenyl group |
| 6 | 2,4,6-trifluorophenyl group |
| 7 | 2,3,4,5,6-pentafluorophenyl group |
| 8 | 2,3-difluorophenyl group |
| 9 | 2-chlorophenyl group |
| 10 | 3-chlorophenyl group |
| 11 | 4-chlorophenyl group |
| 12 | 2,3-dichlorophenyl group |
| 13 | 2,4-dichlorophenyl group |
| 14 | 2,5-dichlorophenyl group |
| 15 | 2,6-dichlorophenyl group |
| 16 | 3,4-dichlorophenyl group |
| 17 | 3,5-dichlorophenyl group |
| 18 | 2,3,4-trichlorophenyl group |
| 19 | 2,3,5-trichlorophenyl group |
| 20 | 2,3,6-trichlorophenyl group |
| 21 | 2,4,5-trichlorophenyl group |
| 22 | 2,4,6-trichlorophenyl group |
| 23 | 3,4,5-trichlorophenyl group |
| 24 | 2,3,4,6-tetrachlorophenyl group |
| 25 | 2,3,5,6-tetrachlorophenyl group |

TABLE 2

| substituents Nos. | A |
|---|---|
| 26 | 2,3,4,5,6-pentachlorophenyl group |
| 27 | 2-bromophenyl group |
| 28 | 3-bromophenyl group |
| 29 | 4-bromophenyl group |
| 30 | 2,4-dibromophenyl group |
| 31 | 2,5-dibromophenyl group |
| 32 | 2,6-dibromophenyl group |
| 33 | 2,4,6-tribromophenyl group |
| 34 | 2,3,4,5,6-pentabromophenyl group |
| 35 | 2-iodophenyl group |
| 36 | 3-iodophenyl group |
| 37 | 4-iodophenyl group |
| 38 | 2,4-diiodophenyl group |
| 39 | 2-chloro-3-fluorophenyl group |
| 40 | 2-chloro-4-fluorophenyl group |
| 41 | 2-chloro-5-fluorophenyl group |
| 42 | 2-chloro-6-fluorophenyl group |
| 43 | 2-chloro-3-bromophenyl group |
| 44 | 2-chloro-4-bromophenyl group |
| 45 | 2-chloro-5-bromophenyl group |
| 46 | 2-chloro-6-bromophenyl group |
| 47 | 2-bromo-3-chlorophenyl group |
| 48 | 2-bromo-4-chlorophenyl group |
| 49 | 2-bromo-5-chlorophenyl group |
| 50 | 2-bromo-3-fluorophenyl group |

TABLE 3

| substituents Nos. | A |
|---|---|
| 51 | 2-bromo-4-fluorophenyl group |
| 52 | 2-bromo-5-fluorophenyl group |
| 53 | 2-bromo-6-fluorophenyl group |
| 54 | 2-fluoro-3-chlorophenyl group |
| 55 | 2-fluoro-4-chlorophenyl group |
| 56 | 2-fluoro-5-chlorophenyl group |
| 57 | 2-fluoro-4-bromophenyl group |
| 58 | 3-chloro-4-fluorophenyl group |
| 59 | 3-chloro-5-fluorophenyl group |
| 60 | 3-chloro-4-bromophenyl group |
| 61 | 3-chloro-5-bromophenyl group |
| 62 | 3-fluoro-4-chlorophenyl group |
| 63 | 3-fluoro-4-bromophenyl group |
| 64 | 3-bromo-4-chlorophenyl group |
| 65 | 3-bromo-4-fluorophenyl group |
| 66 | 2,6-dichloro-4-bromophenyl group |
| 67 | 2,3-difluoro-4-chlorophenyl group |
| 68 | 2,6-difluoro-4-chlorophenyl group |
| 69 | 2,5-difluoro-4-chlorophenyl group |
| 70 | 3,5-difluoro-4-chlorophenyl group |
| 71 | 2,3,5-trifluoro-4-chlorophenyl group |
| 72 | 2,3,6-trifluoro-4-chlorophenyl group |
| 73 | 2,3,5,6-tetrafluoro-4-chlorophenyl group |
| 74 | 2-fluoro-4-bromophenyl group |
| 75 | 2,3-difluoro-4-bromophenyl group |

TABLE 4

| substituents Nos. | A |
|---|---|
| 76 | 2,6-difluoro-4-bromophenyl group |
| 77 | 2,5-difluoro-4-bromophenyl group |
| 78 | 3,5-difluoro-4-bromophenyl group |
| 79 | 2,3,5-trifluoro-4-bromophenyl group |
| 80 | 2,3,6-trifluoro-4-bromophenyl group |
| 81 | 2,3,5,6-tetrafluoro-4-bromophenyl group |
| 82 | 2-fluoro-4-iodophenyl group |
| 83 | 3-fluoro-4-iodophenyl group |
| 84 | 2,3-difluoro-4-iodophenyl group |
| 85 | 2,6-difluoro-4-iodophenyl group |

TABLE 4-continued

| substituents Nos. | A |
|---|---|
| 86 | 2,5-difluoro-4-iodophenyl group |
| 87 | 3,5-difluoro-4-iodophenyl group |
| 88 | 2,3,5-trifluoro-4-iodophenyl group |
| 89 | 2,3,6-trifluoro-4-iodophenyl group |
| 90 | 2,3,5,6-tetrafluoro-4-iodophenyl group |
| 91 | 2-methylphenyl group |
| 92 | 3-methylphenyl group |
| 93 | 4-methylphenyl group |
| 94 | 2,3-dimethylphenyl group |
| 95 | 2,4-dimethylphenyl group |
| 96 | 2,5-dimethylphenyl group |
| 97 | 2,6-dimethylphenyl group |
| 98 | 3,4-dimethylphenyl group |
| 99 | 3,5-dimethylphenyl group |
| 100 | 2,3,5-trimethylphenyl group |

TABLE 5

| substituents Nos. | A |
|---|---|
| 101 | 2,3,4-trimethylphenyl group |
| 102 | 2,3,6-trimethylphenyl group |
| 103 | 2,4,5-trimethylphenyl group |
| 104 | 2,4,6-trimethylphenyl group |
| 105 | 3,4,5-trimethylphenyl group |
| 106 | 2,3,4,6-tetramethylphenyl group |
| 107 | 2,3,5,6-tetramethylphenyl group |
| 108 | 2,3,4,5,6-pentamethylphenyl group |
| 109 | 2-ethylphenyl group |
| 110 | 3-ethylphenyl group |
| 111 | 4-ethylphenyl group |
| 112 | 2,4-diethylphenyl group |
| 113 | 2,6-diethylphenyl group |
| 114 | 3,5-diethylphenyl group |
| 115 | 2,4,6-triethylphenyl group |
| 116 | 2-n-propylphenyl group |
| 117 | 3-n-propylphenyl group |
| 118 | 4-n-propylphenylgroup |
| 119 | 2-isopropylphenyl group |
| 120 | 3-isopropylphenyl group |
| 121 | 4-isopropylphenyl group |
| 122 | 2,4-diisopropylphenyl group |
| 123 | 2,6-diisopropylphenyl group |
| 124 | 3,5-diisopropylphenyl group |
| 125 | 2-s-butylphenyl group |

TABLE 6

| substituents Nos. | A |
|---|---|
| 126 | 3-s-butylphenyl group |
| 127 | 4-s-butylphenyl group |
| 128 | 2-t-butylphenyl group |
| 129 | 3-t-butylphenyl group |
| 130 | 4-t-butylphenyl group |
| 131 | 2-n-butylphenyl group |
| 132 | 3-n-butylphenyl group |
| 133 | 4-n-butylphenyl group |
| 134 | 2-n-nonylphenyl group |
| 135 | 3-n-nonylphenyl group |
| 136 | 4-n-nonylphenyl group |
| 137 | 2-methyl-4-t-butylphenyl group |
| 138 | 2-methyl-6-t-butylphenyl group |
| 139 | 2-methyl-4-isopropylphenyl group |
| 140 | 2-methyl-5-isopropylphenyl group |
| 141 | 3-methyl-4-isopropylphenyl group |
| 142 | 2-cyclohexylphenyl group |
| 143 | 3-cyclohexylphenyl group |
| 144 | 4-cyclohexylphenyl group |
| 145 | 2-cyclopropylphenyl group |

TABLE 6-continued

| substituents Nos. | A |
|---|---|
| 146 | 3-cyclopropylphenyl group |
| 147 | 4-cyclopropylphenyl group |
| 148 | 4-cyclobutylphenyl group |
| 149 | 2-cyclopentylphenyl group |
| 150 | 3-cyclopentylphenyl group |

TABLE 7

| substituents Nos. | A |
|---|---|
| 151 | 4-cyclopentylphenyl group |
| 152 | 2'-chloro[1,1'-biphenyl]-4-yl group |
| 153 | 2'-bromo[1,1'-biphenyl]-4-yl group |
| 154 | 2-hydroxylphenyl group |
| 155 | 3-hydroxylphenyl group |
| 156 | 4-hydroxylphenyl group |
| 157 | 2-methoxyphenyl group |
| 158 | 3-methoxyphenyl group |
| 159 | 4-methoxyphenyl group |
| 160 | 2-ethoxyphenyl group |
| 161 | 3-ethoxyphenyl group |
| 162 | 4-ethoxyphenyl group |
| 163 | 2-n-propyloxyphenyl group |
| 164 | 3-n-propyloxyphenyl group |
| 165 | 4-n-propyloxyphenyl group |
| 166 | 2-isopropyloxyphenyl group |
| 167 | 3-isopropyloxyphenyl group |
| 168 | 4-isopropyloxyphenyl group |
| 169 | 2-n-hexyloxyphenyl group |
| 170 | 3-n-hexyloxyphenyl group |
| 171 | 4-n-hexyloxyphenyl group |
| 172 | 2-benzyloxyphenyl group |
| 173 | 3-benzyloxyphenyl group |
| 174 | 4-benzyloxyphenyl group |
| 175 | 2,3-dimethoxyphenyl group |

TABLE 8

| substituents Nos. | A |
|---|---|
| 176 | 2,4-dimethoxyphenyl group |
| 177 | 2,5-dimethoxyphenyl group |
| 178 | 2,6-dimethoxyphenyl group |
| 179 | 3,4-dimethoxyphenyl group |
| 180 | 3,5-dimethoxyphenyl group |
| 181 | 2-t-butoxyphenyl group |
| 182 | 3-t-butoxyphenyl group |
| 183 | 4-t-butoxyphenyl group |
| 184 | 3-(3'-chlorophenyl)phenyl group |
| 185 | 4-(4'-chlorophenyl)phenyl group |
| 186 | 2-phenoxyphenyl group |
| 187 | 3-phenoxyphenyl group |
| 188 | 4-phenoxyphenyl group |
| 189 | 2-(2'-fluorophenoxy)phenyl group |
| 190 | 3-(3'-chlorophenoxy)phenyl group |
| 191 | 4-(4'-chlorophenoxy)phenyl group |
| 192 | 2,3,6-trimethyl-4-fluorophenyl group |
| 193 | 2,3,6-trimethyl-4-chlorophenyl group |
| 194 | 2,3,6-trimethyl-4-bromophenyl group |
| 195 | 2,4-dimethyl-6-fluorophenyl group |
| 196 | 2,4-dimethyl-6-chlorophenyl group |
| 197 | 2,4-dimethyl-6-bromophenyl group |
| 198 | 2-isopropyl-4-chloro-5-methylphenylgroup |
| 199 | 2-chloro-4-nitrophenyl group |
| 200 | 2-nitro-4-chlorophenyl group |

TABLE 9

| substituents Nos. | A |
| --- | --- |
| 201 | 2-methoxy-5-nitrophenyl group |
| 202 | 2,4-dichloro-5-nitrophenyl group |
| 203 | 2,4-dichloro-6-nitrophenyl group |
| 204 | 2,6-dichloro-4-nitrophenyl group |
| 205 | 2,6-dibromo-4-nitrophenyl group |
| 206 | 2,6-diiodo-4-nitrophenyl group |
| 207 | 2-methyl-5-isopropyl-4-chlorophenylgroup |
| 208 | 2-methoxycarbonylphenyl group |
| 209 | 3-methoxycarbonylphenyl group |
| 210 | 4-methoxycarbonylphenyl group |
| 211 | 2-acetoxyphenyl group |
| 212 | 3-acetoxyphenyl group |
| 213 | 4-acetoxyphenyl group |
| 214 | 2-methoxymethylphenyl group |
| 215 | 3-methoxymethylphenyl group |
| 216 | 4-methoxymethylphenyl group |
| 217 | [1,1'-biphenyl]-4-yl group |
| 218 | [1,1'-biphenyl]-3-yl group |
| 219 | [1,1'-biphenyl]-2-yl group |
| 220 | 2-(2'-fluorophenyl)phenyl group |
| 221 | 2-methyl-5-bromophenyl group |
| 222 | 2-methyl-6-bromophenyl group |
| 223 | 2-chloro-3-methylphenyl group |
| 224 | 2-chloro-4-methylphenyl group |
| 225 | 2-chloro-5-methylphenyl group |

TABLE 10

| substituents Nos. | A |
| --- | --- |
| 226 | 2-fluoro-3-methylphenyl group |
| 227 | 2-fluoro-4-methylphenyl group |
| 228 | 2-fluoro-5-methylphenyl group |
| 229 | 2-bromo-3-methylphenyl group |
| 230 | 2-bromo-4-methylphenyl group |
| 231 | 2-bromo-5-methylphenyl group |
| 232 | 3-methyl-4-chlorophenyl group |
| 233 | 3-methyl-5-chlorophenyl group |
| 234 | 3-methyl-4-fluorophenyl group |
| 235 | 3-methyl-5-fluorophenyl group |
| 236 | 3-methyl-4-bromophenyl group |
| 237 | 3-methyl-5-bromophenyl group |
| 238 | 3-fluoro-4-methylphenyl group |
| 239 | 3-chloro-4-methylphenyl group |
| 240 | 3-bromo-4-methylphenyl group |
| 241 | 2-chloro-4,5-dimethylphenyl group |
| 242 | 2-bromo-4,5-dimethylphenyl group |
| 243 | 2-chloro-3,5-dimethylphenyl group |
| 244 | 2-bromo-3,5-dimethylphenyl group |
| 245 | 2,6-dibromo-4-methylphenyl group |
| 246 | 2,4-dichloro-6-methylphenyl group |
| 247 | 2,6-dichloro-4-methylphenyl group |
| 248 | 2,4-difluoro-6-methylphenyl group |
| 249 | 2,4-dibromo-6-methylphenyl group |
| 250 | 2,6-dimethyl-4-fluorophenyl group |

TABLE 11

| substituents Nos. | A |
| --- | --- |
| 251 | 2,6-dimethyl-4-chlorophenyl group |
| 252 | 2,6-dimethyl-4-bromophenyl group |
| 253 | 3,5-dimethyl-4-fluorophenyl group |
| 254 | 3,5-dimethyl-4-chlorophenyl group |
| 255 | 3,5-dimethyl-4-bromophenyl group |
| 256 | 2,3-difluoro-4-methylphenyl group |
| 257 | 2,5-difluoro-4-methylphenyl group |
| 258 | 3,5-difluoro-4-methylphenyl group |
| 259 | 2,6-difluoro-4-methylphenyl group |
| 260 | 2,3,5-trifluoro-4-methylphenyl group |

TABLE 11-continued

| substituents Nos. | A |
| --- | --- |
| 261 | 2,3,6-trifluoro-4-methylphenyl group |
| 262 | 2,3,5,6-tetrafluoro-4-methylphenyl group |
| 263 | 2-fluoro-4-ethylphenyl group |
| 264 | 3-fluoro-4-ethylphenyl group |
| 265 | 2,3-difluoro-4-ethylphenyl group |
| 266 | 2,6-difluoro-4-ethylphenyl group |
| 267 | 2,5-difluoro-4-ethylphenyl group |
| 268 | 3,5-difluoro-4-ethylphenyl group |
| 269 | 2,3,5-trifluoro-4-ethylphenyl group |
| 270 | 2,3,6-trifluoro-4-ethylphenyl group |
| 271 | 2,3,5,6-tetrafluoro-4-ethylphenyl group |
| 272 | 2-trifluoromethylphenyl group |
| 273 | 3-trifluoromethylphenyl group |
| 274 | 4-trifluoromethylphenyl group |
| 275 | 4-(2,2,2-trifluoro-1-trifluoromethylethyl)phenyl group |

TABLE 12

| substituents Nos. | A |
| --- | --- |
| 276 | 2-trifluoromethoxyphenyl group |
| 277 | 3-trifluoromethoxyphenyl group |
| 278 | 4-trifluoromethoxyphenyl group |
| 279 | 4-(2,2-difluoroethoxy)phenyl group |
| 280 | 4-(2,2,2-trifluoroethoxy)phenyl group |
| 281 | 2-nitrophenyl group |
| 282 | 3-nitrophenyl group |
| 283 | 4-nitrophenyl group |
| 284 | 2-cyanophenyl group |
| 285 | 3-cyanophenyl group |
| 286 | 4-cyanophenyl group |
| 287 | 2-methyl-3-chlorophenyl group |
| 288 | 2-methyl-4-chlorophenyl group |
| 289 | 2-methyl-5-chlorophenyl group |
| 290 | 2-methyl-6-chlorophenyl group |
| 291 | 2-methyl-3-fluorophenyl group |
| 292 | 2-methyl-4-fluorophenyl group |
| 293 | 2-methyl-5-fluorophenyl group |
| 294 | 2-methyl-6-fluorophenyl group |
| 295 | 2-methyl-3-bromophenyl group |
| 296 | 2-methyl-4-bromophenyl group |
| 297 | 2-methylthiophenyl group |
| 298 | 3-methylthiophenyl group |
| 299 | 4-methylthiophenyl group |
| 300 | 2-methylsulfonylphenyl group |

TABLE 13

| substituents Nos. | A |
| --- | --- |
| 301 | 3-methylsulfonylphenyl group |
| 302 | 4-methylsulfonylphenyl group |
| 303 | 2-methylsulfinylphenyl group |
| 304 | 3-methylsulfinylphenyl group |
| 305 | 4-methylsulfinylphenyl group |
| 306 | 2-trifluoromethylthiophenyl group |
| 307 | 3-trifluoromethylthiophenyl group |
| 308 | 4-trifluoromethylthiophenyl group |
| 309 | 2-ethynylphenyl group |
| 310 | 3-ethynylphenyl group |
| 311 | 4-ethynylphenyl group |
| 312 | 2-(1-propenyl)phenyl group |
| 313 | 3-(1-propenyl)phenyl group |
| 314 | 4-(1-propenyl)phenyl group |
| 315 | 2-vinylphenyl group |
| 316 | 3-vinylphenyl group |
| 317 | 4-vinylphenyl group |
| 318 | 4-(2,2-dichlorovinyl)phenyl group |
| 319 | 4-(2,2-difluorovinyl)phenyl group |

TABLE 13-continued

| substituents Nos. | A |
|---|---|
| 320 | cyclohexyl group |
| 321 | 2-chlorocyclohexyl group |
| 322 | 3-chlorocyclohexyl group |
| 323 | 4-chlorocyclohexyl group |
| 324 | 4,4-dichlorocyclohexyl group |
| 325 | 2-bromocyclohexyl group |

TABLE 14

| substituents Nos. | A |
|---|---|
| 326 | 3-bromocyclohexyl group |
| 327 | 4-bromocyclohexyl group |
| 328 | 4,4-dibromocyclohexyl group |
| 329 | 2-iodocyclohexyl group |
| 330 | 3-iodocyclohexyl group |
| 331 | 4-iodocyclohexyl group |
| 332 | 2-fluorocyclohexyl group |
| 333 | 3-fluorocyclohexyl group |
| 334 | 4-fluorocyclohexyl group |
| 335 | 4,4-difluorocyclohexyl group |
| 336 | 4-methylcyclohexyl group |
| 337 | 4-ethylcyclohexyl group |
| 338 | 1-cyclohexenyl group |
| 339 | 2-cyclohexenyl group |
| 340 | 3-cyclohexenyl group |
| 341 | 2-chloro-1-cyclohexenyl group |
| 342 | 3-chloro-1-cyclohexenyl group |
| 343 | 4-chloro-1-cyclohexenyl group |
| 344 | 5-chloro-1-cyclohexenyl group |
| 345 | 6-chloro-1-cyclohexenyl group |
| 346 | 1-chloro-2-cyclohexenyl group |
| 347 | 2-chloro-2-cyclohexenyl group |
| 348 | 3-chloro-2-cyclohexenyl group |
| 349 | 4-chloro-2-cyclohexenyl group |
| 350 | 5-chloro-2-cyclohexenyl group |

TABLE 15

| substituents Nos. | A |
|---|---|
| 351 | 6-chloro-2-cyclohexenyl group |
| 352 | 1-chloro-3-cyclohexenyl group |
| 353 | 2-chloro-3-cyclohexenyl group |
| 354 | 3-chloro-3-cyclohexenyl group |
| 355 | 4-chloro-3-cyclohexenyl group |
| 356 | 5-chloro-3-cyclohexenyl group |
| 357 | 6-chloro-3-cyclohexenyl group |
| 358 | 4-bromo-1-cyclohexenyl group |
| 359 | 4-bromo-2-cyclohexenyl group |
| 360 | 4-bromo-3-cyclohexenyl group |
| 361 | 4-methyl-1-cyclohexenyl group |
| 362 | 4-methyl-2-cyclohexenyl group |
| 363 | 4-methyl-3-cyclohexenyl group |
| 364 | 4-ethyl-1-cyclohexenyl group |
| 365 | 4-ethyl-2-cyclohexenyl group |
| 366 | 4-ethyl-3-cyclohexenyl group |
| 367 | trifluoromethyl group |
| 368 | tert-butyl group |
| 369 | 4-(2-(2-methoxyethoxy)ethoxy)phenyl group |
| 370 | 4-(2-tetrahydropyranyloxy)phenyl group |
| 371 | 4-(N,N-dimethylamino) sulfonylphenyl group |
| 372 | 1-naphthyl group |
| 373 | 2-naphthyl group |
| 374 | adamantane-1-yl group |
| 375 | 3-methyladamantane-1-yl group |

TABLE 16

| substituents Nos. | A |
|---|---|
| 376 | 5-methyladamantane-1-yl group |
| 377 | 5,7-dimethyladamantane-1-yl group |
| 378 | 3,5-dimethyladamantane-1-yl group |
| 379 | 3,5,7-trimethyladamantane-1-yl group |

Next, the Formulation examples are shown below. In the Examples, the term "part(s)" means part(s) by weight unless otherwise specified.

Formulation Example 1

Fifty (50) parts of any one of the present Compounds T001 to T149, 3 parts of calcium lignosulfonate, 2 parts of magnesium lauryl sulfate and 45 parts of synthetic hydrated silicon dioxide are well mixed while grinding to obtain a formulation.

Formulation Example 2

Twenty (20) parts of any one of the present Compounds T001 to T149, 1.5 parts of sorbitan trioleate are mixed with 28.5 parts of an aqueous solution containing 2 parts of polyvinyl alcohol, and the mixture is then finely-ground by a wet grinding method. To this mixture is then added 40 parts of an aqueous solution containing 0.05 parts of xanthane gum and 0.1 parts of magnesium aluminium silicate, and 10 parts of propylene glycol is further added thereto. The mixture is stirred to obtain a formulation.

Formulation Example 3

Two (2) parts of any one of the present Compounds T001 to T149, 88 parts of kaolin clay and 10 parts of talc are mixed-grinding to obtain a formulation.

Formulation Example 4

Five (5) parts of any one of the present Compounds T001 to T149, 14 parts of polyoxyethylene styryl phenyl ether, 6 parts of calcium dodecylbenzene sulfonate and 75 parts of xylene are mixed-grinding to obtain a formulation.

Formulation Example 5

Two (2) parts of any one of the present Compounds T001 to T149, one part of synthetic hydrated silicon dioxide, 2 parts of calcium lignosulfonate, 30 parts of bentonite and 65 parts of kaolin clay are mixed-grinding and thereto is added water and the mixture is well kneaded and is then granulated and dried to obtain a formulation.

Formulation Example 6

Ten (10) parts of any one of the present Compounds T001 to T149, 35 parts of white carbon containing 50 parts of ammonium polyoxyethylene alkyl ether sulfate, and 55 parts of water are mixed, and the mixture is then finely-ground by a wet grinding method to obtain a formulation.

Formulation Example 7

Ten (10) parts of any one of the present Compounds T001 to T147, 35 parts of white carbon containing 50 parts of ammonium polyoxyethylene alkyl ether sulfate, and 55 parts of water are mixed, and the mixture is then finely-ground by a wet grinding method to obtain a formulation.

Next, Test examples are used to show an efficacy of the present Compounds on controlling plant diseases.

Here the controlling effects were evaluated by visually observing a lesion area on the tested plants and followed by comparing the lesion area of the plants treated with the present Compounds with a lesion area of the untreated plants.

Test Example 1

A plastic pot was filled with soils and thereto was seeded rice (cv; Nipponbare) and the plants were grown in a greenhouse for twenty days. Thereafter, each of the present Compounds T026, T032 to T034, T036, T047, T048, T059, T064, T066, T071, T073, T077, T080, T091, T102, T106 to T108, T111, T113, T114, T116, T123 and T135 was made to a formulation according to the above-mentioned Formulation examples and was then diluted with water so as to make a predetermined concentration (500 ppm). The dilutions were sprayed to foliar parts so as to adhere adequately on the leaves of the above-mentioned rice. After spraying the dilutions, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*), and a lesion area was observed. As a result, every of the lesion areas in plants treated with the present Compounds T026, T032 to T034, T036, T047, T048, T059, T064, T066, T071, T073, T077, T080, T091, T102, T106 to T108, T111, T113, T114, T116, T123 and T135 showed 30% or less compared to the lesion area in an untreated plants.

Test Example 2

A plastic pot was filled with soils and thereto was seeded rice (cv; Nipponbare) and the plants were grown in a greenhouse for 20 days. Thereafter, each of the present Compounds T003, T005, T009, T014, T018, T025, T035, T049, T051, T053, T062, T063, T065, T067, T072, T076, T086, T087, T094 to T098, T100, T103, T105, T109, T112, T117, T121, T129, T132, T139, T140, T143, T148 and T149 was made to a formulation according to the above-mentioned Formulation examples and was then diluted with water so as to make a predetermined concentration (200 ppm). The dilutions were sprayed to foliar parts so as to adhere adequately on the leaves of the above-mentioned rice. After spraying the dilutions, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*) and a lesion area was observed. As a result, every of the lesion areas in plants treated with the present Compounds T003, T005, T009, T014, T018, T025, T035, T049, T051, T053, T062, T063, T065, T067, T072, T076, T086, T087, T094 to T098, T100, T103, T105, T109, T112, T117, T121, T129, T132, T139, T140, T143, T148 and T149 showed 30% or less compared to the lesion area in an untreated plants.

Test Example 3

A plastic pot was filled with soils and thereto was seeded rice (cv; Nipponbare) and the plants were grown in a greenhouse for 20 days. Thereafter, each of the present Compounds T099, T101 and T115 was made to a formulation according to the above-mentioned Formulation examples and was then diluted with water so as to make a predetermined concentration (50 ppm). The dilutions were sprayed to foliar parts so as to adhere adequately on the leaves of the above-mentioned rice. After spraying the dilution, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*) and a lesion area was observed. As a result, every of the lesion areas in plants treated with the present Compounds T099, T101 and T115 showed 30% or less compared to the lesion area in an untreated plants.

Test Example 4

A plastic pot was filled with soils and thereto was seeded wheat (cv; Shirogane) and the plants were grown in a greenhouse for 9 days. Thereafter, each of the present Compounds T003, T006, T021, T025, T066, T091, T101, T102, T105, T106, T109, T113, T114, T120, T123, T132 and T143 was made to a formulation according to the above-mentioned Formulation examples and was then diluted with water so as to make a predetermined concentration (500 ppm). The dilutions were sprayed to foliar parts so as to adhere adequately on the leaves of the above-mentioned wheat. After spraying the dilutions, the plants were air-dried and were placed at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, every of the lesion areas in plants treated with the present Compounds T003, T006, T021, T025, T066, T091, T101, T102, T105, T106, T109, T113, T114, T120, T123, T132 and T143 showed 30% or less compared to the lesion area in an untreated plants.

Test Example 5

A plastic pot was filled with soils and thereto was seeded wheat (cv; Shirogane) and the plants were grown in a greenhouse for 9 days. Thereafter, each of the present Compounds T004, T009, T012, T015, T026, T032, T034 to T036, T038, T048, T062, T064, T065, T070 to T072, T080, T081, T087, T094, T096, T097, T104, T107, T108, T110, T111, T116, T121, T127, T129 to T131, T134, T146 and T149 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and were placed at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, every of the lesion areas in plants treated with the present Compounds T004, T009, T012, T015, T026, T032, T034 to T036, T038, T048, T062, T064, T065, T070 to T072, T080, T081, T087, T094, T096, T097, T104, T107, T108, T110, T111, T116, T121, T127, T129 to T131, T134, T146 and T149 showed 300 or less compared to the lesion area in an untreated plants.

Test Example 6

A plastic pot was filled with soils and thereto was seeded wheat (cv; Shirogane) and the plants were grown in a greenhouse for 9 days. Thereafter, to the wheat were sprinkling-inoculated the spores of wheat rust fungi (*Puccinia recondita*). The wheat was placed under a dark and humid condition at 23° C. for 1 day and was air-dried. Each of the present Compounds T003, T004 and T013 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and were placed under lighting for 8 days and a lesion area was observed. As a result, every of the lesion areas in plants treated with the present Compounds T003, T004 and T013 showed 30% or less compared to the lesion area in an untreated plants.

Test Example 7

A plastic pot was filled with soils and thereto was seeded barley (cv; Mikamo Golden) and the plants were grown in a greenhouse for 7 days. Thereafter, each of the present Compounds T008, T026, T028, T030 to T040, T044 to T048, T056 to T066, T068, T070, T072 to T088, T090 to T093, T096, T097, T101 to T111, T113 to T123, T125 to T136, T140, T142, T143, T145 to T147, T148 and T149 was made to a formulation according to the above-mentioned Formulation examples and was then diluted with water so as to make a predetermined concentration (500 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compounds T008, T026, T028, T030 to T040, T044 to T048, T056 to T066, T068, T070, T072 to T088, T090 to T093, T096, T097, T101 to T111, T113 to T123, T125 to T136, T140, T142, T143, T145 to T147, T148 and T149 showed 30% or less compared to the lesion area in an untreated plants.

Test Example 8

A plastic pot was filled with soils and thereto was seeded barley (cv; Mikamo Golden) and the plants were grown in a greenhouse for 7 days. Thereafter, each of the present Compounds T002 to T006, T009 to T015, T017 to T019, T021, T023 to T025, T027, T041, T042, T049 to T054, T067, T071, T094, T098, T100, T112, T137, T139 and T141 was made to a formulation according to the above-mentioned Formulation examples and was then diluted with water so as to make a predetermined concentration (200 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compounds T002 to T006, T009 to T015, T017 to T019, T021, T023 to T025, T027, T041, T042, T049 to T054, T067, T071, T094, T098, T100, T112, T137, T139 and T141 showed 30% or less compared to the lesion area in an untreated plants.

Test Example 9

A plastic pot was filled with soils and thereto was seeded barley (cv; Mikamo Golden) and the plants were grown in a greenhouse for 7 days. Each of the present Compounds T001 and T029 was made to a formulation according to the above-mentioned Formulation examples and was then diluted with water so as to make a predetermined concentration (50 ppm). After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compounds T001 and T029 showed 10% or less compared to the lesion area in an untreated plants.

Test Example 10

A plastic pot was filled with soils and thereto was seeded tomato (cv; Patio) and the plants were grown in a greenhouse for 20 days. The present compound T047 was made to a flowable according to the above-mentioned Formulation examples and was then diluted with water so as to make a predetermined concentration (500 ppm). The dilutions were sprayed to foliar parts so as to adhere adequately on the leaves of the above-mentioned tomato. After the plants were air-dried to such an extent that the dilutions were dried, an aqueous suspension of the spores of tomato late blight fungi (*Phytophthora infestans*) was spraying-inoculated. After inoculation, the plants were at first placed at 23° C. under a high humidity for 1 day and were then cultivated at 20° C. in an air-conditioned room for 4 days, and a lesion area was observed. As a result, every of the lesion areas in plants treated with the present compound T047 showed 30% or less compared to the lesion area in an untreated plants.

Test Example 11

A plastic pot was filled with soils and thereto was seeded tomato (cv; Patio) and the plants were grown in a greenhouse for 20 days. The present Compounds T053 and T127 were made to flowables according to the above-mentioned Formulation examples and were then diluted with water so as to make a predetermined concentration (200 ppm). The dilutions were sprayed to foliar parts so as to adhere adequately on the leaves of the above-mentioned tomato. After the plants were air-dried to such an extent that the dilutions were dried, an aqueous suspension of the spores of tomato late blight fungi (*Phytophthora infestans*) was spraying-inoculated. After inoculation, the plants were at first placed at 23° C. under a high humidity for 1 day and were then cultivated at 20° C. in an air-conditioned room for 4 days, and a lesion area was observed. As a result, every of the lesion areas in plants treated with the present Compounds T053 and T127 showed 30% or less compared to the lesion area in an untreated plants.

Test Example 12

A plastic pot was filled with soils and thereto was seeded Kidney bean (cv; Nagauzura-saitou) and the plants were grown in a greenhouse for 8 days. Either of the present Compounds T029, T031, T039, T040, T045, T047, T058, T062 to T066, T076, T080, T090, T091, T102, T103, T105 to T111, T113, T116, T117, T121, T127, T129, T130, T132 and T146 was made to a formulation according to the above-mentioned Formulation examples and was then diluted with water so as to make a predetermined concentration (500 ppm). The dilutions were sprayed to foliar parts so as to adhere adequately on the leaves of the above-mentioned kidney bean. After spraying the dilutions, the plants were air-dried and a PDA medium containing hyphae of kidney bean *sclerotinia* rot fungi (*Sclerotinia sclerotiorum*) was placed on the leaves of the kidney bean. After inoculation, all kidney beans were placed under a high humidity during only night and after four days, and a lesion area was observed. As a result, every of the lesion areas in plants treated with either the present Compounds T029, T031, T039, T040, T045, T047, T058, T062 to T066, T076, T080, T090, T091, T102, T103, T105 to T111, T113, T116, T117, T121, T127, T129, T130, T132 and T146 showed 30% or less compared to the lesion area in an untreated plants.

Test Example 13

A plastic pot was filled with soils and thereto was seeded Kidney bean (cv; Nagauzura-saitou) and the plants were grown in a greenhouse for 8 days. Either of the present Compounds T059, T061, T087, T093, T094, T097, T120, T125, T131 and T140 was made to a formulation according to the above-mentioned Formulation examples and was then diluted with water so as to make a predetermined concentration (200 ppm). The dilutions were sprayed to foliar parts so as to adhere adequately on the leaves of the above-mentioned kidney bean. After spraying the formulations, the plants were air-dried and a PDA medium containing hyphae of kidney bean *sclerotinia* rot fungi (*Sclerotinia sclerotiorum*) was placed on the leaves of the kidney bean. After inoculation, all kidney beans were placed under a high humidity during only night and after four days, and a lesion area was observed. As a result, every of the lesion areas in plants treated with either the present Compounds T059, T061, T087, T093, T094, T097, T120, T125, T131 and T140 showed 300 or less compared to the lesion area in an untreated plants.

Test Example 14

A plastic pot was filled with soils and thereto was seeded wheat (cv; Apogee) and the plants were grown in a greenhouse for 10 days. Each of the present Compounds T002 to T004, T012, T013, T025 to T027, T029 to T041, T045 to T048, T059 to T066, T070 to T075, T077 to T081, T085 to T088, T090 to T093, T096, T097, T101 to T111, T113, T114, T116 to T118, T120 to T123, T125 to T127, T129 to T132, T134, T135, T137, T138, T140, T142, T143, T145, T146 and T148 was made to a formulation according to the above-mentioned Formulation examples and was then diluted with water so as to make a predetermined concentration (500 ppm). The dilutions were spread to foliar parts so as to adhere adequately on the leaves of the above-mentioned wheat. After spraying the dilutions, the plants were air-dried and after 4 days, an aqueous suspension of the spores of wheat leaf blotch fungi (*Septoria tritici*) was spraying-inoculated. After inoculation, the plants were placed at 18° C. under a high humidity for 3 days and then under lighting for 14 to 18 days, and a lesion area was observed. As a result, every of the lesion areas in plants treated with the present Compounds T002 to T004, T012, T013, T025 to T027, T029 to T041, T045 to T048, T059 to T066, T070 to T075, T077 to T081, T085 to T088, T090 to T093, T096, T097, T101 to T111, T113, T114, T116 to T118, T120 to T123, T125 to T127, T129 to T132, T134, T135, T137, T138, T140, T142, T143, T145, T146 and T148 showed 30% or less compared to the lesion area in an untreated plants.

Test Example 15

A plastic pot was filled with soils and thereto was seeded wheat (cv; Apogee) and the plants were grown in a greenhouse for 10 days. Each of the present Compounds T001, T009, T011, T014, T022, T042, T044, T049 to T053, T056, T058, T067, T076, T094, T095, T098, T100, T112, T133, T136, T139, T144 and T149 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and after 4 days, an aqueous suspension of the spores of wheat leaf blotch fungi (*Septoria tritici*) was spraying-inoculated. After inoculation, the plants were placed at 18° C. under a high humidity for 3 days and then under lighting for 14 to 18 days, and a lesion area was observed. As a result, every of the lesion areas in plants treated with the present Compounds T001, T009, T011, T014, T022, T042, T044, T049 to T053, T056, T058, T067, T076, T094, T095, T098, T100, T112, T133, T136, T139, T144 and T149 showed 30% or less compared to the lesion area in an untreated plants.

Test Example 16

A plastic pot was filled with soils and thereto was seeded wheat (cv; Apogee) and the plants were grown in a greenhouse for 10 days. The present compound T099 was made to a formulation according to the above-mentioned Formulation examples and was then diluted with water so as to make a predetermined concentration (50 ppm). The dilutions were sprayed to foliar parts so as to adhere adequately on the leaves of the above-mentioned wheat. After spraying the dilutions, the plants were air-dried and after 4 days, an aqueous suspension of the spores of wheat leaf blotch fungi (*Septoria tritici*) was spraying-inoculated. After inoculation, the plants were placed at 18° C. under a high humidity for 3 days and then under lighting for 14 to 18 days, and a lesion area was observed. As a result, every of the lesion areas in plants treated with the present compound T099 showed 300 or less compared to the lesion area in an untreated plants.

Test Example 17

A plastic pot was filled with soils and thereto was seeded wheat (cv; Apogee) and the plants were grown in a greenhouse for 10 days. Thereafter, to the wheat was spraying-inoculated an aqueous suspension of the spores of wheat leaf blotch fungi (*Septoria tritici*). The wheat was placed at 18° C. under a high humidity for 3 days and was air-dried. Each of the present Compounds T002 to T004, T025, T026, T030 to T036, T046 to T049, T056, T059 to T066, T070, T072 to T074, T079 to T081, T086 to T088, T091, T094 to T098, T102 to T114, T116, T120, T121, T127, T129, T132, T135, T139, T140 and T143 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and were further placed under lighting for 14 to 18 days, and a lesion area was observed. As a result, every of the lesion areas in plants treated with the present Compounds T002 to T004, T025, T026, T030 to T036, T046 to T049, T056, T059 to T066, T070, T072 to T074, T079 to T081, T086 to T088, T091, T094 to T098, T102 to T114, T116, T120, T121, T127, T129, T132, T135, T139, T140 and T143 showed 30% or less compared to the lesion area in an untreated plants.

Test Example 18

A plastic pot was filled with soils and thereto was seeded wheat (cv; Apogee) and the plants were grown in a greenhouse for 10 days. Thereafter, to the wheat was spraying-inoculated an aqueous suspension of the spores of wheat leaf blotch fungi (*Septoria tritici*). The wheat was placed at 18° C. under a high humidity for 3 days and was air-dried. Each of the present Compounds T099 and T101 was made to a formulation according to the above-mentioned Formulation examples and was then diluted with water so as to make a predetermined concentration (50 ppm). The dilutions were sprayed to foliar parts so as to adhere adequately on the leaves of the above-mentioned wheat. After spraying the dilutions, the plants were air-dried and were further placed under lighting for 14 to 18 days, and a lesion area was observed. As a result, every of the lesion areas in plants treated with the present Compounds T099 and T101 showed 30% or less compared to the lesion area in an untreated plants.

Test Example 19

A plastic pot was filled with soils and thereto was seeded cucumber (cv; Sagamihanjiro) and the plants were grown in a greenhouse for 12 days. Each of the present Compounds T029 to T034, T036 to T040, T046, T047, T060 to T066, T075 to T077, T080, T081, T084, T086 to T088, T091, T093, T096, T097, T102 to T111, T113 to T121, T123, T127, T129 to T132, T134, T136, T138, T140, T142, T143, T145, T146, T148 and T149 was made to a formulation according to the above-mentioned Formulation examples and was then diluted with water so as to make a predetermined concentration (500 ppm). The dilutions were sprayed to foliar parts so as to adhere adequately on the leaves of the above-mentioned cucumber. After spraying the dilutions, the plants were air-dried and the spores of powdery mildew fungi (*Sphaerotheca fuliginea*) were sprinkling-inoculated. The plants were placed in a greenhouse of 24° C. during daytime and 20° C. during nighttime for 8 days, and a lesion area was observed. As a result, every of the lesion areas in plants treated with the present Compounds T029 to T034, T036 to T040, T046, T047, T060 to T066, T075 to T077, T080, T081, T084, T086 to T088, T091, T093, T096, T097, T102 to T111, T113 to T121, T123, T127, T129 to T132, T134, T136, T138, T140, T142, T143, T145, T146, T148 and T149 showed 30% or less compared to the lesion area in an untreated plants.

Test Example 20

A plastic pot was filled with soils and thereto was seeded cucumber (cv; Sagamihanjiro) and the plants were grown in a greenhouse for 12 days. Each of the present Compounds T011, T042, T079, T094 and T101 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and the spores of powdery mildew fungi (*Sphaerotheca fuliginea*) were sprinkling-inoculated. The plants were placed in a greenhouse of 24° C. during daytime and 20° C. during nighttime for 8 days, and a lesion area was observed. As a result, every of the lesion areas in plants treated with the present Compounds T011, T042, T079, T094, T099 and T101 showed 30% or less compared to the lesion area in an untreated plants.

Test Example 21

A plastic pot was filled with soils and thereto was seeded barley (cv; Mikamo Golden) and the plants were grown in a greenhouse for 7 days. The present compound T025 was made to a formulation according to the above-mentioned Formulation examples and was then diluted with water so as to make a predetermined concentration (500 ppm). The dilutions were sprayed to foliar parts so as to adhere adequately on the leaves of the above-mentioned barley. After spraying the dilutions, the plants were air-dried and after 2 days, an aqueous suspension of the spores of barley scald fungi (*Rhynchosporium secalis*) was spraying-inoculated. After inoculation, the plants were placed in a greenhouse of 23° C. during daytime and 20° C. during nighttime under a high humidity for 3 days and were then cultivated in the greenhouse for 7 days, and a lesion area was observed. As a result, the lesion areas in plants treated with the present compound T025 showed 10% or less compared to the lesion area in an untreated plants.

Test Example 22

A plastic pot was filled with soils and thereto was seeded barley (cv; Mikamo Golden) and the plants were grown in a greenhouse for 7 days. Each of the present Compounds T003, T009, T014, T024, T029 to T036, T038 to T042, T045 to T048, T056, T057, T059 to T066, T073, T075 to T077, T079 to T081, T086 to T088, T091 to T098, T100, T102 to T114, T116 to T118, T120, T121, T125 to T127, T129 to T132, T135, T137, T139, T140, T142, T143, T145, T146, T148 and T149 was made to a formulation according to the above-mentioned Formulation examples and was then diluted with water so as to make a predetermined concentration (200 ppm). The dilutions were sprayed, to foliar parts so as to adhere adequately on the leaves of the above-mentioned barley. After spraying the dilutions, the plants were air-dried and after 2 days, an aqueous suspension of the spores of barley scald fungi (*Rhynchosporium secalis*) was spraying-inoculated. After inoculation, the plants were placed in a greenhouse of 23° C. during daytime and 20° C. during nighttime under a high humidity for 3 days and were then cultivated in the greenhouse for 7 days, and a lesion area was observed. As a result, every of the lesion areas in plants treated with the present Compounds T003, T009, T014, T024, T029 to T036, T038 to T042, T045 to T048, T056, T057, T059 to T066, T073, T075 to T077, T079 to T081, T086 to T088, T091 to T098, T100, T102 to T114, T116 to T118, T120, T121, T125 to T127, T129 to T132, T135, T137, T139, T140, T142, T143, T145, T146, T148 and T149 showed 30% or less compared to the lesion area in an untreated plants.

Test Example 23

A plastic pot was filled with soils and thereto was seeded barley (cv; Mikamo Golden) and the plants were grown in a greenhouse for 7 days. Each of the present Compounds T101 and T115 was made to a formulation according to the above-mentioned Formulation examples and was then diluted with water so as to make a predetermined concentration (50 ppm). The dilutions were sprayed to foliar parts so as to adhere adequately on the leaves of the above-mentioned barley. After spraying the dilutions, the plants were air-dried and after 2 days, an aqueous suspension of the spores of barley scald fungi (*Rhynchosporium secalis*) was spraying-inoculated. After inoculation, the plants were placed in a greenhouse of 23° C. during daytime and 20° C. during nighttime under a high humidity for 3 days and were then cultivated in the greenhouse for 7 days, and a lesion area was observed. As a result, every of the lesion areas in plants treated with the present Compounds T101 and T115 showed 30% or less compared to the lesion area in an untreated plants.

Test Example 24

A plastic pot was filled with soils and thereto was seeded soybean (cv: Kurosengoku) and the plants were grown in a greenhouse for 13 days. Each of the present Compounds T038, T047, T066, T105, T106, T116, T120 and T143 was made to a formulation according to the above-mentioned Formulation examples and was then diluted with water so as to make a predetermined concentration (200 ppm). The dilutions were sprayed to foliar parts so as to adhere adequately on the leaves of the above-mentioned soybean. After spraying the dilutions, the plants were air-dried and after 2 days, an aqueous suspension of the spores of soybean rust fungi (*Phakopsora pachyrhizi*) was spraying-inoculated. After inoculation, the plants were placed in a greenhouse of 23° C. during daytime and 20° C. during nighttime under a high humidity for 3 days and were then cultivated in the greenhouse for 14 days, and a lesion area was observed. As a result, every of the lesion areas in plants treated with the present Compounds T038, T047, T066, T105, T106, T116, T120 and T143 showed 30% or less compared to the lesion area in an untreated plants Test Example 25

A plastic pot was filled with soils and thereto was seeded soybean (cv; Kurosengoku) and the plants were grown in a greenhouse for 13 days. Thereafter, to the soybean was spraying-inoculated an aqueous suspension of the spores of soybean rust fungi (*Phakopsora pachyrhizi*). The soybean was placed at 23° C. under a high humidity for one day and was air-dried. The present compound T047 was made to a formulation according to the above-mentioned Formulation examples and was then diluted with water so as to make a predetermined concentration (200 ppm). The dilutions were sprayed to foliar parts so as to adhere adequately on the leaves of the above-mentioned soybean. After spraying the dilutions, the plants were air-dried and were further placed under lighting for 14 days, and a lesion area was observed. As a result, the lesion areas in plants treated with the present compound T047 showed 30% or less compared to the lesion area in an untreated plants.

Test Example 26

A plastic pot was filled with soils and thereto was seeded grapes (Seeding of Chardonnay) and the plants were grown in a greenhouse for 40 days. Each of the present Compounds T001 to T004 and T012 was made to a formulation according to the above-mentioned Formulation examples and was then diluted with water so as to make a predetermined concentration (200 ppm). The dilutions were sprayed to foliar parts so as to adhere adequately on the leaves of the above-mentioned grapes. After spraying the dilutions, the plants were air-dried to such an extent that the dilutions were dried, and a suspension of the zoosporangium of grapes downy mildew fungi was spraying-inoculated. After inoculation, the plants were placed at 23° C. under a high humidity for 1 day and were then transferred to a greenhouse of 23° C. during a daytime and 20° C. during a nighttime and were cultivated therein for 5 days. Thereafter, the plants were placed under a high humidity for 1 day, and a lesion area was observed. As a result, the lesion areas in plants treated with every of the present Compounds T001 to T004 and T012 showed 30% or less compared to the lesion area in an untreated plants.

Test Example 27

A plastic pot was filled with soils and thereto was seeded cucumber (cv; Sagamihanjiro) and the plants were grown in a greenhouse for 19 days. Each of the present Compounds T066, T091, T093, T094, T097, T099, T100, T102 to T108, T111, T113 to T118, T127, T130, T132, T136, T139, T140, T142, T143 and T146 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber target spot fungi (*Corynespora cassiicola*) was spraying-inoculated. After an inoculation, the plants were placed at 24° C. during daytime and 20° C. during nighttime under a high humidity for 7 days, and a lesion area was observed. As a result, every of the lesion areas in plants treated with the present Compounds T066, T091, T093, T094, T097, T099, T100, T102 to T108, T111, T113 to T118, T127, T130, T132, T136, T139, T140, T142, T143 and T146 showed 30% or less compared to the lesion area in an untreated plants.

Test Example 28

A plastic pot was filled with soils and thereto was seeded cucumber (cv; Sagamihanjiro) and the plants were grown in a greenhouse for 19 days. Each of the present Compounds T063, T066, T088, T091, T093, T101, T102, T104 to T108, T110, T111, T113 to T118, T125 to T127, T129 to T132, T134, T136, T139, T140, T142, T143 and T148 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber anthracnose fungi (*Colletotrichum lagenarium*) was spraying-inoculated. After an inoculation, the plants were placed at first at 23° C. under a high humidity for 1 day and were then cultivated in a greenhouse of 24° C. during daytime and 20° C. during nighttime for 6 days, and a lesion area was observed. As a result, every of the lesion areas in plants treated with the present Compounds T063, T066, T088, T091, T093, T101, T102, T104 to T108, T110, T111, T113 to T118, T125 to T127, T129 to T132, T134, T136, T139, T140, T142, T143 and T148 showed 30% or less compared to the lesion area in an untreated plants.

Test Example 29

A plastic pot was filled with soils and thereto was seeded cucumber (cv; Sagamihanjiro) and the plants were grown in a greenhouse for 19 days. Each of the present Compounds T097 and T103 was made to a formulation according to the above-mentioned Formulation examples and was then diluted with water so as to make a predetermined concentration (50 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber anthracnose fungi (*Colletotrichum lagenarium*) was spraying-inoculated. After an inoculation, the plants were placed at first at 23° C. under a high humidity for 1 day and were then cultivated in a greenhouse of 24° C. during daytime and 20° C. during nighttime for 6 days, and a lesion area was observed. As a result, every of the lesion areas in plants treated with the present Compounds T097 and T103 showed 300 or less compared to the lesion area in an untreated plants.

Test Example 30

A plastic pot was filled with soils and thereto was seeded cucumber (cv; Sagamihanjiro) and the plants were grown in a greenhouse for 19 days. The present compound T095 was made to a formulation according to the above-mentioned Formulation examples and was then diluted with water so as to make a predetermined concentration (12.5 ppm). The dilutions were sprayed to foliar parts so as to adhere adequately on the leaves of the above-mentioned cucumber. After spraying the dilutionss, the plants were air-dried and after 1 day, an aqueous suspension of the spores of cucumber anthracnose fungi (*Colletotrichum lagenarium*) was spraying-inoculated. After an inoculation, the plants were placed at first at 23° C. under a high humidity for 1 day and were then cultivated in a greenhouse of 24° C. during daytime and 20° C. during nighttime for 6 days, and a lesion area was observed. As a result, the lesion areas in plants treated with the present compound T095 showed 30% or less compared to the lesion area in an untreated plants.

Test Example 31

Each formulation containing the present Compounds T125 and T143 prepared according to the above-mentioned Formulation examples was diluted with water so that the active ingredient concentration was set to 500 ppm and the testing drug solutions were prepared. The above-mentioned drug solutions 0.7 mL were added to an ion-exchange water 100 mL (an active ingredient concentration: 3.5 ppm). Twenty (20) last instar larva of common house mosquito (*Culex pipiens pallens*) were released into the solutions and after 1 day, the number of the dead insects was counted. The mortality of insects was calculated by the following equation.

Mortality of insects (%)=(Number of dead insects/ Number of tested insects)×100

As a result, the experiments treated with the present compounds T125 and T143 showed 100% as the mortality of insects.

Test Example 32

The testing drug solutions to be used in this Test example were prepared by diluting the formulations prepared according to the above-mentioned Formulation examples with an ion-exchange water so that the active ingredient concentration was set to 500 ppm. The above-mentioned drug solutions 0.7 mL were added to an ion-exchange water 100 mL so that the active ingredient concentration was set to 3.5 ppm. Twenty (20) last instar larva of common house mosquito (*Culex pipiens pallens*) were released into the solutions and after 8 day, the number of the dead insects was counted.

The mortality of insects was calculated by the following equation.

Mortality of insects (%)=(Number of dead insects/ Number of tested insects)×100

As a result, the present Compounds T042, T091, T097, T144, T146, T147 and T148 showed 100% as the mortality of insects.

Test Example 33

Each formulation containing the present Compounds T033 and T039 prepared according to the above-mentioned Formulation examples was diluted with water so that the active ingredient concentration was set to 500 ppm and the testing drug solutions were prepared.

A bottom of a polyethylene cup having 5.5 cm of diameter was lain with filter paper with the same size as the bottom and thereto was added dropwise the above-mentioned testing solutions 0.7 mL onto the filter paper and sucrose 30 mg as feed was placed uniformly thereon. Ten (10) individuals of female adult housefly (*Musca domestica*) was released into the polyethylene cup and the cup was covered with the lid. After 24 hours, the number of the dead insects was counted. The mortality of insects was calculated by the following equation.

Mortality of insects (%)=(Number of dead insects/ Number of tested insects)×100

As a result, the experiments treated with the present compounds T033 and T039 showed 100% as the mortality of insects.

Test Example 34

The testing drug solutions to be used in this Test example were prepared by diluting the formulations prepared according to the above-mentioned Formulation examples with an ion-exchange water so that the active ingredient concentration was set to 500 ppm. Cabbage (green ball) was planted in a polyethylene cup and was grown until the third true leaf or the fourth true leaf was developed. To the cabbage (*Brassicae oleracea*) was sprayed the above-mentioned testing solutions in a ratio of 20 mL/cup. After the drug solutions were dried, to a polyethylene cup (diameter 5.5 cm) covered with a filter paper on the bottom, the cabbage cut out from the root was installed and five heads of cabbage moth (*Plutella xylostella*) at the three instar larval stages were released into the cup and the cup was covered with the lid. The cup was held at 25° C. and after 5 days, the number of the surviving insects was counted and the mortality of insects was calculated by the following equation.

Mortality of insects (%)=(Number of dead insects/ Number of tested insects)×100

As a result, the experiments treated with the present compounds T034, T036, T041, T042, T091, T125 and T145 showed 80% as the mortality of insects.

Test Example 35

The testing drug solutions to be used in this Test example were prepared by diluting the formulations prepared according to the above-mentioned Formulation examples with an ion-exchange water so that the active ingredient concentration was set to 500 ppm.

On the other hand, to a polyethylene cup where the seedling bush bean (cv; Nagauzura-saitou) was planted (at the stage of a primary leaf being developed after 7 days of the seeding) was released about 60 heads of female adult spider mites (*Tetranychus urticae*) and were left to stand for 1 day. To this seedling was sprayed each of the above-mentioned dilutions 30 mL.

At 8 days post the spraying, the number of the surviving mites on the leaves of the bush bean is observed and the controlling ratio was calculated by the following equation.

Controlling ratio (%)=100×{1−(Number of surviving mites in the treated area)/(Number of surviving mites in the untreated area)}

As a result, the treated area that was treated with the testing spray solutions of the present compound T124 showed 900 or more as the controlling ratio.

Test Example 36

The testing drug solutions to be used in this Test example were prepared by diluting the formulations prepared according to the above-mentioned Formulation examples with an ion-exchange water so that the active ingredient concentration was set to 500 ppm.

A bottom of a polyethylene cup having 5.5 cm of diameter was laid with filter paper with the same size as the bottom. An artificial diet: Insecta LF (which manufactured from Nippon Nosan Kogyo Co., Ltd.) was sliced to 6 mm thickness and was further cut to a half, which was then placed on the paper. Thereto was applied the above-mentioned testing dilutions 1 mL. After the testing dilutions were air-dried, five heads of tobacco cutworm (*Spodoptera litura*) at the four-instar larval stages were released into the cup and the cup was covered with the lid. After 6 days, the number of the surviving insects was observed and the mortality of insects was calculated by the following equation.

Mortality of insects (%)=(Number of dead insects/Number of tested insects)×100

As a result, every of the treated area that was treated with the testing spray solutions of the present Compounds T034 and T041 showed 80% or more as the mortality of insects.

Test Example 37

The testing drug solutions to be used in this Test example were prepared by diluting the formulations prepared according to the above-mentioned Formulation examples with an ion-exchange water so that the active ingredient concentration was set to 500 ppm.

A bottom of a polyethylene cup having 5.5 cm of diameter was laid with filter paper with the same size as the bottom. An artificial diet: Insecta LF (which manufactured from Nippon Nosan Kogyo Co., Ltd.) was sliced to 6 mm thickness, which was then placed on the paper. Thereto was applied the above-mentioned testing dilutions 1 mL. After the testing dilutions were air-dried, thirty heads of summer fruit tortrix (*Adoxophyes orana*) at the first instar larval stage were released into the cup and the cup was covered with the lid. After 7 days, the number of the surviving insects was observed and the mortality of insects was calculated by the following equation.

Mortality of insects (%)=(Number of dead insects/Number of tested insects)×100

As a result, every of the treated area that was treated with the testing spray solutions of the present Compounds T041 and T125 showed 90% or more as the mortality of insects.

Test Example 38

The testing drug solutions to be used in this Test example were prepared by diluting the formulations prepared according to the above-mentioned Formulation examples with an ion-exchange water so that the active ingredient concentration was set to 500 ppm.

Cucumber (Sagami-hanjiro-fushinari) was grown in a polyethylene cup until the first true leaf was developed. Thirty (30) heads of cotton aphid (*Aphis gossypii*) (including the adults and the larvae) was released onto the leaves of the cucumber and next day, the above-mentioned testing drug solutions 20 mL were sprayed. After 6 days, the number of the surviving insects was counted and the control value was calculated by the following equation.

Control value (%)={1−($Cb \times Tai$)/($Cai \times Tb$)}×100 wherein the symbols in the formula represent the following descriptions.

Cb: Number of the insects before treatment in untreated area;

Cai: Number of the insects at the time of the observation in untreated area;

Tb: Number of the insects before treatment in treated area;

Tai: Number of the insects at the time of the observation in treated area;

As a result, the present Compounds T019, T034, T076 and T142 showed 90% or more as the control value.

Comparative Test Example

A plastic pot was filled with soils and thereto was seeded barley (cv; Mikamo Golden) and the plants were grown in a greenhouse for 7 days. A control compound, 4-((1-(4,5-dihydro-4-methyl-5-oxo-1H-tetrazole-1-yl)-2-phenyl-2-yl]methyloxy}-4-phenylthiazole was made to a formulation according to the above-mentioned Formulation examples and was then diluted with water so as to make a predetermined concentration (50 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed in a greenhouse of 23° C. during daytime and 20° C. during nighttime under a high humidity for 3 days and were then cultivated in the greenhouse for 7 days, and a lesion area was observed. As a result, the lesion area in plants treated with the control compound, 4-((1-(4,5-dihydro-4-methyl-5-oxo-1H-tetrazole-1-yl)-2-phenyl-2-yl]methyloxy}-4-phenylthiazole showed 70% or more compared to the lesion area in an untreated plants.

The invention claimed is:
1. A tetrazolinone compound of formula (1):

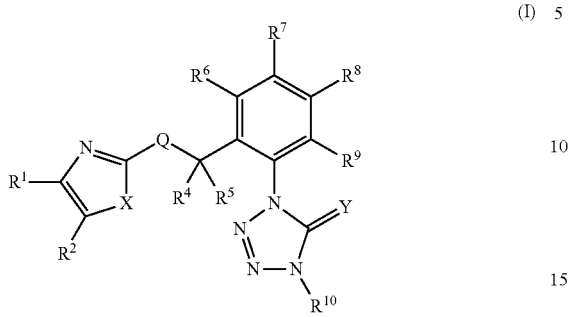

wherein,
R¹ represents an C6-C16 aryl group optionally substituted with one or more substituents selected from the group P¹, an C7-C18 aralkyl group optionally substituted with one or more substituents selected from the group P¹, an C1-C12 alkyl group optionally substituted with one or more substituents selected from the group P¹, an C2-C12 alkenyl group optionally substituted with one or more substituents selected from the group P¹, an C2-C12 alkynyl group optionally substituted with one or more substituents selected from the group P¹, a C3-C12 cycloalkyl group optionally substituted with one or more substituents selected from the group P¹, an C2-C12 acyl group optionally substituted with one or more substituents selected from the group P¹, an adamantyl group optionally substituted with one or more substituents selected from the group P¹, a C3-C12 trialkylsilyl group, a hydrogen atom or a halogen atom with the proviso that when the C6-C16 aryl group, the C7-C18 aralkyl group, the C1-C12 alkyl group, the C2-C12 alkenyl group, the C2-C12 alkynyl group, the C3-C12 cycloalkyl group, the C2-C12 acyl group or the adamantyl group has two or more substituents, the substituents may be same or different to each other;
X represents a sulfur atom or an oxygen atom;
R² represents a hydrogen atom, an C1-C12 alkyl group, a C1-C12 haloalkyl group, an C2-C12 alkenyl group, a C2-C12 haloalkenyl group, an C2-C12 alkynyl group, a C2-C12 haloalkynyl group, an C2-C12 alkoxycarbonyl group, a hydroxycarbonyl group or a halogen atom;
R⁴ and R⁵ represent independently of each other a hydrogen atom, a halogen atom or an C1-C3 alkyl group, or R⁴ and R⁵ combine each other together with the carbon to which they are attached to form a C3-C6 cycloalkane ring;
R⁶, R⁷, R⁸ and R⁹ represent independently of each other an C1-C12 alkyl group, a halogen atom, a C1-C12 haloalkyl group, a C3-C12 cycloalkyl group, a C3-C12 halocycloalkyl group, an C1-C12 alkoxy group, a C1-C12 haloalkoxy group, an C1-C12 alkylthio group, a C1-C12 haloalkylthio group, a nitro group, a cyano group, a hydroxyl group, a thiol group, a pentafluorosulfanyl group, an C2-C12 alkenyl group, a C2-C12 haloalkenyl group, an C2-C12 alkynyl group, a C2-C12 haloalkynyl group, a C3-C12 cycloalkyloxy group, a C3-C12 halocycloalkyloxy group, a C3-C12 cycloalkylthio group, an C2-C12 alkenyloxy group, an C2-C12 alkynyloxy group, a C2-C12 haloalkenyloxy group, a C2-C12 haloalkynyloxy group, an C2-C12 alkynylthio group, an C2-C12 alkenylthio group, a C2-C12 haloalkenylthio group, a C2-C12 haloalkynylthio group, an C2-C12 acyl group, a C2-C12 haloacyl group, an C2-C12 acyloxy group, an C2-C12 acylthio group, an C2-C12 alkoxycarbonyl group, a C3-C12 trialkylsilyl group, a C5-C14 trialkylsilylethynyl group, an C1-C12 alkylsulfonyl group, a C1-C12 haloalkylsulfonyl group, an C1-C12 alkylsulfinyl group, a C1-C12 haloalkylsulfinyl group, an aminosulfonyl group optionally substituted with an C1-C12 alkyl group, an amino group optionally substituted with an C1-C12 alkyl group, an aminocarbonyl group optionally substituted with an C1-C12 alkyl group, a hydrogen atom, a hydroxycarbonyl group, or a formyl group, or
the adjacent R⁶ and R⁷, the adjacent R⁷ and R⁸, or the adjacent R⁸ and R⁹ may connect each other together with the carbon to which they are attached to form a C4-C6 cycloalkene ring, a C5-C6 cycloalkyldiene ring or a benzene ring;
R¹⁰ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group;
Y represents an oxygen atom or a sulfur atom;
Q represents an oxygen atom, a sulfur atom or a NR¹¹ group; and
R¹¹ represents a halogen atom, an C1-C6 alkyl group or a C1-C6 haloalkyl group;
Group P¹: a group consisting of a halogen atom, an C1-C12 alkyl group, a C1-C12 haloalkyl group, an C1-C12 alkoxy group, a C1-C12 haloalkoxy group, an C1-C12 alkylthio group, a C1-C12 haloalkylthio group, a hydroxycarbonyl group, a formyl group, a nitro group, a cyano group, a hydroxyl group, a thiol group, a pentafluorosulfanyl group, an C2-C12 alkenyl group, a C2-C12 haloalkenyl group, an C2-C12 alkynyl group, a C2-C12 haloalkynyl group, a C3-C12 cycloalkyl group, a C3-C12 halocycloalkyl group, a C3-C12 cycloalkyloxy group, a C3-C12 halocycloalkyloxy group, a C3-C12 cycloalkylthio group, an C2-C12 alkenyloxy group, an C2-C12 alkynyloxy group, a C2-C12 haloalkenyloxy group, a C2-C12 haloalkynyloxy group, an C2-C12 alkynylthio group, an C2-C12 alkenylthio group, a C2-C12 haloalkenylthio group, a C2-C12 haloalkynylthio group, an C2-C12 acyl group, a C2-C12 haloacyl group, an C2-C12 acyloxy group, an C2-C12 acylthio group, an C2-C12 alkoxycarbonyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a C3-C12 trialkylsilyl group, a C5-C14 trialkylsilylethynyl group, an C1-C12 alkylsulfonyl group, a C1-C12 haloalkylsulfonyl group, an C6-C16 arylsulfonyl group, a C6-C16 haloarylsulfonyl group, an C1-C12 alkylsulfinyl group, a C1-C12 haloalkylsulfinyl group, an C6-C16 arylsulfinyl group, a C6-C16 haloarylsulfinyl group, a C2-11 polyoxaalkyloxy group, an C2-C5 oxacycloalkyloxy group, an aminocarbonyl group optionally substituted with an C1-C12 alkyl group and/or an C6-C12 aryl group, an aminosulfonyl group optionally substituted with an C1-C12 alkyl group and/or an C6-C12 aryl group, and an amino group optionally substituted with an C1-C12 alkyl group.

2. The tetrazolinone compound according to claim 1 wherein
X represents a sulfur atom;
$R^2$, $R^4$ and $R^5$ represent a hydrogen atom;
$R^{10}$ represents a methyl group; and
Y and Q represent an oxygen atom.

3. The tetrazolinone compound according to claim 2 wherein
$R^1$ represents an C6-C16 aryl group optionally substituted with one or more substituents selected from group $P^1$, an C1-C12 alkyl group optionally substituted with one or more substituents selected from group $P^1$, an C3-C12 cycloalkyl group optionally substituted with one or more substituents selected from group $P^1$, or an adamantyl group optionally substituted with one or more substituents selected from group $P^1$ with the proviso that when the C6-C16 aryl group, the C1-C12 alkyl group, the C3-C12 cycloalkyl group, or the adamantyl group has two or more substituents, the substituents may be same or different to each other;
$R^6$ represents independently of each other an C1-C4 alkyl group, a halogen atom, a C1-C4 haloalkyl group, a C3-C4 cycloalkyl group, a C3-C4 halocycloalkyl group, an C1-C4 alkoxy group, a C1-C4 haloalkoxy group, an C1-C4 alkylthio group, a C1-C4 haloalkylthio group, a nitro group, a cyano group, a hydroxyl group, a thiol group, a trimethylsilylethynyl group, a triethylsilylethynyl group, a pentafluorosulfanyl group, an C2-C4 alkenyl group, a C2-C4 haloalkenyl group, an C2-C4 alkynyl group, a C2-C4 haloalkynyl group, a C3-C4 cycloalkyloxy group, a C3-C4 halocycloalkyloxy group, a C3-C4 cycloalkylthio group, an C2-C4 alkenyloxy group, an C2-C4 alkynyloxy group, a C2-C4 haloalkenyloxy group, a C2-C4 haloalkynyloxy group, an C2-C4 alkynylthio group, an C2-C4 alkenylthio group, a C2-C4 haloalkenylthio group, a C2-C4 haloalkynylthio group, an amino group optionally substituted with an C1-C4 alkyl group, an C2-C4 acyl group, a C2-C4 haloacyl group, an C2-C4 acyloxy group, an C2-C4 acylthio group, an C2-C4 alkoxycarbonyl group, an aminocarbonyl group optionally substituted with an C1-C3 alkyl group, an aminosulfonyl group optionally substituted with an C1-C3 alkyl group, an C1-C4 alkylsulfonyl group, a C1-C4 haloalkylsulfonyl group, an C1-C4 alkylsulfinyl group, a C1-C4 haloalkylsulfinyl group, a hydroxycarbonyl group, or a formyl group; and
$R^7$, $R^8$ and $R^9$ represent independently of each other a hydrogen atom or a fluorine atom.

4. The tetrazolinone compound according to claim 3 wherein $R^1$ represents an C6-C16 aryl group optionally substituted with one or more substituents selected from group $P^1$ with the proviso that when the C6-C16 aryl group has two or more substituents, the substituents may be same or different to each other.

5. The tetrazolinone compound according to claim 3 wherein
$R^1$ represents a formula (2):

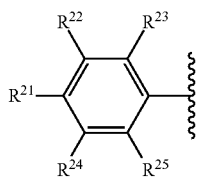

(2)

wherein
$R^{21}$ represents a hydrogen atom, a halogen atom, a nitro group, a cyano group, a trimethylsilyl group, a trimethylsilylethynyl group, a pentafluorosulfanyl group, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C2-C6 alkenyloxy group, an C2-C6 alkynyloxy group, a C2-C6 haloalkenyloxy group, a C2-C6 haloalkynyloxy group, an C2-C6 alkynylthio group, an C2-C6 alkenylthio group, a C2-C6 haloalkenylthio group, a C2-C6 haloalkynylthio group, an amino group optionally substituted with an C1-C6 alkyl group, an C2-C6 acyl group, a C2-C6 haloacyl group, an C2-C6 acyloxy group, an C2-C6 acylthio group, an C1-C6 alkylsulfonyl group, a C1-C6 haloalkylsulfonyl group, an C1-C6 alkylsulfinyl group, a C1-C6 haloalkylsulfinyl group, a C2-C5 polyoxaalkyloxy group or an C2-C5 oxacycloalkyloxy group; and
$R^{22}$, $R^{23}$, $R^{24}$ and $R^{25}$ represent independently of each other a hydrogen atom or a halogen atom.

6. The tetrazolinone compound according to claim 5 wherein
$R^{21}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group; and
$R^6$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom.

7. The tetrazolinone compound according to claim 6 wherein
$R^{21}$ represents a hydrogen atom, a fluorine atom, a chlorine atom, a bromine atom, an iodine atom, a methyl group, an ethyl group, a methoxy group, a methylthio group, a trifluoromethyl group or a trifluoromethoxy group;
$R^{22}$, $R^{23}$, $R^{24}$ and $R^{25}$ represent independently of each other a hydrogen atom or a fluorine atom; and
$R^6$ represents a methyl group, an ethyl group, a cyclopropyl group, a chlorine atom, a bromine atom or a methoxy group.

8. The tetrazolinone compound according to claim 3 wherein
$R^1$ represents a group of formula (3):

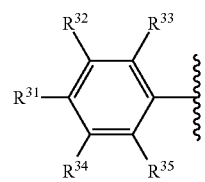

(3)

wherein
$R^{32}$ represents a hydrogen atom, a halogen atom, a nitro group, a cyano group, a trimethylsilyl group, a trimethylsilylethynyl group, a pentafluorosulfanyl group, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C2-C6 alkenyloxy group, an C2-C6 alkynyloxy group, a C2-C6 haloalkenyloxy group, a C2-C6 haloalkynyloxy group, an C2-C6 alkynylthio group, an C2-C6 alkenylthio group, a C2-C6 haloalkenylthio group, a C2-C6 haloalkynylthio group, an amino group optionally substituted with an C1-C6 alkyl group, an C2-C6 acyl group, a C2-C6 haloacyl group, an C2-C6 acyloxy group, an C2-C6 acylthio group, an C1-C6 alkylsulfonyl group, a C1-C6 haloalkylsulfonyl group, an C1-C6 alkylsulfinyl group, a C1-C6 haloalkylsulfinyl group, a C2-C5 polyoxaalkyloxy group or an C2-C5 oxacycloalkyloxy group; and $R^{31}$, $R^{33}$, $R^{34}$ and $R^{35}$ represent independently of each other a hydrogen atom or a halogen atom.

9. The tetrazolinone compound according to claim 8 wherein $R^{32}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group;

$R^6$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom.

10. The tetrazolinone compound according to claim 9 wherein $R^{32}$ represents a hydrogen atom, a fluorine atom, a chlorine atom, a bromine atom, an iodine atom, a methyl group, an ethyl group, a methoxy group, a methylthio group, a trifluoromethyl group or a trifluoromethoxy group;

$R^{31}$, $R^{33}$, $R^{34}$ and $R^{35}$ represent independently of each other a hydrogen atom or a fluorine atom; and $R^6$ represents a methyl group, an ethyl group, a cyclopropyl group, a chlorine atom, a bromine atom or a methoxy group.

11. The tetrazolinone compound according to claim 3 wherein $R^1$ represents a group of formula (4):

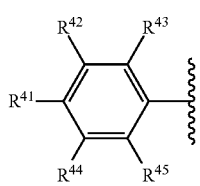

(4)

wherein $R^{43}$ represents a hydrogen atom, a halogen atom, a nitro group, a cyano group, a trimethylsilyl group, a trimethylsilylethynyl group, a pentafluorosulfanyl group, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C2-C6 alkenyloxy group, an C2-C6 alkynyloxy group, a C2-C6 haloalkenyloxy group, a C2-C6 haloalkynyloxy group, an C2-C6 alkynylthio group, an C2-C6 alkenylthio group, a C2-C6 haloalkenylthio group, a C2-C6 haloalkynylthio group, an amino group optionally substituted with an C1-C6 alkyl group, an C2-C6 acyl group, a C2-C6 haloacyl group, an C2-C6 acyloxy group, an C2-C6 acylthio group, an C1-C6 alkylsulfonyl group, a C1-C6 haloalkylsulfonyl group, an C1-C6 alkylsulfinyl group, a C1-C6 haloalkylsulfinyl group, a C2-C5 polyoxaalkyloxy group, or an C2-C5 oxacycloalkyloxy group;

$R^{41}$, $R^{42}$, $R^{44}$ and $R^{45}$ represent independently of each other a hydrogen atom or a halogen atom.

12. The tetrazolinone compound according to claim 11 wherein $R^{43}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group; and $R^6$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom.

13. The tetrazolinone compound according to claim 11 wherein $R^{43}$ represents a hydrogen atom, a fluorine atom, a chlorine atom, a bromine atom, an iodine atom, a methyl group, an ethyl group, a methoxy group, a methylthio group, a trifluoromethyl group or a trifluoromethoxy group;

$R^{41}$, $R^{42}$, $R^{44}$ and $R^{45}$ represent independently of each other a hydrogen atom or a fluorine atom; and $R^6$ represent a methyl group, an ethyl group, a cyclopropyl group, a chlorine atom, a bromine atom or a methoxy group.

14. The tetrazolinone compound according to claim 3 wherein $R^1$ represents an C1-C12 alkyl group optionally substituted with one or more substituents selected from group $P^1$, a C3-C12 cycloalkyl group optionally substituted with one or more substituents selected from group $P^1$, or an adamantyl group optionally substituted with one or more substituents selected from group $P^1$ (with the proviso that when the C1-C12 alkyl group, the C3-C12 cycloalkyl group or the adamantyl group has two or more substituents, the substituents may be same or different to each other).

15. The tetrazolinone compound according to claim 14 wherein $R^6$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom.

16. The tetrazolinone compound according to claim 15 wherein $R^6$ represents a methyl group, an ethyl group, a cyclopropyl group, a chlorine atom, a bromine atom or a methoxy group.

17. The tetrazolinone compound according to claim 1 wherein
X represents an oxygen atom;
$R^2$, $R^4$ and $R^5$ represent a hydrogen atom;
$R^{10}$ represent a methyl group; and
Y and Q represent an oxygen atom.

18. The tetrazolinone compound according to claim 17 wherein
$R^1$ represents an C6-C12 aryl group optionally substituted with one or more substituents selected from group $P^1$, an C1-C12 alkyl group optionally substituted with one or more substituents selected from group $P^1$, a C3-C12 cycloalkyl group optionally substituted with one or more substituents selected from group $P^1$, or an adamantyl group optionally substituted with one or more substituents selected from group $P^1$ with the proviso that when the C6-C16 aryl group, the C1-C12 alkyl group, the C3-C12 cycloalkyl group or the adamantyl group has two or more substituents, the substituents may be same or different to each other;
$R^6$ represents a hydroxycarbonyl group, a formyl group, a halogen atom, a nitro group, a cyano group, a hydroxyl group, a thiol group, a trimethylsilyl group, a trimethylsilylethynyl group, a pentafluorosulfanyl group, an C1-C4 alkyl group, a C1-C4 haloalkyl group, an C2-C4 alkenyl group, a C2-C4 haloalkenyl group, an C2-C4 alkynyl group, a C2-C4 haloalkynyl group, a C3-C4 cycloalkyl group, a C3-C4 halocycloalkyl group, an C1-C4 alkoxy group, a C1-C4 haloalkoxy group, an C1-C4 alkylthio group, a C1-C4 haloalkylthio group, a C3-C4 cycloalkyloxy group, a C3-C4 halocycloalkyloxy group, a C3-C4 cycloalkylthio group, a C2-C4 alkenyloxy group, an C2-C4 alkynyloxy group, a C2-C4 haloalkenyloxy group, a C2-C4 haloalkynyloxy group, an C2-C4 alkynylthio group, an C2-C4 alkenylthio group, a C2-C4 haloalkenylthio group, a C2-C4 haloalkynylthio group, an amino group optionally substituted with an C1-C4 alkyl group, an C2-C4 acyl group, a C2-C4 haloacyl group, an C2-C4 acyloxy group, an C2-C4 acylthio group, an C2-C4 alkoxycarbonyl group, an aminocarbonyl group optionally substituted with an C1-C3 alkyl group, an aminosulfonyl group optionally substituted with an C1-C3 alkyl group, an C1-C4 alkylsulfonyl group, a C1-C4 haloalkylsulfonyl group, an C1-C4 alkylsulfinyl group, or a C1-C4 haloalkylsulfinyl group; and
$R^7$, $R^8$ and $R^9$ represent independently of each other a hydrogen atom or a fluorine atom.

19. The tetrazolinone compound according to claim 18 wherein $R^1$ represents an C6-C12 aryl group optionally substituted with one or more substituents selected from group $P^1$ with the proviso that when the C6-C16 aryl group has two or more substituents, the substituents may be same or different to each other.

20. The tetrazolinone compound according to claim 3 wherein $R^1$ represents a group of formula (2):

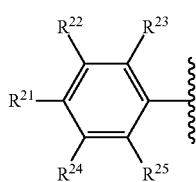

(2)

wherein
$R^{21}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group; and
$R^{22}$, $R^{23}$, $R^{24}$ and $R^{25}$ represent independently of each other a hydrogen atom or a halogen atom;
$R^7$, $R^8$ and $R^9$ represent a hydrogen atom; and
$R^6$ represents a halogen atom, an C1-C3 alkyl group, a C1-C3 haloalkyl group or an C1-C3 alkoxy group.

21. The tetrazolinone compound according to claim 20 wherein
$R^{21}$ represents a halogen atom, a methyl group, a trifluoromethyl group or a methoxy group;
$R^{22}$, $R^{23}$, $R^{24}$ and $R^{25}$ represent independently of each other a hydrogen atom or a fluorine atom; and
$R^6$ represents a chlorine atom, a bromine atom, a methyl group, an ethyl group or a methoxy group.

22. The tetrazolinone compound according to claim 3 wherein $R^1$ represents a group of formula (3):

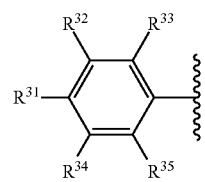

(3)

wherein
$R^{32}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group; and
$R^{31}$, $R^{33}$, $R^{34}$ and $R^{35}$ represent independently of each other a hydrogen atom or a halogen atom;
$R^7$, $R^8$ and $R^9$ represent a hydrogen atom; and
$R^6$ represents a halogen atom, an C1-C3 alkyl group, a C1-C3 haloalkyl group or an C1-C3 alkoxy group.

23. The tetrazolinone compound according to claim 22 wherein
$R^{32}$ represents a halogen atom, a methyl group, a trifluoromethyl group or a methoxy group; and
$R^{31}$, $R^{33}$, $R^{34}$ and $R^{35}$ represent independently of each other a hydrogen atom or a fluorine atom; and
$R^6$ represents a chlorine atom, a bromine atom, a methyl group, an ethyl group or a methoxy group.

24. The tetrazolinone compound according to claim 3 wherein
$R^1$ represents a group of formula (4):

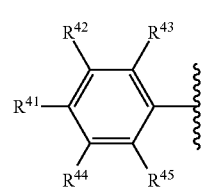

(4)

wherein
$R^{43}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group; and $R^{41}$, $R^{42}$, $R^{44}$ and $R^{45}$ represent independently of each other a hydrogen atom or a halogen atom;

$R^7$, $R^8$ and $R^9$ represent a hydrogen atom; and $R^6$ represents a halogen atom, an C1-C3 alkyl group, a C1-C3 haloalkyl group or an C1-C3 alkoxy group.

25. The tetrazolinone compound according to claim 24 wherein $R^{43}$ represents a halogen atom, a methyl group, a trifluoromethyl group or a methoxy group;

$R^{41}$, $R^{42}$, $R^{44}$ and $R^{45}$ represent independently of each other a hydrogen atom or a fluorine atom; and $R^6$ represents a chlorine atom, a bromine atom, a methyl group, an ethyl group or a methoxy group.

26. The tetrazolinone compound according to claim 3 wherein $R^6$ represents a C3-C4 cycloalkyl group, a C3-C4 halocycloalkyl group, a C1-C3 haloalkoxy group, an C1-C4 alkylthio group, a C1-C4 haloalkylthio group, a nitro group, a cyano group, a hydroxyl group, a thiol group, a trimethylsilylethynyl group, a pentafluorosulfanyl group, an C2-C4 alkenyl group, a C2-C4 haloalkenyl group, an C2-C4 alkynyl group, a C2-C4 haloalkynyl group, a C3-C4 cycloalkyloxy group, a C3-C4 halocycloalkyloxy group, a C3-C4 cycloalkylthio group, a C2-C4 alkenyloxy group, an C2-C4 alkynyloxy group, a C2-C4 haloalkenyloxy group, a C2-C4 haloalkynyloxy group, an C2-C4 alkynylthio group, an C2-C4 alkenylthio group, a C2-C4 haloalkenylthio group, a C2-C4 haloalkynylthio group, an amino group optionally substituted with an C1-C4 alkyl group, an C2-C4 acyl group, a C2-C4 haloacyl group, an C2-C4 acyloxy group, an C2-C4 acylthio group, an C2-C4 alkoxycarbonyl group, an aminocarbonyl group optionally substituted with an C1-C3 alkyl group, an aminosulfonyl group optionally substituted with an C1-C3 alkyl group, an C1-C4 alkylsulfonyl group, a C1-C4 haloalkylsulfonyl group, an C1-C4 alkylsulfinyl group, a C1-C4 haloalkylsulfinyl group, a hydroxycarbonyl group, or a formyl group.

27. An agent for controlling pests comprising the tetrazolinone compound according to claim 1.

28. A method for controlling pests comprising applying an effective amount of the tetrazolinone compound according to claim 1 to plant or soil.

29. A thiazole compound of formula (5):

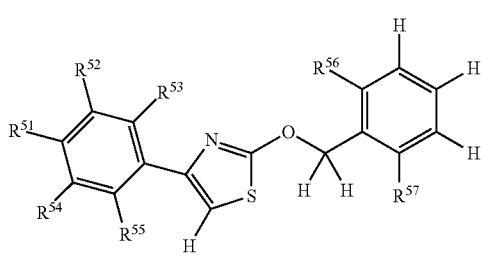

wherein $R^{51}$, $R^{52}$, $R^{53}$, $R^{54}$ and $R^{55}$ represent independently of each other a hydrogen atom, a halogen atom, a nitro group, a cyano group, a trimethylsilyl group, a trimethylsilylethynyl group, a pentafluorosulfanyl group, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C2-C6 alkenyloxy group, an C2-C6 alkynyloxy group, a C2-C6 haloalkenyloxy group, a C2-C6 haloalkynyloxy group, an C2-C6 alkynylthio group, an C2-C6 alkenylthio group, a C2-C6 haloalkenylthio group, a C2-C6 haloalkynylthio group, an amino group optionally substituted with an C1-C6 alkyl group, an C2-C6 acyl group, a C2-C6 haloacyl group, an C2-C6 acyloxy group, an C2-C6 acylthio group, an C1-C6 alkylsulfonyl group, a C1-C6 haloalkylsulfonyl group, an C1-C6 alkylsulfinyl group, a C1-C6 haloalkylsulfinyl group, a C2-O5 polyoxaalkyloxyl group, or an C2-O5 oxacycloalkyloxy group;

$R^{56}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group, or an C1-C4 alkylamino group; and $R^{57}$ represents a group of formula (6):

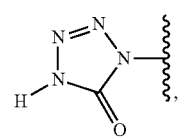

a formyl group, a C2-C6 halogenated acyl group, an C2-C6 alkoxycarbonyl group, a hydroxycarbonyl group, a hydroxymethyl group, an amino group, an isocyanate group, a nitro group, a halomethyl group, a halogen atom, NSO, $CON_3$, or aminocarbonyl group optionally substituted with a chlorine atom, a bromine atom, or a hydroxyl group.

30. The thiazole compound according to claim 29, wherein $R^{51}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group;

$R^{56}$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom;

$R^{52}$, $R^{53}$, $R^{54}$ and $R^{55}$ represent independently of each other a hydrogen atom or a halogen atom.

31. The thiazole compound according to claim 29, wherein $R^{52}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group;

$R^{56}$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom; and $R^{51}$, $R^{53}$, $R^{54}$ and $R^{55}$ represent independently of each other a hydrogen atom or a halogen atom.

32. The thiazole compound according to claim 29, wherein $R^{52}$ represents a hydrogen atom, an C1-C6 alkyl group, a C1-C6 haloalkyl group, an C1-C6 alkoxy group, a C1-C6 haloalkoxy group, an C1-C6 alkylthio group, an C1-C6 haloalkylthio group, an C2-C6 acyl group, a C2-C6 haloacyl group, a halogen atom, a nitro group or a cyano group;

$R^{56}$ represents an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an amino group optionally substituted with an C1-C3 alkyl group, or a halogen atom; and $R^{51}$, $R^{53}$ and $R^{54}$ represent independently of each other a hydrogen atom or a halogen atom.

33. The thiazole compound according to claim 30, wherein $R^{51}$ represents a halogen atom, a methyl group, an ethyl group or a methoxy group;

$R^{56}$ represents a chlorine atom, a bromine atom, a methyl group, an ethyl group, a cyclopropyl group or a methoxy group; and $R^{52}$, $R^{53}$, $R^{54}$ and $R^{55}$ represent independently of each other a hydrogen atom or a fluorine atom.

34. The thiazole compound according to claim 31, wherein $R^{52}$ represents a halogen atom, a methyl group, an ethyl group or a methoxy group;

$R^{56}$ represents a chlorine atom, a bromine atom, a methyl group, an ethyl group, a cyclopropyl group or a methoxy group; and $R^{51}$, $R^{53}$, $R^{54}$ and $R^{55}$ represent independently of each other a hydrogen atom or a fluorine atom.

35. The thiazole compound according to claim 29, wherein $R^{53}$ represents a halogen atom, a methyl group, an ethyl group or a methoxy group;

$R^{56}$ represents a chlorine atom, a bromine atom, a methyl group, an ethyl group, a cyclopropyl group or a methoxy group; and $R^{51}$, $R^{52}$, and $R^{54}$ represent independently of each other a hydrogen atom or a fluorine atom.

* * * * *